United States Patent
Hulme et al.

(10) Patent No.: US 12,054,483 B2
(45) Date of Patent: Aug. 6, 2024

(54) SMALL MOLECULE INHIBITORS OF DYRK/CLK AND USES THEREOF

(71) Applicant: Arizona Board of Regents on Behalf of the University of Arizona, Tucson, AZ (US)

(72) Inventors: Christopher Hulme, Tucson, AZ (US); Christopher Foley, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 498 days.

(21) Appl. No.: 17/280,763

(22) PCT Filed: Sep. 27, 2019

(86) PCT No.: PCT/US2019/053620
§ 371 (c)(1),
(2) Date: Mar. 26, 2021

(87) PCT Pub. No.: WO2020/069418
PCT Pub. Date: Apr. 2, 2020

(65) Prior Publication Data
US 2022/0041590 A1    Feb. 10, 2022

Related U.S. Application Data

(60) Provisional application No. 62/738,540, filed on Sep. 28, 2018.

(51) Int. Cl.
| | | |
|---|---|---|
| C07D 471/04 | (2006.01) | |
| C07D 405/14 | (2006.01) | |
| C07D 487/04 | (2006.01) | |
| C07D 498/08 | (2006.01) | |

(52) U.S. Cl.
CPC ......... *C07D 471/04* (2013.01); *C07D 405/14* (2013.01); *C07D 487/04* (2013.01); *C07D 498/08* (2013.01)

(58) Field of Classification Search
None
See application file for complete search history.

(56) References Cited

U.S. PATENT DOCUMENTS

| | | | |
|---|---|---|---|
| 3,989,816 | A | 11/1976 | Rajadhyaksha |
| 4,444,762 | A | 4/1984 | Rajadhyaksha |
| 2002/0019415 | A1 | 2/2002 | Camden |
| 2013/0102586 | A1 | 4/2013 | Vankayalapati et al. |
| 2016/0326178 | A1 | 11/2016 | Zhuo et al. |
| 2018/0208600 | A1 | 7/2018 | Nacro et al. |

FOREIGN PATENT DOCUMENTS

| | | | |
|---|---|---|---|
| CN | 101641093 | 2/2010 | |
| CN | 103797002 | 5/2014 | |
| CN | 108137581 | 6/2018 | |
| CN | 108137582 | 6/2018 | |
| WO | WO-2015035167 A1 * | 3/2015 | ......... A61K 31/5025 |
| WO | WO-2015108490 A2 * | 7/2015 | ............. A61K 45/06 |
| WO | WO 2015/187818 | 12/2015 | |
| WO | WO 2017/040993 A1 | 3/2017 | |
| WO | WO-2017040993 A1 * | 3/2017 | ......... A61K 31/4184 |
| WO | WO 2017/055530 | 4/2017 | |
| WO | WO 2017/055533 | 4/2017 | |

OTHER PUBLICATIONS

International Search Report and Written Opinion for PCT/US2019/053620. Mailed Feb. 3, 2020. 12 pages.
Arron et al., NFAT dysregulation by increased dosage of DSCR1 and DYRK1A on chromosome 21. Nature. Jun. 1, 2006;441(7093):595-600.
Branca et al., Dyrk1 inhibition improves Alzheimer's disease-like pathology. Aging Cell. Oct. 2017;16(5):1146-1154.
Bullock et al., Kinase domain insertions define distinct roles of CLK kinases in SR protein phosphorylation. Structure. Mar. 11, 2009;17(3):352-62.
Chen et al., Dosage of Dyrk1a shifts cells within a p21-cyclin D1 signaling map to control the decision to enter the cell cycle. Mol Cell. Oct. 10, 2013;52(1):87-100. 26 pages.
Druillennec et al., Alternative splicing in oncogenic kinases: from physiological functions to cancer. J Nucleic Acids. 2012;2012:639062. 14 pages.
Fedorov et al., Specific CLK inhibitors from a novel chemotype for regulation of alternative splicing. Chem Biol. Jan. 28, 2011;18(1):67-76.
Guo et al., DYRK1A and DYRK3 promote cell survival through phosphorylation and activation of SIRT1. J Biol Chem. Apr. 23, 2010;285(17):13223-32.

(Continued)

*Primary Examiner* — Jeffrey S Lundgren
*Assistant Examiner* — Michael J Schmitt
(74) *Attorney, Agent, or Firm* — Casimir Jones, S.C.; Robert A. Goetz

(57) ABSTRACT

This invention is in the field of medicinal chemistry. In particular, the invention relates to a new class of small-molecules having a 6,5-heterocyclic structure (e.g., compounds having a imidazopyridine, imidazopyrimidine, imidazopyrazine, imidazopyridazine, imidazotriazine, benzoimidazole, benzotriazole, benzoisoxazole, purine, indazole, triazolotriazine, triazolopyridazine, triazolopyrimidine, triazolopyrazine, triazolotetrazine, triazolopyridine, pyrazolopyrazine, pyrazolopyrimidine, pyrazolopyridazine, pyrazolotriazine, pyrazolopyridine, isoxazolopyrazine, isoxazolopyrimidine, isoxazolopyrdiazine, isoxazolotriazine, or isoxalopyridine structure) which function as inhibitors of DYRK1A, DYRK1B, and Clk-1, and their use as therapeutics for the treatment of Alzheimer's disease, Down syndrome, diabetes, glioblastoma, autoimmune diseases, cancer (e.g., glioblastoma, prostate cancer), inflammatory disorders (e.g., airway inflammation), and other diseases.

1 Claim, No Drawings

(56) References Cited

OTHER PUBLICATIONS

Hämmerle et al., Transient expression of Mnb/Dyrk1a couples cell cycle exit and differentiation of neuronal precursors by inducing p27KIP1 expression and suppressing NOTCH signaling. Development. Jun. 2011;138(12):2543-54.

Humpfries et al., 8-Fluoroimidazo[1,2-a]pyridine: synthesis, physicochemical properties and evaluation as a bioisosteric replacement for imidazo[1,2-a]pyrimidine in an allosteric modulator ligand of the GABA A receptor. Bioorg Med Chem Lett. Mar. 15, 2006;16(6):1518-22.

Ionescu et al., DYRK1A kinase inhibitors with emphasis on cancer. Mini Rev Med Chem. Nov. 2012;12(13):1315-29. 15 pages.

Jain et al., Human CDC2-like kinase 1 (CLK1): a novel target for Alzheimer's disease. Curr Drug Targets. May 2014;15(5):539-50. 12 pages.

Khor et al., The kinase DYRK1A reciprocally regulates the differentiation of Th17 and regulatory T cells. Elife. May 22, 2015;4:e05920. 27 pages.

Liu et al., Tau exon 10 alternative splicing and tauopathies. Mol Neurodegener. Jul. 10, 2008;3:8. 10 pages.

Mennenga et al., Harmine treatment enhances short-term memory in old rats: Dissociation of cognition and the ability to perform the procedural requirements of maze testing. Physiol Behav. Jan. 2015;138:260-5. 16 pages.

Michan et al., SIRT1 is essential for normal cognitive function and synaptic plasticity. J Neurosci. Jul. 21, 2010;30(29):9695-707.

Seifert et al., DYRK1A phosphorylates caspase 9 at an inhibitory site and is potently inhibited in human cells by harmine. FEBS J. Dec. 2008;275(24):6268-80.

Smith et al., Recent advances in the design, synthesis, and biological evaluation of selective DYRK1A inhibitors: a new avenue for a disease modifying treatment of Alzheimer's? ACS Chem Neurosci. Nov. 21, 2012;3(11):857-72.

Velazquez et al., Chronic Dyrk1 Inhimition Delays the Onset of AD-Like Pathology in 3xTg-AD Mice. Molecular Neurobiology. 2019. 1-12.

Wang et al., Cyclin D1b is aberrantly regulated in response to therapeutic challenge and promotes resistance to estrogen antagonists. Cancer Res. Jul. 15, 2008;68(14):5628-38. 26 pages.

Zheng et al., A palladium-catalyzed regiospecific synthesis of N-aryl benzimidazoles. Angew Chem Int Ed Engl. 2007;46(39):7509-12.

Neumann F. DYRK1A inhibition and cognitive rescue in a Down syndrome mouse model are induced by new fluoro-DANDY derivatives. Sci Rep. Feb. 12, 2018;8(1):2859.

Office Action for CN 201980078361.9, mailed Apr. 27, 2023, 9 pages.

Extended European Search Report for PCT/US2019/053620. Mailed Jun. 9, 2022. 8 pages.

Fernanda Neumann et al; "DYRK1A inhibition and cognitive rescue in a Down syndrome mouse model are induced by new fluoro-DANDY derivatives", Scientific Reports, vol. 8, n. 1, Feb. 12, 2018, pp. 1-12.

* cited by examiner

SMALL MOLECULE INHIBITORS OF DYRK/CLK AND USES THEREOF

CROSS REFERENCE TO RELATED APPLICATIONS

This application is a U.S. 371 national phase entry of International Patent Application No. PCT/US2019/053620, filed Sep. 27, 2019, which claims priority to and the benefit of U.S. Provisional Application No. 62/738,540, filed Sep. 28, 2018, which are hereby incorporated by reference in their entireties.

FIELD OF THE INVENTION

This invention is in the field of medicinal chemistry. In particular, the invention relates to a new class of small-molecules having a 6,5-heterocyclic structure (e.g., compounds having a imidazopyridine, imidazopyrimidine, imidazopyrazine, imidazopyridazine, imidazotriazine, benzoimidazole, benzotriazole, benzoisoxazole, purine, indazole, triazolotriazine, triazolopyridazine, triazolopyrimidine, triazolopyrazine, triazolotetrazine, triazolopyridine, pyrazolopyrazine, pyrazolopyrimidine, pyrazolopyridazine, pyrazolotriazine, pyrazolopyridine, isoxazolopyrazine, isoxazolopyrimidine, isoxazolopyridazine, isoxazolotriazine, or isoxalopyridine structure) which function as inhibitors of DYRK1A, DYRK1B, and Clk-1, and their use as therapeutics for the treatment of Alzheimer's disease, Down syndrome, diabetes, glioblastoma, autoimmune diseases, inflammatory disorders (e.g., airway inflammation), cancer (e.g., glioblastoma, prostate cancer), and other diseases.

INTRODUCTION

With 24.3 million people affected in 2005 and an estimated rise to 42.3 million in 2020, dementia is currently a leading unmet medical need and costly burden on public health. Seventy percent of these cases have been attributed to Alzheimer's disease (AD), a neurodegenerative pathology whose most evident symptom is a progressive decline in cognitive functions.

The underlying treatment of learning and/or memory disorders is a huge and significantly unmet medical need and also included learning and memory repair after, for example, incidents of stroke or significant brain damage. As such, an improved understanding of the dementia (and other neuropathology) and related improved treatment methods are needed.

SUMMARY OF THE INVENTION

In addition to the overwhelmingly prominent β-amyloid hypothesis being evaluated in a multitude of clinical trials through small molecule modulation of γ- and β-secretases and numerous immune-based approaches, aberrant phosphorylation of the tau protein is believed to significantly contribute to the development of AD and thus affords an alternate approach for therapeutic development. Tau is a cytoplasmic protein involved in the stabilization of microtubules under normal conditions. In AD, neuronal tau has been found to be excessively phosphorylated, with subsequent generation of aggregates of phosphorylated tau protein, known as "neurofibrillary tangles" (NFTs). NFTs and amyloid plaques are considered the most common hallmarks of AD and are correlated with neurofibrillary degeneration, neuronal death, and dementia.

Interestingly, several protein kinases have been implicated in neuronal development and, in particular, their overexpression and aberrant activation have been shown to play a significant role in the development of AD via tau phosphorylation. Dual specificity tyrosine phosphorylation regulated kinase-1A (DYRK1A) is important in neuronal development and plays a variety of functional roles within the adult central nervous system. The DYRK1A gene is located within the Down syndrome critical region (DSCR) on human chromosome 21 and current research suggests that overexpression of DYRK1A may be a significant factor leading to cognitive deficits in people with Alzheimer's disease (AD) and Down syndrome (DS).

Currently, treatment options for cognitive deficiencies associated with Down syndrome, as well as Alzheimer's disease, are extremely limited and represent a major unmet therapeutic need. Small molecule inhibition of DYRK1A activity in the brain may provide an avenue for pharmaceutical intervention of mental impairment associated with AD and other neurodegenerative diseases.

Increased expression of the DYRK1A gene has been implicated in both the cognitive deficits of Down syndrome (DS) and the early onset of tau and amyloid neuropathologies that are associated with this genetic disorder. DYRK1A levels are increased in transgenic mouse models of DS and develop DS-like phenotypes including hippocampal-dependent spatial learning and memory deficits and developmental delays. Together these data strongly support a central function for DYRK1A in cognitive deficits associated with DS. Moreover, inhibition of excess DYRK1A activity has been shown to improve these DYRK1A-mediated cognitive deficits after administration of the natural products epigallocatechin-3-gallate (EGCg) and harmine, the standards for DYRK1A inhibition at the on-set of this translational campaign. However, these probes are not significantly selective and have numerous off-target effects that reduce their practical long-term use. To circumvent many of the detrimental issues observed, in particular with harmine, knowledge-based design efforts herein have unearthed novel small molecule series of structurally unique 6,5-heterocyclic DYRK1A inhibitors, amenable to test the benefits of selective DYRK1A inhibition in mouse models of DS/AD and a variety of other disease states including Parkinson's disease, Pick's disease, Huntington's and additional tauopathies.

Experiments conducted during the course of developing embodiments for the present invention designed, synthesized and biologically evaluated compounds having a 6,5-heterocyclic structure (e.g., compounds having a imidazopyridine, imidazopyrimidine, imidazopyrazine, imidazopyridazine, imidazotriazine, benzoimidazole, benzotriazole, benzoisoxazole, purine, indazole, triazolotriazine, triazolopyridazine, triazolopyrimidine, triazolopyrazine, triazolotetrazine, triazolopyridine, pyrazolopyrazine, pyrazolopyrimidine, pyrazolopyridazine, pyrazolotriazine, pyrazolopyridine, isoxazolopyrazine, isoxazolopyrimidine, isoxazolopyrdiazine, isoxazolotriazine, or isoxalopyridine structure) as inhibitors of the dual specificity tyrosine phosphorylation regulated kinase-1A (DYRK1A), and their potential for use as therapeutics against AD and other disorders related to DYRK-1A activity (e.g., DS, other neuropathology, cancer (e.g., glioblastoma, prostate cancer), diabetes, cognitive enhancement). Many of such compounds exhibit activity against dual specificity tyrosine phosphorylation regulated kinase-1B (DYRK1B) and exhibit activity against other kinases implicated in a variety of disease states (e.g., dual specificity protein kinase CLK1 (Clk-1).

The DYRK1A inhibitors described herein can also be considered as potential therapeutics for the treatment of developmental diseases such as Down syndrome, and neurodegenerative diseases such as Parkinson's disease, and Huntington's disease. Moreover, the DYRK1A inhibitors of the present invention have been also implicated as potential therapeutics for the treatment of glioblastomas and further potential utility is highlighted in the oncology arena (see, e.g., Ionescu et al., Mini-reviews in Medicinal Chemistry, 2012, 12, 1315-1329).

These novel DYRK1A inhibitors may also have utility as general cognitive enhancers, given the published findings that DYRK1A can phosphorylate sirtuin 1, a key regulator of learning and memory (see, e.g., Michan et al., J. Neurosci. 2010, 30(29), 9695-9707; Guo et al., J Biol. Chem. 2010, 285 (17), 13223-13232). The potential utility of these DYRK1A compound series is further reinforced by findings that harmine, a potent, but relatively less selective DYRK1A inhibitor, enhances memory performance in wild-type rodents (Mennenga et al., Physiol. Behav. 2015, 138, 260-265). Moreover, the effectiveness of small molecule inhibition of DYRK1A in mitigating both insoluble tau aggregates and amyloid plaques has been demonstrated (see, e.g., Branca et al., Aging Cell, 2017, 16(5), 1146-1154). The mechanistic rational for this was detailed previously (see Smith et al., ACS Chem. Neuroscience, 2012, 3(11), 857-872). These novel DYRK1A inhibitors may also have further utility as results identify DYRK1A as a physiologically relevant regulator of $T_{reg}$ cell differentiation and suggest a broader role for other DYRK family members in immune homeostasis. As such, new roles may be found in autoimmune diseases such as inflammatory bowel disease and type 1 diabetes (see, e.g., Khor B, et al., eLife 2015; 4:e05920).

Accordingly, this invention relates to a new class of small-molecules having a 6,5-heterocyclic structure (e.g., compounds having a imidazopyridine, imidazopyrimidine, imidazopyrazine, imidazopyridazine, imidazotriazine, benzoimidazole, benzotriazole, benzoisoxazole, purine, indazole, triazolotriazine, triazolopyridazine, triazolopyrimidine, triazolopyrazine, triazolotetrazine, triazolopyridine, pyrazolopyrazine, pyrazolopyrimidine, pyrazolopyridazine, pyrazolotriazine, pyrazolopyridine, isoxazolopyrazine, isoxazolopyrimidine, isoxazolopyrdiazine, isoxazolotriazine, or isoxalopyridine structure) which function as inhibitors of DYRK1A protein, and their use as therapeutics for the treatment of disorders related to DYRK1A activity (e.g., AD, DS, neuropathology, glioblastoma, prostate cancer, diabetes, autoimmune diseases, inflammatory disorders (e.g., airway inflammation).

In a particular embodiment, compounds encompassed within the following formulas are provided:

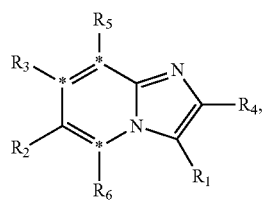

(Formula I)

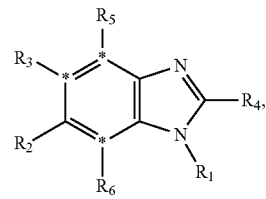

(Formula II)

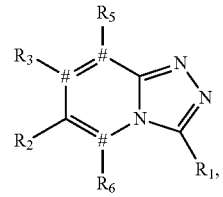

(Formula III)

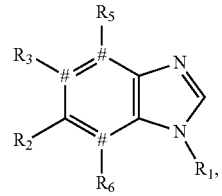

(Formula IV)

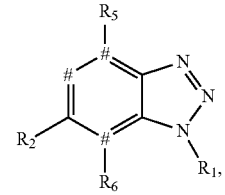

(Formula V)

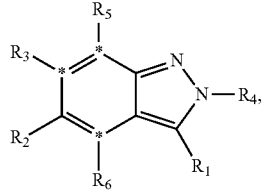

(Formula VI)

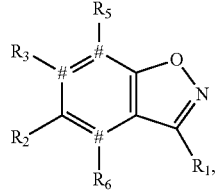

(Formula VII)

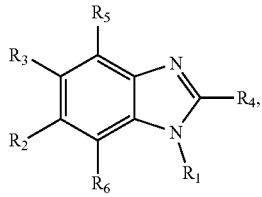

(Formula VIII)

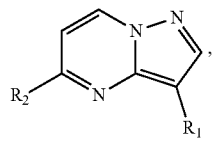

(Formula X)

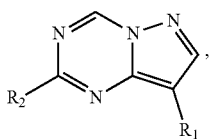
(Formula XI)

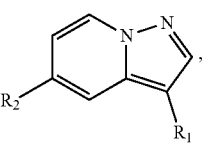
(Formula XII)

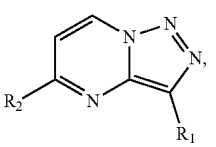
(Formula XIII)

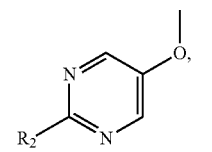
(Formula XIV)

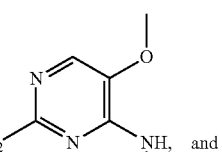
(Formula XV)

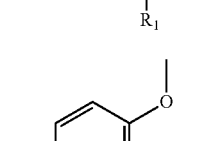
(Formula XVI)

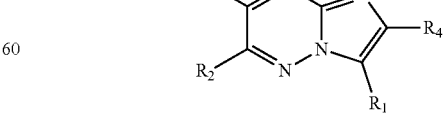
(Formula XVII)

including pharmaceutically acceptable salts, solvates, and/or prodrugs thereof, wherein R5 is present or absent, wherein R6 is present or absent.

Formula I is not limited to a particular chemical moiety for R1, R2, R3, R4, R5, R6, *, # if one or both are present. In some embodiments, the particular chemical moiety for R1, R2, R3, R4, R5, R6, *, # if one or both are present, independently include any chemical moiety that permits the resulting compound to inhibit DYRK1A activity. In some embodiments, the particular chemical moiety for R1, R2, R3, R4, R5, R6, *, # if one or both are present, independently include any chemical moiety that permits the resulting compound to inhibit one or more of: DYRK1A related PI3K/Akt signaling; DYRK1A related tau phosphorylation; DYRK1A related NFAT phosphorylation; DYRK1A related ASK1/JNK1 pathway activation; DYRK1A related p53 phosphorylation; DYRK1A related Amph 1 phosphorylation; DYRK1A related Dynamin 1 phosphorylation; DYRK1A related Synaptojanin phosphorylation; DYRK1A related presenilin 1 (the catalytic sub-unit of γ-secretase) activity; DYRK1A related amyloid precursor protein phosphorylation; DYRK1A related SIRT1 activation; DYRK2 activity; DYRK1B activity; CMGC/CLK kinase activity; CLK2 activity; CLK3 activity; and CLK4 activity.

In some embodiments, the particular chemical moiety for R1, R2, R3, R4, R5, R6, *, # if one or both are present, independently include any chemical moiety that permits the resulting compound to bind a DYRK1A protein at the Lys188 position (e.g., commonly known as the conserved lysine) (e.g., via the R2 moiety). In some embodiments, the particular chemical moiety for R1, R2, R3, R4, R5, R6, *, # if one or both are present, independently include any chemical moiety that permits the resulting compound to bind a DYRK1A protein at the Lys188 position (e.g., commonly known as the conserved lysine) (e.g., via the R2 moiety).

Such embodiments are not limited to a particular definition for the "*" substituents.

In some embodiments, the "*" substituents are two carbons and one nitrogen such that the resulting structure is one of the following formulas:

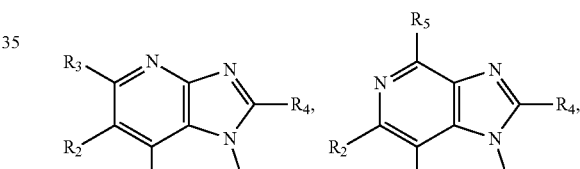


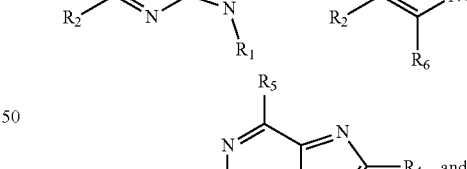

In some embodiments, the "*" substituents are three carbons such that the resulting structure is one of the following formulas:

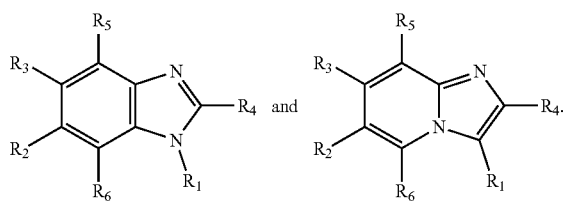

Such embodiments are not limited to a particular definition for the "#" substituents.

In some embodiments, the "#" substituents are selected from two nitrogens and one carbon, three carbons, three nitrogens, or one nitrogen and two carbons. For example, in some embodiments, the "#" substituents are two nitrogens and one carbon such that the resulting structure is represented by one of the following formulas:

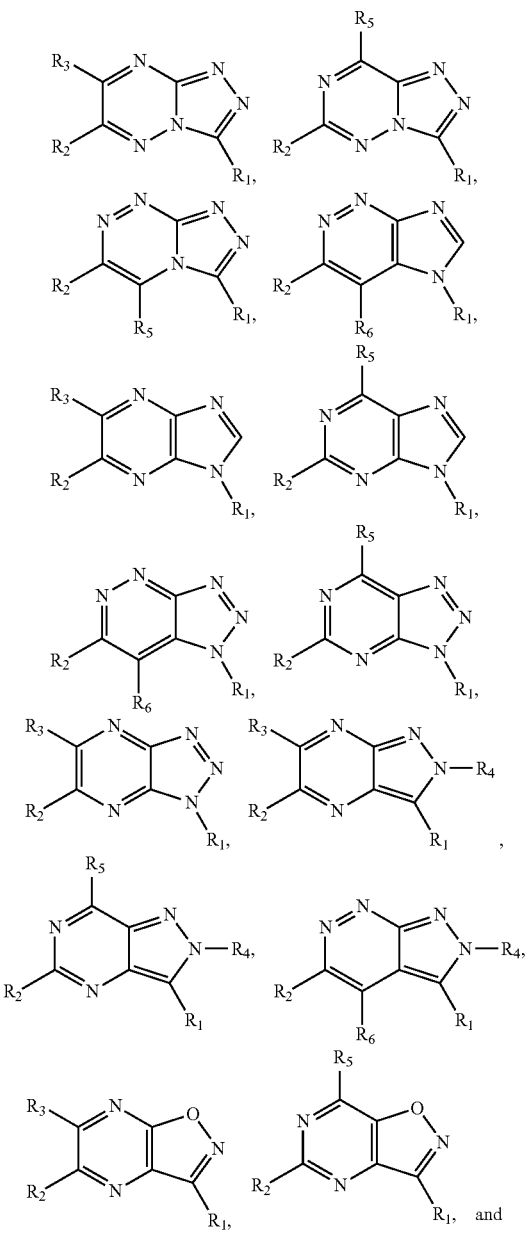

For example, in some embodiments, the "#" substituents are three nitrogens such that the resulting structure is represented by one of the following formulas:

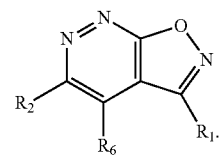

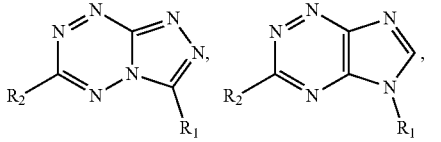

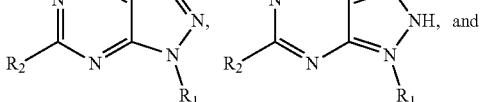

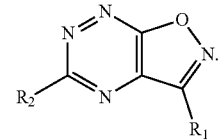

For example, in some embodiments, the "#" substituents are three carbons such that the resulting structure is represented by one of the following formulas:

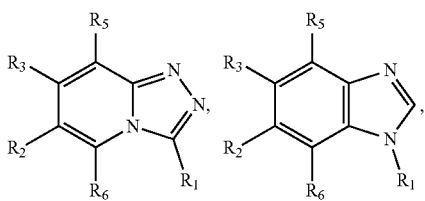

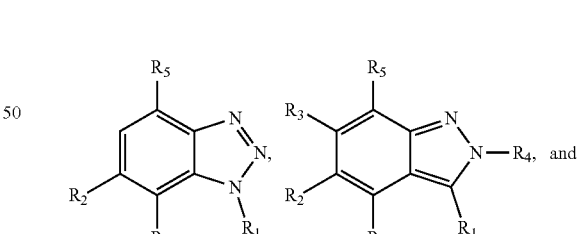

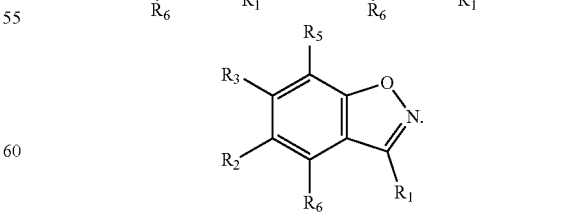

For example, in some embodiments, the "#" substituents are two carbons and one nitrogen such that the resulting structure is represented by one of the following formulas:

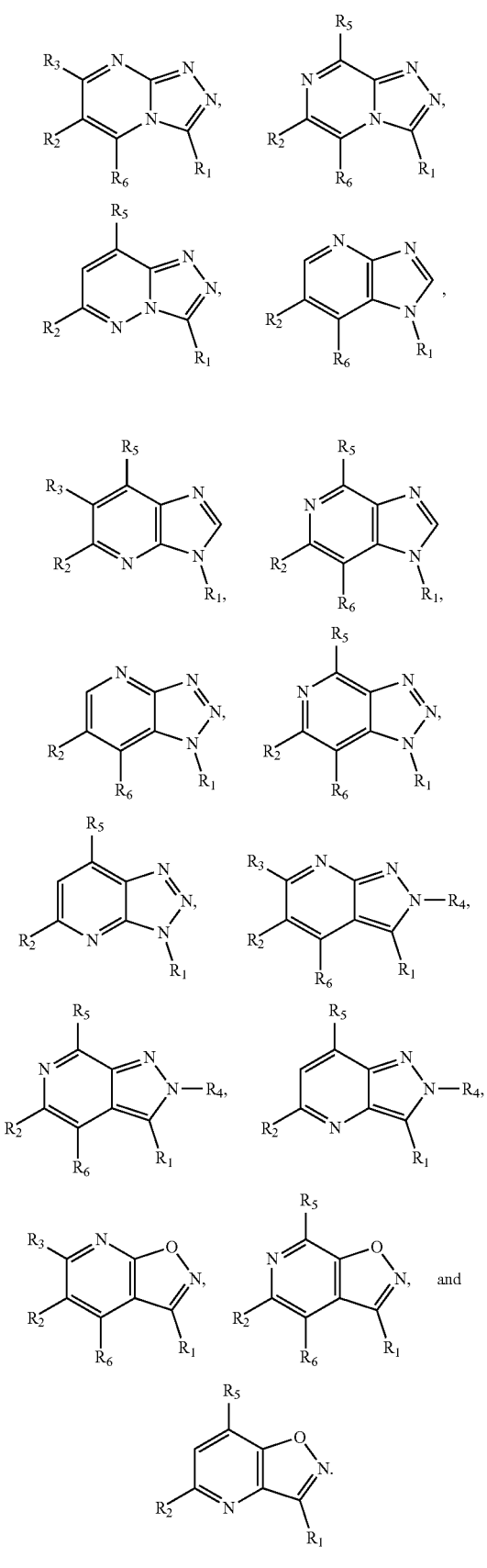
In some embodiments, R1 is selected from hydrogen,
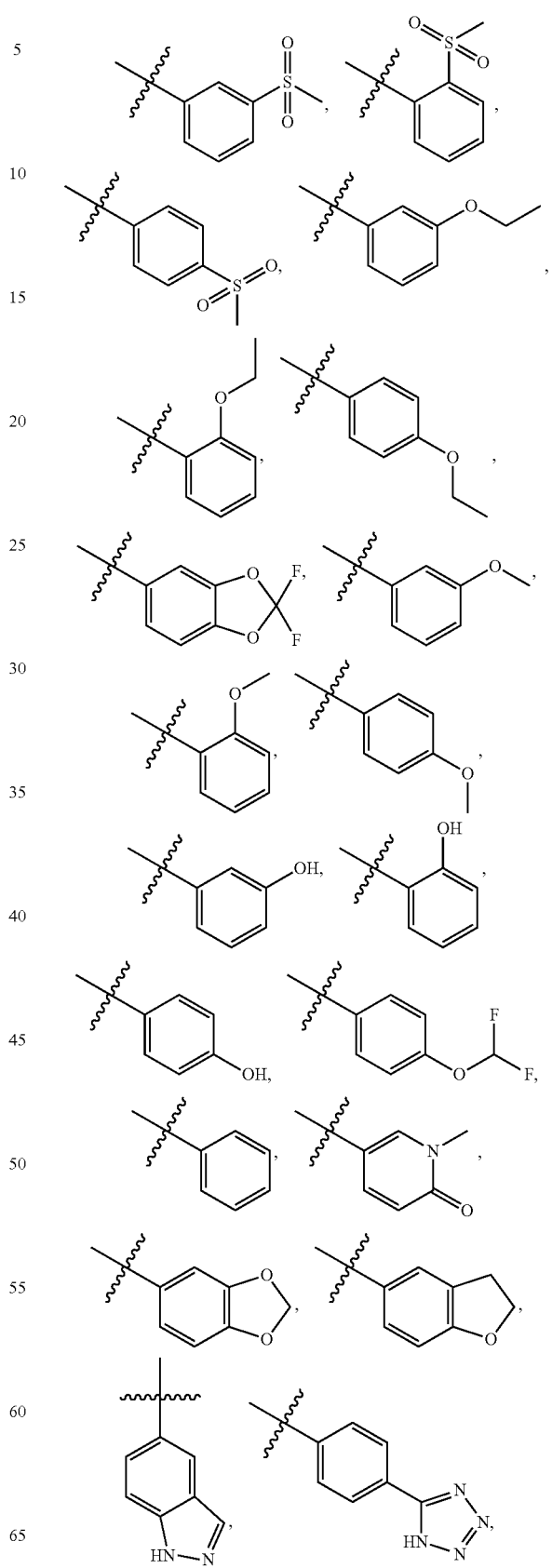

11
-continued
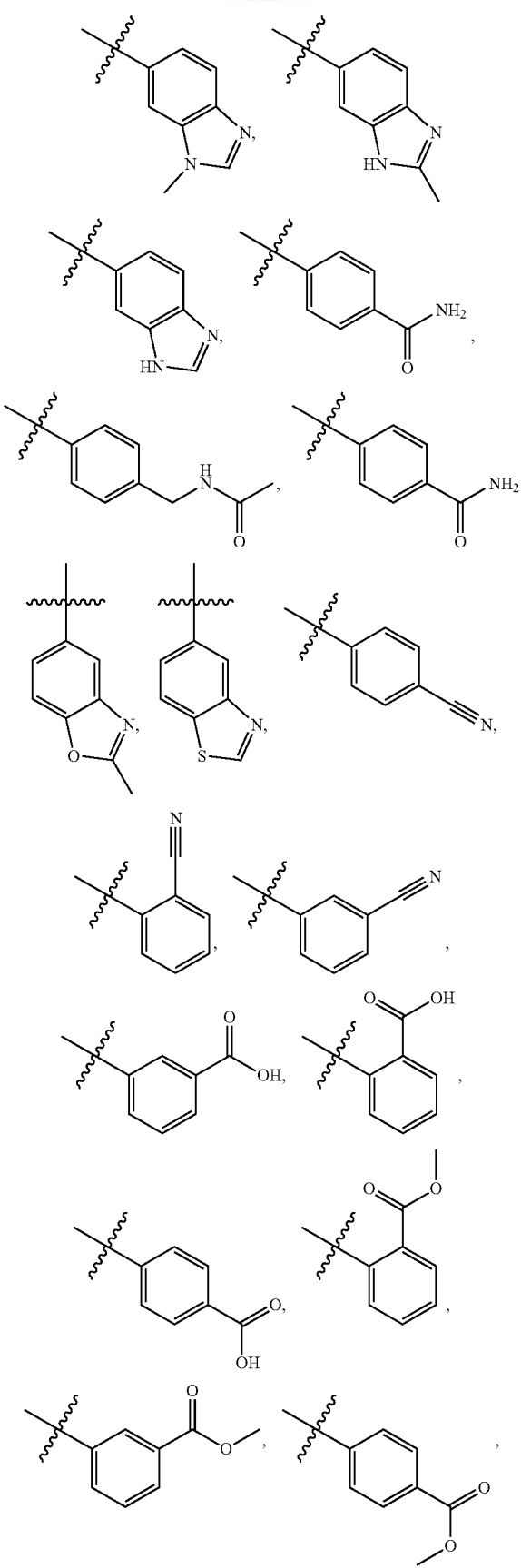
12
-continued
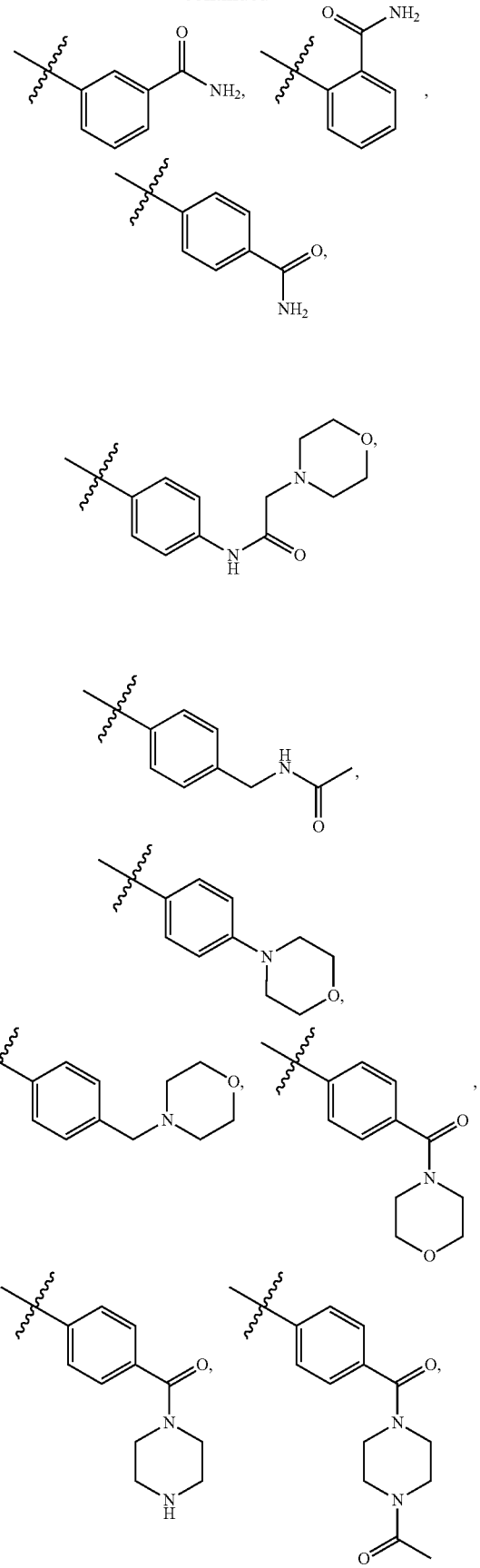

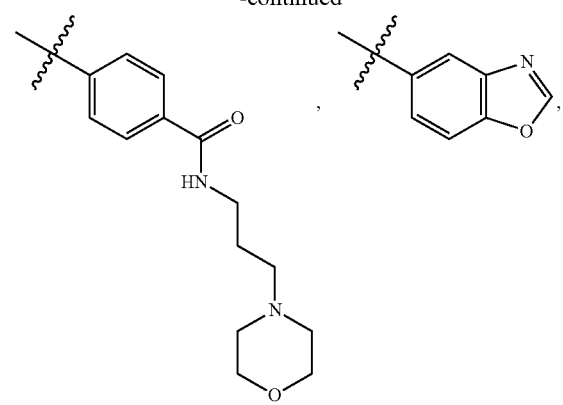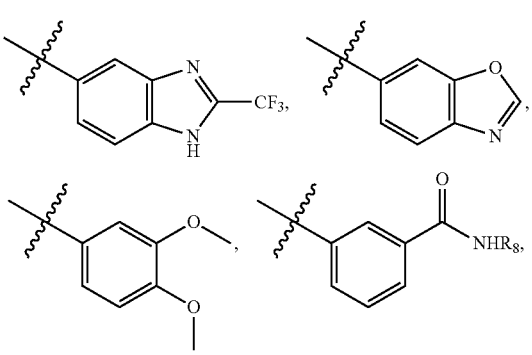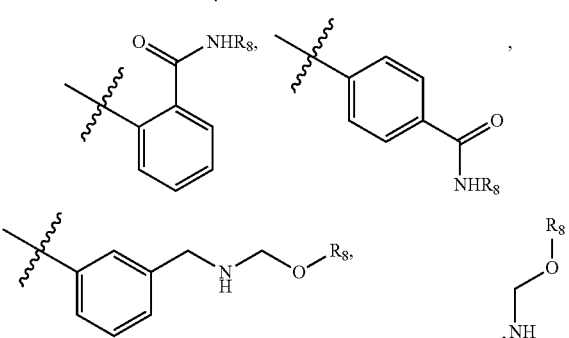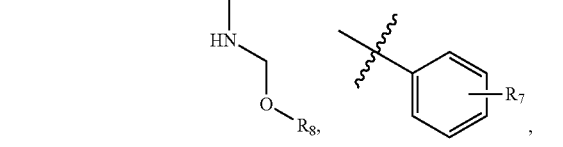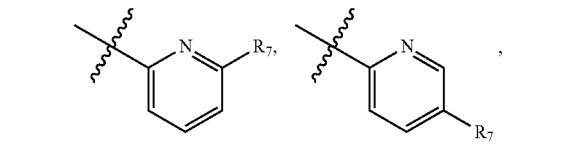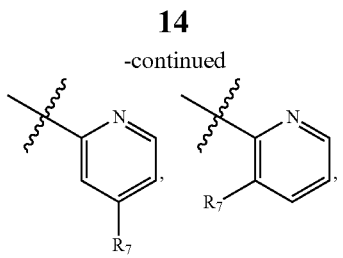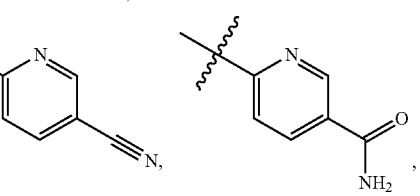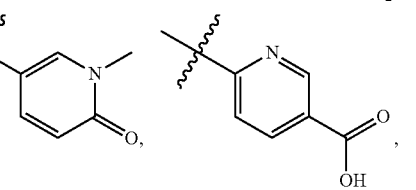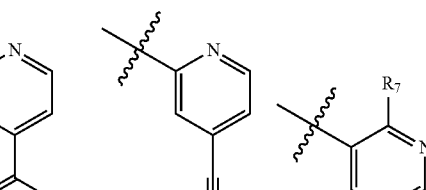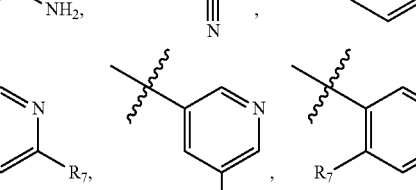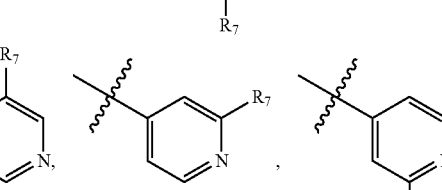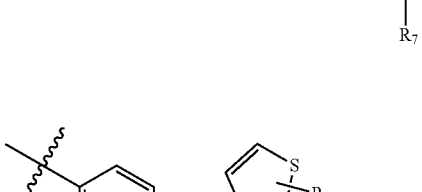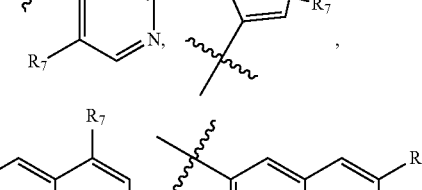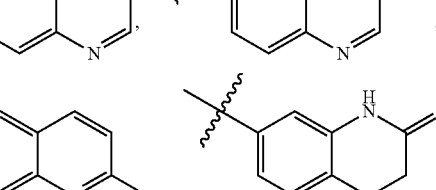

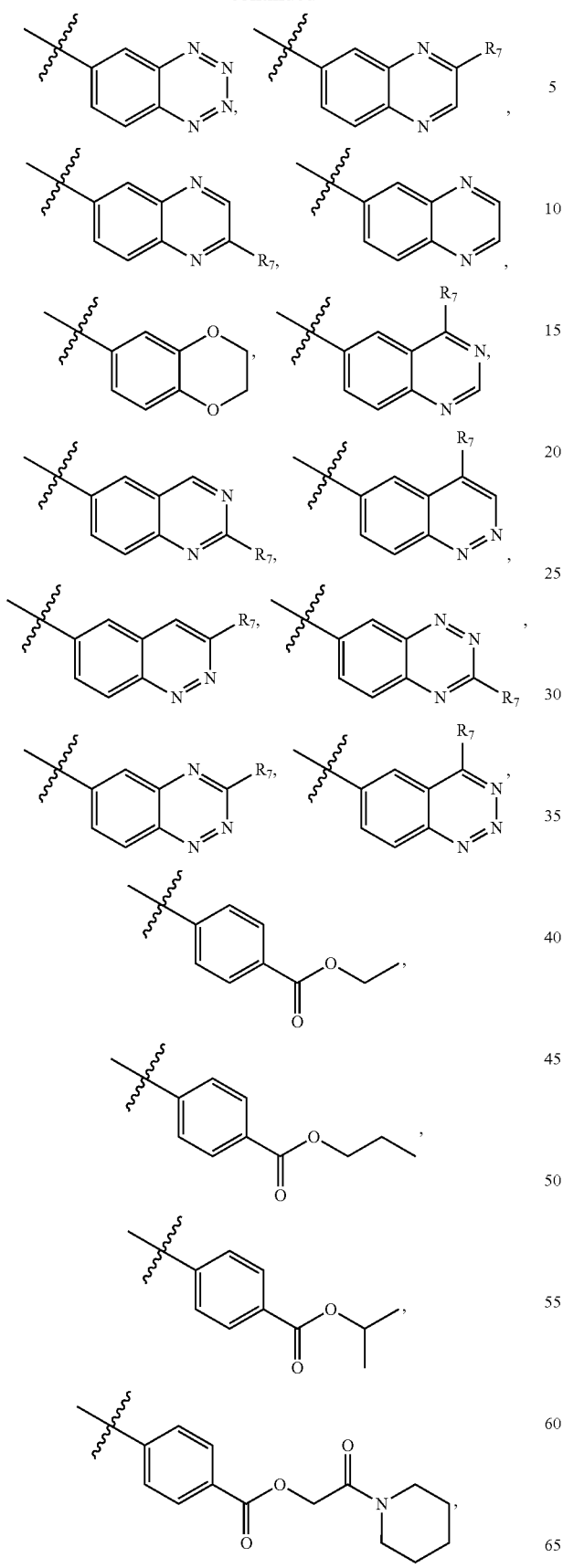
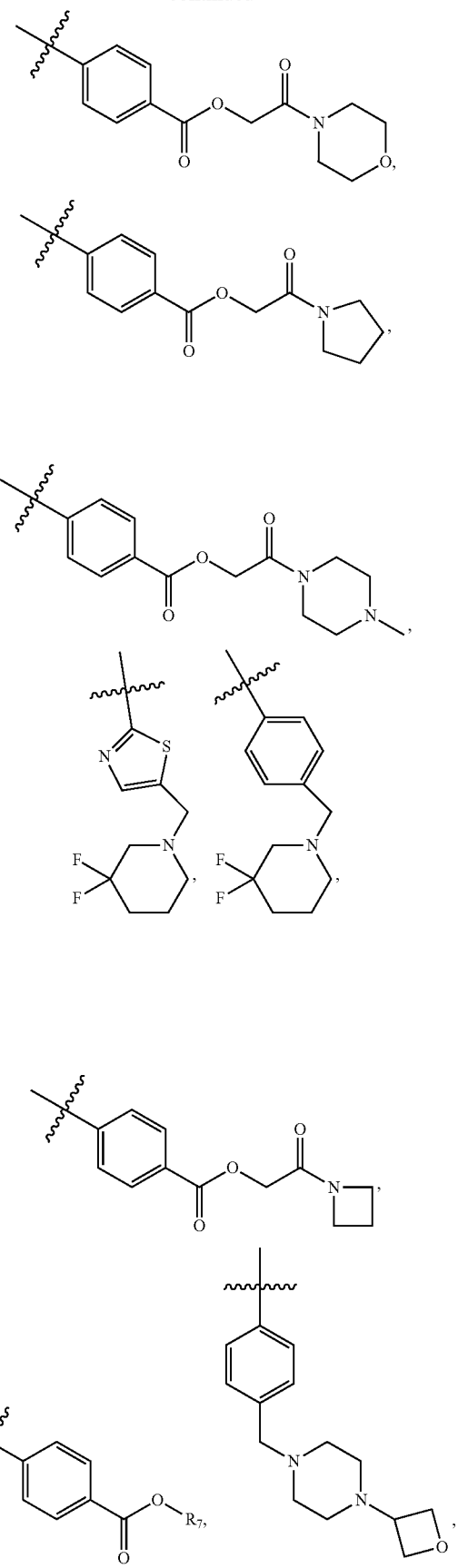

-continued
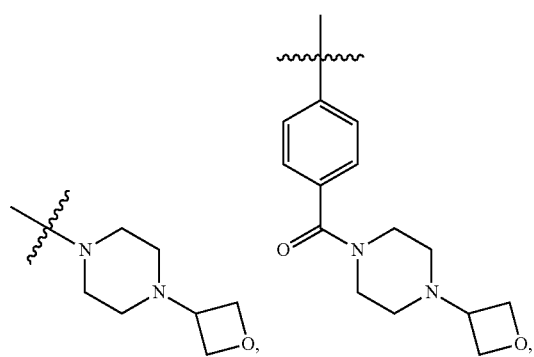
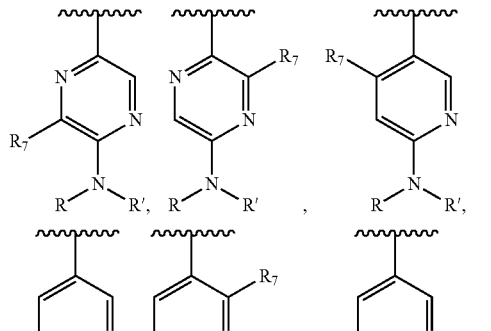
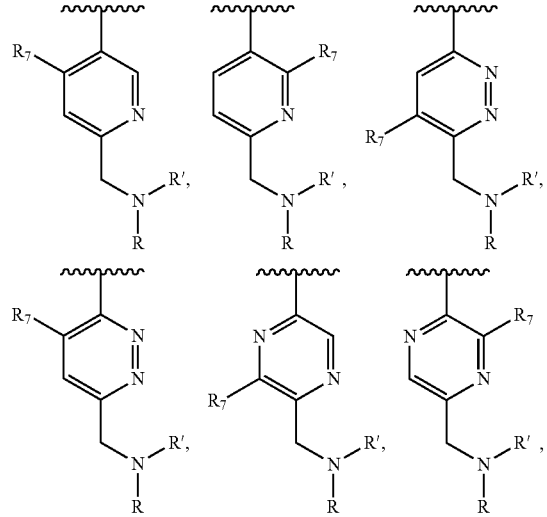
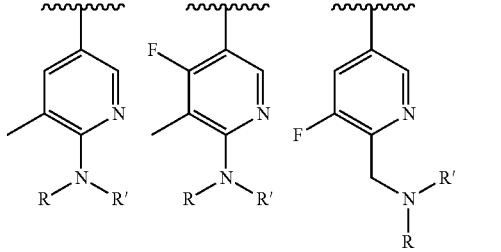
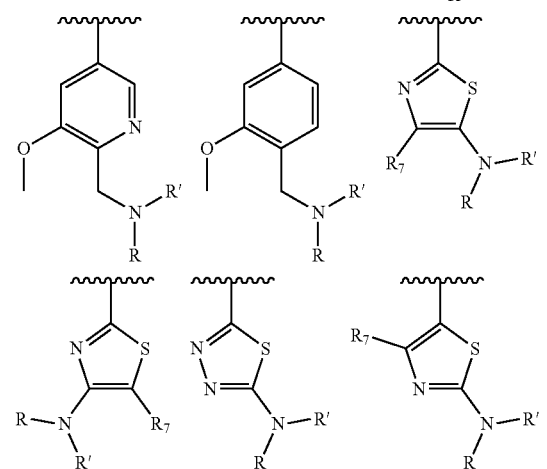

-continued
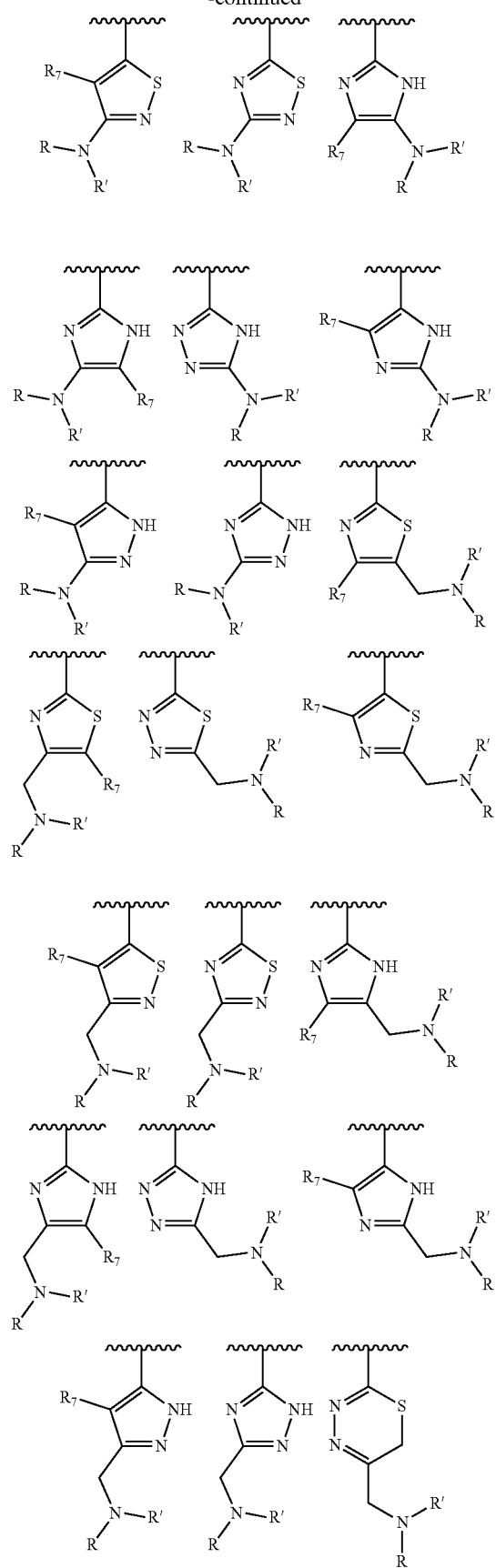
-continued
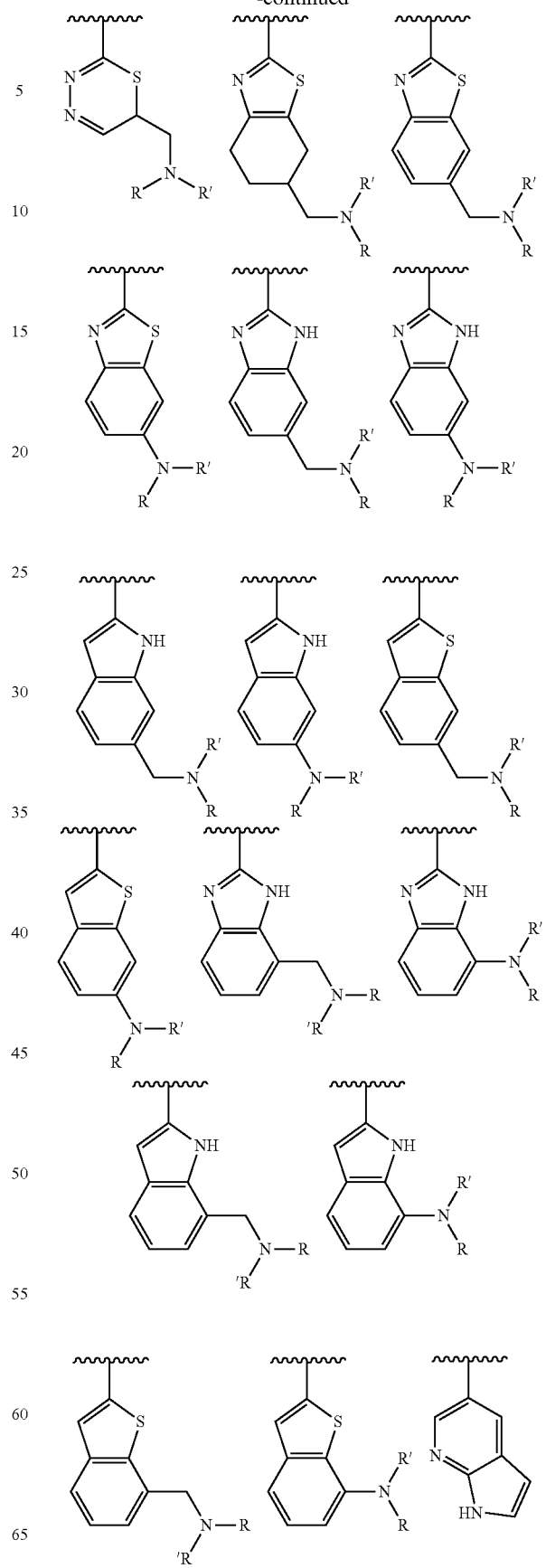

-continued

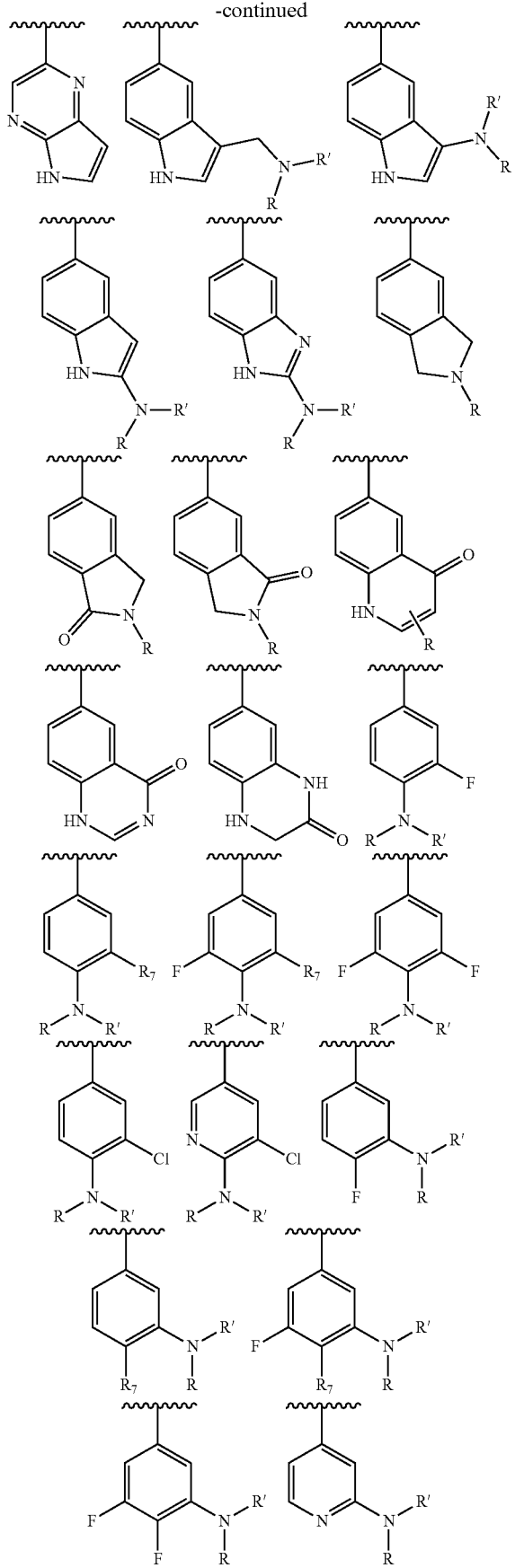

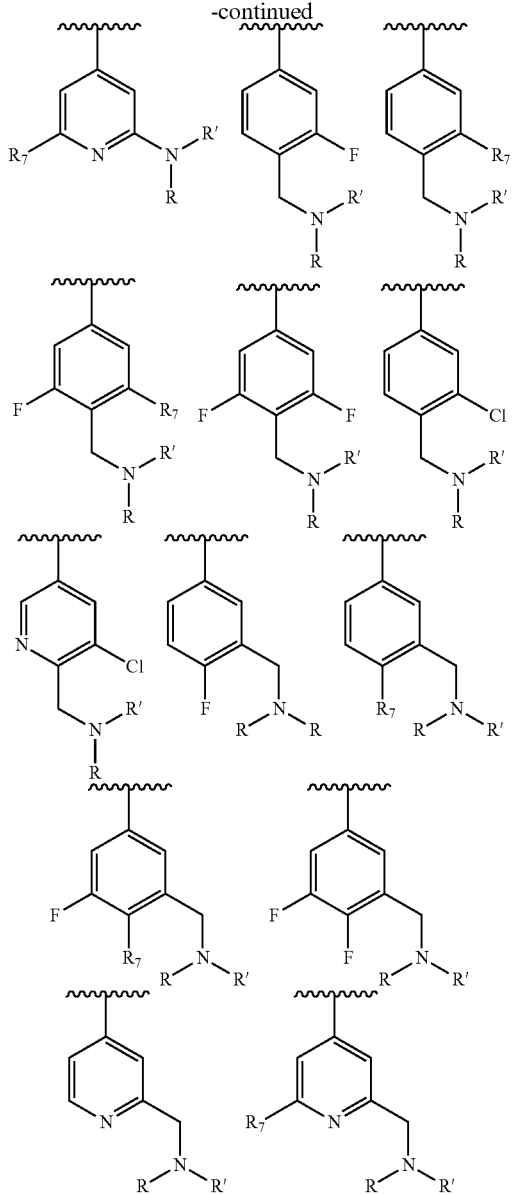

wherein R and R' are independently secondary or tertiary amine moiety consisting of a heterocycloalkyl group that is bioisosteric to secondary amines (e.g., morpholine, piperidine, piperazine).

In some embodiments, R1 is an aryl or heteroaryl ring.
In some embodiments, R7 is

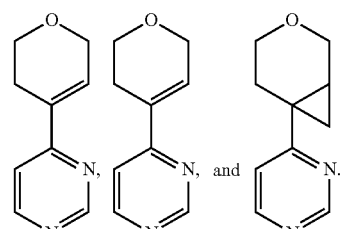

In some embodiments, R7 is an acidic bio-isostere. For example, in some embodiments R7 is selected from

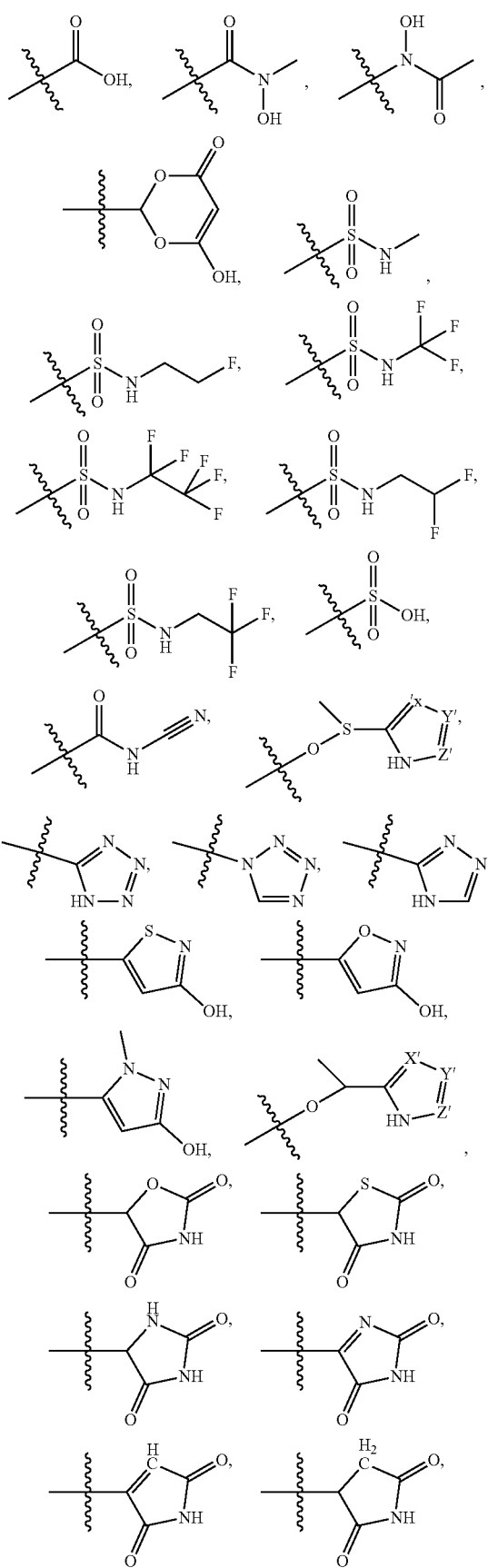

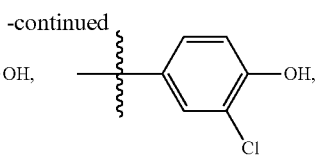

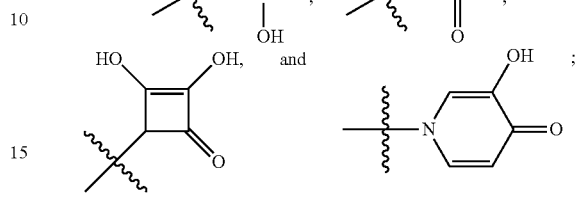

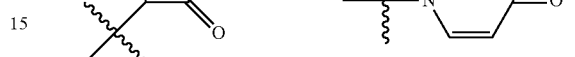

wherein X', Y', Z' are independently N, C or CO.

In some embodiments, R, R', and R7 are independently selected from hydrogen, halogen (e.g., fluorine, bromine, chlorine, iodine), di-halogen (di-fluorine, di-bromine, di-chlorine, di-iodine), $CF_3$, $OCH_3$, $CHF_2H$, $OCF_3$, methyl, di-methyl, alkoxy, alkylsulfonyl, cyano, carboxy, ester, amido, substituted amido, sulfonamide, substituted sulfonamide, methylenedioxy, heterocyclyl alkyl, heterocyclyl, heterocyclyl alkyl amido, a lipophilic moiety comprising ether functionality, methyl, ethyl, $(CH_2)_3$,

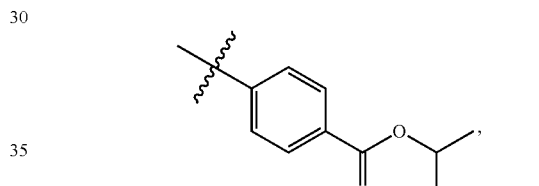

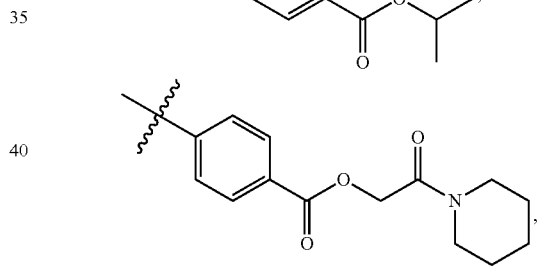

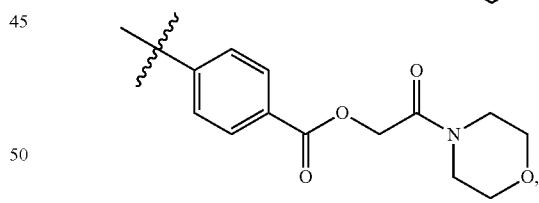

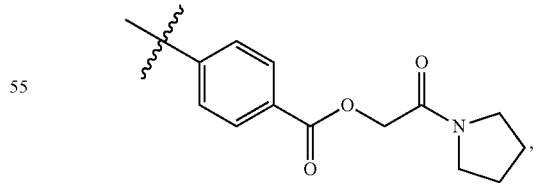

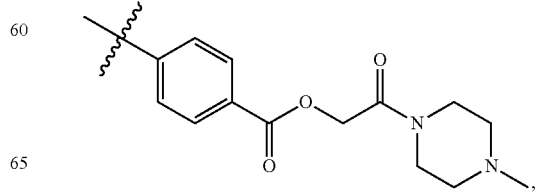, and

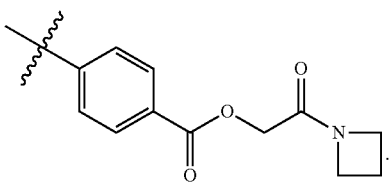
In some embodiments, R8 is selected from hydrogen, C1-C4 alkyl, heterocyclyl alkyl, heteroaryl alkyl, aryl alkyl, aryl, heterocyclyl, and heteroaryl.
In some embodiments, each of R2 and R3 is independently selected from hydrogen, halogen (e.g., fluorine), aryl, substituted aryl, heteroaryl, substituted heteroaryl,
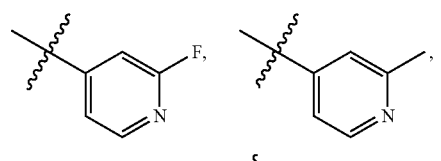
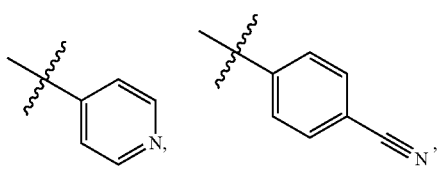
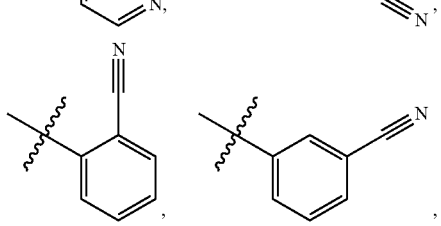
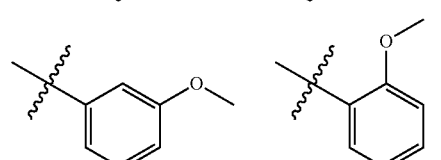
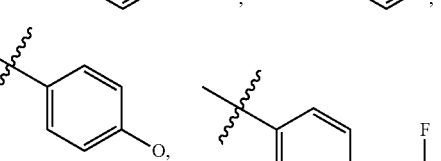
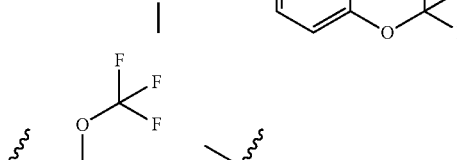
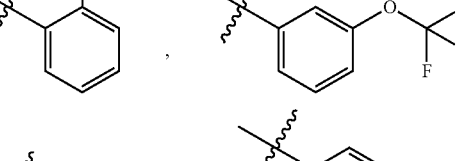
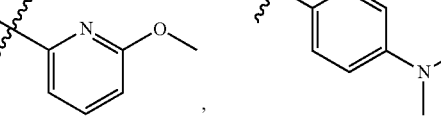
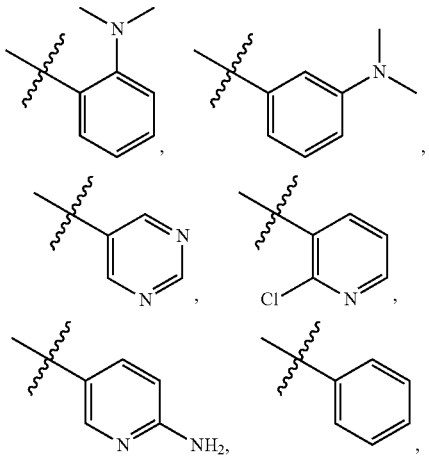
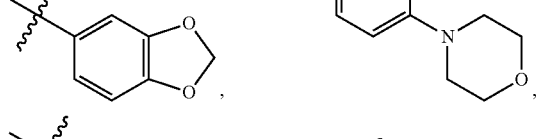
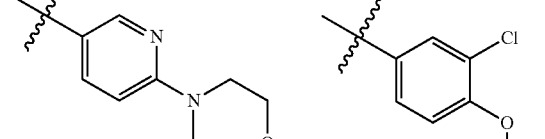
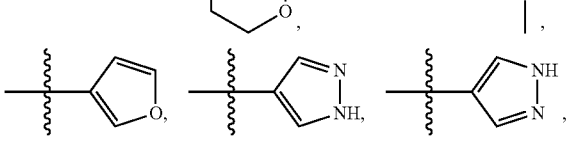
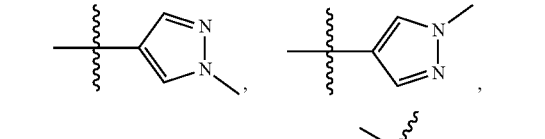
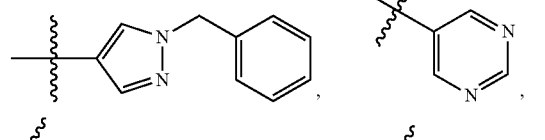
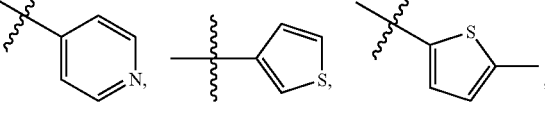

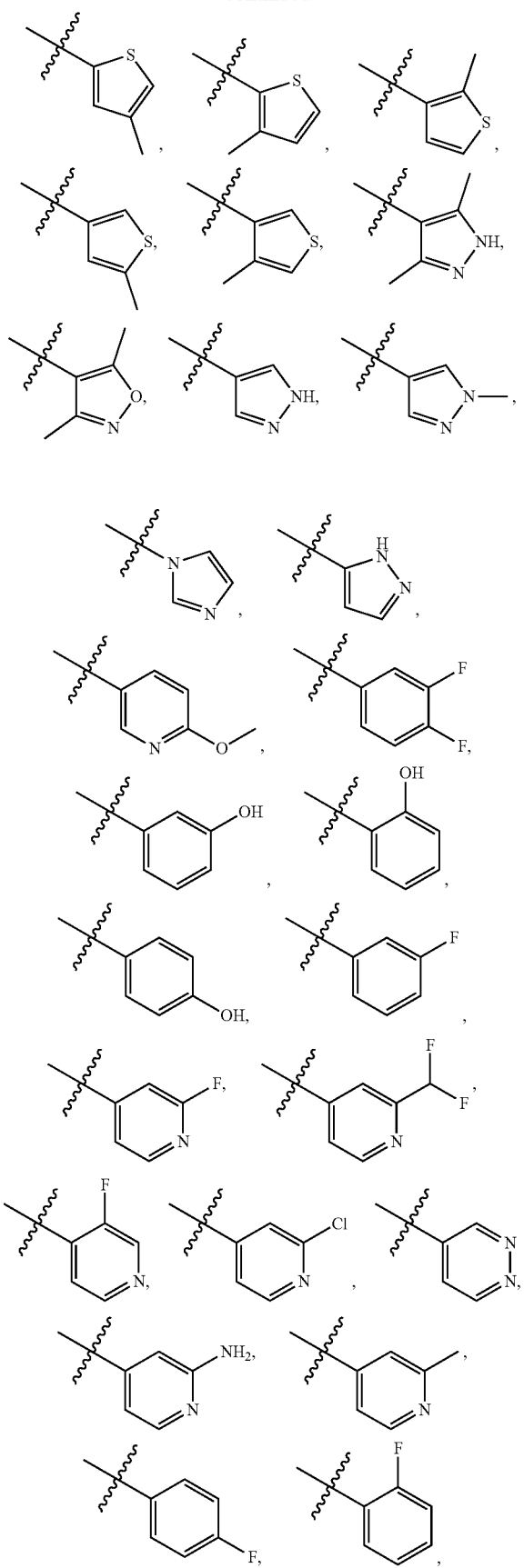
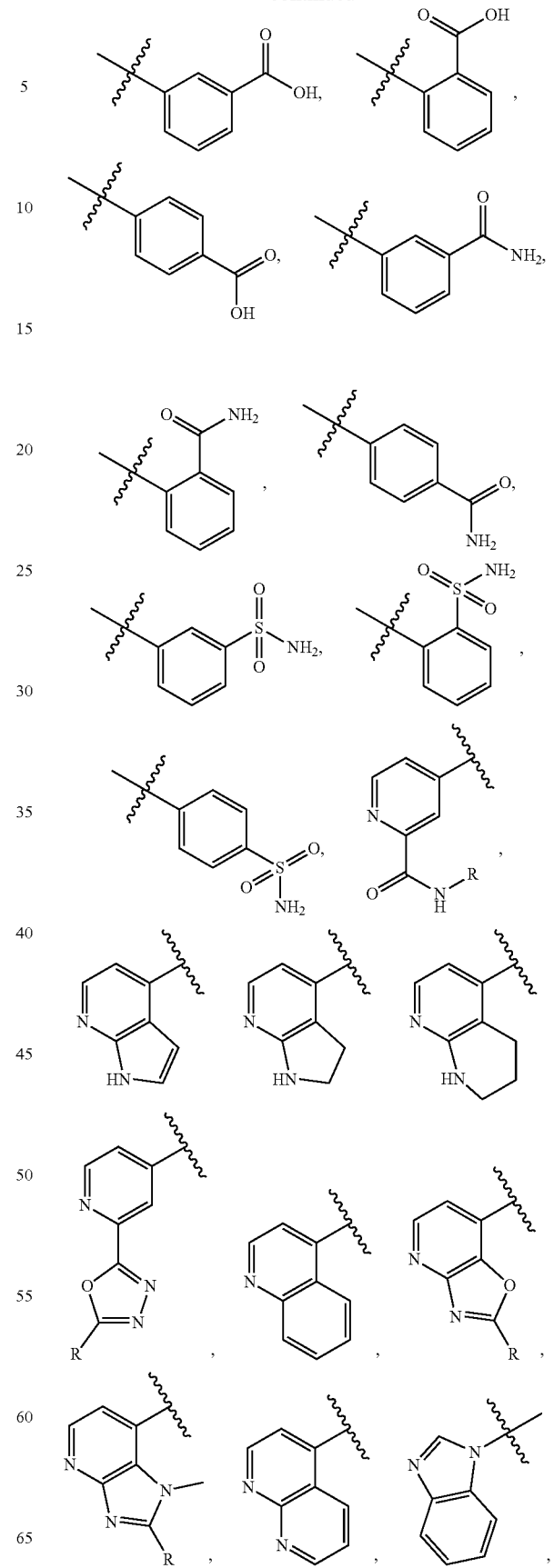

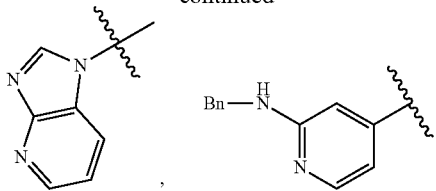

wherein Bn is benzyl or heterobenzyl,

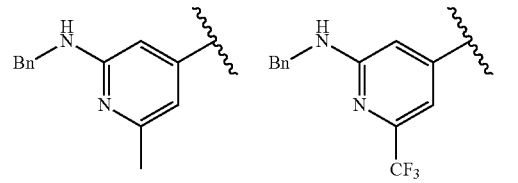
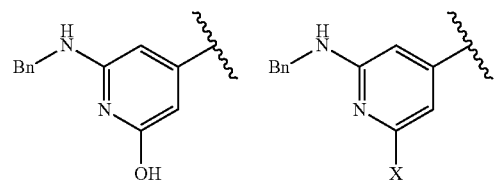
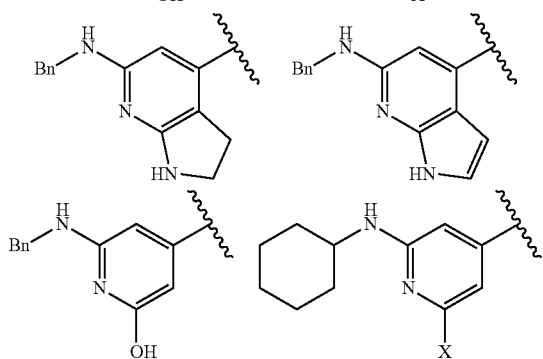
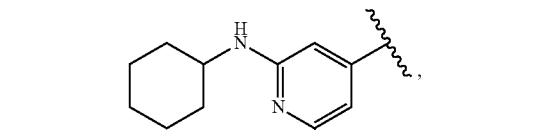
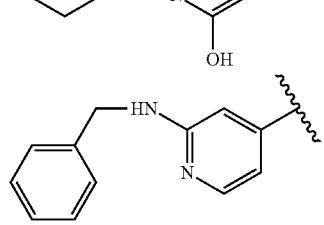
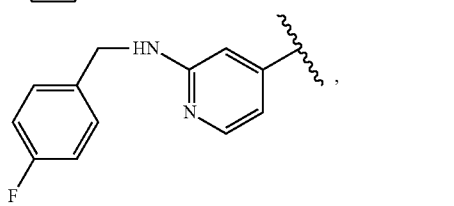
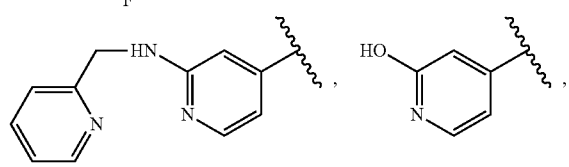

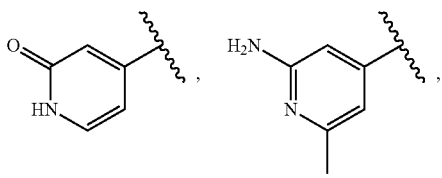
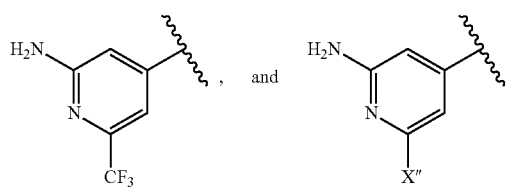

(wherein X'' is selected from alkyl, haloalkyl, amino, alkylamino, hydroxy, fluoro, chloro, bromo, cyano groups).

In some embodiments, R4 is selected from hydrogen, $CH_3$, $NH_2$, CN,

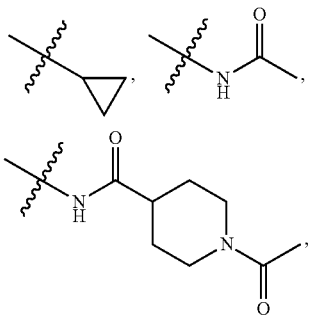

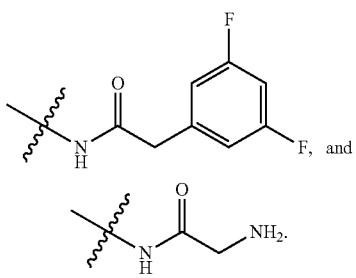

In some embodiments, R5 is present or absent, and if present is selected from hydrogen, halogen (e.g., fluorine), methyl, or methoxy.

In some embodiments, R6 is present or absent, and if present is selected from hydrogen, halogen (e.g., fluorine), methyl, or methoxy.

In some embodiments, the compound is recited in Table 1. Table 1 further includes the results of affinity testing of the compounds of the present invention with DYRK1A (DYRK1A Affinity Key (KD): +++=0.5–100 nM, ++=101 nM–500 nM, +=501 nM–10 uM) (see, Table 1).

TABLE 1
KD (DYRK1A): +++  1
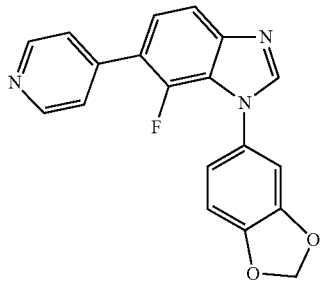
KD (DYRK1A): +++  2
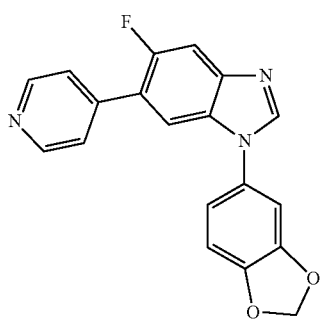 [SMILES: Fc1cc2ncn(-c3ccc4c(c3)OCO4)c2cc1-c1ccncc1]
KD (DYRK1A): +++  3
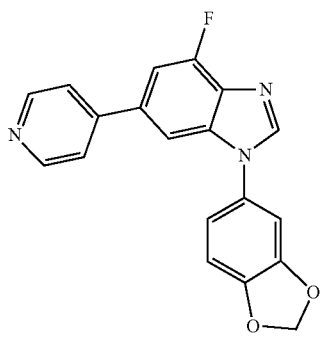 [SMILES: Fc1cc(-c2ccncc2)cc2c1ncn2-c1ccc2c(c1)OCO2]
KD (DYRK1A): +++  4
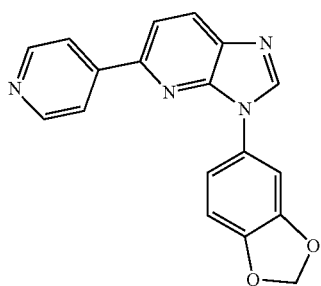 [SMILES: c1cc(-c2ccc3ncn(-c4ccc5c(c4)OCO5)c3n2)ccn1]

TABLE 1-continued
| | |
|---|---|
| KD (DYRK1A): +++ 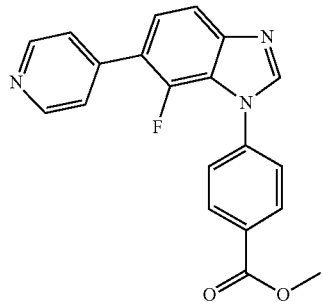 [SMILES: COC(=O)c1ccc(-n2cnc3ccc(-c4ccncc4)c(F)c32)cc1] | 5 |
| KD (DYRK1A): ++ 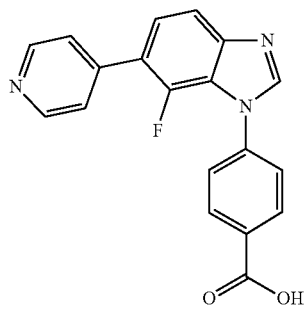 [SMILES: O=C(O)c1ccc(-n2cnc3ccc(-c4ccncc4)c(F)c32)cc1] | 6 |
| KD (DYRK1A): ++ 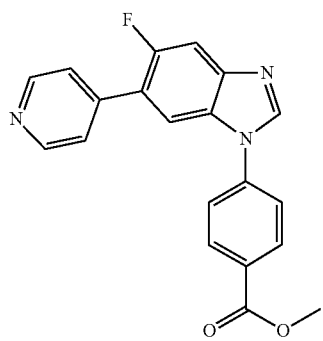 [SMILES: COC(=O)c1ccc(-n2cnc3cc(F)c(-c4ccncc4)cc32)cc1] | 7 |
| KD (DYRK1A): ++ 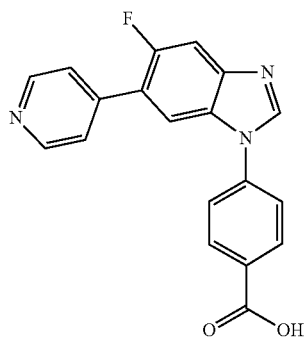 [SMILES: O=C(O)c1ccc(-n2cnc3cc(F)c(-c4ccncc4)cc32)cc1] | 8 |

TABLE 1-continued
| KD (DYRK1A): +++ | 9 |
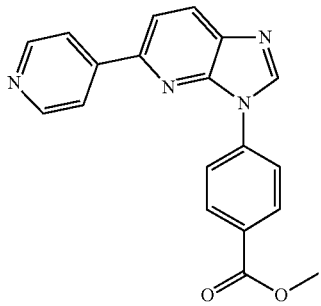 [SMILES: COC(=O)c1ccc(-n2cnc3ccc(-c4ccncc4)nc32)cc1]
| KD (DYRK1A): +++ | 10 |
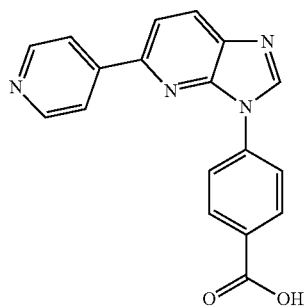 [SMILES: O=C(O)c1ccc(-n2cnc3ccc(-c4ccncc4)nc32)cc1]
| KD (DYRK1A): ++ | 11 |
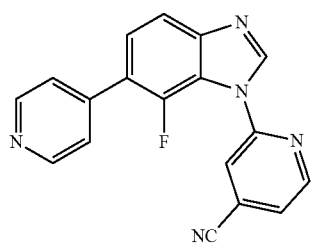 [SMILES: N#Cc1ccnc(-n2cnc3ccc(-c4ccncc4)c(F)c32)c1]
| KD (DYRK1A): ++ | 12 |
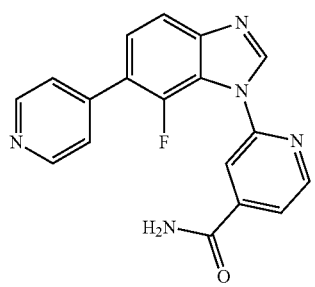 [SMILES: NC(=O)c1ccnc(-n2cnc3ccc(-c4ccncc4)c(F)c32)c1]
| KD (DYRK1A): + | 13 |
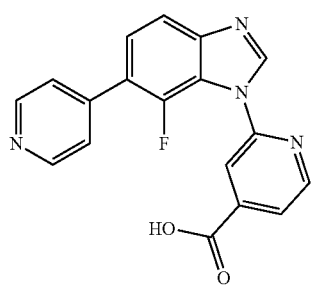 [SMILES: O=C(O)c1ccnc(-n2cnc3ccc(-c4ccncc4)c(F)c32)c1]

TABLE 1-continued
KD (DYRK1A): +++ 14
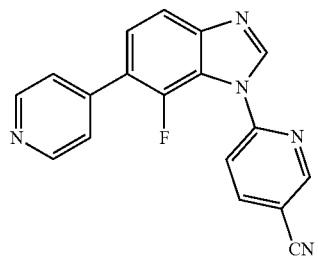 [SMILES: N#Cc1ccc(-n2cnc3ccc(-c4ccncc4)c(F)c32)nc1]
KD (DYRK1A): +++ 15
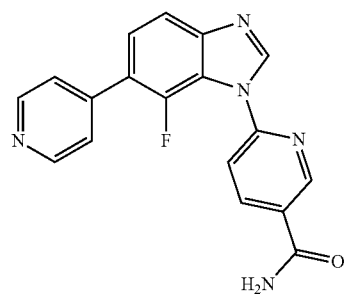 [SMILES: NC(=O)c1ccc(-n2cnc3ccc(-c4ccncc4)c(F)c32)nc1]
16
KD (DYRK1A): +++
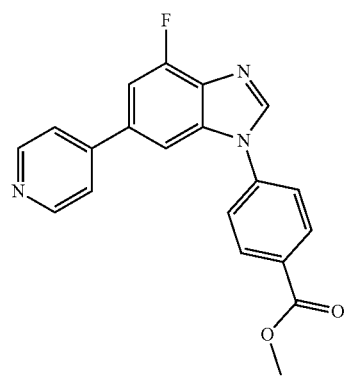 [SMILES: COC(=O)c1ccc(-n2cnc3c(F)cc(-c4ccncc4)cc32)cc1]
KD (DYRK1A): ++ 17
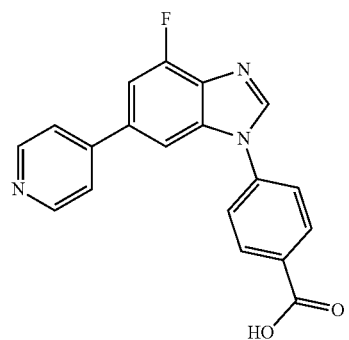 [SMILES: O=C(O)c1ccc(-n2cnc3c(F)cc(-c4ccncc4)cc32)cc1]

TABLE 1-continued
| | |
|---|---|
| KD (DYRK1A): +++ 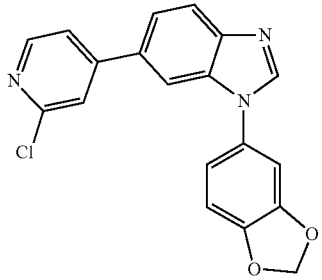 [SMILES: Clc1cc(-c2ccc3ncn(-c4ccc5c(c4)OCO5)c3c2)ccn1] | 18 |
| KD (DYRK1A): +++ 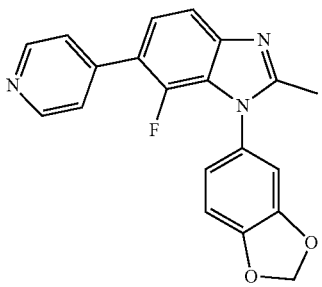 [SMILES: Cc1nc2ccc(-c3ccncc3)c(F)c2n1-c1ccc2c(c1)OCO2] | 19 |
| | 20 |
| KD (DYRK1A): +++ 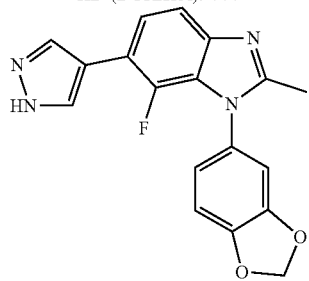 | |
| KD (DYRK1A): + 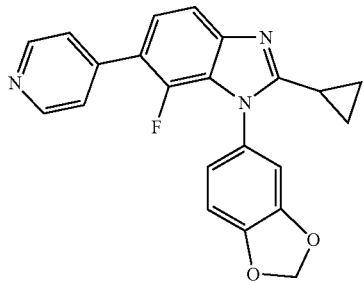 [SMILES: Fc1c(-c2ccncc2)ccc2nc(C3CC3)n(-c3ccc4c(c3)OCO4)c12] | 21 |
| KD (DYRK1A): +++ 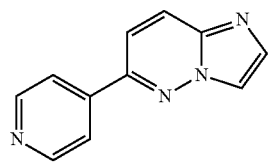 [SMILES: c1cc(-c2ccc3nccn3n2)ccn1] | 22 |

TABLE 1-continued
| | |
|---|---|
| KD (DYRK1A): +++ 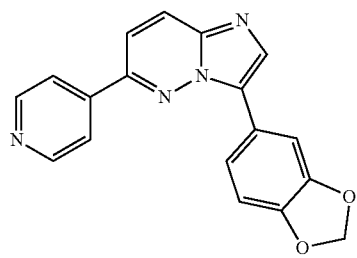 [SMILES: c1cc(-c2ccc3ncc(-c4ccc5c(c4)OCO5)n3n2)ccn1] | 23 |
| KD (DYRK1A): +++ 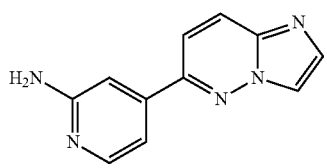 [SMILES: Nc1cc(-c2ccc3nccn3n2)ccn1] | 24 |
| KD (DYRK1A): +++ 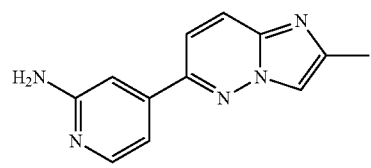 [SMILES: Cc1cn2nc(-c3ccnc(N)c3)ccc2n1] | 25 |
| KD (DYRK1A): ++ 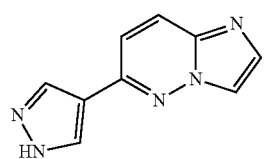 [SMILES: c1cn2nc(-c3cn[nH]c3)ccc2n1] | 26 |
| KD (DYRK1A): +++ 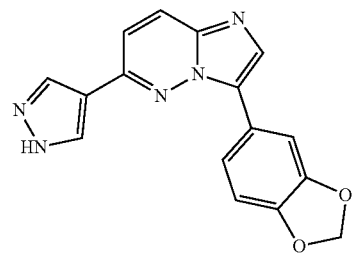 [SMILES: c1n[nH]cc1-c1ccc2ncc(-c3ccc4c(c3)OCO4)n2n1] | 27 |
| KD (DYRK1A): +++ 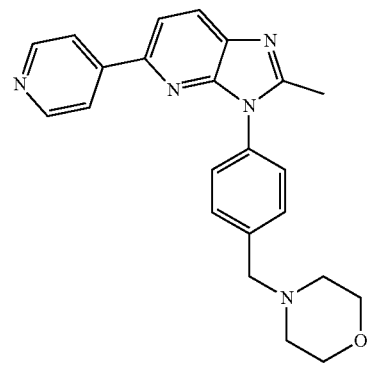 [SMILES: Cc1nc2ccc(-c3ccncc3)nc2n1-c1ccc(CN2CCOCC2)cc1] | 28 |

TABLE 1-continued
| | |
|---|---|
| KD (DYRK1A): +++ 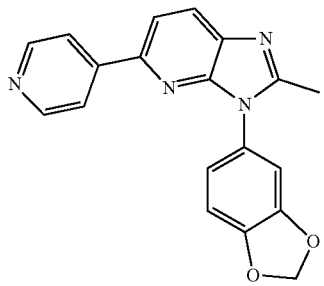 [SMILES: Cc1nc2ccc(-c3ccncc3)nc2n1-c1ccc2c(c1)OCO2] | 29 |
| KD (DYRK1A): +++ 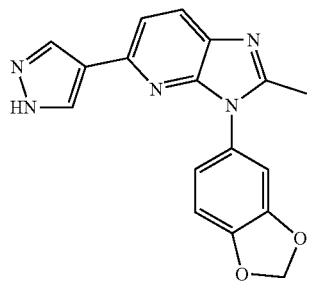 [SMILES: Cc1nc2ccc(-c3cn[nH]c3)nc2n1-c1ccc2c(c1)OCO2] | 30 |
| KD (DYRK1A): ++ 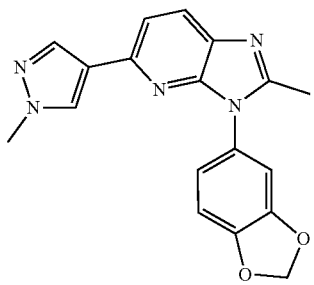 | 31 |
| KD (DYRK1A): +++ 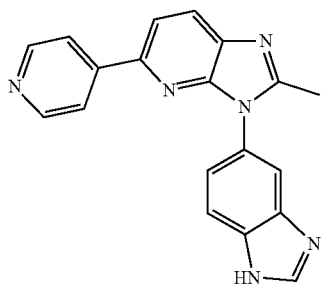 [SMILES: Cc1nc2ccc(-c3ccncc3)nc2n1-c1ccc2[nH]cnc2c1] | 32 |
| KD (DYRK1A): +++ 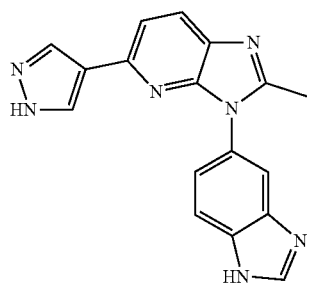 [SMILES: Cc1nc2ccc(-c3cn[nH]c3)nc2n1-c1ccc2[nH]cnc2c1] | 33 |

TABLE 1-continued
KD (DYRK1A): +++  34
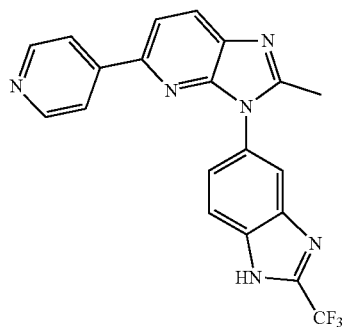 [SMILES: Cc1nc2ccc(-c3ccncc3)nc2n1-c1ccc2[nH]c(C(F)(F)F)nc2c1]
35
KD (DYRK1A): ++
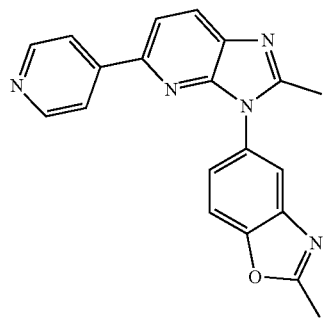 [SMILES: Cc1nc2cc(-n3c(C)nc4ccc(-c5ccncc5)nc43)ccc2o1]
KD (DYRK1A): ++  36
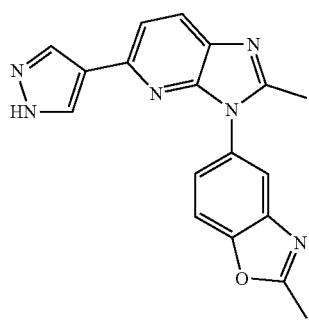 [SMILES: Cc1nc2cc(-n3c(C)nc4ccc(-c5cn[nH]c5)nc43)ccc2o1]
KD (DYRK1A): +++  37
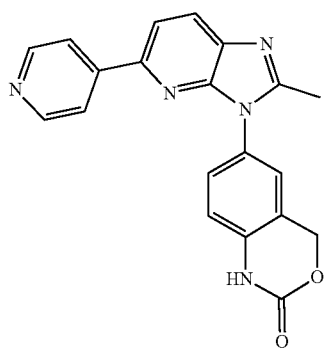 [SMILES: Cc1nc2ccc(-c3ccncc3)nc2n1-c1ccc2c(c1)COC(=O)N2]

TABLE 1-continued
| | |
|---|---|
| KD (DYRK1A): +++ 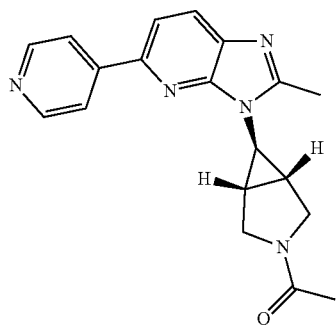 [SMILES: CC(=O)N1C[C@@H]2[C@H](C1)[C@H]2n1c(C)nc2ccc(-c3ccncc3)nc21] | 38 |
| KD (DYRK1A): ++ 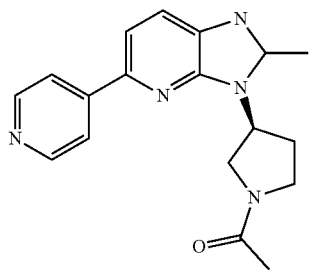 [SMILES: CC(=O)N1CC[C@H](N2c3nc(-c4ccncc4)ccc3NC2C)C1] | 39 |
| KD (DYRK1A): +++ 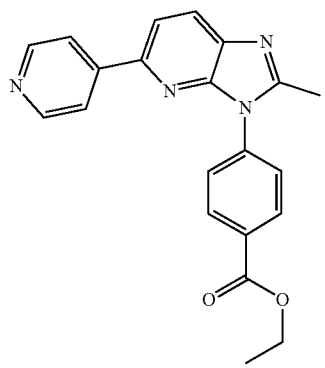 [SMILES: CCOC(=O)c1ccc(-n2c(C)nc3ccc(-c4ccncc4)nc32)cc1] | 40 |
| KD (DYRK1A): ++ 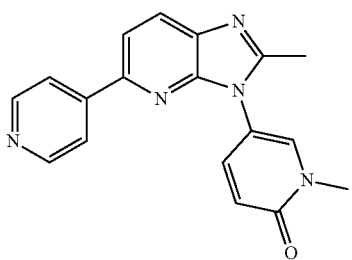 [SMILES: Cc1nc2ccc(-c3ccncc3)nc2n1-c1ccc(=O)n(C)c1] | 41 |

TABLE 1-continued
KD (DYRK1A): +++  42
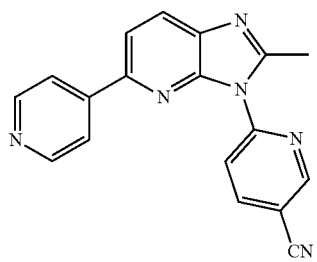 [SMILES: Cc1nc2ccc(-c3ccncc3)nc2n1-c1ccc(C#N)cn1]
KD (DYRK1A): +++  43
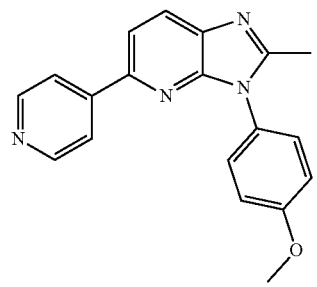 [SMILES: COc1ccc(-n2c(C)nc3ccc(-c4ccncc4)nc32)cc1]
KD (DYRK1A): +++  44
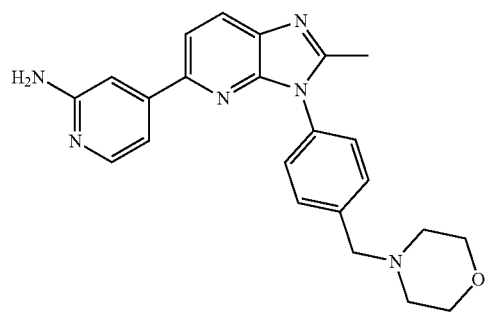 [SMILES: Cc1nc2ccc(-c3ccnc(N)c3)nc2n1-c1ccc(CN2CCOCC2)cc1]
KD (DYRK1A): +  45
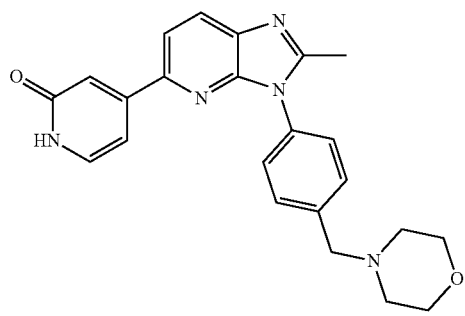 [SMILES: Cc1nc2ccc(-c3cc[nH]c(=O)c3)nc2n1-c1ccc(CN2CCOCC2)cc1]

TABLE 1-continued
KD (DYRK1A): +++     46
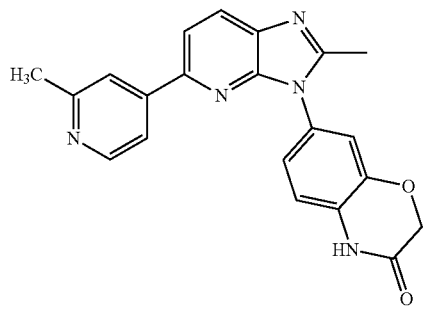 [SMILES: Cc1cc(-c2ccc3nc(C)n(-c4ccc5c(c4)OCC(=O)N5)c3n2)ccn1]
KD (DYRK1A): +++     47
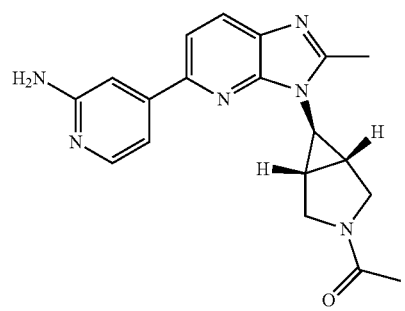 [SMILES: CC(=O)N1C[C@@H]2[C@H](C1)[C@H]2n1c(C)nc2ccc(-c3ccnc(N)c3)nc21]
KD (DYRK1A): +++     48
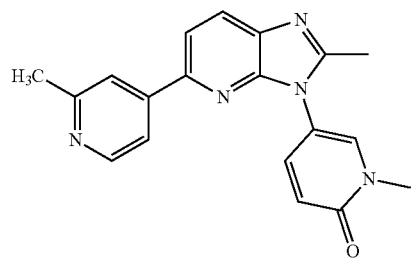
KD (DYRK1A): +++     49
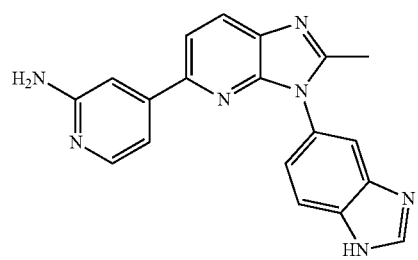
KD (DYRK1A): +++     50
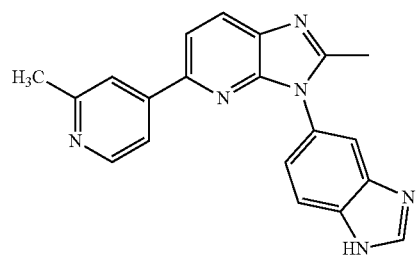 [SMILES: Cc1cc(-c2ccc3nc(C)n(-c4ccc5[nH]cnc5c4)c3n2)ccn1]

TABLE 1-continued
| KD (DYRK1A): ++ | 51 |
|---|---|
| 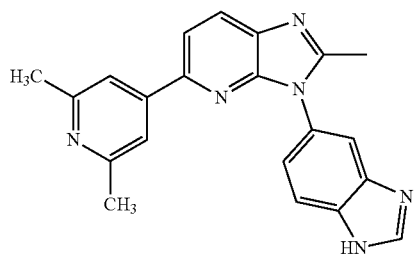 [SMILES: Cc1cc(-c2ccc3nc(C)n(-c4ccc5[nH]cnc5c4)c3n2)cc(C)n1] | |
| KD (DYRK1A): ++ | 52 |
|---|---|
| 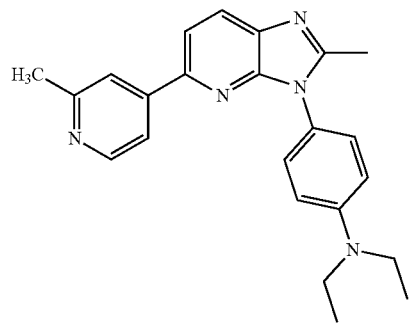 [SMILES: CCN(CC)c1ccc(-n2c(C)nc3ccc(-c4ccnc(C)c4)nc32)cc1] | |
| KD (DYRK1A): + | 53 |
|---|---|
| 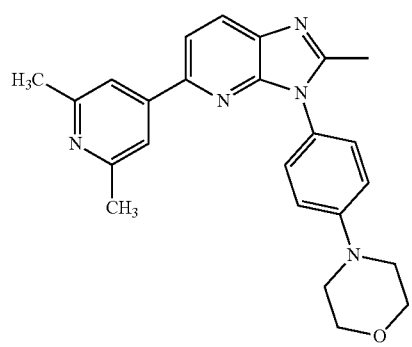 [SMILES: Cc1cc(-c2ccc3nc(C)n(-c4ccc(N5CCOCC5)cc4)c3n2)cc(C)n1] | |
| KD (DYRK1A): + | 54 |
|---|---|
| 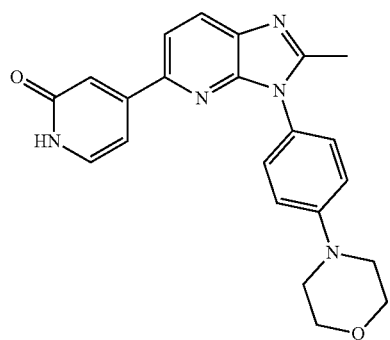 [SMILES: Cc1nc2ccc(-c3cc[nH]c(=O)c3)nc2n1-c1ccc(N2CCOCC2)cc1] | |

TABLE 1-continued
KD (DYRK1A): +++ 55
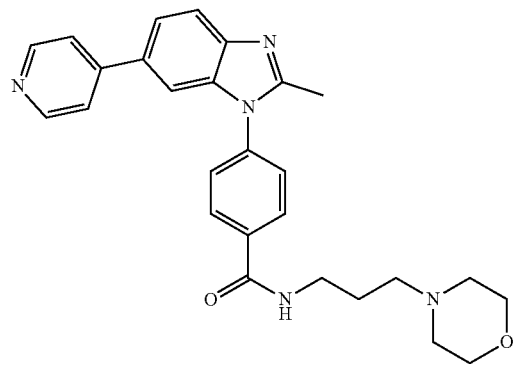 [SMILES: Cc1nc2ccc(-c3ccncc3)cc2n1-c1ccc(C(=O)NCCCN2CCOCC2)cc1]
KD (DYRK1A): ++ 56
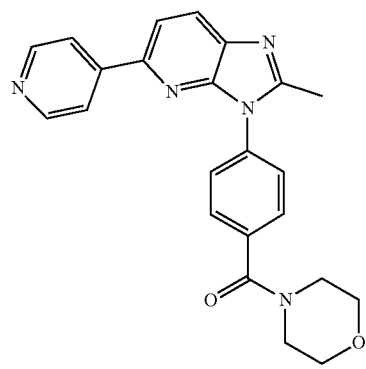 [SMILES: Cc1nc2ccc(-c3ccncc3)nc2n1-c1ccc(C(=O)N2CCOCC2)cc1]
KD (DYRK1A): ++ 57
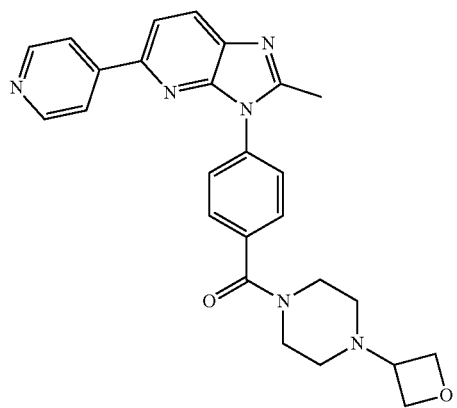 [SMILES: Cc1nc2ccc(-c3ccncc3)nc2n1-c1ccc(C(=O)N2CCN(C3COC3)CC2)cc1]

TABLE 1-continued
| KD (DYRK1A): ++ | 58 |
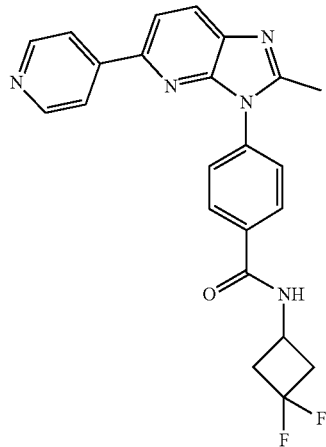 [SMILES: Cc1nc2ccc(-c3ccncc3)nc2n1-c1ccc(C(=O)NC2CC(F)(F)C2)cc1]
| KD (DYRK1A): +++ | 59 |
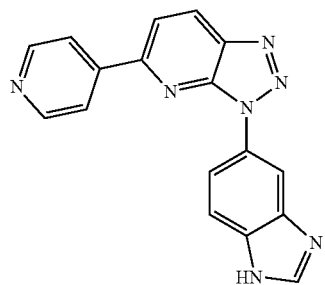 [SMILES: c1cc(-c2ccc3nnn(-c4ccc5[nH]cnc5c4)c3n2)ccn1]
| KD (DYRK1A): + | 60 |
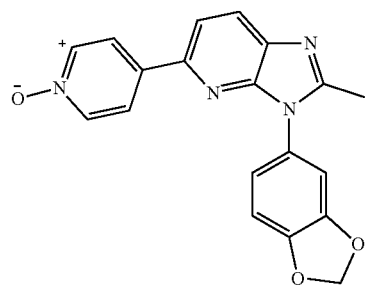
| KD (DYRK1A): + | 61 |
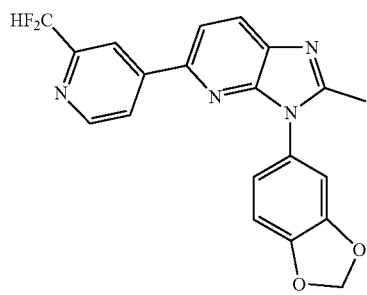

TABLE 1-continued
| KD (DYRK1A): +++ | 62 |
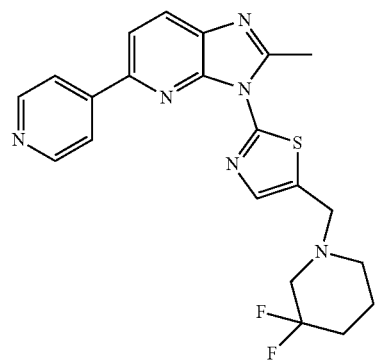 [SMILES: Cc1nc2ccc(-c3ccncc3)nc2n1-c1ncc(CN2CCCC(F)(F)C2)s1]
| KD (DYRK1A): +++ | 63 |
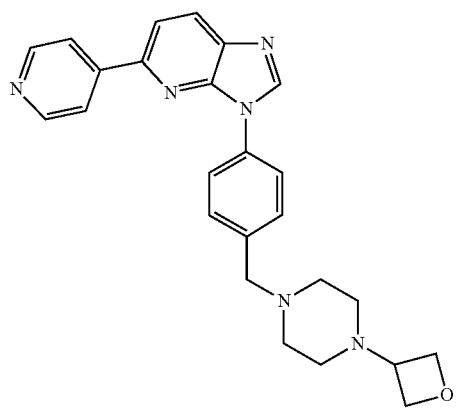 [SMILES: c1cc(-c2ccc3ncn(-c4ccc(CN5CCN(C6COC6)CC5)cc4)c3n2)ccn1]
| KD (DYRK1A): + | 64 |
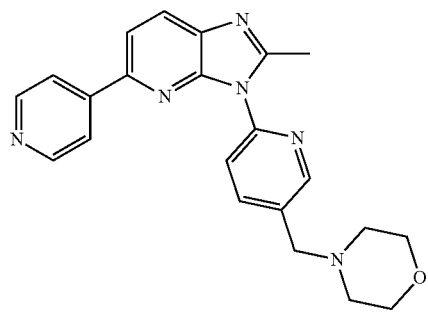 [SMILES: Cc1nc2ccc(-c3ccncc3)nc2n1-c1ccc(CN2CCOCC2)cn1]
| KD (DYRK1A): ++ | 65 |
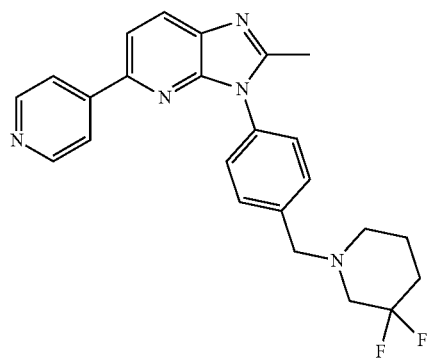 [SMILES: Cc1nc2ccc(-c3ccncc3)nc2n1-c1ccc(CN2CCCC(F)(F)C2)cc1]

TABLE 1-continued
| | |
|---|---|
| KD (DYRK1A): +++ 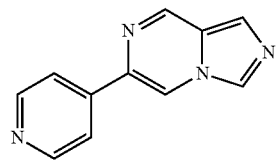 [SMILES: c1cc(-c2cn3cncc3cn2)ccn1] | 66 |
| KD (DYRK1A): +++ 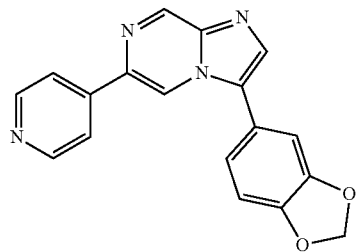 [SMILES: c1cc(-c2cn3c(-c4ccc5c(c4)OCO5)cnc3cn2)ccn1] | 67 |
| KD (DYRK1A): + 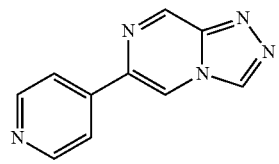 [SMILES: c1cc(-c2cn3cnnc3cn2)ccn1] | 68 |
| KD (DYRK1A): ++ 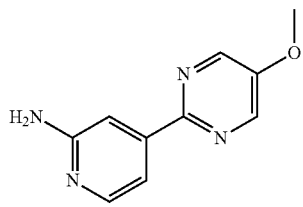 | 69 |
| KD (DYRK1A): + 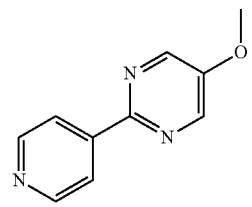 | 70 |
| KD (DYRK1A): +++ 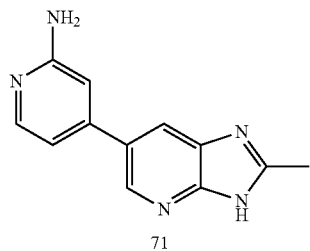 | 71 |

TABLE 1-continued
| | |
|---|---|
| KD (DYRK1A): +++ 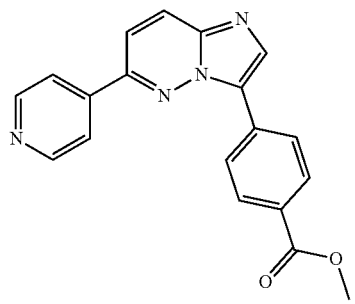 [SMILES: COC(=O)c1ccc(-c2cnc3ccc(-c4ccncc4)nn23)cc1] | 72 |
| KD (DYRK1A): +++ 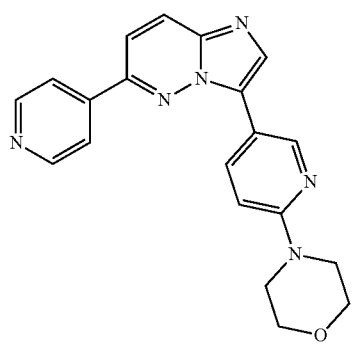 [SMILES: c1cc(-c2ccc3ncc(-c4ccc(N5CCOCC5)nc4)n3n2)ccn1] | 73 |
| KD (DYRK1A): ++ 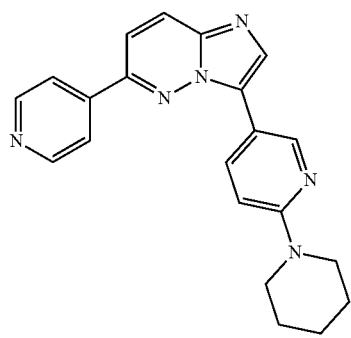 [SMILES: c1cc(-c2ccc3ncc(-c4ccc(N5CCCCC5)nc4)n3n2)ccn1] | 74 |
| KD (DYRK1A): + 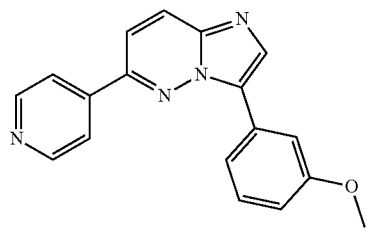 [SMILES: COc1cccc(-c2cnc3ccc(-c4ccncc4)nn23)c1] | 75 |

TABLE 1-continued
| KD (DYRK1A): +++ | 76 |
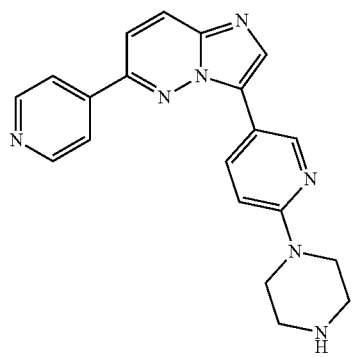 [SMILES: c1cc(-c2ccc3ncc(-c4ccc(N5CCNCC5)nc4)n3n2)ccn1]
| KD (DYRK1A): +++ | 77 |
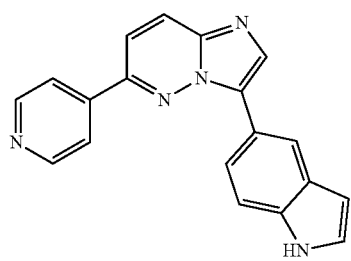 [SMILES: c1cc(-c2ccc3ncc(-c4ccc5[nH]ccc5c4)n3n2)ccn1]
| KD (DYRK1A): ++ | 78 |
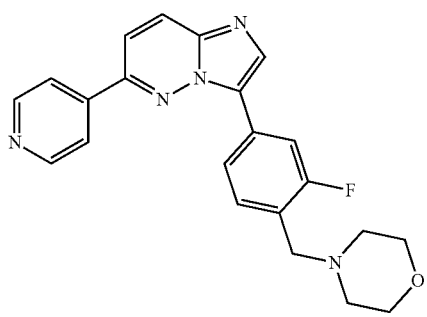 [SMILES: Fc1cc(-c2cnc3ccc(-c4ccncc4)nn23)ccc1CN1CCOCC1]
| KD (DYRK1A): ++ | 79 |
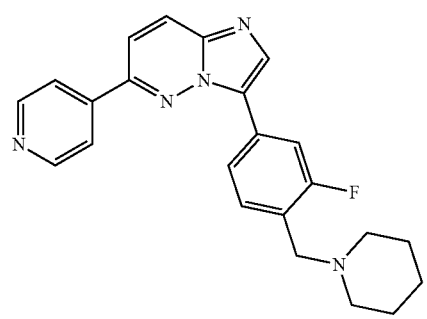 [SMILES: Fc1cc(-c2cnc3ccc(-c4ccncc4)nn23)ccc1CN1CCCCC1]

TABLE 1-continued
| KD (DYRK1A): ++ | 80 |
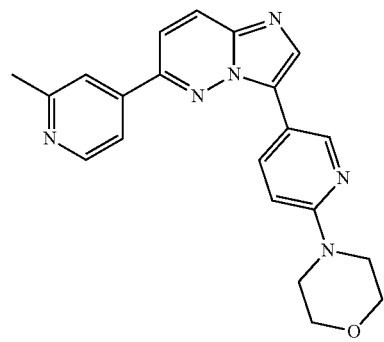 [SMILES: Cc1cc(-c2ccc3ncc(-c4ccc(N5CCOCC5)nc4)n3n2)ccn1]
| KD (DYRK1A): ++ | 81 |
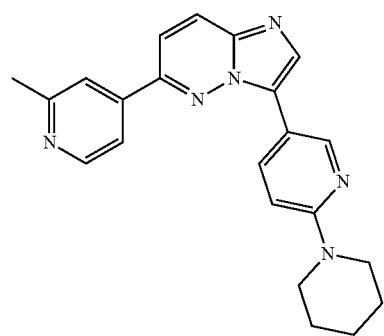 [SMILES: Cc1cc(-c2ccc3ncc(-c4ccc(N5CCCCC5)nc4)n3n2)ccn1]
| KD (DYRK1A): ++ | 82 |
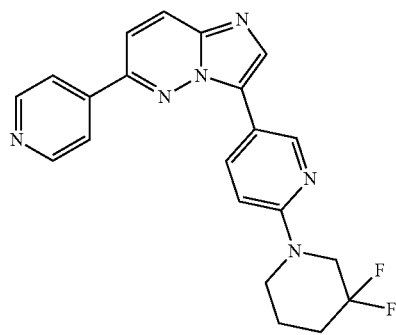 [SMILES: FC1(F)CCCN(c2ccc(-c3cnc4ccc(-c5ccncc5)nn34)cn2)C1]
| KD (DYRK1A): +++ | 83 |
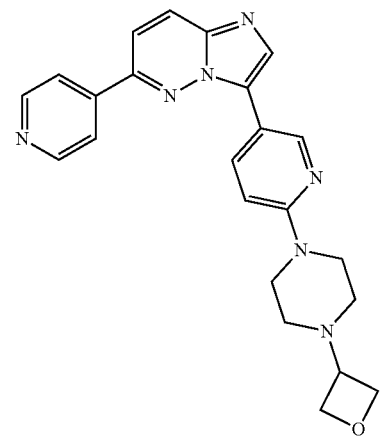 [SMILES: c1cc(-c2ccc3ncc(-c4ccc(N5CCN(C6COC6)CC5)nc4)n3n2)ccn1]

TABLE 1-continued
| | |
|---|---|
| KD (DYRK1A): + 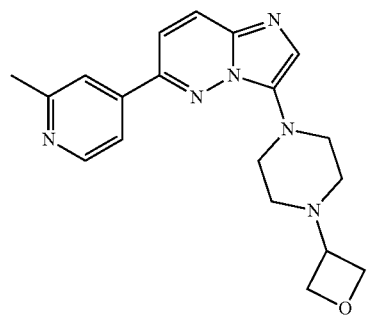 [SMILES: Cc1cc(-c2ccc3ncc(N4CCN(C5COC5)CC4)n3n2)ccn1] | 84 |
| KD (DYRK1A): + 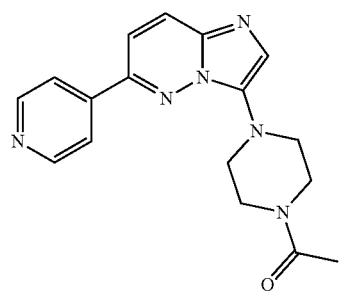 [SMILES: CC(=O)N1CCN(c2cnc3ccc(-c4ccncc4)nn23)CC1] | 85 |
| KD (DYRK1A): + 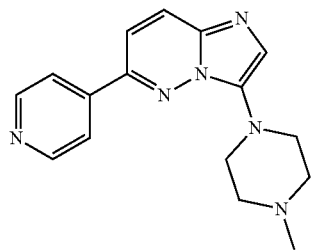 [SMILES: CN1CCN(c2cnc3ccc(-c4ccncc4)nn23)CC1] | 86 |
| KD (DYRK1A): +++ 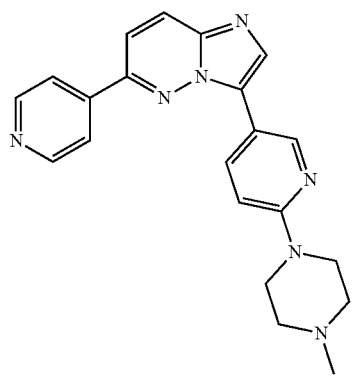 [SMILES: CN1CCN(c2ccc(-c3cnc4ccc(-c5ccncc5)nn34)cn2)CC1] | 87 |

TABLE 1-continued
| | |
|---|---|
| KD (DYRK1A): +++ 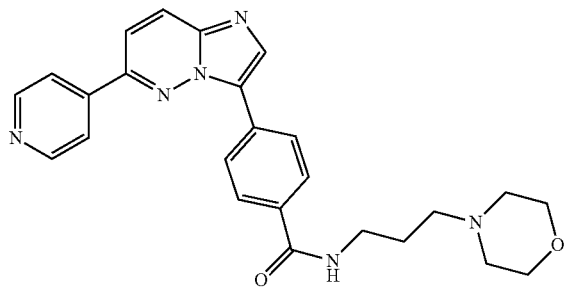 [SMILES: O=C(NCCCN1CCOCC1)c1ccc(-c2cnc3ccc(-c4ccncc4)nn23)cc1] | 88 |
| KD (DYRK1A): ++ 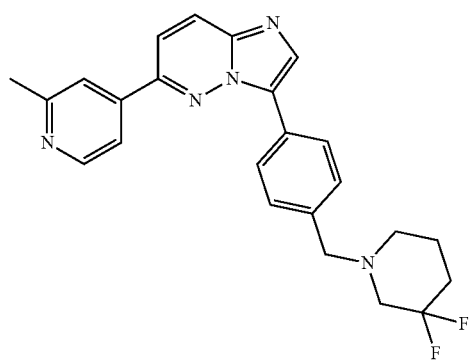 [SMILES: Cc1cc(-c2ccc3ncc(-c4ccc(CN5CCCC(F)(F)C5)cc4)n3n2)ccn1] | 89 |
| KD (DYRK1A): ++ 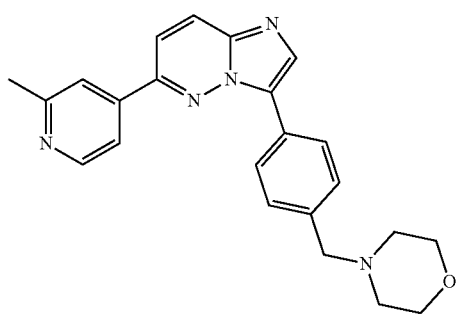 [SMILES: Cc1cc(-c2ccc3ncc(-c4ccc(CN5CCOCC5)cc4)n3n2)ccn1] | 90 |
| KD (DYRK1A): +++ 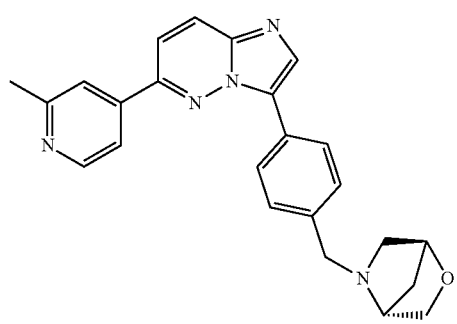 [SMILES: Cc1cc(-c2ccc3ncc(-c4ccc(CN5C[C@@H]6C[C@@H]5CO6)cc4)n3n2)ccn1] | 91 |

TABLE 1-continued
| | |
|---|---|
| KD (DYRK1A): ++ 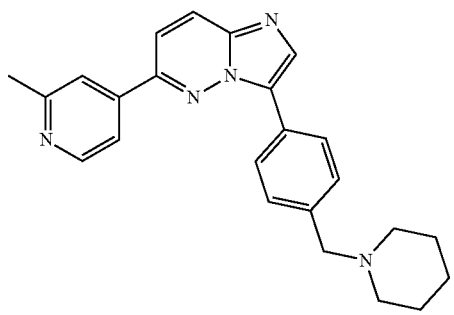 [SMILES: Cc1cc(-c2ccc3ncc(-c4ccc(CN5CCCCC5)cc4)n3n2)ccn1] | 92 |
| KD (DYRK1A): ++ 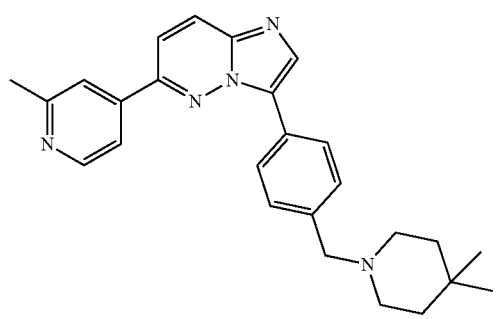 | 93 |
| KD (DYRK1A): +++ 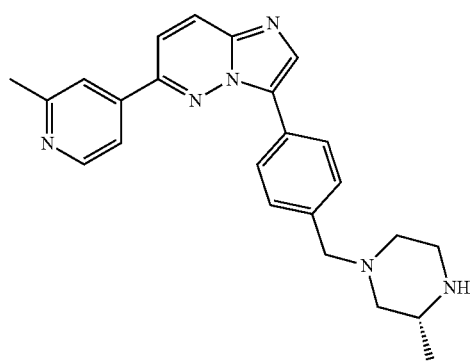 [SMILES: Cc1cc(-c2ccc3ncc(-c4ccc(CN5CCN[C@H](C)C5)cc4)n3n2)ccn1] | 94 |
| KD (DYRK1A): + 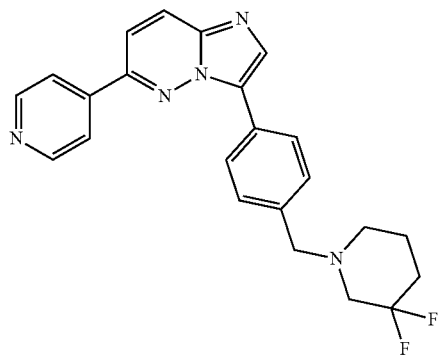 [SMILES: FC1(F)CCCN(Cc2ccc(-c3cnc4ccc(-c5ccncc5)nn34)cc2)C1] | 95 |

TABLE 1-continued
| | |
|---|---|
| KD (DYRK1A): ++ 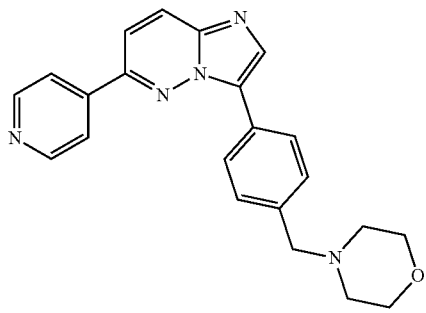 [SMILES: c1cc(-c2ccc3ncc(-c4ccc(CN5CCOCC5)cc4)n3n2)ccn1] | 96 |
| KD (DYRK1A): +++ 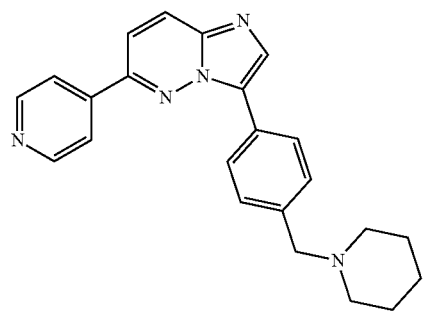 [SMILES: c1cc(-c2ccc3ncc(-c4ccc(CN5CCCCC5)cc4)n3n2)ccn1] | 97 |
| KD (DYRK1A): ++ 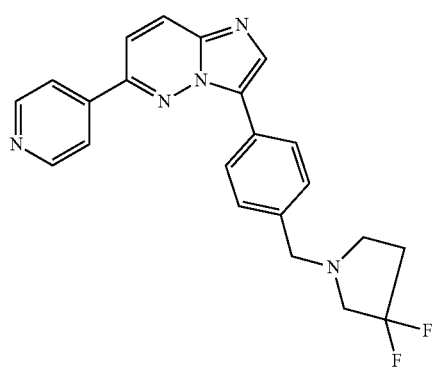 [SMILES: FC1(F)CCN(Cc2ccc(-c3cnc4ccc(-c5ccncc5)nn34)cc2)C1] | 98 |
| KD (DYRK1A): +++ 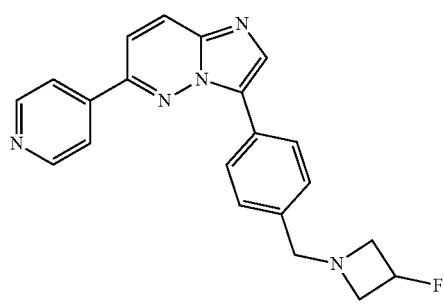 [SMILES: FC1CN(Cc2ccc(-c3cnc4ccc(-c5ccncc5)nn34)cc2)C1] | 99 |

TABLE 1-continued
| | |
|---|---|
| KD (DYRK1A): ++ 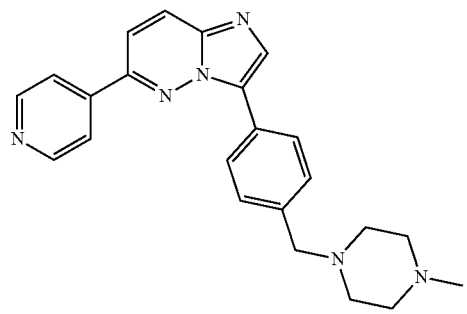 [SMILES: CN1CCN(Cc2ccc(-c3cnc4ccc(-c5ccncc5)nn34)cc2)CC1] | 100 |
| KD (DYRK1A): ++ 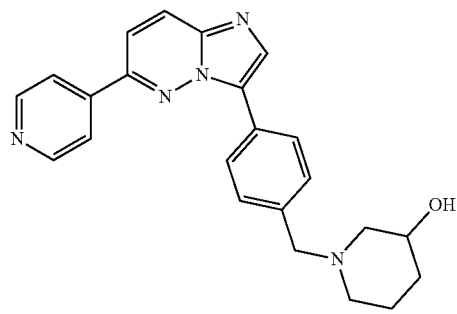 [SMILES: OC1CCCN(Cc2ccc(-c3cnc4ccc(-c5ccncc5)nn34)cc2)C1] | 101 |
| KD (DYRK1A): ++ 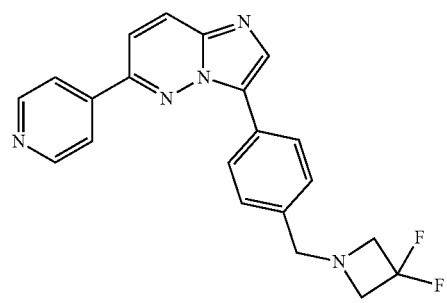 | 102 |
| KD (DYRK1A): ++ 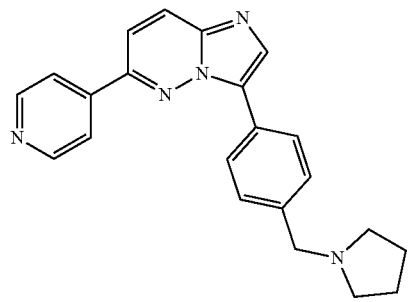 [SMILES: c1cc(-c2ccc3ncc(-c4ccc(CN5CCCC5)cc4)n3n2)ccn1] | 103 |

TABLE 1-continued
| | |
|---|---|
| KD (DYRK1A): +++ 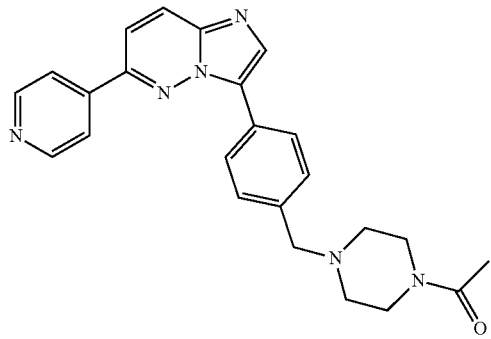 [SMILES: CC(=O)N1CCN(Cc2ccc(-c3cnc4ccc(-c5ccncc5)nn34)cc2)CC1] | 104 |
| KD (DYRK1A): + 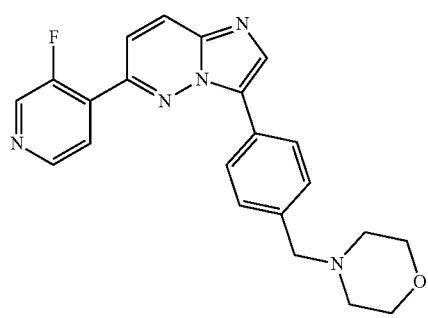 [SMILES: Fc1cnccc1-c1ccc2ncc(-c3ccc(CN4CCOCC4)cc3)n2n1] | 105 |
| KD (DYRK1A): + 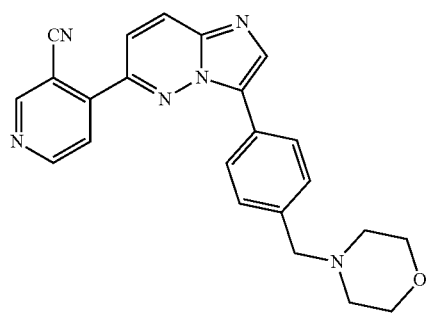 [SMILES: N#Cc1cnccc1-c1ccc2ncc(-c3ccc(CN4CCOCC4)cc3)n2n1] | 106 |
| KD (DYRK1A): ++ 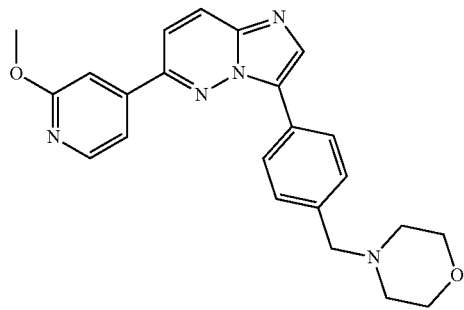 [SMILES: COc1cc(-c2ccc3ncc(-c4ccc(CN5CCOCC5)cc4)n3n2)ccn1] | 107 |

TABLE 1-continued
KD (DYRK1A): +++  108
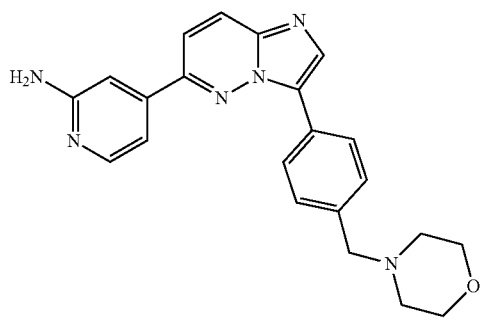 [SMILES: Nc1cc(-c2ccc3ncc(-c4ccc(CN5CCOCC5)cc4)n3n2)ccn1]
KD (DYRK1A): +  109
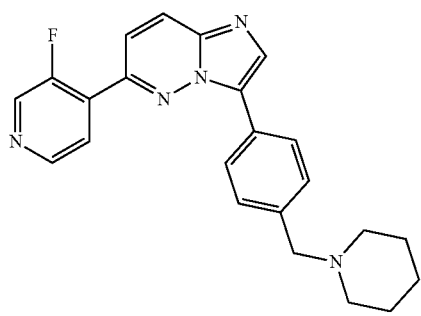 [SMILES: Fc1cnccc1-c1ccc2ncc(-c3ccc(CN4CCCCC4)cc3)n2n1]
KD (DYRK1A): +++  110
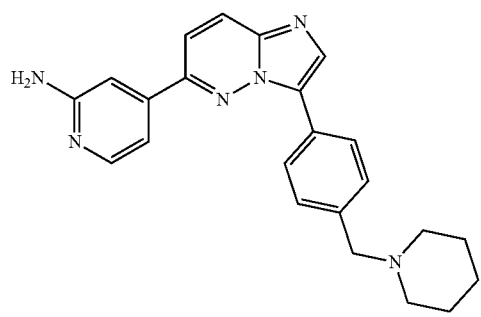 [SMILES: Nc1cc(-c2ccc3ncc(-c4ccc(CN5CCCCC5)cc4)n3n2)ccn1]
KD (DYRK1A): +  111
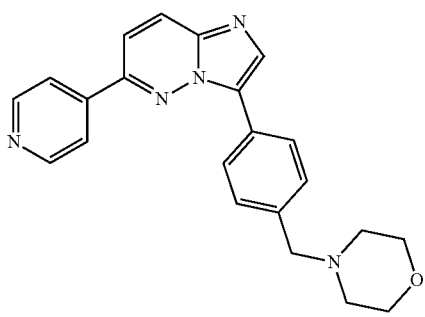 [SMILES: c1cc(-c2ccc3ncc(-c4ccc(CN5CCOCC5)cc4)n3n2)ccn1]

TABLE 1-continued
KD (DYRK1A): + 112
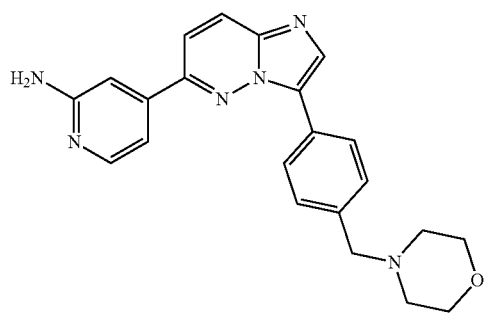 [SMILES: Nc1cc(-c2ccc3ncc(-c4ccc(CN5CCOCC5)cc4)n3n2)ccn1]
KD (DYRK1A): + 113
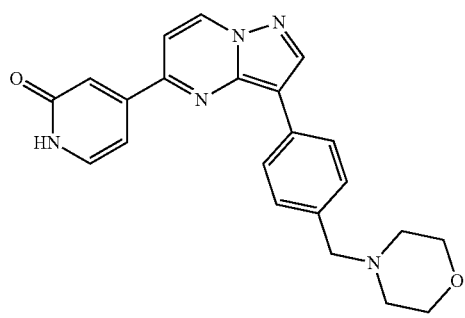 [SMILES: O=c1cc(-c2ccn3ncc(-c4ccc(CN5CCOCC5)cc4)c3n2)cc[nH]1]
KD (DYRK1A): ++ 114
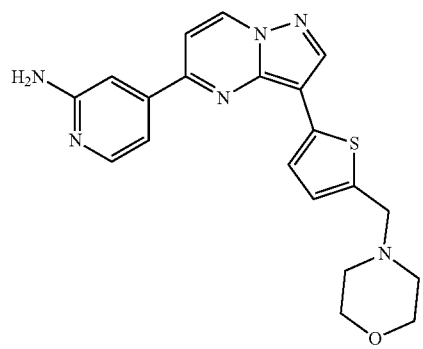 [SMILES: Nc1cc(-c2ccn3ncc(-c4ccc(CN5CCOCC5)s4)c3n2)ccn1]
KD (DYRK1A): +++ 115
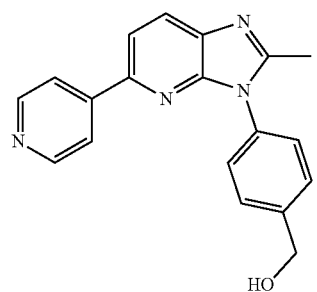 [SMILES: Cc1nc2ccc(-c3ccncc3)nc2n1-c1ccc(CO)cc1]

TABLE 1-continued
KD (DYRK1A): +++ 116
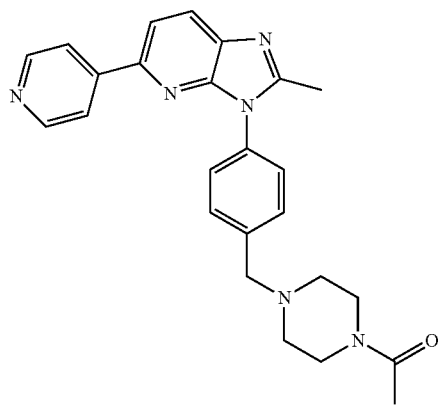 [SMILES: CC(=O)N1CCN(Cc2ccc(-n3c(C)nc4ccc(-c5ccncc5)nc43)cc2)CC1]
117
KD (DYRK1A): ++
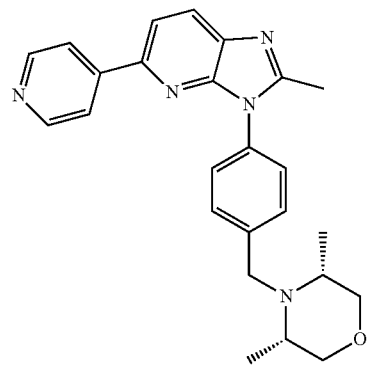 [SMILES: Cc1nc2ccc(-c3ccncc3)nc2n1-c1ccc(CN2[C@H](C)COC[C@@H]2C)cc1]
118
KD (DYRK1A): +++
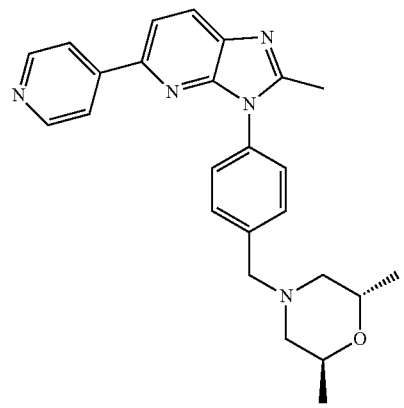 [SMILES: Cc1nc2ccc(-c3ccncc3)nc2n1-c1ccc(CN2C[C@H](C)O[C@@H](C)C2)cc1]

TABLE 1-continued
KD (DYRK1A): +++     119
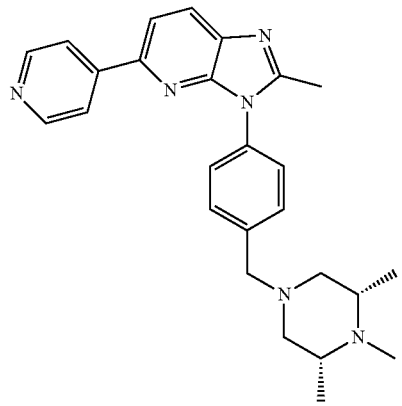 [SMILES: Cc1nc2ccc(-c3ccncc3)nc2n1-c1ccc(CN2C[C@@H](C)N(C)[C@@H](C)C2)cc1]
KD (DYRK1A): +++     120
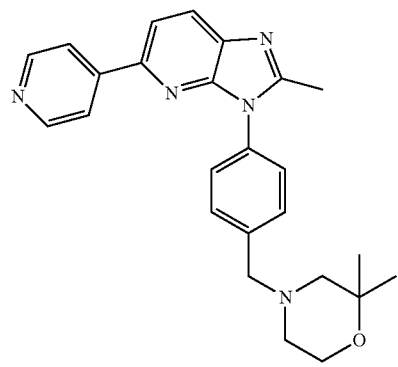 [SMILES: Cc1nc2ccc(-c3ccncc3)nc2n1-c1ccc(CN2CCOC(C)(C)C2)cc1]
KD (DYRK1A): +++     121
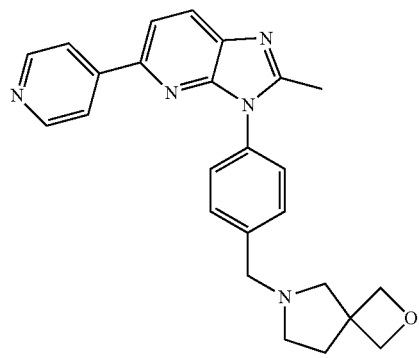 [SMILES: Cc1nc2ccc(-c3ccncc3)nc2n1-c1ccc(CN2CCC3(COC3)C2)cc1]

TABLE 1-continued
| | |
|---|---|
| KD (DYRK1A): +++ 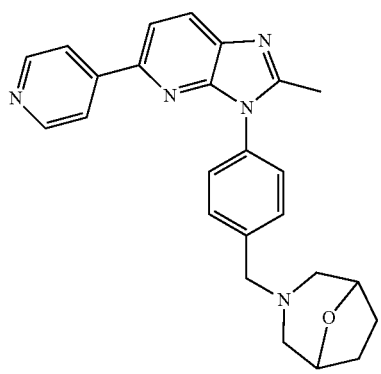 [SMILES: Cc1nc2ccc(-c3ccncc3)nc2n1-c1ccc(CN2CC3CCC(C2)O3)cc1] | 122 |
| KD (DYRK1A): ++ 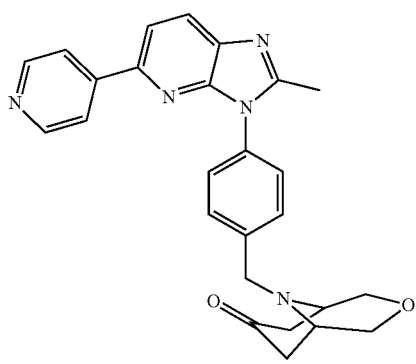 [SMILES: Cc1nc2ccc(-c3ccncc3)nc2n1-c1ccc(CN2C3COCC2CC(=O)C3)cc1] | 123 |
| KD (DYRK1A): +++ 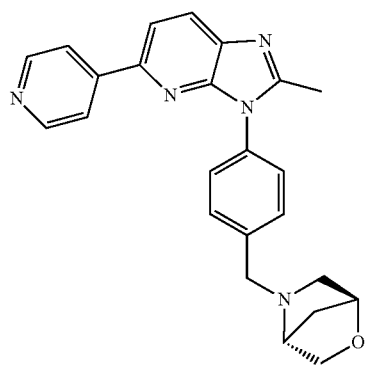 [SMILES: Cc1nc2ccc(-c3ccncc3)nc2n1-c1ccc(CN2C[C@@H]3C[C@@H]2CO3)cc1] | 124 |
| KD (DYRK1A): +++ 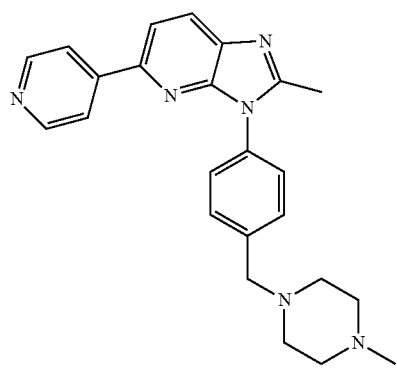 [SMILES: Cc1nc2ccc(-c3ccncc3)nc2n1-c1ccc(CN2CCN(C)CC2)cc1] | 125 |

TABLE 1-continued
KD (DYRK1A): +++  126
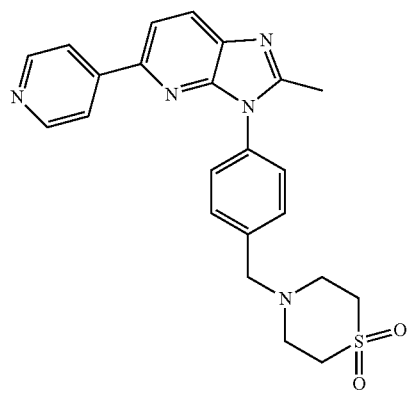 [SMILES: Cc1nc2ccc(-c3ccncc3)nc2n1-c1ccc(CN2CCS(=O)(=O)CC2)cc1]
KD (DYRK1A): +++  127
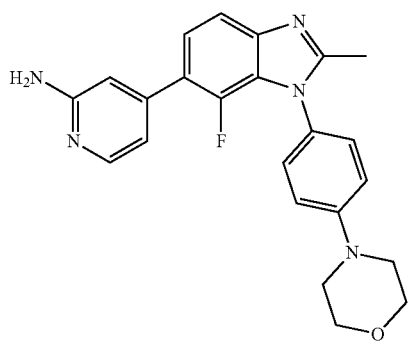 [SMILES: Cc1nc2ccc(-c3ccnc(N)c3)c(F)c2n1-c1ccc(N2CCOCC2)cc1]
KD (DYRK1A): +  128
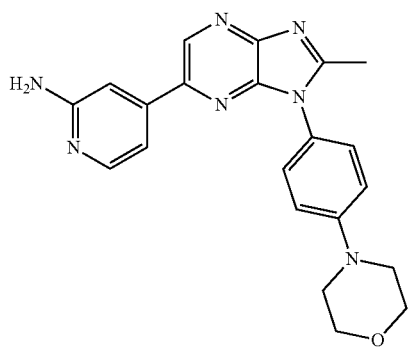 [SMILES: Cc1nc2ncc(-c3ccnc(N)c3)nc2n1-c1ccc(N2CCOCC2)cc1]
KD (DYRK1A): +  129
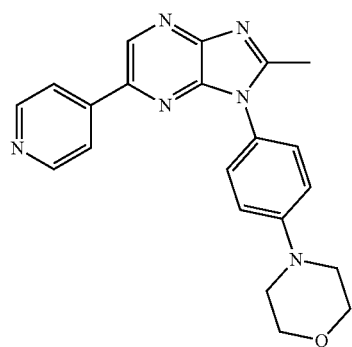

TABLE 1-continued
| | |
|---|---|
| KD (DYRK1A): ++ 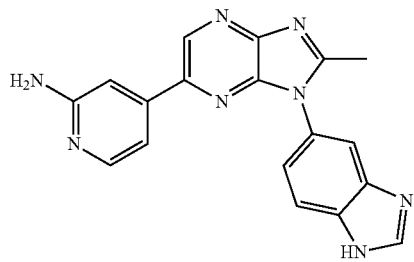 [SMILES: Cc1nc2ncc(-c3ccnc(N)c3)nc2n1-c1ccc2[nH]cnc2c1] | 130 |
| KD (DYRK1A): ++ 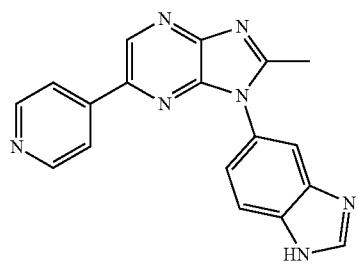 [SMILES: Cc1nc2ncc(-c3ccncc3)nc2n1-c1ccc2[nH]cnc2c1] | 131 |
| KD (DYRK1A): +++ 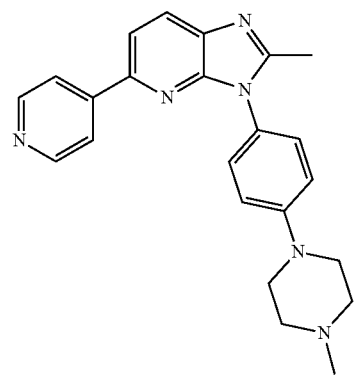 [SMILES: Cc1nc2ccc(-c3ccncc3)nc2n1-c1ccc(N2CCN(C)CC2)cc1] | 132 |
| KD (DYRK1A): ++ 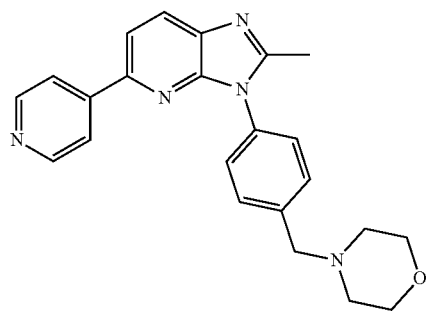 [SMILES: Cc1nc2ccc(-c3ccncc3)nc2n1-c1ccc(CN2CCOCC2)cc1] | 133 |

TABLE 1-continued
| KD (DYRK1A): ++ | 134 |
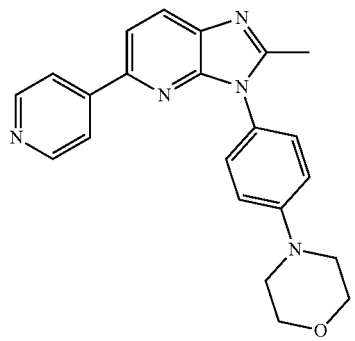 [SMILES: Cc1nc2ccc(-c3ccncc3)nc2n1-c1ccc(N2CCOCC2)cc1]
| | 135 |
| KD (DYRK1A): +++ | |
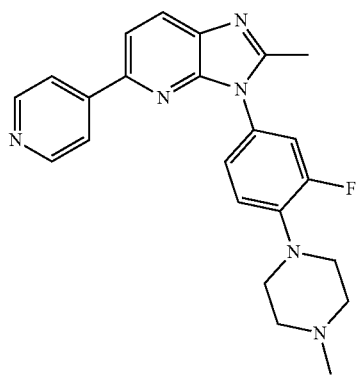 [SMILES: Cc1nc2ccc(-c3ccncc3)nc2n1-c1ccc(N2CCN(C)CC2)c(F)c1]
| KD (DYRK1A): +++ | 136 |
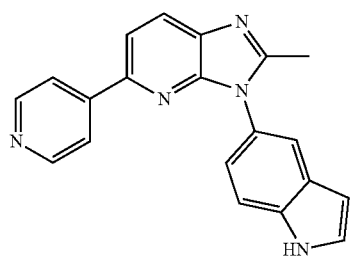
| | 137 |
| KD (DYRK1A): +++ | |
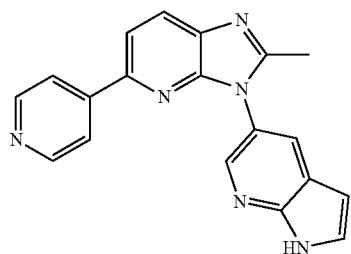 [SMILES: Cc1nc2ccc(-c3ccncc3)nc2n1-c1ccc2[nH]ccc2c1]

TABLE 1-continued
KD (DYRK1A): +++  138
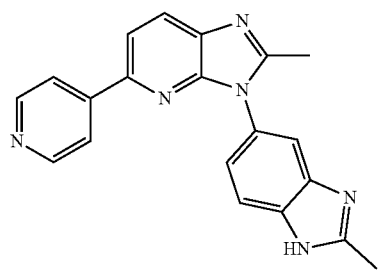 [SMILES: Cc1nc2cc(-n3c(C)nc4ccc(-c5ccncc5)nc43)ccc2[nH]1]
139
KD (DYRK1A): +++
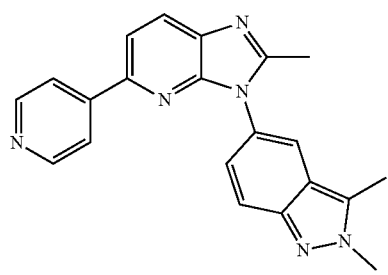 [SMILES: Cc1c2cc(-n3c(C)nc4ccc(-c5ccncc5)nc43)ccc2nn1C]
KD (DYRK1A): +++  140
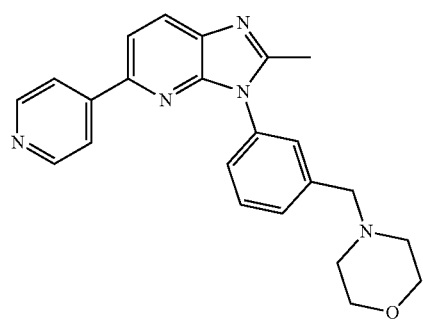 [SMILES: Cc1nc2ccc(-c3ccncc3)nc2n1-c1cccc(CN2CCOCC2)c1]
141
KD (DYRK1A): +++
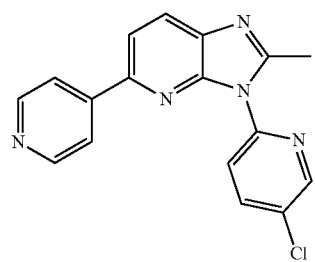 [SMILES: Cc1nc2ccc(-c3ccncc3)nc2n1-c1ccc(Cl)cn1]

TABLE 1-continued
| KD (DYRK1A): ++ | 142 |
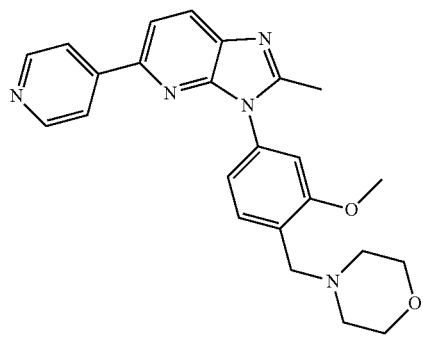 [SMILES: COc1cc(-n2c(C)nc3ccc(-c4ccncc4)nc32)ccc1CN1CCOCC1]
| KD (DYRK1A): +++ | 143 |
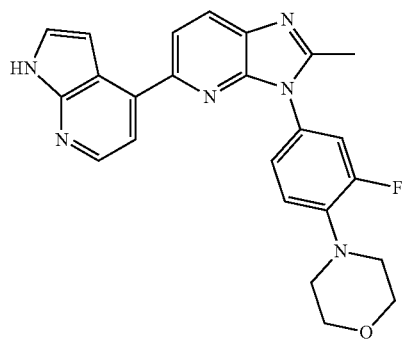 [SMILES: Cc1nc2ccc(-c3ccnc4[nH]ccc34)nc2n1-c1ccc(N2CCOCC2)c(F)c1]
| KD (DYRK1A): +++ | 144 |
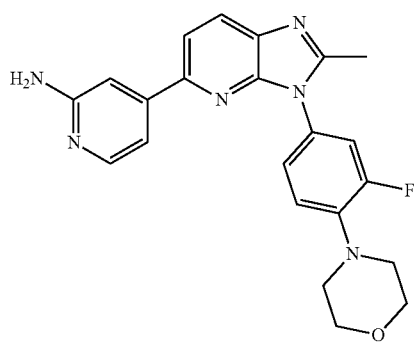
| KD (DYRK1A): +++ | 145 |
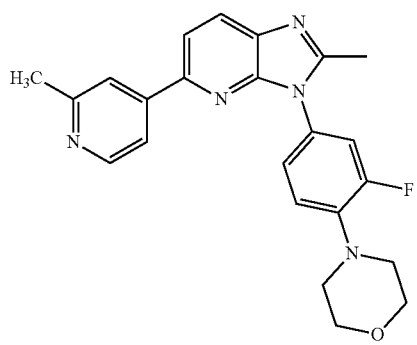 [SMILES: Cc1cc(-c2ccc3nc(C)n(-c4ccc(N5CCOCC5)c(F)c4)c3n2)ccn1]

TABLE 1-continued
| KD (DYRK1A): +++ | 146 |
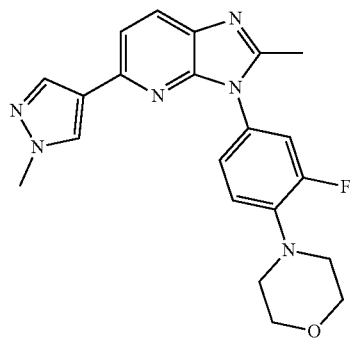 [SMILES: Cc1nc2ccc(-c3cnn(C)c3)nc2n1-c1ccc(N2CCOCC2)c(F)c1]
| KD (DYRK1A): +++ | 147 |
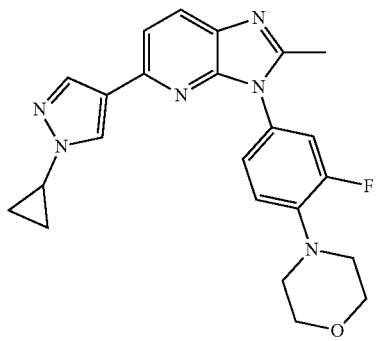 [SMILES: Cc1nc2ccc(-c3cnn(C4CC4)c3)nc2n1-c1ccc(N2CCOCC2)c(F)c1]
| KD (DYRK1A): +++ | 148 |
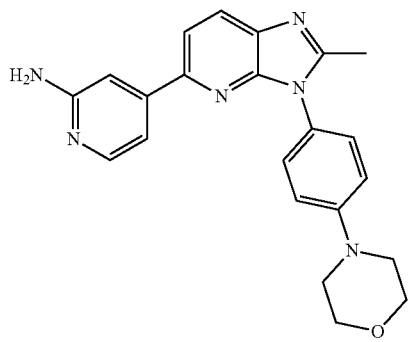 [SMILES: Cc1nc2ccc(-c3ccnc(N)c3)nc2n1-c1ccc(N2CCOCC2)cc1]
| KD (DYRK1A): + | 149 |
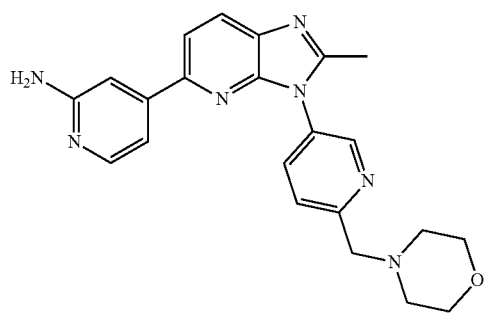 [SMILES: Cc1nc2ccc(-c3ccnc(N)c3)nc2n1-c1ccc(CN2CCOCC2)nc1]

TABLE 1-continued
| KD (DYRK1A): +++ | 150 |
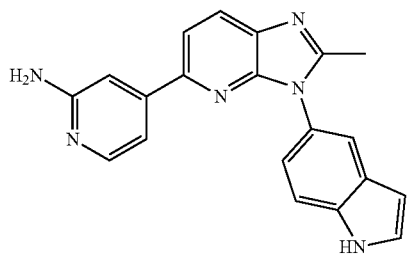 [SMILES: Cc1nc2ccc(-c3ccnc(N)c3)nc2n1-c1ccc2[nH]ccc2c1]
| KD (DYRK1A): +++ | 151 |
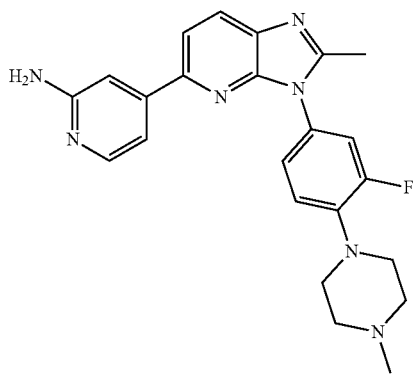 [SMILES: Cc1nc2ccc(-c3ccnc(N)c3)nc2n1-c1ccc(N2CCN(C)CC2)c(F)c1]
| KD (DYRK1A): +++ | 152 |
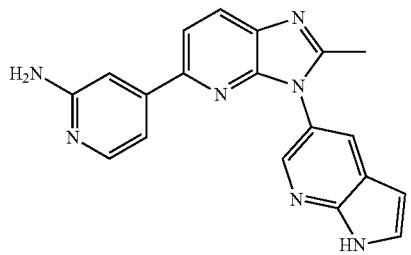
| KD (DYRK1A): +++ | 153 |
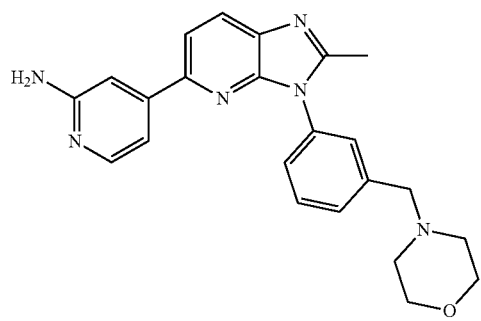 [SMILES: Cc1nc2ccc(-c3ccnc(N)c3)nc2n1-c1cccc(CN2CCOCC2)c1]

TABLE 1-continued
154
KD (DYRK1A): +++
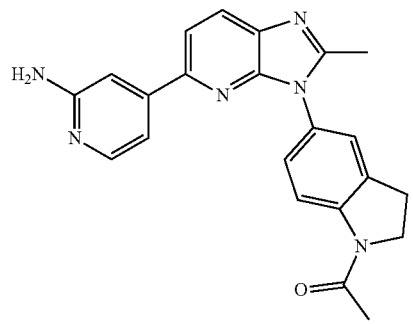 [SMILES: CC(=O)N1CCc2cc(-n3c(C)nc4ccc(-c5ccnc(N)c5)nc43)ccc21]
155
KD (DYRK1A): +++
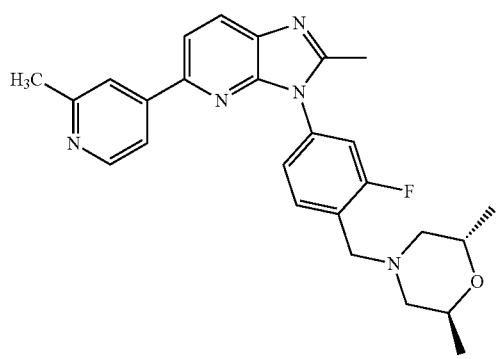
156
KD (DYRK1A): +++
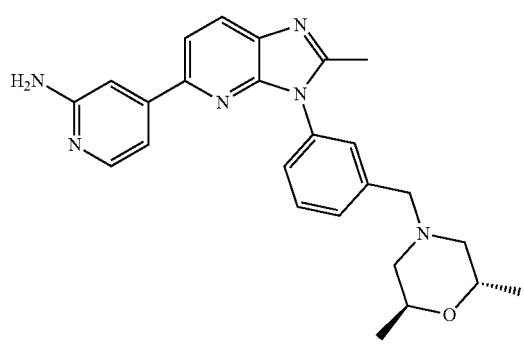 [SMILES: Cc1nc2ccc(-c3ccnc(N)c3)nc2n1-c1cccc(CN2C[C@H](C)O[C@@H](C)C2)c1]
157
KD (DYRK1A): +++
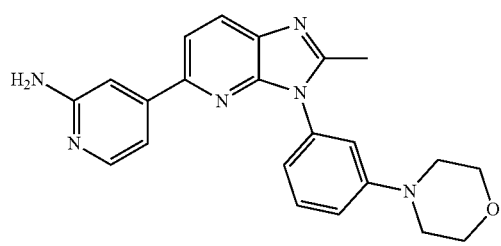 [SMILES: Cc1nc2ccc(-c3ccnc(N)c3)nc2n1-c1cccc(N2CCOCC2)c1]

TABLE 1-continued
KD (DYRK1A): +++ 158
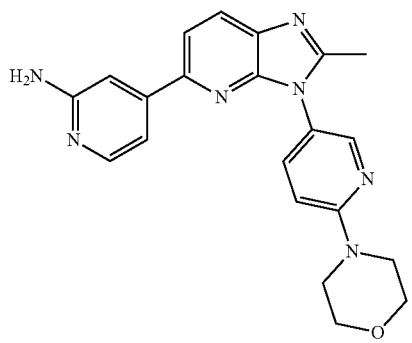 [SMILES: Cc1nc2ccc(-c3ccnc(N)c3)nc2n1-c1ccc(N2CCOCC2)nc1]
KD (DYRK1A): +++ 159
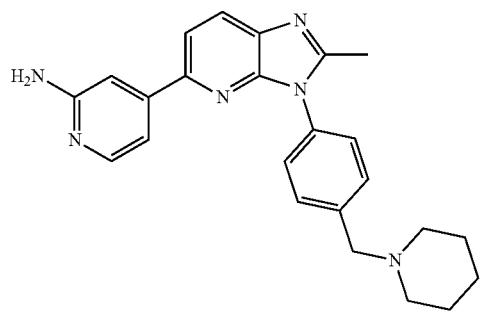 [SMILES: Cc1nc2ccc(-c3ccnc(N)c3)nc2n1-c1ccc(CN2CCCCC2)cc1]
KD (DYRK1A): +++ 160
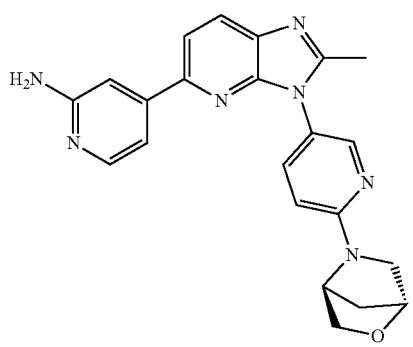 [SMILES: Cc1nc2ccc(-c3ccnc(N)c3)nc2n1-c1ccc(N2C[C@H]3C[C@H]2CO3)nc1]
KD (DYRK1A): +++ 161
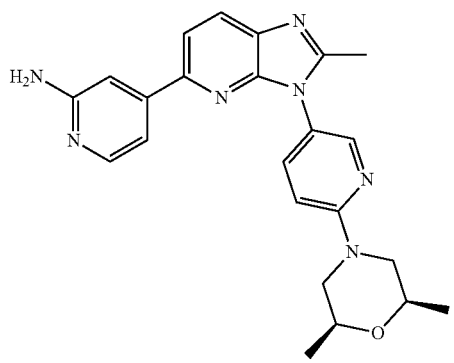 [SMILES: Cc1nc2ccc(-c3ccnc(N)c3)nc2n1-c1ccc(N2C[C@@H](C)O[C@@H](C)C2)nc1]

TABLE 1-continued
KD (DYRK1A): +++ 162
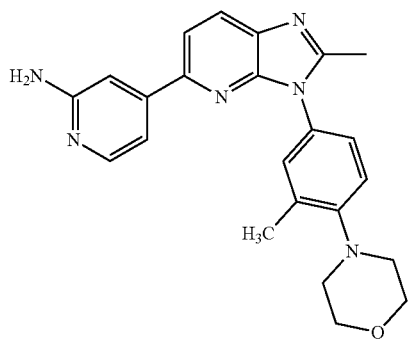 [SMILES: Cc1cc(-n2c(C)nc3ccc(-c4ccnc(N)c4)nc32)ccc1N1CCOCC1]
KD (DYRK1A): +++ 163
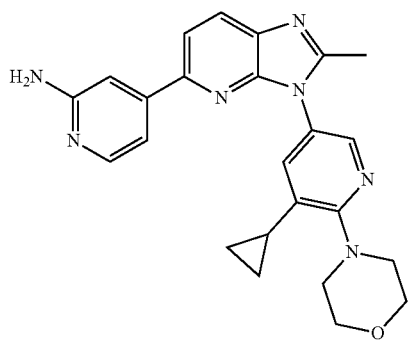 [SMILES: Cc1nc2ccc(-c3ccnc(N)c3)nc2n1-c1cnc(N2CCOCC2)c(C2CC2)c1]
KD (DYRK1A): +++ 164
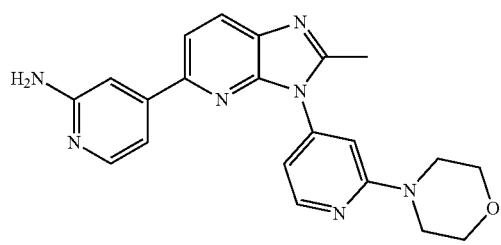
KD (DYRK1A): +++ 165
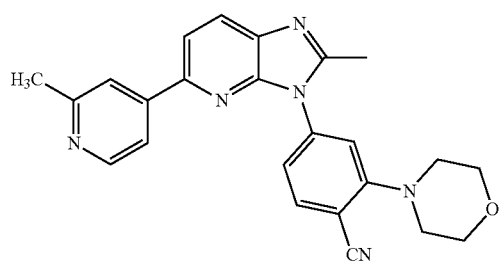

TABLE 1-continued
KD (DYRK1A): +++     166
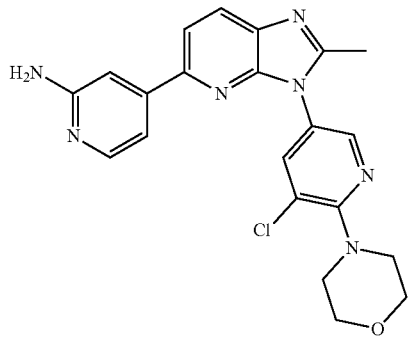 [SMILES: Cc1nc2ccc(-c3ccnc(N)c3)nc2n1-c1cnc(N2CCOCC2)c(Cl)c1]
KD (DYRK1A): +++     167
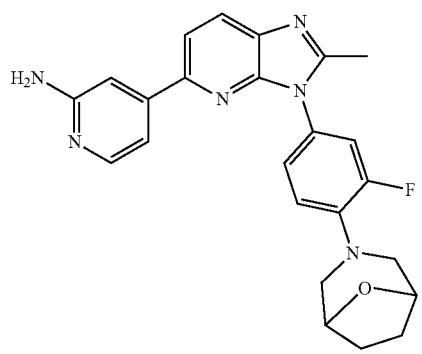 [SMILES: Cc1nc2ccc(-c3ccnc(N)c3)nc2n1-c1ccc(N2CC3CCC(C2)O3)c(F)c1]
KD (DYRK1A): +++     168
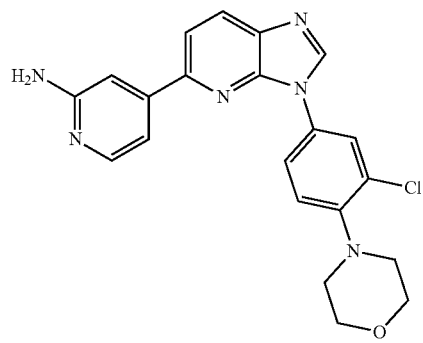 [SMILES: Nc1cc(-c2ccc3ncn(-c4ccc(N5CCOCC5)c(Cl)c4)c3n2)ccn1]
KD (DYRK1A): +++     169
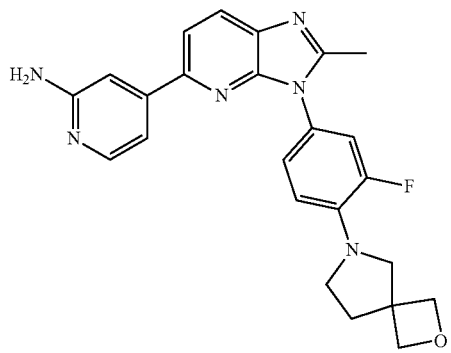 [SMILES: Cc1nc2ccc(-c3ccnc(N)c3)nc2n1-c1ccc(N2CCC3(COC3)C2)c(F)c1]

TABLE 1-continued
| | |
|---|---|
| KD (DYRK1A): +++ 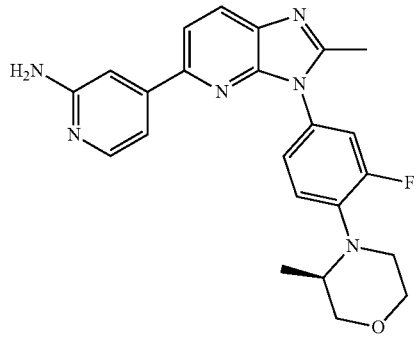 [SMILES: Cc1nc2ccc(-c3ccnc(N)c3)nc2n1-c1ccc(N2CCOC[C@H]2C)c(F)c1] | 170 |
| KD (DYRK1A): +++ 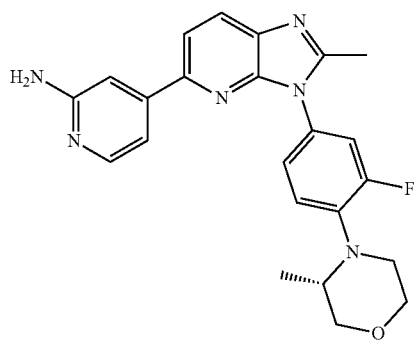 [SMILES: Cc1nc2ccc(-c3ccnc(N)c3)nc2n1-c1ccc(N2CCOC[C@@H]2C)c(F)c1] | 171 |
| KD (DYRK1A): +++ 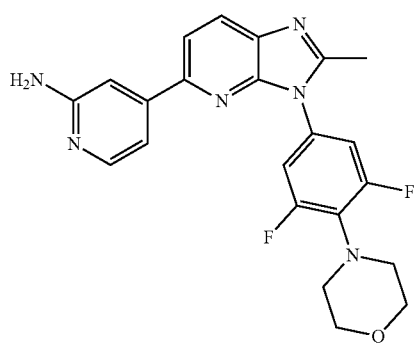 [SMILES: Cc1nc2ccc(-c3ccnc(N)c3)nc2n1-c1cc(F)c(N2CCOCC2)c(F)c1] | 172 |
| KD (DYRK1A): +++ 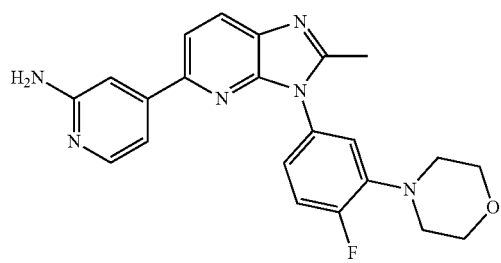 [SMILES: Cc1nc2ccc(-c3ccnc(N)c3)nc2n1-c1ccc(F)c(N2CCOCC2)c1] | 173 |

TABLE 1-continued
| | |
|---|---|
| KD (DYRK1A): +++ 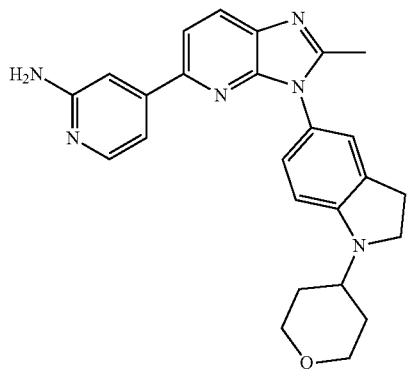 [SMILES: Cc1nc2ccc(-c3ccnc(N)c3)nc2n1-c1ccc2c(c1)CCN2C1CCOCC1] | 174 |
| KD (DYRK1A): +++ 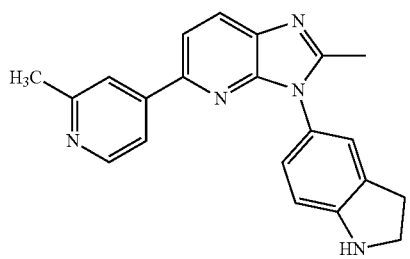 [SMILES: Cc1cc(-c2ccc3nc(C)n(-c4ccc5c(c4)CCN5)c3n2)ccn1] | 175 |
| KD (DYRK1A): +++ 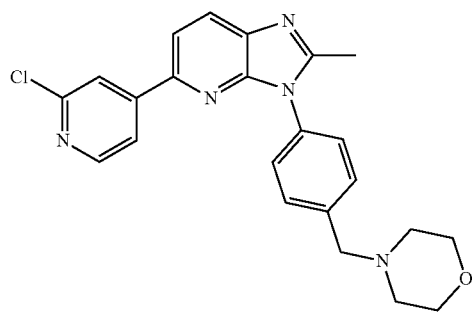 [SMILES: Cc1nc2ccc(-c3ccnc(Cl)c3)nc2n1-c1ccc(CN2CCOCC2)cc1] | 176 |
| KD (DYRK1A): + 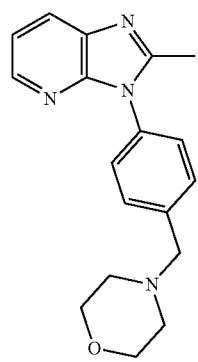 [SMILES: Cc1nc2cccnc2n1-c1ccc(CN2CCOCC2)cc1] | 177 |

TABLE 1-continued
KD (DYRK1A): +++  178
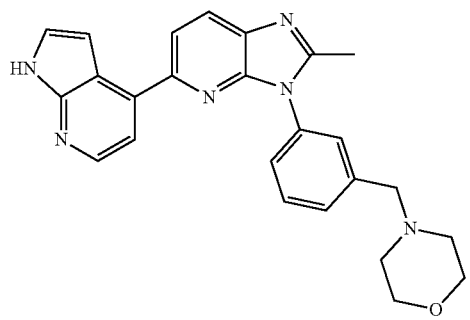 [SMILES: Cc1nc2ccc(-c3ccnc4[nH]ccc34)nc2n1-c1cccc(CN2CCOCC2)c1]
KD (DYRK1A): +++  179
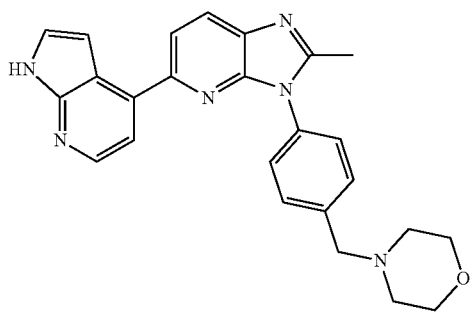 [SMILES: Cc1nc2ccc(-c3ccnc4[nH]ccc34)nc2n1-c1ccc(CN2CCOCC2)cc1]
KD (DYRK1A): ++  180
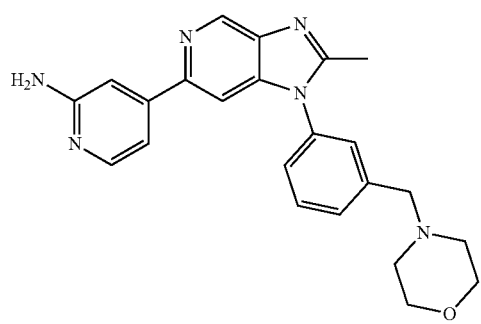 [SMILES: Cc1nc2cnc(-c3ccnc(N)c3)cc2n1-c1cccc(CN2CCOCC2)c1]
KD (DYRK1A): +++  181
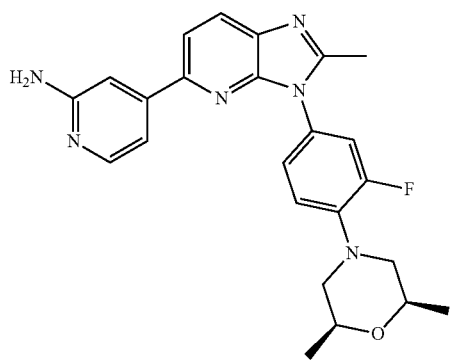 [SMILES: Cc1nc2ccc(-c3ccnc(N)c3)nc2n1-c1ccc(N2C[C@@H](C)O[C@@H](C)C2)c(F)c1]

TABLE 1-continued
KD (DYRK1A): +++ 182
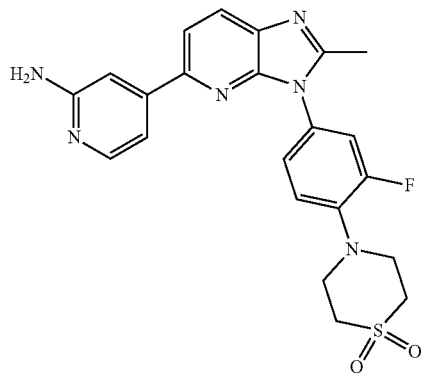 [SMILES: Cc1nc2ccc(-c3ccnc(N)c3)nc2n1-c1ccc(N2CCS(=O)(=O)CC2)c(F)c1]
KD (DYRK1A): +++ 183
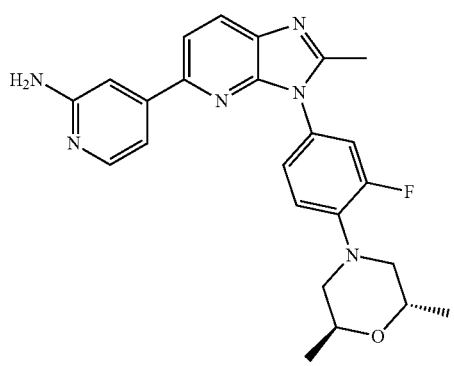 [SMILES: Cc1nc2ccc(-c3ccnc(N)c3)nc2n1-c1ccc(N2C[C@H](C)O[C@@H](C)C2)c(F)c1]
KD (DYRK1A): +++ 184
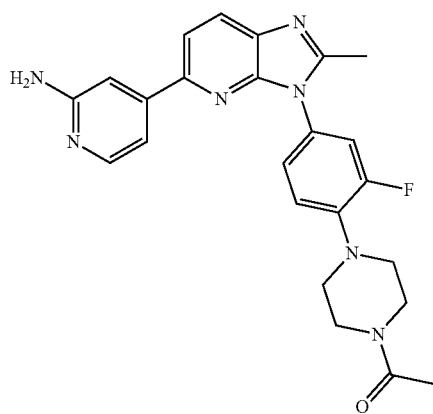 [SMILES: CC(=O)N1CCN(c2ccc(-n3c(C)nc4ccc(-c5ccnc(N)c5)nc43)cc2F)CC1]

TABLE 1-continued

KD (DYRK1A): +++      185

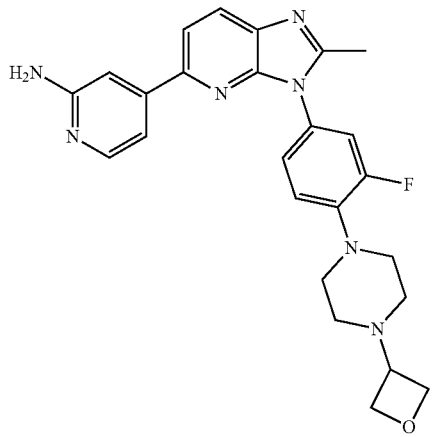 [SMILES: Cc1nc2ccc(-c3ccnc(N)c3)nc2n1-c1ccc(N2CCN(C3COC3)CC2)c(F)c1]

The invention further provides processes for preparing any of the compounds of the present invention.

The invention also provides the use of compounds to not only inhibit DYRK1A activity but also signaling pathways dependent upon DYRK1A phosphorylation (e.g., Tau, PI3K/AKt, APP, PSI, ASF, RCAN-1, NFAT, p53, ASK1/JNK1, SIRT1, GluN2A and other NMDA receptors). The invention also relates to the use of compounds for sensitizing cells to additional agent(s), such as agents known to be effective in the treatment of neurodegenerative disorders.

In certain embodiments, the compounds are used as DYRK protein degraders (see, Valazquez, et al, 2019 Molecular Neurobiology 1-12).

The compounds of the invention are useful for the treatment, amelioration, or prevention of disorders associated with DYRK1A activity (e.g., AD, DS, Parkinson's disease, Huntington's disease, diabetes, glioblastoma), such as those responsive to DYRK1A activity inhibition. In certain embodiments, the compounds can be used to treat, ameliorate, or prevent cancer that is associated with DYRK1A activity (e.g., glioblastoma, prostate cancer). In certain embodiments, the compounds can be used to treat, ameliorate, or prevent autoimmune diseases. In certain embodiments, the compounds can be used to treat, ameliorate, or prevent inflammatory disorders (e.g., airway inflammation).

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., agents useful in treating neurodegenerative disorders and/or anticancer agents.

The present disclosure further provides bifunctional compounds that function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited. An exemplary advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as any type of cancer characterized with AR activity and/or AR expression (e.g., cancer (e.g., CRPC) (e.g., cancers resistant to Enzalutamide treatment)).

In an additional aspect, the disclosure provides bifunctional or PROTAC compounds, which comprise an E3 Ubiquitin Ligase binding moiety (e.g., a ligand for an E3 Ubquitin Ligase or "ULM" group), and a moiety that binds a target protein (e.g., a protein/polypeptide targeting ligand or "PTM" group) (e.g., an AR activity and/or AR expression inhibitor) such that the target protein/polypeptide is placed in proximity to the ubiquitin ligase to effect degradation (and inhibition) of that protein (e.g., inhibit AR receptor activity and/or AR expression). In certain embodiments, the PTM is any of the compounds as described herein showing inhibitory activity against AR activity and/or AR expression. In some embodiments, the ULM is a VHL, cereblon, mouse double minute 2 (MDM2), and/or inhibitor of apoptosis protein (IAP) E3 ligase binding moiety. For example, the structure of the bifunctional compound can be depicted as PTM-ULM.

The respective positions of the PTM and ULM moieties, as well as their number as illustrated herein, is provided by way of example only and is not intended to limit the compounds in any way. As would be understood by the skilled artisan, the bifunctional compounds as described herein can be synthesized such that the number and position of the respective functional moieties can be varied as desired.

In certain embodiments, the bifunctional compound further comprises a chemical linker ("L"). In this example, the structure of the bifunctional compound can be depicted as PTM-L-ULM, where PTM is a protein/polypeptide targeting moiety (e.g., any of the compounds as described herein showing inhibitory activity against AR activity and/or AR expression), L is a linker, and ULM is a VHL, cereblon, MDM2, or IAP E3 ligase binding moiety binding moiety.

Such embodiments are not limited to a specific type of linker. In some embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical. In some embodiments, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

The ULM group and PTM group may be covalently linked to the linker group through any group which is appropriate and stable to the chemistry of the linker. In exemplary aspects of the present invention, the linker is independently covalently bonded to the ULM group and the PTM group in certain embodiments through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. In certain aspects where the PTM group is a ULM group, the target protein for degradation may be the ubiquitin ligase itself. In certain exemplary aspects, the linker may be linked to an optionally substituted alkyl, alkylene, alkene or alkyne group, an aryl group or a heterocyclic group on the ULM and/or PTM groups.

In certain embodiments, the compounds as described herein comprise multiple ULMs, multiple PTMs, multiple chemical linkers, or any combinations thereof.

In some embodiments, the present invention provides a method of ubiquitinating/degrading AR receptor activity and/or AR expression in a cell comprising administering a bifunctional compound as described herein comprising an ULM and a PTM, in certain embodiments linked through a linker moiety, as otherwise described herein, wherein the ULM is coupled to the PTM and wherein the ULM recognizes a ubiquitin pathway protein and the PTM recognizes the target protein such that degradation of the target protein occurs when the target protein is placed in proximity to the ubiquitin ligase, thus resulting in degradation/inhibition of the effects of the target protein and the control of protein levels. The control of protein levels afforded by the present invention provides treatment of a disease state or condition, which is modulated through the target protein by lowering the level of that protein in the cells of a patient.

DETAILED DESCRIPTION OF THE INVENTION

DYRK1A is a member of the DYRK family containing 5 kinases (DYRK1A, DYRK1B, DYRK2, DYRK3 and DYRK4). DYRKs belong to the CMGC group of proline-directed kinases, which also includes cyclin-dependent kinases (CDKs), mitogen-activated protein kinases (MAPKs), glycogen synthase kinases (GSKs) and $CDCl_2$-like kinases (CLKs). While the signaling pathways of CDK and MAPK families have been extensively studied, much less is known on how DYRKs and CLKs are linked to other proteins and various physiological or pathological processes.

The DYRK1A gene is located on chromosome 21 (21q22.2), a region known as the Down-Syndrome Critical Region (DSCR) (see, e.g., Hämmerle et al., 2011 Development 138, 2543-2554). The under- or over-expression of the Dyrk1a gene in mammals or of its orthologous gene minibrain (mnb) in Drosophila causes severe retardation of central nervous system development and maturation. At the molecular level, DYRK1A phosphorylates the nuclear factor of activated T cells (NFAT), counteracting the effect of calcium signaling and maintaining inactive NFAT (see, e.g., Arron et al., 2006 Nature 411, 595-600). DYRK1A has been identified as a negative regulator of the cell cycle that promotes the switch to a quiescent state or differentiation (see, e.g., Chen et al., 2013 Mol. Cell 52, 87-100). In malignant cells, DYRK1A promotes survival via inhibition of pro-apoptotic proteins (see, e.g., Guo et al., 2010 J. Bio. Chem. 285, 13223-13232; Seifert et al., 2008 FEBS J. 275, 6268-6280).

Currently, treatment options for cognitive deficiencies associated with AD and DS are extremely limited and represent a major, extremely significant unmet therapeutic need. The DYRK1A inhibitors of the present invention provide a new avenue for pharmaceutical intervention of mental impairment associated with AD and other neurodegenerative diseases, and address a critical unmet medical need and significantly changing treatment paradigm for AD.

Experiments conducted during the course of developing embodiments for the present invention designed, synthesized and biologically evaluated compounds having a 6,5-heterocyclic structure (e.g., compounds having a imidazopyridine, imidazopyrimidine, imidazopyrazine, imidazopyridazine, imidazotriazine, benzoimidazole, benzotriazole, benzoisoxazole, purine, indazole, triazolotriazine, triazolopyridazine, triazolopyrimidine, triazolopyrazine, triazolotetrazine, triazolopyridine, pyrazolopyrazine, pyrazolopyrimidine, pyrazolopyridazine, pyrazolotriazine, pyrazolopyridine, isoxazolopyrazine, isoxazolopyrimidine, isoxazolopyrdiazine, isoxazolotriazine, or isoxalopyridine structure) as inhibitors of the dual specificity tyrosine phosphorylation regulated kinase-1A (DYRK1A) and their potential for use as therapeutics against AD and other disorders related to DYRK-1A activity (e.g., DS, other neuropathology, cancer (e.g., glioblastoma, prostate cancer)). Many of such compounds exhibit activity against DYRK1B and exhibit activity against other kinases implicated in a variety of disease states (e.g., Clk-1). The DYRK1B gene is not as ubiquitous as the DYRK1A gene and is found in the testis and muscle. DYRK1B plays roles in survival of certain cancer cells and myoblast differentiation.

Moreover, the DYRK1A inhibitors of the present invention can be used for treating other cellular pathways involved in mental impairment and neurodegenerative dementia. Specifically, the DYRK1A inhibitors of the present invention can be used for inhibiting DYRK1A activated PI3K/Akt signaling, a pathway largely involved in neuronal development, growth, and survival. The DYRK1A inhibitors of the present invention DYRK1A can be used for inhibiting DYRK1A stimulated ASK1/JNK1 activity, thereby inducing neuronal death and apoptosis. In addition, the DYRK1A inhibitors of the present invention DYRK1A can be used to inhibit DYRK1A phosphorylation of p53 during embryonic brain development, thereby preventing neuronal proliferation alteration. The DYRK1A inhibitors of the present invention can be used to inhibit DYRK1A phosphorylation of synaptic proteins Amph 1, Dynamin 1, and Synaptojanin, involved in the regulation of endocytosis, thereby retaining synaptic plasticity through preventing alteration of the number, size, and morphology of dendritic spines. The DYRK1A inhibitors of the present invention can be used to inhibit presenilin 1 (the catalytic sub-unit of γ-secretase). The DYRK1A inhibitors of the present invention can be used to inhibit DYRK2 activity. The DYRK1A inhibitors of the present invention can be used to inhibit DYRK1B activity. The DYRK1A inhibitors of the present invention can be used to inhibit CMGC/CLK kinase activity. The DYRK1A inhibitors of the present invention can be used to inhibit CLK2 activity. The DYRK1A inhibitors of the present invention can be used to inhibit CLK3 activity. The DYRK1A inhibitors of the present invention can be used to inhibit CLK4 activity.

As such, the present invention addresses the need for effective therapies for AD and DS by providing potent and selective DYRK1A inhibitors able to permeate the blood-brain barrier (BBB) and elicit on-mechanism therapeutic responses in AD animal models.

Accordingly, this invention relates to a new class of small-molecules having a 6,5-heterocyclic structure (e.g., compounds having a imidazopyridine, imidazopyrimidine, imidazopyrazine, imidazopyridazine, imidazotriazine, benzoimidazole, benzotriazole, benzoisoxazole, purine, indazole, triazolotriazine, triazolopyridazine, triazolopyrimidine, triazolopyrazine, triazolotetrazine, triazolopyridine, pyrazolopyrazine, pyrazolopyrimidine, pyrazolopyridazine, pyrazolotriazine, pyrazolopyridine, isoxazolopyrazine, isoxazolopyrimidine, isoxazolopyrdiazine, isoxazolotriazine, or isoxalopyridine structure) which function as inhibitors of DYRK1A protein, and their use as therapeutics for the treatment of Alzheimer's disease, Down syndrome, diabetes, glioblastoma, autoimmune diseases, inflammatory disorders (e.g., airway inflammation), and other diseases.

The $CDCl_2$-like kinase (CLK) family contains four isoforms which are important in regulating the function of the spliceosome complex (see, e.g., Fedorov et al, Chem Biol. 2011; 18(1):67-76). This complex, comprised of small nuclear RNAs (snRNA) and a large number of associated proteins, regulates the splicing of pre-mRNAs to give mature protein-encoding mRAs. CLK1 is known to regulate the activity of the spliceosome via phosphorylation of the constituent serine-arginine-rich (SR) proteins (see, e.g., Bullock et al, Structure. 2009; 17(3):352-62). By controlling the activity of the spliceosome in this way, many genes are able express more than one mRNA leading to diversity in the translated proteins. The alternative protein iso forms transcribed from the same gene will often have different activities and physiological functions. Deregulation of alternative splicing has been linked to cancer, where a number of cancer-related proteins are known to be alternatively spliced (see, e.g., Druillennec et al, J Nucleic Acids. 2012; 2012: 639062). An example of an alternatively spliced protein in cancer is Cyclin Dl, important for the progression of cancer cells through the cell cycle (see, e.g., Wang et al, Cancer Res. 2008; 68(14):5628-38).

Alternative splicing regulated by CLK1 has also been described to play a role in neurodegenerative diseases, including Alzheimer's and Parkinson's, via phosphorylation of the SR proteins of the spliceosome (see, e.g., Jain et al, Curr Drug Targets. 2014; 15(5):539-50). In the case of Alzheimer's, CLK1 is known to regulate the alternative splicing of the microtubule-associated protein TAU leading to an imbalance between TAU iso forms which is sufficient to cause neurodegeneration and dementia (see, e.g., Liu et al, Mol Neurodegener. 2008; 3:8).

In the treatment of both cancer and neurological disease, there is thus undoubtedly an urgent need for compounds which potently inhibit the DYRK1 and CLK1 kinases whilst not affecting other closely-related kinases. The compounds described herein address this need.

In a particular embodiment, compounds encompassed within the following formulas are provided:

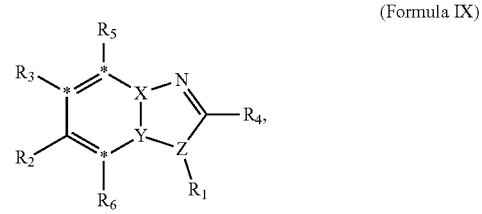

(Formula IX)

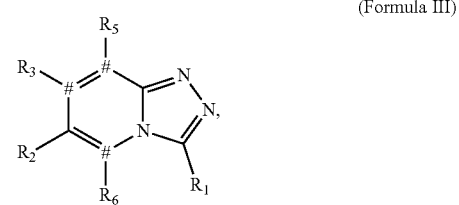

(Formula III)

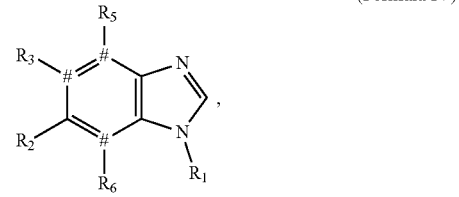

(Formula IV)

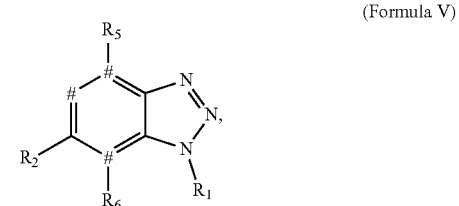

(Formula V)

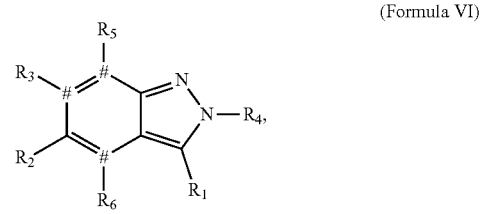

(Formula VI)

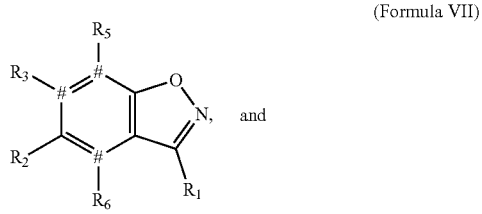

(Formula VII)

and

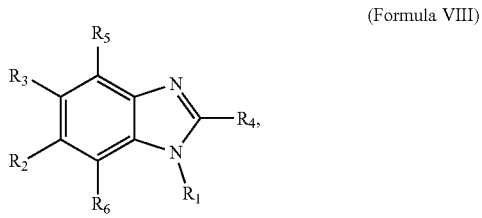

(Formula VIII)

(Formula X)

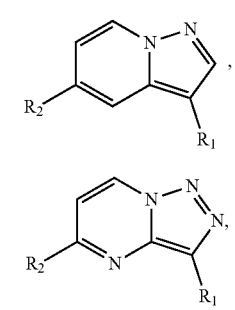
(Formula XI)

(Formula XII)

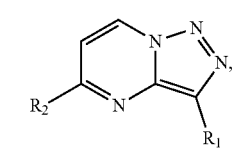
(Formula XIII)

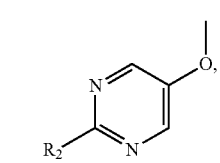
(Formula XIV)

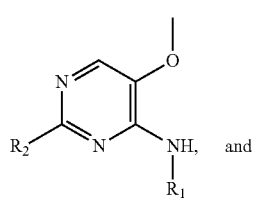
(Formula XV)

(Formula XVI)

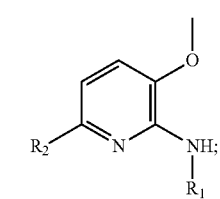
(Formula XVII)

including pharmaceutically acceptable salts, solvates, and/or prodrugs thereof, wherein R5 is present or absent, wherein R6 is present or absent.

Formula I is not limited to a particular chemical moiety for R1, R2, R3, R4, R5, R6, X, Y, Z, *, # if one or both are present. In some embodiments, the particular chemical moiety for R1, R2, R3, R4, R5, R6, X, Y, Z, *, # if one or both are present, independently include any chemical moiety that permits the resulting compound to inhibit DYRK1A activity. In some embodiments, the particular chemical moiety for R1, R2, R3, R4, R5, R6, X, Y, Z, *, # if one or both are present, independently include any chemical moiety that permits the resulting compound to inhibit one or more of: DYRK1A related PI3K/Akt signaling; DYRK1A related tau phosphorylation; DYRK1A related NFAT phosphorylation; DYRK1A related ASK1/JNK1 pathway activation; DYRK1A related p53 phosphorylation; DYRK1A related Amph 1 phosphorylation; DYRK1A related Dynamin 1 phosphorylation; DYRK1A related Synaptojanin phosphorylation; DYRK1A related presenilin 1 (the catalytic subunit of γ-secretase) activity; DYRK1A related amyloid precursor protein phosphorylation; DYRK1A related SIRT1 activation; DYRK2 activity; CMGC/CLK kinase activity; CLK2 activity; CLK3 activity; and CLK4 activity. In some embodiments, the particular chemical moiety for R1, R2, R3, R4, R5, R6, X, Y, Z, *, # if one or both are present, independently include any chemical moiety that permits the resulting compound to bind a DYRK1A protein at the Lys188 position (e.g., commonly known as the conserved lysine) (e.g., via the R2 moiety).

Such embodiments are not limited to a particular definition for the "*" substituents.

In some embodiments, the "*" substituents are selected from two carbons and one nitrogen or three carbons. For example, in some embodiments, the "*" substituents are two carbons and one nitrogen such that the resulting structure is one of the following formulas:

For example, in some embodiments, the "*" substituents are each carbon such that the resulting in the following formula:

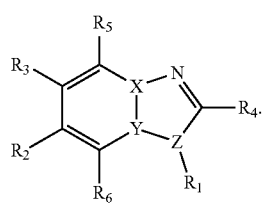

Such embodiments are not limited to a particular definition for the "X—Y—Z" substituents.

In some embodiments, X—Y—Z is

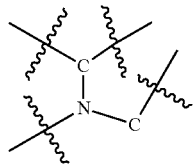 [SMILES: *CN(*)C(*)*]

resulting in the following formula:

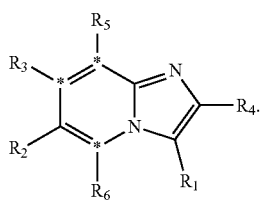

(Formula I)

In some embodiments, X—Y—Z is

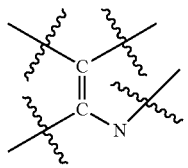 [SMILES: *NC(*)=C(*)*]

resulting in the following formula:

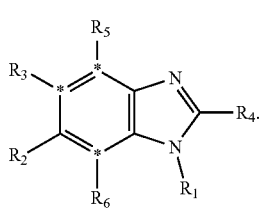

(Formula II)

In some embodiments, X—Y—Z is

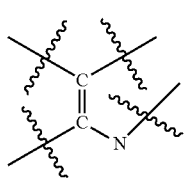 [SMILES: *NC(*)=C(*)*]

and the "*" substituents are two carbons and one nitrogen such that the resulting structure is one of the following formulas:

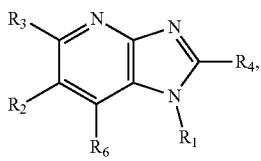

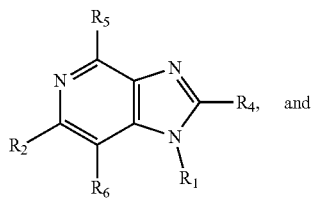

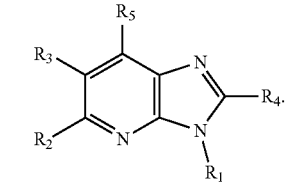

In some embodiments, X—Y—Z is

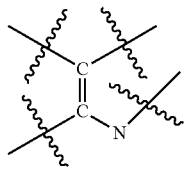 [SMILES: *NC(*)=C(*)*]

and the "*" substituents are three carbons such that the resulting structure is the following formula:

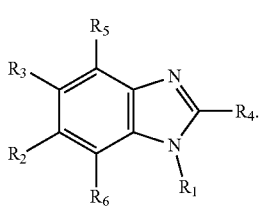

In some embodiments, X—Y—Z is

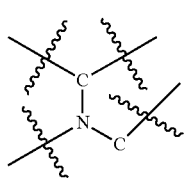 [SMILES: *CN(*)C(*)*]

and the "*" substituents are two carbons and one nitrogen such that the resulting structure is one of the following formulas:

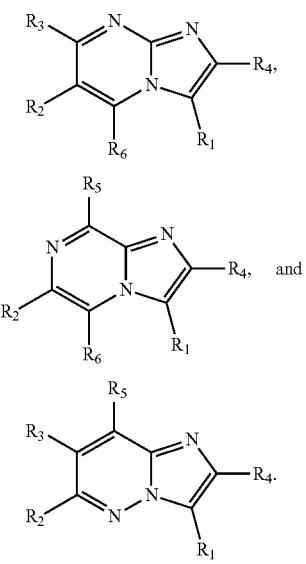

In some embodiments, X—Y—Z is

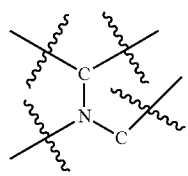 [SMILES: *CN(*)C(*)*]

and the "*" substituents are three carbons such that the resulting structure is the following formula:

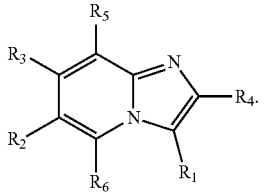

Such embodiments are not limited to a particular definition for the "#" substituents.

In some embodiments, the "#" substituents are selected from two nitrogens and one carbon, three carbons, three nitrogens, or one nitrogen and two carbons. For example, in some embodiments, the "#" substituents are two nitrogens and one carbon such that the resulting structure is represented by one of the following formulas:

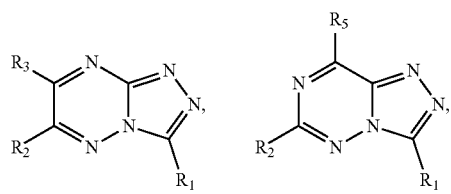

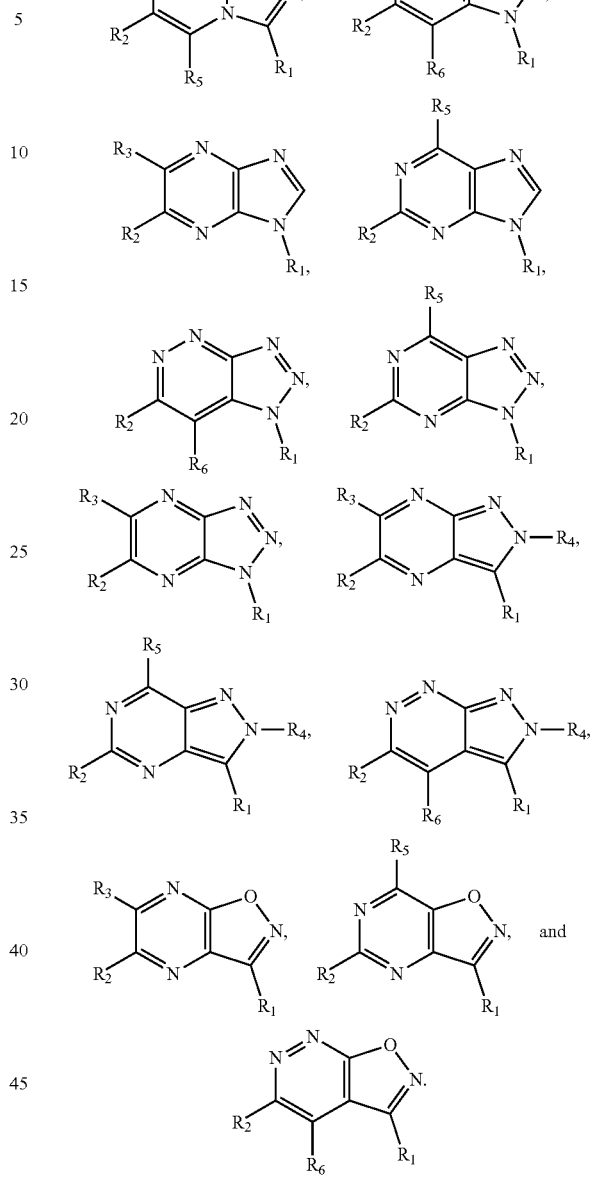

For example, in some embodiments, the "#" substituents are three nitrogens such that the resulting structure is represented by one of the following formulas:

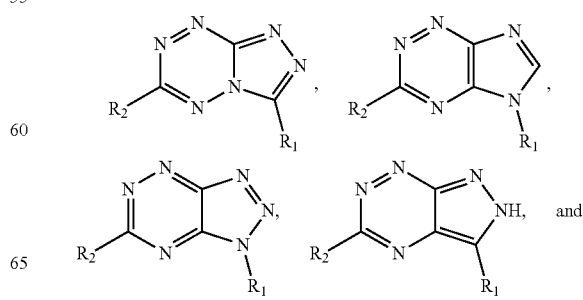

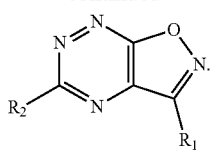

For example, in some embodiments, the "#" substituents are three carbons such that the resulting structure is represented by one of the following formulas:

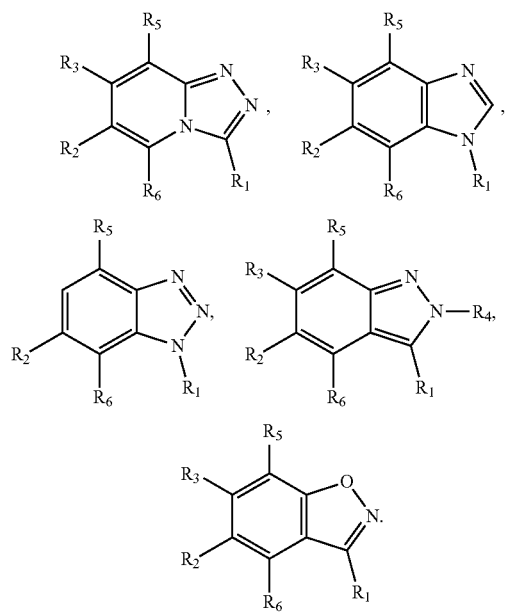

For example, in some embodiments, the "#" substituents are two carbons and one nitrogen such that the resulting structure is represented by one of the following formulas:

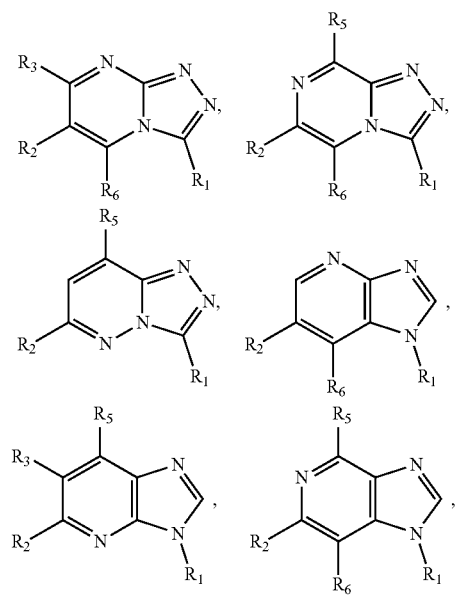

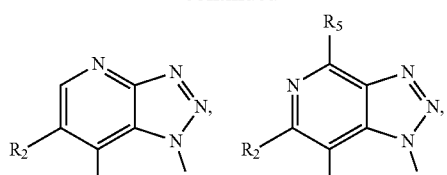

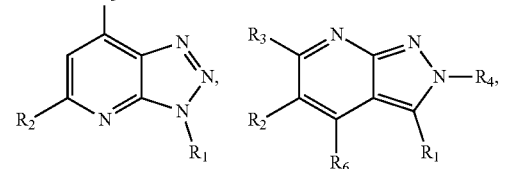

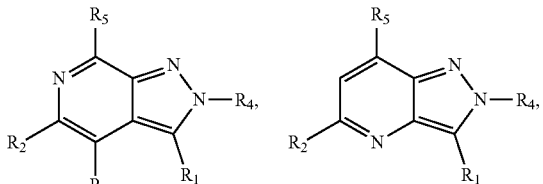

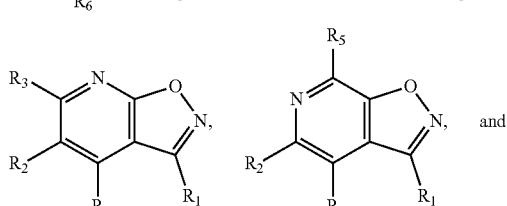

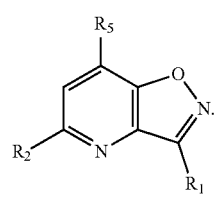

In some embodiments, R1 is selected from hydrogen,

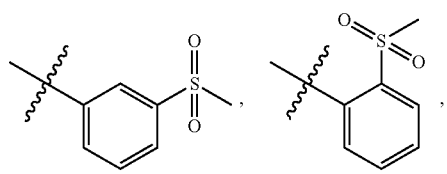

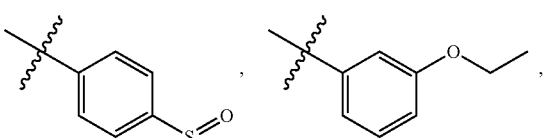

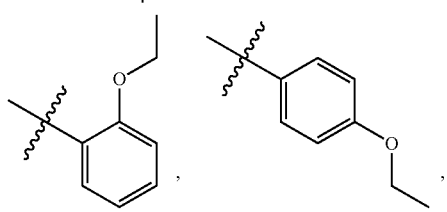

135
-continued
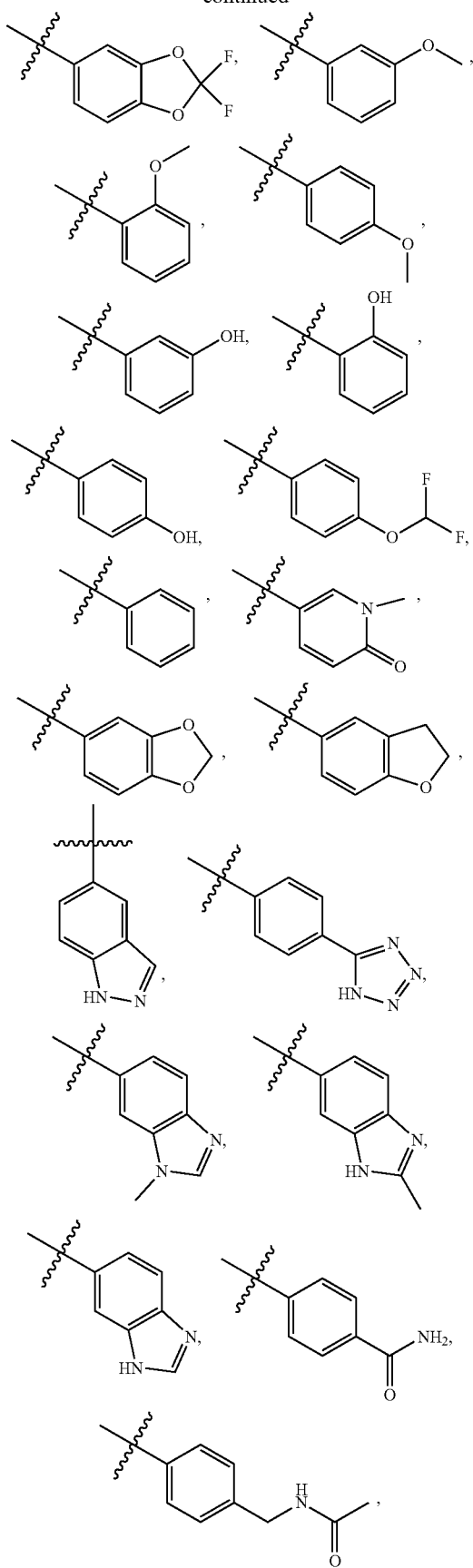
136
-continued
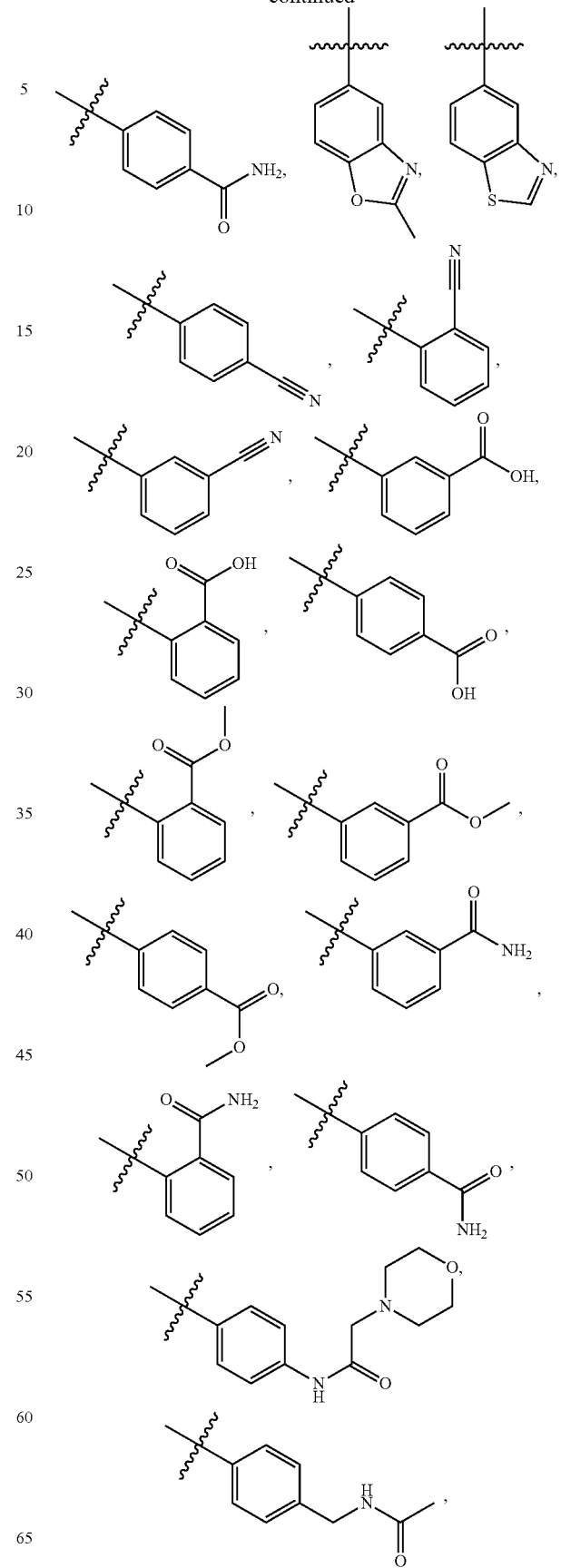

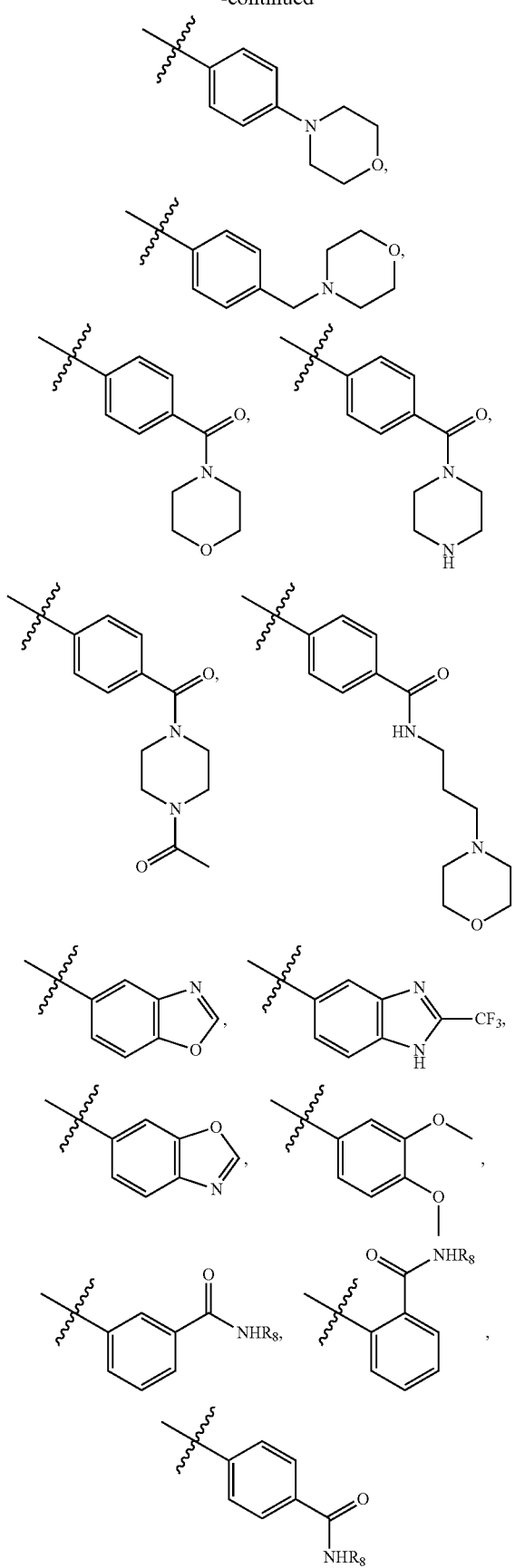
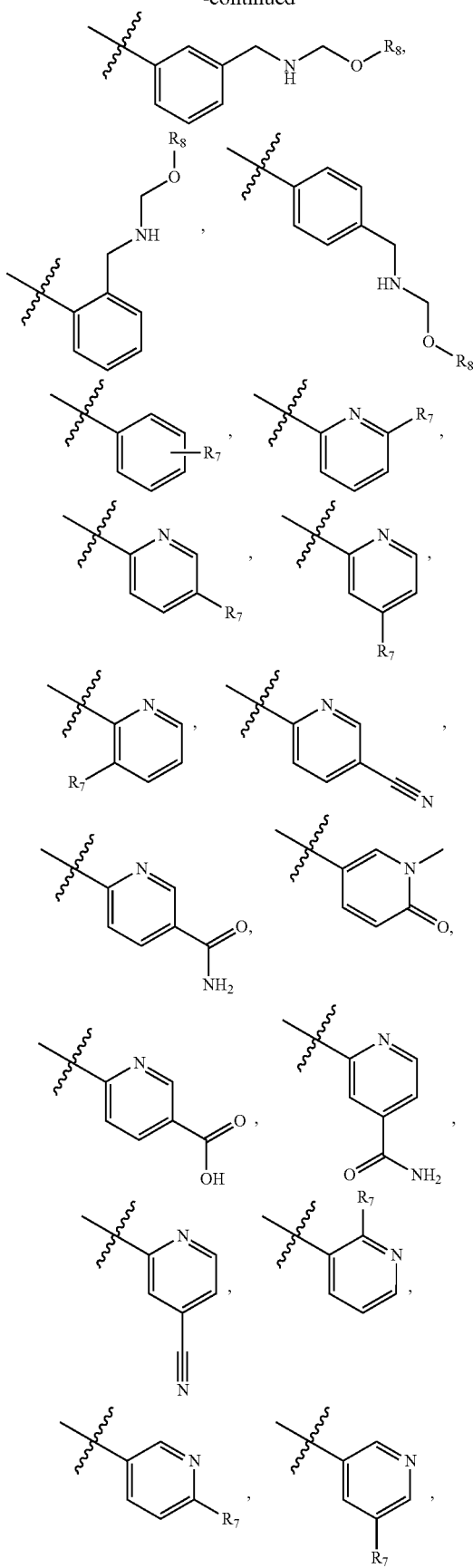

-continued
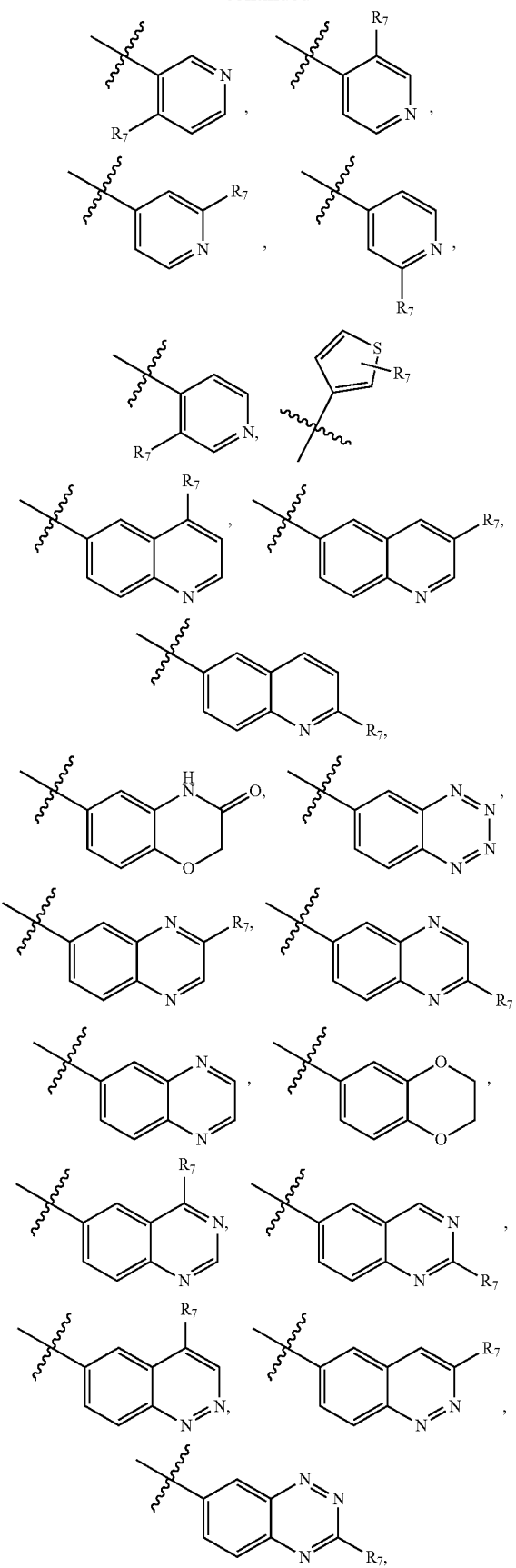
-continued
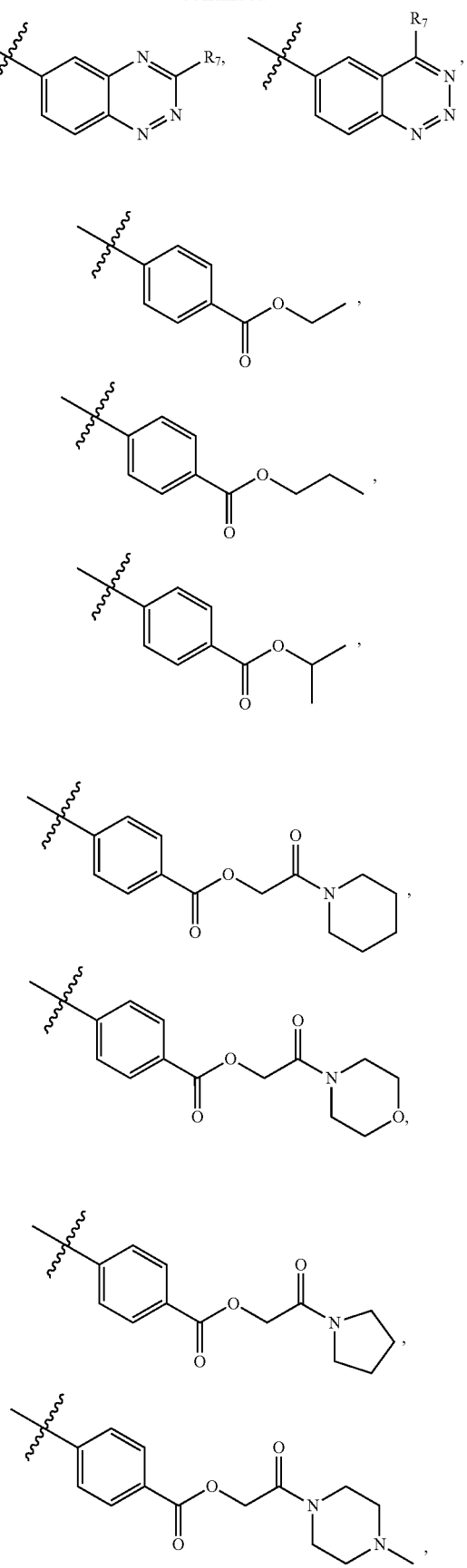

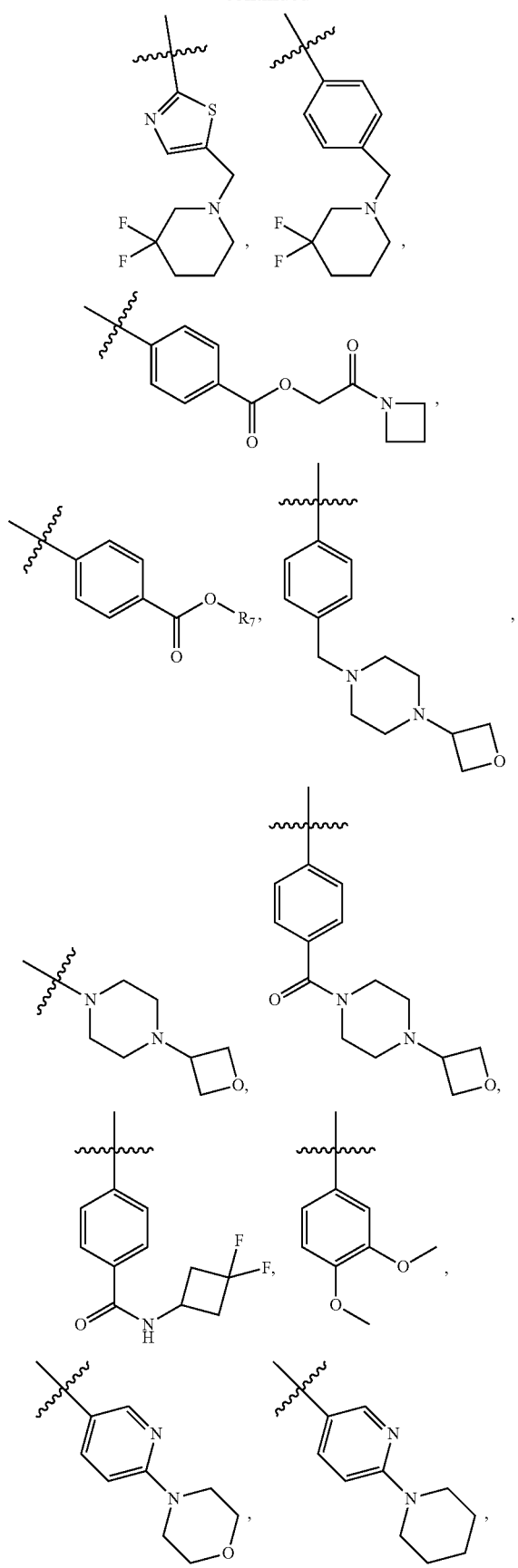
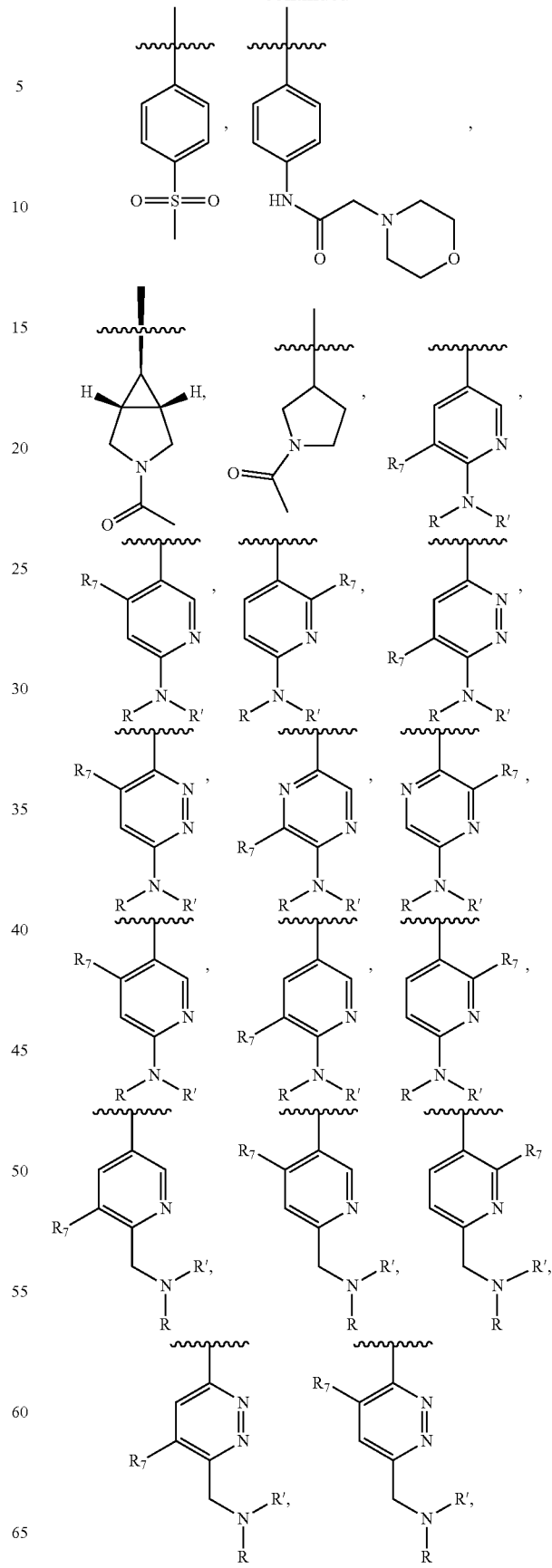

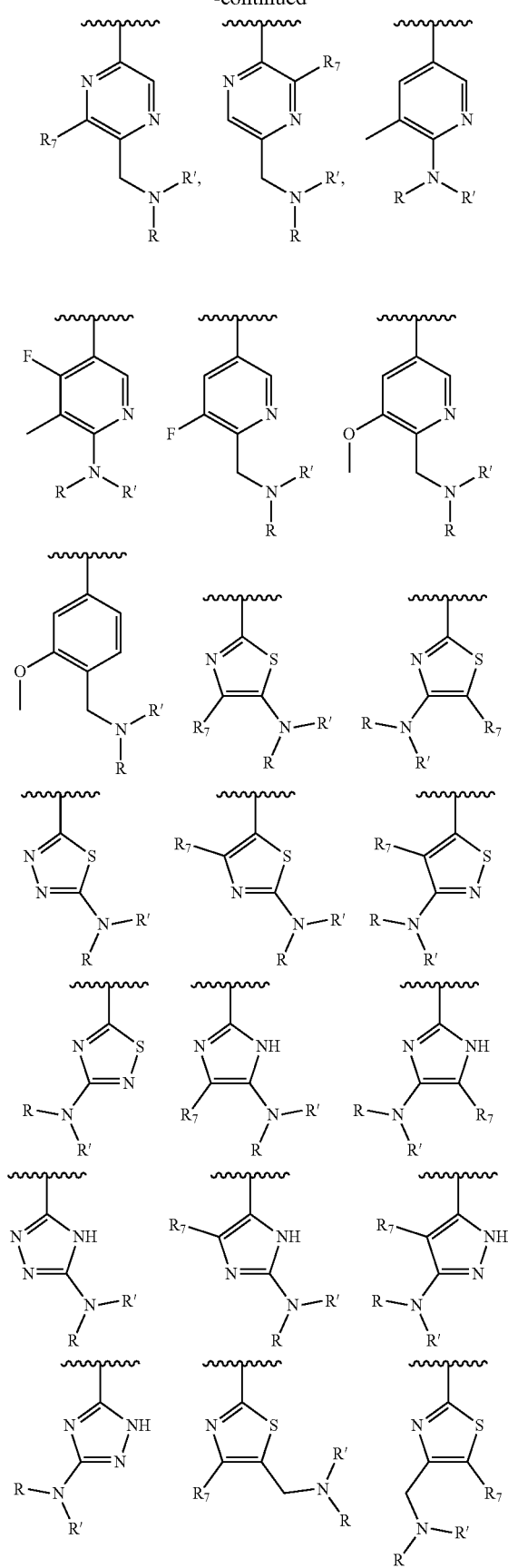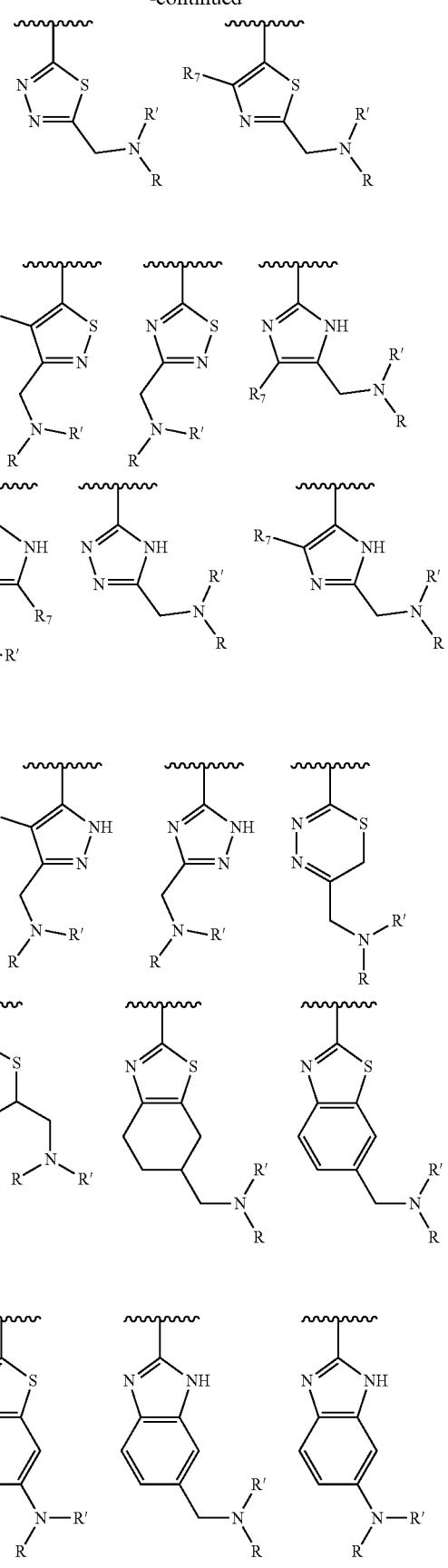

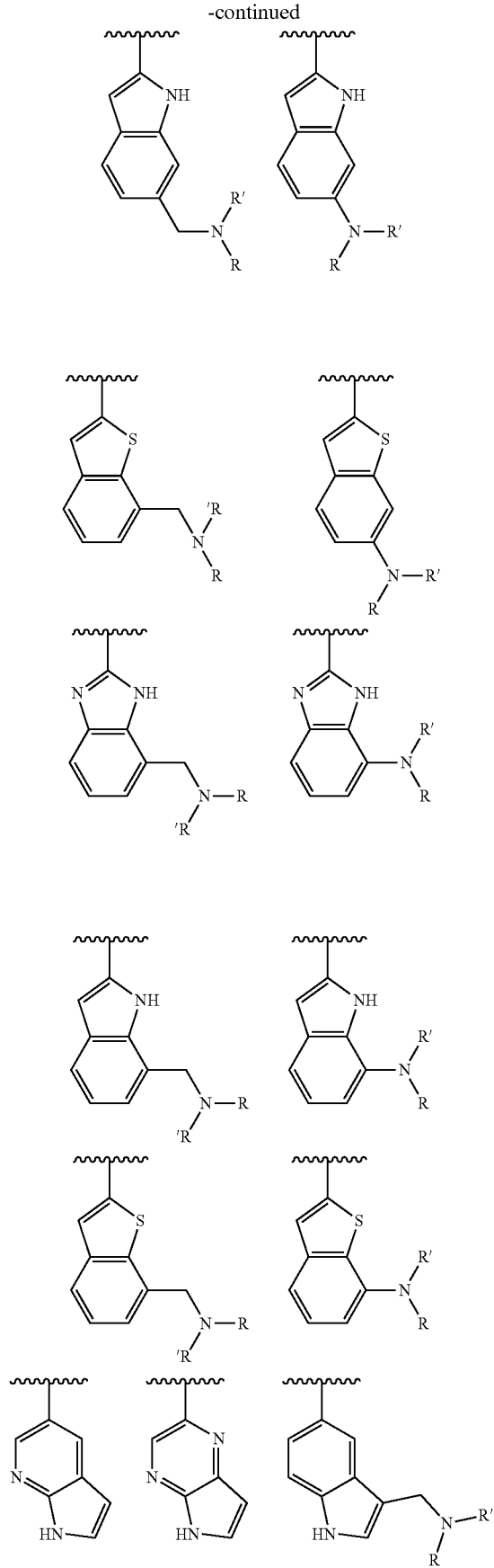
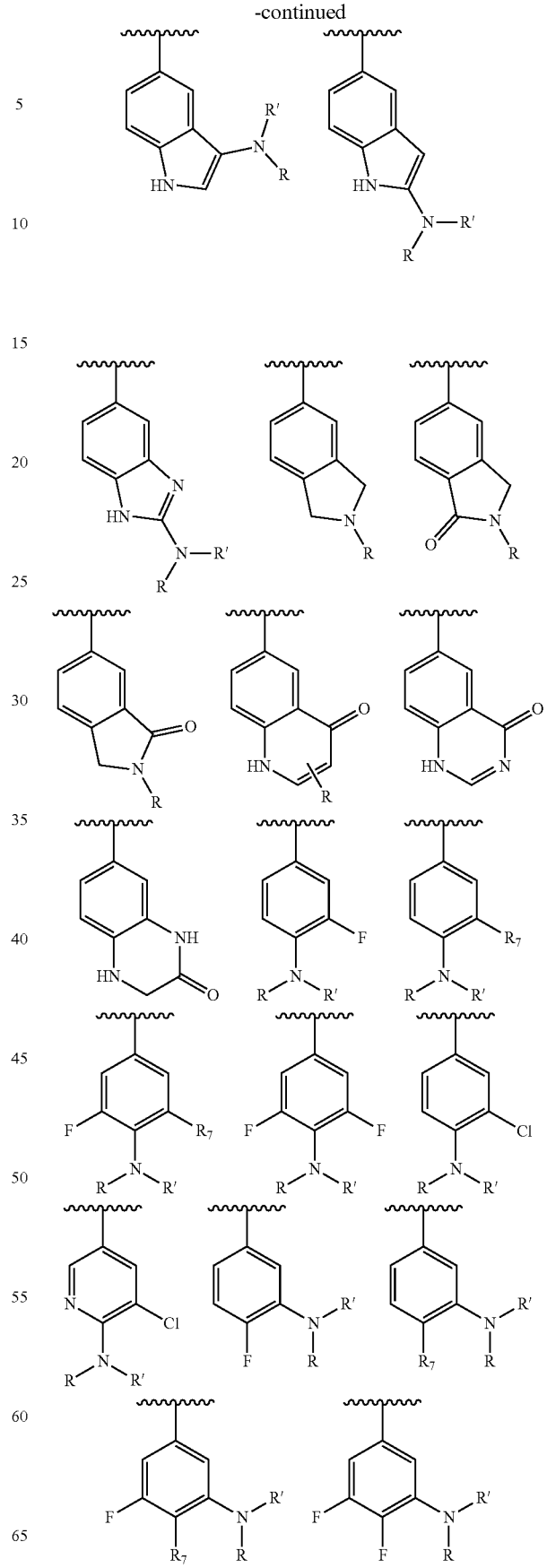

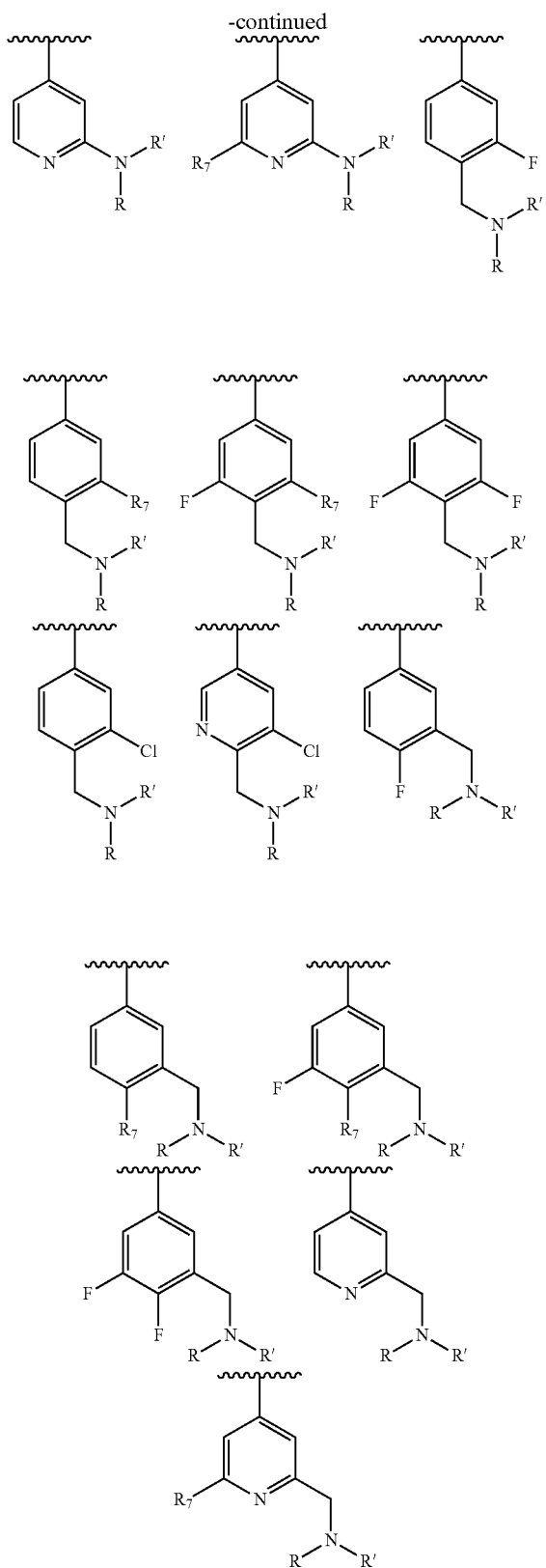

wherein R and R' are independently secondary or tertiary amine moiety consisting of a heterocycloalkyl group that is bioisosteric to secondary amines (e.g., morpholine, piperidine, piperazine).

In some embodiments, R1 is an aryl or heteroaryl ring.

In some embodiments, R7 is

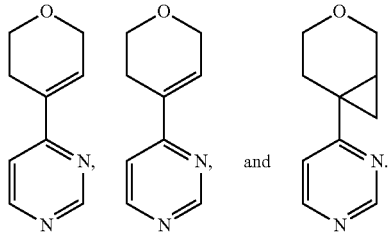

In some embodiments, R7 is an acidic bio-isostere. For example, in some embodiments R7 is selected from

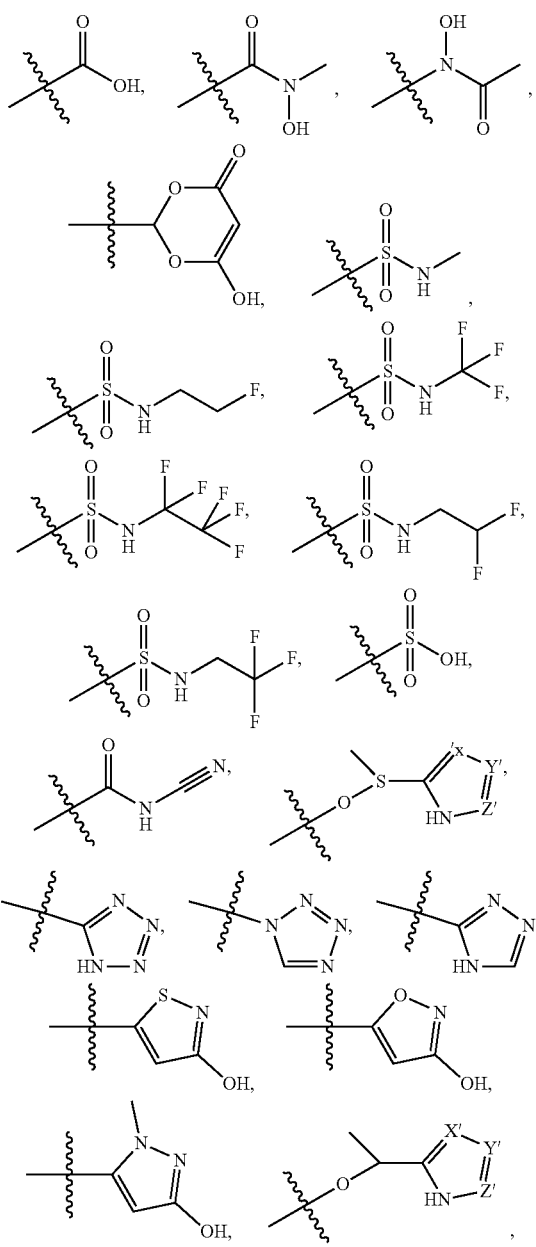

-continued

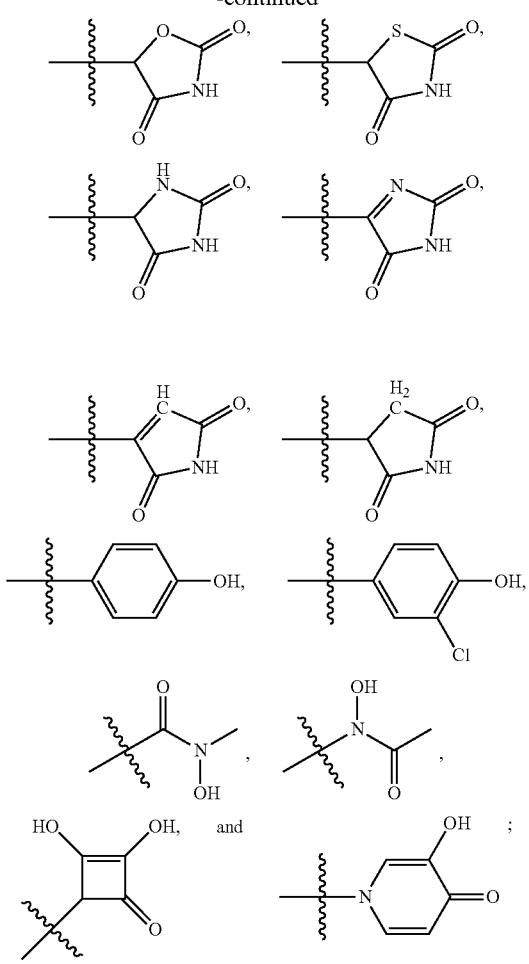

wherein X', Y', Z' are independently N, C or CO.

In some embodiments, R, R', and R7 are independently selected from hydrogen, halogen (e.g., fluorine, bromine, chlorine, iodine), di-halogen (di-fluorine, di-bromine, di-chlorine, di-iodine), CF3, OCH3, CHF2H, OCF3, methyl, di-methyl, alkoxy, alkylsulfonyl, cyano, carboxy, ester, amido, substituted amido, sulfonamide, substituted sulfonamide, methylenedioxy, heterocyclyl alkyl, heterocyclyl, heterocyclyl alkyl amido, a lipophilic moiety comprising ether functionality, methyl, ethyl, $(CH_2)_3$,

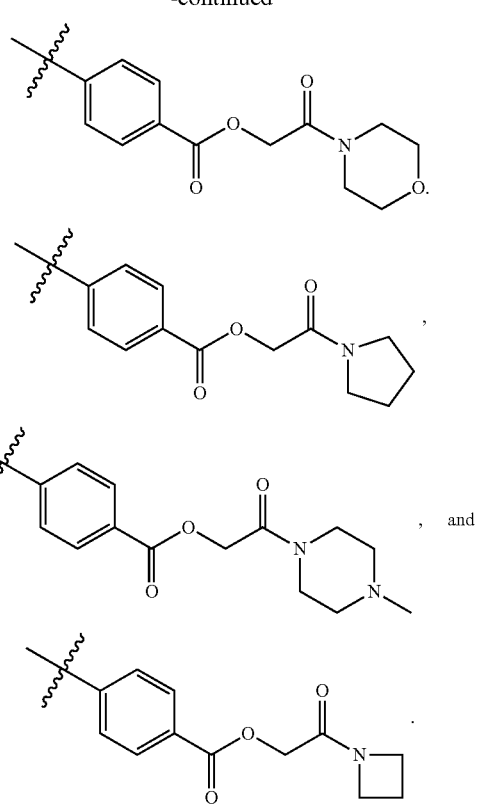

-continued

In some embodiments, R8 is selected from hydrogen, C1-C4 alkyl, heterocyclyl alkyl, heteroaryl alkyl, aryl alkyl, aryl, heterocyclyl, and heteroaryl.

In some embodiments, each of R2 and R3 is independently selected from hydrogen, halogen (e.g., fluorine), aryl, substituted aryl, heteroaryl, substituted heteroaryl,

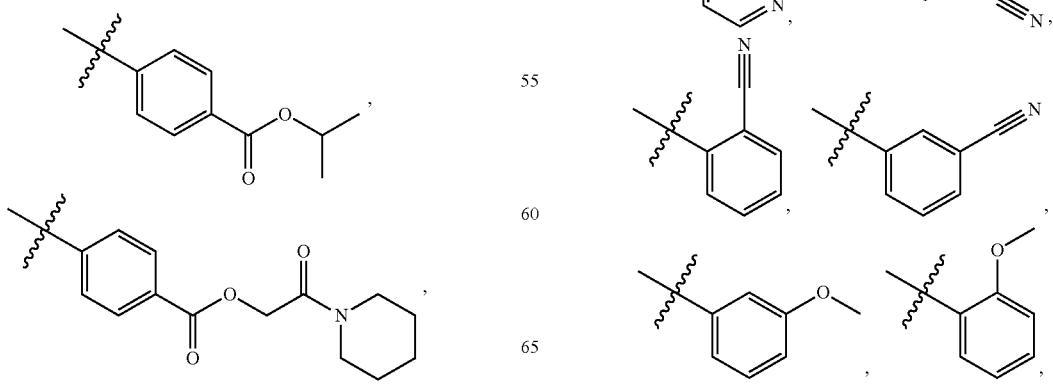

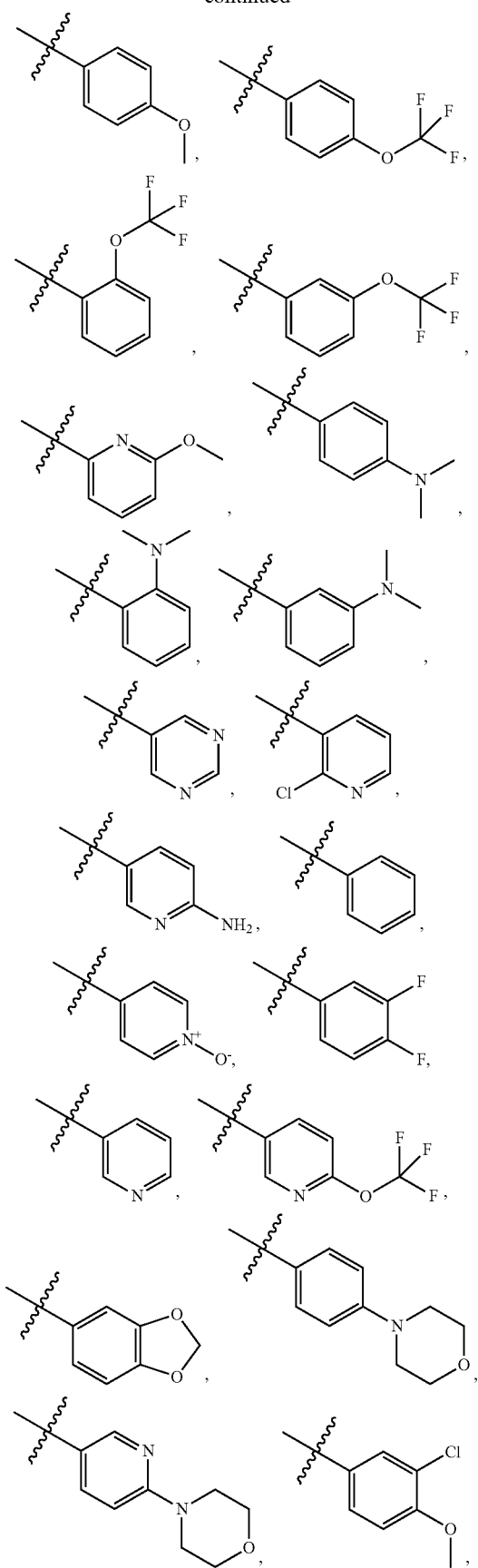
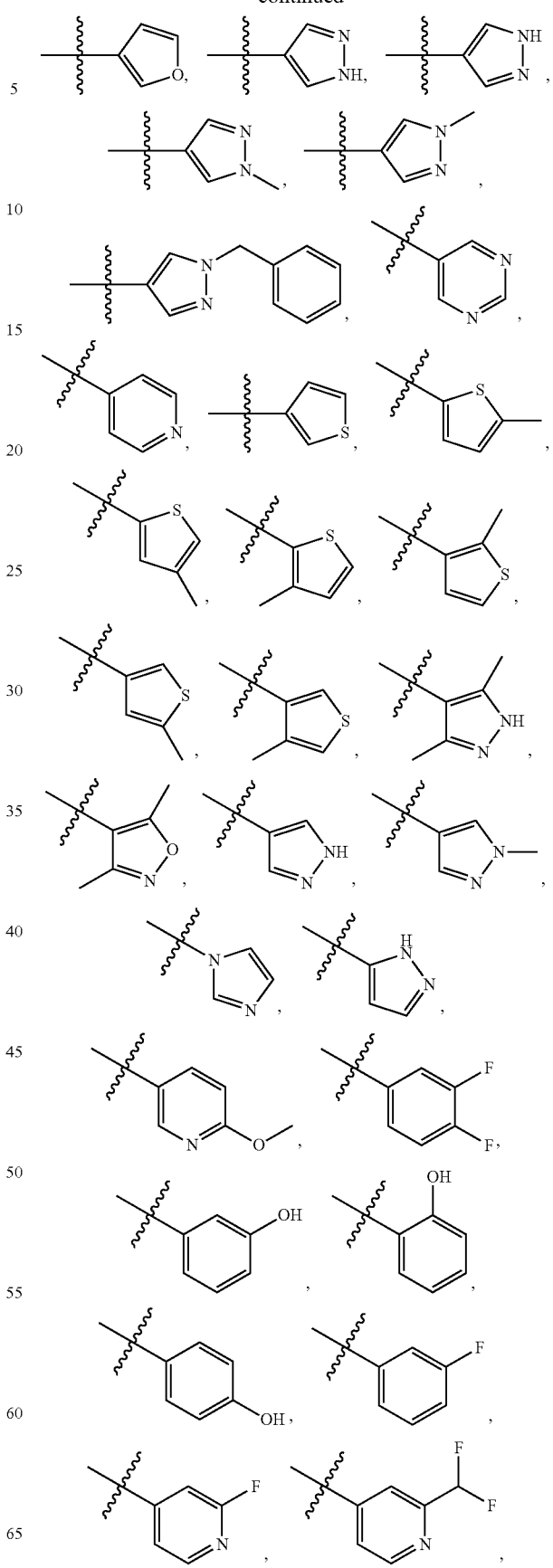

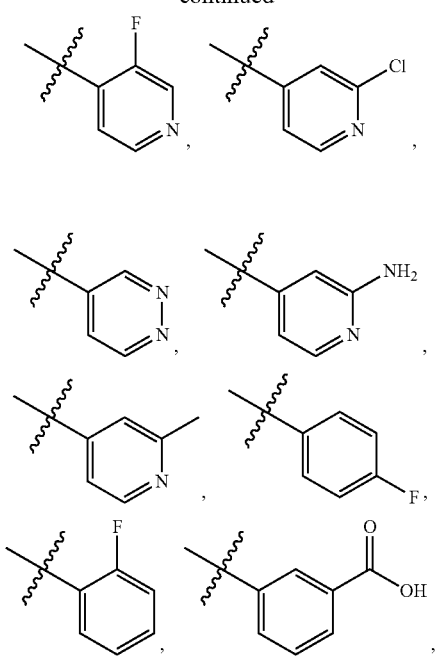
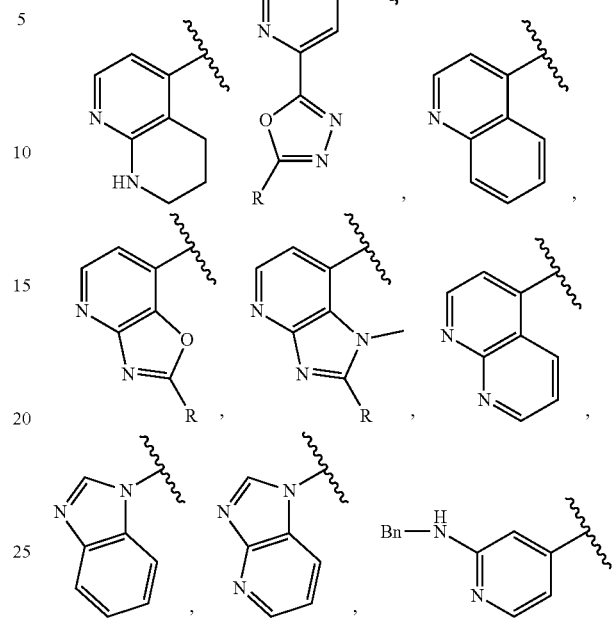
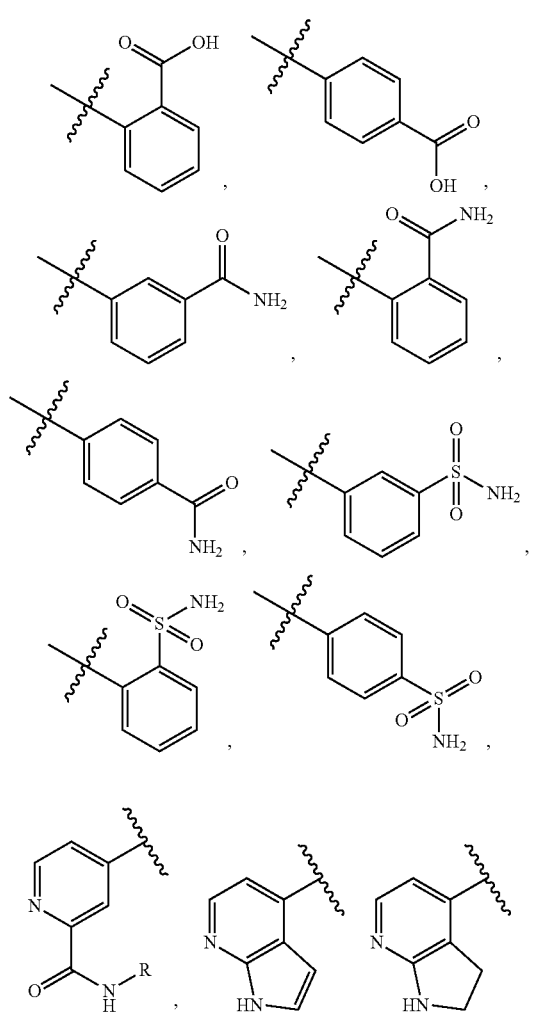
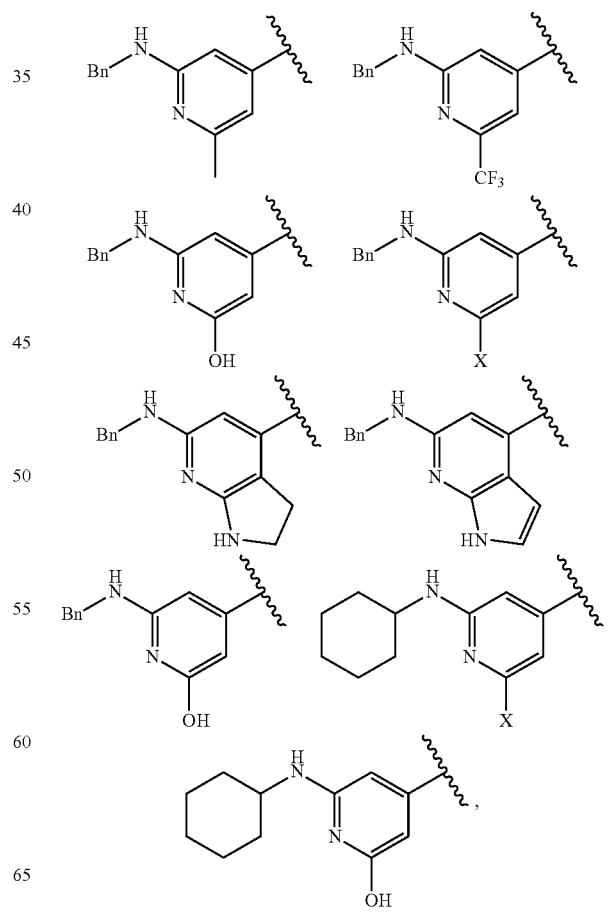
wherein Bn is benzyl or heterobenzyl, -continued

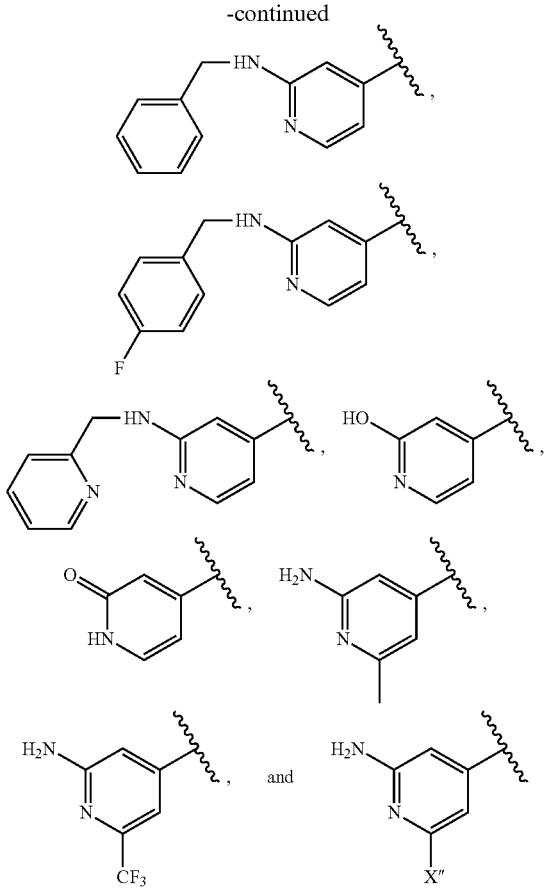

(wherein X″ is selected from alkyl, haloalkyl, amino, alkylamino, hydroxy, fluoro, chloro, bromo, cyano groups).

In some embodiments, R4 is selected from hydrogen, $CH_3$, $NH_2$, CN,

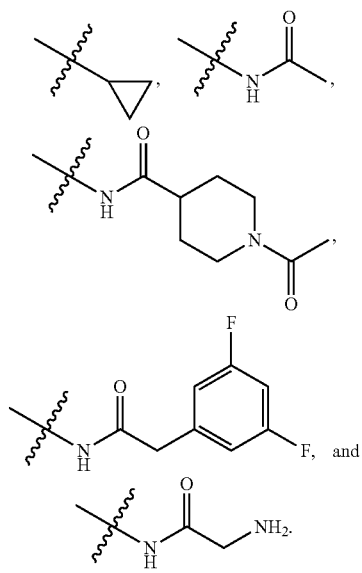

In some embodiments, R5 is present and is selected from hydrogen, halogen (e.g., fluorine), methyl, or methoxy.

In some embodiments, R6 is present and is selected from hydrogen, halogen (e.g., fluorine), methyl, or methoxy.

In some embodiments, the compound is one or more of the compounds recited in Table 1.

The invention further provides processes for preparing any of the compounds of the present invention.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, Alzheimer's disease, Down syndrome, Huntington's disease, Parkinson's disease, autoimmune diseases, cancer (e.g., glioblastoma, prostate cancer), inflammatory disorders (e.g., airway inflammation), any neurodegenerative disorder related to DYRK1A activity, and any type of cancer related to DYRK1A and/or DYRK1B activity.

Some embodiments of the present invention provide methods for administering an effective amount of a compound of the invention and at least one additional therapeutic agent (including, but not limited to, any agent useful in treating Alzheimer's disease, Down syndrome, Huntington's disease, Parkinson's disease, autoimmune diseases, inflammatory disorders (e.g., airway inflammation), any neurodegenerative disorder related to DYRK1A activity, and any type of cancer characterized related to DYRK1A activity).

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than C12). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

The following abbreviations are relevant for the following examples:
1. TEA=triethylamine
2. DMF=Dimethylformamide
3. Fe—Iron
4. NH4Cl—ammonium chloride
5. Pd(PPh3)4—Tetrakis(triphenylphosphine)palladium(0)
6. Ac2O—Acetic anhydride
7. AcOH—Acetic Acid
8. NBS—N-Bromosuiccinimide
9. TBD 1,5,7-Triazabicyclo[4.4.0]dec-5-ene or TBD
10. THF—tetrahydrofuran
11. DFMS Zinc difluoromethanesulfinate
12. TBHP—tert butyl hydrogen peroxide
13. TFA—trifluoroacetic acid
14. DCM—dichloromethane
15. EtOAc—ethyl acetate
16. KOtBu—potassium tert butoxide
17. DIBAL—
18. PPh3—triphenylphosphine
19. NaBH(OAc)3—Sodium triacetoxyborohydride
20. NCS—N-Bromosuiccinimide
21. XPhos 2-Dicyclohexylphosphino-2',4',6'-triisopropylbiphenyl
22. Pd(OAc)2 Palladium(II) acetate
23. Cs2CO3 cesium carbonate
24. RuPhos 2-Dicyclohexylphosphino-2',6'-diisopropoxybiphenyl
25. Pd2(dba)3 Tris(dibenzylideneacetone)dipalladium(II).
26. K3PO4 potassium phosphate tribasic
27. t-BuOH tert-butanol
28. Cu2O—Copper(I) oxide.
29. NMP—N-Methyl-2-pyrrolidone
30. Boc2O—Di-tert-butyl dicarbonate
31. PdCl2(dppf)—[1,1'-Bis(diphenylphosphino)ferrocene]dichloropalladium(II).
32. BrettPhos—2-(Dicyclohexylphosphino)3,6-dimethoxy-2',4',6'-triisopropyl-1,1'-biphenyl
33. [PdCl(allyl)]2—Allylpalladium(II) chloride dimer
34. SPhos—2-Dicyclohexylphosphino-2',6'-dimethoxybiphenyl]
35. P(Cy)3—Tricyclohexylphosphine;
36. DMAP—4-Dimethylaminopyridine
37. DIPEA—N,N-Diisopropylethylamine,
38. KOtBu—potassium t-butoxide
39. NaOtBu—sodium t-butoxide
40. IPA—Isopropanol
41. Na2S2O5—Sodium metabisulfite
42. mCPBA—meta-chloroperbenzoic acid
43. NH4OH—ammonium hydroxide
44. EtOH—absolute ethanol
45. n-BuOH—n-butanol
46. MeOH—methanol
47. BOC or Boc—tert-butyloxycarbonyl protecting group
48. Na2SO4—sodium sulfate
49. K2CO3—potassium carbonate
50. KOAc—potassium acetate
51. HCl—hydrochloric acid
52. H2O—water
53. DMSO—Dimethyl sulfoxide
54. CDCL3—deuterated chloroform Example I Affinity of compounds of the present invention with DYRK1A was tested and the following results obtained (DYRK1A Affinity Key (KD): +++=0.5–100 nM, ++=101 nM–500 nM, +=501 nM–10 uM) (see, Table 1).

Scheme 1

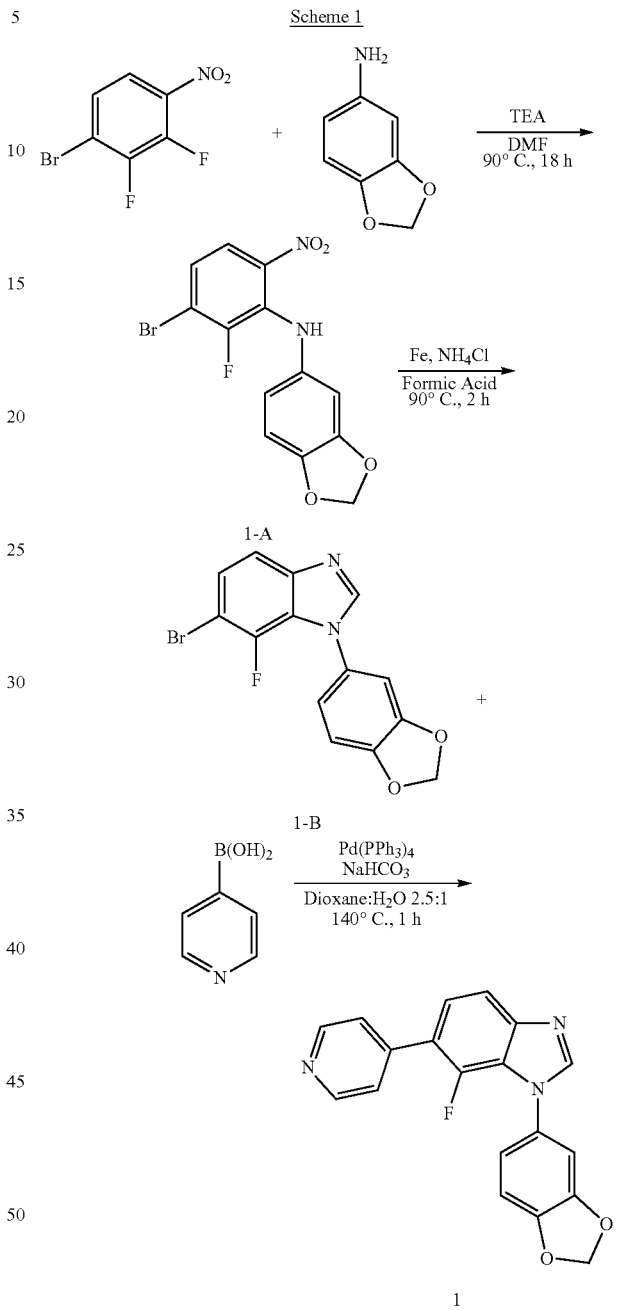

Scheme 1, Step 1

A 20 mL Biotage© microwave vial loaded with 1-bromo-2,3-difluoro-4-nitrobenzene (1.19 g, 5.0 mmol), benzo[d][1,3]dioxol-5-amine (686 mg, 5.0 mmol), DMF (7 mL) and triethylamine (1.394 mL, 10 mmol), was capped, purged with argon, then heated to 90° C. for 18 h in an oil bath. The reaction was cooled, poured into a solution of H2O and the precipitated product was filtered, washed with H2O and hexanes, affording N-(3-bromo-2-fluoro-6-nitrophenyl) benzo[d][1,3]dioxol-5-amine (1-A) as a red solid (1.74 g, 4.65 mmol, 93% yield).

$^1$H NMR (CDCl$_3$) δ: 8.93 (bs, 1H), 7.91 (dd, J=9.3, 1.9 Hz, 1H), 7.07 (dd, J=9.3, 6.0 Hz, 1H), 6.77 (d, J=8.2 Hz, 1H), 6.63 (t, J=2.2 Hz, 1H), 6.60-6.56 (m, 1H), 6.00 (s, 2H).

Scheme 1, Step 2

In a 20 mL Biotage© microwave vial, stir bar, N-(3-bromo-2-fluoro-6-nitrophenyl)benzo[d][1,3]dioxol-5-amine 1-A (426 mg, 1.2 mmol), iron (670 mg, 12.0 mmol), and ammonium chloride (642 mg, 12.0 mmol) were added. The vial was sealed, degassed with Ar for 15 min, injected with IPA (6 mL) and (98%) Formic Acid (7.8 mL). The mixture was heated for 2 h at 90° C. in an oil bath. Upon cooling, the mixture was diluted with EtOAc, solids filtered through celite, and concentrated. The crude was concentrated/dry-loaded onto silica with DCM and purified on a 12 g silica column (DCM/MeOH, 0-4%), affording 1-(benzo[d][1,3]dioxol-5-yl)-6-bromo-7-fluoro-1H-benzo[d]imidazole (1-B) as a gray solid (227 mg, 0.677 mmol, 56% yield, 4% MeOH in DCM). $^1$H NMR (CDCl$_3$) δ: 10.17 (s, 1H), 8.46 (d, J=8.6 Hz, 1H), 7.33 (d, J=2.2 Hz, 1H), 6.95 (ddd, J=8.3, 2.2, 0.5 Hz, 1H), 6.84 (d, J=8.3 Hz, 1H), 6.79 (d, J=8.6 Hz, 1H), 6.04 (s, 2H).

Scheme 1, Step 3

A 2-5 mL Biotage© microwave vial loaded with 1-(benzo[d][1,3]dioxol-5-yl)-6-bromo-7-fluoro-1H-benzo[d]imidazole 1-B (140 mg, 0.417 mmol), pyridin-4-ylboronic acid (61.5 mg, 0.5 mmol), Pd(PPh$_3$)$_4$ (33.7 mg, 0.029 mmol), and NaHCO$_3$ (140 mg, 1.677 mmol), was capped, purged with argon, then injected with degassed dioxane:H$_2$O (2 mL:1 mL, 2.5:1 v/v), and heated to 140° for 1 h in a Biotage Microwave Reactor. The reaction was cooled, diluted with DCM, filtered through celite, concentrated, dryloaded onto silica gel and purified on a 12 g silica gel column (DCM/MeOH, 0-5%), affording 1-(benzo[d][1,3]dioxol-5-yl)-7-fluoro-6-(pyridin-4-yl)-1H-benzo[d]imidazole 1 as a white solid (127 mg, 0.381 mmol, 91% yield, 5% MeOH in DCM). $^1$H NMR (CDCl$_3$) δ: 8.69 (d, J=6.2 Hz, 2H), 8.02 (s, 1H), 7.76 (d, J=8.4 Hz, 1H), 7.54-7.50 (m, 2H), 7.46-7.37 (m, 1H), 7.04-6.71 (m, 3H), 6.12 (s, 2H)

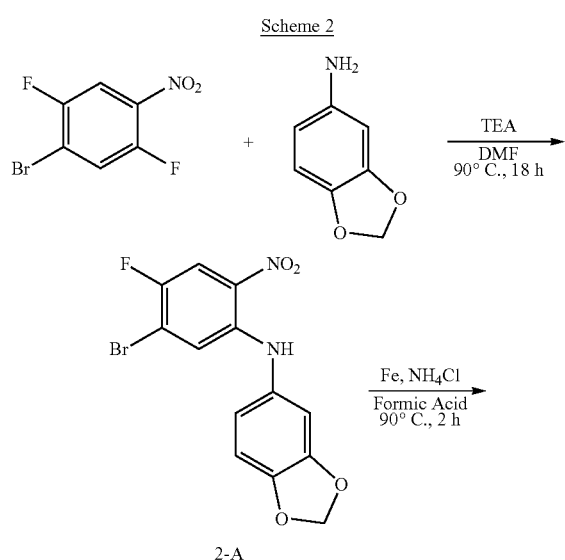

Scheme 2

2-A

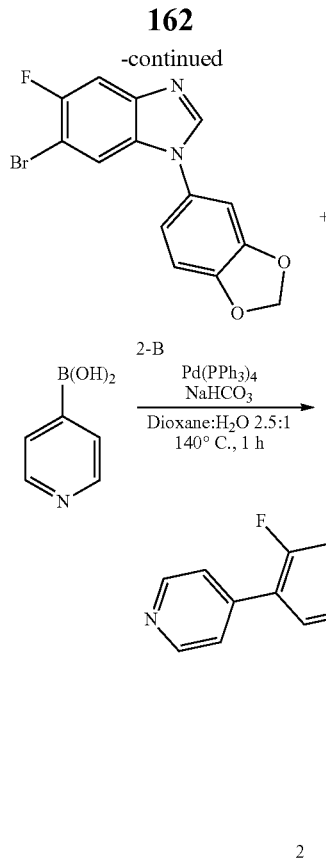

2-B

Scheme 2, Step 1

A 20 mL Biotage© microwave vial loaded with 1-bromo-2,5-difluoro-4-nitrobenzene (714 mg, 3.0 mmol), benzo[d][1,3]dioxol-5-amine (0.411 mg, 3.0 mmol), DMF (7 mL) and triethylamine (0.836 mL, 6 mmol), was capped, purged with argon, then heated to 90° C. for 18 h in an oil bath. The reaction was cooled, poured into a solution of H$_2$O and the precipitated product was filtered, washed with H$_2$O and hexanes, affording N-(5-bromo-4-fluoro-2-nitrophenyl)benzo[d][1,3]dioxol-5-amine 2-A as a red solid (1.05 g, 2.87 mmol, 96% yield).

$^1$H NMR (CDCl$_3$) δ: 9.21 (s, 1H), 7.97 (dd, J=8.6, 0.4 Hz, 1H), 7.24 (dd, J=6.0, 0.4 Hz, 1H), 6.89 (dd, J=7.6, 0.9 Hz, 1H), 6.76-6.72 (m, 2H), 6.07 (s, 2H).

Scheme 2, Step 2

In a 20 mL Biotage© microwave vial, stir bar, N-(5-bromo-4-fluoro-2-nitrophenyl)benzo[d][1,3]dioxol-5-amine 2-A (426 mg, 1.2 mmol), iron (670 mg, 12.0 mmol), and ammonium chloride (642 mg, 12.0 mmol) were added. The vial was sealed, degassed with Ar for 15 min, injected with IPA (6 mL) and Formic Acid (98%, 7.8 mL). The mixture was heated for 2 h at 90° C. in an oil bath. Upon cooling, the mixture was diluted with EtOAc, solids filtered through celite, and concentrated. The crude was concentrated/dry-loaded onto silica with DCM and purified on a 12 g silica column (DCM/MeOH, 0-4%), affording 1-(benzo[d][1,3]dioxol-5-yl)-6-bromo-5-fluoro-1H-benzo[d]imidazole 2-B as a light gray semi-solid (240 mg, 0.716 mmol, 60% yield, 4% MeOH in DCM).

$^1$H NMR (CDCl$_3$) δ: 8.06 (s, 1H), 7.68-7.58 (m, 2H), 7.04-6.91 (m, 3H), 6.14 (s, 2H).

Scheme 2, Step 3

A 2-5 mL Biotage© microwave vial loaded with halide 1-(benzo[d][1,3]dioxol-5-yl)-6-bromo-5-fluoro-1H-benzo

[d]imidazole 2-B (140 mg, 0.417 mmol), pyridin-4-ylboronic acid (61.5 mg, 0.5 mmol), Pd(PPh$_3$)$_4$ (33.7 mg, 0.029 mmol), and NaHCO$_3$ (140 mg, 1.667 mmol), was capped, purged with argon, then injected with degassed dioxane:H$_2$O (2 mL:1 mL, 2.5:1 v/v), and heated to 140° for 1 h in a Biotage Microwave Reactor. The reaction was cooled, diluted with DCM, filtered through celite, concentrated, dryloaded onto silica gel and purified on a 12 g silica gel column (DCM/MeOH, 0-5%), affording 1-(benzo[d][1,3]dioxol-5-yl)-5-fluoro-6-(pyridin-4-yl)-1H-benzo[d]imidazole 2 as a opaque solid (118 mg, 0.354 mmol, 85% yield, 5% MeOH in DCM). $^1$H NMR (CDCl$_3$) δ: 8.69 (d, J=6.2 Hz, 2H), 8.13 (s, 1H), 7.68 (d, J=10.9 Hz, 1H), 7.58-7.44 (m, 3H), 7.07-6.92 (m, 3H), 6.14 (s, 2H)

Scheme 3

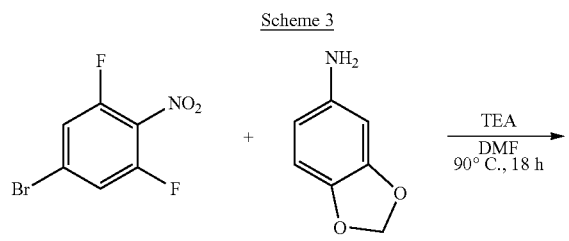

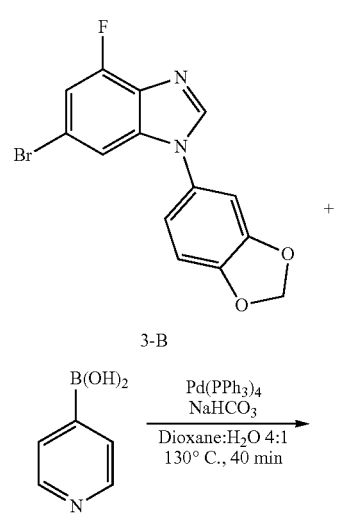

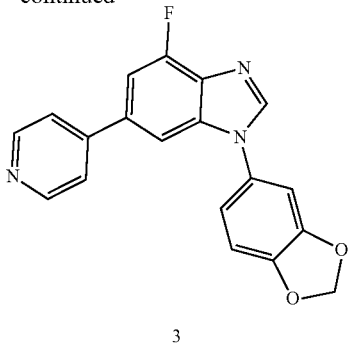

3

Scheme 3, Step 1

A 20 mL Biotage© microwave vial loaded with 5-bromo-1,3-difluoro-2-nitrobenzene (1.19 g, 5.0 mmol), benzo[d][1,3]dioxol-5-amine (0.686 g, 5.0 mmol), DMF (10 mL) and triethylamine (1.394 mL, 10.0 mmol), was capped, purged with argon, then heated to 90° C. for 18 h in an oil bath. The reaction was cooled, poured into a solution of H$_2$O and the precipitated product was filtered, washed with H$_2$O and hexanes, affording N-(5-bromo-3-fluoro-2-nitrophenyl)benzo[d][1,3]dioxol-5-amine 3-A as a red solid (1.6 g, 4.51 mmol, 90% yield).

$^1$H NMR (DMSO) δ: 8.77 (s, 1H), 7.08 (dd, J=10.5, 2.0 Hz, 1H), 6.95 (d, J=8.2 Hz, 1H), 6.88 (d, J=2.1 Hz, 1H), 6.83 (t, J=1.8 Hz, 1H), 6.74 (dd, J=8.2, 2.1 Hz, 1H), 6.07 (s, 2H).

Scheme 3, Step 2

In a 20 mL Biotage© microwave vial, stir bar, N-(5-bromo-4-fluoro-2-nitrophenyl)benzo[d][1,3]dioxol-5-amine 3-A (426 mg, 1.2 mmol), iron (670 mg, 12.0 mmol), and ammonium chloride (642 mg, 12.0 mmol) were added. The vial was sealed, degassed with Ar for 15 min, injected with IPA (6 mL) and Formic Acid (98%, 7.8 mL). The mixture was heated for 2 h at 90° C. in an oil bath. Upon cooling, the mixture was diluted with EtOAc, solids filtered through celite, and concentrated. The crude was concentrated/dryloaded onto silica with DCM and purified on a 12 g silica column (DCM/MeOH, 0-5%), affording 1-(benzo[d][1,3]dioxol-5-yl)-6-bromo-4-fluoro-1H-benzo[d]imidazole 3-B as a pink solid (287 mg, 0.856 mmol, 71% yield, 5% MeOH in DCM).

$^1$H NMR (DMSO) δ: 8.54 (s, 1H), 7.53 (d, J=1.7 Hz, 1H), 7.42 (dd, J=10.2, 1.6 Hz, 1H), 7.34 (t, J=1.3 Hz, 1H), 7.14 (d, J=1.2 Hz, 2H), 6.18 (s, 2H).

Scheme 3, Step 3

A 2-5 mL Biotage© microwave vial loaded with halide 3-B (110 mg, 0.328 mmol), pyridin-4-ylboronic acid (40.3 mg, 0.328 mmol), Pd(PPh$_3$)$_4$ (34.1 mg, 0.030 mmol), and NaHCO$_3$ (110 mg, 1.313 mmol), was capped, purged with argon, then injected with degassed dioxane:H$_2$O (2 mL:1 mL, 2.5:1 v/v), and heated to 130° for 40 min. in a Biotage Microwave Reactor. The reaction was cooled, diluted with DCM, filtered through celite, concentrated, dryloaded onto silica gel and purified on a 12 g silica gel column (DCM/MeOH, 0-5%), affording 1-(benzo[d][1,3]dioxol-5-yl)-4-fluoro-6-(pyridin-4-yl)-1H-benzo[d]imidazole 3 as a tan solid (77 mg, 0.231 mmol, 70% yield, 5% MeOH in DCM). $^1$H NMR (DMSO) δ: 8.63 (d, J=6.2 Hz, 2H), 8.60 (s, 1H), 7.80 (d, J=5.7 Hz, 2H), 7.73 (s, 1H), 7.63 (dd, J=12.0, 1.5 Hz, 1H), 7.42 (d, J=2.1 Hz, 1H), 7.25-7.13 (m, 2H), 6.19 (s, 2H).

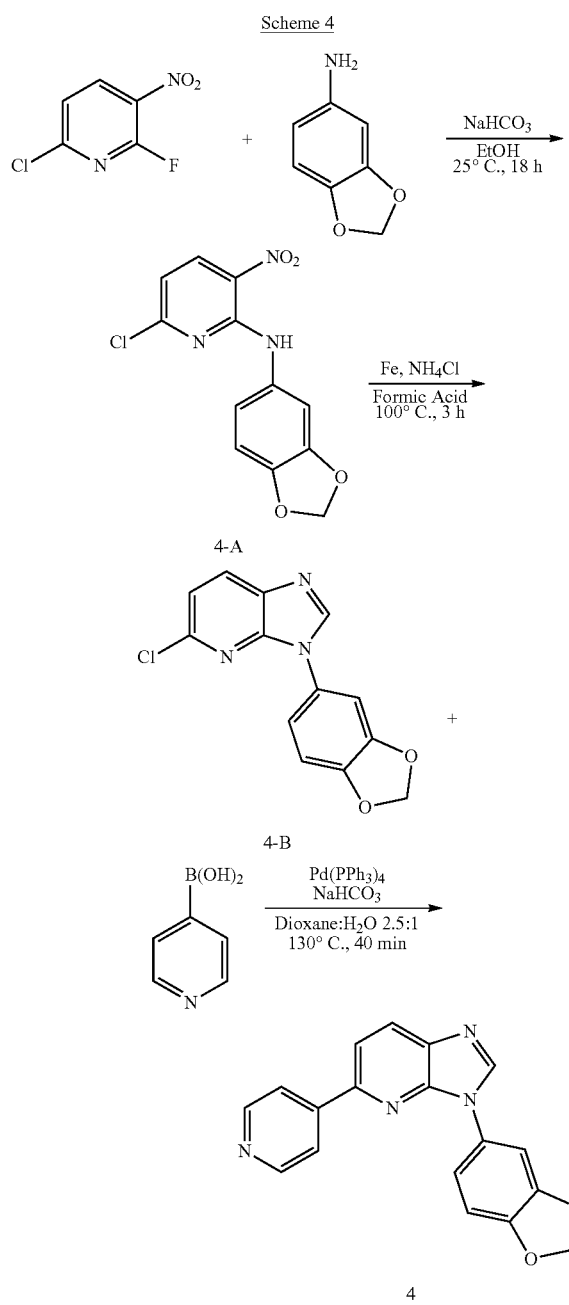

Scheme 4, Step 2

In a 20 mL Biotage© microwave vial, stir bar, N-(benzo[d][1,3]dioxol-5-yl)-6-chloro-3-nitropyridin-2-amine 4-A (350 mg, 1.192 mmol), iron (666 mg, 11.92 mmol), and ammonium chloride (638 mg, 11.92 mmol) were added. The vial was sealed, degassed with Ar for 15 min, injected with IPA (6 mL) and Formic Acid (98%, 7.8 mL). The mixture was heated for 3 h at 100° C. in an oil bath. Upon cooling, the mixture was diluted with EtOAc, solids filtered through celite, and concentrated. The crude was concentrated/dry-loaded onto silica with DCM and purified on a 12 g silica column (DCM), affording 3-(benzo[d][1,3]dioxol-5-yl)-5-chloro-3H-imidazo[4,5-b]pyridine 4-B as a white solid (55 mg, 0.201 mmol, 17% yield, 100% DCM)

$^1$H NMR (CDCl$_3$) δ: 8.24 (s, 1H), 8.10 (d, J=8.4 Hz, 1H), 7.34 (d, J=8.4 Hz, 1H), 7.22 (dd, J=2.2, 0.4 Hz, 1H), 7.11 (dd, J=8.2, 2.2 Hz, 1H), 6.98 (dd, J=8.2, 0.4 Hz, 1H), 6.11 (s, 2H).

Scheme 4, Step 3

A 2-5 mL Biotage© microwave vial loaded with 4-B (55 mg, 0.201 mmol), pyridin-4-ylboronic acid (29.6 mg, 0.241 mmol), Pd(PPh$_3$)$_4$ (16.26 mg, 0.014 mmol), and NaHCO$_3$ (67.5 mg, 0.804 mmol), was capped, purged with argon, then injected with degassed dioxane:H$_2$O (1.44 mL:0.574 mL, 2.5:1 v/v), and heated to 130° C. for 40 min in a Biotage Microwave Reactor. The reaction was cooled, diluted with DCM, filtered through celite, concentrated, dryloaded onto silica gel and purified on a 12 g silica gel column (DCM/MeOH, 0-5.5%), affording 3-(benzo[d][1,3]dioxol-5-yl)-5-(pyridin-4-yl)-3H-imidazo[4,5-b]pyridine 4 as a light yellow solid (61 mg, 0.193 mmol, 96% yield, 5.5% MeOH in DCM). $^1$H NMR (DMSO) δ: 8.90 (s, 1H), 8.72 (d, J=5.6 Hz, 2H), 8.35 (d, J=8.4 Hz, 1H), 8.14 (d, J=8.4 Hz, 1H), 8.10 (d, J=5.1 Hz, 2H), 7.62 (d, J=2.1 Hz, 1H), 7.47 (dd, J=8.3, 2.2 Hz, 1H), 7.19 (d, J=8.3 Hz, 1H), 6.19 (s, 2H).

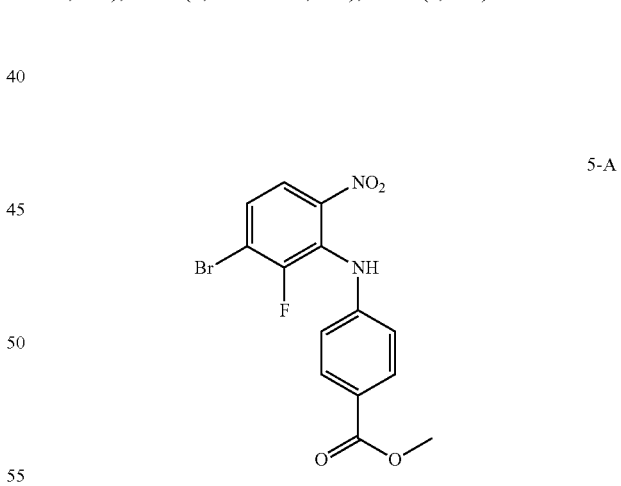

5-A

Scheme 4, Step 1

In a 20 mL Biotage© microwave vial, stir bar, benzo[d][1,3]dioxol-5-amine (1 g, 7.29 mmol), NaHCO$_3$ (1.225 g, 14.58 mmol) and EtOH (14.6 mL) were added and stirred for 5 min. 2,6-Dichloro-3-nitropyridine (1.4 g, 7.29 mmol) was added and the vial sealed, then stirred at 25° C. for 18 h. The mixture was filtered and the precipitated product was washed with cold EtOH, H2O, and hexanes, affording N-(benzo[d][1,3]dioxol-5-yl)-6-chloro-3-nitropyridin-2-amine 4-A as a red solid (1.66 g, 5.65 mmol, 78% yield). $^1$H NMR (DMSO) δ: 10.02 (s, 1H), 8.52 (d, J=8.6 Hz, 1H), 7.22 (dd, J=2.1, 0.4 Hz, 1H), 7.03-6.89 (m, 3H), 6.06 (s, 2H). $^{13}$C NMR (DMSO) δ: 154.76, 150.01, 147.59, 145.09, 139.23, 132.00, 128.09, 117.45, 114.05, 108.37, 106.05, 101.80.

5-A Was synthesized in a similar manner as depicted in Scheme 1, Step 1 using methyl 4-aminobenzoate (1 equiv.) and replacing the base/solvent with potassium tert butoxide (2 equiv) and dioxane (0.5 Molar).

methyl 4-((3-bromo-2-fluoro-6-nitrophenyl)amino)benzoate 5-A.

Orange solid (1.73 g, 4.45 mmol, 89% yield).

$^1$H NMR (CDCl$_3$) δ: 8.73 (s, 1H), 8.02 (d, J=8.6 Hz, 2H), 7.93 (dd, J=9.3, 1.9 Hz, 1H), 7.33-7.28 (m, 1H), 6.99 (dd, J=8.6, 3.1 Hz, 2H), 3.93 (s, 3H).

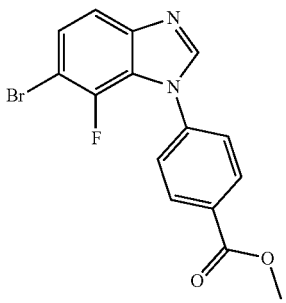

5-B

5-B Was synthesized in a similar manner as depicted in Scheme 1, Step 2.

methyl 4-(6-bromo-7-fluoro-1H-benzo[d]imidazole-1-yl)benzoate 5-B.

White solid (125 mg, 0.358 mmol, 30% yield, 5% MeOH in DCM).

$^1$H NMR (DMSO) δ: 8.63 (s, 1H), 8.16 (d, J=8.6 Hz, 2H), 7.84 (dd, J=8.7, 2.9 Hz, 2H), 7.66-7.53 (m, 2H), 3.93 (s, 3H).

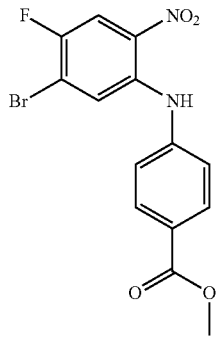

5

5 Was synthesized in a similar manner as depicted in Scheme 1, Step 3.

methyl 4-(7-fluoro-6-(pyridin-4-yl)-1H-benzo[d]imidazol-1-yl)benzoate 5.

White semi-solid (58 mg, 0.167 mmol, 56% yield, 5% MeOH in DCM).

$^1$H NMR (DMSO) δ: 8.69-8.63 (m, 3H), 8.15 (d, J=7.8 Hz, 2H), 7.89 (dd, J=8.7, 2.9 Hz, 2H), 7.77 (d, J=8.4 Hz, 1H), 7.66-7.61 (m, 2H), 7.59-7.48 (m, 1H), 3.92 (s, 3H).

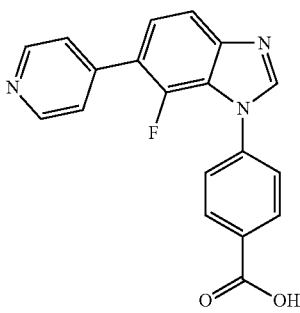

6

6 Formed from 5 as a hydrolytic side product of the conditions depicted in Scheme 1, Step 3.

4-(7-fluoro-6-(pyridin-4-yl)-1H-benzo[d]imidazol-1-yl)benzoic acid 6.

White oil (15 mg, 0.045 mmol, 15% yield, 30% MeOH in DCM).

$^1$H NMR (DMSO) δ: 8.65 (d, J=6.1 Hz, 2H), 8.58 (s, 1H), 8.01 (d, J=8.3 Hz, 2H), 7.74 (d, J=8.4 Hz, 1H), 7.69-7.59 (m, 2H), 7.60-7.55 (m, 2H), 7.55-7.47 (m, 1H), COOH H absent.

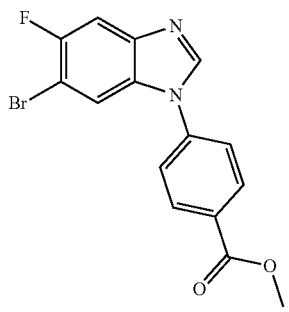

7-A

7-A Was synthesized in a similar manner as depicted in Scheme 2, using methyl 4-aminobenzoate (1 equiv.) and replacing the base/solvent with potassium tert butoxide (2 equiv) and dioxane (0.5 Molar).

methyl 4-((5-bromo-4-fluoro-2-nitrophenyl)amino)benzoate 7-A.

Orange solid (440 mg, 1.192 mmol, 40% yield).

$^1$H NMR (CDCl$_3$) δ: 9.36 (s, 1H), 8.12 (d, J=8.7 Hz, 2H), 8.01 (d, J=8.4 Hz, 1H), 7.64 (d, J=5.9 Hz, 1H), 7.31 (d, J=8.6 Hz, 2H), 3.96 (s, 3H)

7-B

7-B Was synthesized in a similar manner as depicted in Scheme 2, Step 2.

methyl 4-(6-bromo-5-fluoro-1H-benzo[d]77midazole-1-yl)benzoate 7-B.

Red semi-solid (121 mg, 0.347 mmol, 46% yield, 5% MeOH in DCM).

$^1$H NMR (CDCl$_3$) δ: 8.30 (d, J=8.9 Hz, 2H), 8.21 (s, 1H), 7.77 (d, J=5.9 Hz, 1H), 7.65 (d, J=8.6 Hz, 1H), 7.61 (d, J=8.9 Hz, 2H), 4.02 (s, 3H).

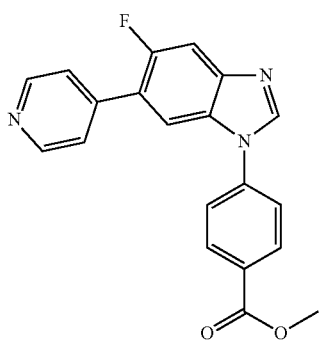

7

7 Was synthesized in a similar manner as depicted in Scheme 2, Step 3.

methyl 4-(5-fluoro-6-(pyridin-4-yl)-1H-benzo[d]imidazol-1-yl)benzoate 7.

Orange solid (11 mg, 0.032 mmol, 12% yield, 5% MeOH in DCM).

$^1$H NMR (DMSO) δ: 8.85 (s, 1H), 8.68 (d, J=5.9 Hz, 2H), 8.19 (d, J=8.6 Hz, 2H), 7.98 (d, J=8.8 Hz, 2H), 7.88 (d, J=6.6 Hz, 1H), 7.84 (d, J=11.3 Hz, 1H), 7.76-7.63 (m, 2H), 3.92 (s, 3H).

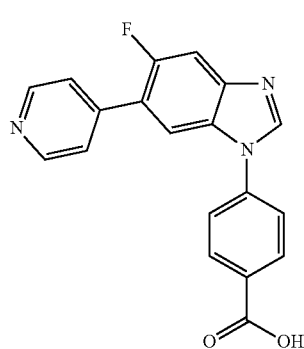

8

8 Formed from 7 as a hydrolytic side product of the conditions depicted in Scheme 2, Step 3.

4-(5-fluoro-6-(pyridin-4-yl)-1H-benzo[d]imidazol-1-yl)benzoic acid 8.

Yellow solid (23 mg, 0.069 mmol, 27% yield, 15% MeOH in DCM).

$^1$H NMR (DMSO) δ: 13.20 (bs, 1H), 8.83 (s, 1H), 8.67 (d, J=6.2 Hz, 2H), 8.17 (dd, J=8.7, 2.0 Hz, 2H), 7.94 (d, J=8.8 Hz, 2H), 7.88 (d, J=6.7 Hz, 1H), 7.83 (d, J=11.3 Hz, 1H), 7.70-7.63 (m, 2H).

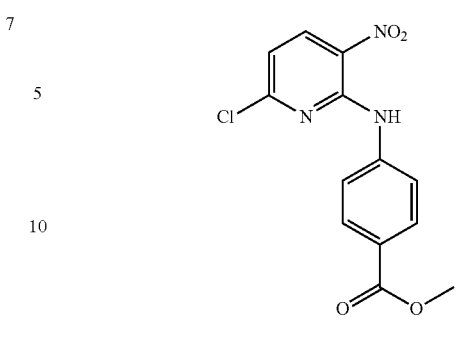

9-A

9-A Was synthesized in a similar manner as depicted in Scheme 4, Step 1.

methyl 4-((6-chloro-3-nitropyridin-2-yl)amino)benzoate 9-A.

Light Orange solid (950 mg, 3.09 mmol, 21% yield).

$^1$H NMR (DMSO) δ: 10.26 (s, 1H), 8.54 (d, J=8.6 Hz, 1H), 7.96 (d, J=8.5 Hz, 2H), 7.75 (d, J=8.1 Hz, 2H), 7.05 (d, J=8.6 Hz, 1H), 3.85 (s, 3H). $^{13}$C NMR (DMSO) δ: 166.26, 154.07, 148.93, 143.88, 139.26, 130.40, 129.50, 125.01, 122.17, 114.82, 52.42.

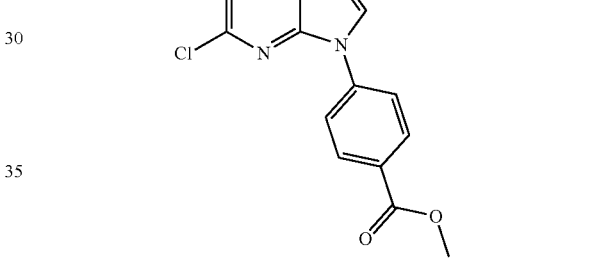

9-B

9-B Was synthesized in a similar manner as depicted in Scheme 4, Step 2.

methyl 4-(5-chloro-3H-imidazo[4,5-b]pyridin-3-yl)benzoate 9-B.

Gray oil (145 mg, 0.252 mmol, 25% yield, 100% DCM).

$^1$H NMR (CDCl$_3$) δ: 8.87 (d, J=11.2 Hz, 1H), 8.46 (d, J=1.7 Hz, 1H), 8.17 (bs, 1H), 8.11-7.94 (m, 5H), 7.65 (d, J=8.9 Hz, 2H), 7.15 (d, J=8.6 Hz, 2H), 3.93 (s, 3H).

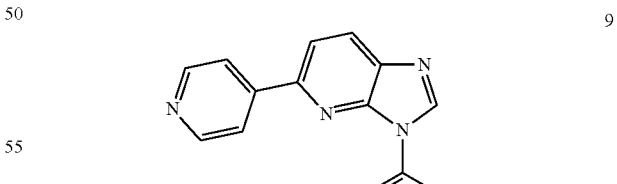

9

9 Was synthesized in a similar manner as depicted in Scheme 4, Step 3.

methyl 4-(5-(pyridin-4-yl)-3H-imidazo[4,5-b]pyridin-3-yl)benzoate 9.

Beige semi-solid (23 mg, 0.070 mmol, 28% yield, 5% MeOH in DCM).

$^1$H NMR (CDCl$_3$) δ: 8.76 (d, J=6.1 Hz, 2H), 8.53 (s, 1H), 8.33 (d, J=8.4 Hz, 2H), 8.29 (d, J=8.4 Hz, 1H), 8.07 (d, J=8.7 Hz, 2H), 8.00 (d, J=6.3 Hz, 2H), 7.93 (d, J=8.4 Hz, 1H), 4.02 (s, 3H).

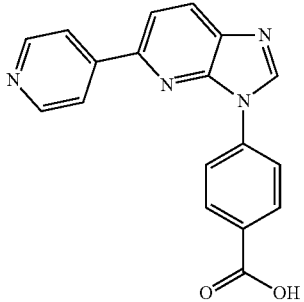

10

10 Formed from 9 as a hydrolytic side product of the conditions depicted in Scheme 4, Step 3.

4-(5-(pyridin-4-yl)-3H-imidazo[4,5-b]pyridin-3-yl)benzoic acid 10.

Yellow-tan solid (11 mg, 0.035 mmol, 68% yield, 3% MeOH in DCM).

$^1$H NMR (DMSO) δ: 9.22 (s, 1H), 8.91 (d, J=6.0 Hz, 2H), 8.56 (d, J=5.6 Hz, 2H), 8.48 (d, J=8.4 Hz, 1H), 8.38 (d, J=8.4 Hz, 1H), 8.29 (d, J=8.8 Hz, 2H), 8.22 (d, J=8.8 Hz, 2H).

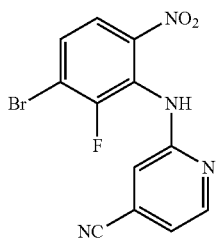

11-A

11-A Was synthesized in a similar manner as depicted in Scheme 1, Step 1, using 2-aminoisonicotinonitrile (1 equiv.) and replacing the base/solvent with potassium tert butoxide (2 equiv) and dioxane (0.5 Molar).

2-((3-bromo-2-fluoro-6-nitrophenyl)amino)isonicotinonitrile 11-A.

Orange solid (575 mg, 1.706 mmol, 68% yield).

$^1$H NMR (CDCl$_3$) δ: 8.45 (s, 1H), 8.39 (dd, J=5.1, 0.9 Hz, 1H), 7.90 (dd, J=9.1, 1.8 Hz, 1H), 7.48 (dd, J=9.1, 6.3 Hz, 1H), 7.15 (dd, J=5.1, 1.3 Hz, 1H), 7.10-7.04 (m, 1H).

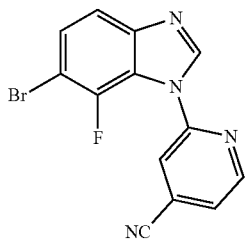

11-B

11-B Was synthesized in a similar manner as depicted in Scheme 2, Step 2.

2-(6-bromo-7-fluoro-1H-benzo[d]imidazol-1-yl)isonicotinonitrile 11-B.

Yellow solid (160 mg, 0.505 mmol, 42% yield).

$^1$H NMR (CDCl$_3$) δ: 8.79 (dd, J=5.0, 0.9 Hz, 1H), 8.53 (s, 1H), 7.85-7.80 (m, 1H), 7.69-7.52 (m, 3H).

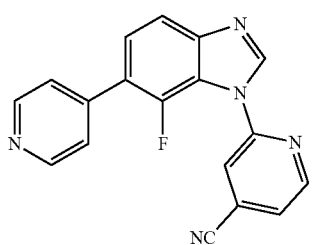

11

11 Was synthesized in a similar manner as depicted in Scheme 1, Step 3.

2-(7-fluoro-6-(pyridin-4-yl)-1H-benzo[d]imidazol-1-yl)isonicotinonitrile 11.

Tan solid (26 mg, 0.079 mmol, 26% yield, 5% MeOH in DCM).

$^1$H NMR (CDCl$_3$) δ: 8.81 (dd, J=5.0, 0.9 Hz, 1H), 8.75 (d, J=6.1 Hz, 2H), 8.60 (s, 1H), 7.87-7.84 (m, 1H), 7.81 (d, J=8.4 Hz, 1H), 7.64 (dd, J=5.0, 1.2 Hz, 1H), 7.58-7.53 (m, 2H), 7.53-7.45 (m, 1H).

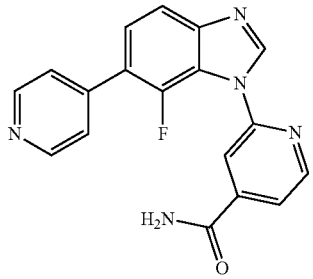

12

12 & 13 were formed from 11 as hydrolytic side products of the conditions depicted in Scheme 1, Step 3.

2-(7-fluoro-6-(pyridin-4-yl)-1H-benzo[d]imidazol-1-yl)isonicotinamide 12.

Beige solid (63 mg, 0.189 mmol, 63% yield, 15% MeOH in DCM).

$^1$H NMR (DMSO) δ: 8.81 (s, 1H), 8.78 (dd, J=5.1, 0.7 Hz, 1H), 8.68 (d, J=6.3 Hz, 2H), 8.36 (bs, 1H), 8.26-8.18 (m, 1H), 7.94 (dd, J=5.1, 1.4 Hz, 1H), 7.93 (bs, 1H), 7.79 (d, J=8.4 Hz, 1H), 7.67-7.61 (m, 2H), 7.60-7.50 (m, 1H).

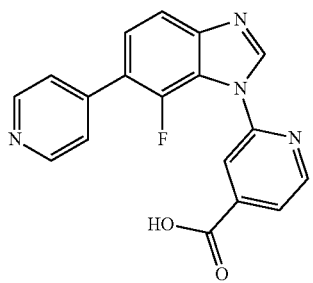

13

12 & 13 were formed from 11 as hydrolytic side products of the conditions depicted in Scheme 1, Step 3.

2-(7-fluoro-6-(pyridin-4-yl)-1H-benzo[d]imidazol-1-yl)isonicotinic acid 13.

Green semi-solid (4 mg, 0.012 mmol, 20% yield, 20% MeOH in DCM).

$^1$H NMR (DMSO) δ: 14.06 (bs, 1H), 8.96-8.80 (m, 2H), 8.80-8.69 (m, 2H), 8.22 (s, 1H), 7.97 (d, J=4.4 Hz, 1H), 7.79 (d, J=8.0 Hz, 1H), 7.76-7.69 (m, 2H), 7.61-7.51 (m, 1H).

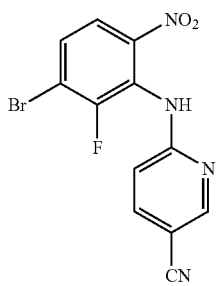

14-A

14-A Was synthesized in a similar manner as depicted in Scheme 1, Step 1, using 6-aminonicotinonitrile (1 equiv.) and replacing the base/solvent with potassium tert butoxide (2 equiv) and dioxane (0.5 Molar).

6-((3-bromo-2-fluoro-6-nitrophenyl)amino)nicotinonitrile 14-A.

Orange solid (450 mg, 1.335 mmol, 53% yield).

$^1$H NMR (CDCl$_3$) δ: 8.50 (d, J=1.6 Hz, 1H), 8.38 (s, 1H), 7.87 (ddd, J=16.4, 8.9, 2.0 Hz, 2H), 7.54 (dd, J=9.1, 6.3 Hz, 1H), 6.88 (d, J=8.2 Hz, 1H).

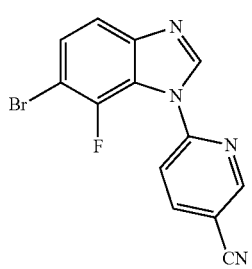

14-B

14-B Was synthesized in a similar manner as depicted in Scheme 1, Step 2.

6-(6-bromo-7-fluoro-1H-benzo[d]imidazol-1-yl)nicotinonitrile 14-B.

Gray solid (118 mg, 0.372 mmol, 31% yield, EtOAc trituration).

$^1$H NMR (CDCl$_3$) δ: 8.88 (dd, J=2.2, 0.8 Hz, 1H), 8.60 (s, 1H), 8.21 (dd, J=8.5, 2.2 Hz, 1H), 7.73 (ddd, J=8.5, 4.3, 0.8 Hz, 1H), 7.67-7.53 (m, 2H).

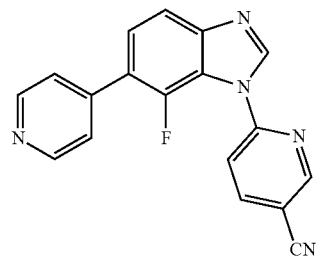

14

14 Was synthesized in a similar manner as depicted in Scheme 1, Step 3.

6-(7-fluoro-6-(pyridin-4-yl)-1H-benzo[d]imidazol-1-yl)nicotinonitrile 14.

White solid (17 mg, 0.054 mmol, 18% yield, 5% MeOH in DCM).

$^1$H NMR (DMSO) δ: 9.13 (dd, J=2.2, 0.8 Hz, 1H), 8.87 (s, 1H), 8.69 (d, J=5.9 Hz, 2H), 8.64 (dd, J=8.5, 2.2 Hz, 1H), 8.12 (ddd, J=8.5, 3.8, 0.8 Hz, 1H), 7.80 (d, J=8.4 Hz, 1H), 7.68-7.63 (m, 2H), 7.59 (dd, J=8.4, 6.9 Hz, 1H).

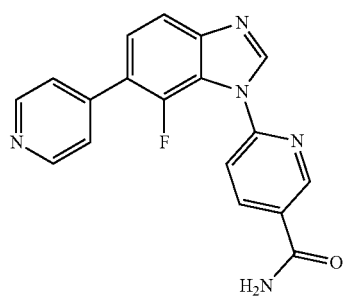

15

15 Formed from 14 as a hydrolytic side product of the conditions depicted in Scheme 1, Step 3.

6-(7-fluoro-6-(pyridin-4-yl)-1H-benzo[d]imidazol-1-yl)nicotinamide 15.

White solid (28 mg, 0.084 mmol, 28% yield, 15% MeOH in DCM)

$^1$H NMR (DMSO) δ: 9.06 (d, J=2.3 Hz, 1H), 8.83 (s, 1H), 8.69 (d, J=5.1 Hz, 2H), 8.49 (dd, J=8.4, 2.3 Hz, 1H), 8.29 (bs, 1H), 7.98 (dd, J=8.5, 3.7 Hz, 1H), 7.79 (d, J=8.4 Hz, 1H), 7.74 (bs, 1H), 7.67 (d, J=4.7 Hz, 2H), 7.60-7.52 (m, 1H).

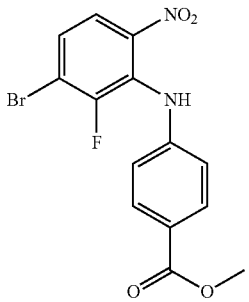

16-A

16-A Was synthesized in a similar manner as depicted in Scheme 3, Step 1, using methyl 4-aminobenzoate (1 equiv.) and replacing the base/solvent with potassium tert butoxide (2 equiv) and dioxane (0.5 Molar).

methyl 4-((5-bromo-3-fluoro-2-nitrophenyl)amino)benzoate 16-A.

Orange solid (810 mg, 2.194 mmol, 44% yield).

$^1$H NMR (DMSO) δ: 9.15-9.10 (m, 1H), 7.90 (d, J=8.3 Hz, 2H), 7.50-7.33 (m, 2H), 7.21 (d, J=8.4 Hz, 2H), 3.83 (s, 3H).

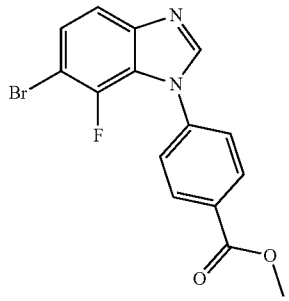

16-B

16-B Was synthesized in a similar manner as depicted in Scheme 3, Step 2.

methyl 4-(6-bromo-4-fluoro-1H-benzo[d]imidazol-1-yl)benzoate 16-B.

Tan solid (270 mg, 0.773 mmol, 64% yield, 5% MeOH in DCM).

$^1$H NMR (DMSO) δ: 8.76 (s, 1H), 8.19 (d, J=8.5 Hz, 2H), 7.89 (d, J=8.8 Hz, 2H), 7.73 (d, J=1.5 Hz, 1H), 7.48 (dd, J=10.2, 1.6 Hz, 1H), 3.92 (s, 3H).

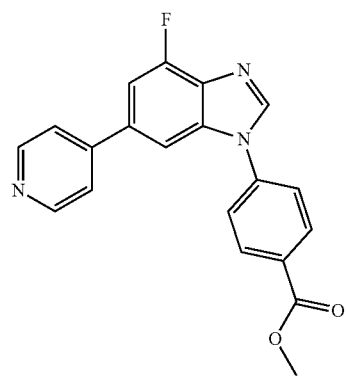

16

16 Was synthesized in a similar manner as depicted in Scheme 3, Step 3.

methyl 4-(4-fluoro-6-(pyridin-4-yl)-1H-benzo[d]imidazol-1-yl)benzoate 16.

Gray solid (60 mg, 0.173 mmol, 43% yield, 4% MeOH in DCM).

$^1$H NMR (DMSO) δ: 8.81 (s, 1H), 8.64 (d, J=6.2 Hz, 2H), 8.21 (d, J=8.8 Hz, 2H), 7.98 (d, J=8.6 Hz, 2H), 7.91 (d, J=1.4 Hz, 1H), 7.83 (d, J=6.1 Hz, 2H), 7.69 (dd, J=12.0, 1.4 Hz, 1H), 3.93 (s, 3H).

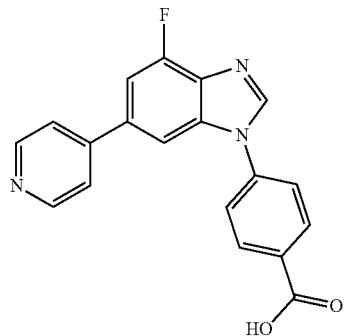

17

17 Formed from 16 as a hydrolytic side product of the conditions depicted in Scheme 3, Step 3.

4-(4-fluoro-6-(pyridin-4-yl)-1H-benzo[d]imidazol-1-yl)benzoic acid 17.

Red solid (18 mg, 0.054 mmol, 13% yield, 25% MeOH in DCM).

$^1$H NMR (DMSO) δ: 8.77 (s, 1H), 8.63 (dd, J=6.0, 1.8 Hz, 2H), 8.17 (d, J=7.9 Hz, 2H), 7.91-7.81 (m, 5H), 7.68 (dd, J=12.0, 1.4 Hz, 1H), note: COOH H absent.

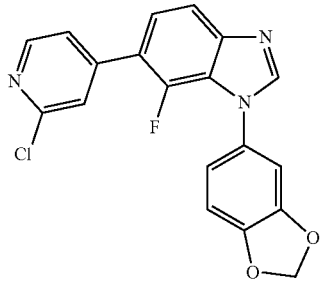

18

18 Was synthesized in a similar manner as depicted in Scheme 1, Step 3 using (2-chloropyridin-4-yl)boronic acid.

1-(benzo[d][1,3]dioxol-5-yl)-6-(2-chloropyridin-4-yl)-7-fluoro-1H-benzo[d]imidazole 18.

White solid (13 mg, 0.035 mmol, 24% yield, 50% EtOAC in hexanes).

$^1$H NMR (CDCl$_3$) δ: 8.45 (dd, J=5.9, 0.7 Hz, 1H), 8.03 (s, 1H), 7.76 (d, J=8.5 Hz, 1H), 7.61-7.55 (m, 1H), 7.48-7.43 (m, 1H), 7.43-7.34 (m, 1H), 7.06-6.91 (m, 3H), 6.13 (s, 2H).

Scheme 5

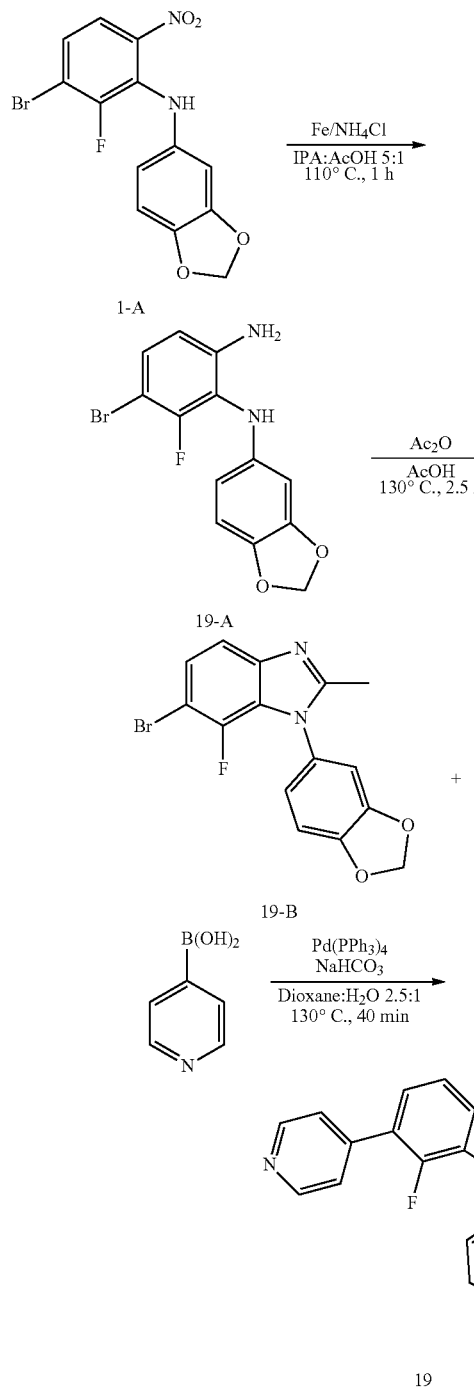

Scheme 5, Step 1

In a 20 mL Biotage© microwave vial, stir bar, N-(3-bromo-2-fluoro-6-nitrophenyl)benzo[d][1,3]dioxol-5-amine (300 mg, 0.845 mmol), iron (472 mg, 8.45 mmol), and ammonium chloride (452 mg, 8.45 mmol) were added. The vial was sealed, degassed with Ar for 15 min, injected with IPA:AcOH (10 mL:2 mL, 5:1 v/v) and purged with Ar for another 5 min. The mixture was heated at 110° C. for 1 h in an oil bath. Upon cooling, the mixture was diluted with EtOAc, solids filtered through celite, and the mixture concentrated/dryloaded onto silica with DCM and purified on a 12 g silica column (DCM), affording $N^1$-(benzo[d][1,3]dioxol-5-yl)-5-bromo-6-fluorobenzene-1,2-diamine 19-A as a tan solid (190 mg, 0.584 mmol, 69% yield, 100% DCM). $^1$H NMR (DMSO) δ: 7.16 (dd, J=8.8, 7.5 Hz, 1H), 7.06 (s, 1H), 6.69 (d, J=8.3 Hz, 1H), 6.55 (dd, J=8.8, 1.5 Hz, 1H), 6.20 (d, J=2.1 Hz, 1H), 5.95 (dd, J=8.4, 2.3 Hz, 1H), 5.87 (s, 2H), 5.28 (s, 2H).

Scheme 5, Step 2

A 5 mL Biotage© microwave vial loaded with $N^1$-(benzo[d][1,3]dioxol-5-yl)-5-bromo-6-fluorobenzene-1,2-diamine 19-A was dissolved in AcOH (0.563 mL), Ac₂O (0.3 mL) was injected and the mixture was purged with Ar for 15 min and heated at 130° C. for 2.5 h. Upon cooling, the mixture was azeotroped with toluene. The crude was concentrated/dryloaded onto silica with DCM and purified on a 4 g silica column (DCM/MeOH, 0-5%), affording 1-(benzo[d][1,3]dioxol-5-yl)-6-bromo-7-fluoro-2-methyl-1H-benzo[d]imidazole 19-B as a tan solid (76 mg, 0.218 mmol, 88% yield, 4.5% MeOH in DCM). $^1$H NMR (CDCl₃) δ: 7.43-7.34 (m, 2H), 6.94 (dd, J=7.9, 0.6 Hz, 1H), 6.87 (dd, J=2.1, 0.9 Hz, 1H), 6.85-6.81 (m, 1H), 6.13 (s, 2H), 2.46 (s, 3H).

Scheme 5, Step 3

A 2-5 mL Biotage© microwave vial loaded with 1-(benzo[d][1,3]dioxol-5-yl)-6-bromo-7-fluoro-2-methyl-1H-benzo[d]imidazole 19-B (62 mg, 0.178 mmol), pyridin-4-ylboronic acid (21.83 mg, 0.178 mmol), Pd(PPh₃)₄ (18.47 mg, 0.016 mmol), and NaHCO₃ (59.7 mg, 0.016 mmol), was capped, purged with argon, then injected with degassed dioxane:H₂O (1.268 mL:0.5 mL, 2.5:1 v/v), and heated at 130° for 40 min in a Biotage Microwave Reactor. The reaction was cooled, diluted with DCM, filtered through celite, concentrated, dryloaded onto silica gel and purified on a 12 g silica gel column (DCM/MeOH, 0-5%), affording 1-(benzo[d][1,3]dioxol-5-yl)-7-fluoro-2-methyl-6-(pyridin-4-yl)-1H-benzo[d]imidazole 19 as a clear oil (54 mg, 0.155 mmol, 88% yield, 5% MeOH in DCM). $^1$H NMR (CDCl₃) δ: 8.64 (d, J=6.2 Hz, 2H), 7.61 (d, J=8.3 Hz, 1H), 7.53-7.43 (m, 2H), 7.37-7.30 (m, 1H), 6.98-6.79 (m, 3H), 6.12 (s, 2H), 2.49 (s, 3H).

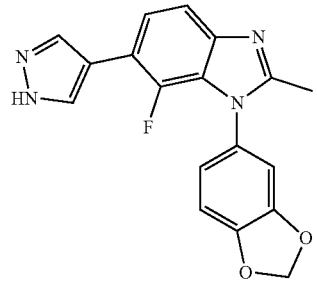

20

20 Was synthesized in a similar manner as depicted in Scheme 5, Step 3, using 4-(4,4,5,5-tetramethyl-1,3,2-dioxaborolan-2-yl)-1H-pyrazole.

1-(benzo[d][1,3]dioxol-5-yl)-7-fluoro-2-methyl-6-(1H-pyrazol-4-yl)-1H-benzo[d]imidazole 20.

Purple oil (8 mg, 0.024 mmol, 15% yield, 9% MeOH in DCM).

$^1$H NMR (CDCl₃) δ: 7.95 (d, J=1.8 Hz, 2H), 7.54 (d, J=8.4 Hz, 1H), 7.49-7.38 (m, 1H), 6.96 (dd, J=7.7, 0.9 Hz, 1H), 6.92-6.85 (m, 2H), 6.15 (s, 2H), 2.47 (s, 3H).

Scheme 6

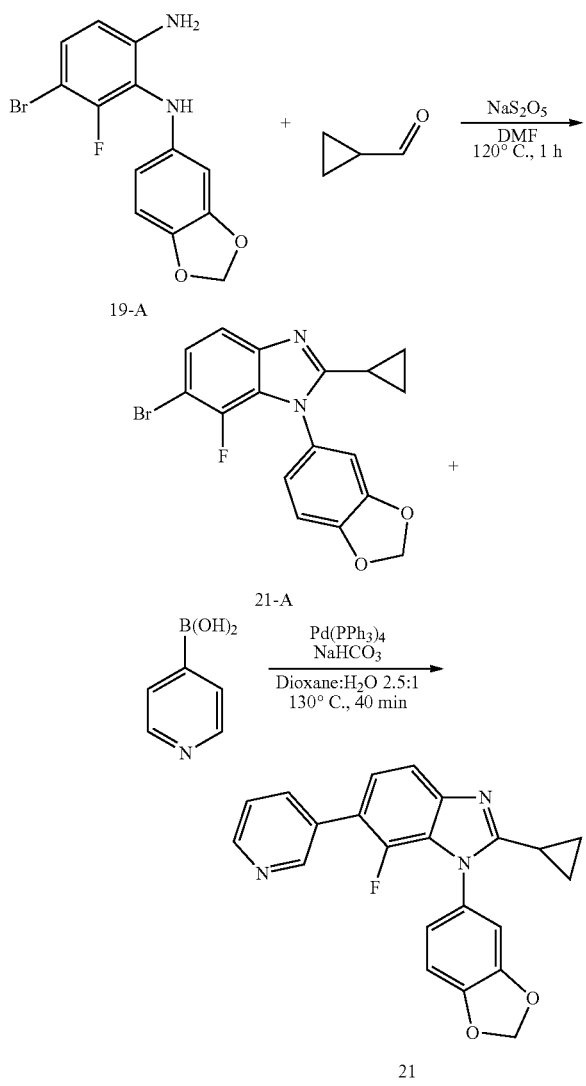

Scheme 6, Step 1

A 2-5 mL Biotage© microwave vial loaded with N¹-(benzo[d][1,3]dioxol-5-yl)-5-bromo-6-fluorobenzene-1,2-diamine 19-A (75 mg, 0.231 mmol), cyclopropanecarboxaldehyde (0.026 mL, 0.346 mL), DMF (0.95 mL), was capped, purged with argon, and heated to 120° C. for 1 h in a Biotage Microwave Reactor. The vial was diluted with H$_2$O and then extracted multiple times with Et$_2$O, washed with H$_2$O, brine, the organic layer was dried over Na$_2$SO$_4$ and concentrated, affording 1-(benzo[d][1,3]dioxol-5-yl)-6-bromo-2-cyclopropyl-7-fluoro-1H-benzo[d]imidazole 21-A as a green oil (60 mg, 0.160 mmol, 69% yield). $^1$H NMR (CDCl$_3$) δ: 7.37-7.33 (m, 2H), 6.99-6.91 (m, 3H), 6.13 (s, 2H), 1.85-1.74 (m, 1H), 1.30 (dq, J=5.5, 3.4 Hz, 2H), 1.12-1.03 (m, 2H).

Scheme 6, Step 2

A 2-5 mL Biotage© microwave vial loaded with 1-(benzo[d][1,3]dioxol-5-yl)-6-bromo-2-cyclopropyl-7-fluoro-1H-benzo[d]imidazole 21-A (53 mg, 0.141 mmol), pyridin-4-ylboronic acid (17.36 mg, 0.141 mmol), Pd(PPh$_3$)$_4$ (11.43 mg, 0.00989 mmol), and NaHCO$_3$ (47.5 mg, 0.565 mmol), was capped, purged with argon, then injected with degassed dioxane:H$_2$O (1 mL:0.4 mL, 2.5:1 v/v), and heated to 130° for 40 min in a Biotage Microwave Reactor. The reaction was cooled, diluted with DCM, filtered through celite, concentrated, dryloaded onto silica gel and purified on a 12 g silica gel column (Hexanes/EtOAc, 0-80%), affording 1-(benzo[d][1,3]dioxol-5-yl)-2-cyclopropyl-7-fluoro-6-(pyridin-4-yl)-1H-benzo[d]imidazole 21 as a clear oil (28 mg, 0.075 mmol, 53% yield, 80% EtOAc). $^1$H NMR (CDCl$_3$) δ: 8.64 (d, J=6.1 Hz, 2H), 7.57 (d, J=8.4 Hz, 1H), 7.53-7.42 (m, 2H), 7.36-7.29 (m, 1H), 7.05-6.88 (m, 3H), 6.13 (s, 2H), 1.86-1.75 (m, 1H), 1.37-1.29 (m, 2H), 1.17-0.97 (m, 2H).

Scheme 7

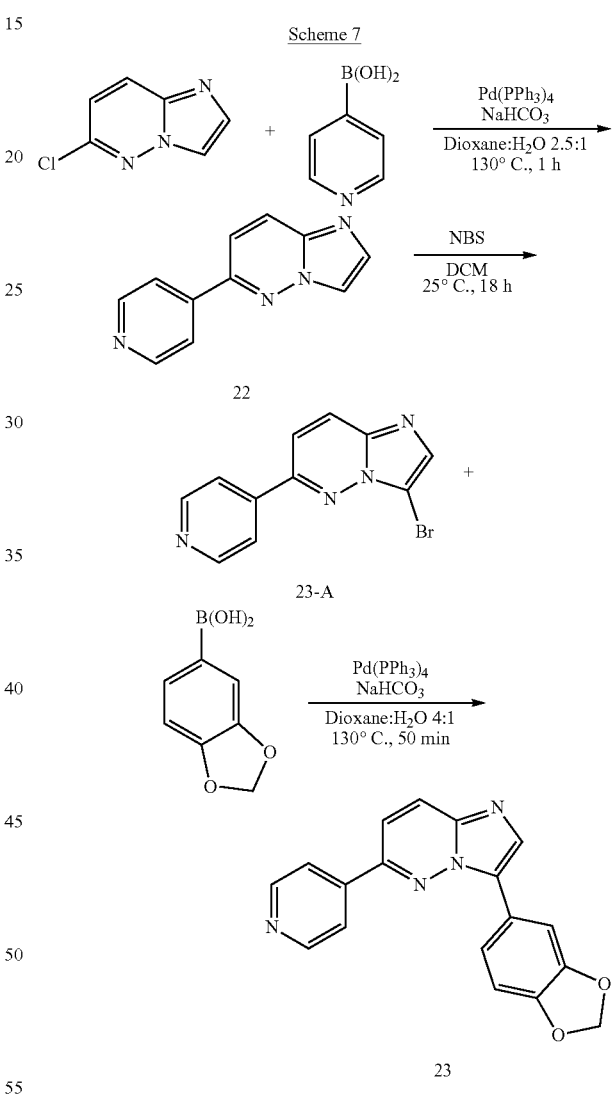

Scheme 7, Step 1

A 2-5 mL Biotage© microwave vial loaded with 6-chloro-imidazo[1,2-b]pyridazine (115 mg, 0.749 mmol), pyridin-4-ylboronic acid (92 mg, 0.749 mmol), Pd(PPh$_3$)$_4$ (60.6 mg, 0.052 mmol), and NaHCO$_3$ (252 mg, 3.0 mmol), was capped, purged with argon, then injected with degassed dioxane:H$_2$O (2.674 mL:1.07 mL, 2.5:1 v/v), and heated to 130° for 1 h in a Biotage Microwave Reactor. The reaction was cooled, diluted with DCM, filtered through celite, concentrated, dryloaded onto silica gel and purified on a 12 g silica gel column (DCM/MeOH, 0-11%), affording 6-(pyridin-4-yl)imidazo[1,2-b]pyridazine 22 as a white solid (375 mg, 1.911 mmol, 65% yield, 11% MeOH in DCM). ¹H NMR (CDCl₃) δ: 8.81 (d, J=6.0 Hz, 2H), 8.16-8.05 (m, 2H), 7.93-7.83 (m, 3H), 7.53 (d, J=9.4 Hz, 1H). ¹³C NMR (CDCl₃) δ: 150.74, 149.30, 142.80, 138.48, 135.07, 126.26, 120.98, 117.27, 115.24.

Scheme 7, Step 2

A 20 mL screw cap vial loaded with 6-(pyridin-4-yl)imidazo[1,2-b]pyridazine 22 (275 mg, 1.402 mmol), was dissolved in DCM (10.8 mL), and N-Bromosuccinimide (299 mg, 1.682 mmol), was added in portions, and the mixture was sealed and stirred at 25° C. for 18 h. The vial was diluted with DCM and 10% NaOH, then extracted multiple times with DCM, washed with 10% NaOH, H₂O, brine, and the organic layer was dried over Na₂SO₄, concentrated, dryloaded onto silica gel and purified on a 12 g silica gel column (DCM/MeOH, 0-9%), affording 3-bromo-6-(pyridin-4-yl)imidazo[1,2-b]pyridazine 23-A as a pink solid (265 mg, 0.963 mmol, 69% yield, 9% MeOH in DCM). ¹H NMR (CDCl₃) δ: 8.84 (d, J=6.1 Hz, 2H), 8.09 (d, J=9.5 Hz, 1H), 7.96 (d, J=6.1 Hz, 2H), 7.88 (s, 1H), 7.60 (d, J=9.5 Hz, 1H). ¹³C NMR (CDCl₃) δ: 150.82, 149.99, 142.42, 139.24, 135.38, 126.41, 121.08, 115.21, 101.61.

Scheme 7, Step 3

A 2-5 mL Biotage© microwave vial loaded with 3-bromo-6-(pyridin-4-yl)imidazo[1,2-b]pyridazine 23-A (50 mg, 0.182 mmol), benzo[d][1,3]dioxol-5-ylboronic acid (33.2 mg, 0.20 mmol), Pd(PPh₃)₄ (14.7 mg, 0.013 mmol), and NaHCO₃ (61.1 mg, 0.727 mmol), was capped, purged with argon, then injected with degassed dioxane:H₂O (2.4 mL:0.6 mL, 4:1 v/v), and heated to 130° for 50 min in a Biotage Microwave Reactor. The reaction was cooled, diluted with DCM, filtered through celite, concentrated, dryloaded onto silica gel and purified on a 12 g silica gel column (DCM/MeOH, 0-8%), affording 3-(benzo[d][1,3]dioxol-5-yl)-6-(pyridin-4-yl)imidazo[1,2-b]pyridazine 23 as a orange solid (42 mg, 0.133 mmol, 73% yield, 8% MeOH in DCM). ¹H NMR (CDCl₃) δ: 8.88-8.75 (m, 2H), 8.13 (d, J=9.4 Hz, 1H), 8.08-7.83 (m, 3H), 7.69-7.47 (m, 3H), 7.00 (d, J=8.0 Hz, 1H), 6.08 (s, 2H). ¹³C NMR (CDCl₃) δ: 150.78, 149.00, 147.94, 147.62, 142.98, 139.25, 133.64, 128.90, 126.51, 122.18, 121.05, 120.98, 114.21, 108.77, 107.42, 101.35.

24

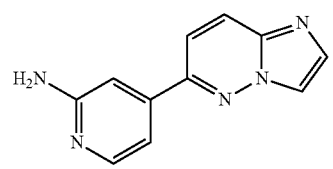

Compound 24 was synthesized in a similar manner as depicted in Scheme 7, Step 1 using 4-(4,4,5,5-tetramethyl-1,3,2-dioxaborolan-2-yl)pyridin-2-amine 4-(imidazo[1,2-b]pyridazin-6-yl)pyridin-2-amine 24.

Yellow solid (34 mg, 0.161 mmol, 82% yield, 12% MeOH in DCM).

¹H NMR (DMSO) δ: 8.37 (s, 1H), 8.25 (d, J=9.5 Hz, 1H), 8.09 (d, J=5.2 Hz, 1H), 7.86 (d, J=1.2 Hz, 1H), 7.69 (d, J=9.5 Hz, 1H), 7.14-7.06 (m, 2H), 6.20 (s, 2H). ¹³C NMR (DMSO) δ: 161.01, 150.35, 149.38, 143.58, 135.03, 126.58, 117.75, 116.37, 114.25, 109.80, 105.45.

25

Compound 25 was synthesized in a similar manner as depicted in Scheme 7, Step 1 using 4-(4,4,5,5-tetramethyl-1,3,2-dioxaborolan-2-yl)pyridin-2-amine and 6-chloro-2-methylimidazo[1,2-b]pyridazine.

4-(2-methylimidazo[1,2-b]pyridazin-6-yl)pyridin-2-amine 25.

Yellow solid (32 mg, 0.142 mmol, 79% yield, 10% MeOH in DCM).

¹H NMR (CDCl₃) δ: 8.24 (d, J=5.4 Hz, 1H), 7.93 (d, J=9.4 Hz, 1H), 7.83 (s, 1H), 7.40 (d, J=9.4 Hz, 1H), 7.18 (d, J=5.3 Hz, 1H), 7.09 (s, 1H), 4.65 (s, 2H), 2.56 (s, 3H).

Scheme 8

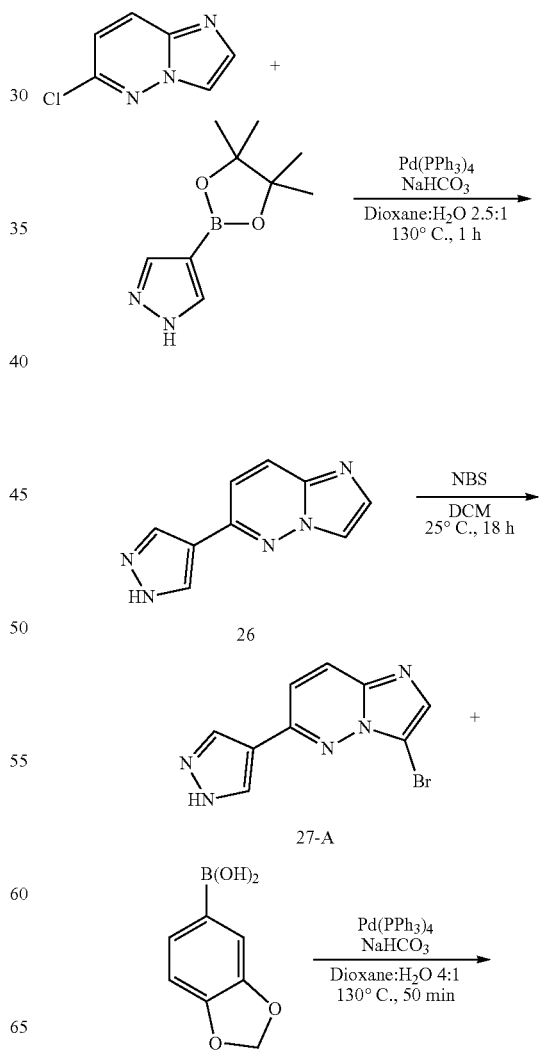

183

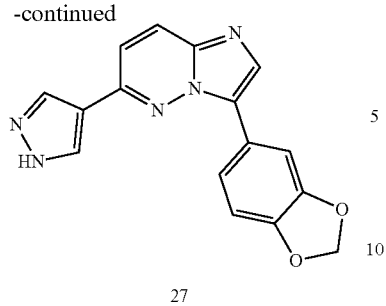

27

Scheme 8, Step 1

A 2-5 mL Biotage© microwave vial loaded with 6-chloroimidazo[1,2-b]pyridazine (180 mg, 1.172 mmol), 4-(4,4,5,5-tetramethyl-1,3,2-dioxaborolan-2-yl)-1H-pyrazole (250 mg, 1.29 mmol), Pd(PPh$_3$)$_4$ (95 mg, 0.082 mmol), and NaHCO$_3$ (394 mg, 4.69 mmol), was capped, purged with argon, then injected with degassed dioxane:H$_2$O (7 mL:2.8 mL, 4:1 v/v), and heated to 130° for 1 h in a Biotage Microwave Reactor. The reaction was cooled, diluted with DCM, filtered through celite, concentrated, dryloaded onto silica gel and purified on a 12 g silica gel column (DCM/MeOH, 0-10%), affording 6-(1H-pyrazol-4-yl)imidazo[1,2-b]pyridazine 26 as a tan solid (117 mg, 0.632 mmol, 54% yield, 10% MeOH in DCM). $^1$H NMR (DMSO) δ: 13.29 (s, 1H), 8.47 (bs, 2H), 8.21 (dd, J=1.1, 0.7 Hz, 1H), 8.12 (dd, J=9.5, 0.7 Hz, 1H), 7.72 (d, J=1.2 Hz, 1H), 7.62 (d, J=9.5 Hz, 1H).

Scheme 8, Step 2

A 20 mL screw cap vial loaded with 6-(1H-pyrazol-4-yl)imidazo[1,2-b]pyridazine 26 (100 mg, 0.54 mmol), was dissolved in DCM (5.4 mL), and N-Bromosuccinimide (115 mg, 0.648 mmol), was added in portions, and the mixture was sealed and stirred at 25° C. for 18 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-8%), affording 3-bromo-6-(1H-pyrazol-4-yl)imidazo[1,2-b]pyridazine 27-A as a tan solid (58 mg, 0.220 mmol, 41% yield, 8% MeOH in DCM). $^1$H NMR (CDCl$_3$) δ: 8.23 (s, 2H), 7.96 (d, J=9.4 Hz, 1H), 7.76 (s, 1H), 7.36 (d, J=9.4 Hz, 1H), (Note: N—H of Pyrazole is absent).

Scheme 8, Step 3

A 2-5 mL Biotage© microwave vial loaded with 3-bromo-6-(1H-pyrazol-4-yl)imidazo[1,2-b]pyridazine 27-A (52 mg, 0.197 mmol), benzo[d][1,3]dioxol-5-ylboronic acid (39.2 mg, 0.236 mmol), Pd(PPh$_3$)$_4$ (15.93 mg, 0.014 mmol), and NaHCO$_3$ (66.2 mg, 0.788 mmol), was capped, purged with argon, then injected with degassed dioxane:H$_2$O (1.97 mL:0.492 mL, 4:1 v/v), and heated to 130° for 50 min in a Biotage Microwave Reactor. The reaction was cooled, diluted with DCM, filtered through celite, concentrated, dryloaded onto silica gel and purified on a 12 g silica gel column (DCM/MeOH, 0-9%), affording 3-(benzo[d][1,3]dioxol-5-yl)-6-(1H-pyrazol-4-yl)imidazo[1,2-b]pyridazine 27 as a yellow solid (16 mg, 0.052 mmol, 27% yield, 9% MeOH in DCM). $^1$H NMR (CDCl$_3$) δ: 8.20 (s, 2H), 8.02 (d, J=9.4 Hz, 1H), 7.97 (s, 1H), 7.70 (d, J=1.5 Hz, 1H), 7.62 (dd, J=9.7, 1.9 Hz, 1H), 7.36 (bs, 1H), 7.32 (d, J=9.4 Hz, 1H), 6.99 (d, J=8.2 Hz, 1H), 6.08 (s, 2H).

184

Scheme 9

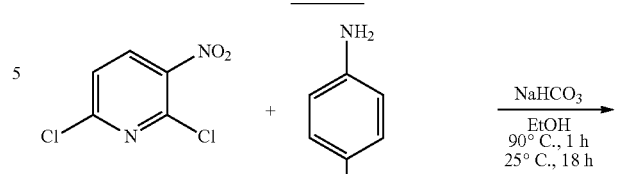

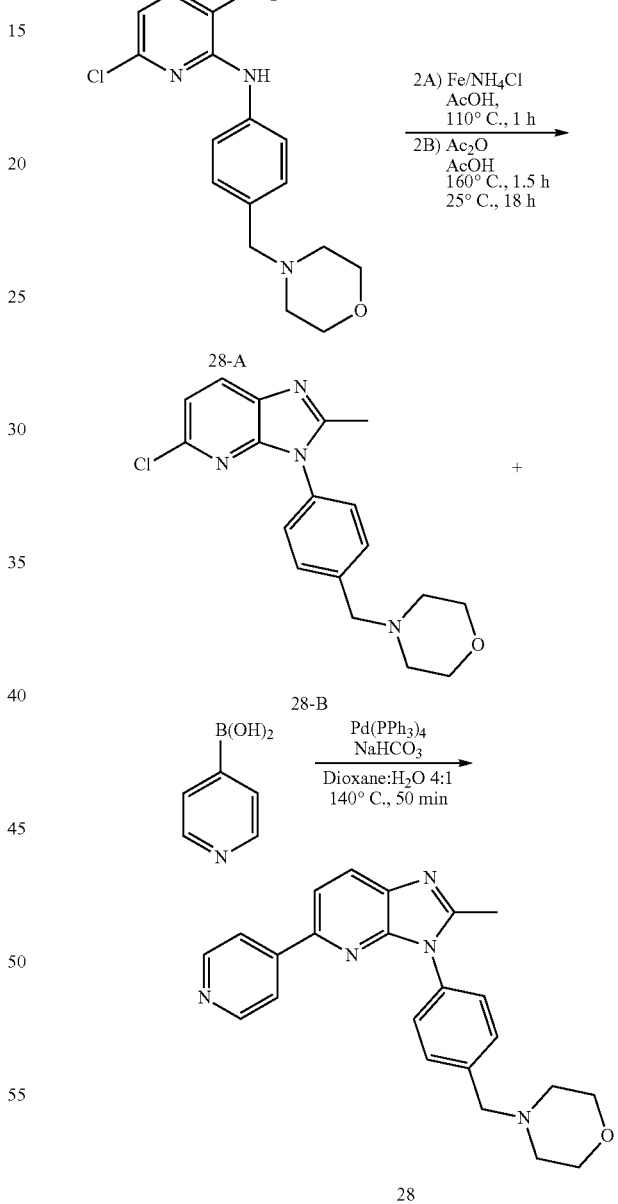

Scheme 9, Step 1

In a 20 mL Biotage© microwave vial, stir bar, 4-(morpholinomethyl)aniline (1.992 g, 10.36 mmol), NaHCO$_3$ (1.741 g, 20.73 mmol) and EtOH (5.18 mL) were added and stirred for 5 min. 2,6-Dichloro-3-nitropyridine (2 g, 10.36 mmol) was added and the vial sealed, then heated at 90° C.

for 1 h in an oil bath, ensuring to vent with a needle when necessary. The mixture was then stirred at 25° C. for 18 h, filtered, and the precipitated product was washed with cold EtOH, H₂O, and hexanes, affording 6-chloro-N-(4-(morpholinomethyl)phenyl)-3-nitropyridin-2-amine 28-A as a orange solid (2.625 g, 7.53 mmol, 73% yield). ¹H NMR (DMSO) δ: 10.10 (s, 1H), 8.53 (d, J=8.6 Hz, 1H), 7.55 (d, J=8.4 Hz, 2H), 7.32 (d, J=8.4 Hz, 2H), 7.00 (d, J=8.6 Hz, 1H), 3.61-3.56 (m, 4H), 3.46 (s, 2H), 2.41-2.33 (m, 4H).

Step 9, Step 2A

To (2) 20 mL Biotage© microwave vials, stir bars, 6-chloro-N-(4-(morpholinomethyl)phenyl)-3-nitropyridin-2-amine 28-A (1.3 g, 3.73 mmol), iron (1.665 g, 29.8 mmol), and ammonium chloride (0.798 mg, 14.91 mmol) were added to each individual vial. The vials were sealed, degassed with Ar for 15 min, injected with AcOH (11.3 mL each) and purged with Ar for another 5 min. Both vials were heated at 110° C. for 1 h in an oil bath. Upon cooling, both vials were diluted with EtOAc, solids filtered through celite, and the combined mixture concentrated.

Scheme 9, Step 2B

The crude residue from Step 2A was dissolved in AcOH (12.8 mL), gently warmed and pipetted repeatedly into one 20 mL Biotage© microwave vial equipped with a stir bar. Ac₂O (0.881 mL, 9.32 mmol) was injected and the mixture was purged with Ar for 15 min and heated at 160° C. for 1.5 h and then at 25° C. for 18 h. The mixture was poured into a 500 mL RBF and azeotroped with toluene repeatedly. DCM was added, followed by 7M NH₃ in MeOH (10 mL) with subsequent concentration. The crude freebase was concentrated/dryloaded onto silica with DCM and purified on a 40 g silica column (DCM/MeOH, 0-10%), affording 4-(4-(5-chloro-2-methyl-3H-imidazo[4,5-b]pyridin-3-yl)benzyl)morpholine 28-B as a orange oil (2 g, 5.54 mmol, 74% yield, 10% MeOH in DCM). ¹H NMR (CDCl₃) δ: 7.96 (d, J=8.3 Hz, 1H), 7.55 (d, J=8.4 Hz, 2H), 7.35 (d, J=8.4 Hz, 2H), 7.25 (d, J=8.3 Hz, 1H), 3.80-3.73 (m, 4H), 3.62 (s, 2H), 2.59-2.51 (m, 7H).

Scheme 9, Step 3

A 2-5 mL Biotage© microwave vial loaded with 4-(4-(5-chloro-2-methyl-3H-imidazo[4,5-b]pyridin-3-yl)benzyl)morpholine 28-B (65 mg, 0.190 mmol), pyridin-4-ylboronic acid (25.6 mg, 0.209 mmol), Pd(PPh₃)₄ (17.53 mg, 0.015 mmol), and NaHCO₃ (63.7 mg, 0.758 mmol), was capped, purged with argon, then injected with degassed dioxane:H₂O (1.52 mL:0.38 mL, 4:1 v/v), and heated to 140° for 50 min in a Biotage Microwave Reactor. The reaction was cooled, diluted with DCM, filtered through celite, concentrated, dryloaded onto silica gel and purified on a 12 g silica gel column (DCM/MeOH, 0-10%), affording 4-(4-(2-methyl-5-(pyridin-4-yl)-3H-imidazo[4,5-b]pyridin-3-yl)benzyl)morpholine 28 as a green semi-solid (15 mg, 0.044 mmol, 23% yield, 10% MeOH in DCM). ¹H NMR (CDCl₃) δ: 8.66 (d, J=6.2 Hz, 2H), 8.10 (d, J=8.3 Hz, 1H), 7.89 (d, J=6.1 Hz, 2H), 7.81 (d, J=8.3 Hz, 1H), 7.61 (d, J=8.2 Hz, 2H), 7.46 (d, J=8.4 Hz, 2H), 3.87-3.72 (m, 4H), 3.66 (s, 2H), 2.63 (s, 3H), 2.60-2.51 (m, 4H). ¹³C NMR (CDCl₃) δ: 154.64, 150.26, 149.19, 148.61, 146.60, 138.98, 135.23, 133.34, 130.09, 127.10, 127.01, 121.05, 116.17, 67.04, 62.87, 53.76, 15.45.

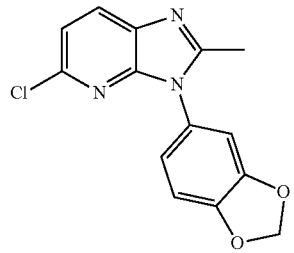

29-B

29-B Was synthesized in a similar manner as depicted in Scheme 9, Step 2, using 4-A.

3-(benzo[d][1,3]dioxol-5-yl)-5-chloro-2-methyl-3H-imidazo[4,5-b]pyridine 29-B.

Tan solid (390 mg, 1.356 mmol, 49% yield, 80% EtOAc in hexanes).

¹H NMR (CDCl₃) δ: 7.93 (d, J=8.3 Hz, 1H), 7.25 (d, J=8.3 Hz, 1H), 6.97 (d, J=8.7 Hz, 1H), 6.87-6.81 (m, 2H), 6.11 (s, 2H), 2.54 (s, 3H). ¹³C NMR (CDCl₃) δ: 153.90, 148.62, 148.47, 148.33, 145.15, 133.54, 128.76, 127.53, 121.17, 118.81, 108.78, 108.47, 102.11, 15.01.

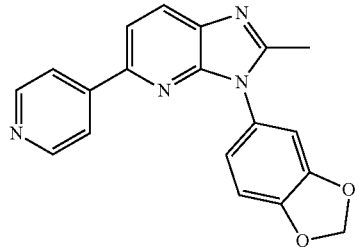

29

29 Was synthesized in a similar manner as depicted in Scheme 9, Step 3, 3-(benzo[d][1,3]dioxol-5-yl)-2-methyl-5-(pyridin-4-yl)-3H-imidazo[4,5-b]pyridine 29.

Tan solid (85 mg, 0.257 mmol, 74% yield, 100% EtOAc).

¹H NMR (CDCl₃) δ: 8.64 (d, J=6.2 Hz, 2H), 8.05 (d, J=8.3 Hz, 1H), 7.87 (d, J=6.1 Hz, 2H), 7.76 (d, J=8.2 Hz, 1H), 6.99 (d, J=8.1 Hz, 1H), 6.96-6.71 (m, 2H), 6.12 (s, 2H), 2.58 (s, 3H).

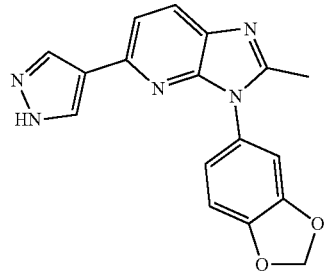

30

30 Was synthesized in a similar manner as depicted in Scheme 9, Step 3, using 4-(4,4,5,5-tetramethyl-1,3,2-dioxaborolan-2-yl)-1H-pyrazole.

3-(benzo[d][1,3]dioxol-5-yl)-2-methyl-5-(1H-pyrazol-4-yl)-3H-imidazo[4,5-b]pyridine 30.

Tan solid (43 mg, 0.135 mmol, 48% yield, 100% EtOAc).

¹H NMR (DMSO) δ: 12.97 (bs, 1H), 8.31-7.77 (m, 3H), 7.59 (d, J=8.2 Hz, 1H), 7.21 (d, J=2.0 Hz, 1H), 7.14 (d, J=8.2 Hz, 1H), 7.04 (dd, J=8.2, 2.1 Hz, 1H), 6.19 (s, 2H), 2.45 (s, 3H).

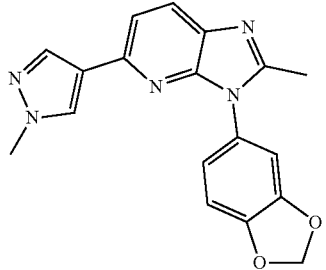

31

31 Was synthesized in a similar manner as depicted in Scheme 9, Step 3, using 1-methyl-4-(4,4,5,5-tetramethyl-1,3,2-dioxaborolan-2-yl)-1H-pyrazole.

3-(benzo[d][1,3]dioxol-5-yl)-2-methyl-5-(1-methyl-1H-pyrazol-4-yl)-3H-imidazo[4,5-b]pyridine 31.

Green semi-solid (38 mg, 0.114 mmol, 55% yield, 7% MeOH in DCM)

¹H NMR (CDCl₃) δ: 7.98-7.77 (m, 2H), 7.55 (s, 1H), 7.42 (d, J=8.3 Hz, 1H), 7.22-6.76 (m, 3H), 6.13 (s, 2H), 3.93 (s, 3H), 2.56 (s, 3H).

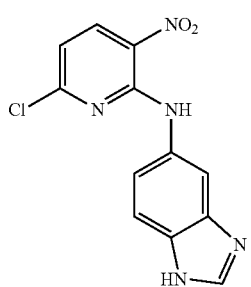

32-A

32-A Was synthesized in a similar manner as depicted in Scheme 9, Step 1, using 1H-benzo[d]imidazol-5-amine.

N-(6-chloro-3-nitropyridin-2-yl)-1H-benzo[d]imidazol-5-amine 32-A.

Red solid (1.24 g, 4.28 mmol, 86% yield).

¹H NMR (DMSO) δ: 10.22 (s, 1H), 8.54 (d, J=8.5 Hz, 1H), 8.25 (s, 1H), 7.90 (d, J=2.0 Hz, 1H), 7.60 (d, J=8.6 Hz, 1H), 7.31 (dd, J=8.6, 2.0 Hz, 1H), 6.96 (d, J=8.6 Hz, 1H), 3.57 (bs, 1H).

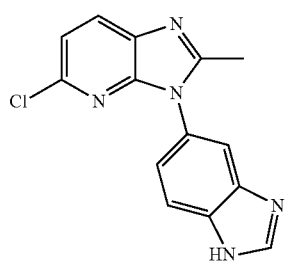

32-B

32-B Was synthesized in a similar manner as depicted in Scheme 9, Step 2.

3-(1H-benzo[d]imidazol-5-yl)-5-chloro-2-methyl-3H-imidazo[4,5-b]pyridine 32-B.

White solid (222 mg, 0.782 mmol, 23% yield, 18% MeOH in DCM).

¹H NMR (DMSO) δ: 12.79 (s, 1H), 8.41 (s, 1H), 8.10 (d, J=8.3 Hz, 1H), 7.84-7.76 (m, 2H), 7.38-7.29 (m, 2H), 2.46 (s, 3H).

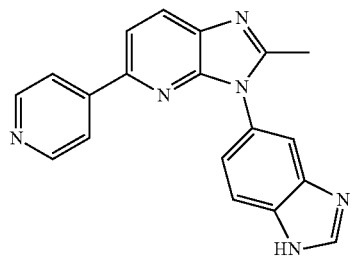

32

32 Was synthesized in a similar manner as depicted in Scheme 9, Step 3.

3-(1H-benzo[d]imidazol-5-yl)-2-methyl-5-(pyridin-4-yl)-3H-imidazo[4,5-b]pyridine 32.

White semi-solid (40 mg, 0.123 mmol, 58% yield, 20% MeOH in DCM).

¹H NMR (CDCl₃) δ: 8.64 (d, J=6.3 Hz, 2H), 8.25 (s, 1H), 8.13 (d, J=8.3 Hz, 1H), 7.90 (d, J=6.2 Hz, 2H), 7.86-7.78 (m, 3H), 7.38 (dd, J=8.5, 2.0 Hz, 1H), 2.65 (s, 3H).

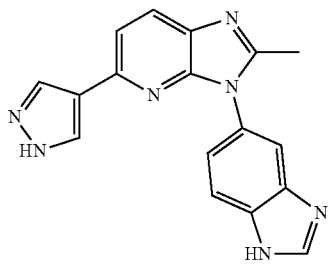

33

33 Was synthesized in a similar manner as depicted in Scheme 9, Step 3, using 4-(4,4,5,5-tetramethyl-1,3,2-dioxaborolan-2-yl)-1H-pyrazole.

3-(1H-benzo[d]imidazol-5-yl)-2-methyl-5-(1H-pyrazol-4-yl)-3H-imidazo[4,5-b]pyridine 33.

White solid (50 mg, 0.159 mmol, 56% yield, 100% EtOAc).

¹H NMR (DMSO) δ: 12.92 (bs, 2H), 8.40 (s, 1H), 8.05-7.89 (m, 3H), 7.86-7.71 (m, 2H), 7.60 (d, J=8.3 Hz, 1H), 7.36 (dd, J=8.4, 1.9 Hz, 1H), 2.46 (s, 3H).

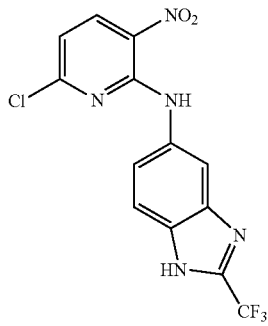

34-A

34-A Was synthesized in a similar manner as depicted in Scheme 9, Step 1, using 2-(trifluoromethyl)-1H-benzo[d]imidazol-5-amine.

N-(6-chloro-3-nitropyridin-2-yl)-2-(trifluoromethyl)-1H-benzoimidazol-5-amine 34-A.

Orange solid (730 mg, 2.041 mmol, 68% yield).

$^1$H NMR (DMSO) δ: 13.99 (bs, 1H), 10.26 (s, 1H), 8.55 (d, J=8.6 Hz, 1H), 8.07 (d, J=2.0 Hz, 1H), 7.74 (bs, J=8.9 Hz, 1H), 7.54-7.45 (m, 1H), 7.00 (d, J=8.6 Hz, 1H).

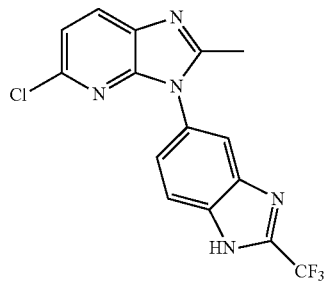

34-B

34-B Was synthesized in a similar manner as depicted in Scheme 9, Step 2.

5-chloro-2-methyl-3-(2-(trifluoromethyl)-1H-benzo[d]imidazol-5-yl)-3H-imidazo[4,5-b]pyridine 34-B.

Tan solid (61 mg, 0.173 mmol, 9% yield, 9% MeOH in DCM).

$^1$H NMR (CDCl$_3$) δ: 13.29 (bs, 1H), 8.07 (d, J=8.3 Hz, 1H), 7.82 (bs, 1H), 7.57 (bs, 1H), 7.34 (d, J=8.3 Hz, 1H), 7.25 (d, J=8.4 Hz, 1H), 2.53 (s, 3H).

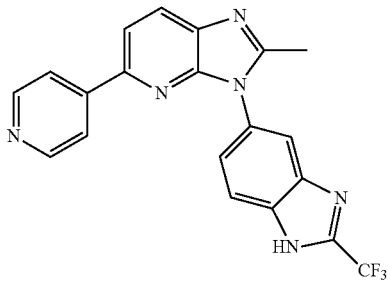

34

34 Was synthesized in a similar manner as depicted in Scheme 9, Step 3.

2-methyl-5-(pyridin-4-yl)-3-(2-(trifluoromethyl)-1H-benzo[d]imidazol-5-yl)-3H-imidazo[4,5-b]pyridine 34.

Tan solid (41 mg, 0.104 mmol, 61% yield, 8% MeOH in DCM).

$^1$H NMR (CDCl$_3$) δ: 8.69 (d, J=5.1 Hz, 2H), 8.13 (d, J=8.3 Hz, 1H), 7.96 (d, J=4.9 Hz, 3H), 7.90 (s, 1H), 7.83 (d, J=8.3 Hz, 1H), 7.44 (dd, J=8.6, 1.9 Hz, 1H), 2.69 (s, 3H).

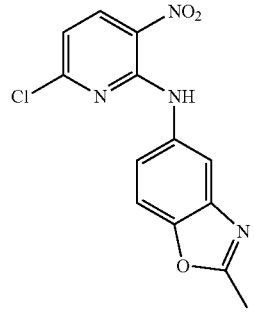

35-A

35-A Was synthesized in a similar manner as depicted in Scheme 9, Step 1, using 2-methylbenzo[d]oxazol-5-amine.

N-(6-chloro-3-nitropyridin-2-yl)-2-methylbenzo[d]oxazol-5-amine 35-A.

Red solid (1.14 g, 3.74 mmol, 94% yield).

$^1$H NMR (DMSO) δ: 10.20 (s, 1H), 8.54 (d, J=8.6 Hz, 1H), 7.90 (d, J=2.1 Hz, 1H), 7.66 (d, J=8.7 Hz, 1H), 7.46 (dd, J=8.7, 2.2 Hz, 1H), 6.99 (d, J=8.5 Hz, 1H), 2.63 (s, 3H).

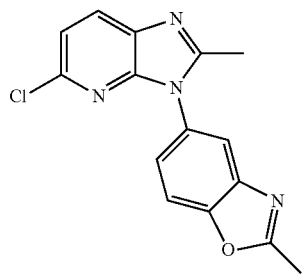

35-B

35-B Was synthesized in a similar manner as depicted in Scheme 9, Step 2.

5-(5-chloro-2-methyl-3H-imidazo[4,5-b]pyridin-3-yl)-2-methylbenzo[d]oxazole 35-B.

Tan solid (343 mg, 1.148 mmol, 39% yield, 100% EtOAc).

$^1$H NMR (CDCl$_3$) δ: 7.97 (d, J=8.3 Hz, 1H), 7.70-7.65 (m, 2H), 7.33 (dd, J=8.5, 2.1 Hz, 1H), 7.27 (d, J=8.3 Hz, 1H), 2.73 (s, 3H), 2.55 (s, 3H). $^{13}$C NMR (CDCl$_3$) δ: 165.84, 153.79, 151.12, 148.39, 145.26, 142.64, 133.58, 130.26, 128.85, 124.00, 118.96, 118.88, 111.27, 15.10, 14.64.

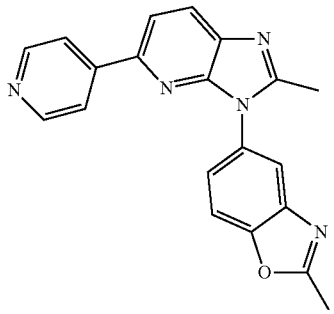

35 Was synthesized in a similar manner as depicted in Scheme 9, Step 3, 2-methyl-5-(2-methyl-5-(pyridin-4-yl)-3H-imidazo[4,5-b]pyridin-3-yl)benzo[d]oxazole 35.

Green semi-solid (29 mg, 0.085 mmol, 25% yield, 100% EtOAc).

$^1$H NMR (CDCl$_3$) δ: 8.64 (d, J=5.2 Hz, 2H), 8.13 (d, J=8.3 Hz, 1H), 7.93-7.69 (m, 5H), 7.42 (dd, J=8.6, 2.1 Hz, 1H), 2.76 (s, 3H), 2.63 (s, 3H).

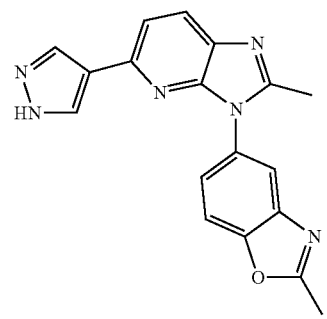

36 Was synthesized in a similar manner as depicted in Scheme 9, Step 3, using 4-(4,4,5,5-tetramethyl-1,3,2-dioxaborolan-2-yl)-1H-pyrazole.

2-methyl-5-(2-methyl-5-(1H-pyrazol-4-yl)-3H-imidazo[4,5-b]pyridin-3-yl)benzo oxazole 36.

Tan solid (33 mg, 0.100 mmol, 30% yield, 8% MeOH in DCM).

$^1$H NMR (CDCl$_3$) δ: 8.02 (s, 2H), 8.00 (d, J=8.2 Hz, 1H), 7.77 (d, J=2.0 Hz, 1H), 7.68 (dd, J=8.5, 0.6 Hz, 1H), 7.49 (d, J=8.2 Hz, 1H), 7.41 (dd, J=8.5, 2.1 Hz, 1H), 2.74 (s, 3H), 2.59 (s, 3H).

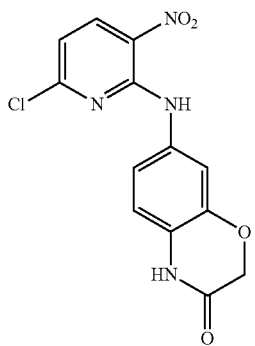

37-A Was synthesized in a similar manner as depicted in Scheme 9, Step 1, using 7-amino-2H-benzo[b][1,4]oxazin-3(4H)-one.

7-((6-chloro-3-nitropyridin-2-yl)amino)-2H-benzo[b][1,4]oxazin-3(4H)-one 37-A.

Black solid (815 mg, 2.54 mmol, 83% yield).

$^1$H NMR (DMSO) δ: 10.74 (s, 1H), 10.03 (s, 1H), 8.52 (d, J=8.6 Hz, 1H), 7.32 (d, J=2.3 Hz, 1H), 7.12 (dd, J=8.5, 2.3 Hz, 1H), 6.98 (d, J=8.6 Hz, 1H), 6.89 (d, J=8.4 Hz, 1H), 4.60 (s, 2H). $^{13}$C NMR (DMSO) δ: 164.95, 154.66, 149.53, 143.47, 139.24, 133.20, 128.23, 124.70, 117.80, 115.98, 114.28, 111.81, 67.20.

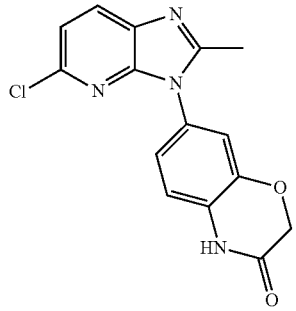

37-B Was synthesized in a similar manner as depicted in Scheme 9, Step 2.

7-(5-chloro-2-methyl-3H-imidazo[4,5-b]pyridin-3-yl)-2H-benzo[b][1,4]oxazin-3(4H)-one 37-B.

Tan solid (100 mg, 0.318 mmol, 13% yield, 100% EtOAc).

$^1$H NMR (DMSO) δ: 10.97 (s, 1H), 8.06 (d, J=8.2 Hz, 1H), 7.33 (d, J=8.2 Hz, 1H), 7.22 (s, 1H), 7.17-7.05 (m, 2H), 4.70 (s, 2H), 2.45 (s, 3H).

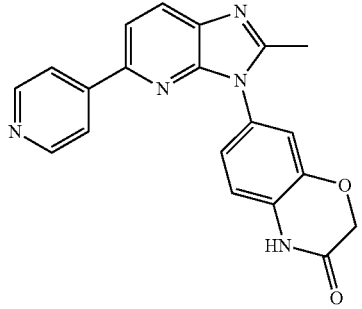

37 Was synthesized in a similar manner as depicted in Scheme 9, Step 3.

7-(2-methyl-5-(pyridin-4-yl)-3H-imidazo[4,5-b]pyridin-3-yl)-2H-benzo[b][1,4]oxazin-3(4H)-one 37.

Yellow solid (31 mg, 0.087 mmol, 27% yield, 10% MeOH in DCM).

$^1$H NMR (DMSO) δ: 10.98 (s, 1H), 8.64 (d, J=6.0 Hz, 2H), 8.16 (d, J=8.3 Hz, 1H), 8.03 (d, J=8.3 Hz, 1H), 7.97 (d, J=6.1 Hz, 2H), 7.31 (d, J=2.3 Hz, 1H), 7.22 (dd, J=8.3, 2.2 Hz, 1H), 7.12 (d, J=8.3 Hz, 1H), 4.72 (s, 2H), 2.52 (s, 3H). $^{13}$C NMR (DMSO) δ: 165.11, 155.47, 150.71, 149.42, 147.69, 146.26, 143.94, 135.41, 129.37, 128.20, 127.30, 122.15, 121.10, 116.61, 116.57, 116.09, 67.18, 15.42.

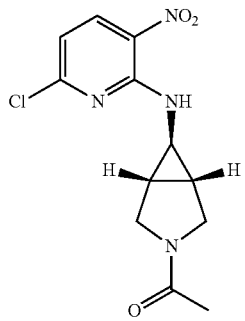

38-A

38-A Was synthesized in a similar manner as depicted in Scheme 9, Step 1, using 1-((1R,5S,6s)-6-amino-3-azabicyclo[3.1.0]hexan-3-yl)ethan-1-one.

1-((1R,5S,6s)-6-(((6-chloro-3-nitropyridin-2-yl)amino)-3-azabicyclo[3.1.0]hexan-3-yl)ethan-1-one 38-A.

Yellow solid (460 mg, 1.297 mmol, 51% yield).

$^1$H NMR (DMSO) δ: 8.50 (s, 1H), 8.43 (d, J=8.5 Hz, 1H), 6.88 (d, J=8.5 Hz, 1H), 3.60-3.51 (m, 2H), 3.45-3.35 (m, 2H), 3.33 (s, 3H), 2.55 (t, J=2.4 Hz, 1H), 1.98-1.91 (m, 2H)

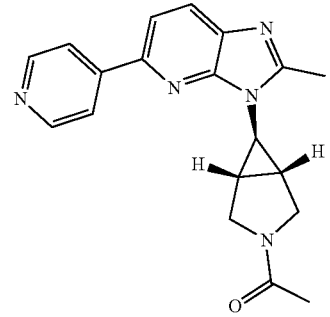

38

38 Was synthesized in a similar manner as depicted in Scheme 9, Step 3.

1-((1R,5S,6s)-6-(2-methyl-5-(pyridin-4-yl)-3H-imidazo[4,5-b]pyridin-3-yl)-3-azabicyclo[3.1.0]hexan-3-yl)ethan-1-one 38.

Green oil (99 mg, 0.297 mmol, 86% yield, 15% MeOH in DCM).

$^1$H NMR (CDCl$_3$) δ: 8.90-8.53 (m, 2H), 8.07-7.85 (m, 3H), 7.74 (d, J=8.3 Hz, 1H), 4.23 (d, J=12.1 Hz, 1H), 4.03 (d, J=10.4 Hz, 1H), 3.90 (dd, J=10.4, 4.5 Hz, 1H), 3.68 (dd, J=12.2, 4.7 Hz, 1H), 3.01 (t, J=2.3 Hz, 1H), 2.79-2.74 (m, 1H), 2.72 (s, 3H), 2.49-2.33 (m, 1H), 2.12 (s, 3H). $^{13}$C NMR (CDCl$_3$) δ: 169.86, 156.21, 150.38, 149.16, 147.92, 146.55, 135.12, 127.03, 120.85, 115.65, 49.22, 47.43, 34.22, 24.89, 24.14, 22.75, 15.38.

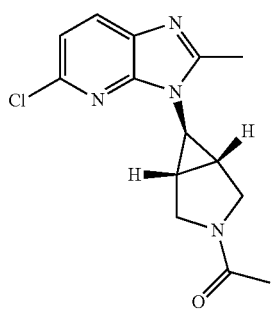

38-B

38-B Was synthesized in a similar manner as depicted in Scheme 9, Step 2.

1-((1R,5S,6s)-6-(5-chloro-2-methyl-3H-imidazo[4,5-b]pyridin-3-yl)-3-azabicyclo[3.1.0]hexan-3-yl)ethan-1-one 38-B.

Light yellow solid (203 mg, 0.698 mmol, 62% yield, 8% MeOH in DCM).

$^1$H NMR (CDCl$_3$) δ: 7.71 (d, J=8.3 Hz, 1H), 7.05 (d, J=8.3 Hz, 1H), 4.04 (d, J=12.2 Hz, 1H), 3.91 (d, J=10.5 Hz, 1H), 3.74 (dd, J=10.5, 4.6 Hz, 1H), 3.51 (dd, J=12.2, 4.7 Hz, 1H), 2.84 (t, J=2.3 Hz, 1H), 2.62-2.55 (m, 1H), 2.57 (s, 3H), 2.23 (ddd, J=7.9, 4.5, 2.3 Hz, 1H), 1.97 (s, 3H)

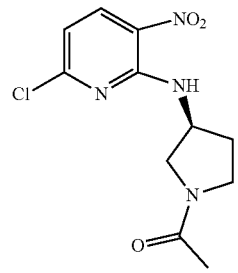

39-A

39-A Was synthesized in a similar manner as depicted in Scheme 9, Step 1, using (S)-1-(3-aminopyrrolidin-1-yl)ethan-1-one.

(S)-1-(3-((6-chloro-3-nitropyridin-2-yl)amino)pyrrolidin-1-yl)ethan-1-one 39-A.

Yellow-green oil (559 mg, 1.631 mmol, 54% yield, 18% EtOAc in hexanes).

$^1$H NMR (CDCl$_3$) δ: 8.36 (d, J=8.6 Hz, 2H), 6.68 (d, J=8.6 Hz, 1H), 4.80 (bs, 1H), 3.82 (dd, J=11.4, 6.3 Hz, 1H), 3.55-3.46 (m, 2H), 3.46-3.09 (m, 1H), 2.34 (ddt, J=12.9, 7.7, 6.4 Hz, 1H), 2.10-1.89 (m, 1H), 1.49 (s, 3H).

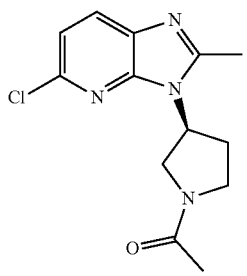

39-B

39-B Was synthesized in a similar manner as depicted in Scheme 9, Step 2.

(S)-1-(3-(5-chloro-2-methyl-3H-imidazo[4,5-b]pyridin-3-yl)pyrrolidin-1-yl)ethan-1-one 39-B.

Red oil (407 mg, 1.46 mmol, 90% yield, 13% MeOH in DCM).

$^1$H NMR (CDCl$_3$) δ: 7.85 (dd, J=8.3, 6.6 Hz, 1H), 7.18 (t, J=8.2 Hz, 1H), 5.11-4.93 (m, 1H), 4.44-3.48 (m, 4H), 3.18-2.91 (m, 1H), 2.73-2.64 (m, 3H), 2.52-2.23 (m, 1H), 2.18-2.08 (m, 3H)

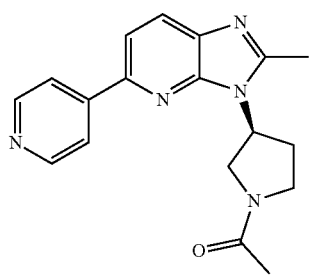

39

39 Was synthesized in a similar manner as depicted in Scheme 9, Step 3.

(S)-1-(3-(2-methyl-5-(pyridin-4-yl)-3H-imidazo[4,5-b]pyridin-3-yl)pyrrolidin-1-yl)ethan-1-one 39.

Orange semi-solid (44 mg, 0.137 mmol, 38% yield, 16% MeOH in DCM).

$^1$H NMR (CDCl$_3$) δ: 8.81-8.65 (m, 2H), 8.03 (dd, J=8.3, 6.3 Hz, 1H), 7.94-7.83 (m, 2H), 7.76 (dd, J=15.3, 8.3 Hz, 1H), 5.21-4.99 (m, 1H), 4.61-4.29 (m, 1H), 4.24-3.89 (m, 2H), 3.82-3.57 (m, 1H), 3.26-3.08 (m, 1H), 2.74 (d, J=8.8 Hz, 3H), 2.57-2.31 (m, 1H), 2.20-2.09 (m, 3H).

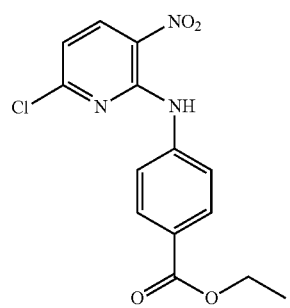

40-A

40-A Was synthesized in a similar manner as depicted in Scheme 9, Step 1 using ethyl 4-aminobenzoate.

ethyl 4-((6-chloro-3-nitropyridin-2-yl)amino)benzoate 40-A.

Yellow solid (1.2 g, 3.73 mmol, 55% yield).

$^1$H NMR (DMSO) δ: 10.26 (s, 1H), 8.51 (d, J=8.6 Hz, 1H), 7.94 (d, J=8.9 Hz, 2H), 7.70 (d, J=8.9 Hz, 2H), 6.98 (d, J=8.5 Hz, 1H), 4.31 (q, J=7.1 Hz, 2H), 1.34 (t, J=7.0 Hz, 3H).

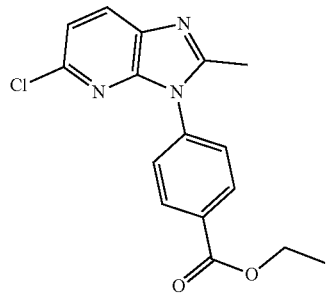

40-B

40-B Was synthesized in a similar manner as depicted in Scheme 9, Step 2.

ethyl 4-(5-chloro-2-methyl-3H-imidazo[4,5-b]pyridin-3-yl)benzoate 40-B.

Yellow oil (148 mg, 0.469 mmol, 46% yield, 100% DCM).

$^1$H NMR (CDCl$_3$) δ: 8.24 (d, J=8.9 Hz, 2H), 7.93 (d, J=8.3 Hz, 1H), 7.50 (d, J=8.7 Hz, 2H), 7.23 (d, J=8.3 Hz, 1H), 4.42 (q, J=7.1 Hz, 2H), 2.56 (s, 3H), 1.42 (t, J=7.1 Hz, 3H).

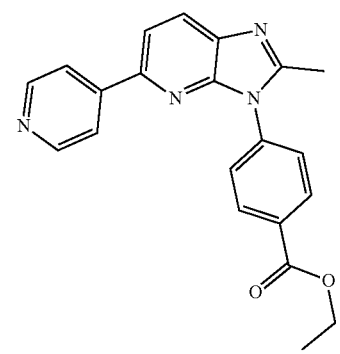

40

40 Was synthesized in a similar manner as depicted in Scheme 9, Step 3.

ethyl 4-(2-methyl-5-(pyridin-4-yl)-3H-imidazo[4,5-b]pyridin-3-yl)benzoate 40.

White solid (133 mg, 0.371 mmol, 84% yield, 8% MeOH).

$^1$H NMR (CDCl$_3$) δ: 8.67 (d, J=6.3 Hz, 2H), 8.33 (d, J=8.8 Hz, 2H), 8.12 (d, J=8.3 Hz, 1H), 7.90 (d, J=6.2 Hz, 2H), 7.84 (d, J=8.3 Hz, 1H), 7.62 (d, J=8.7 Hz, 2H), 4.48 (q, J=7.1 Hz, 2H), 2.67 (s, 3H), 1.48 (t, J=7.1 Hz, 3H). $^{13}$C NMR (CDCl$_3$) δ: 165.63, 154.04, 150.24, 148.88, 148.75, 146.37, 138.27, 135.25, 130.94, 130.82, 127.26, 127.08, 120.98, 116.41, 61.48, 15.52, 14.37.

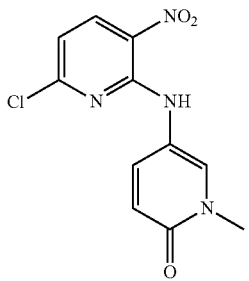

41-A

41-A Was synthesized in a similar manner as depicted in Scheme 9, Step 1 using 5-amino-1-methylpyridin-2(1H)-one.

5-((6-chloro-3-nitropyridin-2-yl)amino)-1-methylpyridin-2(1H)-one 41-A.

Red solid (313 mg, 1.115 mmol, 28% yield).

¹H NMR (DMSO) δ: 9.83 (s, 1H), 8.52 (d, J=8.6 Hz, 1H), 7.84 (d, J=2.9 Hz, 1H), 7.52 (dd, J=9.6, 2.9 Hz, 1H), 6.96 (d, J=8.6 Hz, 1H), 6.43 (d, J=9.5 Hz, 1H), 3.45 (s, 3H).

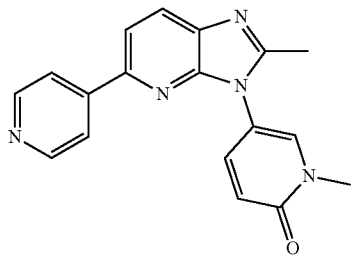

41-B

41-B Was synthesized in a similar manner as depicted in Scheme 9, Step 2.

5-(5-chloro-2-methyl-3H-imidazo[4,5-b]pyridin-3-yl)-1-methylpyridin-2(1H)-one 41-B.

Green solid (203 mg, 0.739 mmol, 66% yield, 12% MeOH in DCM).

¹H NMR (CDCl₃) δ: 7.86 (d, J=8.3 Hz, 1H), 7.56 (d, J=2.9 Hz, 1H), 7.28 (dd, J=9.6, 2.9 Hz, 1H), 7.19 (d, J=8.3 Hz, 1H), 6.64 (d, J=9.6 Hz, 1H), 3.57 (s, 3H), 2.50 (s, 3H). ¹³C NMR (CDCl₃) δ: 161.79, 153.80, 148.07, 145.28, 138.88, 137.97, 133.46, 129.10, 121.32, 119.21, 114.06, 38.16, 14.80.

41

41 Was synthesized in a similar manner as depicted in Scheme 9, Step 3.

1-methyl-5-(2-methyl-5-(pyridin-4-yl)-3H-imidazo[4,5-b]pyridin-3-yl)pyridin-2(1H)-one 41.

White semi-solid (75 mg, 0.236 mmol, 65% yield, 10% MeOH in DCM).

¹H NMR (CDCl₃) δ: 8.71 (d, J=5.1 Hz, 2H), 8.10 (d, J=8.2 Hz, 1H), 7.90 (d, J=5.6 Hz, 2H), 7.82 (d, J=8.3 Hz, 1H), 7.59 (dd, J=2.8, 0.6 Hz, 1H), 7.42 (dd, J=9.6, 2.9 Hz, 1H), 6.79 (dd, J=9.6, 0.6 Hz, 1H), 3.69 (s, 3H), 2.64 (s, 3H).

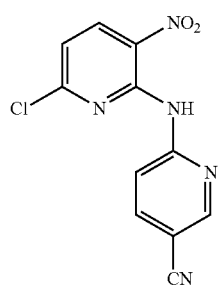

42-A

42-A Was synthesized in a similar manner as depicted in Scheme 9, Step 1 using 6-aminonicotinonitrile.

6-((6-chloro-3-nitropyridin-2-yl)amino)nicotinonitrile 42-A.

Brown solid (1.3 g, 4.72 mmol, 67% yield).

¹H NMR (DMSO) δ: 10.76 (bs, 1H), 8.72 (dd, J=2.3, 0.8 Hz, 1H), 8.60 (d, J=8.6 Hz, 1H), 8.29 (dd, J=8.8, 2.3 Hz, 1H), 8.03 (dd, J=8.8, 0.9 Hz, 1H), 7.34 (d, J=8.6 Hz, 1H). ¹³C NMR (DMSO) δ: 154.22, 153.35, 152.47, 146.45, 142.50, 139.13, 132.22, 118.10, 117.73, 113.17, 103.41.

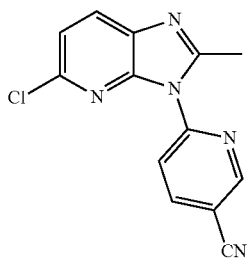

42-B

42-B Was synthesized in a similar manner as depicted in Scheme 9, Step 2.

6-(5-chloro-2-methyl-3H-imidazo[4,5-b]pyridin-3-yl)nicotinonitrile 42-B.

White solid (279 mg, 1.035 mmol, 37% yield, 30% EtOAc in hexanes).

¹H NMR (CDCl₃) δ: 8.89 (dd, J=2.3, 0.8 Hz, 1H), 8.37 (dd, J=8.5, 0.8 Hz, 1H), 8.26 (dd, J=8.5, 2.3 Hz, 1H), 7.98 (d, J=8.3 Hz, 1H), 7.34 (d, J=8.3 Hz, 1H), 2.91 (s, 3H). ¹³C NMR (CDCl₃) δ: 154.10, 151.78, 150.74, 146.42, 145.26, 141.86, 133.89, 129.44, 120.05, 119.50, 116.02, 108.63, 17.83.

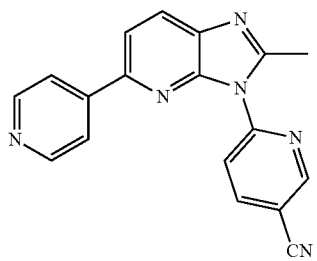

42

42 Was synthesized in a similar manner as depicted in Scheme 9, Step 3.

6-(2-methyl-5-(pyridin-4-yl)-3H-imidazo[4,5-b]pyridin-3-yl)nicotinonitrile 42.

Light yellow semi-solid (62 mg, 0.199 mmol, 67% yield, 100% EtOAc).

$^1$H NMR (CDCl$_3$) δ: 8.93 (dd, J=2.3, 0.9 Hz, 1H), 8.74 (d, J=6.1 Hz, 2H), 8.56 (dd, J=8.5, 0.9 Hz, 1H), 8.31 (dd, J=8.5, 2.3 Hz, 1H), 8.14 (d, J=8.3 Hz, 1H), 7.92 (d, J=5.9 Hz, 2H), 7.89 (d, J=8.3 Hz, 1H), 2.98 (s, 3H). $^{13}$C NMR (CDCl$_3$) δ: 155.23, 151.83, 151.15, 150.50, 148.90, 147.62, 146.08, 141.53, 135.45, 127.82, 120.96, 119.47, 117.25, 116.10, 108.41, 18.09.

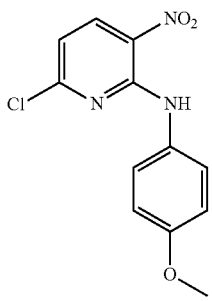

43-A

43-A Was synthesized in a similar manner as depicted in Scheme 9, Step 1 using 4-methoxyaniline.

6-chloro-N-(4-methoxyphenyl)-3-nitropyridin-2-amine 43-A.

Orange solid (927 mg, 3.31 mmol, 53% yield).

$^1$H NMR (DMSO) δ: 10.05 (s, 1H), 8.51 (d, J=8.6 Hz, 1H), 7.47 (d, J=9.3 Hz, 2H), 6.97 (d, J=9.3 Hz, 2H), 6.94 (d, J=8.6 Hz, 1H), 3.78 (s, 3H). $^{13}$C NMR (DMSO) δ: 157.19, 154.86, 150.08, 139.22, 130.79, 127.92, 125.66, 114.33, 113.83, 55.73.

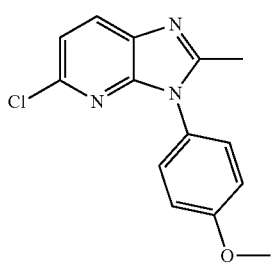

43-B

43-B Was synthesized in a similar manner as depicted in Scheme 9, Step 2.

5-chloro-3-(4-methoxyphenyl)-2-methyl-3H-imidazo[4,5-b]pyridine 43-B.

Pink solid (305 mg, 1.114 mmol, 34% yield, 40% EtOAc in hexanes).

$^1$H NMR (CDCl$_3$) δ: 7.93 (d, J=8.2 Hz, 1H), 7.30 (d, J=8.9 Hz, 2H), 7.23 (d, J=8.2 Hz, 1H), 7.07 (d, J=9.0 Hz, 2H), 3.89 (s, 3H), 2.52 (s, 3H) $^{13}$C NMR (CDCl$_3$) δ: 160.06, 154.01, 148.37, 145.06, 133.57, 128.69, 128.51, 126.61, 118.72, 115.05, 55.61, 15.03.

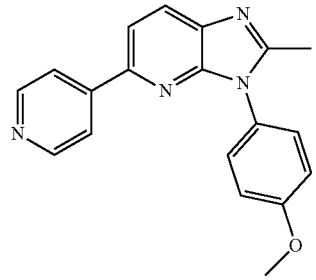

43

43 Was synthesized in a similar manner as depicted in Scheme 9, Step 3.

3-(4-methoxyphenyl)-2-methyl-5-(pyridin-4-yl)-3H-imidazo[4,5-b]pyridine 43.

Green semi-solid (7 mg, 0.022 mmol, 3% yield, 20% EtOAc in hexanes).

$^1$H NMR (CDCl$_3$) δ: 8.67 (d, J=6.2 Hz, 2H), 8.10 (d, J=8.3 Hz, 1H), 7.90 (d, J=6.3 Hz, 2H), 7.81 (d, J=8.3 Hz, 1H), 7.41 (d, J=9.1 Hz, 2H), 7.14 (d, J=9.1 Hz, 2H), 3.96 (s, 3H), 2.61 (s, 3H).

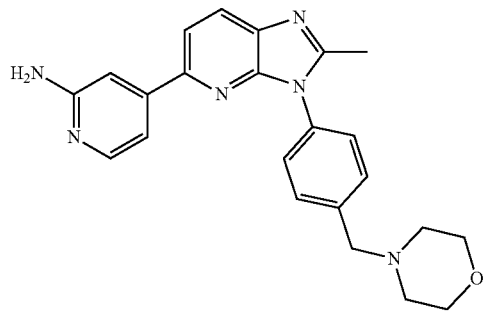

44

44 Was synthesized in a similar manner as depicted in Scheme 9, Step 3 using 4-(4,4,5,5-tetramethyl-1,3,2-dioxaborolan-2-yl)pyridin-2-amine.

4-(2-methyl-3-(4-(morpholinomethyl)phenyl)-3H-imidazo[4,5-b]pyridin-5-yl)pyridin-2-amine 44.

White semi-solid (280 mg, 0.699 mmol, 60% yield, 11% MeOH in DCM).

$^1$H NMR (CDCl$_3$) δ: 8.13 (dd, J=5.4, 0.8 Hz, 1H), 8.07 (d, J=8.3 Hz, 1H), 7.74 (d, J=8.3 Hz, 1H), 7.60 (d, J=8.2 Hz, 2H), 7.45 (d, J=8.6 Hz, 2H), 7.24 (dd, J=5.4, 1.5 Hz, 1H), 7.17-7.10 (m, 1H), 4.52 (bs, 2H), 3.82-3.75 (m, 4H), 3.65 (s, 2H), 2.62 (s, 3H), 2.61-2.44 (m, 4H). $^{13}$C NMR (CDCl$_3$) δ: 159.00, 154.37, 149.23, 149.04, 148.97, 148.54, 138.88, 135.08, 133.44, 130.09, 127.14, 126.86, 116.24, 112.18, 106.04, 67.04, 62.88, 53.76, 15.45.

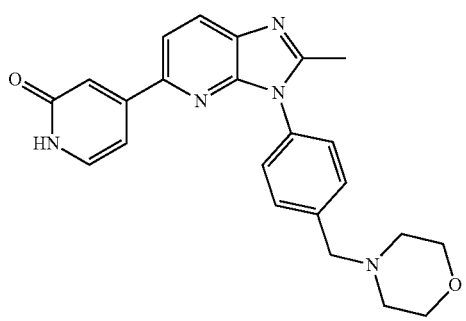

45

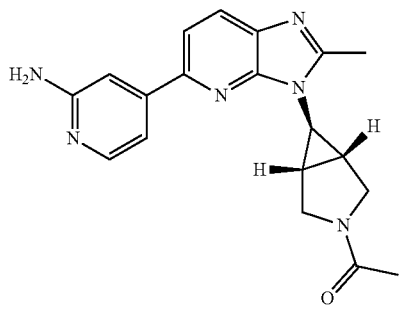

47

45 Was synthesized in a similar manner as depicted in Scheme 9, Step 3 using (2-hydroxypyridin-4-yl)boronic acid.

4-(2-methyl-3-(4-(morpholinomethyl)phenyl)-3H-imidazo[4,5-b]pyridin-5-yl)pyridin-2(1H)-one 45.

White solid (14 mg, 0.035 mmol, 60% yield, 20% MeOH in DCM).

$^1$H NMR (CDCl$_3$) δ: 13.14 (bs, 1H), 8.09 (d, J=8.3 Hz, 1H), 7.75 (d, J=8.3 Hz, 1H), 7.59 (d, J=8.3 Hz, 2H), 7.46-7.37 (m, 3H), 7.24 (s, 1H), 6.98 (d, J=6.8 Hz, 1H), 3.85-3.74 (m, 4H), 3.65 (s, 2H), 2.72-2.46 (m, 7H). $^{13}$C NMR (CDCl$_3$) δ: 155.03, 152.09, 149.04, 147.78, 139.07, 135.48, 134.27, 133.20, 130.11, 127.09, 126.88, 116.79, 116.57, 105.89, 67.04, 62.85, 53.77, 15.42. (Note: Pyridone C=O absent, also observed in other related pyridone compounds).

47 Was synthesized in a similar manner as depicted in Scheme 9, Step 3 using 4-(4,4,5,5-tetramethyl-1,3,2-dioxaborolan-2-yl)pyridin-2-amine.

1-((1R,5S,6s)-6-(5-(2-aminopyridin-4-yl)-2-methyl-3H-imidazo[4,5-b]pyridin-3-yl)-3-azabicyclo[3.1.0]hexan-3-yl)ethan-1-one 47.

Tan semi-solid (17 mg, 0.049 mmol, 47% yield, 25% MeOH in DCM).

$^1$H NMR (CDCl$_3$) δ: 8.19 (d, J=5.4 Hz, 1H), 7.96 (d, J=8.3 Hz, 1H), 7.68 (d, J=8.3 Hz, 1H), 7.32 (dd, J=5.4, 1.5 Hz, 1H), 7.19 (s, 1H), 4.66 (bs, 2H), 4.25 (d, J=12.2 Hz, 1H), 4.04 (d, J=10.4 Hz, 1H), 3.90 (dd, J=10.4, 4.5 Hz, 1H), 3.69 (dd, J=12.2, 4.7 Hz, 1H), 3.02 (t, J=2.3 Hz, 1H), 2.80-2.71 (m, 1H), 2.73 (s, 3H), 2.52-2.41 (m, 1H), 2.14 (s, 3H). $^{13}$C NMR (CDCl$_3$) δ: 169.94, 159.10, 155.94, 148.97, 148.62, 148.57, 134.91, 126.89, 115.75, 112.00, 105.81, 49.26, 47.48, 34.24, 24.90, 24.14, 22.75, 15.37.

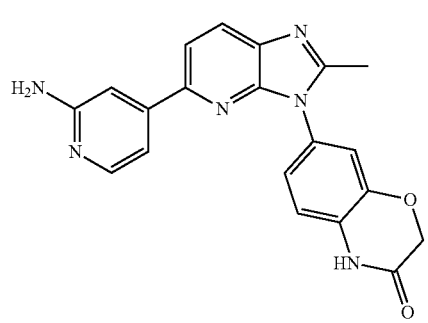

46

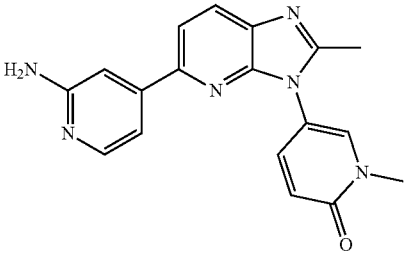

48

46 Was synthesized in a similar manner as depicted in Scheme 9, Step 3 using 4-(4,4,5,5-tetramethyl-1,3,2-dioxaborolan-2-yl)pyridin-2-amine.

7-(5-(2-aminopyridin-4-yl)-2-methyl-3H-imidazo[4,5-b]pyridin-3-yl)-2H-benzo[b][1,4]oxazin-3(4H)-one 46.

Off-white semi-solid (8 mg, 0.021 mmol, 34% yield, 15% MeOH in DCM).

$^1$H NMR (DMSO) δ: 10.99 (s, 1H), 8.10 (d, J=8.2 Hz, 1H), 7.96 (d, J=5.4 Hz, 1H), 7.80 (d, J=8.4 Hz, 1H), 7.28 (d, J=2.2 Hz, 1H), 7.19 (dd, J=8.3, 2.2 Hz, 1H), 7.11 (d, J=8.3 Hz, 1H), 7.05 (d, J=5.5 Hz, 1H), 7.00 (s, 1H), 5.98 (s, 2H), 4.72 (s, 2H), 2.49 (s, 3H).

48 Was synthesized in a similar manner as depicted in Scheme 9, Step 3 using 4-(4,4,5,5-tetramethyl-1,3,2-dioxaborolan-2-yl)pyridin-2-amine.

5-(5-(2-aminopyridin-4-yl)-2-methyl-3H-imidazo[4,5-b]pyridin-3-yl)-1-methylpyridin-2(1H)-one 48.

Green solid (50 mg, 0.150 mmol, 92% yield, 13% MeOH in DCM).

$^1$H NMR (CDCl$_3$) δ: 8.15 (d, J=5.4 Hz, 1H), 8.05 (dd, J=8.3, 1.0 Hz, 1H), 7.74 (d, J=8.3 Hz, 1H), 7.57 (d, J=2.9 Hz, 1H), 7.41 (dd, J=9.6, 2.9 Hz, 1H), 7.22 (dd, J=5.4, 1.5 Hz, 1H), 7.15 (s, 1H), 6.78 (d, J=9.6 Hz, 1H), 4.61 (s, 2H), 3.68 (s, 3H), 2.62 (s, 3H).

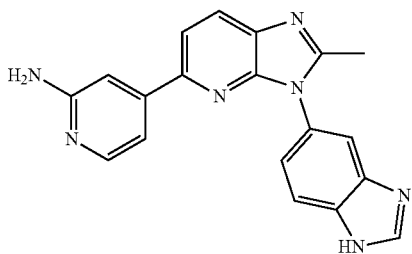

49

49 Was synthesized in a similar manner as depicted in Scheme 9, Step 3 using 4-(4,4,5,5-tetramethyl-1,3,2-dioxaborolan-2-yl)pyridin-2-amine.

4-(3-(1H-benzo[d]imidazol-5-yl)-2-methyl-3H-imidazo[4,5-b]pyridin-5-yl)pyridin-2-amine 49.

White semi-solid (20 mg, 0.059 mmol, 83% yield, 10% MeOH in DCM).

$^1$H NMR (MeOD) δ: 8.40 (s, 1H), 8.11 (d, J=8.3 Hz, 1H), 7.94-7.89 (m, 2H), 7.85 (bs, 2H), 7.45 (d, J=8.9 Hz, 1H), 7.27-7.13 (m, 2H), 5.51 (s, 1H), 2.60 (s, 3H), note: NH$_2$ absent.

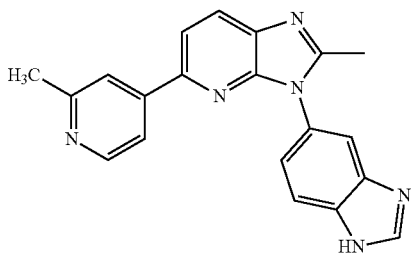

50

50 Was synthesized in a similar manner as depicted in Scheme 9, Step 3 using (2-methylpyridin-4-yl)boronic acid.

3-(1H-benzo[d]imidazol-5-yl)-2-methyl-5-(2-methylpyridin-4-yl)-3H-imidazo[4,5-b]pyridine 50.

White semi-solid (12 mg, 0.035 mmol, 50% yield, 11% MeOH in DCM).

$^1$H NMR (Acetone) δ: 11.90 (bs, 1H), 8.46 (dd, J=5.2, 0.9 Hz, 1H), 8.37 (s, 1H), 8.10 (d, J=8.3 Hz, 1H), 7.98 (d, J=8.3 Hz, 1H), 7.92-7.86 (m, 2H), 7.84-7.80 (m, 1H), 7.78-7.72 (m, 1H), 7.45 (dd, J=8.5, 2.0 Hz, 1H), 2.57 (s, 3H), 2.51 (s, 3H).

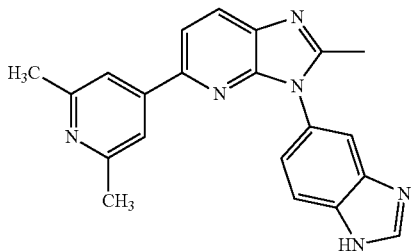

51

51 Was synthesized in a similar manner as depicted in Scheme 9, Step 3 using (2,6-dimethylpyridin-4-yl)boronic acid.

3-(1H-benzo[d]imidazol-5-yl)-5-(2,6-dimethylpyridin-4-yl)-2-methyl-3H-imidazo[4,5-b]pyridine 51.

Clear semi-solid (5 mg, 0.014 mmol, 20% yield, 11% MeOH in DCM).

$^1$H NMR (Acetone) δ: 11.96 (bs, 1H), 8.37 (s, 1H), 8.08 (d, J=8.4 Hz, 1H), 7.95 (d, J=8.4 Hz, 1H), 7.90 (bs, 2H), 7.62 (s, 2H), 7.44 (d, J=8.4 Hz, 1H), 2.56 (s, 3H), 2.45 (s, 6H).

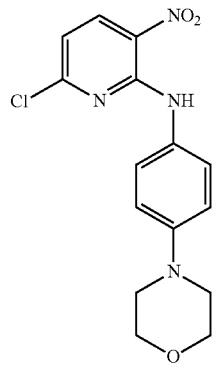

52-A

52-A Was synthesized in a similar manner as depicted in Scheme 9, Step 1 using 4-morpholinoaniline.

6-chloro-N-(4-morpholinophenyl)-3-nitropyridin-2-amine 52-A.

Black solid (1.95 g, 5.83 mmol, 87% yield).

$^1$H NMR (DMSO) δ: 10.04 (s, 1H), 8.51 (d, J=8.6 Hz, 1H), 7.43 (d, J=8.8 Hz, 2H), 6.98 (d, J=9.1 Hz, 2H), 6.93 (d, J=8.6 Hz, 1H), 3.78-3.71 (m, 4H), 3.17-3.09 (m, 4H). $^{13}$C NMR (DMSO) δ: 154.91, 149.95, 149.03, 139.25, 129.56, 127.82, 124.89, 115.47, 113.69, 66.55, 48.95.

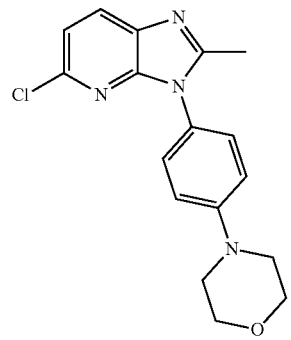

52-B

52-B Was synthesized in a similar manner as depicted in Scheme 9, Step 2.

4-(4-(5-chloro-2-methyl-3H-imidazo[4,5-b]pyridin-3-yl)phenyl)morpholine 52-B.

White solid (865 mg, 2.63 mmol, 55% yield, 100% DCM).

$^1$H NMR (Acetone) δ: 7.97 (d, J=8.2 Hz, 1H), 7.39 (d, J=8.6 Hz, 2H), 7.28 (d, J=8.2 Hz, 1H), 7.17 (d, J=8.8 Hz, 2H), 3.88-3.81 (m, 4H), 3.33-3.26 (m, 4H), 2.48 (s, 3H). $^{13}$C NMR (Acetone) δ: 154.39, 151.83, 148.76, 143.97, 133.94, 128.63, 128.23, 125.44, 117.91, 115.42, 66.42, 48.44, 14.12.

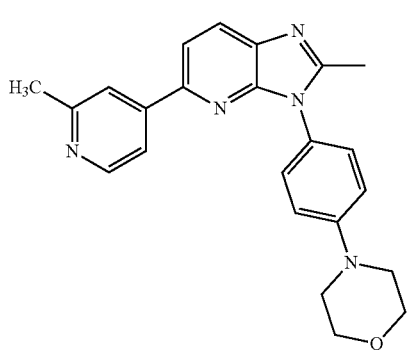

52

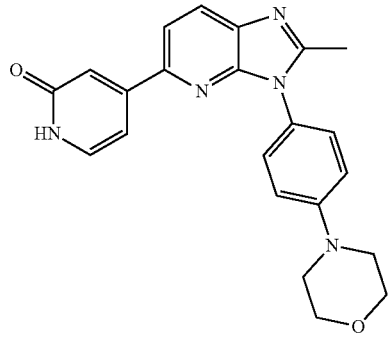

54

52 Was synthesized in a similar manner as depicted in Scheme 9, Step 3 using (2-methylpyridin-4-yl)boronic acid.

4-(4-(2-methyl-5-(2-methylpyridin-4-yl)-3H-imidazo[4,5-b]pyridin-3-yl)phenyl)morpholine 52.

Clear oil (54 mg, 0.140 mmol, 92% yield, 10% MeOH in DCM).

$^1$H NMR (CD$_2$Cl$_2$) δ: 8.52 (d, J=5.2 Hz, 1H), 8.07 (d, J=8.3 Hz, 1H), 7.80 (d, J=8.3 Hz, 1H), 7.75 (s, 1H), 7.69 (d, J=5.3 Hz, 1H), 7.39 (d, J=8.5 Hz, 2H), 7.14 (d, J=8.9 Hz, 2H), 3.96-3.89 (m, 4H), 3.36-3.29 (m, 4H), 2.61 (s, 3H), 2.57 (s, 3H). $^{13}$C NMR (CD$_2$Cl$_2$) δ: 158.93, 155.14, 151.51, 149.43, 148.69, 147.04, 135.22, 128.12, 126.59, 125.93, 120.28, 118.22, 115.89, 115.63, 66.73, 48.76, 24.32, 14.99.

54 Was synthesized in a similar manner as depicted in Scheme 9, Step 3 using (2-hydroxypyridin-4-yl)boronic acid.

4-(2-methyl-3-(4-morpholinophenyl)-3H-imidazo[4,5-b]pyridin-5-yl)pyridin-2(1H)-one 54.

Yellow solid (21 mg, 0.054 mmol, 36% yield, 11% MeOH in DCM).

$^1$H NMR (DMSO) δ: 11.56 (bs, 1H), 8.09 (d, J=8.3 Hz, 1H), 7.91 (d, J=8.3 Hz, 1H), 7.47-7.38 (m, 3H), 7.19-7.13 (m, 2H), 6.97-6.91 (m, 1H), 6.80 (dd, J=6.9, 1.8 Hz, 1H), 3.83-3.76 (m, 4H), 3.30-3.23 (m, 4H), 2.49 (s, 3H)

Scheme 10

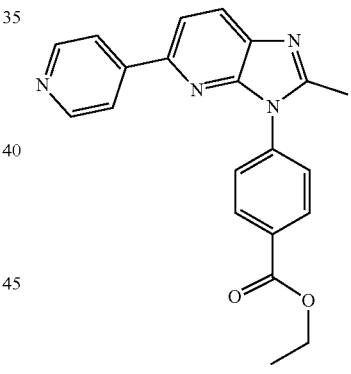

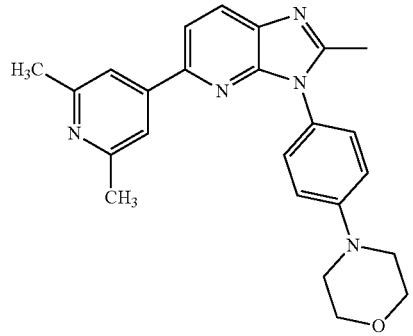

53

53 Was synthesized in a similar manner as depicted in Scheme 9, Step 3 using (2,6-dimethylpyridin-4-yl)boronic acid.

4-(4-(5-(2,6-dimethylpyridin-4-yl)-2-methyl-3H-imidazo[4,5-b]pyridin-3-yl)phenyl)morpholine 53.

White solid (8 mg, 0.020 mmol, 13% yield, 8% MeOH in DCM).

$^1$H NMR (Acetone) δ: 8.05 (d, J=8.3 Hz, 1H), 7.93 (d, J=8.3 Hz, 1H), 7.65 (s, 2H), 7.48 (d, J=8.9 Hz, 2H), 7.22 (d, J=8.5 Hz, 2H), 3.90-3.83 (m, 4H), 3.36-3.29 (m, 4H), 2.52 (s, 3H), 2.49 (s, 6H).

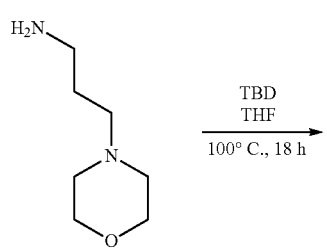

TBD
THF
100° C., 18 h

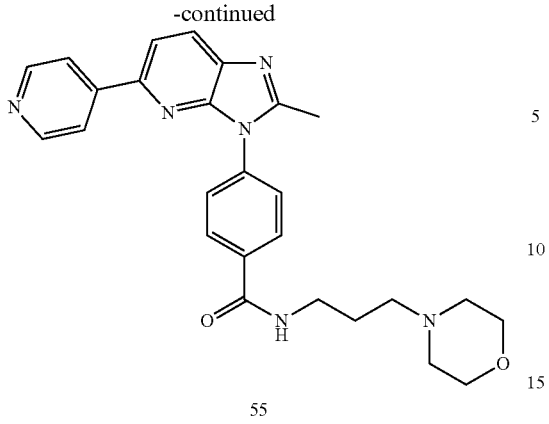

55

A 2-5 mL Biotage© microwave vial loaded with ethyl 4-(2-methyl-5-(pyridin-4-yl)-3H-imidazo[4,5-b]pyridin-3-yl)benzoate 40 (11 mg, 0.031 mmol), 3-morpholinopropan-1-amine (6.64 mg, 0.046 mmol), THF (0.29 mL), and 1,5,7-Triazabicyclo[4.4.0]dec-5-ene (2.56 mg, 0.018 mmol) was added and the mixture was sealed, degassed with argon and stirred at 100° C. for 18 h. The vial was diluted with DCM and dryloaded onto silica gel and purified on a 4 g silica gel column (DCM/MeOH, 0-9%), affording 4-(2-methyl-5-(pyridin-4-yl)-3H-imidazo[4,5-b]pyridin-3-yl)-N-(3-morpholinopropyl)benzamide 55 as a white semi-solid (12 mg, 0.026 mmol, 86% yield, 9% MeOH in DCM). $^1$H NMR (CDCl$_3$) δ: 8.67 (d, J=5.9 Hz, 2H), 8.30 (t, J=4.3 Hz, 1H), 8.18-8.06 (m, 3H), 7.90 (d, J=5.9 Hz, 2H), 7.85 (d, J=8.3 Hz, 1H), 7.63 (d, J=8.5 Hz, 2H), 3.87-3.75 (m, 4H), 3.68 (q, J=5.5 Hz, 2H), 2.82-2.48 (m, 9H), 2.01-1.83 (m, 2H).

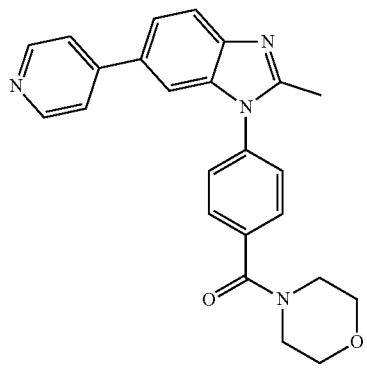

56

Compound 56 was synthesized in a similar manner as depicted in Scheme 10, using morpholine.

(4-(2-methyl-5-(pyridin-4-yl)-3H-imidazo[4,5-b]pyridin-3-yl)phenyl)(morpholino)methanone 56.

Light green semi-solid (12 mg, 0.030 mmol, 98% yield, 10% MeOH in DCM).

$^1$H NMR (CDCl$_3$) δ: 8.69 (d, J=6.2 Hz, 2H), 8.14 (d, J=8.3 Hz, 1H), 7.90 (d, J=6.2 Hz, 2H), 7.85 (d, J=8.3 Hz, 1H), 7.72 (d, J=8.6 Hz, 2H), 7.61 (d, J=8.6 Hz, 2H), 4.03-3.58 (m, 8H), 2.67 (s, 3H).

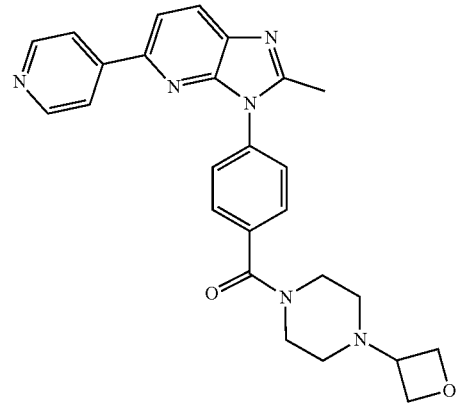

57

Compound 57 was synthesized in a similar manner as depicted in Scheme 10, using 1-(oxetan-3-yl)piperazine.

(4-(2-methyl-5-(pyridin-4-yl)-3H-imidazo[4,5-b]pyridin-3-yl)phenyl)(4-(oxetan-3-yl)piperazin-1-yl)methanone 57.

Green-white-semi-solid (4 mg, 0.0088 mmol, 32% yield, 10% MeOH in DCM).

$^1$H NMR (CDCl$_3$) δ: 8.69 (d, J=6.1 Hz, 2H), 8.13 (d, J=8.3 Hz, 1H), 7.90 (d, J=6.3 Hz, 2H), 7.84 (d, J=8.3 Hz, 1H), 7.70 (d, J=8.6 Hz, 2H), 7.60 (d, J=8.7 Hz, 2H), 4.78-4.57 (m, 4H), 4.00-3.66 (m, 4H), 3.64-3.52 (m, 1H), 2.66 (s, 3H), 2.54-2.28 (m, 4H).

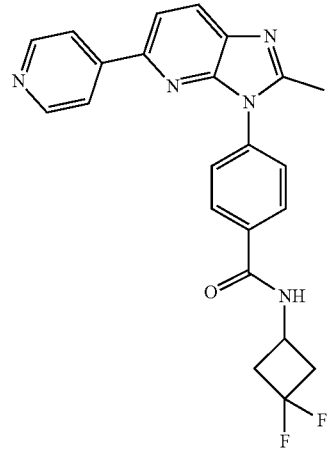

58

Compound 58 was synthesized in a similar manner as depicted in Scheme 10, using 3,3-difluorocyclobutan-1-amine.

N-(3,3-difluorocyclobutyl)-4-(2-methyl-5-(pyridin-4-yl)-3H-imidazo[4,5-b]pyridin-3-yl)benzamide 58.

White semi-solid (7 mg, 0.017 mmol, 60% yield, 15% MeOH).

$^1$H NMR (DMSO) δ: 9.04 (d, J=6.5 Hz, 1H), 8.64 (d, J=6.0 Hz, 2H), 8.21 (d, J=8.2 Hz, 1H), 8.14-8.07 (m, 3H), 7.99 (d, J=6.3 Hz, 2H), 7.82 (d, J=8.6 Hz, 2H), 4.38-4.21 (m, 1H), 2.58 (s, 3H), 1.26-1.22 (m, 4H).

Scheme 11

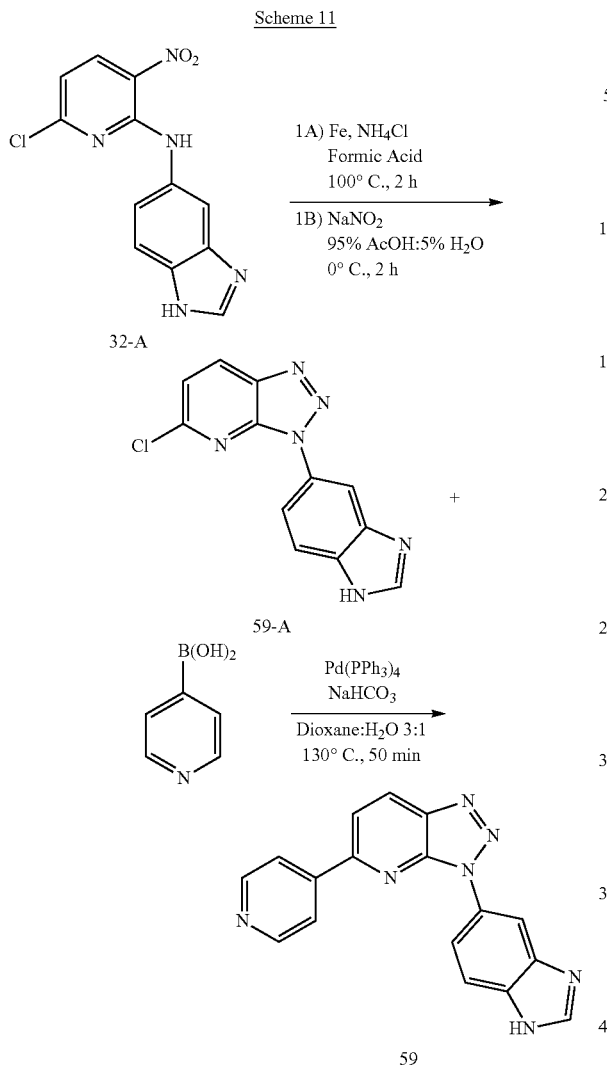

Scheme 11, Step 1A

In a 20 mL Biotage© microwave vial, stir bar, N-(6-chloro-3-nitropyridin-2-yl)-1H-benzo[d]imidazol-5-amine 32-A (150 mg, 0.518 mmol), iron (289 mg, 5.18 mmol), ammonium chloride (277 mg, 5.18 mmol), and EtOH:AcOH (1.94 mL:0.65 mL, 3:1 v/v), were added. The vial was sealed, degassed with Ar for 15 min, and heated for 2 h at 100° C. in an oil bath. Upon cooling, the mixture was diluted with EtOAc, solids filtered through celite, and concentrated. The crude dianiline was transferred to a 20 mL dram vial.

Scheme 11, Step 1B

In a 20 mL dram vial, stir bar, crude dianiline from Step 1A, and 95% AcOH: 5% $H_2O$ (3.96 mL:0.21 mL) were added, dissolved and then cooled to 0° C. $NaNO_2$ (104 mg, 1.502 mmol) was added and the mixture was stirred at 0° C. for 2 h then warmed to 25° C. over 30 min. The reaction was diluted with $H_2O$ and basified with 10% NaOH. The precipitate was filtered, dryloaded onto silica gel and purified on a 12 g silica gel column (DCM/MeOH, 0-12%), affording 3-(1H-benzo[d]imidazol-5-yl)-5-chloro-3H-[1,2,3]triazolo[4,5-b]pyridine 59-A as a tan solid (120 mg, 0.443 mmol, 89% yield, 12% MeOH in DCM). $^1$H NMR (DMSO) δ: 12.85 (bs, 1H), 8.81-8.76 (m, 1H), 8.43 (s, 1H), 8.30 (s, 1H), 7.91-7.86 (m, 2H), 7.73-7.68 (m, 1H).

Scheme 11, Step 2

A 2-5 mL Biotage© microwave vial loaded with 3-(1H-benzo[d]imidazol-5-yl)-5-chloro-3H-[1,2,3]triazolo[4,5-b]pyridine 59-A (100 mg, 0.369 mmol), pyridin-4-ylboronic acid (54.5 mg, 0.443 mmol), $Pd(PPh_3)_4$ (29.9 mg, 0.026 mmol), and $NaHCO_3$ (140 mg, 1.662 mmol), was capped, purged with argon, then injected with degassed dioxane:$H_2O$ (2.77 mL:0.92 mL, 3:1 v/v), and heated to 130° for 50 min in a Biotage Microwave Reactor. The reaction was cooled, diluted with DCM, filtered through celite, concentrated, dryloaded onto silica gel and purified on a 12 g silica gel column (DCM/MeOH, 0-13%), affording 3-(1H-benzo[d]imidazol-5-yl)-5-(pyridin-4-yl)-3H-[1,2,3]triazolo[4,5-b]pyridine 59 as a tan solid (40 mg, 0.128 mmol, 35% yield, 13% MeOH in DCM). $^1$H NMR (DMSO) δ: 12.86 (bs, 1H), 8.87 (d, J=8.7 Hz, 1H), 8.79 (d, J=6.2 Hz, 2H), 8.49 (d, J=2.0 Hz, 1H), 8.43 (s, 1H), 8.34 (d, J=8.7 Hz, 1H), 8.20 (d, J=5.9 Hz, 2H), 8.06 (dd, J=8.6, 2.0 Hz, 1H), 7.91 (d, J=8.6 Hz, 1H).

Scheme 12

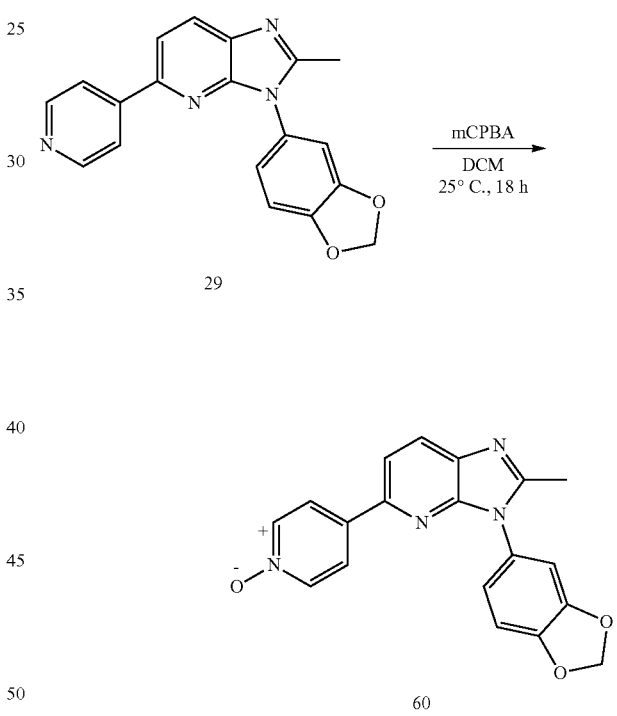

A 2-5 mL Biotage© microwave vial loaded with 3-(benzo[d][1,3]dioxol-5-yl)-2-methyl-5-(pyridin-4-yl)-3H-imidazo[4,5-b]pyridine 29 (20 mg, 0.061 mmol), was dissolved in DCM (0.3 mL), and 70% mCPBA (23.88 mg, 0.097 mmol) was added and the mixture was capped, stirred at 25° C. for 18 h. The reaction was quenched dropwise with methanol and dryloaded onto silica gel and purified on a 4 g silica gel column (DCM/MeOH, 0-11%), affording 4-(3-(benzo[d][1,3]dioxol-5-yl)-2-methyl-3H-imidazo[4,5-b]pyridin-5-yl)-1$\lambda^4$-pyridin-2-ylium-1-olate 60 as a white solid (6 mg, 0.017 mmol, 29% yield, 11% MeOH in DCM). $^1$H NMR (CDCl$_3$) δ: 8.24 (d, J=7.2 Hz, 2H), 8.08 (d, J=8.3 Hz, 1H), 7.95 (d, J=7.4 Hz, 2H), 7.73 (d, J=8.3 Hz, 1H), 7.03 (dd, J=7.7, 0.8 Hz, 1H), 6.96-6.87 (m, 2H), 6.17 (s, 2H), 2.61 (s, 3H).

Scheme 13

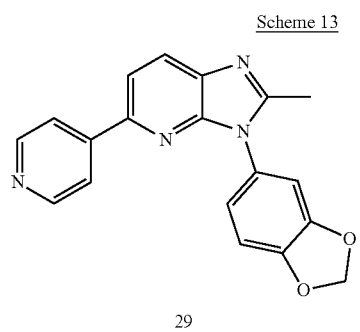

29

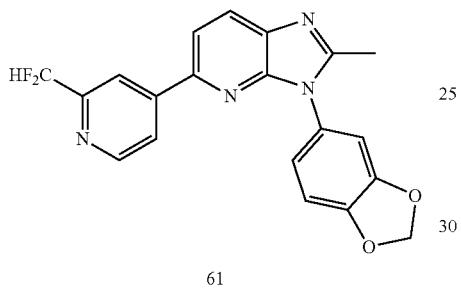

61

A 2-5 mL Biotage© microwave vial loaded with 3-(benzo[d][1,3]dioxol-5-yl)-2-methyl-5-(pyridin-4-yl)-3H-imidazo[4,5-b]pyridine 29 (30 mg, 0.091 mmol), was dissolved in DCM:H$_2$O (0.364 mL:0.146 mL, 2.5:1 v/v), Zinc difluoromethanesulfinate (DFMS) (75 mg, 0.254 mmol), and TFA (0.007 mL, 0.091 mmol) were added. The reaction is stirred rapidly and 70% aqueous TBHP (0.063 mL, 0.454 mmol) is added dropwise and the mixture was capped and stirred at 25° C. for 18 h. The vial was diluted with DCM and saturated sodium bicarbonate, then extracted multiple times with DCM, washed with saturated sodium bicarbonate, brine, and the organic layer was dried over Na$_2$SO$_4$, concentrated, dryloaded onto silica gel and purified on a 4 g silica gel column (DCM), affording 3-(benzo[d][1,3]dioxol-5-yl)-5-(2-(difluoromethyl)pyridin-4-yl)-2-methyl-3H-imidazo[4,5-b]pyridine 61 as a yellow semi-solid (13 mg, 0.034 mmol, 38% yield, 100% DCM). $^1$H NMR (CDCl$_3$) δ: 8.70 (d, J=5.8 Hz, 1H), 8.22 (s, 1H), 8.12 (d, J=8.3 Hz, 1H), 8.04 (d, J=5.2 Hz, 1H), 7.85 (d, J=8.3 Hz, 1H), 7.03 (d, J=8.8 Hz, 1H), 6.95-6.90 (m, 2H), 6.71 (t, J=55.5 Hz, 1H), 6.17 (s, 2H), 2.62 (s, 3H).

Scheme 14

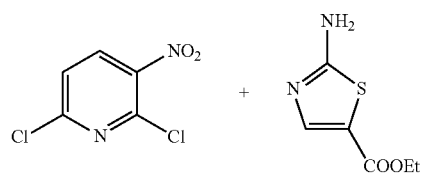

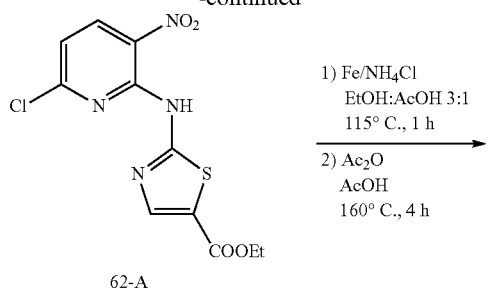

62-A

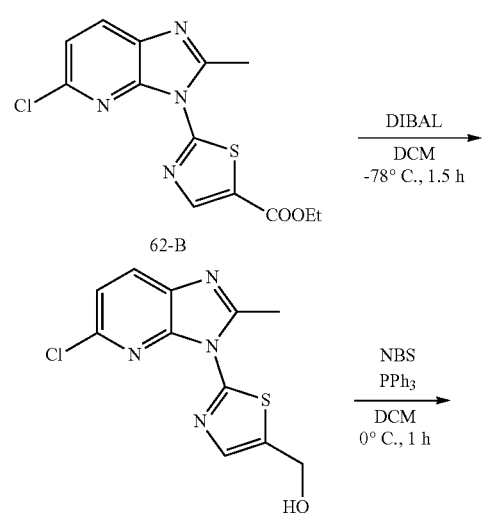

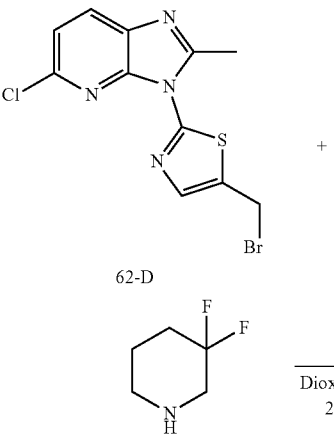

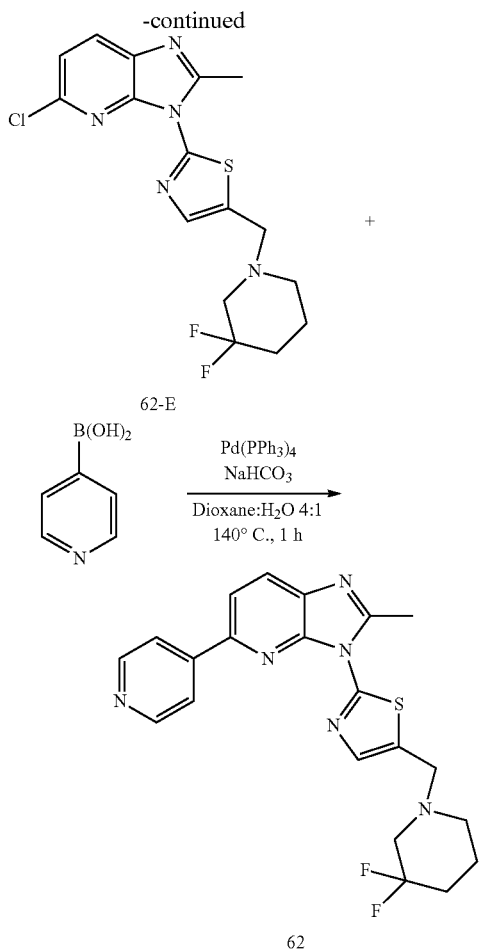

Scheme 14, Step 1

A 125 mL Erlenmyer flask was loaded with a stir bar, ethyl 2-aminothiazole-5-carboxylate (800 mg, 4.65 mmol), 2,6-dichloro-3-nitropyridine (897 mg, 4.65 mmol), Potassium tert butoxide (1.043 g, 9.29 mmol), Dioxane (18 mL), sealed and stirred at 25° C. for 4 days. The mixture was poured into H$_2$O and saturated ammonium chloride was added until precipitate formed, this was filtered, washed with H$_2$O, and hexanes, affording ethyl 2-((6-chloro-3-nitropyridin-2-yl)amino)thiazole-5-carboxylate 62-A as a dark green solid (300 mg, 0.913 mmol, 20% yield). 1H NMR (DMSO) δ: 11.95 (bs, 1H), 8.58 (d, J=8.4 Hz, 1H), 8.20 (s, 1H), 7.33 (d, J=8.5 Hz, 1H), 4.32 (q, J=7.1 Hz, 2H), 1.32 (t, J=7.1 Hz, 3H).

Scheme 14, Step 2A

In a 20 mL Biotage© microwave vial, stir bar, ethyl 2-((6-chloro-3-nitropyridin-2-yl)amino)thiazole-5-carboxylate 62-A (310 mg, 0.943 mmol), iron (527 mg, 9.43 mmol), and ammonium chloride (504 mg, 9.43 mmol) were added. The vial was sealed, degassed with Ar for 15 min, injected with EtOH:AcOH (2.83 mL:0.94 mL, 3:1 v/v), and purged with Ar for another 5 min. The mixture was heated for 1 h at 115° C. in an oil bath. Upon cooling, the mixture was diluted with EtOAc, solids filtered through celite, and the mixture concentrated and used in Step 2B.

Scheme 14, Step 2B

The crude residue from Step 2A was dissolved in AcOH (5.3 mL), gently warmed and pipetted repeatedly into a 20 mL Biotage© microwave vial equipped with a stir bar. Ac$_2$O (0.357 mL, 3.77 mmol) was injected and the mixture was purged with Ar for 15 min and heated 4 h at 160° C. Upon cooling, the mixture was azeotroped with toluene then DCM, followed by addition of 7M NH$_3$ in MeOH (10 mL) with subsequent concentration. The crude was concentrated/dryloaded onto silica with DCM and purified on a 4 g silica column (hexanes/EtOAc, 0-30%), affording ethyl 2-(5-chloro-2-methyl-3H-imidazo[4,5-b]pyridin-3-yl)thiazole-5-carboxylate 62-B as a light yellow solid (134 mg, 0.415 mmol, 44% yield, 30% EtOAc). $^1$H NMR (CDCl$_3$) δ: 8.31 (s, 1H), 7.98 (d, J=8.3 Hz, 1H), 7.38 (d, J=8.3 Hz, 1H), 4.46 (q, J=7.1 Hz, 2H), 3.08 (s, 3H), 1.46 (t, J=7.1 Hz, 3H). $^{13}$C NMR (CDCl$_3$) δ: 161.37, 158.32, 153.98, 145.43, 144.86, 133.42, 129.48, 127.46, 120.40, 61.84, 18.72, 14.36.

Scheme 14, Step 3

A 5 mL Biotage© microwave vial loaded with a stir bar, ethyl 2-(5-chloro-2-methyl-3H-imidazo[4,5-b]pyridin-3-yl)thiazole-5-carboxylate 62-B (132 mg, 0.409 mmol) and DCM (2.27 mL), under an argon balloon, was cooled to −78° C. DIBAL in toluene (1.2M, 0.443 mL, 0.532 mmol) was added dropwise over 15 minutes. After 1.5 h at −78° C., the reaction was quenched dropwise with MeOH, warmed to RT and then with H$_2$O and 10% NaOH. The vial was uncapped, MgSO$_4$ was added, stirred for 15 min and filtered through celite. Saturated sodium bicarbonate solution was added and then the mixture was extracted multiple times with DCM, washed with saturated sodium bicarbonate, brine, and the organic layer was dried over MgSO$_4$, concentrated, dryloaded onto silica gel and purified on a 12 g silica gel column (Hexanes/EtOAc, 0-100%), affording (2-(5-chloro-2-methyl-3H-imidazo[4,5-b]pyridin-3-yl)thiazol-5-yl)methanol 62-C as a yellow solid (30 mg, 0.107 mmol, 26% yield, 100% EtOAc). $^1$H NMR (CDCl$_3$) δ: 7.97 (d, J=8.3 Hz, 1H), 7.62 (t, J=0.9 Hz, 1H), 7.34 (d, J=8.3 Hz, 1H), 4.99 (d, J=0.9 Hz, 2H), 2.98 (s, 3H), 1.29 (bs, 1H).

Scheme 14, Step 4

In a 5 mL Biotage© microwave vial, stir bar, (2-(5-chloro-2-methyl-3H-imidazo[4,5-b]pyridin-3-yl)thiazol-5-yl)methanol 62-C (30 mg, 0.107 mmol) was dissolved in DCM (0.822 mL) and cooled to 0° C. NBS (22.82 mg, 0.128 mmol) and triphenylphosphine (33.6 mg, 0.128 mmol) were added and stirred for 1 h. The mixture was diluted with DCM, concentrated, dryloaded onto silica gel and purified on a 4 g silica gel column (Hexanes/EtOAc, 0-50%), affording 5-(bromomethyl)-2-(5-chloro-2-methyl-3H-imidazo[4,5-b]pyridin-3-yl)thiazole 62-D as a white solid (20 mg, 0.058 mmol, 55% yield, 50% EtOAc). $^1$H NMR (CDCl$_3$) δ: 7.97 (d, J=8.3 Hz, 1H), 7.67 (t, J=0.8 Hz, 1H), 7.35 (d, J=8.3 Hz, 1H), 4.79 (d, J=0.8 Hz, 2H), 3.02 (s, 3H). $^{13}$C NMR (CDCl$_3$) δ: 155.23, 153.84, 145.57, 145.27, 138.53, 134.40, 133.30, 129.37, 120.11, 22.87, 18.22.

Scheme 14, Step 5

A 5 mL Biotage© microwave vial loaded with a, stir bar, NaOH (4.89 mg, 0.122 mmol), dioxane:H$_2$O (1 mL:0.2 mL, 5:1 v/v), 3,3-difluoropiperidine (8.14 mg, 0.061 mmol) and 5-(bromomethyl)-2-(5-chloro-2-methyl-3H-imidazo[4,5-b]pyridin-3-yl)thiazole 62-D (21 mg, 0.061 mmol), was capped and stirred at 25° C. for 5 h. The mixture is diluted with toluene, azeotroped with toluene, concentrated, dryloaded onto silica gel and purified on a 4 g silica gel column (Hexanes/EtOAc, 0-50%), affording 2-(5-chloro-2-methyl-3H-imidazo[4,5-b]pyridin-3-yl)-5-((3,3-difluoropiperidin-1-yl)methyl)thiazole 62-E as a white solid (20 mg, 0.052 mmol, 85% yield, 50% EtOAc). $^1$H NMR (CDCl$_3$) δ: 7.96 (d, J=8.3 Hz, 1H), 7.54 (t, J=1.0 Hz, 1H), 7.34 (d, J=8.3 Hz, 1H), 3.93 (s, 2H), 2.99 (s, 3H), 2.78 (t, J=11.2 Hz, 2H), 2.62 (t, J=5.3 Hz, 2H), 2.02-1.89 (m, 2H), 1.88-1.80 (m, 2H).

Scheme 14, Step 6

A 2-5 mL Biotage© microwave vial loaded with 2-(5-chloro-2-methyl-3H-imidazo[4,5-b]pyridin-3-yl)-5-((3,3-difluoropiperidin-1-yl)methyl)thiazole 62-E (14 mg, 0.036 mmol), pyridin-4-ylboronic acid (5.38 mg, 0.044 mmol), Pd(PPh$_3$)$_4$ (3.37 mg, 0.00292 mmol), and NaHCO$_3$ (12.26 mg, 0.146 mmol), was capped, purged with argon, then injected with degassed dioxane:H$_2$O (0.547 mL:0.182 mL, 3:1 v/v), and heated to 130° for 40 min in a Biotage Microwave Reactor. The reaction was cooled, diluted with DCM, filtered through celite, concentrated, dryloaded onto silica gel and purified on a 4 g silica gel column (Hexanes/EtOAc, 0-100%), affording 5-((3,3-difluoropiperidin-1-yl)methyl)-2-(2-methyl-5-(pyridin-4-yl)-3H-imidazo[4,5-b]pyridin-3-yl)thiazole 62 as a white semi-solid (5 mg, 0.012 mmol, 32% yield, 100% EtOAc). $^1$H NMR (CDCl$_3$) δ: 8.77 (d, J=6.3 Hz, 2H), 8.12 (d, J=8.3 Hz, 1H), 8.08 (d, J=6.1 Hz, 2H), 7.91 (d, J=8.3 Hz, 1H), 7.54 (t, J=1.1 Hz, 1H), 3.97 (s, 2H), 3.10 (s, 3H), 2.83 (t, J=11.1 Hz, 2H), 2.66 (t, J=5.3 Hz, 2H), 2.10-1.83 (m, 4H).

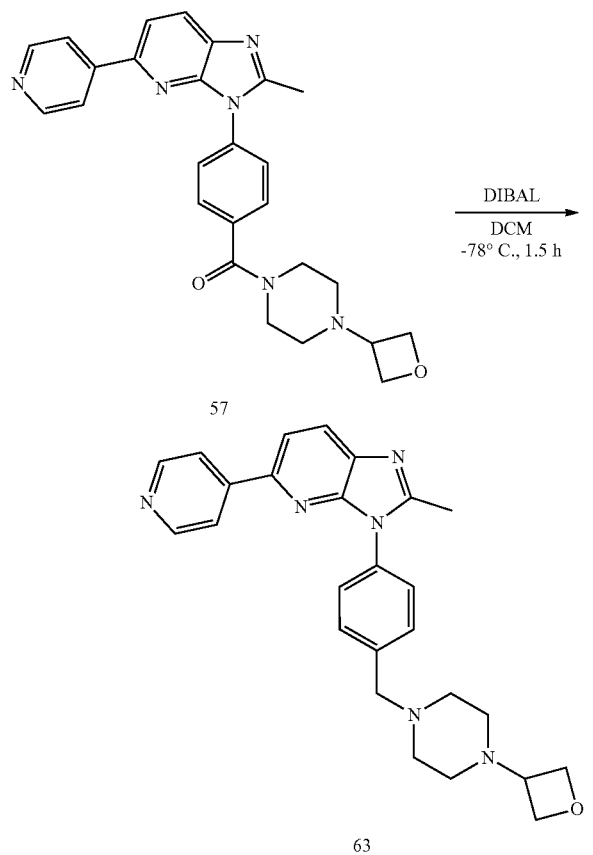

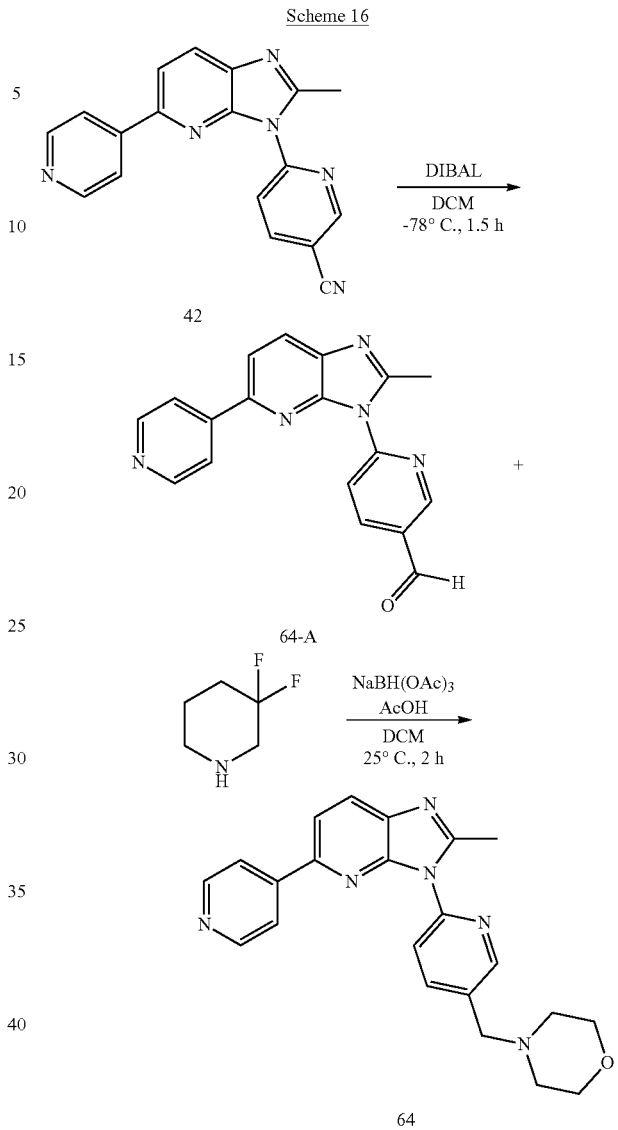

Scheme 16, Step 1

Compound 64-A was synthesized in a similar manner as depicted in Scheme 14, Step 3, by reduction of 42, the crude material was used in Step 2.

Scheme 16, Step 2

A 5 mL screw cap vial loaded with 6-(2-methyl-5-(pyridin-4-yl)-3H-imidazo[4,5-b]pyridin-3-yl)nicotinaldehyde 64-A (16 mg, 0.036 mmol), Morpholine (0.004 mL, 0.046 mmol), DCM (0.8 mL), and AcOH (2 drops), were stirred for 5 minutes. NaBH(OAc)$_3$ (12.80 mg, 0.060 mmol) was added, the mixture was sealed and stirred at 25° C. for 2 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 4 g silica gel column (DCM/MeOH, 0-20%), affording 4-((6-(2-methyl-5-(pyridin-4-yl)-3H-imidazo[4,5-b]pyridin-3-yl)pyridin-3-yl)methyl)morpholine 64 as a clear semi-solid (1 mg, 0.00259 mmol, 7% yield, 19% MeOH in DCM). $^1$H NMR (CDCl$_3$) δ: 8.71 (d, J=6.2 Hz, 2H), 8.62 (s, 1H), 8.12 (d, J=8.3 Hz, 1H), 8.07-8.02 (m, 2H), 7.94 (d, J=6.2 Hz, Compound 63 was synthesized in a similar manner as depicted in Scheme 14, Step 3, by reduction of 57.

2-methyl-3-(4-((4-(oxetan-3-yl)piperazin-1-yl)methyl)phenyl)-5-(pyridin-4-yl)-3H-imidazo[4,5-b]pyridine 63.

White semi-solid (3 mg, 0.0068 mmol, 10% yield, 13% MeOH in DCM).

$^1$H NMR (DMSO) δ: 8.64 (d, J=6.0 Hz, 2H), 8.20 (d, J=8.3 Hz, 1H), 8.17 (d, J=7.9 Hz, 2H), 8.08 (d, J=8.3 Hz, 1H), 7.99 (d, J=6.1 Hz, 2H), 7.74 (d, J=8.0 Hz, 2H), 3.35-3.29 (m, 15H), 2.58 (s, 3H).

2H), 7.85 (dd, J=8.3, 1.1 Hz, 1H), 3.85-3.77 (m, 4H), 3.67 (s, 2H), 2.89 (s, 3H), 2.65-2.43 (m, 4H).

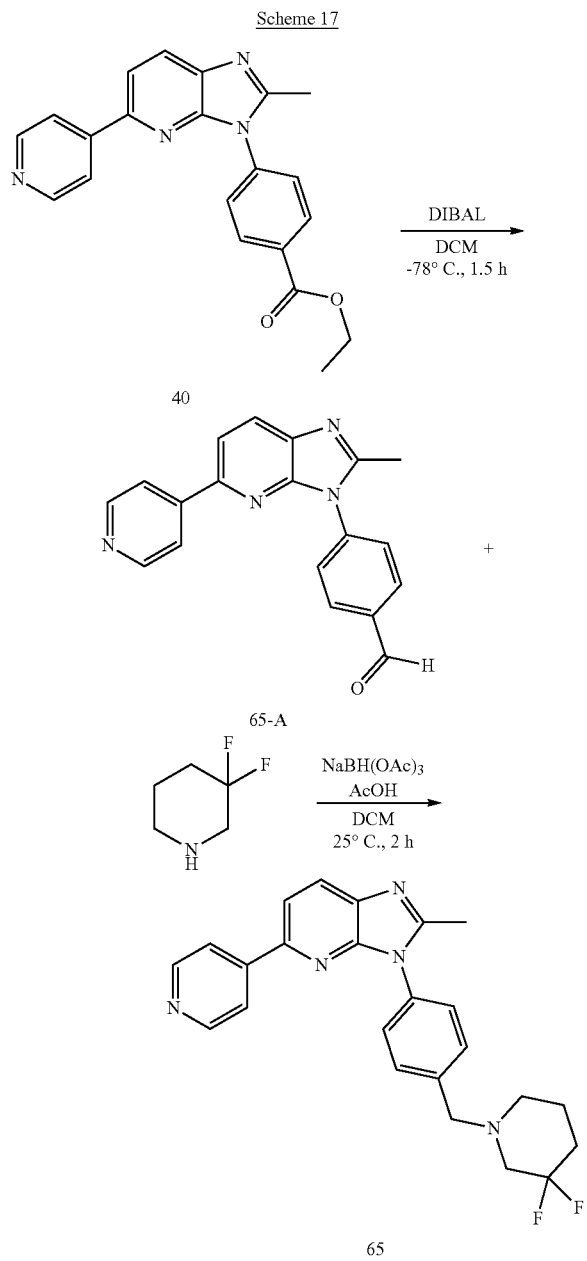

Scheme 17, Step 1

Compound 65-A was synthesized in a similar manner as depicted in Scheme 14, Step 3, by reduction of 40.

4-(2-methyl-5-(pyridin-4-yl)-3H-imidazo[4,5-b]pyridin-3-yl)benzaldehyde 65-A.

White solid (12 mg, 0.038 mmol, 58% yield, 13% MeOH in DCM).

$^1$H NMR (CDCl$_3$) δ: 10.18 (s, 1H), 8.66 (d, J=6.5 Hz, 2H), 8.18 (d, J=8.7 Hz, 2H), 8.13 (d, J=8.3 Hz, 1H), 7.89 (d, J=6.1 Hz, 2H), 7.85 (d, J=8.3 Hz, 1H), 7.75 (d, J=8.3 Hz, 2H), 2.69 (s, 3H). $^{13}$C NMR (CDCl$_3$) δ: 190.95, 153.86, 150.23, 148.90, 148.76, 146.31, 139.53, 136.09, 135.23, 130.91, 127.75, 127.40, 120.99, 116.62, 15.59.

Scheme 17, Step 2

A 5 mL screw cap vial loaded with 4-(2-methyl-5-(pyridin-4-yl)-3H-imidazo[4,5-b]pyridin-3-yl)benzaldehyde 65-A (15 mg, 0.048 mmol), 3,3-difluoropiperidine (6.94 mg, 0.057 mmol), DCM (0.477 mL), and AcOH (1 drop), were stirred for 5 minutes. NaBH(OAc)$_3$ (17.19 mg, 0.081 mmol) was added, the mixture was sealed and stirred at 25° C. for 2 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-20%), affording 3-(4-((3,3-difluoropiperidin-1-yl)methyl)phenyl)-2-methyl-5-(pyridin-4-yl)-3H-imidazo[4,5-b]pyridine 65 as a clear semi-solid (1 mg, 0.002384 mmol, 5% yield, 9% MeOH in DCM).

$^1$H NMR (CDCl$_3$) δ: 8.67 (d, J=6.2 Hz, 2H), 8.12 (d, J=8.3 Hz, 1H), 7.90 (d, J=6.2 Hz, 2H), 7.83 (d, J=8.3 Hz, 1H), 7.62 (d, J=8.5 Hz, 2H), 7.48 (d, J=8.5 Hz, 2H), 3.75 (s, 2H), 2.77 (t, J=11.2 Hz, 2H), 2.65 (s, 3H), 2.59 (t, J=5.3 Hz, 2H), 2.03-1.77 (m, 4H).

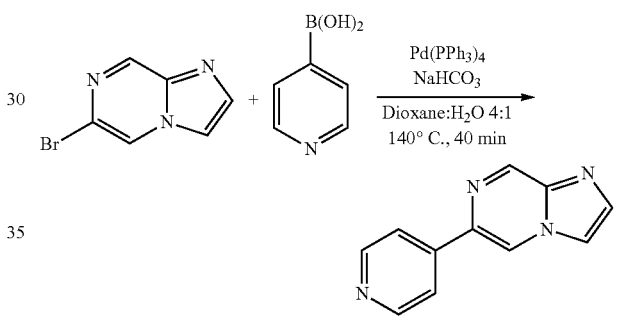

A 20 mL Biotage© microwave vial loaded with 6-bromoimidazo[1,2-a]pyrazine (120 mg, 0.606 mmol), pyridin-4-ylboronic acid (82 mg, 0.667 mmol), Pd(PPh$_3$)$_4$ (63 mg, 0.055 mmol), and NaHCO$_3$ (204 mg, 2.424 mmol), was capped, purged with argon, then injected with degassed dioxane:H$_2$O (3.73 mL:0.93 mL, 4:1 v/v), and heated to 140° for 40 min in a Biotage Microwave Reactor. The reaction was cooled, diluted with DCM, filtered through celite, concentrated, dryloaded onto silica gel and purified on a 12 g silica gel column (DCM/MeOH, 0-8%), affording 6-(pyridin-4-yl)imidazo[1,2-a]pyrazine 66 as a white solid (85 mg, 0.433 mmol, 72% yield, 8% MeOH). $^1$H NMR (DMSO) δ: 9.45 (d, J=1.5 Hz, 1H), 9.21 (dd, J=1.5, 0.7 Hz, 1H), 8.70 (d, J=6.2 Hz, 2H), 8.18 (s, 1H), 8.01 (d, J=6.2 Hz, 2H), 7.91 (d, J=1.1 Hz, 1H). $^{13}$C NMR (DMSO) δ: 150.78, 144.04, 143.05, 140.21, 136.70, 135.33, 120.33, 119.05, 116.10.

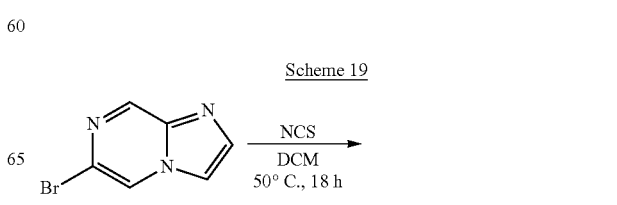

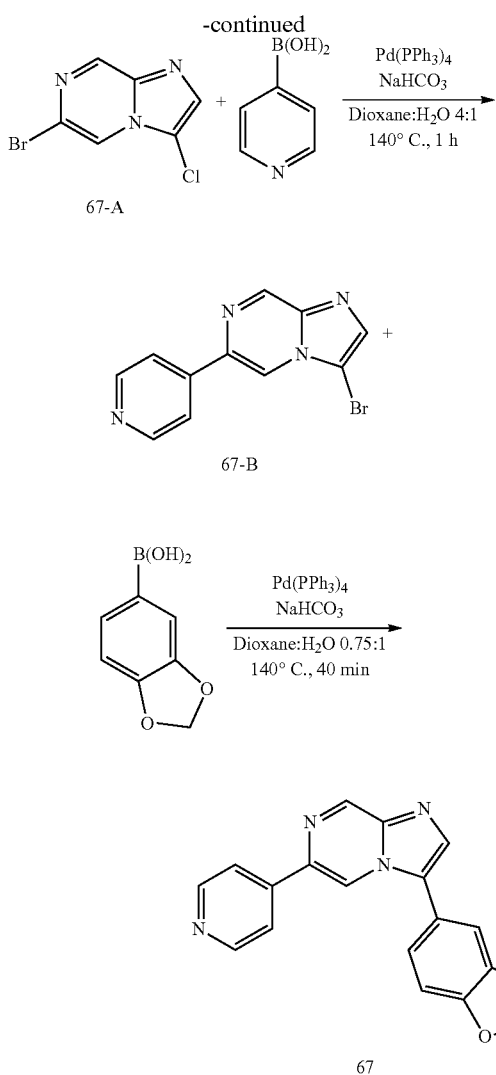

on a 12 g silica gel column (DCM/MeOH, 0-6%), affording 3-bromo-6-(pyridin-4-yl)imidazo[1,2-a]pyrazine 67-B as a white solid (296 mg, 1.283 mmol, 60% yield, 6% MeOH). $^1$H NMR (DMSO) δ: 9.26 (d, J=1.5 Hz, 1H), 9.13 (d, J=1.5 Hz, 1H), 8.71 (d, J=5.9 Hz, 2H), 8.16 (d, J=6.2 Hz, 2H), 8.04 (s, 1H). $^{13}$C NMR (DMSO) δ: 150.72, 143.57, 143.34, 139.49, 136.64, 133.76, 120.82, 115.37, 112.90.

Scheme 19, Step 3

A 2-5 mL Biotage© microwave vial loaded with 3-bromo-6-(pyridin-4-yl)imidazo[1,2-a]pyrazine 67-B (70 mg, 0.243 mmol), benzo[d][1,3]dioxol-5-ylboronic acid (44.3 mg, 0.267 mmol), Pd(PPh$_3$)$_4$ (25.3 mg, 0.022 mmol), and NaHCO$_3$ (82 mg, 0.971 mmol), was capped, purged with argon, then injected with degassed dioxane:H$_2$O (1.5 mL:2 mL, 0.75:1 v/v), and heated to 140° for 40 min in a Biotage Microwave Reactor. The reaction was cooled, diluted with DCM, filtered through celite, concentrated, dryloaded onto silica gel and purified on a 12 g silica gel column (DCM/MeOH, 0-5%), affording 3-(benzo[d][1,3]dioxol-5-yl)-6-(pyridin-4-yl)imidazo[1,2-a]pyrazine 67 as a white solid (40 mg, 0.126 mmol, 52% yield, 5% MeOH in DCM). $^1$H NMR (DMSO) δ: 9.26 (d, J=1.5 Hz, 1H), 9.04 (d, J=1.5 Hz, 1H), 8.68 (d, J=6.2 Hz, 2H), 8.07 (d, J=6.3 Hz, 2H), 8.03 (s, 1H), 7.44 (d, J=1.7 Hz, 1H), 7.30 (dd, J=8.0, 1.8 Hz, 1H), 7.15 (d, J=8.0 Hz, 1H), 6.16 (s, 2H). $^{13}$C NMR (DMSO) δ: 150.61, 148.55, 148.34, 144.13, 143.54, 140.61, 136.28, 135.73, 127.98, 122.85, 121.37, 120.91, 116.05, 109.67, 109.06, 101.99.

Scheme 20

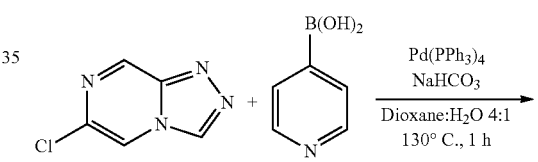

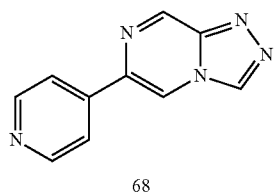

68

A 20 mL Biotage© microwave vial loaded with 6-chloro-[1,2,4]triazolo[4,3-a]pyrazine (386 mg, 2.5 mmol), pyridin-4-ylboronic acid (369 mg, 3 mmol), Pd(PPh$_3$)$_4$ (202 mg, 0.175 mmol), and NaHCO$_3$ (840 mg, 10 mmol), was capped, purged with argon, then injected with degassed dioxane:H$_2$O (12.1 mL:3 mL, 4:1 v/v), and heated to 130° for 1 h in a Biotage Microwave Reactor. The reaction was cooled, diluted with DCM, filtered through celite, concentrated, dryloaded onto silica gel and purified on a 12 g silica gel column (DCM/MeOH, 0-11%), affording 6-(pyridin-4-yl)-[1,2,4]triazolo[4,3-a]pyrazine 68 as a tan solid (56 mg, 0.284 mmol, 11% yield, 11% MeOH in DCM). $^1$H NMR (DMSO) δ: 9.58 (dd, J=1.7, 0.7 Hz, 1H), 9.50 (d, J=0.7 Hz, 1H), 9.42 (d, J=1.7 Hz, 1H), 8.74 (d, J=6.2 Hz, 2H), 8.02 (d, J=6.1 Hz, 2H).

Scheme 19, Step 1

A 20 mL Biotage© microwave vial loaded with 6-bromoimidazo[1,2-a]pyrazine (1.188 g, 6 mmol) was dissolved in DCM (15 mL), and N-chlorosuccinimide (881 mg, 6.60 mmol) was added in portions, and the mixture was sealed and stirred at 50° C. for 18 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (hexanes/EtOAc, 0-25%), affording 6-bromo-3-chloroimidazo[1,2-a]pyrazine 67-A as a white solid (916 mg, 3.94 mmol, 66% yield, 25% EtOAc in hexanes). $^1$H NMR (DMSO) δ: 8.98 (d, J=1.3 Hz, 1H), 8.77 (d, J=1.3 Hz, 1H), 8.01 (s, 1H). $^{13}$C NMR (DMSO) δ: 143.03, 139.15, 134.20, 123.70, 117.92, 112.33.

Scheme 19, Step 2

A 20 mL Biotage© microwave vial loaded with 6-bromo-3-chloroimidazo[1,2-a]pyrazine 67-A (500 mg, 2.151 mmol), pyridin-4-ylboronic acid (291 mg, 2.366 mmol), Pd(PPh$_3$)$_4$ (224 mg, 0.194 mmol), and NaHCO$_3$ (723 mg, 8.60 mmol), was capped, purged with argon, then injected with degassed dioxane:H$_2$O (13.2 mL:3.3 mL, 4:1 v/v), and heated to 140° for 1 h in a Biotage Microwave Reactor. The reaction was cooled, diluted with DCM, filtered through celite, concentrated, dryloaded onto silica gel and purified

Scheme 21

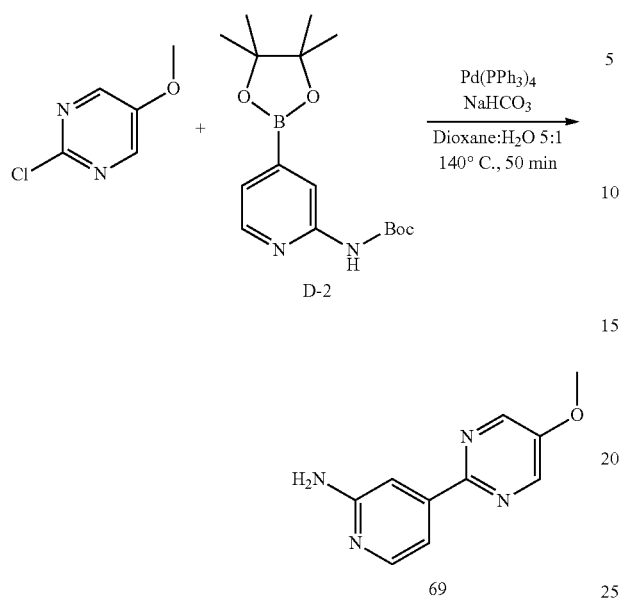

A 2-5 mL Biotage© microwave vial loaded with 2-chloro-5-methoxypyrimidine (12.3 mg, 0.085 mmol), tert-butyl (4-(4,4,5,5-tetramethyl-1,3,2-dioxaborolan-2-yl)pyridin-2-yl)carbamate D-2 (30 mg, 0.094 mmol), Pd(PPh$_3$)$_4$ (7.87 mg, 0.00681 mmol), and NaHCO$_3$ (28.6 mg, 0.341 mmol), was capped, purged with argon, then injected with degassed dioxane:H$_2$O (0.89 mL:0.177 mL, 5:1 v/v), and heated to 140° for 50 min in a Biotage Microwave Reactor. The reaction was cooled, 37% conc. HCl (0.3 mL) was added, stirred for 1 h and basified with 10% NaOH. The mixture was extracted with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-11%), affording 4-(5-methoxypyrimidin-2-yl)pyridin-2-amine 69 as a white semi-solid (12 mg, 0.059 mmol, 70% yield, 11% MeOH in DCM). $^1$H NMR (CDCl$_3$) δ: 8.51 (s, 2H), 8.21 (d, J=5.3 Hz, 1H), 7.59 (dd, J=5.4, 1.5 Hz, 1H), 7.48 (s, 1H), 4.55 (s, 2H), 4.00 (s, 3H). $^{13}$C NMR (CDCl$_3$) δ: 159.13, 155.91, 152.79, 148.78, 146.38, 143.36, 112.37, 106.58, 56.06, 29.70.

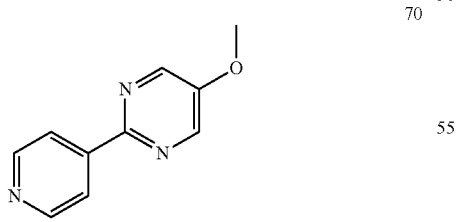

70

Compound 70 was synthesized in a similar manner as depicted in Scheme 21, using pyridin-4-ylboronic acid.

5-methoxy-2-(pyridin-4-yl)pyrimidine 70.

White solid (380 mg, 2.03 mmol, 98% yield, 8% MeOH).

$^1$H NMR (DMSO) δ: 8.77-8.61 (m, 4H), 8.18 (d, J=6.1 Hz, 2H), 4.00 (s, 3H).

Scheme 22

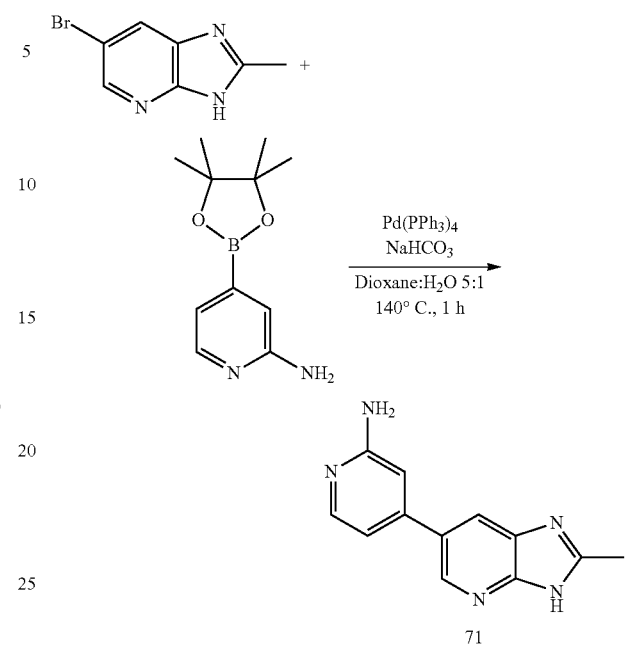

A 2-5 mL Biotage© microwave vial loaded with 6-bromo-2-methyl-3H-imidazo[4,5-b]pyridine (50 mg, 0.236 mmol), 4-(4,4,5,5-tetramethyl-1,3,2-dioxaborolan-2-yl)pyridin-2-amine (51.9 mg, 0.236 mmol), Pd(PPh$_3$)$_4$ (21.80 mg, 0.019 mmol), and NaHCO$_3$ (79 mg, 0.943 mmol), was capped, purged with argon, then injected with degassed dioxane:H$_2$O (1.965 mL:0.393 mL, 5:1 v/v), and heated to 140° for 1 h in a Biotage Microwave Reactor. The reaction was cooled, diluted with DCM, filtered through celite, concentrated, dryloaded onto silica gel and purified on a 12 g silica gel column (DCM/MeOH, 0-18%), affording 4-(2-methyl-3H-imidazo[4,5-b]pyridin-6-yl)pyridin-2-amine 71 as a white semi-solid (14 mg, 0.062 mmol, 26% yield, 18% MeOH in DCM). $^1$H NMR (DMSO) δ: 13.11-12.35 (m, 1H), 8.53 (s, 1H), 8.07 (s, 1H), 7.99 (d, J=5.4 Hz, 1H), 6.88 (dd, J=5.4, 1.6 Hz, 1H), 6.78 (s, 1H), 6.03 (s, 2H), 2.56 (s, 3H).

Scheme 23

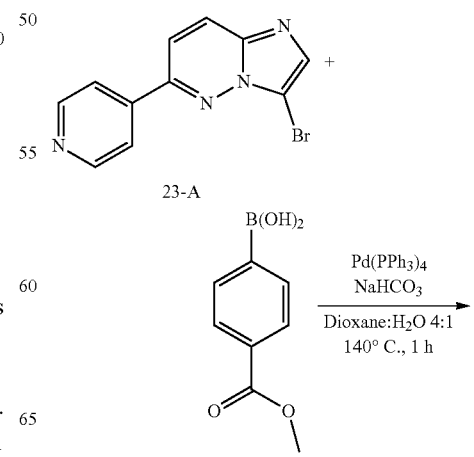

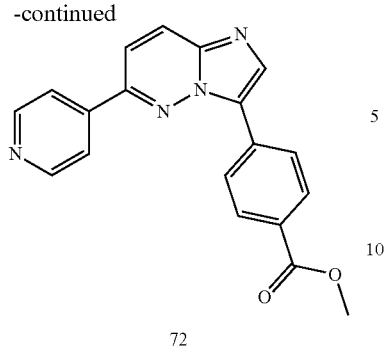

72

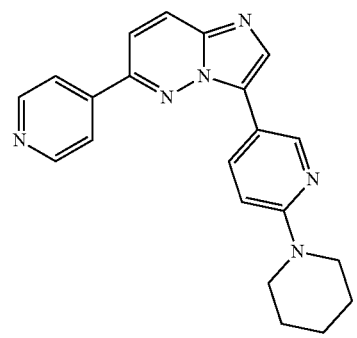

74

Step 1

A 2-5 mL Biotage© microwave vial loaded with 3-bromo-6-(pyridin-4-yl)imidazo[1,2-b]pyridazine (170 mg, 0.618 mmol) 23-A, (4-(methoxycarbonyl)phenyl)boronic acid (122 mg, 0.68 mmol), Pd(PPh$_3$)$_4$ (50 mg, 0.043 mmol), and NaHCO$_3$ (208 mg, 2.47 mmol), was capped, purged with argon, then injected with degassed dioxane:H$_2$O (3.3 mL:0.82 mL, 4:1 v/v), and heated to 130° for 50 min in a Biotage Microwave Reactor. The reaction was cooled, diluted with DCM, filtered through celite, concentrated, dryloaded onto silica gel and purified on a 12 g silica gel column (DCM/MeOH, 0-6%), affording methyl 4-(6-(pyridin-4-yl)imidazo[1,2-b]pyridazin-3-yl)benzoate 72 as a yellow solid (150 mg, 0.454 mmol, 74% yield, 6% MeOH in DCM).

$^1$H NMR (CDCl$_3$) δ: 8.85 (d, J=6.2 Hz, 2H), 8.38-8.16 (m, 6H), 7.93 (d, J=6.1 Hz, 2H), 7.64 (d, J=9.5 Hz, 1H), 4.00 (s, 3H). $^{13}$C NMR (CDCl$_3$) δ: 166.66, 150.87, 149.37, 142.75, 140.16, 135.07, 132.69, 130.09, 129.36, 128.06, 126.76, 126.28, 120.98, 115.13, 52.24.

Compound 74 was synthesized in a similar manner as depicted in Scheme 23, using 2-(piperidin-1-yl)-5-(4,4,5,5-tetramethyl-1,3,2-dioxaborolan-2-yl)pyridine.

3-(6-(piperidin-1-yl)pyridin-3-yl)-6-(pyridin-4-yl)imidazo[1,2-b]pyridazine 74.

Orange solid (23 mg, 0.065 mmol, 71% yield, 11% MeOH in DCM).

$^1$H NMR (CDCl$_3$) δ: 8.96 (dd, J=2.5, 0.8 Hz, 1H), 8.82 (d, J=6.3 Hz, 2H), 8.17 (dd, J=9.0, 2.5 Hz, 1H), 8.14 (d, J=9.4 Hz, 1H), 8.05 (s, 1H), 7.93 (d, J=6.3 Hz, 2H), 7.54 (d, J=9.4 Hz, 1H), 6.84 (dd, J=9.0, 0.8 Hz, 1H), 3.85-3.48 (m, 4H), 1.88-1.58 (m, 6H). $^{13}$C NMR (CDCl$_3$) δ: 150.77, 149.02, 146.60, 143.03, 139.22, 137.48, 135.80, 134.60, 133.41, 132.55, 126.42, 121.02, 113.91, 106.49, 46.20, 25.57, 24.74.

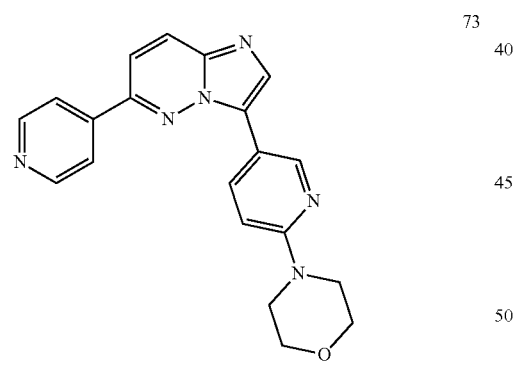

73

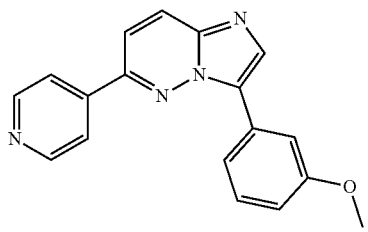

75

Compound 73 was synthesized in a similar manner as depicted in Scheme 23, using 4-(5-(4,4,5,5-tetramethyl-1,3,2-dioxaborolan-2-yl)pyridin-2-yl)morpholine. 4-(5-(6-(pyridin-4-yl)imidazo[1,2-b]pyridazin-3-yl)pyridin-2-yl)morpholine 73.

Orange solid (20 mg, 0.056 mmol, 61% yield, 15% MeOH in DCM).

$^1$H NMR (CDCl$_3$) δ: 8.99 (dd, J=2.4, 0.8 Hz, 1H), 8.82 (d, J=6.1 Hz, 2H), 8.24 (dd, J=8.9, 2.5 Hz, 1H), 8.15 (d, J=9.4 Hz, 1H), 8.07 (s, 1H), 7.92 (d, J=6.1 Hz, 2H), 7.56 (d, J=9.5 Hz, 1H), 6.84 (dd, J=9.0, 0.8 Hz, 1H), 4.05-3.78 (m, 4H), 3.78-3.44 (m, 4H). $^{13}$C NMR (CDCl$_3$) δ: 158.76, 150.79, 149.14, 146.50, 142.95, 139.25, 135.96, 132.79, 127.11, 126.51, 121.01, 114.59, 114.18, 106.47, 66.73, 45.46.

Compound 75 was synthesized in a similar manner as depicted in Scheme 23, using (3-methoxyphenyl)boronic acid.

3-(3-methoxyphenyl)-6-(pyridin-4-yl)imidazo[1,2-b]pyridazine 75.

Green semi-solid (68 mg, 0.225 mmol, 79% yield, 9% MeOH in DCM).

$^1$H NMR (CDCl$_3$) δ: 8.80 (d, J=6.1 Hz, 2H), 8.17-8.11 (m, 2H), 7.91 (d, J=6.1 Hz, 2H), 7.77 (dd, J=2.6, 1.6 Hz, 1H), 7.69 (ddd, J=7.7, 1.6, 0.9 Hz, 1H), 7.56 (d, J=9.5 Hz, 1H), 7.46 (t, J=8.2, 7.7 Hz, 1H), 6.98 (dd, J=8.3, 2.6 Hz, 1H), 3.92 (s, 3H). $^{13}$C NMR (CDCl$_3$) δ: 159.78, 150.73, 148.97, 142.99, 139.59, 134.27, 129.81, 129.52, 128.82, 126.52, 120.96, 119.26, 114.44, 113.82, 112.35, 55.35.

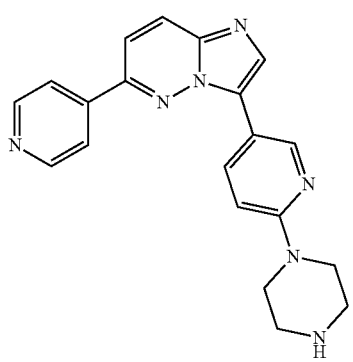

76

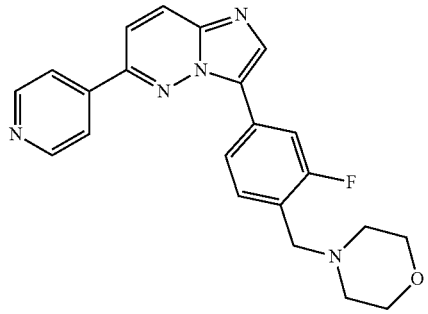

78

Compound 76 was synthesized in a similar manner as depicted in Scheme 23, using 1-(5-(4,4,5,5-tetramethyl-1,3,2-dioxaborolan-2-yl)pyridin-2-yl)piperazine.

3-(6-(piperazin-1-yl)pyridin-3-yl)-6-(pyridin-4-yl)imidazo[1,2-b]pyridazine 76.

Yellow semi-solid (22 mg, 0.062 mmol, 68% yield, 30% MeOH in DCM).

$^1$H NMR (CDCl$_3$) δ: 8.96 (dd, J=2.5, 0.8 Hz, 1H), 8.80 (d, J=6.2 Hz, 2H), 8.19 (dd, J=8.9, 2.5 Hz, 1H), 8.12 (d, J=9.4 Hz, 1H), 8.04 (s, 1H), 7.90 (d, J=6.0 Hz, 2H), 7.52 (d, J=9.5 Hz, 1H), 6.82 (dd, J=9.0, 0.8 Hz, 1H), 3.77-3.53 (m, 4H), 3.19-2.95 (m, 4H), 2.14 (bs, 1H). $^{13}$C NMR (CDCl$_3$) δ: 158.85, 150.73, 149.05, 146.47, 142.96, 139.16, 135.85, 132.62, 127.24, 126.42, 121.00, 114.06, 113.92, 106.50, 46.18, 45.92.

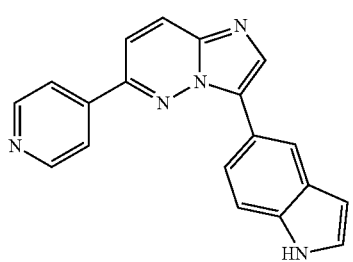

77

Compound 77 was synthesized in a similar manner as depicted in Scheme 23, using 5-(4,4,5,5-tetramethyl-1,3,2-dioxaborolan-2-yl)-1H-indole.

3-(1H-indol-5-yl)-6-(pyridin-4-yl)imidazo[1,2-b]pyridazine 77.

Yellow solid (26 mg, 0.084 mmol, 85% yield, 9% MeOH in DCM).

$^1$H NMR (CDCl$_3$) δ: 8.81 (d, J=6.2 Hz, 2H), 8.66 (bs, 1H), 8.45 (s, 1H), 8.15 (t, J=4.7 Hz, 2H), 7.95 (d, J=6.2 Hz, 2H), 7.93-7.87 (m, 1H), 7.62-7.47 (m, 2H), 7.38-7.31 (m, 1H), 6.79-6.47 (m, 1H).

Compound 78 was synthesized in a similar manner as depicted in Scheme 23, using 4-(2-fluoro-4-(4,4,5,5-tetramethyl-1,3,2-dioxaborolan-2-yl)benzyl)morpholine.

4-(2-fluoro-4-(6-(pyridin-4-yl)imidazo[1,2-b]pyridazin-3-yl)benzyl)morpholine 78.

Green semi-solid (1.8 mg, 0.00462. mmol, 16% yield, 9% MeOH in DCM).

$^1$H NMR (CDCl$_3$) δ: 8.86 (d, J=6.2 Hz, 2H), 8.21-8.12 (m, 2H), 8.02-7.85 (m, 4H), 7.62 (d, J=9.5 Hz, 1H), 7.58 (d, J=7.8 Hz, 1H), 3.85-3.74 (m, 4H), 3.69 (s, 2H), 2.69-2.49 (m, 4H).

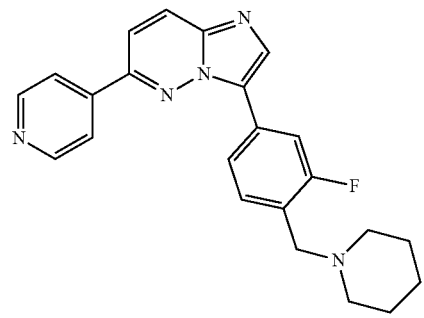

79

Compound 79 was synthesized in a similar manner as depicted in Scheme 23, using 1-(2-fluoro-4-(4,4,5,5-tetramethyl-1,3,2-dioxaborolan-2-yl)benzyl)piperidine.

3-(3-fluoro-4-(piperidin-1-ylmethyl)phenyl)-6-(pyridin-4-yl)imidazo[1,2-b]pyridazine 79.

Green semi-solid (6 mg, 0.015 mmol, 55% yield, 9% MeOH in DCM).

$^1$H NMR (CDCl$_3$) δ: 8.87 (d, J=5.1 Hz, 2H), 8.20 (d, J=8.3 Hz, 2H), 8.02 (d, J=11.5 Hz, 1H), 7.98-7.90 (m, 3H), 7.77-7.60 (m, 1H), 7.63 (d, J=9.4 Hz, 1H), 2.83-2.46 (m, 4H), 1.84-1.74 (m, 4H), 1.63-1.53 (m, 2H), 1.00-0.76 (m, 2H).

Scheme 24

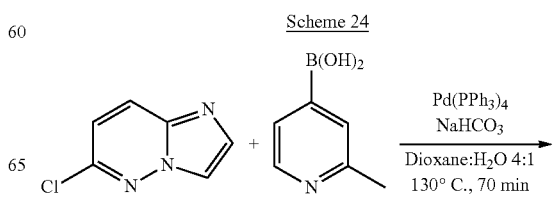

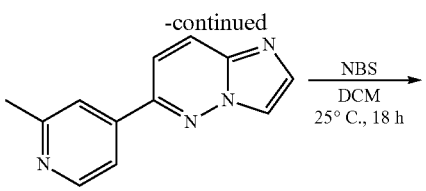

80-A

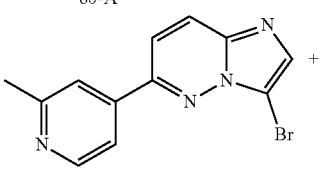

80-B

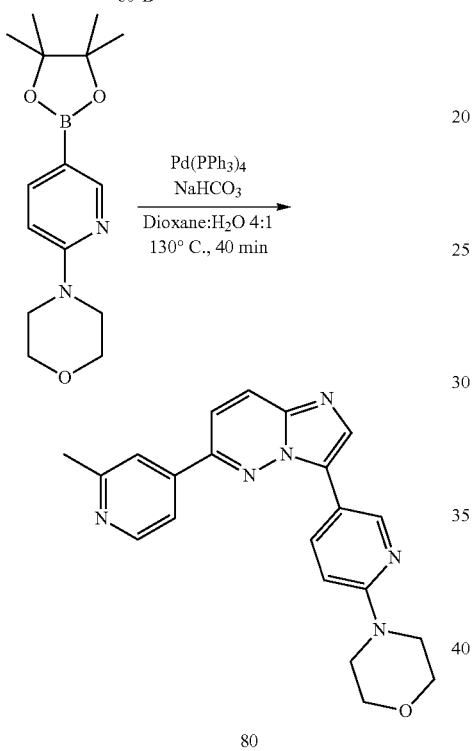

80

Scheme 24, Step 1

A 20 mL Biotage© microwave vial loaded with 6-chloro-imidazo[1,2-b]pyridazine (115 mg, 0.749 mmol), (2-methylpyridin-4-yl)boronic acid (411 mg, 3.0 mmol), Pd(PPh$_3$)$_4$ (202 mg, 0.175 mmol), and NaHCO$_3$ (840 mg, 10.0 mmol), was capped, purged with argon, then injected with degassed dioxane:H$_2$O (12.1 mL:3 mL, 4:1 v/v), and heated to 130° for 70 min in a Biotage Microwave Reactor. The reaction was cooled, diluted with DCM, filtered through celite, concentrated, dryloaded onto silica gel and purified on a 12 g silica gel column (DCM/MeOH, 0-10%), affording 6-(2-methylpyridin-4-yl)imidazo[1,2-b]pyridazine 80-A. as a white solid (353 mg, 1.679 mmol, 67% yield, 10% MeOH in DCM). $^1$H NMR (CDCl$_3$) δ: 8.63 (s, 1H), 8.14-7.41 (m, 6H), 2.65 (s, 3H). $^{13}$C NMR (CDCl$_3$) δ: 159.52, 149.99, 149.59, 143.03, 138.42, 134.83, 126.06, 120.50, 118.15, 117.18, 115.44, 24.62

Scheme 24, Step 2

A 20 mL screw cap vial loaded with 6-(2-methylpyridin-4-yl)imidazo[1,2-b]pyridazine 80-A (353 mg, 1.679 mmol), was dissolved in DCM (12.9 mL), and N-Bromosuccinimide (359 mg, 2.015 mmol), was added in portions, and the mixture was sealed and stirred at 25° C. for 18 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-7%), affording 3-bromo-6-(2-methylpyridin-4-yl)imidazo[1,2-b]pyridazine 80-B as a yellow-orange solid (320 mg, 1.107 mmol, 66% yield, 7% MeOH in DCM)

$^1$H NMR (CDCl$_3$) δ: 8.70 (d, J=5.2 Hz, 1H), 8.07 (d, J=9.5 Hz, 1H), 7.86 (d, J=0.7 Hz, 1H), 7.81 (s, 1H), 7.74 (d, J=5.4 Hz, 1H), 7.57 (d, J=9.5 Hz, 1H), 2.72 (s, 3H). $^{13}$C NMR (CDCl$_3$) δ: 159.69, 150.33, 150.15, 142.73, 139.25, 135.25, 126.30, 120.63, 118.29, 115.43, 101.52, 24.74.

Scheme 24, Step 3

A 2-5 mL Biotage© microwave vial loaded with 3-bromo-6-(2-methylpyridin-4-yl)imidazo[1,2-b]pyridazine 80-B (20 mg, 0.069 mmol), 4-(5-(4,4,5,5-tetramethyl-1,3,2-dioxaborolan-2-yl)pyridin-2-yl)morpholine (24.09 mg, 0.083 mmol), Pd(PPh$_3$)$_4$ (5.6 mg, 0.00484 mmol), and NaHCO$_3$ (23.24 mg, 0.277 mmol), was capped, purged with argon, then injected with degassed dioxane:H$_2$O (0.8 mL:0.2 mL, 4:1 v/v), and heated to 130° for 50 min in a Biotage Microwave Reactor. The reaction was cooled, diluted with DCM, filtered through celite, concentrated, dryloaded onto silica gel and purified on a 12 g silica gel column (DCM/MeOH, 0-10%), affording 4-(5-(6-(2-methylpyridin-4-yl)imidazo[1,2-b]pyridazin-3-yl)pyridin-2-yl)morpholine 80 as a light orange solid (6.5 mg, 0.017 mmol, 25% yield, 10% MeOH in DCM).

$^1$H NMR (CDCl$_3$) δ: 8.98 (dd, J=2.4, 0.8 Hz, 1H), 8.70 (dd, J=5.0, 1.1 Hz, 1H), 8.25 (dd, J=8.9, 2.4 Hz, 1H), 8.13 (d, J=9.4 Hz, 1H), 8.06 (s, 1H), 7.76-7.65 (m, 2H), 7.53 (d, J=9.4 Hz, 1H), 6.84 (dd, J=8.9, 0.8 Hz, 1H), 3.93-3.82 (m, 4H), 3.74-3.59 (m, 4H), 2.72 (s, 3H). $^{13}$C NMR (CDCl$_3$) δ: 159.57, 158.75, 152.21, 150.13, 149.52, 146.52, 143.34, 135.96, 133.12, 132.67, 127.06, 126.41, 120.58, 118.29, 114.45, 106.45, 66.74, 45.46, 24.78.

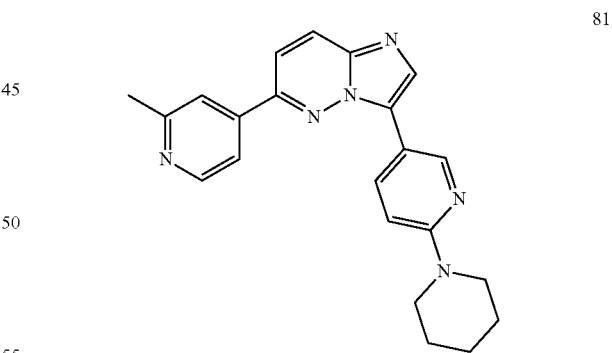

81

Compound 81 was synthesized in a similar manner as depicted in Scheme 24, Step 3 using 2-(piperidin-1-yl)-5-(4,4,5,5-tetramethyl-1,3,2-dioxaborolan-2-yl)pyridine.

6-(2-methylpyridin-4-yl)-3-(6-(piperidin-1-yl)pyridin-3-yl)imidazo[1,2-b]pyridazine 81.

Yellow solid (23 mg, 0.062 mmol, 90% yield, 9% MeOH in DCM).

$^1$H NMR (CDCl$_3$) δ: 8.94 (d, J=2.6 Hz, 1H), 8.68 (dd, J=4.9, 1.1 Hz, 1H), 8.17 (dd, J=9.0, 2.5 Hz, 1H), 8.11 (d, J=9.4 Hz, 1H), 8.03 (s, 1H), 7.76-7.68 (m, 2H), 7.50 (d, J=9.4 Hz, 1H), 6.83 (d, J=8.9 Hz, 1H), 3.90-3.39 (m, 4H), 2.71 (s, 3H), 1.80-1.53 (m, 6H). $^{13}$C NMR (CDCl$_3$) δ: 159.51, 158.76, 150.08, 149.39, 146.59, 143.40, 139.11, 135.78, 132.41, 127.44, 126.29, 120.58, 118.31, 114.17, 113.06, 106.46, 46.20, 25.57, 24.77, 24.74.

Scheme 25

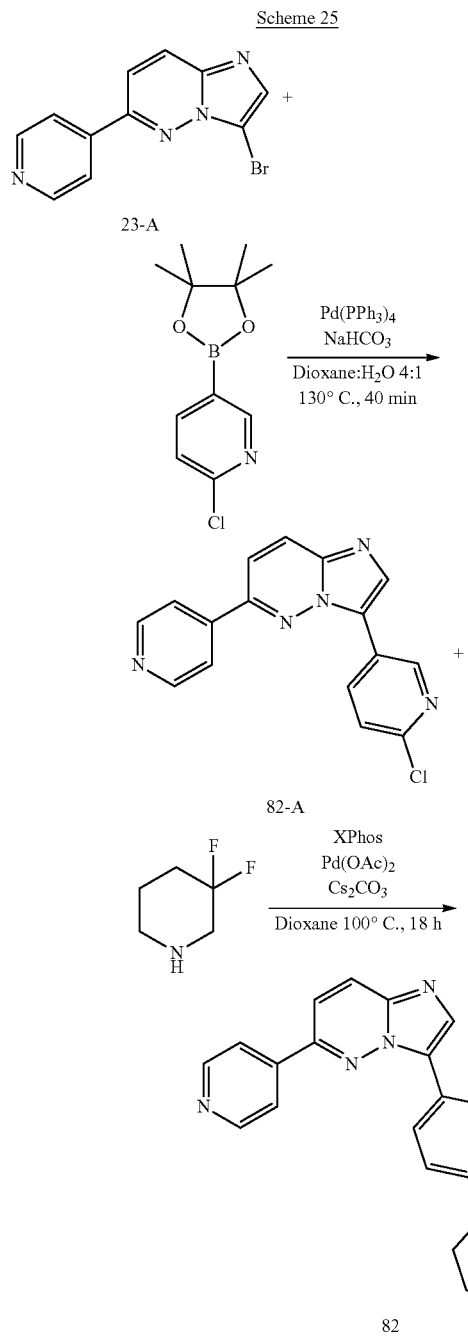

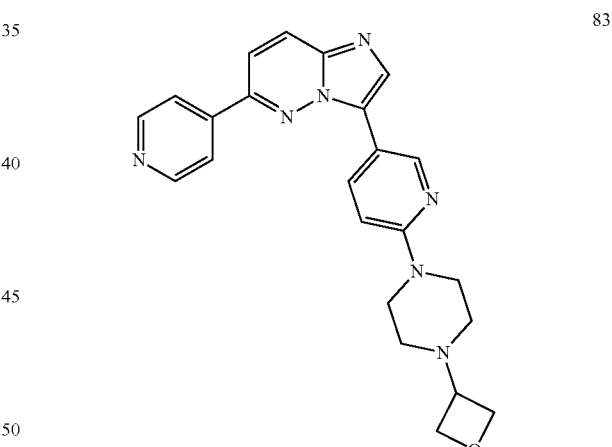

Scheme 25, Step 1

A 2-5 mL Biotage© microwave vial loaded with 3-bromo-6-(pyridin-4-yl)imidazo[1,2-b]pyridazine 23-A (100 mg, 0.363 mmol), 2-chloro-5-(4,4,5,5-tetramethyl-1,3,2-dioxaborolan-2-yl)pyridine (96 mg, 0.4 mmol), Pd(PPh$_3$)$_4$ (29.4 mg, 0.025 mmol), and NaHCO$_3$ (122 mg, 1.454 mmol), was capped, purged with argon, then injected with degassed degassed dioxane:H$_2$O (2.644 mL:0.66 mL, 4:1 v/v), and heated to 130° for 40 min in a Biotage Microwave Reactor. The reaction was cooled, diluted with DCM, filtered through celite, concentrated, dryloaded onto silica gel and purified on a 12 g silica gel column (DCM/MeOH, 0-9%), affording 3-(6-chloropyridin-3-yl)-6-(pyridin-4-yl)imidazo[1,2-b]pyridazine 82-A as a yellow solid (95 mg, 0.309 mmol, 85% yield, 9% MeOH in DCM).

$^1$H NMR (CDCl$_3$) δ: 9.27 (dd, J=2.5, 0.7 Hz, 1H), 8.85 (d, J=6.1 Hz, 2H), 8.41 (dd, J=8.4, 2.5 Hz, 1H), 8.24-8.20 (m, 2H), 7.91 (d, J=6.0 Hz, 2H), 7.66 (d, J=9.5 Hz, 1H), 7.55 (dd, J=8.4, 0.7 Hz, 1H).

Scheme 25, Step 2

A 2-5 mL Biotage© microwave vial loaded with Pd(OAc)$_2$ (2.63 mg, 0.012 mmol), XPhos (11.15 mg, 0.023 mmol), 3-(6-chloropyridin-3-yl)-6-(pyridin-4-yl)imidazo[1,2-b]pyridazine 82-A (40 mg, 0.130 mmol), 3,3-difluoropiperidine (22 mg, 0.182 mmol), Cs$_2$CO$_3$ (127 mg, 0.390 mmol), and dioxane (0.9 mL) was capped, purged with argon, heated to 100° C. for 18 h in an oil bath. The reaction was cooled, diluted with DCM, filtered through celite, concentrated, dryloaded onto silica gel and purified on a 12 g silica gel column (DCM/MeOH, 0-8%), affording 3-(6-(3,3-difluoropiperidin-1-yl)pyridin-3-yl)-6-(pyridin-4-yl) imidazo[1,2-b]pyridazine 82 as a yellow-green semi-solid (11 mg, 0.028 mmol, 22% yield, 8% MeOH in DCM). $^1$H NMR (CDCl$_3$) δ: 8.96 (dd, J=2.5, 0.8 Hz, 1H), 8.82 (d, J=6.0 Hz, 2H), 8.23 (dd, J=8.9, 2.5 Hz, 1H), 8.14 (d, J=9.4 Hz, 1H), 8.06 (s, 1H), 7.92 (d, J=6.2 Hz, 2H), 7.55 (d, J=9.5 Hz, 1H), 6.88 (dd, J=9.0, 0.8 Hz, 1H), 3.97 (t, J=11.7 Hz, 2H), 3.77-3.56 (m, 2H), 2.26-2.05 (m, 2H), 2.02-1.88 (m, 2H).

Compound 83 was synthesized in a similar manner as depicted in Scheme 25, Step 2 using 1-(oxetan-3-yl)piperazine.

3-(6-(4-(oxetan-3-yl)piperazin-1-yl)pyridin-3-yl)-6-(pyridin-4-yl)imidazo[1,2-b]pyridazine 83.

Green semi-solid (8 mg, 0.019 mmol, 15% yield, 19% MeOH in DCM).

$^1$H NMR (CDCl$_3$) δ: 8.98 (dd, J=2.5, 0.7 Hz, 1H), 8.82 (d, J=6.3 Hz, 2H), 8.23 (dd, J=8.9, 2.4 Hz, 1H), 8.15 (d, J=9.4 Hz, 1H), 8.06 (s, 1H), 7.92 (d, J=6.1 Hz, 2H), 7.55 (d, J=9.4 Hz, 1H), 6.85 (dd, J=9.0, 0.8 Hz, 1H), 4.73 (p, J=6.3 Hz, 4H), 3.85-3.67 (m, 4H), 3.59 (p, J=6.4 Hz, 1H), 2.61-2.36 (m, 4H).

Scheme 26

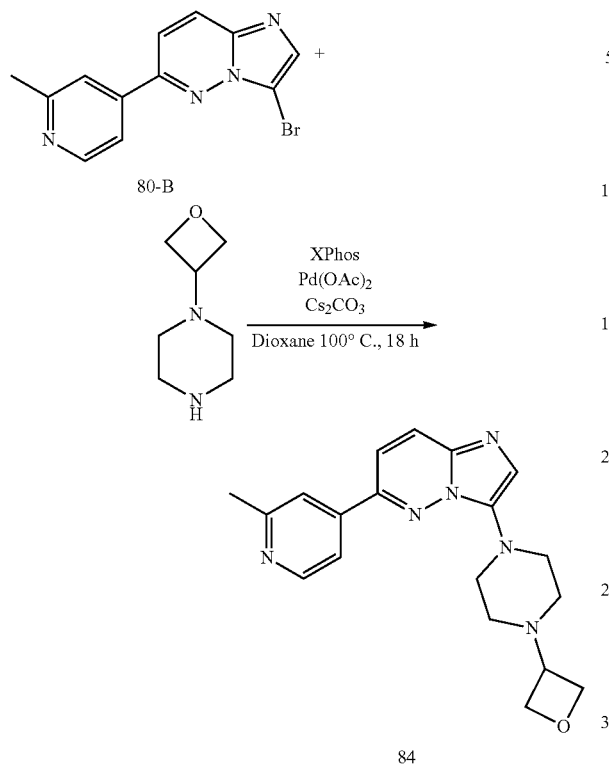

84

A 2-5 mL Biotage© microwave vial loaded with Pd(OAc)₂ (4.24 mg, 0.019 mmol), XPhos (18 mg, 0.038 mmol), 3-bromo-6-(2-methylpyridin-4-yl)imidazo[1,2-b]pyridazine 80-B (60.7 mg, 0.210 mmol), 1-(oxetan-3-yl)piperazine (38.8 mg, 0.273 mmol), Cs₂CO₃ (205 mg, 0.629 mmol), and dioxane (1.05 mL) was capped, purged with argon, heated to 100° C. for 18 h in an oil bath. The reaction was cooled, diluted with DCM, filtered through celite, concentrated, dryloaded onto silica gel and purified on a 12 g silica gel column (DCM/MeOH, 0-10%), affording 6-(2-methylpyridin-4-yl)-3-(4-(oxetan-3-yl)piperazin-1-yl)imidazo[1,2-b]pyridazine 84 as a yellow semi-solid (8 mg, 0.023 mmol, 11% yield, 10% MeOH in DCM). $^1$H NMR (CDCl₃) δ: 8.67 (d, J=5.3 Hz, 1H), 8.00 (d, J=9.4 Hz, 1H), 7.72 (s, 1H), 7.69 (dd, J=5.2, 1.8 Hz, 1H), 7.42 (d, J=9.5 Hz, 1H), 7.39 (s, 1H), 4.87-4.67 (m, 4H), 3.73-3.62 (m, 1H), 3.51-3.40 (m, 4H), 2.71 (s, 3H), 2.70-2.64 (m, 4H).

85

Compound 85 was synthesized in a similar manner as depicted in Scheme 26, using 1-(piperazin-1-yl)ethan-1-one.

1-(4-(6-(pyridin-4-yl)imidazo[1,2-b]pyridazin-3-yl)piperazin-1-yl)ethan-1-one 85.

Green semi-solid (3 mg, 0.00931 mmol, 6% yield, 9% MeOH in DCM).

$^1$H NMR (CDCl₃) δ: 8.82 (d, J=6.2 Hz, 2H), 8.04 (d, J=9.4 Hz, 1H), 7.89 (d, J=6.0 Hz, 2H), 7.47 (d, J=9.5 Hz, 1H), 7.40 (s, 1H), 4.05-3.69 (m, 4H), 3.48-3.13 (m, 4H), 2.21 (s, 3H).

86

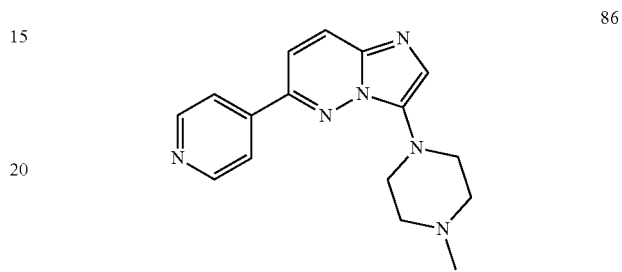

Compound 86 was synthesized in a similar manner as depicted in Scheme 26, using 1-(piperazin-1-yl)ethan-1-one.

3-(4-methylpiperazin-1-yl)-6-(pyridin-4-yl)imidazo[1,2-b]pyridazine 86.

Green semi-solid (5 mg, 0.017 mmol, 11% yield, 30% MeOH in DCM).

$^1$H NMR (CDCl₃) δ: 8.81 (d, J=6.2 Hz, 2H), 8.01 (d, J=9.4 Hz, 1H), 7.90 (d, J=6.1 Hz, 2H), 7.43 (d, J=9.4 Hz, 1H), 7.39 (s, 1H), 3.52-3.41 (m, 4H), 2.82-2.65 (m, 4H), 2.46 (s, 3H).

Scheme 27

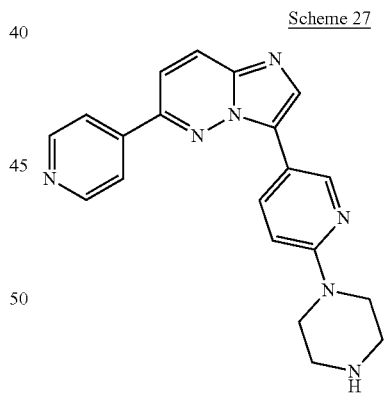

76

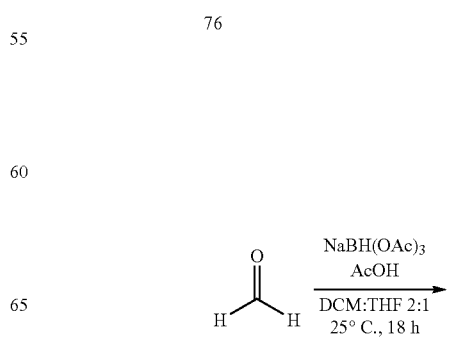

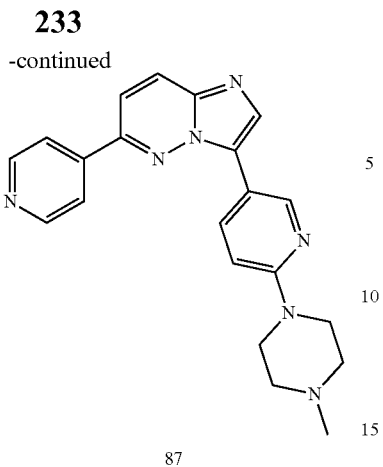

87

A 5 mL screw cap vial loaded with 3-(6-(piperazin-1-yl)pyridin-3-yl)-6-(pyridin-4-yl)imidazo[1,2-b]pyridazine 76 (11 mg, 0.031 mmol), 37% aq formaldehyde (0.007 mL, 0.092 mmol), DCM (1 mL), THF (0.5 mL), and AcOH (1 drop), were stirred for 5 minutes. NaBH(OAc)₃ (19.57 mg, 0.092 mmol), was added and the mixture was sealed and stirred at 25° C. for 18 h. The vial was diluted with DCM and 10% NaOH, then extracted multiple times with DCM, washed with 10% NaOH, H2O, brine, and the organic layer was dried over Na₂SO₄, concentrated, dryloaded onto silica gel and purified on a 4 g silica gel column (DCM/MeOH, 0-29%), affording 3-(6-(4-methylpiperazin-1-yl)pyridin-3-yl)-6-(pyridin-4-yl)imidazo[1,2-b]pyridazine 87 as a orange semi-solid (11 mg, 0.030 mmol, 96% yield, 29% MeOH in DCM).

¹H NMR (CDCl₃) δ: 8.97 (dd, J=2.5, 0.8 Hz, 1H), 8.82 (d, J=6.1 Hz, 2H), 8.21 (dd, J=8.9, 2.4 Hz, 1H), 8.14 (d, J=9.4 Hz, 1H), 8.06 (s, 1H), 7.92 (d, J=6.3 Hz, 2H), 7.54 (d, J=9.4 Hz, 1H), 6.85 (dd, J=9.0, 0.8 Hz, 1H), 3.75-3.68 (m, 4H), 2.64-2.56 (m, 4H), 2.41 (s, 3H). ¹³C NMR (CDCl₃) δ: 158.65, 150.77, 149.09, 146.51, 142.98, 139.20, 135.90, 132.69, 127.25, 126.47, 121.01, 114.09, 114.01, 106.59, 54.86, 46.23, 45.03.

Scheme 28

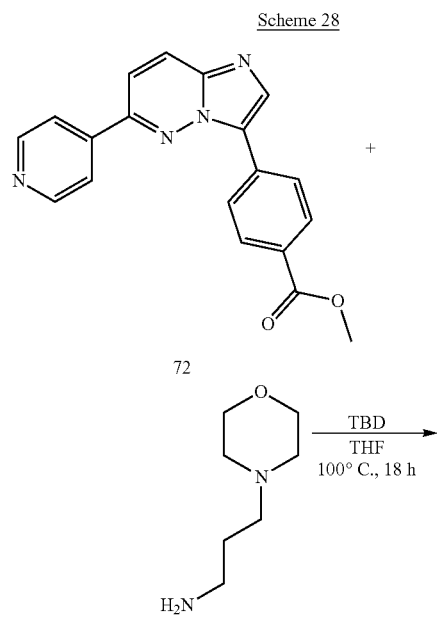

88

A 2-5 mL Biotage© microwave vial loaded with methyl 4-(6-(pyridin-4-yl)imidazo[1,2-b]pyridazin-3-yl)benzoate 72 (15 mg, 0.045 mmol), 3-morpholinopropan-1-amine (19.65 mg, 0.136 mmol), THF (0.43 mL), and 1,5,7-Triazabicyclo[4.4.0]dec-5-ene (6.32 mg, 0.045 mmol), was added and the mixture was sealed, degassed with argon for 10 minutes and stirred at 100° C. for 18 h. The vial was diluted with DCM and dryloaded onto silica gel and purified on a 4 g silica gel column (DCM/MeOH, 0-30%), affording N-(3-morpholinopropyl)-4-(6-(pyridin-4-yl)imidazo[1,2-b]pyridazin-3-yl)benzamide 88 as a yellow solid (9 mg, 0.020 mmol, 45% yield, 30% MeOH in DCM). ¹H NMR (CDCl₃) δ: 8.85 (d, J=6.1 Hz, 2H), 8.73 (s, 1H), 8.28 (d, J=8.7 Hz, 2H), 8.25 (s, 1H), 8.20 (d, J=9.5 Hz, 1H), 8.03 (d, J=8.2 Hz, 2H), 7.94 (d, J=6.3 Hz, 2H), 7.64 (d, J=9.4 Hz, 1H), 3.85-3.74 (m, 4H), 3.67 (q, J=5.5 Hz, 2H), 3.41-3.30 (m, 2H), 2.69-2.43 (m, 4H), 2.05 (t, J=5.9 Hz, 2H).

Scheme 29

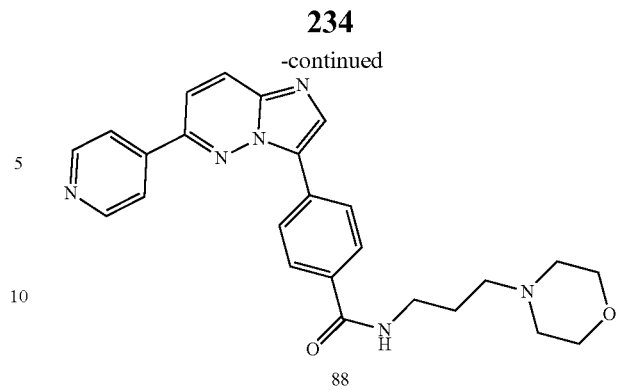

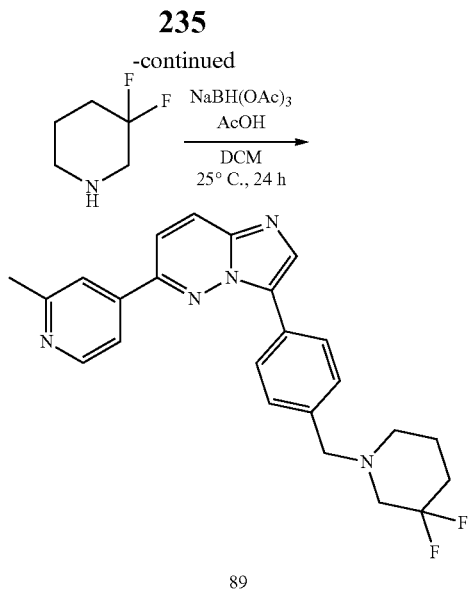

89

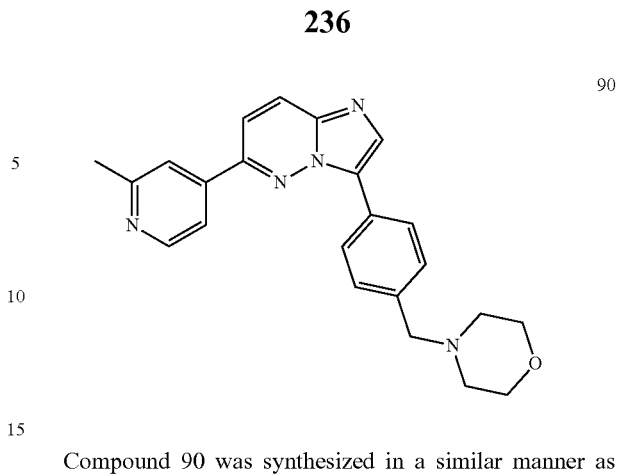

90

Compound 90 was synthesized in a similar manner as depicted in Scheme 26, using morpholine.

4-(4-(6-(2-methylpyridin-4-yl)imidazo[1,2-b]pyridazin-3-yl)benzyl)morpholine 90.

Green semi-solid (26 mg, 0.067 mmol, 71% yield, 11% MeOH).

$^1$H NMR (CDCl$_3$) δ: 8.69 (dd, J=5.2, 0.9 Hz, 1H), 8.23-8.04 (m, 4H), 7.77-7.69 (m, 2H), 7.58-7.48 (m, 3H), 3.84-3.69 (m, 4H), 3.60 (s, 2H), 2.71 (s, 3H), 2.58-2.43 (m, 4H). $^{13}$C NMR (CDCl$_3$) δ: 159.56, 150.11, 149.37, 143.35, 139.53, 138.05, 133.91, 129.54, 128.88, 127.28, 126.67, 126.43, 120.57, 118.24, 114.61, 67.04, 63.21, 53.71, 24.76.

Scheme 29, Step 1

A 2-5 mL Biotage© microwave vial loaded with 3-bromo-6-(2-methylpyridin-4-yl)imidazo[1,2-b]pyridazine 80-B (170 mg, 0.588 mmol), 4-(4,4,5,5-tetramethyl-1,3,2-dioxaborolan-2-yl)benzaldehyde (164 mg, 0.706 mmol), Pd(PPh$_3$)$_4$ (47.6 mg, 0.041 mmol), and NaHCO$_3$ (198 mg, 2.352 mmol), was capped, purged with argon, then injected with degassed dioxane:H$_2$O (3.136 mL:0.784 mL, 4:1 v/v), and heated to 130° for 50 min in a Biotage Microwave Reactor. The reaction was cooled, diluted with DCM, filtered through celite, concentrated, dryloaded onto silica gel and purified on a 12 g silica gel column (DCM/MeOH, 0-7%), affording 4-(6-(2-methylpyridin-4-yl)imidazo[1,2-b]pyridazin-3-yl)benzaldehyde 89-A as a green solid (175 mg, 0.557 mmol, 95% yield, 7% MeOH in DCM). $^1$H NMR (CDCl$_3$) δ: 10.10 (s, 1H), 8.73 (dd, J=5.2, 0.8 Hz, 1H), 8.39 (d, J=8.2 Hz, 2H), 8.29 (s, 1H), 8.20 (d, J=9.5 Hz, 1H), 8.08 (d, J=8.2 Hz, 2H), 7.78-7.72 (m, 2H), 7.64 (d, J=9.5 Hz, 1H), 2.74 (s, 3H)

Scheme 29, Step 2

A 5 mL screw cap vial loaded with 4-(6-(2-methylpyridin-4-yl)imidazo[1,2-b]pyridazin-3-yl)benzaldehyde 89-A (30 mg, 0.095 mmol), 3,3-difluoropiperidine (13.87 mg, 0.115 mmol), DCM (1 mL), and AcOH (1 drop) were stirred for 5 minutes. NaBH(OAc)$_3$ (34.4 mg, 0.162 mmol) was added and the mixture was sealed and stirred at 25° C., for 24 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-11%), affording 3-(4-((3,3-difluoropiperidin-1-yl)methyl)phenyl)-6-(2-methylpyridin-4-yl)imidazo[1,2-b]pyridazine 89 as a yellow semi-solid (28 mg, 0.067 mmol, 70% yield, 11% MeOH in DCM). $^1$H NMR (CDCl$_3$) δ: 8.69 (dd, J=5.2, 0.8 Hz, 1H), 8.23-8.01 (m, 4H), 7.78-7.67 (m, 2H), 7.60-7.48 (m, 3H), 3.70 (s, 2H), 2.71 (s, 5H), 2.54 (t, J=5.3 Hz, 2H), 2.05-1.73 (m, 4H).

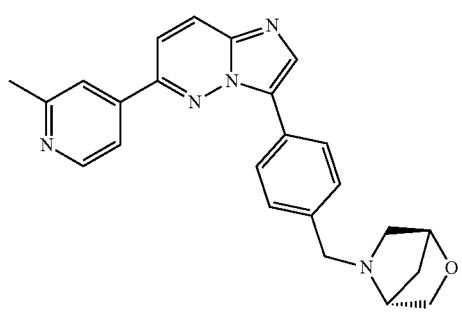

91

Compound 91 was synthesized in a similar manner as depicted in Scheme 29, Step 2, using (1S,4R)-2-oxa-5-azabicyclo[2.2.1]heptane.

(1S,4R)-5-(4-(6-(2-methylpyridin-4-yl)imidazo[1,2-b]pyridazin-3-yl)benzyl)-2-oxa-5-azabicyclo[2.2.1]heptane 91.

Green semi-solid (9 mg, 0.023 mmol, 36% yield, 13% MeOH).

$^1$H NMR (CDCl$_3$) δ: 8.71 (d, J=5.3 Hz, 1H), 8.17-8.10 (m, 4H), 7.77 (s, 1H), 7.75 (d, J=5.4 Hz, 1H), 7.63-7.52 (m, 3H), 4.48 (s, 1H), 4.20 (d, J=7.7 Hz, 1H), 3.98-3.80 (m, 2H), 3.71 (dd, J=7.7, 1.8 Hz, 1H), 3.58 (s, 1H), 2.98 (d, J=11.3 Hz, 1H), 2.85-2.58 (m, 4H), 1.99 (d, J=9.7 Hz, 1H), 1.81 (d, J=9.9 Hz, 1H).

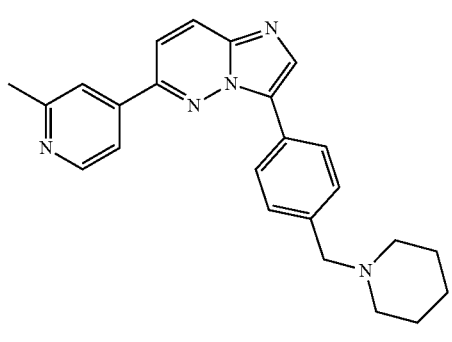

92

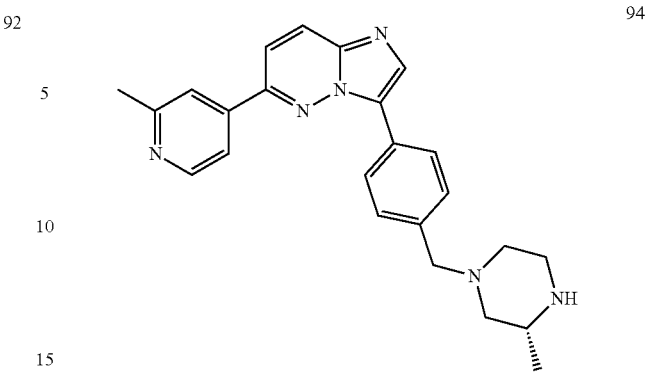

94

Compound 92 was synthesized in a similar manner as depicted in Scheme 29, Step 2, using piperidine.

6-(2-methylpyridin-4-yl)-3-(4-(piperidin-1-ylmethyl)phenyl)imidazo[1,2-b]pyridazine 92.

Yellow semi-solid (18 mg, 0.047 mmol, 74% yield, 20% MeOH in DCM).

$^1$H NMR (CDCl$_3$) δ: 8.70 (dd, J=5.2, 0.9 Hz, 1H), 8.18-7.99 (m, 4H), 7.78-7.69 (m, 2H), 7.60 (d, J=8.4 Hz, 2H), 7.56 (d, J=9.5 Hz, 1H), 3.73 (s, 2H), 2.71 (s, 3H), 2.69-2.45 (m, 4H), 1.80-1.68 (m, 4H), 1.62-1.39 (m, 2H).

Compound 94 was synthesized in a similar manner as depicted in Scheme 29, Step 2, using tert-butyl (R)-2-methylpiperazine-1-carboxylate, followed by hydrolysis with 37% conc. HCl.

(R)-3-(4-((3-methylpiperazin-1-yl)methyl)phenyl)-6-(2-methylpyridin-4-yl)imidazo[1,2-b]pyridazine 94.

Green oil (7 mg, 0.014 mmol, 22% yield, 20% MeOH in DCM).

$^1$H NMR (CDCl$_3$) δ: 8.71 (dd, J=5.3, 0.8 Hz, 1H), 8.18-8.10 (m, 4H), 7.80-7.76 (m, 1H), 7.75 (dd, J=5.2, 1.8 Hz, 1H), 7.57 (d, J=9.4 Hz, 1H), 7.54 (d, J=8.5 Hz, 2H), 3.61 (d, J=1.9 Hz, 2H), 3.04-2.98 (m, 2H), 2.98-2.90 (m, 1H), 2.89-2.82 (m, 2H), 2.73 (s, 3H), 2.15-2.02 (m, 1H), 1.82-1.74 (m, 1H), 1.71 (bs, 1H), 1.07 (d, J=6.4 Hz, 3H).

93

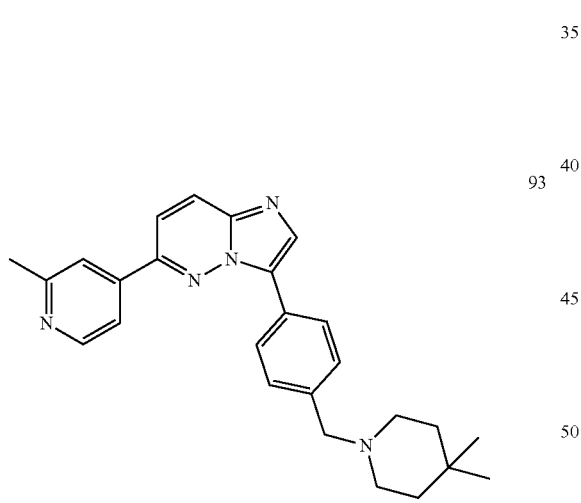

Compound 93 was synthesized in a similar manner as depicted in Scheme 29, Step 2, using 4,4-dimethylpiperidine.

3-(4-((4,4-dimethylpiperidin-1-yl)methyl)phenyl)-6-(2-methylpyridin-4-yl)imidazo[1,2-b]pyridazine 93.

Yellow solid (9 mg, 0.022 mmol, 34% yield, 25% MeOH in DCM).

$^1$H NMR (CDCl$_3$) δ: 8.71 (d, J=6.2 Hz, 1H), 8.20 (d, J=8.2 Hz, 2H), 8.18-8.12 (m, 2H), 7.81-7.69 (m, 4H), 7.58 (d, J=9.5 Hz, 1H), 4.04 (bs, 2H), 3.23-3.11 (m, 2H), 3.01-2.81 (m, 4H), 2.72 (s, 3H), 1.82-1.59 (m, 2H), 1.03 (s, 6H).

Scheme 30

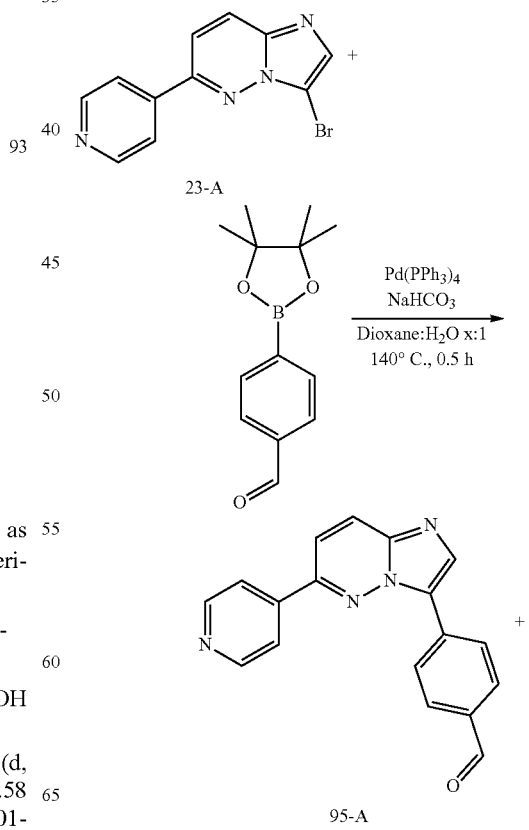

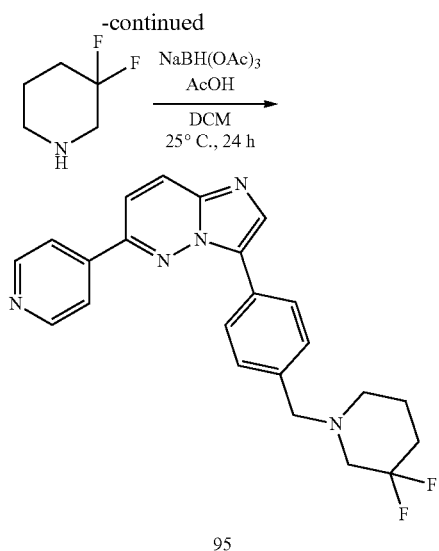

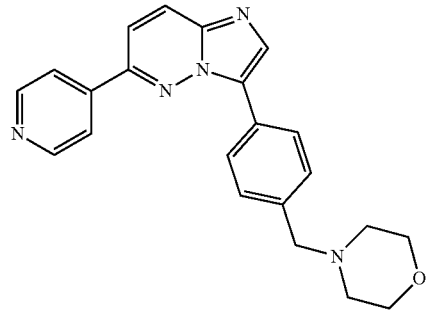

Scheme 30, Step 1

A 2-5 mL Biotage© microwave vial loaded with 3-bromo-6-(pyridin-4-yl)imidazo[1,2-b]pyridazine 23-A (170 mg, 0.618 mmol), 4-(4,4,5,5-tetramethyl-1,3,2-dioxaborolan-2-yl)benzaldehyde (172 mg, 0.742 mmol), Pd(PPh$_3$)$_4$ (50 mg, 0.043 mmol), and NaHCO$_3$ (208 mg, 2.472 mmol), was capped, purged with argon, then injected with degassed dioxane:H$_2$O (3.296 mL:0.824 mL, 4:1 v/v), and heated to 140° for 0.5 h in a Biotage Microwave Reactor. The reaction was cooled, diluted with DCM, filtered through celite, concentrated, dryloaded onto silica gel and purified on a 12 g silica gel column (DCM/MeOH, 0-8%), affording 4-(6-(pyridin-4-yl)imidazo[1,2-b]pyridazin-3-yl)benzaldehyde 95-A as a yellow solid (110 mg, 0.366 mmol, 59% yield, 8% MeOH in DCM). $^1$H NMR (CDCl$_3$) δ: 10.09 (s, 1H), 8.85 (d, J=6.0 Hz, 2H), 8.37 (d, J=8.4 Hz, 2H), 8.29 (s, 1H), 8.20 (d, J=9.4 Hz, 1H), 8.07 (d, J=8.7 Hz, 2H), 7.92 (d, J=6.2 Hz, 2H), 7.65 (d, J=9.5 Hz, 1H). $^{13}$C NMR (CDCl$_3$) δ: 191.47, 150.92, 149.56, 142.66, 140.42, 135.50, 135.41, 134.14, 130.22, 127.76, 126.86, 126.68, 120.99, 115.46.

Scheme 30, Step 2

A 5 mL screw cap vial loaded with 4-(6-(pyridin-4-yl)imidazo[1,2-b]pyridazin-3-yl)benzaldehyde 95-A (20 mg, 0.067 mmol), 3,3-difluoropiperidine (12.1 mg, 0.10 mmol), DCM (1 mL), and AcOH (1 drop), were stirred for 5 minutes. NaBH(OAc)$_3$ (24 mg, 0.113 mmol), was added and the mixture was sealed and stirred at 25° C. for 24 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-10%), affording 3444(3,3-difluoropiperidin-1-yl)methyl)phenyl)-6-(pyridin-4-yl)imidazo[1,2-b]pyridazine 95 as a yellow semi-solid (10 mg, 0.025 mmol, 37% yield, 10% MeOH in DCM). $^1$H NMR (CDCl$_3$) δ: 8.84 (d, J=6.2 Hz, 2H), 8.21-8.11 (m, 4H), 7.94 (d, J=6.2 Hz, 2H), 7.59 (d, J=9.4 Hz, 1H), 7.54 (d, J=8.2 Hz, 2H), 3.71 (s, 2H), 2.73 (t, J=11.3 Hz, 2H), 2.67-2.41 (m, 2H), 2.08-1.77 (m, 4H).

Compound 96 was synthesized in a similar manner as depicted in Scheme 30, Step 2, using morpholine.

4-(4-(6-(pyridin-4-yl)imidazo[1,2-b]pyridazin-3-yl)benzyl)morpholine 96.

Yellow semi-solid (11 mg, 0.030 mmol, 45% yield, 14% MeOH in DCM).

$^1$H NMR (CDCl$_3$) δ: 8.83 (d, J=6.2 Hz, 2H), 8.21-8.14 (m, 2H), 8.13 (d, J=8.4 Hz, 2H), 7.94 (d, J=6.1 Hz, 2H), 7.59 (d, J=9.5 Hz, 1H), 7.54 (d, J=8.7 Hz, 2H), 3.87-3.69 (m, 4H), 3.61 (s, 2H), 2.68-2.38 (m, 4H).

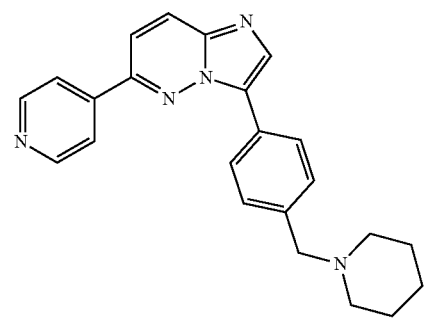

Compound 97 was synthesized in a similar manner as depicted in Scheme 30, Step 2, using morpholine.

3-(4-(piperidin-1-ylmethyl)phenyl)-6-(pyridin-4-yl)imidazo[1,2-b]pyridazine 97.

Green semi-solid (12 mg, 0.032 mmol, 49% yield, 21% MeOH in DCM).

$^1$H NMR (CDCl$_3$) δ: 8.83 (d, J=6.1 Hz, 2H), 8.26-8.12 (m, 4H), 7.92 (d, J=6.1 Hz, 2H), 7.74 (d, J=8.0 Hz, 2H), 7.60 (d, J=9.5 Hz, 1H), 4.00 (s, 2H), 2.98-2.67 (m, 4H), 2.03-1.82 (m, 4H), 1.69-1.49 (m, 2H).

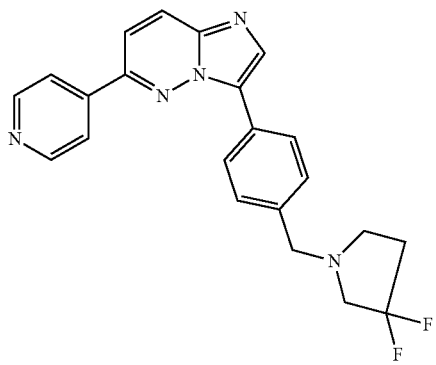

98

Compound 98 was synthesized in a similar manner as depicted in Scheme 30, Step 2, using 3,3-difluoropyrrolidine.

3-(4-((3,3-difluoropyrrolidin-1-yl)methyl)phenyl)-6-(pyridin-4-yl)imidazo[1,2-b]pyridazine 98.

Green semi-solid (12 mg, 0.031 mmol, 46% yield, 9% MeOH in DCM).

$^1$H NMR (CDCl$_3$) δ: 8.83 (d, J=6.1 Hz, 2H), 8.20-8.15 (m, 2H), 8.13 (d, J=8.6 Hz, 2H), 7.93 (d, J=6.1 Hz, 2H), 7.59 (d, J=9.5 Hz, 1H), 7.53 (d, J=8.0 Hz, 2H), 3.75 (s, 2H), 2.98 (t, J=13.2 Hz, 2H), 2.84 (t, J=6.9 Hz, 2H), 2.42-2.26 (m, 2H).

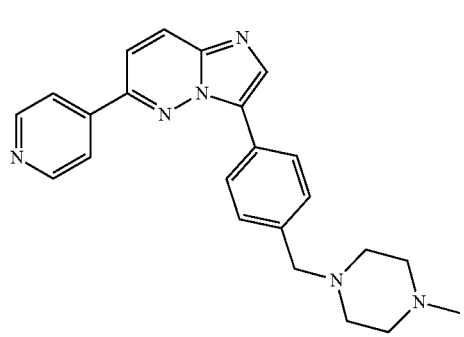

100

Compound 100 was synthesized in a similar manner as depicted in Scheme 30, Step 2, using 4-methylpiperazine.

3-(4-((4-methylpiperazin-1-yl)methyl)phenyl)-6-(pyridin-4-yl)imidazo[1,2-b]pyridazine 100.

Yellow-Green oil (15 mg, 0.039 mmol, 59% yield, 32% MeOH in DCM).

$^1$H NMR (CDCl$_3$) δ: 8.83 (d, J=6.0 Hz, 2H), 8.16 (d, J=9.5 Hz, 2H), 8.11 (d, J=8.5 Hz, 2H), 7.93 (d, J=6.2 Hz, 2H), 7.58 (d, J=9.4 Hz, 1H), 7.53 (d, J=8.5 Hz, 2H), 3.63 (s, 2H), 2.56 (s, 8H), 2.35 (s, 3H). $^{13}$C NMR (CDCl$_3$) δ: 150.78, 149.00, 143.01, 139.50, 138.47, 134.01, 129.55, 129.02, 127.12, 126.69, 126.54, 121.00, 114.35, 62.75, 55.12, 53.07, 45.98.

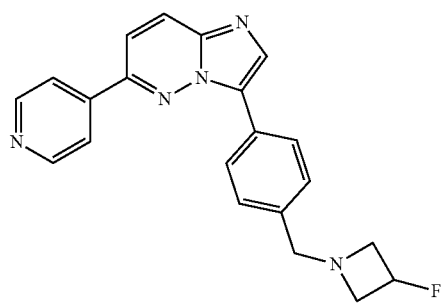

99

Compound 99 was synthesized in a similar manner as depicted in Scheme 30, Step 2, using 3-fluoroazetidine.

3-(4-((3-fluoroazetidin-1-yl)methyl)phenyl)-6-(pyridin-4-yl)imidazo[1,2-b]pyridazine 99.

Yellow-Green semi-solid (9 mg, 0.025 mmol, 38% yield, 9% MeOH in DCM).

$^1$H NMR (CDCl$_3$) δ: 8.83 (d, J=6.2 Hz, 2H), 8.25-8.04 (m, 4H), 7.94 (d, J=6.1 Hz, 2H), 7.59 (d, J=9.4 Hz, 1H), 7.49 (d, J=8.3 Hz, 2H), 5.33-5.08 (m, 1H), 3.91-3.59 (m, 4H), 3.34-3.18 (m, 2H).

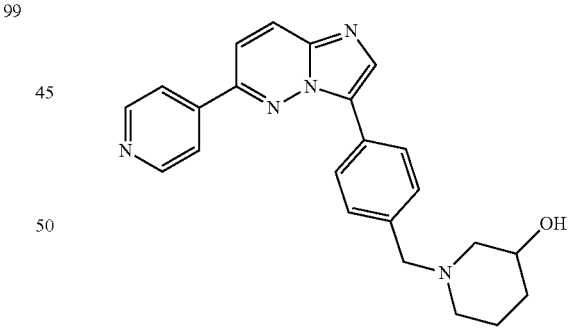

101

Compound 101 was synthesized in a similar manner as depicted in Scheme 30, Step 2, using piperidin-3-ol.

1-(4-(6-(pyridin-4-yl)imidazo[1,2-b]pyridazin-3-yl)benzyl)piperidin-3-ol 101.

Green oil (17 mg, 0.044 mmol, 66% yield, 21% MeOH in DCM).

$^1$H NMR (CDCl$_3$) δ: 8.83 (d, J=5.9 Hz, 2H), 8.20-8.08 (m, 4H), 7.94 (d, J=5.9 Hz, 2H), 7.59 (d, J=9.5 Hz, 1H), 7.53 (d, J=8.2 Hz, 2H), 3.92 (s, 1H), 3.67 (s, 2H), 2.66-2.56 (m, 4H), 2.46-2.33 (m, 2H), 1.90 (bs, 1H), 1.70-1.60 (m, 2H).

102

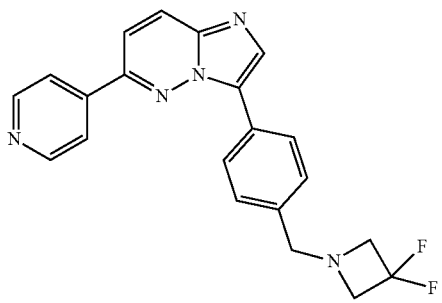

Compound 102 was synthesized in a similar manner as depicted in Scheme 30, Step 2, using 3,3-difluoroazetidine.

3-(4-((3,3-difluoroazetidin-1-yl)methyl)phenyl)-6-(pyridin-4-yl)imidazo[1,2-b]pyridazine 102.

Green semi-solid (17 mg, 0.045 mmol, 85% yield, 8% MeOH in DCM).

$^1$H NMR (CDCl$_3$) δ: 8.84 (d, J=6.2 Hz, 2H), 8.22-8.16 (m, 2H), 8.14 (d, J=8.7 Hz, 2H), 7.94 (d, J=6.1 Hz, 2H), 7.59 (d, J=9.4 Hz, 1H), 7.51 (d, J=8.6 Hz, 2H), 3.86 (s, 2H), 3.69 (t, J=12.0 Hz, 4H).

103

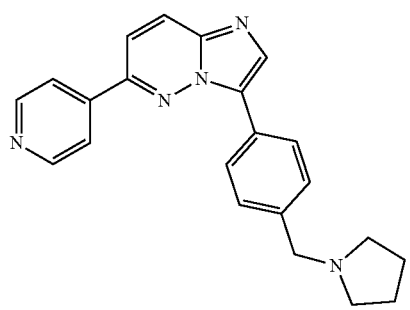

Compound 103 was synthesized in a similar manner as depicted in Scheme 30, Step 2, using pyrrolidine.

6-(pyridin-4-yl)-3-(4-(pyrrolidin-1-ylmethyl)phenyl)imidazo[1,2-b]pyridazine 103.

Yellow-green semi-solid (6 mg, 0.017 mmol, 36% yield, 30% MeOH in DCM).

$^1$H NMR (CDCl$_3$) δ: 8.84 (d, J=6.1 Hz, 2H), 8.21 (d, J=8.3 Hz, 2H), 8.19-8.09 (m, 2H), 7.93 (d, J=6.1 Hz, 2H), 7.76 (d, J=7.9 Hz, 2H), 7.61 (d, J=9.5 Hz, 1H), 4.10 (s, 2H), 3.26-2.92 (m, 4H), 2.22-1.88 (m, 4H).

104

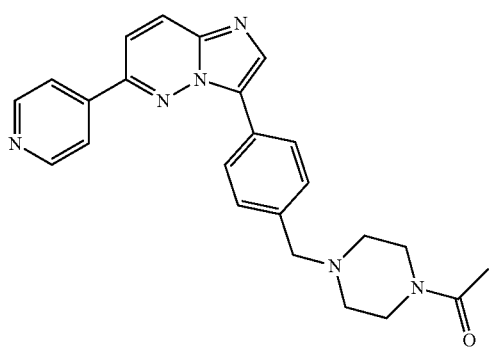

Compound 104 was synthesized in a similar manner as depicted in Scheme 30, Step 2, using 1-(piperazin-1-yl)ethan-1-one.

1-(4-(4-(6-(pyridin-4-yl)imidazo[1,2-b]pyridazin-3-yl)benzyl)piperazin-1-yl)ethan-1-one 104.

Green semi-solid (14 mg, 0.034 mmol, 73% yield, 10% MeOH in DCM).

$^1$H NMR (CDCl$_3$) δ: 8.83 (d, J=6.0 Hz, 2H), 8.29-8.06 (m, 4H), 7.94 (d, J=6.1 Hz, 2H), 7.59 (d, J=9.4 Hz, 1H), 7.53 (d, J=8.4 Hz, 2H), 3.76-3.64 (m, 2H), 3.63 (s, 2H), 3.58-3.45 (m, 2H), 2.64-2.44 (m, 4H), 2.12 (s, 3H).

Scheme 31

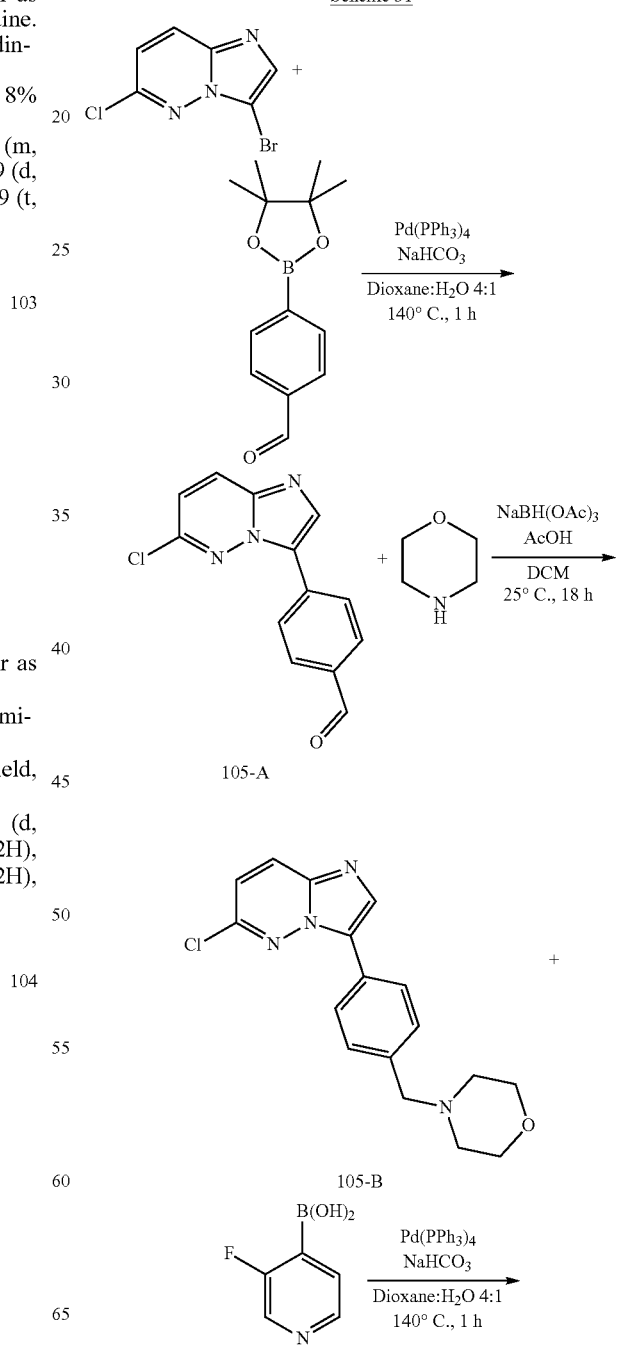

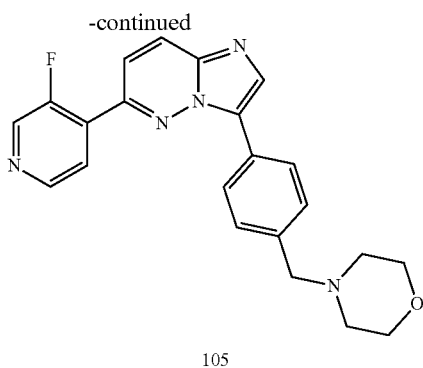

105

Scheme 31, Step 1

A 20 mL Biotage© microwave vial loaded with 3-bromo-6-chloroimidazo[1,2-b]pyridazine (500 mg, 2.151 mmol), 4-(4,4,5,5-tetramethyl-1,3,2-dioxaborolan-2-yl)benzaldehyde (549 mg, 2.366 mmol), Pd(PPh$_3$)$_4$ (124 mg, 0.108 mmol), and NaHCO$_3$, (723 mg, 8.6 mmol), was capped, purged with argon, then injected with degassed dioxane:H$_2$O (12.3 mL:3.07 mL, 4:1 v/v), and heated to 140° for 1 h in an oil bath. The reaction was cooled, diluted with DCM, filtered through celite, concentrated, dryloaded onto silica gel and purified on a 12 g silica gel column (DCM/MeOH, 0-8%), affording 4-(6-chloroimidazo[1,2-b]pyridazin-3-yl)benzaldehyde 105-A as an orange semi-solid (520 mg, 2.018 mmol, 94% yield, 8% MeOH in DCM). $^1$H NMR (CDCl$_3$) δ: 10.05 (s, 1H), 8.27 (d, J=8.6 Hz, 2H), 8.21 (s, 1H), 8.05-7.96 (m, 3H), 7.16 (d, J=9.4 Hz, 1H).

Scheme 31, Step 2

A 20 mL screw cap vial loaded with 4-(6-chloroimidazo[1,2-b]pyridazin-3-yl)benzaldehyde 105-A (200 mg, 0.776 mmol), Morpholine (0.1 mL, 1.164 mmol), DCM (7.76 mL), and AcOH (5 drops), were stirred for 5 minutes. NaBH(OAc)$_3$ (214 mg, 1.009 mmol), was added and the mixture was sealed and stirred at 25° C. for 24 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-7%), affording 4-(4-(6-chloroimidazo[1,2-b]pyridazin-3-yl)benzyl)morpholine 105-B as a green semi-solid (99 mg, 0.301 mmol, 39% yield, 7% MeOH in DCM). $^1$H NMR (CDCl$_3$) δ: 8.08 (s, 1H), 8.01 (d, J=8.2 Hz, 2H), 7.98 (d, J=9.4 Hz, 1H), 7.51 (d, J=7.6 Hz, 2H), 7.11 (d, J=9.4 Hz, 1H), 3.80-3.73 (m, 4H), 3.59 (s, 2H), 2.63-2.43 (m, 4H).

Scheme 31, Step 3

A 2-5 mL Biotage© microwave vial loaded with 4-(4-(6-chloroimidazo[1,2-b]pyridazin-3-yl)benzyl)morpholine 105-B (33 mg, 0.1 mmol), (3-fluoropyridin-4-yl)boronic acid (14.14 mg, 0.1 mmol), Pd(PPh$_3$)$_4$ (4.64 mg, 0.004 mmol), and NaHCO$_3$, (33.7 mg, 0.401 mmol), was capped, purged with argon, then injected with degassed dioxane:H$_2$O (0.8 mL:0.2 mL, 4:1 v/v), and heated to 140° for 1 h in an oil bath. The reaction was cooled, diluted with DCM, filtered through celite, concentrated, dryloaded onto silica gel and purified on a 12 g silica gel column (DCM/MeOH, 0-5%), affording 4-(4-(6-(3-fluoropyridin-4-yl)imidazo[1,2-b]pyridazin-3-yl)benzyl)morpholine 105 as a yellow semi-solid (10 mg, 0.026 mmol, 26% yield, 5% MeOH in DCM).

$^1$H NMR (CDCl$_3$) δ: 8.70 (d, J=2.7 Hz, 1H), 8.63 (dd, J=5.0, 1.0 Hz, 1H), 8.18 (s, 1H), 8.16 (d, J=9.4 Hz, 1H), 8.10 (d, J=8.3 Hz, 2H), 7.93 (ddd, J=6.5, 5.0, 0.5 Hz, 1H), 7.64 (dd, J=9.5, 1.8 Hz, 1H), 7.53 (d, J=8.4 Hz, 2H), 3.83-3.72 (m, 4H), 3.60 (s, 2H), 2.62-2.41 (m, 4H).

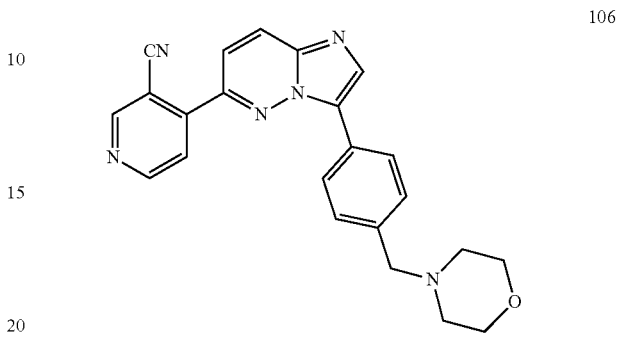

106

Compound 106 was synthesized in a similar manner as depicted in Scheme 31, Step 3, using 4-(4,4,5,5-tetramethyl-1,3,2-dioxaborolan-2-yl)nicotinonitrile.

4-(3-(4-(morpholinomethyl)phenyl)imidazo[1,2-b]pyridazin-6-yl)nicotinonitrile 106.

Clear semi-solid (4 mg, 0.01009 mmol, 10% yield, 9% MeOH in DCM).

$^1$H NMR (CDCl$_3$) δ: 9.12 (d, J=0.8 Hz, 1H), 8.98 (d, J=5.2 Hz, 1H), 8.25 (d, J=9.4 Hz, 1H), 8.21 (s, 1H), 8.13 (d, J=8.4 Hz, 2H), 7.80 (dd, J=5.2, 0.8 Hz, 1H), 7.56-7.50 (m, 3H), 3.80-3.69 (m, 4H), 3.60 (s, 2H), 2.59-2.45 (m, 4H).

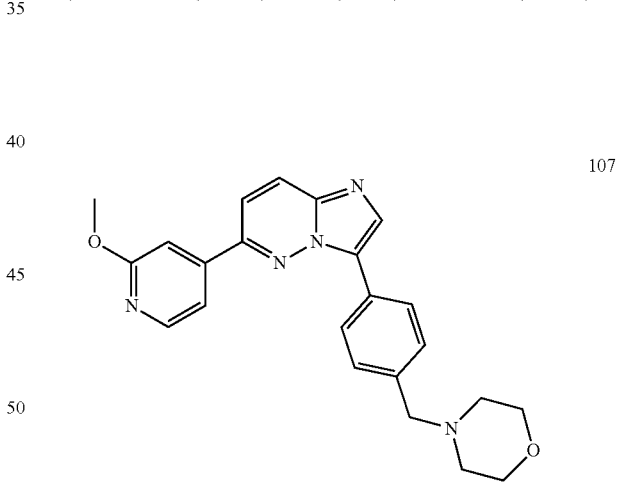

107

Compound 107 was synthesized in a similar manner as depicted in Scheme 31, Step 3, using 2-methoxy-4-(4,4,5,5-tetramethyl-1,3,2-dioxaborolan-2-yl)pyridine.

4-(4-(6-(2-methoxypyridin-4-yl)imidazo[1,2-b]pyridazin-3-yl)benzyl)morpholine 107.

Green semi-solid (12 mg, 0.030 mmol, 30% yield, 6% MeOH in DCM).

$^1$H NMR (CDCl$_3$) δ: 8.35 (dd, J=5.4, 0.7 Hz, 1H), 8.17-8.08 (m, 4H), 7.57-7.49 (m, 4H), 7.39-7.31 (m, 1H), 4.05 (s, 3H), 3.81-3.72 (m, 4H), 3.60 (s, 2H), 2.59-2.46 (m, 4H).

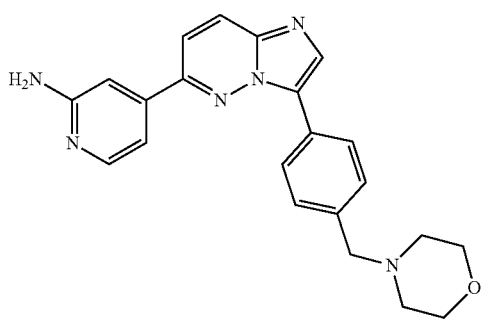

108

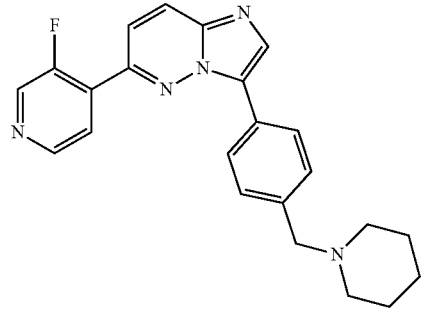

109

Compound 108 was synthesized in a similar manner as depicted in Scheme 31, Step 3, using 4-(4,4,5,5-tetramethyl-1,3,2-dioxaborolan-2-yl)pyridin-2-amine.

4-(3-(4-(morpholinomethyl)phenyl)imidazo[1,2-b]pyridazin-6-yl)pyridin-2-amine 108.

Yellow green semi-solid (15 mg, 0.039 mmol, 37% yield, 15% MeOH).

$^1$H NMR (CDCl$_3$) δ: 8.27 (d, J=5.3 Hz, 1H), 8.16-8.05 (m, 4H), 7.55-7.45 (m, 3H), 7.26 (dd, J=5.4, 1.5 Hz, 1H), 7.16-7.08 (m, 1H), 4.71 (s, 2H), 3.82-3.69 (m, 4H), 3.61 (s, 2H), 2.64-2.47 (m, 4H). $^{13}$C NMR (CDCl$_3$) δ: 159.14, 149.62, 149.27, 144.88, 139.61, 137.89, 133.80, 129.54, 128.82, 127.38, 126.69, 126.29, 114.78, 111.81, 105.92, 67.03, 63.22, 53.71.

Compound 109 was synthesized in a similar manner as depicted, using 1-(4-(4,4,5,5-tetramethyl-1,3,2-dioxaborolan-2-yl)benzyl)piperidine in Scheme 31, Step 1 and in Scheme 31, Step 3, using (3-fluoropyridin-4-yl)boronic acid.

6-(3-fluoropyridin-4-yl)-3-(4-(piperidin-1-ylmethyl)phenyl)imidazo[1,2-b]pyridazine 109.

Yellow-green semi-solid (5.5 mg, 0.014 mmol, 19% yield, 18% MeOH in DCM).

$^1$H NMR (CDCl$_3$) δ: 8.69 (d, J=2.8 Hz, 1H), 8.63 (dd, J=4.9, 1.1 Hz, 1H), 8.18 (s, 1H), 8.15 (d, J=9.5 Hz, 1H), 8.09 (d, J=8.4 Hz, 2H), 7.94 (ddd, J=6.6, 5.0, 0.5 Hz, 1H), 7.64 (dd, J=9.5, 1.9 Hz, 1H), 7.51 (dd, J=8.0, 0.6 Hz, 2H), 3.58 (s, 2H), 2.51-2.42 (m, 4H), 1.70-1.56 (m, 4H), 1.55-1.40 (m, 2H).

110

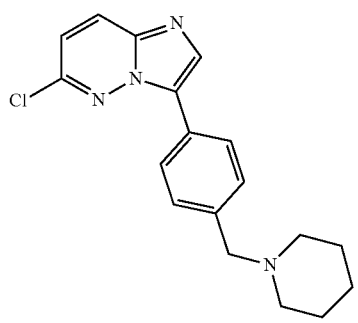 [SMILES: Clc1ccc2ncc(-c3ccc(CN4CCCCC4)cc3)n2n1]

6-chloro-3-(4-(piperidin-1-ylmethyl)phenyl)imidazo[1,2-b]pyridazine

Green semi-solid (30 mg, 0.092 mmol, 12% yield, 8% MeOH in DCM).

$^1$H NMR (CDCl$_3$) δ: 8.07 (s, 1H), 8.02 (d, J=8.1 Hz, 2H), 7.97 (d, J=9.4 Hz, 1H), 7.55 (d, J=8.0 Hz, 2H), 7.10 (d, J=9.4 Hz, 1H), 3.67 (s, 2H), 2.58-2.53 (m, 4H), 1.77-1.63 (m, 4H), 1.63-1.36 (m, 2H).

Compound 110 was synthesized in a similar manner as depicted, using 1-(4-(4,4,5,5-tetramethyl-1,3,2-dioxaborolan-2-yl)benzyl)piperidine in Scheme 31, Step 1 and in Scheme 31, Step 3, using 4-(4,4,5,5-tetramethyl-1,3,2-dioxaborolan-2-yl)pyridin-2-amine.

4-(3-(4-(piperidin-1-ylmethyl)phenyl)imidazo[1,2-b]pyridazin-6-yl)pyridin-2-amine 110.

Yellow green semi-solid (5 mg, 0.013 mmol, 20% yield, 14% MeOH in DCM).

$^1$H NMR (CDCl$_3$) δ: 8.27 (dd, J=5.4, 0.8 Hz, 1H), 8.13-8.07 (m, 4H), 7.54-7.47 (m, 3H), 7.27 (dd, J=5.4, 1.6 Hz, 1H), 7.17-7.08 (m, 1H), 4.67 (s, 2H), 3.58 (s, 2H), 2.56-2.36 (m, 4H), 1.75-1.59 (m, 4H), 1.55-1.42 (m, 2H).

Scheme 32

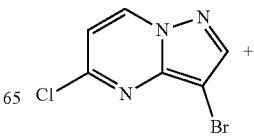

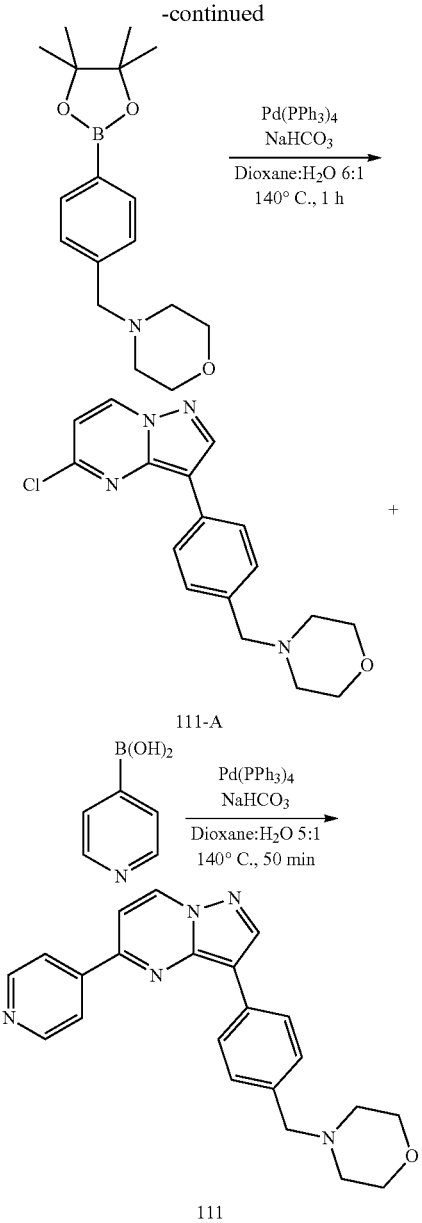

111-A

111

Scheme 32, Step 1

A 20 mL Biotage© microwave vial loaded with 3-bromo-5-chloropyrazolo[1,5-a]pyrimidine (250 mg, 1.075 mmol), 4-(4-(4,4,5,5-tetramethyl-1,3,2-dioxaborolan-2-yl)benzyl)morpholine (272 mg, 0.896 mmol), Pd(PPh$_3$)$_4$ (62 mg, 0.054 mmol), and NaHCO$_3$ (301 mg, 3.58 mmol), was capped, purged with argon, then injected with degassed dioxane:H$_2$O (6.4 mL:1.06 mL, 6:1 v/v), and heated to 140° for 1 h in a Biotage Microwave Reactor. The reaction was cooled, diluted with DCM, filtered through celite, concentrated, dryloaded onto silica gel and purified on a 12 g silica gel column (DCM/MeOH, 0-20%), affording 4-(4-(5-chloropyrazolo[1,5-a]pyrimidin-3-yl)benzyl)morpholine 111-A as a yellow solid (262 mg, 0.797 mmol, 89% yield, 5% MeOH in DCM). $^1$H NMR (CDCl$_3$) δ: 8.65 (d, J=7.4 Hz, 1H), 8.16-8.08 (m, 3H), 7.50 (d, J=8.4 Hz, 2H), 7.32 (d, J=7.4 Hz, 1H), 3.78-3.69 (m, 4H), 3.59 (s, 2H), 2.53-2.46 (m, 4H).

Scheme 32, Step 2

A 2-5 mL Biotage© microwave vial loaded with 4-(4-(5-chloropyrazolo[1,5-a]pyrimidin-3-yl)benzyl)morpholine 111-A (70 mg, 0.192 mmol), pyridin-4-ylboronic acid (25.9 mg, 0.211 mmol), Pd(PPh$_3$)$_4$ (13.28 mg, 0.011 mmol), and NaHCO$_3$, (64.4 mg, 0.766 mmol), was capped, purged with argon, then injected with degassed dioxane:H$_2$O (1.33 mL:0.266 mL, 5:1 v/v), and heated to 140° C. for 50 min in a Biotage Microwave Reactor. The reaction was cooled, diluted with DCM, filtered through celite, concentrated, dryloaded onto silica gel and purified on a 12 g silica gel column (DCM/MeOH, 0-10%), affording 4-(4-(5-(pyridin-4-yl)pyrazolo[1,5-a]pyrimidin-3-yl)benzyl)morpholine 111 as a yellow solid (44 mg, 0.118 mmol, 62% yield, 10% MeOH in DCM).

$^1$H NMR (CDCl$_3$) δ: 8.71 (d, J=7.4 Hz, 1H), 8.65 (d, J=6.2 Hz, 2H), 8.52 (s, 1H), 8.15 (d, J=8.4 Hz, 2H), 8.08 (d, J=6.1 Hz, 2H), 7.55 (d, J=8.4 Hz, 2H), 7.38 (d, J=7.4 Hz, 1H), 3.85-3.69 (m, 4H), 3.62 (s, 2H), 2.62-2.26 (m, 4H). $^{13}$C NMR (CDCl$_3$) δ: 157.00, 150.12, 145.56, 143.53, 141.43, 139.77, 135.63, 135.52, 129.77, 127.42, 120.10, 107.62, 105.96, 67.02, 63.00, 53.69.

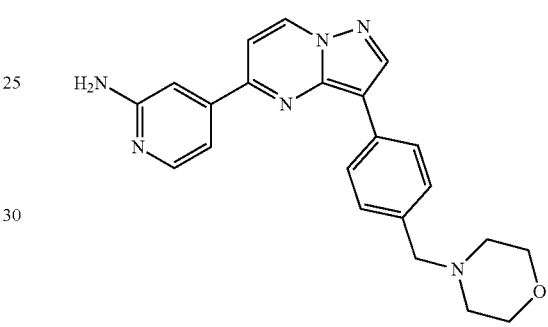

112

Compound 112 was synthesized in a similar manner as depicted in Scheme 32, Step 2, using 4-(4,4,5,5-tetramethyl-1,3,2-dioxaborolan-2-yl)pyridin-2-amine.

4-(3-(4-(morpholinomethyl)phenyl)pyrazolo[1,5-a]pyrimidin-5-yl)pyridin-2-amine 112.

Yellow solid (19 mg, 0.049 mmol, 26% yield, 10% MeOH in DCM).

$^1$H NMR (CDCl$_3$) δ: 8.73 (d, J=7.4 Hz, 1H), 8.48 (s, 1H), 8.21-8.05 (m, 3H), 7.55 (d, J=8.0 Hz, 2H), 7.47 (d, J=6.8 Hz, 1H), 7.43-7.34 (m, 2H), 4.59 (s, 2H), 3.85-3.72 (m, 4H), 3.62 (s, 2H), 2.65-2.44 (m, 4H).

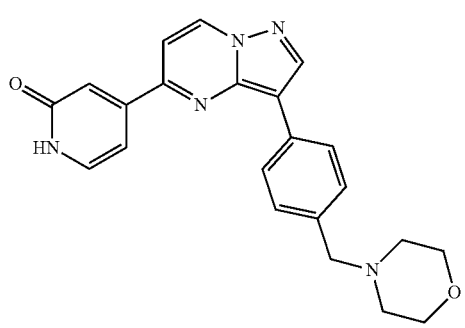

113

Compound 113 was synthesized in a similar manner as depicted in Scheme 32, Step 2, using (2-hydroxypyridin-4-yl)boronic acid.

4-(3-(4-(morpholinomethyl)phenyl)pyrazolo[1,5-a]pyrimidin-5-yl)pyridin-2(1H)-one 113.

Green semi-solid (5 mg, 0.013 mmol, 6% yield, 11% MeOH in DCM).

$^1$H NMR (CDCl$_3$) δ: 12.23 (bs, 1H), 8.76 (d, J=7.4 Hz, 1H), 8.49 (s, 1H), 8.18 (d, J=8.4 Hz, 2H), 7.57 (d, J=8.2 Hz, 2H), 7.53-7.46 (m, 2H), 7.44 (d, J=7.3 Hz, 1H), 7.24 (dd, J=6.9, 1.7 Hz, 1H), 3.82-3.74 (m, 4H), 3.64 (s, 2H), 2.57-2.50 (m, 4H).

Scheme 33

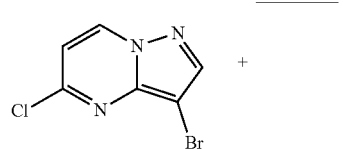

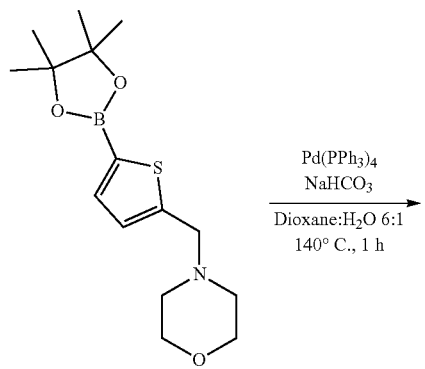

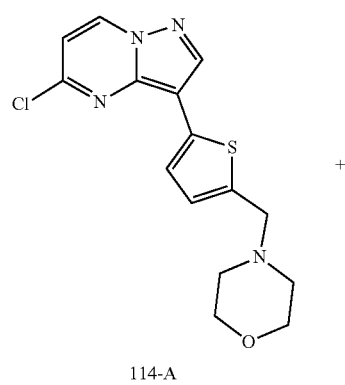

114-A

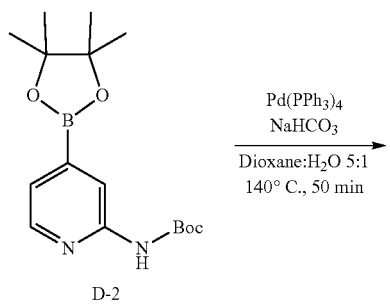

D-2

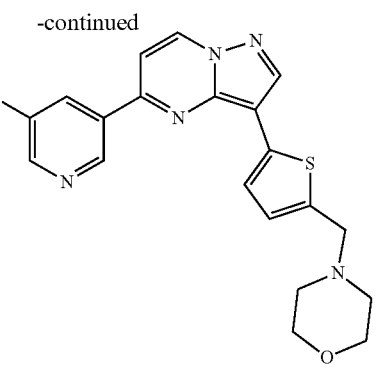

114

Scheme 33, Step 1

A 20 mL Biotage© microwave vial loaded with 3-bromo-5-chloropyrazolo[1,5-a]pyrimidine (366 mg, 1.183 mmol), 4-((5-(4,4,5,5-tetramethyl-1,3,2-dioxaborolan-2-yl)thiophen-2-yl)methyl)morpholine (250 mg, 1.075 mmol), Pd(PPh$_3$)$_4$ (74.6 mg, 0.065 mmol), and NaHCO$_3$, (361 mg, 4.3 mmol), was capped, purged with argon, then injected with degassed dioxane:H$_2$O (7.68 mL:1.28 mL, 6:1 v/v), and heated to 140° for 1 h in a Biotage Microwave Reactor. The reaction was cooled, diluted with DCM, filtered through celite, concentrated, dryloaded onto silica gel and purified on a 12 g silica gel column (DCM/MeOH, 0-7%), affording 4-((5-(5-chloropyrazolo[1,5-a]pyrimidin-3-yl)thiophen-2-yl)methyl)morpholine 114-A as a green semi solid (272 mg, 0.812 mmol, 76% yield, 7% MeOH in DCM).

$^1$H NMR (CDCl$_3$) δ: 8.48 (d, J=7.4 Hz, 1H), 7.99 (s, 1H), 7.50 (d, J=3.7 Hz, 1H), 7.08 (d, J=7.4 Hz, 1H), 6.90 (d, J=3.7 Hz, 1H), 3.74-3.66 (m, 4H), 2.53-2.47 (m, 4H), 1.21 (d, J=8.6 Hz, 2H).

Scheme 33, Step 2

A 2-5 mL Biotage© microwave vial loaded with 4-((5-(5-chloropyrazolo[1,5-a]pyrimidin-3-yl)thiophen-2-yl)methyl)morpholine 114-A (100 mg, 0.239 mmol), tert-butyl (4-(4,4,5,5-tetramethyl-1,3,2-dioxaborolan-2-yl)pyridin-2-yl)carbamate D-2 (84 mg, 0.263 mmol), Pd(PPh$_3$)$_4$ (16.57 mg, 0.014 mmol), and NaHCO$_3$, (80 mg, 0.956 mmol), was capped, purged with argon, then injected with degassed dioxane:H$_2$O (1.66 mL:0.33 mL, 5:1 v/v), and heated to 140° C. for 50 min in a Biotage Microwave Reactor. The reaction was cooled, 37% conc. HCl (0.7 mL) was added, stirred for 1 h and basified with 10% NaOH. The mixture was extracted with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-10%), affording 4-(3-(5-(morpholinomethyl)thiophen-2-yl)pyrazolo[1,5-a]pyrimidin-5-yl)pyridin-2-amine 114 as a green semi-solid (7 mg, 0.018 mmol, 7% yield, 10% MeOH in DCM). $^1$H NMR (CDCl$_3$) δ: 8.63 (d, J=7.4 Hz, 1H), 8.45 (s, 1H), 8.16 (d, J=6.2 Hz, 1H), 7.62 (d, J=3.7 Hz, 1H), 7.44-7.38 (m, 2H), 7.21 (d, J=7.4 Hz, 1H), 7.03 (dt, J=3.7, 0.9 Hz, 1H), 4.58 (s, 2H), 3.92-3.60 (m, 6H), 2.66-2.54 (m, 4H).

Scheme 34

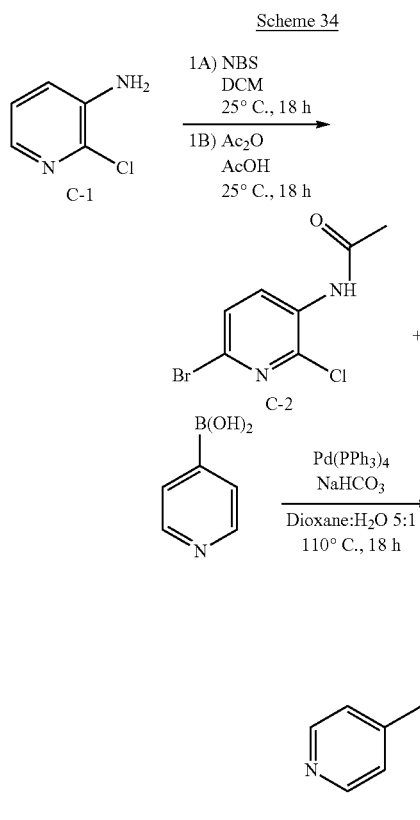

The reaction was cooled, diluted with DCM, filtered through celite, concentrated, dryloaded onto silica gel and purified on a 40 g silica gel column (DCM/MeOH, 0-9%), affording N-(6-chloro-[2,4'-bipyridin]-5-yl)acetamide C-3 as a gray powder (840 mg, 3.39 mmol, 60% yield, 9% MeOH in DCM). $^1$H NMR (CDCl$_3$) δ: 8.87 (d, J=8.4 Hz, 1H), 8.71 (d, J=6.5 Hz, 2H), 7.87 (d, J=6.5 Hz, 2H), 7.79 (d, J=8.4 Hz, 1H), 3.50 (s, 1H), 2.33 (s, 3H). $^{13}$C NMR (CDCl$_3$) δ: 168.77, 150.47, 148.82, 144.22, 139.66, 132.05, 129.37, 120.52, 120.26, 50.77.

Scheme 35

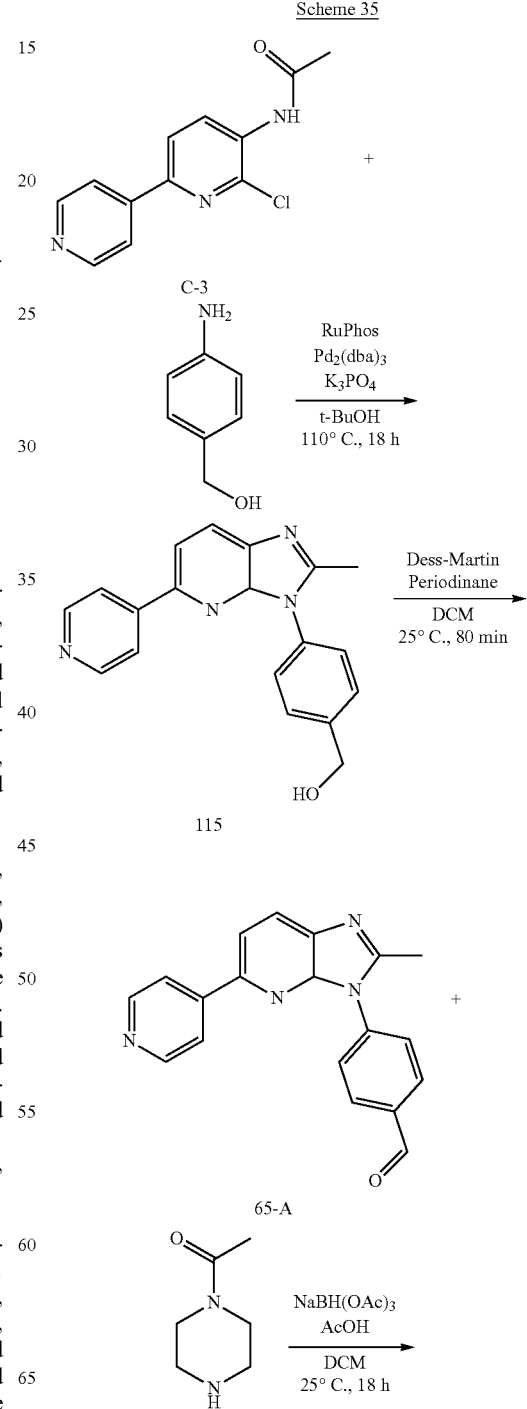

Scheme 34, Step 1A

To a 250 mL erlenmyer loaded with a stir bar, 2-chloro-pyridin-3-amine C-1 (4 g, 31.1 mmol) and DCM (104 mL), N-Bromosuccinimide (6.09 g, 34.2 mmol) was added portionwise over 15 minutes, sealed with parafilm, and stirred at 25° C. for 18 h. The flask was diluted with DCM and saturated sodium bicarbonate solution then extracted multiple times with DCM, washed with 10% NaOH, H$_2$O, brine, and the organic layer was dried over Na$_2$SO$_4$, concentrated and used crude in Step 1B.

Scheme 34, Step 1B

A 500 mL round bottom flask was loaded with a stir bar, crude 6-bromo-2-chloropyridin-3-amine (from Step 1A), and AcOH (35.6 mL, 622 mmol). Ac$_2$O (3.52 mL, 37.3 mL) was added dropwise over 15 minutes and the mixture was sealed with parafilm and stirred at 25° C., 18 h. The mixture is azeotroped with toluene repeatedly, followed by hexanes. Diethyl ether is added and the mixture is gently warmed and cooled until precipitation results. The product is filtered and washed with diethyl ether and hexanes, affording N-(6-bromo-2-chloropyridin-3-yl)acetamide C-2 as a tan solid (5.5 g, 22.04 mmol, 71% yield over two steps).

$^1$H NMR (CDCl$_3$) δ: 8.65 (d, J=8.5 Hz, 1H), 7.60 (s, 1H), 7.43 (d, J=8.5 Hz, 1H), 2.29 (s, 3H).

Scheme 34, Step 2

A 2-5 mL Biotage© microwave vial loaded with N-(6-bromo-2-chloropyridin-3-yl)acetamide C-1 (700 mg, 2.81 mmol), pyridin-4-ylboronic acid (345 mg, 2.81 mmol), Pd(PPh$_3$)$_4$ (292 mg, 0.253 mmol), and NaHCO$_3$, (943 mg, 11.22 mmol), was capped, purged with argon, then injected with degassed dioxane:H$_2$O (13.8 mL:2.75 mL, 5:1 v/v), and heated to 110° C. for 18 h in an oil bath. (Two vials, of the reaction conditions above were ran and purified together).

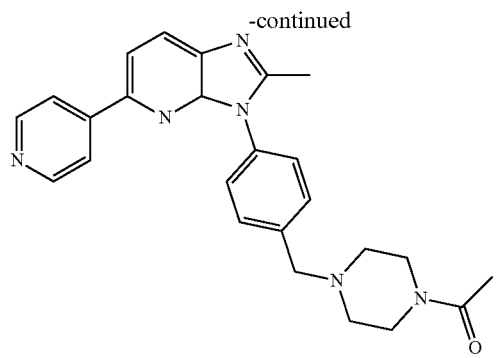

116

Scheme 35, Step 1

A 2-5 mL Biotage© microwave vial loaded with Pd$_2$(dba)$_3$ (22.18 mg, 0024 mmol), RuPhos (60.3 mg, 0.129 mmol), N-(6-chloro-[2,4'-bipyridin]-5-yl)acetamide C-3 (400 mg, 1.615 mmol), 4-aminophenyl)methanol (239 mg, 1.938 mmol), K$_3$PO$_4$ (1.028 g, 4.84 mmol), and t-BuOH (4.04 mL) was capped, purged with argon for 15 min, and then heated to 110° C. for 18 h in an oil bath. The reaction was cooled, diluted with DCM, filtered through celite, concentrated, dryloaded onto silica gel and purified on a 12 g silica gel column (DCM/MeOH, 0-18%), affording (4-(2-methyl-5-(pyridin-4-yl)-3H-imidazo[4,5-b]pyridin-3-yl)phenyl)methanol 115 as a clear semi-solid (8 mg, 0.025 mmol, 27% yield, 18% MeOH in DCM). $^1$H NMR (CDCl$_3$) δ: 8.60 (d, J=6.2 Hz, 2H), 8.10 (d, J=8.3 Hz, 1H), 7.89 (d, J=6.1 Hz, 2H), 7.82 (d, J=8.2 Hz, 1H), 7.66 (d, J=8.6 Hz, 2H), 7.49 (d, J=8.6 Hz, 2H), 4.90 (s, 2H), 3.11 (bs, 1H), 2.61 (s, 3H). This methodology and later related examples are based on Buchwald, et al. *Angew. Chem. Int. Ed.*, 2007, 46, 7509-7512, although in the article they do not describe examples of this process on compounds containing multiple and or complex heterocyclic systems.

Scheme 35, Step 2

A 20 mL dram vial loaded with (4-(2-methyl-5-(pyridin-4-yl)-3H-imidazo[4,5-b]pyridin-3-yl)phenyl)methanol 115 (420 mg, 1.328 mmol), DCM (13.3 mL), and Dess-Martin Periodinane (676 mg, 1.593 mmol) was sealed and stirred at 25° C. for 80 min. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-5%), affording 4-(2-methyl-5-(pyridin-4-yl)-3H-imidazo[4,5-b]pyridin-3-yl)benzaldehyde 65-A as a pink solid (66 mg, 0.875 mmol, 66% yield, 5% MeOH in DCM). $^1$H NMR (CDCl$_3$) δ: 10.18 (s, 1H), 8.66 (d, J=6.5 Hz, 2H), 8.18 (d, J=8.7 Hz, 2H), 8.13 (d, J=8.3 Hz, 1H), 7.89 (d, J=6.1 Hz, 2H), 7.85 (d, J=8.3 Hz, 1H), 7.75 (d, J=8.3 Hz, 2H), 2.69 (s, 3H). $^{13}$C NMR (CDCl$_3$) δ: 190.95, 153.86, 150.23, 148.90, 148.76, 146.31, 139.53, 136.09, 135.23, 130.91, 127.75, 127.40, 120.99, 116.62, 15.59.

Scheme 35, Step 3

A 5 mL screw cap vial loaded with 4-(2-methyl-5-(pyridin-4-yl)-3H-imidazo[4,5-b]pyridin-3-yl)benzaldehyde 65-A (30 mg, 0.095 mmol), 1-(piperazin-1-yl)ethan-1-one (18.35 mg, 0.143 mmol), DCM (0.954 mL), and AcOH (1 drop), were stirred for 5 minutes. NaBH(OAc)$_3$ (30.3 mg, 0.143 mmol) was added and the mixture was sealed and stirred at 25° C. for 18 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-22%), affording 1-(4-(4-(2-methyl-5-(pyridin-4-yl)-3H-imidazo[4,5-b]pyridin-3-yl)benzyl)piperazin-1-yl)ethan-1-one 116 as a green semi-solid (28 mg, 0.066 mmol, 69% yield, 22% MeOH in DCM). $^1$H NMR (CDCl$_3$) δ: 8.64 (d, J=5.8 Hz, 2H), 8.09 (d, J=8.3 Hz, 1H), 7.88 (d, J=5.9 Hz, 2H), 7.80 (d, J=8.3 Hz, 1H), 7.59 (d, J=8.2 Hz, 2H), 7.46 (d, J=8.4 Hz, 2H), 3.79-3.67 (m, 2H), 3.66 (s, 2H), 3.60-3.39 (m, 2H), 2.63 (s, 3H), 2.59-2.50 (m, 4H), 2.12 (s, 3H).

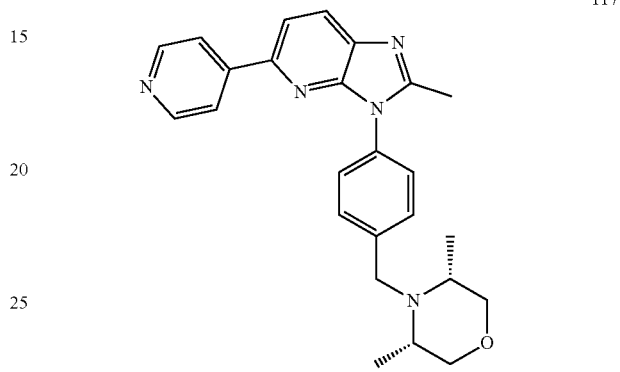

117

Compound 117 was synthesized in a similar manner as depicted in Scheme 35, Step 3, using (3S,5R)-3,5-dimethylmorpholine.

(3S,5R)-3,5-dimethyl-4-(4-(2-methyl-5-(pyridin-4-yl)-3H-imidazo[4,5-b]pyridin-3-yl)benzyl)morpholine 117.

Clear semi-solid (1.5 mg, 0.002418 mmol, 4.5% yield, 10% MeOH in DCM).

$^1$H NMR (Acetone) δ: 8.63 (d, J=5.7 Hz, 2H), 8.11 (d, J=8.5 Hz, 1H), 8.02 (d, J=8.3 Hz, 1H), 7.99 (d, J=6.2 Hz, 2H), 7.74 (d, J=8.2 Hz, 2H), 7.65-7.56 (m, 2H), 3.96 (s, 2H), 3.86-3.68 (m, 2H), 3.29-3.19 (m, 1H), 2.73-2.63 (m, 1H), 2.57 (s, 3H), 1.19-1.10 (m, 2H), 1.00 (s, 3H), 0.98 (s, 3H).

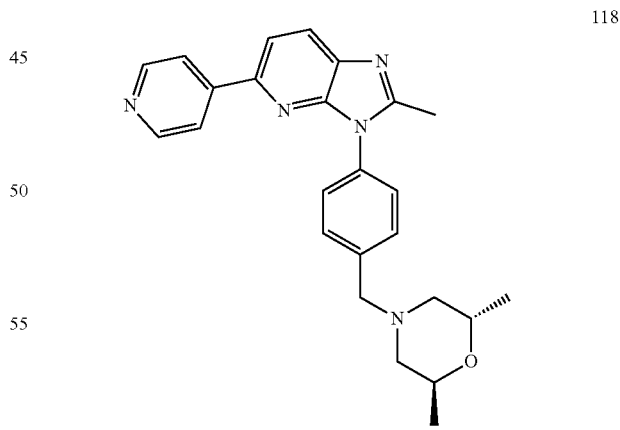

118

Compound 118 was synthesized in a similar manner as depicted in Scheme 35, Step 3, using (2S,6S)-2,6-dimethylmorpholine.

(2S,6S)-2,6-dimethyl-4-(4-(2-methyl-5-(pyridin-4-yl)-3H-imidazo[4,5-b]pyridin-3-yl)benzyl)morpholine 118.

White solid (19 mg, 0.046 mmol, 48% yield, 8% MeOH in DCM).

¹H NMR (CDCl₃) δ: 8.79-8.45 (m, 2H), 8.10 (d, J=8.3 Hz, 1H), 7.90 (d, J=5.6 Hz, 2H), 7.82 (d, J=8.3 Hz, 1H), 7.61 (d, J=8.2 Hz, 2H), 7.45 (d, J=8.6 Hz, 2H), 4.16-4.01 (m, 2H), 3.70-3.53 (m, 2H), 2.64 (s, 3H), 2.59 (dd, J=11.0, 3.1 Hz, 2H), 2.33-2.22 (m, 2H), 1.32 (s, 3H), 1.30 (s, 3H).

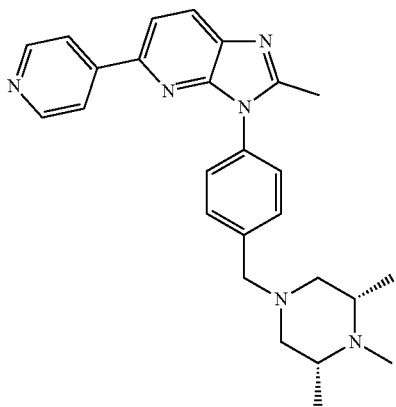

119

Compound 119 was synthesized in a similar manner as depicted in Scheme 35, Step 3, using (2R,6S)-1,2,6-trimethylpiperazine.

2-methyl-5-(pyridin-4-yl)-3-(4-(((3R,5S)-3,4,5-trimethylpiperazin-1-yl)methyl)phenyl)-3H-imidazo[4,5-b]pyridine 119.

Green oil (25 mg, 0.059 mmol, 61% yield, 31% MeOH in DCM).

¹H NMR (CDCl₃) δ: 8.65 (d, J=6.5 Hz, 2H), 8.10 (d, J=8.3 Hz, 1H), 7.88 (d, J=6.3 Hz, 2H), 7.80 (d, J=8.3 Hz, 1H), 7.58 (d, J=8.3 Hz, 2H), 7.45 (d, J=8.0 Hz, 2H), 3.62 (s, 2H), 2.85 (d, J=10.3 Hz, 2H), 2.63 (s, 3H), 2.55-2.47 (m, 2H), 2.40 (s, 3H), 2.18 (t, J=10.9 Hz, 2H), 1.21 (s, 3H), 1.19 (s, 3H).

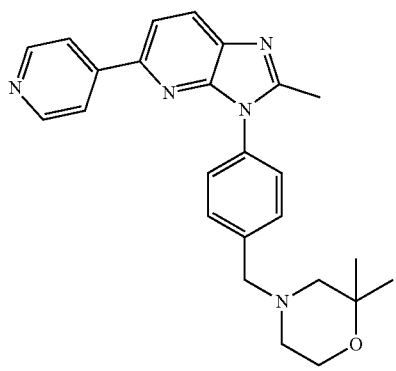

120

Compound 120 was synthesized in a similar manner as depicted in Scheme 35, Step 3, using 2,2-dimethylmorpholine.

2,2-dimethyl-4-(4-(2-methyl-5-(pyridin-4-yl)-3H-imidazo[4,5-b]pyridin-3-yl)benzyl)morpholine 120.

Clear semi-solid (20 mg, 0.048 mmol, 51% yield, 9% MeOH in DCM).

¹H NMR (CDCl₃) δ: 8.65 (d, J=6.1 Hz, 2H), 8.11 (d, J=8.3 Hz, 1H), 7.90 (d, J=6.2 Hz, 2H), 7.82 (d, J=8.3 Hz, 1H), 7.62 (d, J=8.0 Hz, 2H), 7.48-7.43 (m, 2H), 3.88-3.80 (m, 2H), 3.61 (s, 2H), 2.64 (s, 3H), 2.56-2.45 (m, 2H), 2.33 (s, 2H), 1.32 (s, 6H).

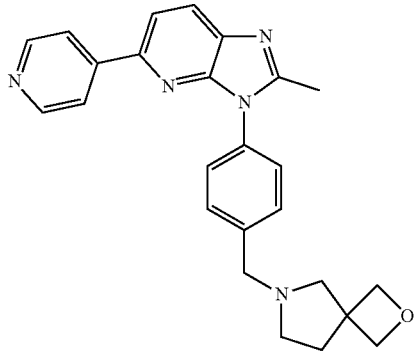

121

Compound 121 was synthesized in a similar manner as depicted in Scheme 35, Step 3, using 2-oxa-6-azaspiro[3.4]octane.

6-(4-(2-methyl-5-(pyridin-4-yl)-3H-imidazo[4,5-b]pyridin-3-yl)benzyl)-2-oxa-6-azaspiro[3.4]octane 121.

Clear semi-solid (18 mg, 0.044 mmol, 46% yield, 11% MeOH in DCM).

¹H NMR (CDCl₃) δ: 8.67 (d, J=6.3 Hz, 2H), 8.11 (d, J=8.3 Hz, 1H), 7.90 (d, J=6.6 Hz, 2H), 7.82 (d, J=8.3 Hz, 1H), 7.59 (d, J=8.0 Hz, 2H), 7.46 (d, J=8.4 Hz, 2H), 4.79-4.38 (m, 4H), 3.76 (s, 2H), 2.97 (s, 2H), 2.73-2.52 (m, 5H), 2.22 (t, J=7.0 Hz, 2H).

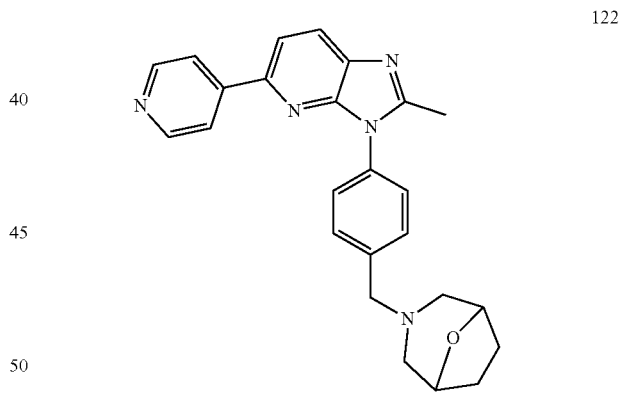

122

Compound 122 was synthesized in a similar manner as depicted in Scheme 35, Step 3, using 8-oxa-3-azabicyclo[3.2.1]octane.

3-(4-(2-methyl-5-(pyridin-4-yl)-3H-imidazo[4,5-b]pyridin-3-yl)benzyl)-8-oxa-3-azabicyclo[3.2.1]octane 122.

White semi-solid (20 mg, 0.049 mmol, 51% yield, 9% MeOH in DCM).

¹H NMR (CDCl₃) δ: 8.66 (d, J=5.6 Hz, 2H), 8.11 (d, J=8.3 Hz, 1H), 7.90 (d, J=6.1 Hz, 2H), 7.81 (d, J=8.3 Hz, 1H), 7.59 (d, J=8.5 Hz, 2H), 7.44 (d, J=8.3 Hz, 2H), 4.43-4.26 (m, 2H), 3.62 (s, 2H), 2.71-2.61 (m, 5H), 2.47 (dd, J=11.2, 2.1 Hz, 2H), 2.12-2.02 (m, 2H), 1.96-1.91 (m, 2H).

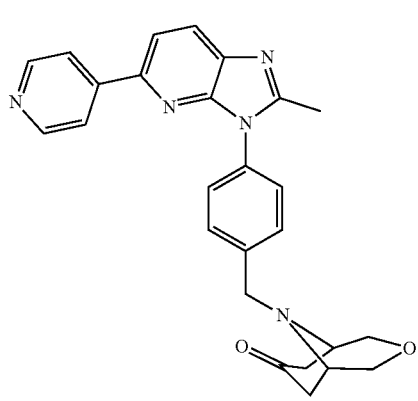

123

Compound 123 was synthesized in a similar manner as depicted in Scheme 35, Step 3, using (1R,5S)-3-oxa-9-azabicyclo[3.3.1]nonan-7-one.

(1R,5S)-9-(4-(2-methyl-5-(pyridin-4-yl)-3H-imidazo[4,5-b]pyridin-3-yl)benzyl)-3-oxa-9-azabicyclo[3.3.1]nonan-7-one 123.

Clear semi-solid (2 mg, 0.00455 mmol, 5% yield, 20% MeOH in DCM)

$^1$H NMR (Acetone) δ: 8.63 (d, J=6.2 Hz, 2H), 8.12 (d, J=8.3 Hz, 1H), 8.02 (d, J=8.3 Hz, 1H), 7.99 (d, J=6.0 Hz, 2H), 7.80 (d, J=8.2 Hz, 2H), 7.66 (d, J=8.5 Hz, 2H), 4.21 (s, 2H), 3.87 (d, J=11.2 Hz, 2H), 3.75 (d, J=10.7 Hz, 2H), 3.36-3.25 (m, 2H), 2.58 (s, 3H), 2.33-2.17 (m, 2H), 1.91 (p, J=2.2 Hz, 1H), 1.24 (d, J=6.4 Hz, 1H).

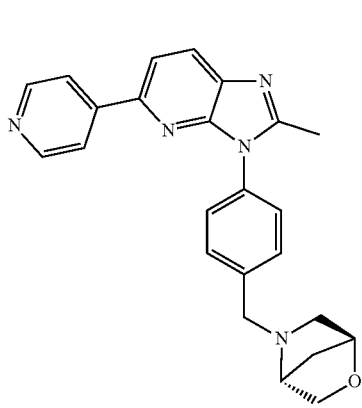

124

Compound 124 was synthesized in a similar manner as depicted in Scheme 35, Step 3, using (1S,4R)-2-oxa-5-azabicyclo[2.2.1]heptane.

(1S,4R)-5-(4-(2-methyl-5-(pyridin-4-yl)-3H-imidazo[4,5-b]pyridin-3-yl)benzyl)-2-oxa-5-azabicyclo[2.2.1]heptane 124.

Green semi-solid (11 mg, 0.028 mmol, 29% yield, 19% MeOH in DCM).

$^1$H NMR (CDCl$_3$) δ: 8.67 (d, J=5.9 Hz, 2H), 8.11 (d, J=8.3 Hz, 1H), 7.90 (d, J=6.2 Hz, 2H), 7.82 (d, J=8.3 Hz, 1H), 7.63 (d, J=8.3 Hz, 2H), 7.46 (d, J=8.4 Hz, 2H), 4.59-4.43 (m, 1H), 4.21 (d, J=7.8 Hz, 1H), 3.95 (d, J=6.3 Hz, 2H), 3.74 (dd, J=7.8, 1.8 Hz, 1H), 3.61 (s, 1H), 3.02 (d, J=10.5 Hz, 1H), 2.71 (d, J=10.2 Hz, 1H), 2.64 (s, 3H), 2.01 (d, J=10.2 Hz, 1H), 1.84 (d, J=9.8, 1.7 Hz, 1H).

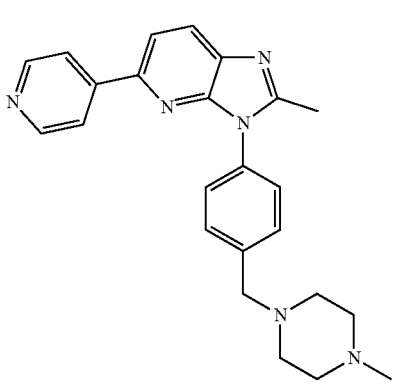

125

Compound 125 was synthesized in a similar manner as depicted in Scheme 35, Step 3, using 1-methylpiperazine.

2-methyl-3-(4-((4-methylpiperazin-1-yl)methyl)phenyl)-5-(pyridin-4-yl)-3H-imidazo[4,5-b]pyridine 125.

White semi-solid (19 mg, 0.048 mmol, 50% yield, 30% MeOH in DCM).

$^1$H NMR (CDCl$_3$) δ: 8.66 (d, J=6.2 Hz, 2H), 8.10 (d, J=8.3 Hz, 1H), 7.88 (d, J=6.3 Hz, 2H), 7.81 (d, J=8.3 Hz, 1H), 7.59 (d, J=8.4 Hz, 2H), 7.46 (d, J=8.5 Hz, 2H), 3.72 (s, 2H), 2.94-2.71 (m, 8H), 2.63 (s, 3H), 2.56 (s, 3H).

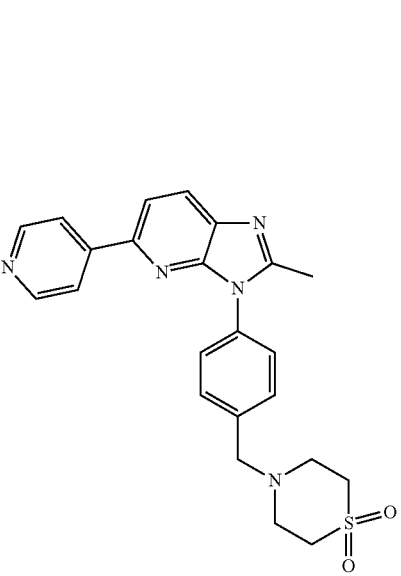

126

Compound 126 was synthesized in a similar manner as depicted in Scheme 35, Step 3, using thiomorpholine 1,1-dioxide.

4-(4-(2-methyl-5-(pyridin-4-yl)-3H-imidazo[4,5-b]pyridin-3-yl)benzyl)thiomorpholine 1,1-dioxide 126.

Clear semi-solid (6 mg, 0.014 mmol, 15% yield, 18% MeOH in DCM).

$^1$H NMR (CDCl$_3$) δ: 8.68 (d, J=5.8 Hz, 2H), 8.13 (d, J=8.3 Hz, 1H), 7.89 (d, J=6.2 Hz, 2H), 7.83 (d, J=8.3 Hz, 1H), 7.61 (d, J=8.3 Hz, 2H), 7.51 (d, J=8.3 Hz, 2H), 3.83 (s, 2H), 3.23-3.08 (m, 8H), 2.66 (s, 3H).

Scheme 36

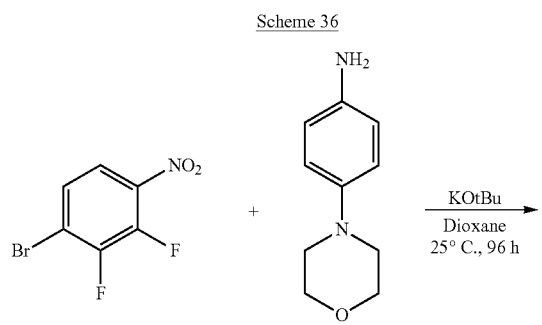

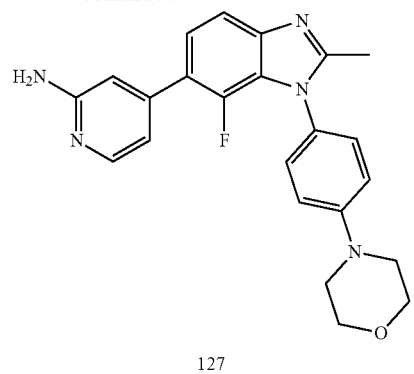

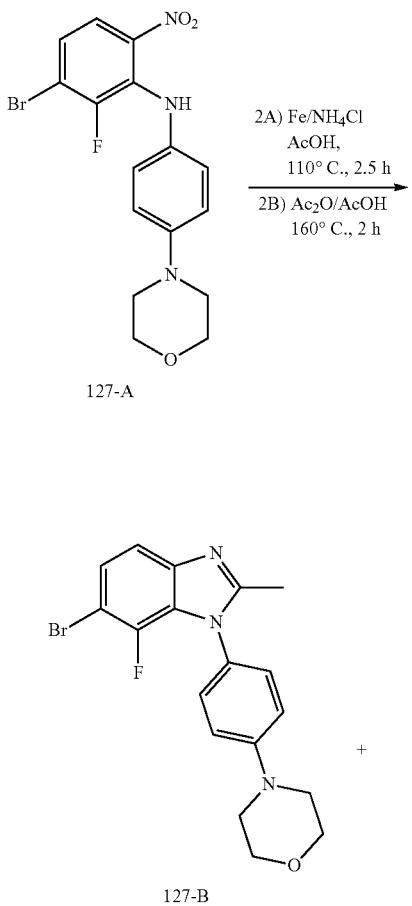

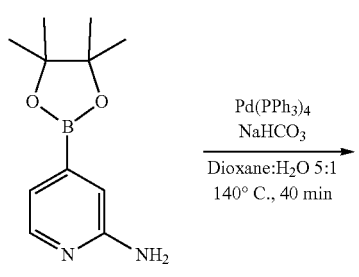

Scheme 36, Step 1

In a 20 mL Biotage© microwave vial, stir bar, 4-morpholinoaniline (599 mg, 3.36 mmol), Dioxane (6.72 mL) were added and stirred. 1-Bromo-2,3-difluoro-4-nitrobenzene (800 mg, 3.36 mmol) was then added followed by Potassium tert butoxide (754 mg, 6.72 mmol), the vial sealed, and stirred at 25° C. for 96 h The mixture was poured into H$_2$O, acidified with saturated ammonium chloride solution and filtered. the precipitated product was washed with H$_2$O, and hexanes, affording 3-bromo-2-fluoro-N-(4-morpholinophenyl)-6-nitroaniline 127-A as a black solid (920 mg, 2.322 mmol, 69% yield). $^1$H NMR (DMSO) δ: 8.81 (bs, 1H), 7.83 (dd, J=9.2, 1.8 Hz, 1H), 7.34-7.25 (m, 1H), 6.93 (d, J=8.9 Hz, 2H), 6.87 (d, J=8.9 Hz, 2H), 3.77-3.71 (m, 4H), 3.09-3.02 (m, 4H).

Scheme 36, Step 2

Compound 127-B was synthesized in a similar manner as depicted in Scheme 9, Step 2.

4-(4-(6-bromo-7-fluoro-2-methyl-1H-benzo[d]imidazol-1-yl)phenyl)morpholine 127-B.

Tan solid (220 mg, 0.564 mmol, 47% yield, 60% EtOAc in hexanes)

$^1$H NMR (CDCl$_3$) δ: 7.43-7.33 (m, 2H), 7.27 (dd, J=8.7, 1.3 Hz, 2H), 7.02 (d, J=8.7 Hz, 2H), 3.96-3.84 (m, 4H), 3.33-3.24 (m, 4H), 2.45 (s, 3H).

Scheme 36, Step 3

A 2-5 mL Biotage© microwave vial loaded with 4-(4-(6-bromo-7-fluoro-2-methyl-1H-benzo[d]imidazol-1-yl)phenyl)morpholine 127-B (55 mg, 0.141 mmol), 4-(4,4,5,5-tetramethyl-1,3,2-dioxaborolan-2-yl)pyridin-2-amine (34.1 mg, 0.155 mmol), Pd(PPh$_3$)$_4$ (13 mg, 0.011 mmol), and NaHCO$_3$ (47.4 mg, 0.564 mmol), was capped, purged with argon, then injected with degassed dioxane:H$_2$O (0.78 mL:0.157 mL, 5:1 v/v), and heated to 140° for 40 min in a Biotage Microwave Reactor. The reaction was cooled, diluted with DCM, filtered through celite, concentrated, dryloaded onto silica gel and purified on a 12 g silica gel column (DCM/MeOH, 0-10%), affording 4-(7-fluoro-2-methyl-1-(4-morpholinophenyl)-1H-benzo[d]imidazol-6-yl)pyridin-2-amine 127 as a tan solid (20 mg, 0.050 mmol, 35% yield, 10% MeOH in DCM).

$^1$H NMR (DMSO) δ: 7.93 (d, J=5.3 Hz, 1H), 7.52 (d, J=8.3 Hz, 1H), 7.43 (d, J=8.6 Hz, 2H), 7.29 (t, J=8.5, 7.7 Hz, 1H), 7.09 (d, J=8.7 Hz, 2H), 6.67-6.56 (m, 2H), 5.94 (s, 2H), 3.88-3.69 (m, 4H), 3.28-3.19 (m, 4H), 2.36 (s, 3H).

Scheme 37

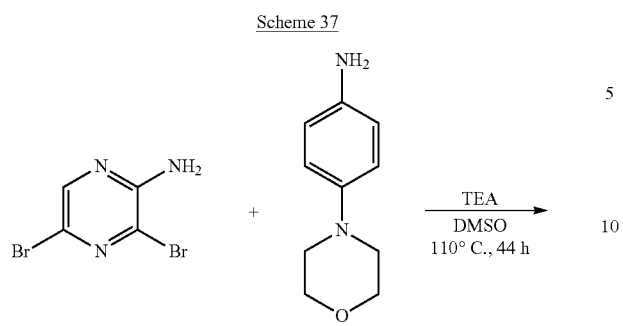

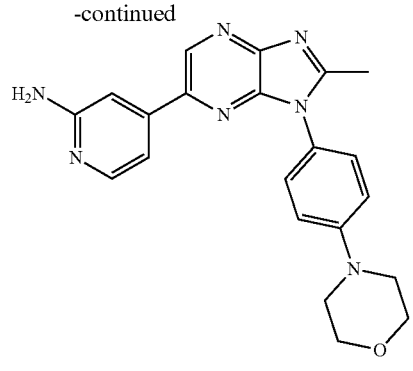

128

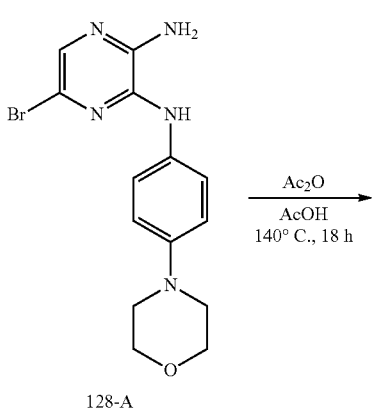

128-A

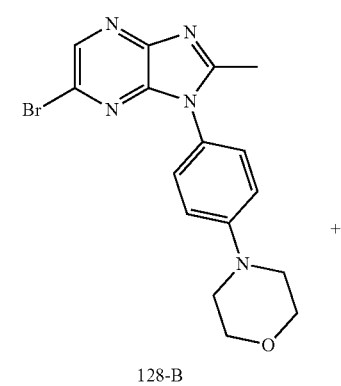

128-B

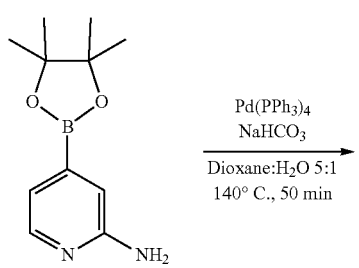

Scheme 37, Step 1

A 2-5 mL Biotage© microwave vial loaded with 3,5-dibromopyrazin-2-amine xx (437 mg, 1.726 mmol), 4-morpholinoaniline (400 mg, 2.244 mmol), DMSO (0.959 mL) and triethylamine (0.794 mL 5.7 mmol), was capped, purged with argon, then heated to 110° for 44 h in an oil bath. The reaction was cooled, evaporated by azeotroping with toluene, diluted with DCM, filtered through celite, concentrated, dryloaded onto silica gel and purified on a 12 g silica gel column (DCM/MeOH, 0-5%), affording 6-bromo-$N^2$-(4-morpholinophenyl)pyrazine-2,3-diamine 128-A as a black solid (450 mg, 1.171 mmol, 68% yield, 5% MeOH in DCM). $^1$H NMR (DMSO) δ: 8.27 (s, 1H), 7.52 (d, J=9.2 Hz, 2H), 7.38 (s, 1H), 6.94 (d, J=9.2 Hz, 2H), 6.44 (s, 2H), 3.78-3.71 (m, 4H), 3.10-3.03 (m, 4H). $^{13}$C NMR (DMSO) δ: 147.17, 144.00, 139.99, 132.57, 130.11, 121.22, 121.11, 116.04, 66.61, 49.48.

Scheme 37, Step 2

A 20 mL Biotage© microwave vial equipped with a stir bar. was loaded with 6-bromo-$N^2$-(4-morpholinophenyl)pyrazine-2,3-diamine 128-A (160 mg, 0.457 mmol), AcOH (1.3 mL, 22.84 mmol), Ac$_2$O (0.216 mL, 2.284 mmol), and the mixture was purged with Ar for 15 min and heated at 140° C. for 18 h. Upon cooling, the mixture was concentrated with toluene, then DCM, followed by addition of 7M NH3 in MeOH (5 mL) with subsequent concentration. The crude was concentrated/dryloaded onto silica with DCM and purified on a 12 g silica column (DCM/MeOH, 0-5%), affording 4-(4-(6-bromo-2-methyl-1H-imidazo[4,5-b]pyrazin-1-yl)phenyl)morpholine 128-B as a tan solid (300 mg, 0.802 mmol, 69% yield, 5% MeOH in DCM). $^1$H NMR (DMSO) δ: 8.59 (s, 1H), 7.43 (d, J=8.9 Hz, 2H), 7.15 (d, J=8.8 Hz, 2H), 3.82-3.75 (m, 4H), 3.29-3.22 (m, 4H), 2.51 (s, 3H). $^{13}$C NMR (DMSO) δ: 159.12, 151.97, 147.63, 142.01, 140.60, 132.35, 128.59, 124.12, 115.64, 66.49, 48.24, 15.51.

Scheme 37, Step 3

A 2-5 mL Biotage© microwave vial loaded with 4-(4-(6-bromo-2-methyl-1H-imidazo[4,5-b]pyrazin-1-yl)phenyl)morpholine 9-1 (55 mg, 0.147 mmol), 4-(4,4,5,5-tetramethyl-1,3,2-dioxaborolan-2-yl)pyridin-2-amine 128-B (35.6 mg, 0.162 mmol), Pd(PPh$_3$)$_4$ (13.59 mg, 0.012 mmol), and NaHCO$_3$ (49.4 mg, 0.588 mmol), was capped, purged with argon, then injected with degassed dioxane:H$_2$O (1.225 mL:0.245 mL, 5:1 v/v), and heated to 140° for 50 min in a Biotage Microwave Reactor. The reaction was cooled, diluted with DCM, filtered through celite, concentrated, dryloaded onto silica gel and purified on a 12 g silica gel column (DCM/MeOH, 0-20%), affording 4-(2-methyl-1-(4-morpholinophenyl)-1H-imidazo[4,5-b]pyrazin-6-yl)pyridin-2-amine 128 as a white solid (49 mg, 0.126 mmol, 86% yield, 10% MeOH in DCM). ¹H NMR (CDCl₃) δ: 8.99 (s, 1H), 8.17 (d, J=5.4 Hz, 1H), 7.35 (d, J=8.8 Hz, 2H), 7.26 (d, J=5.5 Hz, 1H), 7.18-7.07 (m, 3H), 4.57 (s, 2H), 4.11-3.84 (m, 4H), 3.47-3.10 (m, 4H), 2.68 (s, 3H).

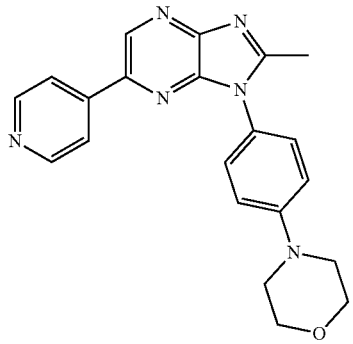

129

Compound 129 was synthesized in a similar manner as depicted in Scheme 37, Step 3 using pyridin-4-ylboronic acid.

4-(4-(2-methyl-6-(pyridin-4-yl)-1H-imidazo[4,5-b]pyrazin-1-yl)phenyl)morpholine 129.

White solid (30 mg, 0.081 mmol, 55% yield, 9% MeOH in DCM).

¹H NMR (CDCl₃) δ: 9.05 (s, 1H), 8.70 (d, J=5.0 Hz, 2H), 7.91 (d, J=6.0 Hz, 2H), 7.35 (d, J=9.2 Hz, 2H), 7.11 (d, J=9.2 Hz, 2H), 4.03-3.82 (m, 4H), 3.40-3.16 (m, 4H), 2.69 (s, 3H). ¹³C NMR (CDCl₃) δ: 159.20, 151.70, 150.42, 149.01, 144.34, 143.54, 141.85, 137.63, 128.00, 124.65, 120.90, 115.76, 66.75, 48.55, 15.60.

Scheme 38

Scheme 38, Step 1

A 5 mL Biotage© microwave vial loaded with 3,5-dibromopyrazin-2-amine (365 mg, 1.444 mmol), 1H-benzo[d]imidazol-5-amine (250 mg, 1.878 mmol), DMSO (0.8 mL) and triethylamine (0.66 mL, 4.77 mmol), was capped, purged with argon, then heated to 110° for 18 h in an oil bath. Upon cooling, the mixture was concentrated with toluene, diluted with DCM, filtered through celite, concentrated, dryloaded onto silica gel and purified on a 12 g silica gel column (DCM/MeOH, 0-5%), affording N²-(1H-benzo[d]imidazol-5-yl)-6-bromopyrazine-2,3-diamine 130-A as a gray solid (159 mg, 0.521 mmol, 36% yield, 5% MeOH in DCM). ¹H NMR (DMSO) δ: 12.18 (bs, 1H), 9.05 (s, 1H), 8.75 (s, 1H), 8.38 (s, 1H), 7.73 (d, J=8.8 Hz, 1H), 7.59 (d, J=8.9 Hz, 1H), 7.51 (s, 1H), 6.65 (s, 2H).

Scheme 38, Step 2

A 20 mL Biotage© microwave vial equipped with a stir bar. was loaded with N²-(1H-benzo[d]imidazol-5-yl)-6-bromopyrazine-2,3-diamine 130-A (150 mg, 0.492 mmol), AcOH (1.4 mL, 24.58 mmol), Ac₂O (0.232 mL, 2.458 mmol), and the mixture was purged with Ar for 15 min and heated at 140° C. for 18 h. Upon cooling, the mixture was concentrated with toluene then DCM, followed by addition of 7M NH₃ in MeOH (5 mL) with subsequent concentration. The crude was concentrated/dryloaded onto silica with DCM and purified on a 12 g silica column (DCM/MeOH, 0-15%), affording 1-(1H-benzo[d]imidazol-5-yl)-6-bromo-2-methyl-1H-imidazo[4,5-b]pyrazine 130-B as a tan solid (79 mg, 0.240 mmol, 49% yield, 15% MeOH in DCM). ¹H NMR (DMSO) δ: 12.83 (s, 1H), 8.62 (s, 1H), 8.43 (s, 1H), 7.99-7.72 (m, 2H), 7.39 (d, J=8.3 Hz, 1H), 2.53 (s, 3H).

Scheme 38, Step 3

A 2-5 mL Biotage© microwave vial loaded with 1-(1H-benzo[d]imidazol-5-yl)-6-bromo-2-methyl-1H-imidazo[4,5-b]pyrazine 130-B (50 mg, 0.122 mmol), 4-(4,4,5,5-tetramethyl-1,3,2-dioxaborolan-2-yl)pyridin-2-amine (29.4 mg, 0.134 mmol), Pd(PPh$_3$)$_4$ (11.23 mg, 0.00972 mmol), and NaHCO$_3$ (40.8 mg, 0.486 mmol), was capped, purged with argon, then injected with degassed dioxane:H$_2$O (1 mL:0.2 mL, 5:1 v/v), and heated to 140° for 1 h in a Biotage Microwave Reactor. The reaction was cooled, diluted with DCM, filtered through celite, concentrated, dryloaded onto silica gel and purified on a 12 g silica gel column (DCM/MeOH, 0-20%), affording 4-(1-(1H-benzo[d]imidazol-5-yl)-2-methyl-1H-imidazo[4,5-b]pyrazin-6-yl)pyridin-2-amine 130 as a white solid (21 mg, 0.067 mmol, 55% yield, 20% MeOH in DCM)

$^1$H NMR (DMSO) δ: 12.85 (bs, 1H), 9.04 (s, 1H), 8.43 (s, 1H), 7.98 (d, J=5.5 Hz, 1H), 7.92 (bs, 1H), 7.83 (bs, 1H), 7.43 (dd, J=8.4, 2.0 Hz, 1H), 7.14 (dd, J=5.5, 1.6 Hz, 1H), 7.03 (s, 1H), 6.15 (bs, 2H), 2.56 (s, 3H).

131

Compound 131 was synthesized in a similar manner as depicted in Scheme 38, Step 3 using pyridin-4-ylboronic acid.

1-(1H-benzo[d]imidazol-5-yl)-2-methyl-6-(pyridin-4-yl)-1H-imidazo[4,5-b]pyrazine 131.

White solid (14 mg, 0.043 mmol, 59% yield, 18% MeOH in DCM).

$^1$H NMR (DMSO) δ: 12.84 (bs, 1H), 9.25 (s, 1H), 8.65 (d, J=6.2 Hz, 2H), 8.43 (s, 1H), 8.00 (d, J=6.2 Hz, 2H), 7.94 (d, J=1.9 Hz, 1H), 7.84 (d, J=8.5 Hz, 1H), 7.45 (dd, J=8.5, 2.0 Hz, 1H), 2.60 (s, 3H).

Scheme 39

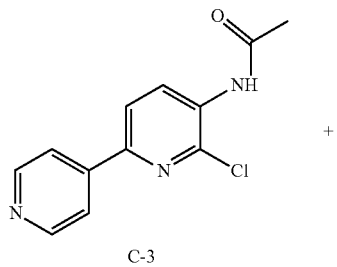

C-3

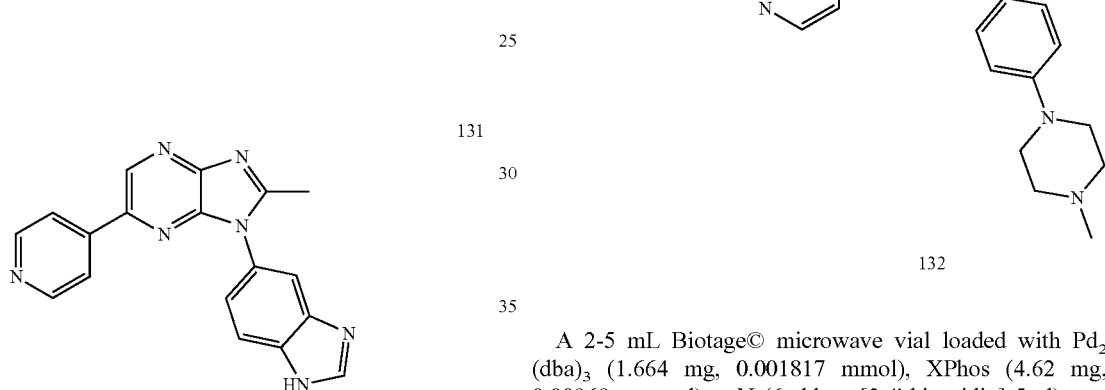

132

A 2-5 mL Biotage© microwave vial loaded with Pd$_2$(dba)$_3$ (1.664 mg, 0.001817 mmol), XPhos (4.62 mg, 0.00969 mmol), N-(6-chloro-[2,4'-bipyridin]-5-yl)acetamide C-3 (30 mg, 0.121 mmol), 4-(4-methylpiperazin-1-yl)aniline (27.8 mg, 0.145 mmol), and K$_3$PO$_4$ (77 mg, 0.363 mmol), and t-BuOH (0.4 mL) are added, the vial sealed, purged with argon for 15 min and heated to 110° C. for 18 h in an oil bath. The reaction was cooled, diluted with DCM, filtered through celite, concentrated, dryloaded onto silica gel and purified on a 12 g silica gel column (DCM/MeOH, 0-15%), affording 2-methyl-3-(4-(4-methylpiperazin-1-yl)phenyl)-5-(pyridin-4-yl)-3H-imidazo[4,5-b]pyridine 132 as a pink-white solid (17 mg, 0.044 mmol, 37% yield, 15% MeOH in DCM). $^1$H NMR (CDCl$_3$) δ: 8.65 (d, J=6.4 Hz, 2H), 8.08 (d, J=8.3 Hz, 1H), 7.91 (d, J=6.4 Hz, 2H), 7.80 (d, J=8.3 Hz, 1H), 7.35 (d, J=9.7 Hz, 2H), 7.12 (d, J=8.8 Hz, 2H), 3.42-3.19 (m, 4H), 2.70-2.62 (m, 4H), 2.61 (s, 3H), 2.42 (s, 3H).

Scheme 40

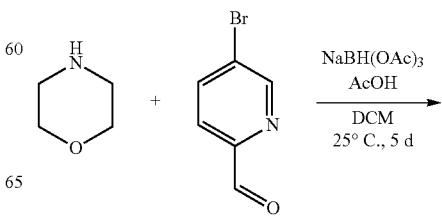

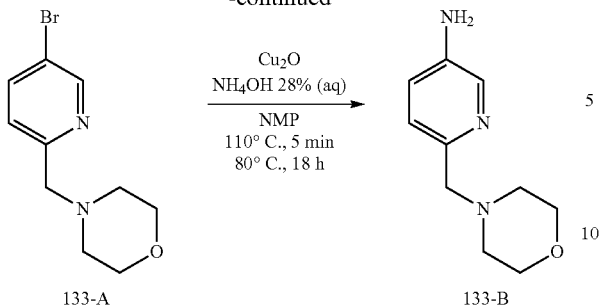

Scheme 40, Step 1

A 20 mL screw cap vial loaded with 5-bromopicolinaldehyde (300 mg, 1.613 mmol), morpholine (0.211 mL, 2.419 mmol), DCM (10.8 mL), and AcOH (5 drops), were stirred for 5 minutes. NaBH(OAc)$_3$ (513 mg, 2.419 mmol) was added and the mixture was stirred at 25° C. for 5 days. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM), affording 4-((5-bromopyridin-2-yl)methyl)morpholine 133-A as a green oil (308 mg, 1.198 mmol, 74% yield, 100% DCM). $^1$H NMR (CDCl$_3$) δ: 8.63 (dd, J=2.4, 0.7 Hz, 1H), 7.79 (dd, J=8.3, 2.4 Hz, 1H), 7.35 (d, J=8.3 Hz, 1H), 3.78-3.71 (m, 4H), 3.62 (s, 2H), 2.55-2.47 (m, 4H).

$^{13}$C NMR (CDCl$_3$) δ: 156.81, 150.34, 139.02, 124.52, 119.09, 66.90, 64.21, 53.72.

Scheme 40, Step 2

In a 20 mL Biotage© microwave vial, a stir bar, N-Methyl-2-pyrrolidone (2.186 mL), 4-((5-bromopyridin-2-yl)methyl)morpholine 133-A, 28% NH$_4$OH (1.52 mL 10.93 mmol) were added followed by Cu$_2$O (7.82 mg, 0.055 mmol). The vial was sealed and heated at 110° C. for 5 minutes and then at 80° C. for 18 h. Upon cooling, the mixture is diluted with brine, ether and poured into separatory funnel and extracted with diethyl ether multiple times. The pooled ether layers were washed with H$_2$O, brine, then dried with Na$_2$SO$_4$, concentrated, dryloaded onto silica gel and purified on a 12 g silica gel column (DCM/MeOH, 0-20%), affording 6-(morpholinomethyl)pyridin-3-amine 133-B as a green oil (45 mg, 0.233 mmol, 21% yield, 20% MeOH in DCM). $^1$H NMR (CDCl$_3$) δ: 8.07 (dd, J=2.9, 0.7 Hz, 1H), 7.16 (d, J=8.2 Hz, 1H), 6.97 (dd, J=8.3, 2.8 Hz, 1H), 3.77-3.70 (m, 4H), 3.56 (s, 2H), 2.54-2.46 (m, 4H). (Note: NH$_2$ is absent in CDCL$_3$, present in DMSO).

133

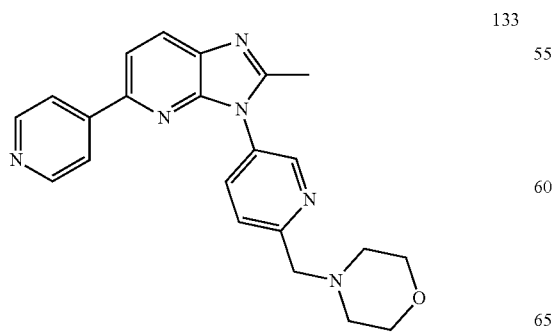

Compound 133 was synthesized in a similar manner as depicted in Scheme 39, using 6-(morpholinomethyl)pyridin-3-amine 133-B, the synthesis of 133-B is described in Scheme 40.

4-((5-(2-methyl-5-(pyridin-4-yl)-3H-imidazo[4,5-b]pyridin-3-yl)pyridin-2-yl)methyl)morpholine 133.

Green semi-solid (14 mg, 0.036 mmol, 18% yield, 10% MeOH in DCM).

$^1$H NMR (CDCl$_3$) δ: 8.78 (s, 1H), 8.68 (d, J=5.3 Hz, 2H), 8.13 (d, J=8.3 Hz, 1H), 7.93-7.81 (m, 4H), 7.76 (d, J=8.6 Hz, 1H), 3.87-3.79 (m, 6H), 2.70-2.62 (m, 7H).

134

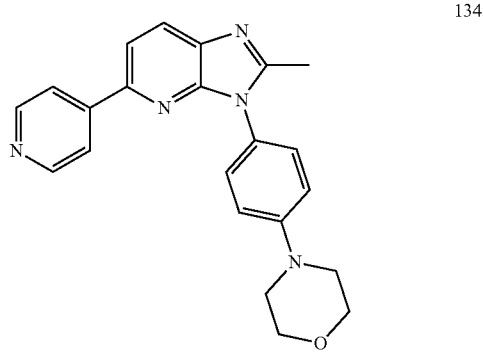 [SMILES: Cc1nc2ccc(-c3ccncc3)nc2n1-c1ccc(N2CCOCC2)cc1]

Compound 134 was synthesized in a similar manner as depicted in Scheme 39, using 4-morpholinoaniline.

4-(4-(2-methyl-5-(pyridin-4-yl)-3H-imidazo[4,5-b]pyridin-3-yl)phenyl)morpholine 134.

Pink solid (9 mg, 0.078 mmol, 65% yield, 9% MeOH in DCM).

$^1$H NMR (CDCl$_3$) δ: 8.65 (d, J=6.5 Hz, 2H), 8.08 (d, J=8.2 Hz, 1H), 7.90 (d, J=6.5 Hz, 2H), 7.80 (d, J=8.3 Hz, 1H), 7.37 (d, J=9.2 Hz, 2H), 7.11 (d, J=9.4 Hz, 2H), 3.98-3.88 (m, 4H), 3.40-3.16 (m, 4H), 2.61 (s, 3H). $^{13}$C NMR (CDCl$_3$) δ: 155.10, 151.31, 150.23, 149.48, 148.42, 146.69, 135.20, 128.12, 126.84, 125.95, 121.05, 115.95, 115.75, 66.81, 48.76, 15.30.

135

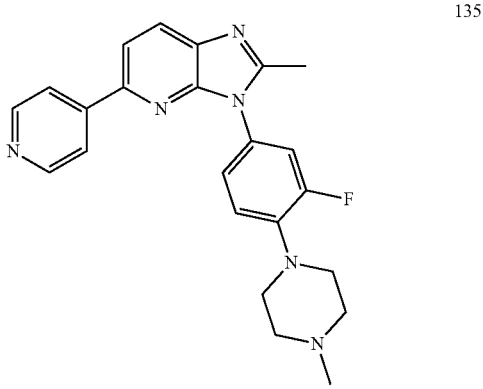 [SMILES: Cc1nc2ccc(-c3ccncc3)nc2n1-c1ccc(N2CCN(C)CC2)c(F)c1]

Compound 135 was synthesized in a similar manner as depicted in Scheme 39, using 3-fluoro-4-(4-methylpiperazin-1-yl)aniline.

3-(3-fluoro-4-(4-methylpiperazin-1-yl)phenyl)-2-methyl-5-(pyridin-4-yl)-3H-imidazo[4,5-b]pyridine 135.

Green semi-solid (23 mg, 0.029 mmol, 24% yield, 25% MeOH in DCM).

¹H NMR (CDCl₃) δ: 8.67 (d, J=5.3 Hz, 2H), 8.10 (d, J=8.3 Hz, 1H), 7.91 (d, J=6.0 Hz, 2H), 7.82 (d, J=8.3 Hz, 1H), 7.24-7.04 (m, 3H), 3.35-3.19 (m, 4H), 2.70 (t, J=4.9 Hz, 4H), 2.63 (s, 3H), 2.43 (s, 3H).

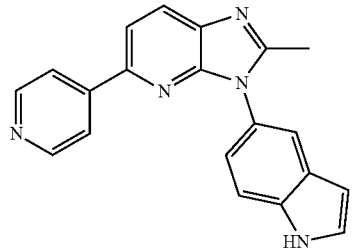

136

Compound 136 was synthesized in a similar manner as depicted in Scheme 39, using 1H-indol-5-amine.

3-(1H-indol-5-yl)-2-methyl-5-(pyridin-4-yl)-3H-imidazo[4,5-b]pyridine 136.

White solid (295 mg, 0.907 mmol, 80% yield, 10% MeOH in DCM).

¹H NMR (DMSO) δ: 11.47 (s, 1H), 8.70-8.49 (m, 2H), 8.23-7.44 (m, 7H), 7.24 (d, J=8.5 Hz, 1H), 6.58 (s, 1H), 2.50 (s, 3H). ¹³C NMR (DMSO) δ: 156.11, 150.64, 150.00, 147.52, 146.38, 136.02, 135.45, 128.35, 127.63, 127.10, 126.29, 121.05, 120.97, 119.74, 116.32, 112.60, 102.22, 49.07, 15.41.

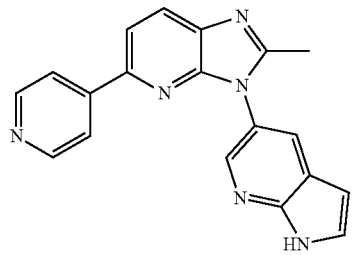

137

Compound 137 was synthesized in a similar manner as depicted in Scheme 39, using 1H-pyrrolo[2,3-b]pyridin-5-amine.

2-methyl-5-(pyridin-4-yl)-3-(1H-pyrrolo[2,3-b]pyridin-5-yl)-3H-imidazo[4,5-b]pyridine 137.

Tan solid (23 mg, 0.070 mmol, 23% yield, 20% MeOH in DCM).

¹H NMR (CDCl₃) δ: 10.82 (s, 1H), 8.67-8.56 (m, 2H), 8.51-8.37 (m, 1H), 8.14 (dd, J=8.3, 1.9 Hz, 1H), 8.10-8.00 (m, 1H), 7.88 (d, J=5.2 Hz, 2H), 7.84 (dd, J=8.2, 1.9 Hz, 1H), 7.56 (s, 1H), 6.68 (dd, J=3.6, 1.9 Hz, 1H), 2.64 (s, 3H). ¹³C NMR (CDCl₃) δ: 155.34, 150.12, 149.82, 148.73, 148.25, 146.58, 141.48, 135.16, 127.91, 127.35, 127.12, 124.32, 121.11, 120.56, 116.32, 101.60, 50.63, 15.25.

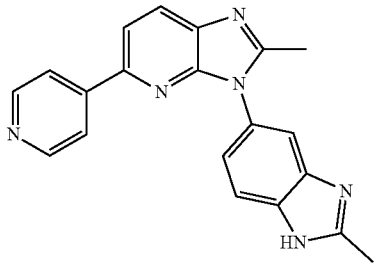

138

Compound 138 was synthesized in a similar manner as depicted in Scheme 39, using 2-methyl-1H-benzo[d]imidazol-5-amine.

2-methyl-3-(2-methyl-1H-benzo[d]imidazol-5-yl)-5-(pyridin-4-yl)-3H-imidazo[4,5-b]pyridine 138.

White solid (53 mg, 0.156 mmol, 66% yield, 100% EtOAc).

¹H NMR (CDCl₃) δ: 8.62 (d, J=6.2 Hz, 2H), 8.12 (d, J=8.2 Hz, 1H), 8.05 (s, 1H), 7.91 (d, J=1.9 Hz, 1H), 7.87 (d, J=6.9 Hz, 2H), 7.82 (d, J=8.3 Hz, 1H), 7.63 (d, J=8.5 Hz, 1H), 7.44 (dd, J=8.5, 1.9 Hz, 1H), 4.00 (s, 3H), 2.63 (s, 3H).

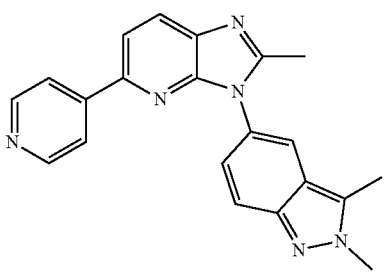

139

Compound 139 was synthesized in a similar manner as depicted in Scheme 39, using 2,3-dimethyl-2H-indazol-5-amine.

3-(2,3-dimethyl-2H-indazol-5-yl)-2-methyl-5-(pyridin-4-yl)-3H-imidazo[4,5-b]pyridine 139.

White semi-solid (2 mg, 0.00566 mmol, 5% yield, 10% MeOH in DCM).

¹H NMR (CDCl₃) δ: 8.63 (d, J=5.1 Hz, 2H), 8.12 (d, J=8.3 Hz, 1H), 7.90 (d, J=6.0 Hz, 2H), 7.83 (d, J=8.3 Hz, 1H), 7.80 (d, J=8.7 Hz, 1H), 7.77-7.68 (m, 1H), 7.13 (dd, J=8.7, 1.8 Hz, 1H), 4.22 (s, 3H), 2.75 (s, 3H), 2.66 (s, 3H).

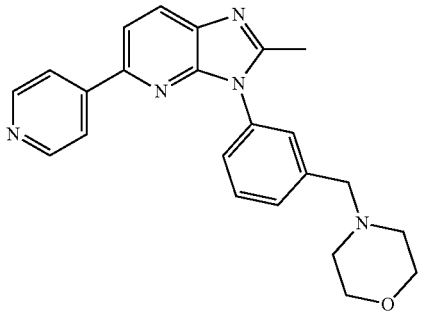

140

Compound 140 was synthesized in a similar manner as depicted in Scheme 39, using 3-(morpholinomethyl)aniline.

4-(3-(2-methyl-5-(pyridin-4-yl)-3H-imidazo[4,5-b]pyridin-3-yl)benzyl)morpholine 140.

Green semi-solid (8 mg, 0.021 mmol, 10% yield, 10% MeOH in DCM).

$^1$H NMR (CDCl$_3$) δ: 8.66 (d, J=4.8 Hz, 2H), 8.11 (d, J=8.3 Hz, 1H), 7.90 (d, J=6.2 Hz, 2H), 7.83 (d, J=8.3 Hz, 1H), 7.64-7.55 (m, 1H), 7.55-7.49 (m, 2H), 7.40 (d, J=8.7 Hz, 1H), 3.82-3.72 (m, 4H), 3.66 (s, 2H), 2.65 (s, 3H), 2.60-2.48 (m, 4H).

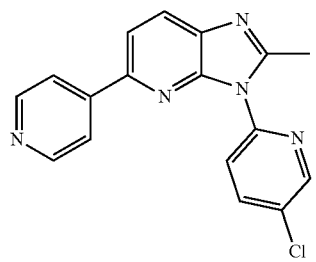

141

Compound 141 was synthesized in a similar manner as depicted in Scheme 39, using 5-chloropyridin-2-amine.

3-(5-chloropyridin-2-yl)-2-methyl-5-(pyridin-4-yl)-3H-imidazo[4,5-b]pyridine 141.

Tan solid (19 mg, 0.059 mmol, 15% yield, 10% MeOH in DCM).

$^1$H NMR (CDCl$_3$) δ: 8.71 (d, J=6.1 Hz, 2H), 8.63 (dd, J=2.6, 0.8 Hz, 1H), 8.12 (d, J=8.3 Hz, 1H), 8.09 (dd, J=8.6, 0.7 Hz, 1H), 8.03 (dd, J=8.6, 2.6 Hz, 1H), 7.93 (d, J=6.3 Hz, 2H), 7.86 (d, J=8.3 Hz, 1H), 2.88 (s, 3H)

Scheme 41

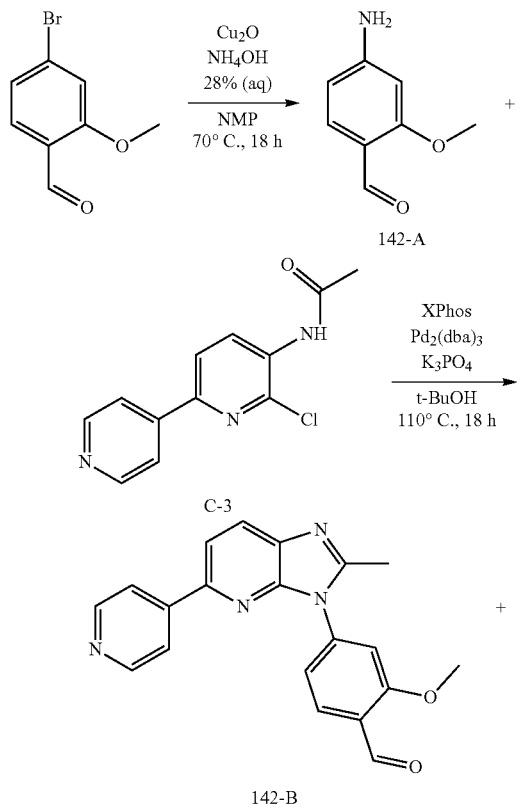

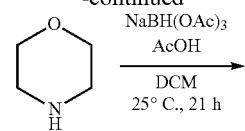

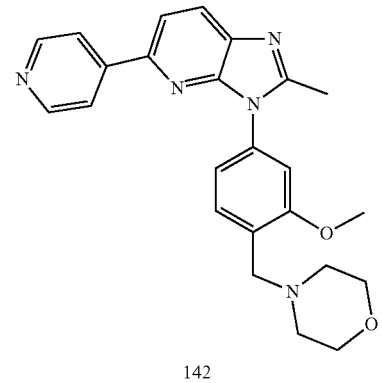

142

Scheme 41, Step 1

In a 5 mL Biotage© microwave vial, a stir bar, N-Methyl-2-pyrrolidone (1.333 mL), 4-bromo-2-methoxybenzaldehyde (430 mg, 2.0 mmol), 28% NH$_4$OH (2.686 mL 20 mmol) were added followed by Cu$_2$O (14.31 mg, 0.100 mmol). The vial was sealed and heated at 70° C. for 18 h. Upon cooling, the mixture is diluted with brine, ether and poured into separatory funnel and extracted with diethyl ether multiple times. The pooled ether layers were washed with H$_2$O, brine, then dried with Na$_2$SO$_4$, concentrated, dryloaded onto silica gel and purified on a 12 g silica gel column (DCM), affording 4-amino-2-methoxybenzaldehyde 142-A as a orange semi-solid (53 mg, 0.351 mmol, 18% yield 100% DCM). $^1$H NMR (CDCl$_3$) δ: 10.18 (d, J=0.8 Hz, 1H), 7.69 (d, J=8.4 Hz, 1H), 6.29-6.26 (m, 1H), 6.15 (d, J=2.0 Hz, 1H), 4.33 (bs, 2H), 3.88 (s, 3H). $^{13}$C NMR (CDCl$_3$) δ: 187.66, 164.08, 154.10, 131.10, 116.61, 107.18, 96.05, 55.39.

Scheme 41, Step 2

A 2-5 mL Biotage© microwave vial loaded with Pd$_2$(dba)$_3$ (2.66 mg, 0.00291 mmol), XPhos (7.39 mg, 0.016 mmol), N-(6-chloro-[2,4'-bipyridin]-5-yl)acetamide C-3 (48 mg, 0.194 mmol), 4-amino-2-methoxybenzaldehyde 142-A (35.2 mg, 0.233 mmol), and K$_3$PO$_4$ (123 mg, 0.581 mmol), and t-BuOH (0.65 mL) are added, the vial sealed, purged with argon for 15 min and heated to 110° C. for 18 h in an oil bath. The reaction was cooled, diluted with DCM, filtered through celite, concentrated, dryloaded onto silica gel and purified on a 12 g silica gel column (DCM/MeOH, 0-10%), affording 2-methoxy-4-(2-methyl-5-(pyridin-4-yl)-3H-imidazo[4,5-b]pyridin-3-yl)benzaldehyde 142-B as a green semi-solid (10 mg, 0.194 mmol, 15% yield, 10% MeOH). $^1$H NMR (CDCl$_3$) δ: 10.58 (d, J=0.8 Hz, 1H), 8.69 (d, J=6.2 Hz, 2H), 8.14 (d, J=8.3 Hz, 1H), 8.10 (d, J=8.2 Hz, 1H), 7.92 (d, J=6.3 Hz, 2H), 7.87 (d, J=8.2 Hz, 1H), 7.26 (d, J=1.8 Hz, 1H), 7.18 (ddd, J=8.2, 1.8, 0.8 Hz, 1H), 3.51 (s, 3H), 2.71 (s, 3H).

Scheme 41, Step 3

A 5 mL screw cap vial loaded with 2-methoxy-4-(2-methyl-5-(pyridin-4-yl)-3H-imidazo[4,5-b]pyridin-3-yl)benzaldehyde 142-B (10 mg, 0.029 mmol), morpholine (0.0076 mL, 0.087 mmol), DCM (0.29 mL), and AcOH (1 drop), were stirred for 5 minutes. NaBH(OAc)$_3$ (6.77 mg, 0.032 mmol) was added and the mixture was sealed and stirred at 25° C. for 21 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-12%), affording 4-(2-methoxy-4-(2-methyl-5-(pyridin-4-yl)-3H-imidazo[4,5-b]pyridin-3-yl)benzyl)morpholine 142 as a green semi-solid (6.5 mg, 0.016 mmol, 54% yield, 12% MeOH). $^1$H NMR (CDCl$_3$) δ: 8.68 (d, J=6.1 Hz, 2H), 8.12 (d, J=8.3 Hz, 1H), 7.91 (d, J=6.1 Hz, 2H), 7.83 (d, J=8.3 Hz, 1H), 7.64 (d, J=7.9 Hz, 1H), 7.10-7.00 (m, 2H), 3.91 (s, 3H), 3.88-3.78 (m, 4H), 3.69 (s, 2H), 2.66 (s, 3H), 2.65-2.61 (m, 4H).

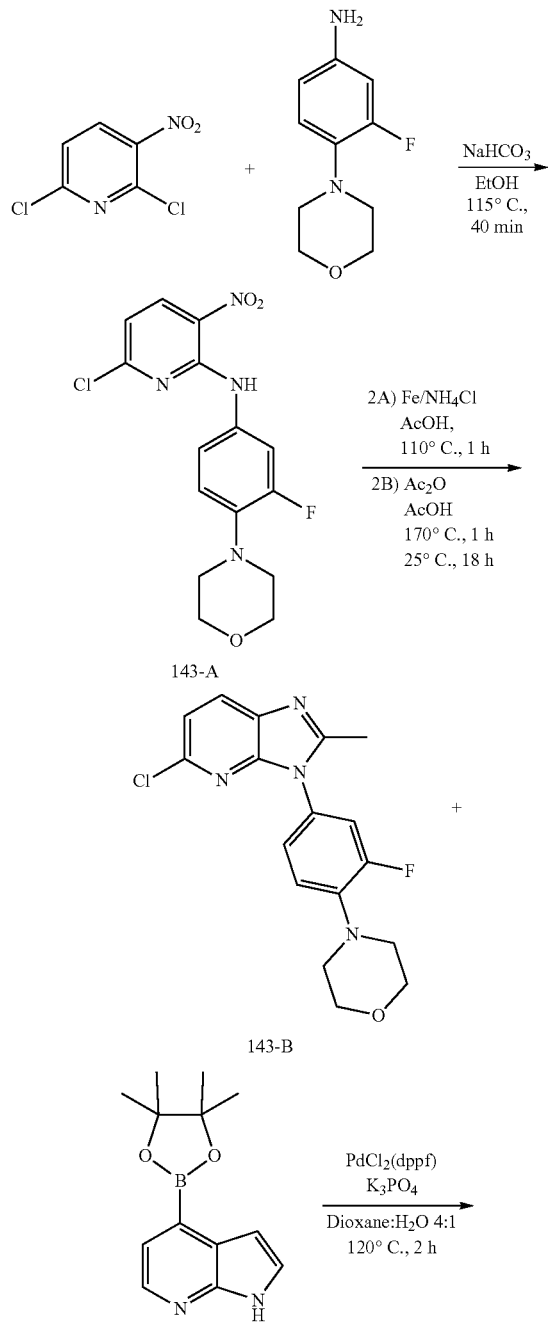

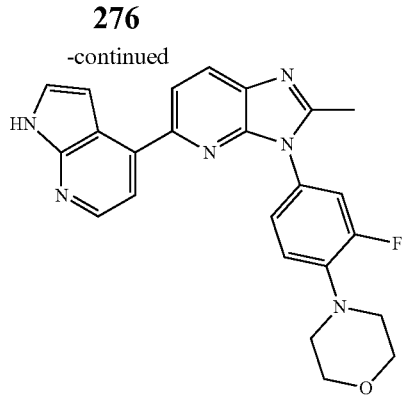

143

Scheme 42, Step 1

In a 20 mL Biotage© microwave vial, stir bar, 3-fluoro-4-morpholinoaniline (1.2 g, 6.12 mmol), NaHCO$_3$ (1.130 g, 13.45 mmol), and EtOH (4.08 mL) were added and stirred for 5 min. 2,6-Dichloro-3-nitropyridine (1.18 g, 6.12 mmol) was added and the vial sealed, then heated at 115° C. for 40 min in an oil bath, ensuring to vent with a needle when necessary. The mixture was then filtered and the precipitated product was washed with cold EtOH, H$_2$O, and hexanes, affording 6-chloro-N-(3-fluoro-4-morpholinophenyl)-3-nitropyridin-2-amine (143-A) as a black solid (1.86 g, 5.27 mmol, 86% yield). $^1$H NMR (DMSO) δ: 10.08 (s, 1H), 8.54 (d, J=8.6 Hz, 1H), 7.53 (dd, J=14.7, 2.4 Hz, 1H), 7.35 (dd, J=8.7, 2.4 Hz, 1H), 7.06 (t, J=9.2 Hz, 1H), 7.01 (d, J=8.6 Hz, 1H), 3.81-3.71 (m, 4H), 3.07-2.98 (m, 4H).

Scheme 42, Step 2A

To (2) 20 mL Biotage© microwave vials, stir bars, 6-chloro-N-(3-fluoro-4-morpholinophenyl)-3-nitropyridin-2-amine 143-A (750 mg, 2.126 mmol), iron (1.187 g, 21.26 mmol), and ammonium chloride (796 mg, 14.88 mmol) were added to each individual vial. The vials were sealed, degassed with Ar for 15 min, injected with AcOH (7.5 mL each) and purged with Ar for another 5 min. Both vials were heated at 110° C. for 1 h in an oil bath. Upon cooling, both vials were diluted with EtOAc, solids filtered through celite, and the combined mixture concentrated and the residue used in Step 2B.

Scheme 42, Step 2B

The crude residue from Step 2A was dissolved in AcOH (17 mL), gently warmed and pipetted repeatedly into one 20 mL Biotage© microwave vial equipped with a stir bar. Ac$_2$O (1.005 mL, 10.63 mmol) was injected and the mixture was purged with Ar for 15 min and heated at 170° C. for 2 h. The mixture was poured into a 500 mL RBF and azeotroped with toluene repeatedly. DCM was added followed by 7M NH$_3$ in MeOH (10 mL) with subsequent concentration. The crude freebase was concentrated/dryloaded onto silica with DCM and purified on a 40 g silica column (DCM/MeOH, 0-5%), affording 4-(4-(5-chloro-2-methyl-3H-imidazo[4,5-b]pyridin-3-yl)-2-fluorophenyl)morpholine 143-B as a white solid (1.02 g, 2.94 mmol, 69% yield, 5% MeOH in DCM). $^1$H NMR (DMSO) δ: 8.08 (d, J=8.3 Hz, 1H), 7.51 (dd, J=13.3, 2.4 Hz, 1H), 7.34 (d, J=8.4 Hz, 2H), 7.24 (t, J=9.0 Hz, 1H), 3.83-3.76 (m, 4H), 3.17-3.10 (m, 4H), 2.46 (s, 3H).

Scheme 42, Step 3

A 2-5 mL Biotage© microwave vial loaded with 4-(4-(5-chloro-2-methyl-3H-imidazo[4,5-b]pyridin-3-yl)-2-fluorophenyl)morpholine 143-A (75 mg, 0.216 mmol), 4-(4,4,5,5-tetramethyl-1,3,2-dioxaborolan-2-yl)-1H-pyrrolo[2,3-b]pyridine (68.6 mg, 0.281 mmol), PdCl$_2$(dppf) (15.87 mg, 0.022 mmol), and K₃PO₄, (101 mg, 0.476 mmol) was capped, purged with argon, then injected with degassed dioxane:H₂O (0.692 mL:0.173 mL, 4:1 v/v), and heated to 120° C. for 2 h in an oil bath. The reaction was cooled, diluted with DCM, filtered through celite, concentrated, dryloaded onto silica gel and purified on a 12 g silica gel column (DCM/MeOH, 0-6%), affording 4-(2-fluoro-4-(2-methyl-5-(1H-pyrrolo[2,3-b]pyridin-4-yl)-3H-imidazo[4,5-b]pyridin-3-yl)phenyl)morpholine 143 as a tan solid (70 mg, 0.163 mmol, 76% yield, 6% MeOH in DCM). ¹H NMR (CDCl₃) δ: 11.42 (s, 1H), 8.39 (d, J=5.1 Hz, 1H), 8.12 (d, J=8.3 Hz, 1H), 7.93 (d, J=8.3 Hz, 1H), 7.57 (d, J=5.1 Hz, 1H), 7.43 (s, 1H), 7.32-7.21 (m, 2H), 7.10 (t, J=8.8 Hz, 1H), 7.01 (s, 1H), 3.96-3.89 (m, 4H), 3.24-3.16 (m, 4H), 2.62 (s, 3H).

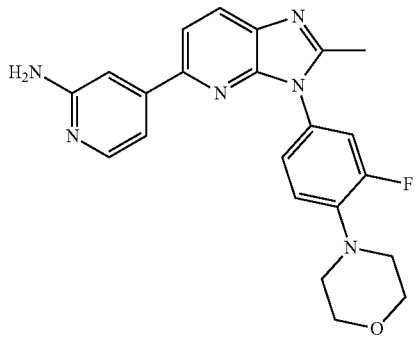

144

Compound 144 was synthesized in a similar manner as depicted in Scheme 42, Step 3 using 4-(4,4,5,5-tetramethyl-1,3,2-dioxaborolan-2-yl)pyridin-2-amine and 4-(4-(5-chloro-2-methyl-3H-imidazo[4,5-b]pyridin-3-yl)-2-fluorophenyl)morpholine 143-B.

4-(3-(3-fluoro-4-morpholinophenyl)-2-methyl-3H-imidazo[4,5-b]pyridin-5-yl)pyridin-2-amine 144.

Tan solid (60 mg, 0.148 mmol, 69% yield, 9% MeOH in DCM).

¹H NMR (CDCl₃) δ: 8.13 (d, J=5.3 Hz, 1H), 8.05 (d, J=8.3 Hz, 1H), 7.72 (d, J=8.3 Hz, 1H), 7.27-7.07 (m, 5H), 4.56 (s, 2H), 3.98-3.90 (m, 4H), 3.27-3.20 (m, 4H), 2.61 (s, 3H).

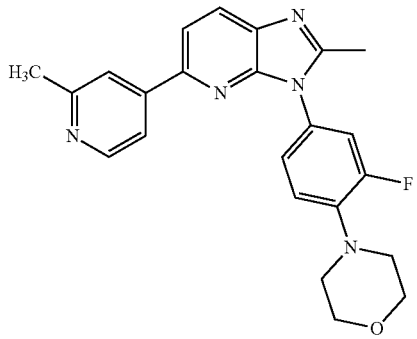

145

Compound 145 was synthesized in a similar manner as depicted in Scheme 42, Step 3 using (2-methylpyridin-4-yl) boronic acid and 4-(4-(5-chloro-2-methyl-3H-imidazo[4,5-b]pyridin-3-yl)-2-fluorophenyl)morpholine 143-B.

4-(2-fluoro-4-(2-methyl-5-(2-methylpyridin-4-yl)-3H-imidazo[4,5-b]pyridin-3-yl)phenyl)morpholine 145.

Tan solid (52 mg, 0.129 mmol, 64% yield, 10% MeOH in DCM)

¹H NMR (CDCl₃) δ: 8.55 (d, J=5.3 Hz, 1H), 8.08 (d, J=8.3 Hz, 1H), 7.78 (d, J=8.3 Hz, 1H), 7.73 (s, 1H), 7.69 (d, J=5.3 Hz, 1H), 7.27-7.09 (m, 3H), 3.99-3.91 (m, 4H), 3.28-3.21 (m, 4H), 2.63 (s, 3H), 2.62 (s, 3H).

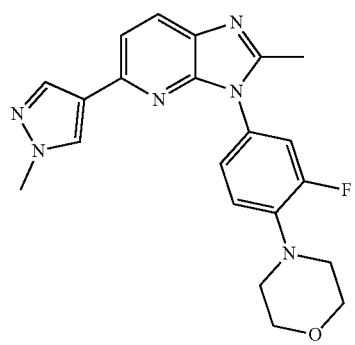

146

Compound 146 was synthesized in a similar manner as depicted in Scheme 42, Step 3 using 1-methyl-4-(4,4,5,5-tetramethyl-1,3,2-dioxaborolan-2-yl)-1H-pyrazole and 4-(4-(5-chloro-2-methyl-3H-imidazo[4,5-b]pyridin-3-yl)-2-fluorophenyl)morpholine 143-B.

4-(2-fluoro-4-(2-methyl-5-(1-methyl-1H-pyrazol-4-yl)-3H-imidazo[4,5-b]pyridin-3-yl)phenyl)morpholine 146.

White solid (92 mg, 0.234 mmol, 81% yield, 7% MeOH in DCM).

¹H NMR (CDCl₃) δ: 7.90 (d, J=8.2 Hz, 1H), 7.88 (s, 1H), 7.79 (s, 1H), 7.38 (d, J=8.2 Hz, 1H), 7.23-7.11 (m, 2H), 7.05 (t, J=8.8 Hz, 1H), 3.93-3.88 (m, 4H), 3.87 (s, 3H), 3.21-3.14 (m, 4H), 2.53 (s, 3H).

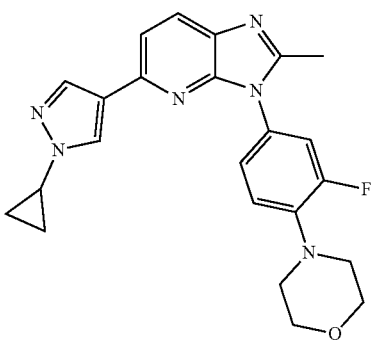

147

Compound 147 was synthesized in a similar manner as depicted in Scheme 42, Step 3 using 1-cyclopropyl-4-(4,4,5,5-tetramethyl-1,3,2-dioxaborolan-2-yl)-1H-pyrazole and 4-(4-(5-chloro-2-methyl-3H-imidazo[4,5-b]pyridin-3-yl)-2-fluorophenyl)morpholine 143-B.

4-(4-(5-(1-cyclopropyl-1H-pyrazol-4-yl)-2-methyl-3H-imidazo[4,5-b]pyridin-3-yl)-2-fluorophenyl)morpholine 147.

White solid (105 mg, 0.251 mmol, 97% yield, 5% MeOH in DCM).

¹H NMR (CDCl₃) δ: 7.92 (d, J=8.3 Hz, 1H), 7.89 (d, J=2.0 Hz, 2H), 7.40 (d, J=8.2 Hz, 1H), 7.25-7.05 (m, 3H), 3.97-3.89 (m, 4H), 3.66-3.55 (m, 1H), 3.25-3.18 (m, 4H), 2.55 (s, 3H), 1.19-0.98 (m, 4H).

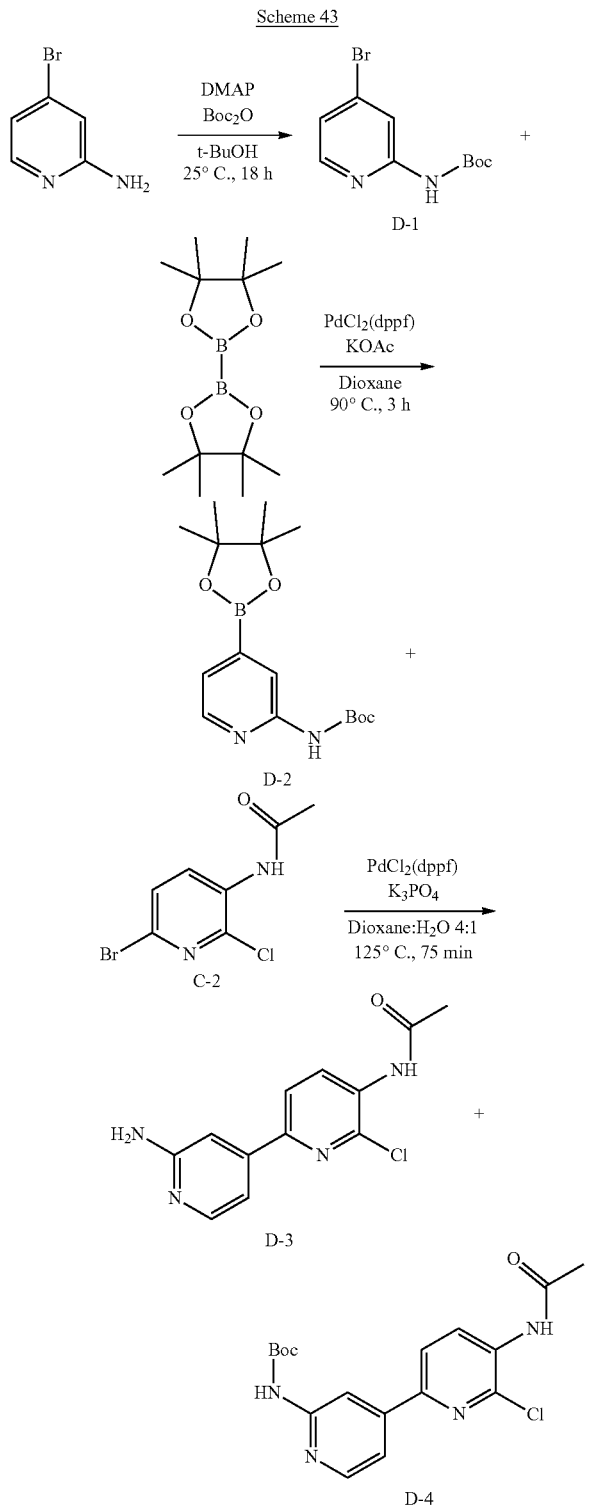

Scheme 43

Scheme 43, Step 1

A 500 mL round bottom flask was loaded with 4-bromopyridin-2-amine (5 g, 28.9 mmol), DMAP (353 mg, 2.89 mmol) and t-BuOH (65 mL). Warm Boc$_2$O (7.72 mL, 33.2 mmol) was added dropwise and the mixture was stirred at 25° C. for 18 h. Solvent is evaporated and the mixture is azeotroped with hexanes, then heated/cooled repeatedly with Et$_2$O and filtered, affording tert-butyl (4-bromopyridin-2-yl)carbamate D-1 as a white solid (3.6 g, 13.18 mmol, 46% yield). $^1$H NMR (DMSO) δ: 10.09 (bs, 1H), 8.15 (d, J=5.3 Hz, 1H), 8.04 (d, J=1.7 Hz, 1H), 7.28 (dd, J=5.3, 1.8 Hz, 1H), 1.48 (s, 9H). $^{13}$C NMR (DMSO) δ: 153.96, 153.09, 149.63, 133.39, 121.62, 115.13, 80.59, 28.42.

Scheme 43, Step 2

A 20 mL Biotage© microwave vial loaded with tert-butyl (4-bromopyridin-2-yl)carbamate D-1 (1 g, 3.66 mmol), 4,4,4',4',5,5,5',5'-octamethyl-2,2'-bi(1,3,2-dioxaborolane) (1.3 g, 5.13 mmol), PdCl$_2$(dppf) (215 mg, 0.293 mmol), and KOAc (1.15 g, 11.72 mmol) was capped, purged with argon, then injected with degassed dioxane (8.14 mL), and heated to 90° C. for 3 h in an oil bath. The reaction was cooled, diluted with EtOAC, poured into a separatory funnel containing EtOAc, saturated ammonium chloride solution, the mixture was shaken, and filtered through celite. After multiple extractions with EtOAc, the organics were washed with saturated ammonium chloride solution and brine. After concentration, the mixture was dissolved in Et$_2$O and then heated/cooled repeatedly with Et$_2$O, filtered, and washed with Et$_2$O affording tert-butyl (4-(4,4,5,5-tetramethyl-1,3,2-dioxaborolan-2-yl)pyridin-2-yl)carbamate D-2 White solid (540 mg, 1.686 mmol, 46% yield). $^1$H NMR (DMSO) δ: 9.76 (s, 1H), 8.27 (dd, J=4.7, 1.0 Hz, 1H), 8.09 (s, 1H), 7.19 (dd, J=4.8, 0.9 Hz, 1H), 1.49 (s, 9H), 1.33 (s, 12H).

Scheme 43, Step 3

A 20 mL Biotage© microwave vial loaded with N-(6-bromo-2-chloropyridin-3-yl)acetamide C-2 (748 mg, 3 mmol), tert-butyl (4-(4,4,5,5-tetramethyl-1,3,2-dioxaborolan-2-yl)pyridin-2-yl)carbamate D-2 (1.057 g, 3.3 mmol), PdCl$_2$(dppf) (220 mg, 0.300 mmol), and K$_3$PO$_4$, (1.4 g, 6.6 mmol) was capped, purged with argon, then injected with degassed dioxane:H$_2$O (9.6 mL:2.4 mL, 4:1 v/v), and heated to 125° C. for 75 min in an oil bath. The reaction was cooled, diluted with DCM, filtered through celite, concentrated, dryloaded onto silica gel and purified on a 40 g silica gel column (DCM/MeOH, 0-6%), affording N-(2'-amino-6-chloro-[2,4'-bipyridin]-5-yl)acetamide D-3 as a beige solid (392 mg, 1.492 mmol, 50% yield). $^1$H NMR (DMSO) δ: 9.76 (s, 1H), 8.35 (d, J=8.3 Hz, 1H), 8.02 (d, J=5.4 Hz, 1H), 7.95 (d, J=8.4 Hz, 1H), 7.10 (s, 1H), 7.06 (dd, J=5.4, 1.6 Hz, 1H), 6.11 (s, 2H), 2.18 (s, 3H). $^{13}$C NMR (DMSO) δ: 169.78, 161.09, 150.47, 149.14, 144.97, 142.59, 134.54, 132.51, 120.45, 109.30, 104.94, 24.03. The product tert-butyl (5-acetamido-6-chloro-[2,4'-bipyridin]-2'-yl)carbamate D-4 was also afforded, white solid (370 mg, 1.020 mmol, 34% yield, 5% MeOH). $^1$H NMR (CDCl$_3$) δ: 8.86 (d, J=8.5 Hz, 1H), 8.49 (s, 1H), 8.37 (d, J=5.3 Hz, 1H), 7.95 (s, 1H), 7.86 (d, J=8.5 Hz, 1H), 7.75 (bs, 1H), 7.62 (dd, J=5.3, 1.6 Hz, 1H), 2.33 (s, 3H), 1.59 (s, 9H).

Scheme 44

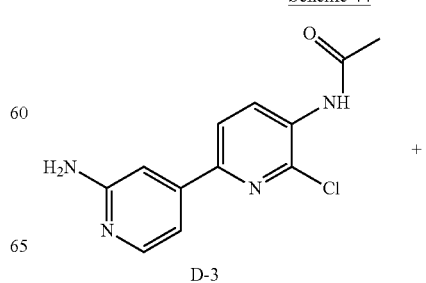

D-3

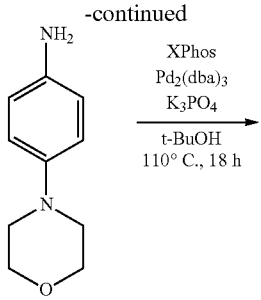

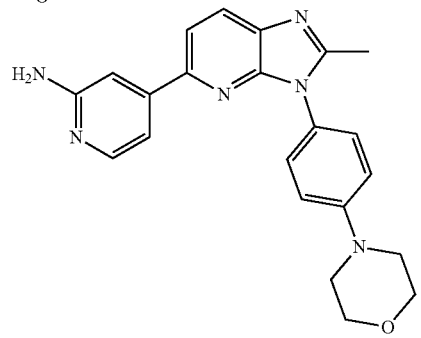

148

A 2-5 mL Biotage© microwave vial loaded with Pd₂(dba)₃ (3 mg, 0.0037 mmol), XPhos (8 mg, 0.017 mmol), and t-BuOH (0.42 mL) was capped, purged with argon, heated to 110° C. for 1 minute in an oil bath and cooled. The vial was uncapped, a mixture of N-(2'-amino-6-chloro-[2,4'-bipyridin]-5-yl)acetamide D-3 (48.6 mg, 0.185 mmol), 4-morpholinoaniline (30 mg, 0.168 mmol), and K₃PO₄ (107 mg, 0.505 mmol) added, the vial sealed and heated to 110° C. for 18 h in an oil bath. The reaction was cooled, diluted with DCM, filtered through celite, concentrated, dryloaded onto silica gel and purified on a 12 g silica gel column (DCM/MeOH, 0-8%), affording 4-(2-methyl-3-(4-morpholinophenyl)-3H-imidazo[4,5-b]pyridin-5-yl)pyridin-2-amine 148 as a white solid (8 mg, 0.021 mmol, 12% yield, 8% MeOH in DCM). ¹H NMR (CDCl₃) δ: 8.13 (d, J=5.4 Hz, 1H), 8.06 (d, J=8.3 Hz, 1H), 7.73 (d, J=8.3 Hz, 1H), 7.37 (d, J=8.4 Hz, 2H), 7.25 (dd, J=5.4, 1.5 Hz, 1H), 7.16 (s, 1H), 7.10 (d, J=8.4 Hz, 2H), 4.49 (s, 2H), 4.18-3.77 (m, 4H), 3.36-3.18 (m, 4H), 2.60 (s, 3H).

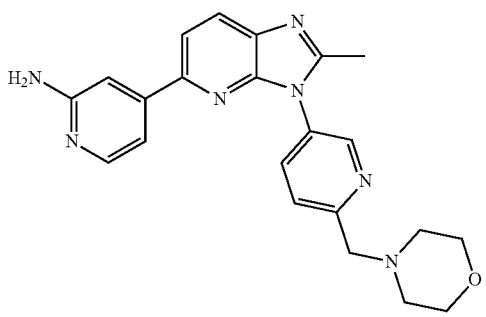

149

Compound 149 was synthesized in a similar manner as depicted in Scheme 44, using 6-(morpholinomethyl)pyridin-3-amine.

4-(2-methyl-3-(6-(morpholinomethyl)pyridin-3-yl)-3H-imidazo[4,5-b]pyridin-5-yl)pyridin-2-amine 149.

Green semi-solid (14 mg, 0.036 mmol, 18% yield, 12% MeOH in DCM).

¹H NMR (Acetone) δ: 9.21 (s, 1H), 8.81 (s, 1H), 8.06 (d, J=7.6 Hz, 1H), 7.90 (d, J=7.9 Hz, 1H), 7.44 (dd, J=8.2, 3.6 Hz, 2H), 7.27-7.21 (m, 1H), 7.19 (d, J=5.5 Hz, 1H), 5.51 (s, 2H), 3.69-3.62 (m, 4H), 3.60 (s, 2H), 2.52-2.46 (m, 4H), 2.21 (s, 3H).

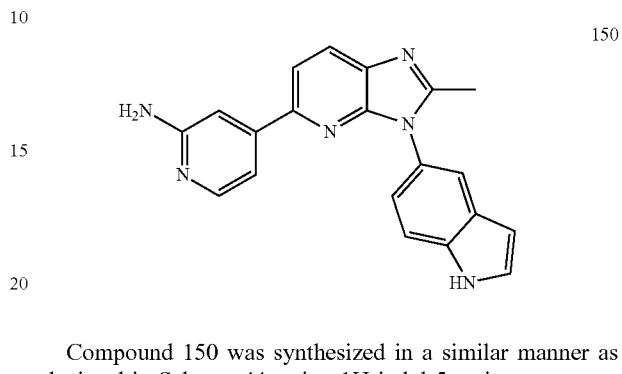

150

Compound 150 was synthesized in a similar manner as depicted in Scheme 44, using 1H-indol-5-amine 4-(3-(1H-indol-5-yl)-2-methyl-3H-imidazo[4,5-b]pyridin-5-yl)pyridin-2-amine 150.

White semi-solid (17 mg, 0.050 mmol, 29% yield, 10% MeOH in DCM).

¹H NMR (DMSO) δ: 11.45 (bs, 1H), 8.11 (d, J=8.3 Hz, 1H), 7.93 (dd, J=5.4, 0.8 Hz, 1H), 7.80 (d, J=8.3 Hz, 1H), 7.73 (d, J=2.0 Hz, 1H), 7.62 (d, J=8.4 Hz, 1H), 7.54 (t, J=2.8 Hz, 1H), 7.22 (dd, J=8.5, 2.1 Hz, 1H), 7.02 (dd, J=5.4, 1.6 Hz, 1H), 6.95 (s, 1H), 6.64-6.46 (m, 1H), 5.93 (s, 2H), 2.46 (s, 3H).

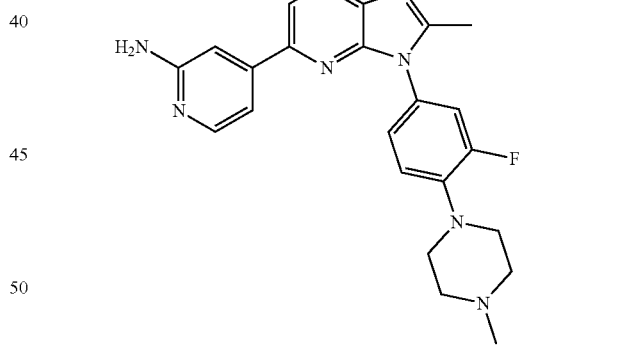

151

Compound 151 was synthesized in a similar manner as depicted in Scheme 44, using 3-fluoro-4-(4-methylpiperazin-1-yl)aniline.

4-(3-(3-fluoro-4-(4-methylpiperazin-1-yl)phenyl)-2-methyl-3H-imidazo[4,5-b]pyridin-5-yl)pyridin-2-amine 151.

White solid (11 mg, 0.026 mmol, 22% yield, 30% MeOH in DCM).

¹H NMR (CDCl₃) δ: 8.13 (d, J=5.5 Hz, 1H), 8.06 (d, J=8.3 Hz, 1H), 7.74 (d, J=8.3 Hz, 1H), 7.27-7.09 (m, 5H), 4.62 (s, 2H), 3.33-3.25 (m, 4H), 2.76-2.66 (m, 4H), 2.62 (s, 3H), 2.43 (s, 3H).

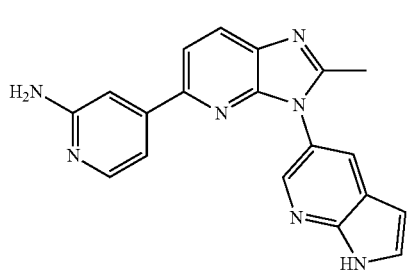

152

Compound 152 was synthesized in a similar manner as depicted in Scheme 44, using 1H-pyrrolo[2,3-b]pyridin-5-amine.

4-(2-methyl-3-(1H-pyrrolo[2,3-b]pyridin-5-yl)-3H-imidazo[4,5-b]pyridin-5-yl)pyridin-2-amine 152.

Light yellow solid (26 mg, 0.076 mmol, 40% yield, 15% MeOH in DCM).

$^1$H NMR (CDCl$_3$) δ: 9.56 (s, 1H), 8.43 (s, 1H), 8.11 (d, J=7.3 Hz, 2H), 8.05 (s, 1H), 7.77 (d, J=8.4 Hz, 1H), 7.52 (s, 1H), 7.22 (d, J=5.4 Hz, 1H), 7.14 (s, 1H), 6.68 (s, 1H), 4.53 (s, 2H), 2.63 (s, 3H).

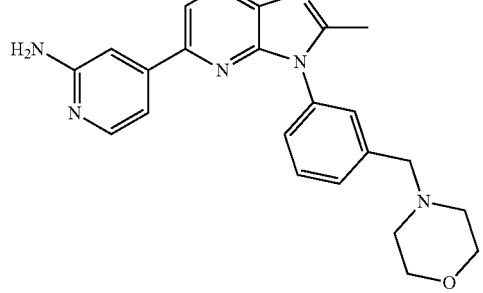

153

Compound 153 was synthesized in a similar manner as depicted in Scheme 44, using 3-(morpholinomethyl)aniline.

4-(2-methyl-3-(3-(morpholinomethyl)phenyl)-3H-imidazo[4,5-b]pyridin-5-yl)pyridin-2-amine 153.

Clear semi-solid (16 mg, 0.040 mmol, 21% yield, 15% MeOH in DCM).

$^1$H NMR (CDCl$_3$) δ: 8.12 (d, J=5.4 Hz, 1H), 8.08 (d, J=8.3 Hz, 1H), 7.75 (d, J=8.3 Hz, 1H), 7.58 (t, J=8.0 Hz, 1H), 7.51 (d, J=7.0 Hz, 2H), 7.40 (d, J=7.8, 1.7 Hz, 1H), 7.23 (dd, J=5.5, 1.5 Hz, 1H), 7.14 (s, 1H), 4.54 (s, 2H), 3.78-3.71 (m, 4H), 3.68 (s, 2H), 2.63 (s, 3H), 2.60-2.53 (m, 4H). $^{13}$C NMR (CDCl$_3$) δ: 159.09, 154.24, 149.18, 149.05, 148.57, 148.47, 139.56, 135.09, 134.57, 129.50, 129.45, 127.95, 126.85, 126.03, 116.19, 112.02, 105.84, 66.99, 62.77, 53.41, 15.40.

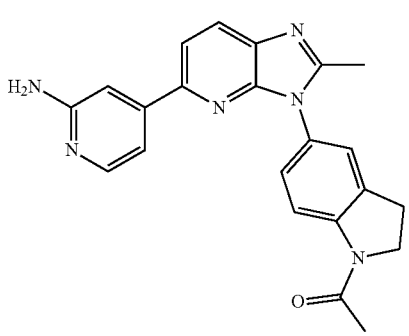

154

Compound 154 was synthesized in a similar manner as depicted in Scheme 44, using 1-(5-aminoindolin-1-yl)ethan-1-one.

1-(5-(5-(2-aminopyridin-4-yl)-2-methyl-3H-imidazo[4,5-b]pyridin-3-yl)indolin-1-yl)ethan-1-one 154.

Tan solid (57 mg, 0.148 mmol, 19% yield, 10% MeOH in DCM).

$^1$H NMR (CDCl$_3$) δ: 8.44 (d, J=8.3 Hz, 1H), 8.12 (d, J=5.4 Hz, 1H), 8.06 (d, J=8.3 Hz, 1H), 7.73 (d, J=8.3 Hz, 1H), 7.32-7.25 (m, 2H), 7.23 (d, J=5.5 Hz, 1H), 7.15 (s, 1H), 4.57 (s, 2H), 4.22 (t, J=8.5 Hz, 2H), 3.35 (t, J=8.4 Hz, 2H), 2.59 (s, 3H), 2.32 (s, 3H).

Scheme 45

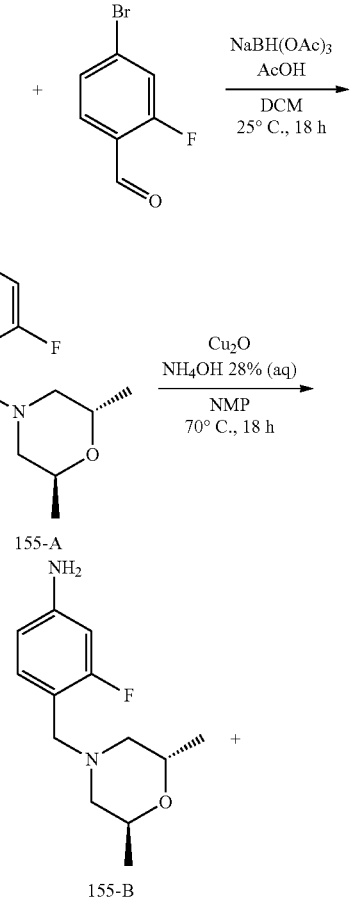

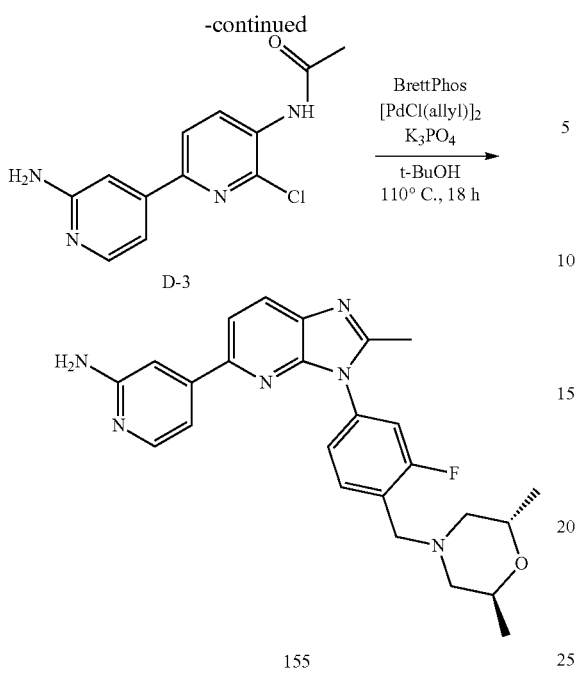

Scheme 45, Step 1

A 5 mL screw cap vial loaded with 4-bromo-2-fluorobenzaldehyde (200 mg, 0.985 mmol), (2S,6S)-2,6-dimethylmorpholine (136 mg, 1.182 mmol), DCM (4.926 mL), and AcOH (3 drops), were stirred for 5 minutes. NaBH(OAc)$_3$ (251 mg, 1.182 mmol), was added and the mixture was sealed and stirred at 25° C. for 48 h. The vial was diluted with DCM and 10% NaOH, then extracted multiple times with DCM, washed with 10% NaOH, H$_2$O, brine, and the organic layer was dried over Na$_2$SO$_4$, concentrated, and used crude in the next step, affording (2S,6S)-4-(4-bromo-2-fluorobenzyl)-2,6-dimethylmorpholine 155-A.

Scheme 45, Step 2

In a 20 mL Biotage© microwave vial, a stir bar, N-Methyl-2-pyrrolidone (2.25 mL), crude (2S,6S)-4-(4-bromo-2-fluorobenzyl)-2,6-dimethylmorpholine 155-A (340 mg, 1.125 mmol), 28% NH$_4$OH (3.13 mL 22.50 mmol) were added followed by Cu$_2$O (16.1 mg, 0.113 mmol). The vial was sealed and heated at 70° C. for 18 h. Upon cooling, the mixture is diluted with brine, ether and poured into separatory funnel and extracted with diethyl ether multiple times. The pooled ether layers were washed with H$_2$O, brine, then dried with Na$_2$SO$_4$, concentrated, dryloaded onto silica gel and purified on a 12 g silica gel column (DCM/MeOH, 0-9%), affording 4-(((2S,6S)-2,6-dimethylmorpholino)methyl)-3-fluoroaniline 155-B as a green oil (96 mg, 0.403 mmol, 36% yield, 9% MeOH in DCM). $^1$H NMR (CDCl$_3$) δ: 7.12 (t, J=8.2 Hz, 1H), 6.43 (dd, J=8.1, 2.3 Hz, 1H), 6.37 (dd, J=11.6, 2.3 Hz, 1H), 4.09-3.95 (m, 2H), 3.75 (s, 2H), 3.41 (s, 2H), 2.56-2.35 (m, 2H), 2.16 (dd, J=11.1, 5.8 Hz, 2H), 1.23 (d, J=6.5 Hz, 6H)

Scheme 45, Step 3

A 2-5 mL Biotage© microwave vial loaded with [PdCl(allyl)]$_2$ (2.09 mg, 0.00571 mmol), BrettPhos (15.32 mg, 0.029 mmol), and t-BuOH (0.95 mL) was capped, purged with argon, heated to 60° C. for 10 min in an oil bath and cooled. The vial was uncapped, a mixture of N-(2'-amino-6-chloro-[2,4'-bipyridin]-5-yl)acetamide D-3 (50 mg, 0.190 mmol), 4-(((2S,6S)-2,6-dimethylmorpholino)methyl)-3-fluoroaniline 155-B (49.9 mg, 0.209 mmol), and K$_3$PO$_4$ (121 mg, 0.571 mmol), added, the vial sealed and heated to 110° C. for 18 h in an oil bath. The reaction was cooled, diluted with DCM, filtered through celite, concentrated, dryloaded onto silica gel and purified on a 12 g silica gel column (DCM/MeOH, 0-8%), affording 4-(3-(4-(((2S,6S)-2,6-dimethylmorpholino)methyl)-3-fluorophenyl)-2-methyl-3H-imidazo[4,5-b]pyridin-5-yl)pyridin-2-amine 155 as a clear semi-solid (10 mg, 0.022 mmol, 12% yield, 8% MeOH in DCM). $^1$H NMR (CDCl$_3$) δ: 8.14 (d, J=5.4 Hz, 1H), 8.09 (d, J=8.3 Hz, 1H), 7.80-7.68 (m, 2H), 7.34-7.21 (m, 3H), 7.15 (s, 1H), 4.59 (s, 2H), 4.17-4.03 (m, 2H), 3.66 (s, 2H), 3.52 (s, 1H), 2.68-2.59 (m, 4H), 2.31 (dd, J=10.9, 5.7 Hz, 2H), 1.32 (d, J=6.4 Hz, 6H).

Scheme 46

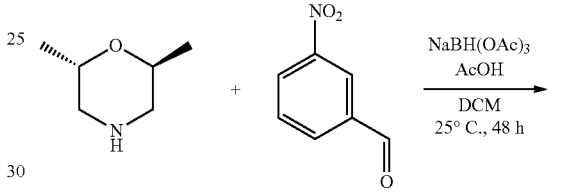

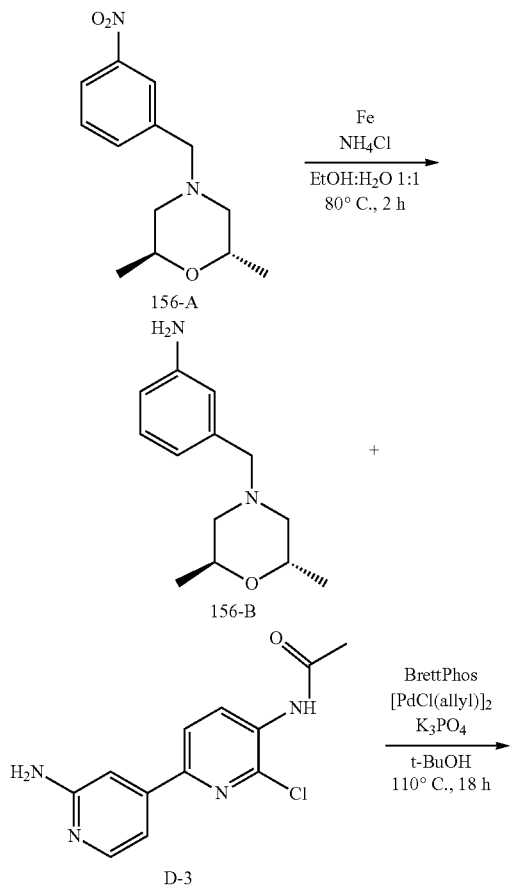

-continued

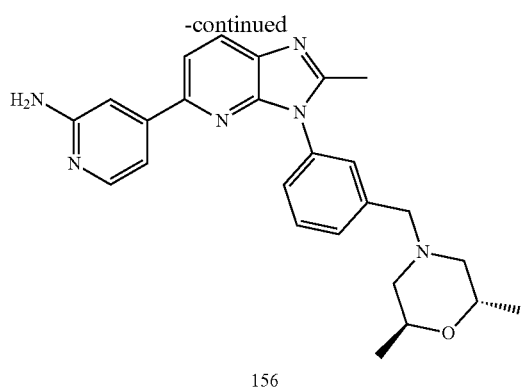

156

Scheme 46, Step 1

A 20 mL screw cap vial loaded with 3-nitrobenzaldehyde (200 mg, 1.323 mmol), (2S,6S)-2,6-dimethylmorpholine (183 mg, 1.588 mmol), DCM (6.62 mL), and AcOH 3 drops), were stirred for 5 minutes. NaBH(OAc)$_3$ (337 mg, 1.588 mmol), was added and the mixture was sealed and stirred at 25° C. for 48 h. The vial was diluted with DCM and 10% NaOH, then extracted multiple times with DCM, washed with 10% NaOH, H$_2$O, brine, and the organic layer was dried over Na$_2$SO$_4$, concentrated, and used crude in the next step, (2S,6S)-2,6-dimethyl-4-(3-nitrobenzyl)morpholine 156-A.

Scheme 46, Step 2

In a 20 mL Biotage© microwave vial, a stir bar, ((2S, 6S)-2,6-dimethyl-4-(3-nitrobenzyl)morpholine 156-A (0.340 g, 1.358 mmol), iron (379 mg, 6.79 mmol), and ammonium chloride (73 mg, 1.358 mmol), were added. The vial was sealed, degassed with Ar for 15 min, and degassed EtOH:H$_2$O (4.07 mL:4.07 mL, 1:1 v/v) injected. The mixture was heated at 80° C. for 2 h in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na$_2$SO$_4$. Solvent was concentrated, the crude was triturated with hot hexanes and the hexane soluble fraction afforded the pure product, 3-(((2S,6S)-2,6-dimethylmorpholino)methyl)aniline 156-B, White solid (95 mg, 0.345 mmol, 25% yield). $^1$H NMR (CDCl$_3$) δ: 7.11 (t, J=7.7 Hz, 1H), 6.78-6.69 (m, 2H), 6.59 (dd, J=7.9, 2.5 Hz, 1H), 4.11-3.98 (m, 2H), 3.68 (bs, 2H), 3.42-3.29 (m, 2H), 2.48 (dd, J=10.9, 3.2 Hz, 2H), 2.21-2.09 (m, 2H), 1.27 (s, 3H), 1.26 (s, 3H).

Scheme 46, Step 3

A 2-5 mL Biotage© microwave vial loaded with [PdCl(allyl)]$_2$ (2.09 mg, 0.00571 mmol), BrettPhos (15.32 mg, 0.029 mmol), and t-BuOH (0.95 mL) was capped, purged with argon, heated to 60° C. for 10 min in an oil bath and cooled. The vial was uncapped, a mixture of N-(2'-amino-6-chloro-[2,4'-bipyridin]-5-yl)acetamide D-3 (50 mg, 0.190 mmol), 3-(((2S,6S)-2,6-dimethylmorpholino)methyl)aniline 156-B (57.7 mg, 0.209 mmol), and K$_3$PO$_4$ (121 mg, 0.571 mmol), added, the vial sealed and heated to 110° C. for 18 h in an oil bath. The reaction was cooled, diluted with DCM, filtered through celite, concentrated, dryloaded onto silica gel and purified on a 12 g silica gel column (DCM/MeOH, 0-9%), affording 4-(3-(3-(((2S,6S)-2,6-dimethylmorpholino)methyl)phenyl)-2-methyl-3H-imidazo[4,5-b]pyridin-5-yl)pyridin-2-amine 156 as a white semi-solid (5 mg, 0.012 mmol, 6% yield, 9% MeOH in DCM). $^1$H NMR (CDCl$_3$) δ: 8.12 (s, 1H), 8.08 (d, J=8.2 Hz, 1H), 7.75 (d, J=8.3 Hz, 1H), 7.58 (t, J=7.7 Hz, 1H), 7.53-7.45 (m, 2H), 7.40 (d, J=8.8 Hz, 1H), 7.24 (d, J=5.5 Hz, 1H), 7.14 (s, 1H), 4.57 (s, 2H), 4.12-4.01 (m, 1H), 3.70-3.50 (m, 3H), 2.70-2.54 (m, 5H), 2.31-2.22 (m, 2H), 1.26 (s, 3H), 1.25 (s, 3H).

Scheme 47

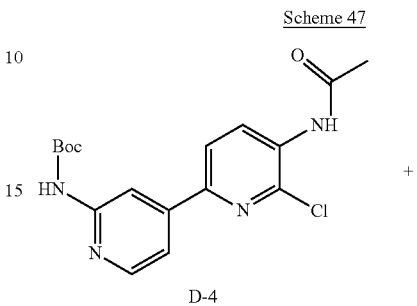

D-4

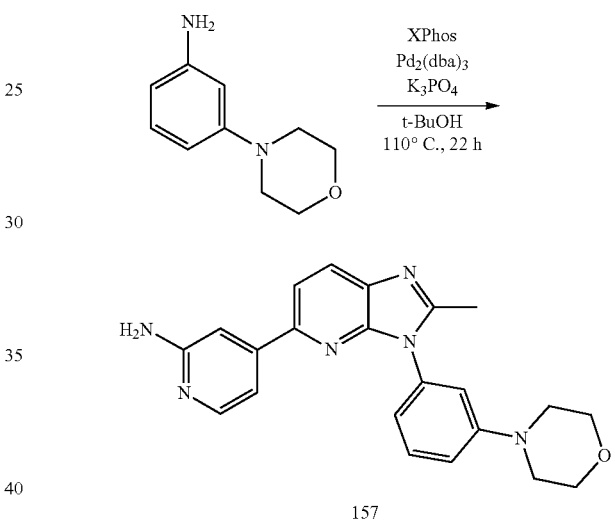

157

A 2-5 mL Biotage© microwave vial loaded with Pd$_2$(dba)$_3$ (5.67 mg, 0.0062 mmol), XPhos (11.83 mg, 0.025 mmol), and t-BuOH (0.69 mL) was capped, purged with argon, heated to 110° C. for 1 minute in an oil bath and cooled. The vial was uncapped, a mixture of tert-butyl (5-acetamido-6-chloro-[2,4'-bipyridin]-2'-yl)carbamate D-4 (75 mg, 0.207 mmol), 3-morpholinoaniline (40.5 mg, 0.227 mmol), and K$_3$PO$_4$ (145 mg, 0.682 mmol), added, the vial sealed and heated to 110° C. for 22 h in an oil bath. The reaction was cooled, 37% conc. HCl (0.7 mL) was added, stirred for 1 h and basified with 10% NaOH. The mixture was extracted with ethyl acetate, washed with 10% NaOH, H$_2$O, brine, and the organic layer was dried over Na$_2$SO$_4$, concentrated, dryloaded onto silica gel and purified on a 12 g silica gel column (DCM/MeOH, 0-9%), affording 4-(2-methyl-3-(3-morpholinophenyl)-3H-imidazo[4,5-b]pyridin-5-yl)pyridin-2-amine 157 as a white solid (30 mg, 0.078 mmol, 38% yield, 9% MeOH in DCM). $^1$H NMR (CDCl$_3$) δ: 8.12 (d, J=5.4 Hz, 1H), 8.05 (d, J=8.3 Hz, 1H), 7.72 (d, J=8.3 Hz, 1H), 7.48 (t, J=8.3 Hz, 1H), 7.24 (dd, J=5.4, 1.5 Hz, 1H), 7.18-7.13 (m, 1H), 7.07 (dd, J=8.4, 2.5 Hz, 1H), 6.98 (t, J=2.2 Hz, 1H), 6.94 (dd, J=7.7, 1.9 Hz, 1H), 4.57 (s, 2H), 3.92-3.87 (m, 4H), 3.29-3.22 (m, 4H), 2.62 (s, 3H).

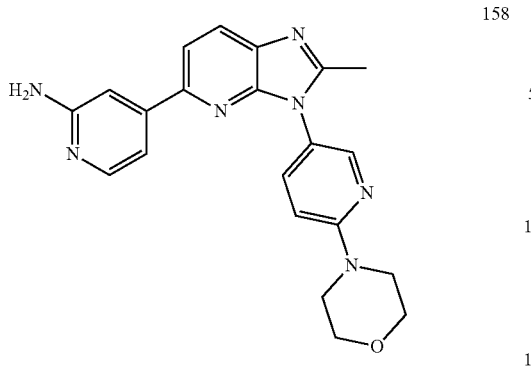

158

Compound 158 was synthesized in a similar manner as depicted in Scheme 47, using 6-morpholinopyridin-3-amine.

4-(2-methyl-3-(6-morpholinopyridin-3-yl)-3H-imidazo[4,5-b]pyridin-5-yl)pyridin-2-amine 158.

Red semi-solid (9 mg, 0.023 mmol, 11% yield, 10% MeOH in DCM).

$^1$H NMR (CDCl$_3$) δ: 8.31 (s, 1H), 8.14 (d, J=5.4 Hz, 1H), 8.07 (dd, J=8.3, 1.6 Hz, 1H), 7.74 (dd, J=8.3, 1.6 Hz, 1H), 7.62 (d, J=9.0 Hz, 1H), 7.24 (d, J=5.4 Hz, 1H), 7.16 (s, 1H), 6.85 (d, J=8.8 Hz, 1H), 4.50 (s, 2H), 3.95-3.87 (m, 4H), 3.75-3.61 (m, 4H), 2.61 (s, 3H).

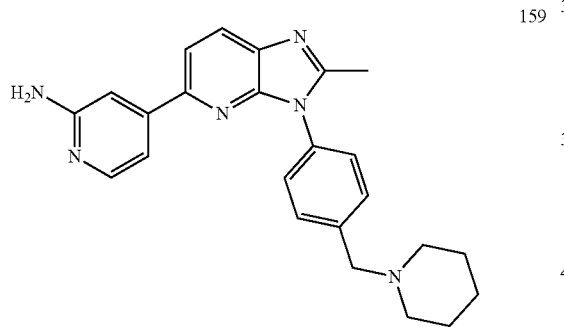

159

Compound 159 was synthesized in a similar manner as depicted in Scheme 47, using 4-(piperidin-1-ylmethyl)aniline.

4-(2-methyl-3-(4-(piperidin-1-ylmethyl)phenyl)-3H-imidazo[4,5-b]pyridin-5-yl)pyridin-2-amine 159.

Green semi-solid (29 mg, 0.073 mmol, 37% yield, 25% MeOH in DCM).

$^1$H NMR (CDCl$_3$) δ: 8.12 (d, J=5.4 Hz, 1H), 8.06 (d, J=8.3 Hz, 1H), 7.73 (d, J=8.3 Hz, 1H), 7.59 (d, J=8.3 Hz, 2H), 7.43 (d, J=8.3 Hz, 2H), 7.23 (d, J=5.4 Hz, 1H), 7.15 (s, 1H), 4.57 (s, 2H), 3.63 (s, 2H), 2.62 (s, 3H), 2.56-2.51 (m, 4H), 1.72-1.62 (m, 4H), 1.57-1.48 (m, 2H).

Scheme 48

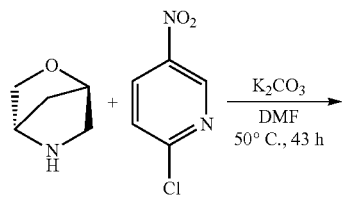

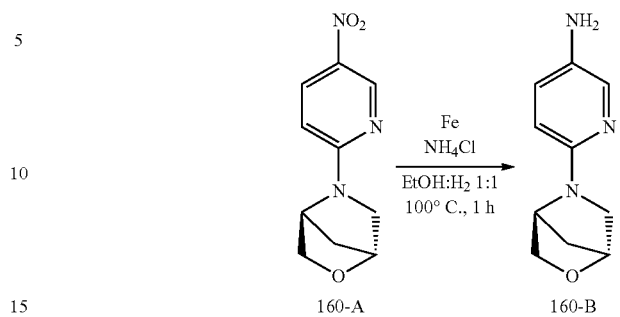

Scheme 48, Step 1

In a 5 mL Biotage© microwave vial, a stir bar, K$_2$CO$_3$ (697 mg, 5.05 mmol), 2-Chloro-5-nitropyridine (400 mg, 2.52 mmol), and (1R,4S)-2-oxa-5-azabicyclo[2.2.1]heptane (250 mg, 2.52 mmol), were added. The vial was sealed, and purged with Ar for 15 min, DMF (2.52 mL) was then added injected into the vial and the mixture was heated at 50° C. for 43 h. Upon cooling, the mixture is transferred to a separatory funnel, H$_2$O was added, and the aq layer was extracted with ethyl acetate and the pooled organics were washed with saturated brine and dried with Na$_2$SO$_4$. Solvent was concentrated, obtaining the pure product, (1R,4S)-5-(5-nitropyridin-2-yl)-2-oxa-5-azabicyclo[2.2.1]heptane 160-A as a red solid (280 mg, 1.266 mmol, 50% yield). $^1$H NMR (CDCl$_3$) δ: 9.05 (d, J=2.7 Hz, 1H), 8.23 (dd, J=9.3, 2.7 Hz, 1H), 6.31 (s, 1H), 4.80 (s, 1H), 3.96 (dd, J=7.6, 1.5 Hz, 1H), 3.89 (d, J=7.6 Hz, 1H), 3.67-3.26 (m, 3H), 2.13-1.98 (m, 2H).

Scheme 48, Step 2

In a 20 mL Biotage© microwave vial, a stir bar, (1R,4S)-5-(5-nitropyridin-2-yl)-2-oxa-5-azabicyclo[2.2.1]heptane 160-A (280 mg, 1.266 mmol), iron (353 mg, 6.33 mmol), and ammonium chloride (135 mg, 2.53 mmol), were added. The vial was sealed, degassed with Ar for 15 min, and degassed EtOH:H$_2$O (3.164 mL:3.164 mL, 1:1 v/v) injected. The mixture was heated for 1 h at 100° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na$_2$SO$_4$. Solvent was concentrated, redissolved in DCM, dryloaded onto silica and chromatographed on a 12 g silica column, (DCM/MeOH, 0-5%), affording 6-((1R,4S)-2-oxa-5-azabicyclo[2.2.1]heptan-5-yl)pyridin-3-amine 160-B as a purple oil (94 mg, 0.489 mmol, 39% yield, 5% MeOH). $^1$H NMR (CDCl$_3$) δ: 7.74 (d, J=2.3 Hz, 1H), 6.97 (dd, J=8.7, 2.9 Hz, 1H), 6.29 (d, J=8.7 Hz, 1H), 4.75-4.59 (m, 2H), 3.89-3.84 (m, 2H), 3.49 (dd, J=9.5, 1.6 Hz, 1H), 3.32-3.11 (m, 3H), 2.03-1.87 (m, 2H). $^{13}$C NMR (CDCl$_3$) δ: 152.45, 152.33, 135.53, 133.33, 126.70, 107.90, 76.69, 72.93, 57.06, 56.99, 36.62.

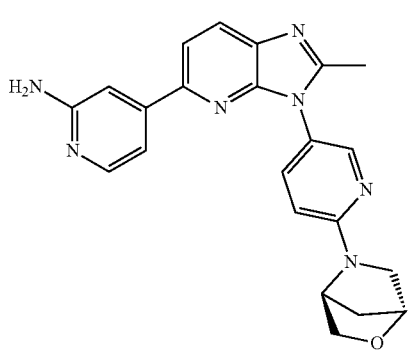

Compound 160 was synthesized in a similar manner as depicted in Scheme 47, using 6-((1R,4S)-2-oxa-5-azabicyclo[2.2.1]heptan-5-yl)pyridin-3-amine 160-B.

4-(3-(6-((1R,4S)-2-oxa-5-azabicyclo[2.2.1]heptan-5-yl)pyridin-3-yl)-2-methyl-3H-imidazo[4,5-b]pyridin-5-yl)pyridin-2-amine 160.

Red semi-solid (39 mg, 0.098 mmol, 45% yield, 9% MeOH in DCM).

$^1$H NMR (CDCl$_3$) δ: 8.23 (dd, J=2.7, 0.7 Hz, 1H), 8.13 (dd, J=5.4, 0.8 Hz, 1H), 8.05 (d, J=8.2 Hz, 1H), 7.72 (d, J=8.3 Hz, 1H), 7.55 (dd, J=8.8, 2.6 Hz, 1H), 7.23 (dd, J=5.4, 1.5 Hz, 1H), 7.19-7.13 (m, 1H), 6.55 (d, J=8.9 Hz, 1H), 5.02 (s, 1H), 4.80-4.77 (m, 1H), 4.54 (s, 2H), 4.05-3.93 (m, 2H), 3.63-3.57 (m, 1H), 3.49 (d, J=9.6 Hz, 2H), 2.60 (s, 3H), 2.05 (s, 1H). $^{13}$C NMR (CDCl$_3$) δ: 159.08, 156.79, 154.81, 149.37, 149.26, 148.57, 148.45, 146.66, 136.31, 135.06, 126.86, 120.57, 116.20, 112.11, 106.89, 106.04, 76.57, 73.67, 56.92, 56.56, 36.78, 15.17.

Scheme 49

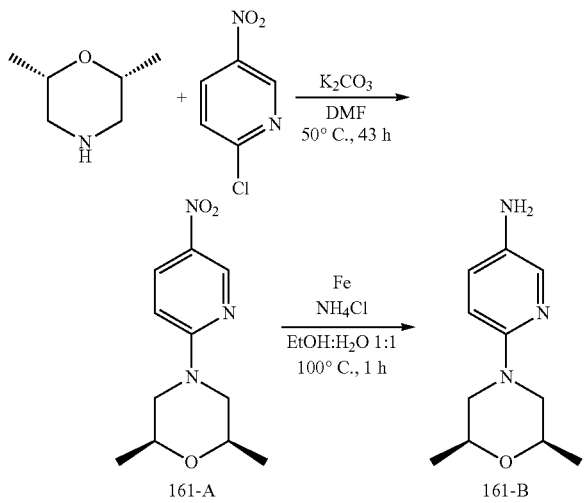

Scheme 49, Step 1

In a 5 mL Biotage© microwave vial, a stir bar, K$_2$CO$_3$ (697 mg, 5.05 mmol), 2-Chloro-5-nitropyridine (400 mg, 2.52 mmol), and (2S,6R)-2,6-dimethylmorpholine (291 mg, 2.52 mmol), were added. The vial was sealed, and purged with Ar for 15 min, DMF (2.523 mL) was then added injected into the vial and the mixture was heated at 50° C. for 43 h. Upon cooling, the mixture is transferred to a separatory funnel, H$_2$O was added, and the aq layer was extracted with ethyl acetate and the pooled organics were washed with saturated brine and dried with Na$_2$SO$_4$. Solvent was concentrated and the pure product was obtained, affording (2S,6R)-2,6-dimethyl-4-(5-nitropyridin-2-yl)morpholine 161-A as a yellow solid (542 mg, 2.284 mmol, 91% yield). $^1$H NMR (CDCl$_3$) δ: 9.04 (d, J=2.7 Hz, 1H), 8.22 (dd, J=9.5, 2.8 Hz, 1H), 6.58 (d, J=9.5 Hz, 1H), 4.32 (d, J=13.0 Hz, 2H), 3.76-3.63 (m, 2H), 2.73 (dd, J=13.1, 10.6 Hz, 2H), 1.33-1.28 (m, 6H). $^{13}$C NMR (CDCl$_3$) δ: 160.14, 146.37, 135.18, 133.04, 104.57, 71.52, 50.17, 18.85.

Scheme 49, Step 2

In a 20 mL Biotage© microwave vial, a stir bar, (2S,6R)-2,6-dimethyl-4-(5-nitropyridin-2-yl)morpholine 161-A (542 mg, 2.284 mmol), iron (638 mg, 11.42 mmol), and ammonium chloride (244 mg, 4.57 mmol), were added. The vial was sealed, degassed with Ar for 15 min, and degassed EtOH:H$_2$O (5.7 mL:5.7 mL, 1:1 v/v) injected. The mixture was heated for 1 h at 100° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na$_2$SO$_4$. Solvent was concentrated, redissolved in DCM, dryloaded onto silica and chromatographed on a 12 g silica column, (DCM/MeOH, 0-4.5%), affording 6-((2S,6R)-2,6-dimethylmorpholino)pyridin-3-amine 161-B as a purple oil (414 mg, 1.997 mmol, 87% yield, 4.5% MeOH). $^1$H NMR (CDCl$_3$) δ: 7.76 (d, J=2.9 Hz, 1H), 6.96 (dd, J=8.8, 3.0 Hz, 1H), 6.53 (d, J=8.8 Hz, 1H), 3.79 (d, J=12.7 Hz, 2H), 3.76-3.65 (m, 2H), 3.31 (bs, 2H), 2.44-2.33 (m, 2H), 1.26-1.22 (m, 6H). $^{13}$C NMR (CDCl$_3$) δ: 154.10, 135.16, 134.85, 126.08, 108.32, 71.60, 52.40, 19.05.

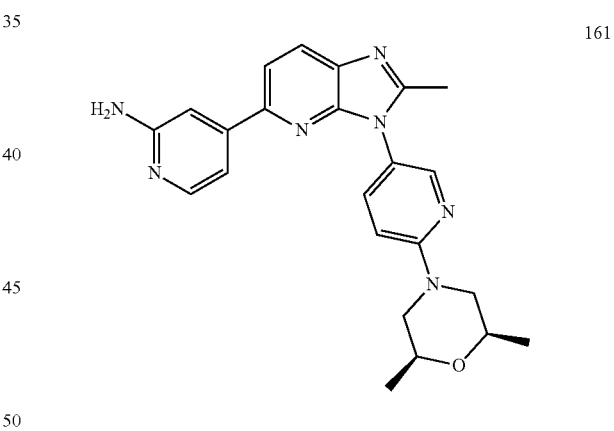

Compound 161 was synthesized in a similar manner as depicted in Scheme 47, using 6-((2S,6R)-2,6-dimethylmorpholino)pyridin-3-amine 161-B.

4-(3-(6-((2S,6R)-2,6-dimethylmorpholino)pyridin-3-yl)-2-methyl-3H-imidazo[4,5-b]pyridin-5-yl)pyridin-2-amine 161.

Purple semi-solid (12 mg, 0.029 mmol, 13% yield, 9% MeOH in DCM).

$^1$H NMR (CDCl$_3$) δ: 8.29 (d, J=2.7 Hz, 1H), 8.14 (d, J=5.4 Hz, 1H), 8.06 (d, J=8.2 Hz, 1H), 7.73 (d, J=8.3 Hz, 1H), 7.61 (dd, J=9.0, 2.7 Hz, 1H), 7.24 (dd, J=5.4, 1.5 Hz, 1H), 7.16 (s, 1H), 6.84 (d, J=9.1 Hz, 1H), 4.53 (s, 2H), 4.24-4.15 (m, 2H), 3.87-3.74 (m, 2H), 2.75-2.64 (m, 2H), 2.61 (s, 3H), 1.36-1.33 (m, 6H). $^{13}$C NMR (CDCl$_3$) δ: 159.06, 158.62, 154.69, 149.33, 149.29, 148.57, 148.45, 146.33, 136.47, 135.08, 126.92, 121.34, 116.25, 112.13, 106.83, 106.05, 71.60, 50.59, 19.00, 15.17.

Scheme 50

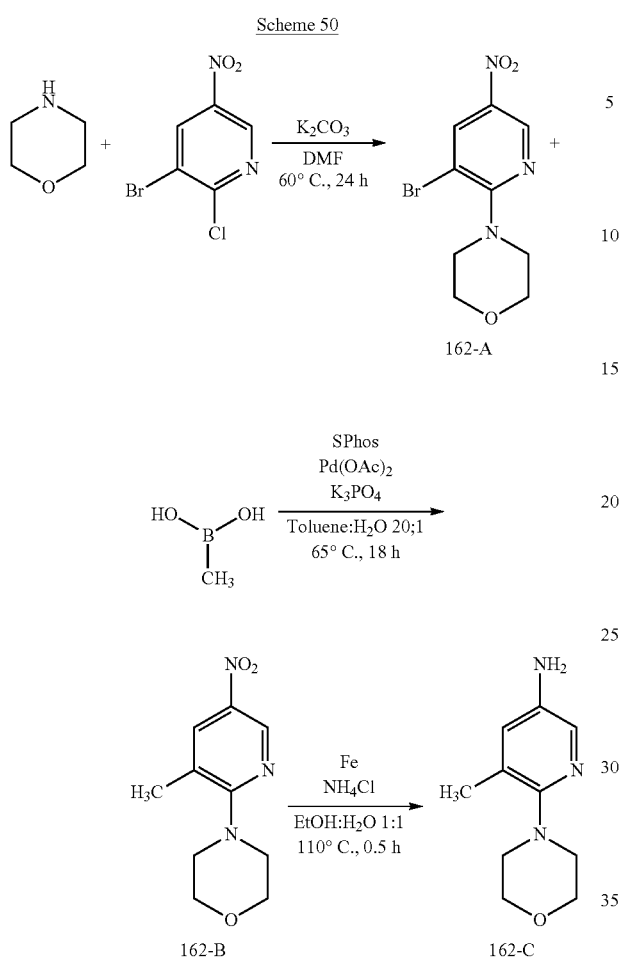

Scheme 50, Step 1

In a 2-5 mL Biotage© microwave vial, a stir bar, K₂CO₃ (1.314 g, 9.5 mmol), DMF (4.75 mL), 3-bromo-2-chloro-5-nitropyridine (1 g, 4.75 mmol), were added, the vial sealed, and purged with Ar for 15 min. Morpholine (0.538 mL, 6.18 mmol), was injected into the vial and the mixture was heated at 60° C. for 24 h. Upon cooling, the mixture is transferred to a separatory funnel, H₂O was added, and the aq layer was extracted with ethyl acetate and the pooled organics were washed with saturated brine and dried with Na₂SO₄. The solvent was evaporated and the residue triturated with hexanes and filtered, affording 4-(3-bromo-5-nitropyridin-2-yl)morpholine 162-A as an Orange solid (2.73 g, 9.48 mmol, 90% yield). $^1$H NMR (CDCl₃) δ: 9.03 (s, 1H), 8.54 (s, 1H), 3.90-3.82 (m, 4H), 3.75-3.68 (m, 4H). $^{13}$C NMR (CDCl₃) δ: 160.99, 142.86, 138.08, 137.85, 106.77, 66.63, 49.37.

Scheme 50, Step 2

In a 20 mL Biotage© microwave vial, a stir bar, Pd(OAc)₂ (28.1 mg, 0.125 mmol), SPhos (103 mg, 0.25 mmol), 4-(3-bromo-5-nitropyridin-2-yl)morpholine 162-A (884 mg, 4.17 mmol), K₃PO₄ (884 mg, 4.17 mmol), and methylboronic acid (162 mg, 2.71 mmol), were added. The vial was sealed, Toluene:H₂O (6.61 mL:0.33 mL, 20:1 v/v) was injected, the vial degassed with Ar for 15 min, and heated at 65° C. for 18 h in an oil bath. Upon cooling, the mixture was diluted with EtOAc, filtered through celite, transferred to a separatory funnel and 10% NaOH was added. The aq layer was extracted with ethyl acetate and the pooled organics were washed with brine and dried with Na₂SO₄. Solvent was concentrated, redissolved in DCM, dryloaded onto silica and chromatographed on a 12 g silica column, (DCM/MeOH, 0-2%), affording 4-(3-methyl-5-nitropyridin-2-yl)morpholine 162-B as a red semi-solid (410 mg, 1.837 mmol, 88% yield, 2% MeOH in DCM). $^1$H NMR (CDCl₃) δ: 8.96 (d, J=2.6 Hz, 1H), 8.13 (dd, J=2.7, 1.0 Hz, 1H), 3.89-3.79 (m, 4H), 3.51-3.44 (m, 4H), 2.37 (s, 3H). $^{13}$C NMR (CDCl₃) δ: 163.90, 142.23, 138.38, 134.57, 121.93, 66.78, 49.20, 19.76.

Scheme 50, Step 3

In a 20 mL Biotage© microwave vial, a stir bar, 4-(3-methyl-5-nitropyridin-2-yl)morpholine 162-B (410 mg, 1.837 mmol), iron (513 mg, 9.18 mmol), and ammonium chloride (196 mg, 3.67 mmol), were added. The vial was sealed, degassed with Ar for 15 min, and degassed EtOH:H₂O (4.592 mL:4.592 mL, 1:1 v/v) injected. The mixture was heated for 0.5 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed with brine, dried with Na₂SO₄. Solvent was concentrated, redissolved in DCM, dryloaded onto silica and chromatographed on a 12 g silica column, (DCM/MeOH, 0-5%), affording 5-methyl-6-morpholinopyridin-3-amine 162-C as a red semi-solid (90 mg, 0.466 mmol, 25% yield, 5% MeOH in DCM). $^1$H NMR (CDCl₃) δ: 7.67 (d, J=2.8 Hz, 1H), 6.83 (d, J=2.8 Hz, 1H), 3.86-3.78 (m, 4H), 3.49 (bs, 2H), 3.03-2.96 (m, 4H), 2.22 (s, 3H). $^{13}$C NMR (CDCl₃) δ: 154.34, 138.62, 132.29, 126.73, 126.23, 67.31, 50.75, 17.65.

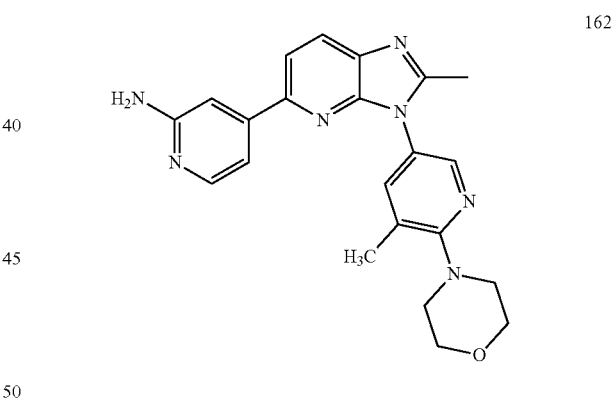

Compound 162 was synthesized in a similar manner as depicted in Scheme 47, using 5-methyl-6-morpholinopyridin-3-amine 162-C.

4-(2-methyl-3-(5-methyl-6-morpholinopyridin-3-yl)-3H-imidazo[4,5-b]pyridin-5-yl)pyridin-2-amine 162.

Red semi-solid (31 mg, 0.077 mmol, 28% yield, 8% MeOH in DCM).

$^1$H NMR (CDCl₃) δ: 8.30 (d, J=2.5 Hz, 1H), 8.12 (d, J=5.4 Hz, 1H), 8.06 (d, J=8.3 Hz, 1H), 7.72 (d, J=8.3 Hz, 1H), 7.54 (d, J=2.5 Hz, 1H), 7.21 (dd, J=5.4, 1.5 Hz, 1H), 7.12 (s, 1H), 4.57 (s, 2H), 3.96-3.89 (m, 4H), 3.35-3.26 (m, 4H), 2.60 (s, 3H), 2.42 (s, 3H). $^{13}$C NMR (CDCl₃) δ: 161.24, 159.08, 154.38, 149.50, 149.16, 148.59, 148.39, 143.47, 138.04, 135.06, 127.03, 125.75, 125.37, 116.44, 112.12, 106.08, 67.06, 49.93, 18.80, 15.28.

Scheme 51

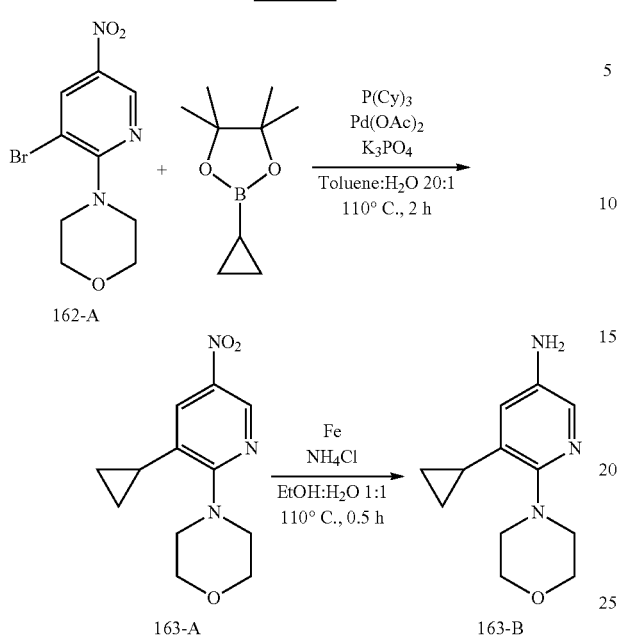

Scheme 51, Step 1

In a 20 mL Biotage© microwave vial, a stir bar, Pd(OAc)₂ (23.38 mg, 0.104 mmol), tricyclohexylphosphine (P(Cy)₃) (58 mg, 0.208 mmol), 4-(3-bromo-5-nitropyridin-2-yl)morpholine 162-A (600 mg, 2.083 mmol), K₃PO₄ (1.591 g, 7.5 mmol), and 2-cyclopropyl-4,4,5,5-tetramethyl-1,3,2-dioxaborolane (455 mg, 2.71 mmol), were added. The vial was sealed, Toluene:H₂O (6.6 mL:0.33 mL, 20:1 v/v) was injected, the vial degassed with Ar for 15 min, and heated for 2 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed 2× with sat. brine, dried with Na₂SO₄. Solvent was concentrated, redissolved in DCM, dryloaded onto silica and chromatographed on a 12 g silica column, (DCM/MeOH, 0-1%), affording 4-(3-cyclopropyl-5-nitropyridin-2-yl)morpholine 163-A as an orange solid (186 mg, 0.748 mmol, 36% yield, 1% MeOH in DCM). ¹H NMR (CDCl₃) δ: 8.93 (d, J=2.6 Hz, 1H), 7.95 (d, J=2.6 Hz, 1H), 3.91-3.85 (m, 4H), 3.71-3.65 (m, 4H), 1.98-1.83 (m, 1H), 1.20-1.07 (m, 2H), 0.93-0.79 (m, 2H).

Scheme 51, Step 2

In a 20 mL Biotage© microwave vial, a stir bar, 4-(3-cyclopropyl-5-nitropyridin-2-yl)morpholine 163-A (233 mg, 0.748 mmol), iron (209 mg, 3.74 mmol), and ammonium chloride (80 mg, 1.496 mmol), were added. The vial was sealed, degassed with Ar for 15 min, and degassed EtOH:H₂O (1.87 mL:1.87 mL, 1:1 v/v) injected. The mixture was heated for 0.5 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na₂SO₄. Solvent was concentrated, redissolved in DCM, dryloaded onto silica and chromatographed on a 12 g silica column, (DCM/MeOH, 0-5%), affording 5-cyclopropyl-6-morpholinopyridin-3-amine 163-B as a purple oil (105 mg, 0.479 mmol, 64% yield, 5% MeOH in DCM). ¹H NMR (CDCl₃) δ: 7.67 (d, J=2.8 Hz, 1H), 6.48 (d, J=2.8 Hz, 1H), 3.91-3.84 (m, 4H), 3.43 (bs, 2H), 3.19-3.12 (m, 4H), 2.20-2.11 (m, 1H), 1.07-0.96 (m, 2H), 0.74-0.65 (m, 2H). ¹³C NMR (CDCl₃) δ: 154.77, 138.52, 131.65, 131.56, 119.87, 67.39, 51.04, 10.77, 9.26.

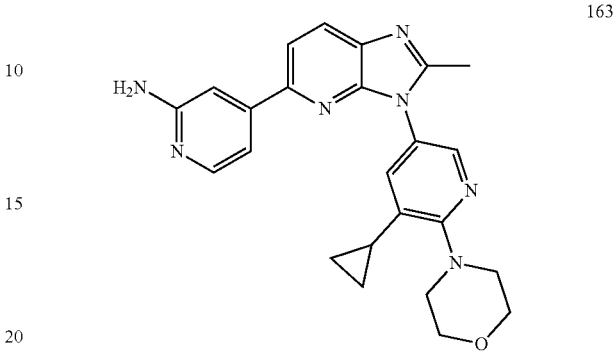

Compound 163 was synthesized in a similar manner as depicted in Scheme 47, using 5-cyclopropyl-6-morpholinopyridin-3-amine 163-B.

4-(3-(5-cyclopropyl-6-morpholinopyridin-3-yl)-2-methyl-3H-imidazo[4,5-b]pyridin-5-yl)pyridin-2-amine 163.

Red semi-solid (7 mg, 0.016 mmol, 7% yield, 7.5% MeOH in DCM).

¹H NMR (CDCl₃) δ: 8.26 (d, J=2.5 Hz, 1H), 8.15 (d, J=5.4 Hz, 1H), 8.07 (d, J=8.3 Hz, 1H), 7.74 (d, J=8.3 Hz, 1H), 7.32 (d, J=2.6 Hz, 1H), 7.24 (dd, J=5.4, 1.5 Hz, 1H), 7.15 (s, 1H), 4.51 (s, 2H), 4.00-3.94 (m, 4H), 3.53-3.46 (m, 4H), 2.63 (s, 3H), 2.21-2.09 (m, 1H), 1.22-1.12 (m, 2H), 0.89-0.81 (m, 2H).

Scheme 52

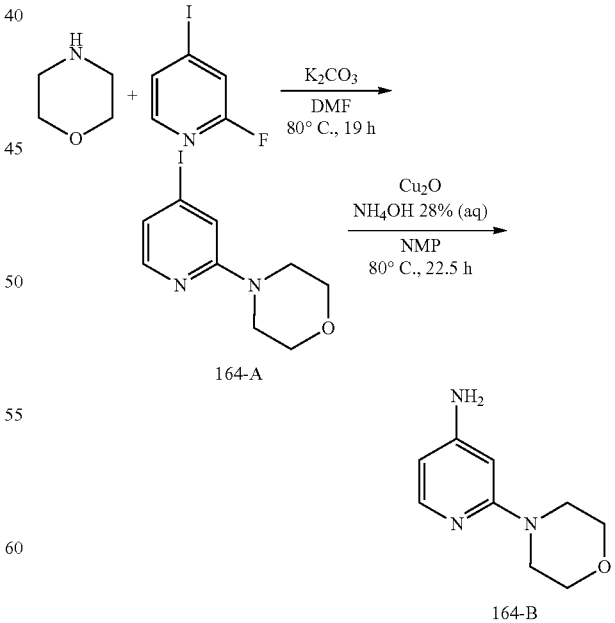

Scheme 52, Step 1

In a 5 mL Biotage© microwave vial, a stir bar, K₂CO₃ (954 mg, 6.91 mmol), 2-fluoro-4-iodopyridine (700 mg, 3.14 mmol), and DMF (3.139 mL) were added, the vial sealed, and purged with Ar for 15 min. Morpholine (0.328 mL, 3.77 mmol), was injected into the vial and heated at 80° C. for 19 h. Upon cooling, the mixture is poured into 100 mL H$_2$O, filtered, thoroughly washed with H$_2$O, and then hexanes, affording 4-(4-iodopyridin-2-yl)morpholine 164-A as a white solid (300 mg, 1.034 mmol, 33% yield). $^1$H NMR (CDCl$_3$) δ: 7.85 (d, J=5.1 Hz, 1H), 7.04-6.97 (m, 2H), 3.84-3.78 (m, 4H), 3.54-3.46 (m, 4H). $^{13}$C NMR (CDCl$_3$) δ: 159.69, 148.24, 122.51, 115.95, 106.67, 66.61, 45.33.

Scheme 52, Step 2

In a 20 mL Biotage© microwave vial, a stir bar, N-Methyl-2-pyrrolidone (1.26 mL), 4-(4-iodopyridin-2-yl)morpholine 164-A (280 mg, 0.965 mmol), 28% NH$_4$OH (1.745 mL 12.55 mmol) were added followed by Cu$_2$O (11.05 mg, 0.077 mmol). The vial was sealed and heated at 80° C. for 22.5 h. Upon cooling, the mixture is diluted with brine, ether and poured into separatory funnel and extracted with diethyl ether multiple times. The pooled ether layers were washed with H$_2$O, brine, then dried with Na$_2$SO$_4$, concentrated, and triturated with hexanes, affording 2-morpholinopyridin-4-amine 164B as a tan solid (49 mg, 0.273 mmol, 28% yield). $^1$H NMR (CDCl$_3$) δ: 7.89 (d, J=5.6 Hz, 1H), 6.04 (dd, J=5.6, 1.9 Hz, 1H), 5.85 (s, 1H), 4.08 (bs, 2H), 3.85-3.77 (m, 4H), 3.47-3.40 (m, 4H). $^{13}$C NMR (CDCl$_3$) δ: 161.13, 154.32, 148.55, 102.49, 91.37, 66.81, 45.86.

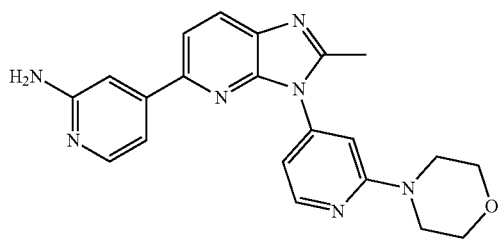

164

Compound 164 was synthesized in a similar manner as depicted in Scheme 47, using 2-morpholinopyridin-4-amine 164-B.

4-(2-methyl-3-(2-morpholinopyridin-4-yl)-3H-imidazo[4,5-b]pyridin-5-yl)pyridin-2-amine 164.

Green semi-solid (6 mg, 0.015 mmol, 7% yield, 9% MeOH in DCM).

$^1$H NMR (CDCl$_3$) δ: 8.44 (d, J=6.0 Hz, 1H), 8.16 (d, J=5.4 Hz, 1H), 8.08 (d, J=8.3 Hz, 1H), 7.77 (d, J=8.3 Hz, 1H), 7.26 (dd, J=5.4, 1.5 Hz, 1H), 7.17 (s, 1H), 6.85-6.78 (m, 2H), 4.56 (s, 2H), 3.93-3.86 (m, 4H), 3.67-3.60 (m, 4H), 2.70 (s, 3H).

Scheme 53

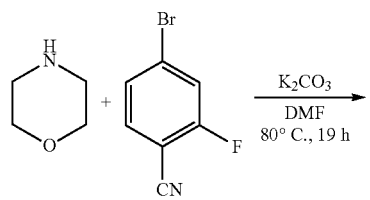

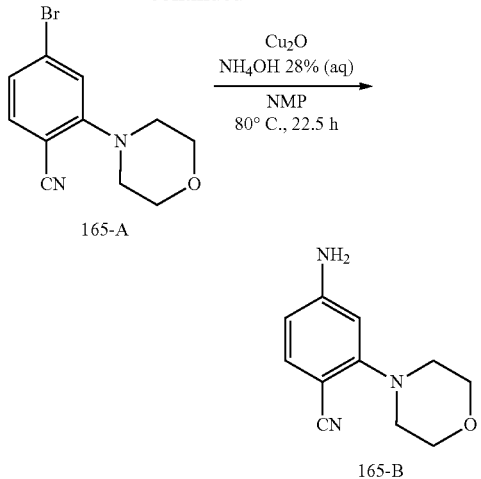

Scheme 53, Step 1

In a 5 mL Biotage© microwave vial, a stir bar, K$_2$CO$_3$ (1.064 g, 7.7 mmol), 4-bromo-2-fluorobenzonitrile (700 mg, 3.5 mmol), and DMF (3.5 mL) were added, the vial sealed, and purged with Ar for 15 min. Morpholine (0.366 mL, 4.2 mmol), was injected into the vial and heated at 80° C. for 19 h. Upon cooling, the mixture is poured into 100 mL H$_2$O, filtered, thoroughly washed with H$_2$O, and then hexanes, affording 4-bromo-2-morpholinobenzonitrile 165-A as a tan solid (760 mg, 2.85 mmol, 81% yield). $^1$H NMR (CDCl$_3$) δ: 7.44 (d, J=8.2 Hz, 1H), 7.19 (dd, J=8.2, 1.8 Hz, 1H), 7.15 (d, J=1.8 Hz, 1H), 3.95-3.88 (m, 4H), 3.28-3.21 (m, 4H). $^{13}$C NMR (CDCl$_3$) δ: 156.13, 135.28, 128.81, 125.18, 122.07, 117.71, 104.43, 66.73, 51.55.

Scheme 53, Step 2

In a 20 mL Biotage© microwave vial, a stir bar, N-Methyl-2-pyrrolidone (3.276 mL), 4-bromo-2-morpholinobenzonitrile 165-A (700 mg, 2.62 mmol), 28% NH$_4$OH (4.738 mL, 34.1 mmol) were added followed by Cu$_2$O (37.5 mg, 0.262 mmol). The vial was sealed and heated at 80° C. for 22.5 h. Upon cooling, the mixture is diluted with brine, ether and poured into separatory funnel and extracted with diethyl ether multiple times. The pooled ether layers were washed with H$_2$O, brine, then dried with Na$_2$SO$_4$, concentrated, and triturated with hexanes, affording 4-amino-2-morpholinobenzonitrile 165-B as a tan solid (280 mg, 1.378 mmol, 53% yield).

$^1$H NMR (CDCl$_3$) δ: 7.34 (d, J=8.3 Hz, 1H), 6.29 (dd, J=8.3, 2.1 Hz, 1H), 6.20 (d, J=2.1 Hz, 1H), 4.17 (bs, 2H), 3.93-3.85 (m, 4H), 3.21-3.14 (m, 4H). $^{13}$C NMR (CDCl$_3$) δ: 157.30, 151.58, 135.84, 119.59, 108.36, 103.58, 94.31, 66.95, 51.72.

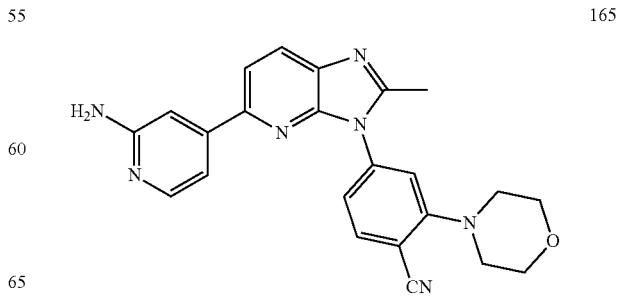

165

Compound 165 was synthesized in a similar manner as depicted in Scheme 56, using 4-amino-2-morpholinobenzonitrile 165-B, affording 4-(5-(2-aminopyridin-4-yl)-2-methyl-3H-imidazo[4,5-b]pyridin-3-yl)-2-morpholinobenzonitrile as a red oil (17 mg, 0.041 mmol, 15% yield, 8% MeOH in DCM). $^1$H NMR (CDCl$_3$) δ: 8.15 (d, J=5.4 Hz, 1H), 8.09 (d, J=8.3 Hz, 1H), 7.83 (d, J=8.0 Hz, 1H), 7.77 (d, J=8.3 Hz, 1H), 7.27-7.17 (m, 3H), 7.13 (s, 1H), 4.58 (bs, 2H), 4.00-3.92 (m, 4H), 3.37-3.31 (m, 4H), 2.68 (s, 3H). $^{13}$C NMR (CDCl$_3$) δ: 159.11, 156.35, 153.29, 149.57, 148.72, 148.44, 148.13, 139.41, 135.62, 135.10, 127.36, 120.10, 117.58, 117.42, 116.70, 111.92, 105.81, 105.46, 66.73, 51.69, 15.67.

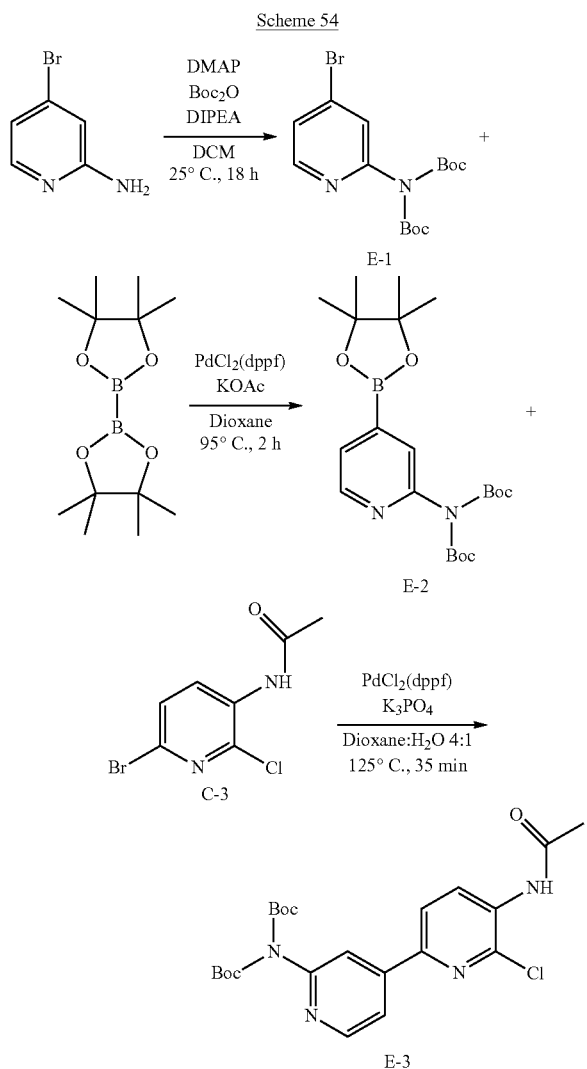

E-1

E-2

C-3

E-3

Scheme 54, Step 1

A 500 mL round bottom flask was loaded with a stir bar, 4-bromopyridin-2-amine (5 g, 28.9 mmol), DMAP (353 mg, 2.89 mmol) and DCM (38.5 mL). Warmed Boc$_2$O (14.76 mL, 63.6 mmol) was added dropwise followed by DIPEA (11.61 mL, 66.5 mmol) and the mixture is stirred at 25° C. for 18 h. Solvent is evaporated and a mixture of 5:1 Et$_2$O:hexanes are added, and the mono-boc intermediate is filtered. The filtrate is concentrated, dryloaded onto silica gel and purified on a 40 g silica gel column (DCM/MeOH, 0-10%), affording Compound E-1 as a white solid (6.38 g, 17.09 mmol, 59% yield, 100% DCM). $^1$H NMR (DMSO) δ: 8.35 (d, J=5.3 Hz, 1H), 7.78 (d, J=1.7 Hz, 1H), 7.62 (dd, J=5.4, 1.7 Hz, 1H), 1.42 (s, 18H). $^{13}$C NMR (DMSO) δ: 153.09, 150.87, 149.85, 133.21, 125.95, 124.67, 83.41, 27.88.

Scheme 54, Step 2

A 20 mL Biotage© microwave vial loaded with Compound E-1 (1.75 g, 4.69 mmol), 4,4,4',4',5,5,5',5'-octamethyl-2,2'-bi(1,3,2-dioxaborolane) (1.786 g, 7.03 mmol), PdCl$_2$(dppf) (0.344 g, 0.469 mmol), and KOAc, (1.472 g, 15.0 mmol) was capped, purged with argon, then injected with degassed dioxane (10.42 mL), and heated to 95° C. for 2 h in an oil bath. (Note: two reaction vials of above were ran and purified together). The reaction was cooled, diluted with EtOAC, poured into a separatory funnel containing EtOAc, saturated ammonium chloride solution, the mixture was shaken, and filtered through celite. After multiple extractions with EtOAc, the organics were washed with saturated ammonium chloride solution and brine. After concentration, the mixture was dissolved in hexanes and then heated/cooled repeatedly with hexanes and filtered to remove the dppf ligand impurity. The hexane soluble filtrate is evaporated, affording the product Compound E-2 as a clear viscous semi-solid (3 g, 7.14 mmol, 76% yield). $^1$H NMR (CDCl$_3$) δ: 8.42 (d, J=4.7 Hz, 1H), 7.49 (s, 1H), 7.47 (d, J=4.7 Hz, 1H), 1.37 (s, 18H), 1.27 (s, 12H).

Scheme 54, Step 3

A 20 mL Biotage© microwave vial loaded with N-(6-bromo-2-chloropyridin-3-yl)acetamide C-3 (499 mg, 2.00 mmol), E-2 (883 mg, 2.1 mmol), PdCl$_2$(dppf) (161 mg, 0.220 mmol), and K$_3$PO$_4$, (1.104 g, 5.2 mmol) was capped, purged with argon, then injected with degassed dioxane:H$_2$O (6.4 mL:1.6 mL, 4:1 v/v), and heated to 125° C. for 35 min in an oil bath. The reaction was cooled, diluted with DCM, filtered through celite, concentrated, dryloaded onto silica gel and purified on a 24 g silica gel column (DCM/MeOH, 0-8%), affording Compound E-3 as a tan solid (540 mg, 1.166 mmol, 58% yield, 8% MeOH in DCM). $^1$H NMR (CDCl$_3$) δ: 8.70 (dd, J=8.7, 5.2 Hz, 1H), 8.56-8.47 (m, 1H), 7.95 (s, 1H), 7.81 (s, 1H), 7.75-7.60 (m, 2H), 2.29-2.16 (m, 3H), 1.56-1.39 (m, 18H).

Scheme 55

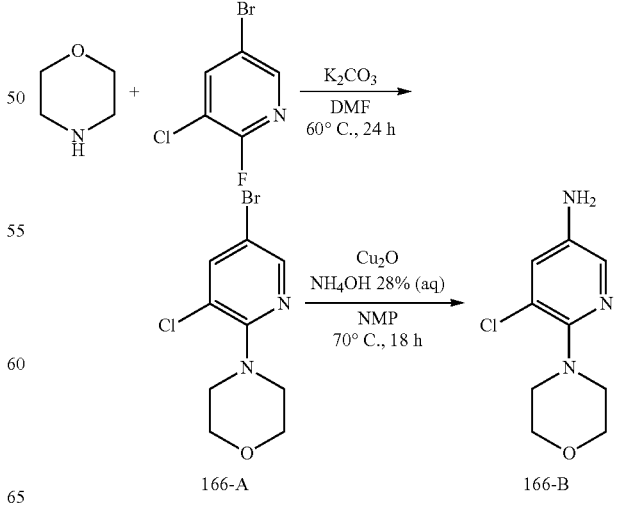

166-A

166-B

Scheme 55, Step 1

In a 5 mL Biotage© microwave vial, a stir bar, K₂CO₃ (1.314 g, 9.50 mmol), 5-bromo-3-chloro-2-fluoropyridine (1 g, 4.75 mmol), DMF (4.75 mL) were added, the vial sealed, and purged with Ar for 15 min. Morpholine (0.538 mL, 6.18 mmol), was injected into the vial and heated at 60° C. for 24 h. Upon cooling, the mixture is transferred to a separatory funnel, H₂O was added, and the aq layer was extracted with diethyl ether and the pooled organics were washed with saturated brine and dried with Na₂SO₄. The solvent was evaporated and the residue triturated with hot hexanes, cooled, and filtered, affording 4-(5-bromo-3-chloropyridin-2-yl)morpholine 166-A as a white solid (700 mg, 2.52 mmol, 53% yield). $^1$H NMR (CDCl₃) δ: 8.22 (d, J=2.2 Hz, 1H), 7.73 (d, J=2.2 Hz, 1H), 3.89-3.81 (m, 4H), 3.37-3.33 (m, 4H). $^{13}$C NMR (CDCl₃) δ: 156.86, 146.56, 140.76, 122.80, 111.87, 66.75, 49.38.

Scheme 55, Step 2

In a 20 mL Biotage© microwave vial, a stir bar, N-Methyl-2-pyrrolidone (3.6 mL), 4-(5-bromo-3-chloropyridin-2-yl)morpholine 166-A, 28% NH₄OH (3.908 mL, 28.1 mmol) were added followed by Cu₂O (30.9 mg, 0.216 mmol). The vial was sealed and heated at 70° C. for 18 h. Upon cooling, the mixture is diluted with brine, ether and poured into separatory funnel and extracted with diethyl ether multiple times. The pooled ether layers were washed with H₂O, brine, then dried with Na₂SO₄. The solvent was evaporated and the residue triturated with hot hexanes, cooled, and filtered, affording 5-chloro-6-morpholinopyridin-3-amine 166-B as a white solid (340 mg, 1.591 mmol, 74% yield). $^1$H NMR (CDCl₃) δ: 7.74 (d, J=2.7 Hz, 1H), 7.06 (d, J=2.7 Hz, 1H), 3.90-3.82 (m, 4H), 3.56 (s, 2H), 3.22-3.15 (m, 4H). $^{13}$C NMR (CDCl₃) δ: 151.14, 138.93, 132.90, 125.74, 123.94, 67.06, 50.21.

Scheme 56

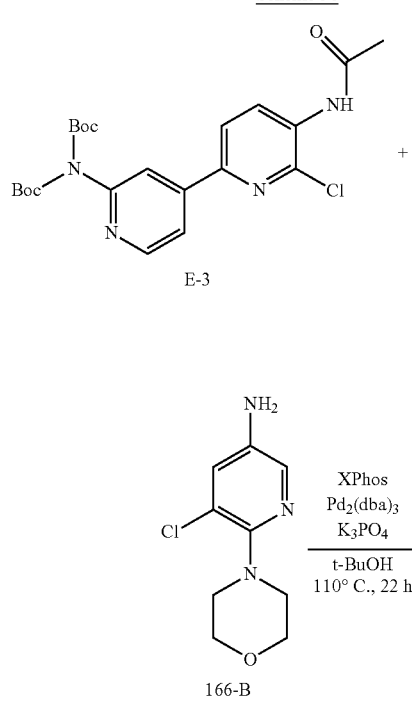

A 2-5 mL Biotage© microwave vial loaded with Pd₂(dba)₃ (5.93 mg, 0.00648 mmol), XPhos (9.27 mg, 0.019 mmol), and t-BuOH (0.72 mL) was capped, purged with argon, heated to 110° C. for 1 minute in an oil bath and cooled. The vial was uncapped, a mixture of E-3 (100 mg, 0.216 mmol), 5-chloro-6-morpholinopyridin-3-amine 166-B (50.8 mg, 0.238 mmol), and K₃PO₄ (151 mg, 0.713 mmol), added, the vial sealed and heated to 110° C. for 22 h in an oil bath. The reaction was cooled, 37% conc. HCl (0.7 mL, 50 equiv.) was added, stirred for 1 h and basified with 10% NaOH. The mixture was extracted with ethyl acetate, washed with 10% NaOH, H₂O, brine, and the organic layer was dried over Na₂SO₄, concentrated, dryloaded onto silica gel and purified on a 12 g silica gel column (DCM/MeOH, 0-7%), affording 4-(3-(5-chloro-6-morpholinopyridin-3-yl)-2-methyl-3H-imidazo[4,5-b]pyridin-5-yl)pyridin-2-amine 166 as a white solid (19 mg, 0.045 mmol, 21% yield, 7% MeOH in DCM). $^1$H NMR (CDCl₃) δ: 8.35 (d, J=2.4 Hz, 1H), 8.15 (dd, J=5.4, 0.8 Hz, 1H), 8.08 (d, J=8.3 Hz, 1H), 7.80 (d, J=2.3 Hz, 1H), 7.75 (d, J=8.3 Hz, 1H), 7.23 (dd, J=5.4, 1.5 Hz, 1H), 7.14 (s, 1H), 4.55 (s, 2H), 3.97-3.90 (m, 4H), 3.59-3.52 (m, 4H), 2.64 (s, 3H). $^{13}$C NMR (CDCl₃) δ: 159.08, 157.77, 153.97, 149.71, 148.95, 148.71, 148.18, 143.92, 137.63, 135.00, 127.27, 125.29, 121.95, 116.68, 112.09, 106.01, 66.86, 49.39, 15.27.

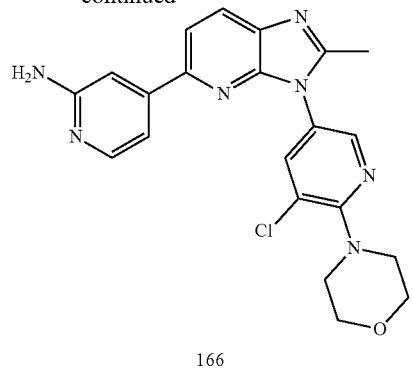

166

Scheme 57

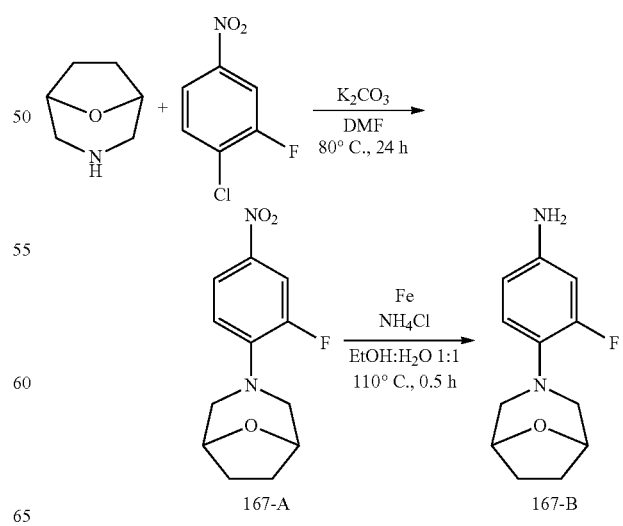

Scheme 57, Step 1

In a 5 mL Biotage© microwave vial, a stir bar, K₂CO₃ (1.386 mg, 10.03 mmol), 1-chloro-2-fluoro-4-nitrobenzene (587 mg, 3.34 mmol), and 8-oxa-3-azabicyclo[3.2.1]octane hydrochloride (500 mg, 3.34 mmol), were added, the vial sealed, and purged with Ar for 15 min. DMF (3.34 mL) was injected into the vial and heated at 80° C. for 24 h. Upon cooling, the mixture is transferred to a separatory funnel, H₂O was added, and the aq layer was extracted with diethyl ether and the pooled organics were washed with saturated brine and dried with Na₂SO₄. The solvent was evaporated and the residue triturated with hot hexanes, cooled, and filtered, affording 3-(2-fluoro-4-nitrophenyl)-8-oxa-3-azabicyclo[3.2.1]octane 167-A as an orange solid (330 mg, 1.308 mmol, 39% yield). ¹H NMR (CDCl₃) δ: 7.98 (dd, J=9.0, 2.6 Hz, 1H), 7.90 (dd, J=13.6, 2.6 Hz, 1H), 6.85 (t, J=8.8 Hz, 1H), 4.51-4.44 (m, 2H), 3.39 (d, J=10.8 Hz, 2H), 3.23 (d, J=10.8 Hz, 2H), 2.06-2.02 (m, 4H).

Scheme 57, Step 2

In a 20 mL Biotage© microwave vial, a stir bar, 3-(2-fluoro-4-nitrophenyl)-8-oxa-3-azabicyclo[3.2.1]octane 167-A (330 mg, 1.308 mmol), iron (365 mg, 6.54 mmol), and ammonium chloride (140 mg, 2.62 mmol), were added. The vial was sealed, degassed with Ar for 15 min, and degassed EtOH:H₂O (3.27 mL:3.27 mL, 1:1 v/v) injected. The mixture was heated for 0.5 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na₂SO₄. Solvent was concentrated, redissolved in DCM, dryloaded onto silica and chromatographed on a 12 g silica column, (DCM/MeOH, 0-5%), affording 4-(8-oxa-3-azabicyclo[3.2.1]octan-3-yl)-3-fluoroaniline 167-B as a pink solid (240 mg, 1.080 mmol, 83% yield, 5% MeOH in DCM). ¹H NMR (CDCl₃) δ: 6.78-6.69 (m, 1H), 6.46-6.37 (m, 2H), 4.45-4.35 (m, 2H), 3.55 (s, 2H), 3.06-2.89 (m, 4H), 2.20-2.09 (m, 2H), 2.00-1.91 (m, 2H).

167

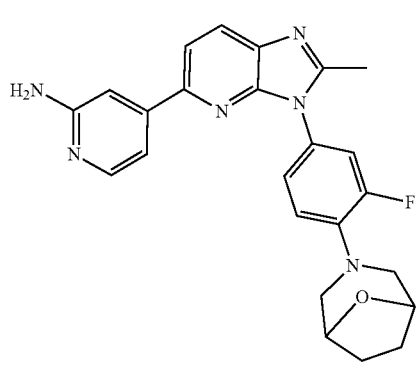

Compound 167 was synthesized in a similar manner as depicted in Scheme 56, using 4-(8-oxa-3-azabicyclo[3.2.1]octan-3-yl)-3-fluoroaniline 167-B.

4-(3-(4-(8-oxa-3-azabicyclo[3.2.1]octan-3-yl)-3-fluorophenyl)-2-methyl-3H-imidazo[4,5-b]pyridin-5-yl)pyridin-2-amine 167.

Tan solid (30 mg, 0.070 mmol, 32% yield, 9% MeOH in DCM).

¹H NMR (CDCl₃) δ: 8.15 (d, J=5.5 Hz, 1H), 8.06 (d, J=8.2 Hz, 1H), 7.73 (d, J=8.3 Hz, 1H), 7.27-7.13 (m, 4H), 7.05 (t, J=9.1 Hz, 1H), 4.54-4.46 (m, 4H), 3.30 (d, J=11.1 Hz, 2H), 3.20 (d, J=11.4 Hz, 2H), 2.61 (s, 3H), 2.22-2.13 (m, 2H), 2.08-2.00 (m, 2H).

Scheme 58

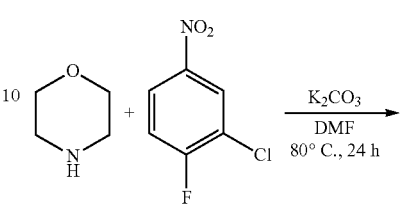

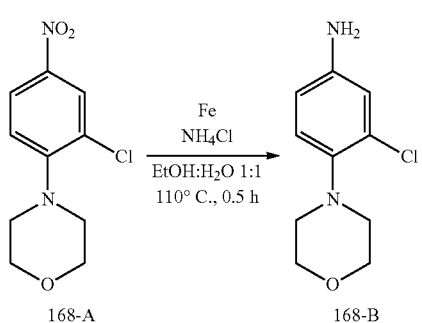

Scheme 58, Step 1

In a 20 mL Biotage© microwave vial, a stir bar, K₂CO₃ (1.212 g, 8.77 mmol), 2-chloro-1-fluoro-4-nitrobenzene (700 mg, 3.99 mmol), DMF (4 mL) were added, the vial sealed, and purged with Ar for 15 min. Morpholine (0.417 mL, 4.79 mmol), was injected into the vial and the mixture was heated at 80° C. for 24 h. Upon cooling, the mixture is poured into H₂O, filtered, thoroughly washed with H₂O, and then hexanes, affording 4-(2-chloro-4-nitrophenyl)morpholine 168-A as a yellow solid (750 mg, 3.09 mmol, 78% yield)

¹H NMR (CDCl₃) δ: 8.26 (s, 1H), 8.12 (dd, J=8.9, 2.7 Hz, 1H), 7.07 (d, J=8.9 Hz, 1H), 3.95-3.88 (m, 4H), 3.27-3.20 (m, 4H). ¹³C NMR (CDCl₃) δ: 154.53, 142.39, 127.64, 126.68, 123.45, 119.26, 66.72, 51.01.

Scheme 58, Step 2

In a 20 mL Biotage© microwave vial, a stir bar, 4-(2-chloro-4-nitrophenyl)morpholine 168-A (500 mg, 2.061 mmol), iron (575 mg, 10.30 mmol), and ammonium chloride (220 mg, 4.12 mmol), were added. The vial was sealed, degassed with Ar for 15 min, and degassed EtOH:H₂O (5.15 mL:5.15 mL, 1:1 v/v) injected. The mixture was heated for 0.5 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na₂SO₄. Solvent was concentrated, redissolved in DCM, dryloaded onto silica and chromatographed on a 12 g silica column, (DCM/MeOH, 0-5%), affording 3-chloro-4-morpholinoaniline 168-B as a pink solid (420 mg, 1.975 mmol, 96% yield, 5% MeOH). ¹H NMR (CDCl₃) δ: 6.89 (d, J=8.5 Hz, 1H), 6.74 (d, J=2.7 Hz, 1H), 6.56 (dd, J=8.5, 2.7 Hz, 1H), 3.90-3.82 (m, 4H), 3.61 (s, 2H), 2.98-2.91 (m, 4H). ¹³C NMR (CDCl₃) δ: 143.20, 140.65, 129.87, 121.31, 117.10, 114.17, 67.30, 52.28.

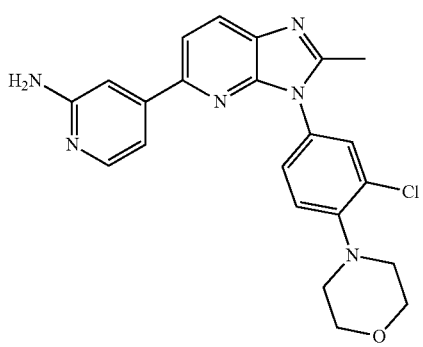

168

Compound 168 was synthesized in a similar manner as depicted in Scheme 56, using 3-chloro-4-morpholinoaniline 168-B.

4-(3-(3-chloro-4-morpholinophenyl)-2-methyl-3H-imidazo[4,5-b]pyridin-5-yl)pyridin-2-amine 168.

Red oil (7 mg, 0.017 mmol, 6% yield, 7% MeOH in DCM).

$^1$H NMR (CDCl$_3$) δ: 8.16-8.11 (m, 1H), 8.09-8.02 (m, 1H), 7.74 (dd, J=8.3, 5.7 Hz, 1H), 7.54 (d, J=2.4 Hz, 1H), 7.42-7.35 (m, 1H), 7.28-7.06 (m, 3H), 4.53 (s, 2H), 4.00-3.92 (m, 4H), 3.26-3.18 (m, 4H), 2.63 (s, 3H).

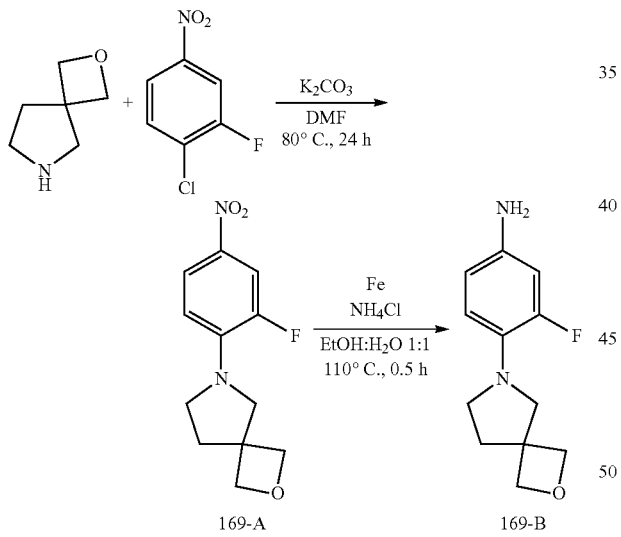

Scheme 59

Scheme 59, Step 1

In a 5 mL Biotage© microwave vial, a stir bar, K$_2$CO$_3$ (804 mg, 5.82 mmol), 1-chloro-2-fluoro-4-nitrobenzene (255 mg, 1.454 mmol), and 2-oxa-6-azaspiro[3.4]octane hemioxalate 169-A (460 mg, 1.454 mmol), were added, the vial sealed, and purged with Ar for 15 min. DMF (1.45 mL) was injected into the vial and heated at 80° C. for 24 h. Upon cooling, the mixture is transferred to a separatory funnel, H$_2$O was added, and the aq layer was extracted with diethyl ether and the pooled organics were washed with saturated brine and dried with Na$_2$SO$_4$. The solvent was evaporated and the residue triturated with hot hexanes, cooled, and filtered, affording 6-(2-fluoro-4-nitrophenyl)-2-oxa-6-azaspiro[3.4]octane 169-A as a yellow solid (280 mg, 1.110 mmol, 76% yield). $^1$H NMR (CDCl$_3$) δ: 7.93 (d, J=9.2 Hz, 1H), 7.86 (d, J=14.0 Hz, 1H), 6.54 (t, J=8.9 Hz, 1H), 4.73 (d, J=6.0 Hz, 2H), 4.67 (d, J=6.0 Hz, 2H), 3.85 (d, J=3.1 Hz, 2H), 3.65-3.58 (m, 1H), 3.52 (t, J=8.8 Hz, 1H), 2.36-2.29 (m, 2H).

Scheme 59, Step 2

In a 20 mL Biotage© microwave vial, a stir bar, 6-(2-fluoro-4-nitrophenyl)-2-oxa-6-azaspiro[3.4]octane 169-A (220 mg, 0.872 mmol), iron (244 mg, 4.36 mmol), and ammonium chloride (93 mg, 1.744 mmol), were added. The vial was sealed, degassed with Ar for 15 min, and degassed EtOH:H$_2$O (2.18 mL:2.18 mL, 1:1 v/v) injected. The mixture was heated for 0.5 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na$_2$SO$_4$. Solvent was concentrated, redissolved in DCM, dryloaded onto silica and chromatographed on a 12 g silica column, (DCM/MeOH, 0-5%), affording 3-fluoro-4-(2-oxa-6-azaspiro[3.4]octan-6-yl)aniline 169-B as a grey solid (190 mg, 0.855 mmol, 98% yield, 5% MeOH). $^1$H NMR (CDCl$_3$) δ: 6.58 (t, J=8.8 Hz, 1H), 6.46 (dd, J=14.3, 2.6 Hz, 1H), 6.40 (dd, J=8.5, 2.6 Hz, 1H), 4.72 (d, J=6.0 Hz, 2H), 4.67 (d, J=6.0 Hz, 2H), 3.51 (d, J=1.7 Hz, 2H), 3.46 (bs, 2H), 3.26 (td, J=7.0, 1.7 Hz, 2H), 2.26 (t, J=7.0 Hz, 2H).

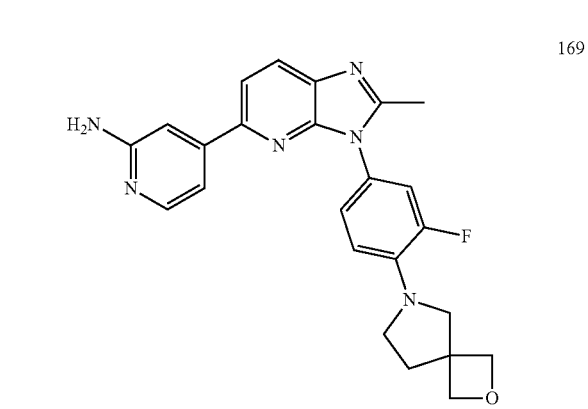 [SMILES: Cc1nc2ccc(-c3ccnc(N)c3)nc2n1-c1ccc(N2CCC3(COC3)C2)c(F)c1]

169

Compound 169 was synthesized in a similar manner as depicted in Scheme 56, using (3-fluoro-4-(2-oxa-6-azaspiro[3.4]octan-6-yl)aniline 169-B.

4-(3-(3-fluoro-4-(2-oxa-6-azaspiro[3.4]octan-6-yl)phenyl)-2-methyl-3H-imidazo[4,5-b]pyridin-5-yl)pyridin-2-amine 169.

Red semi-solid (20 mg, 0.046 mmol, 21% yield, 10% MeOH in DCM).

$^1$H NMR (CDCl$_3$) δ: 8.13 (d, J=5.4 Hz, 1H), 8.05 (d, J=8.2 Hz, 1H), 7.73 (d, J=8.3 Hz, 1H), 7.24 (dd, J=5.5, 1.5 Hz, 1H), 7.18-7.08 (m, 3H), 6.82 (t, J=9.0 Hz, 1H), 4.52 (s, 2H), 3.83 (s, 2H), 3.80 (d, J=1.9 Hz, 2H), 3.65 (td, J=7.1, 2.3 Hz, 2H), 3.50 (t, J=2.4 Hz, 2H), 2.60 (s, 3H), 2.05 (td, J=7.0, 1.7 Hz, 2H).

Scheme 60

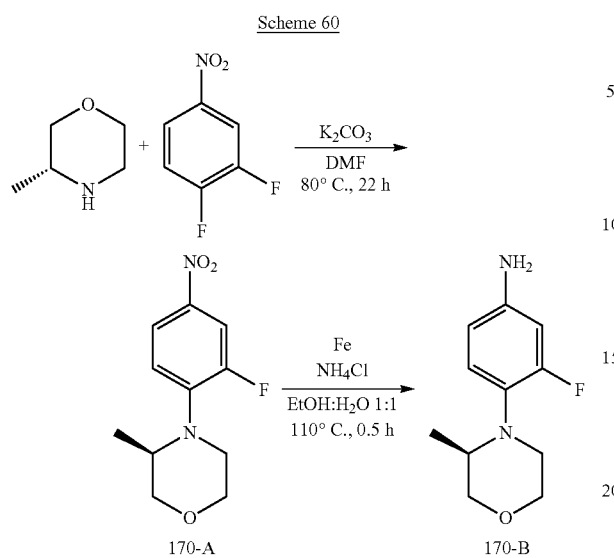

Scheme 60, Step 1

In a 5 mL Biotage© microwave vial, a stir bar, K₂CO₃ (1.096 g, 7.93 mmol), 1,2-difluoro-4-nitrobenzene (420 mg, 2.64 mmol), and (R)-3-methylmorpholine hydrochloride (400 mg, 2.91 mmol), were added, the vial sealed, and purged with Ar for 15 min. DMF (2.643 mL) was injected into the vial and heated at 80° C. for 22 h. Upon cooling, the mixture is poured into 100 mL H₂O, filtered, thoroughly washed with H₂O, and then hexanes. Upon cooling, the mixture is transferred to a separatory funnel, H₂O was added, and the aq layer was extracted with diethyl ether and the pooled organics were washed with saturated brine and dried with Na₂SO₄. The solvent was evaporated, affording (R)-4-(2-fluoro-4-nitrophenyl)-3-methylmorpholine 170A as a yellow oil (591 mg, 2.46 mmol, 93% yield). ¹H NMR (CDCl₃) δ: 7.79 (dd, J=9.1, 2.7 Hz, 1H), 7.68 (dd, J=13.5, 2.7 Hz, 1H), 6.81 (t, J=8.8 Hz, 1H), 3.90-3.72 (m, 3H), 3.66-3.51 (m, 2H), 3.42-3.30 (m, 1H), 3.00 (dt, J=12.4, 2.8 Hz, 1H), 1.08 (d, J=6.7 Hz, 3H).

Scheme 60, Step 2

In a 20 mL Biotage© microwave vial, a stir bar, (R)-4-(2-fluoro-4-nitrophenyl)-3-methylmorpholine 170-A (657 mg, 2.461 mmol), iron (687 mg, 12.31 mmol), and ammonium chloride (263 mg, 4.92 mmol), were added. The vial was sealed, degassed with Ar for 15 min, and degassed EtOH:H₂O (6.15 mL:6.15 mL, 1:1 v/v) injected. The mixture was heated for 0.5 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na₂SO₄. Solvent was concentrated, redissolved in DCM, dryloaded onto silica and chromatographed on a 12 g silica column, (DCM/MeOH, 0-5%), affording (R)-3-fluoro-4-(3-methylmorpholino)aniline 170B as a brown solid (510 mg, 2.123 mmol, 86% yield, 5% MeOH in DCM). ¹H NMR (CDCl₃) δ: 7.00-6.89 (m, 1H), 6.47-6.36 (m, 2H), 3.90-3.72 (m, 3H), 3.68 (bs, 2H), 3.44-3.34 (m, 1H), 3.29-3.16 (m, 1H), 3.00-2.95 (m, 2H), 0.85 (d, J=6.3 Hz, 3H).

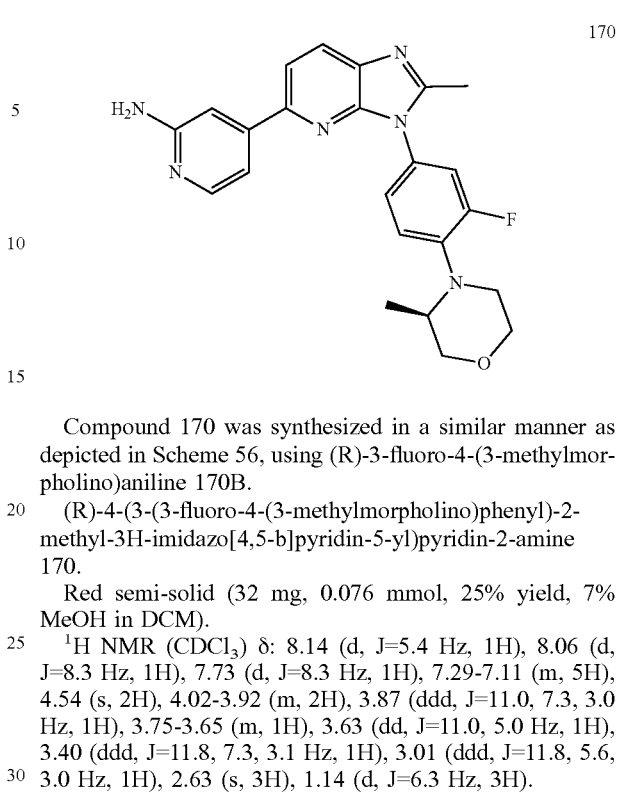

170

Compound 170 was synthesized in a similar manner as depicted in Scheme 56, using (R)-3-fluoro-4-(3-methylmorpholino)aniline 170B.

(R)-4-(3-(3-fluoro-4-(3-methylmorpholino)phenyl)-2-methyl-3H-imidazo[4,5-b]pyridin-5-yl)pyridin-2-amine 170.

Red semi-solid (32 mg, 0.076 mmol, 25% yield, 7% MeOH in DCM).

¹H NMR (CDCl₃) δ: 8.14 (d, J=5.4 Hz, 1H), 8.06 (d, J=8.3 Hz, 1H), 7.73 (d, J=8.3 Hz, 1H), 7.29-7.11 (m, 5H), 4.54 (s, 2H), 4.02-3.92 (m, 2H), 3.87 (ddd, J=11.0, 7.3, 3.0 Hz, 1H), 3.75-3.65 (m, 1H), 3.63 (dd, J=11.0, 5.0 Hz, 1H), 3.40 (ddd, J=11.8, 7.3, 3.1 Hz, 1H), 3.01 (ddd, J=11.8, 5.6, 3.0 Hz, 1H), 2.63 (s, 3H), 1.14 (d, J=6.3 Hz, 3H).

Scheme 61

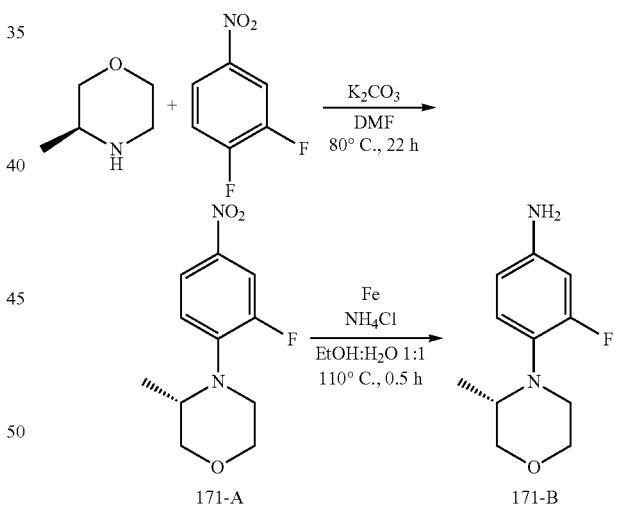

Step 1

In a 5 mL Biotage© microwave vial, a stir bar, K₂CO₃ (1.096 g, 7.93 mmol), 1,2-difluoro-4-nitrobenzene (420 mg, 2.64 mmol), and (S)-3-methylmorpholine hydrochloride (400 mg, 2.91 mmol), were added, the vial sealed, and purged with Ar for 15 min. DMF (2.643 mL) was injected into the vial and heated at 80° C. for 22 h. Upon cooling, the mixture is poured into 100 mL H₂O, filtered, thoroughly washed with H₂O, and then hexanes. Upon cooling, the mixture is transferred to a separatory funnel, H₂O was added, and the aq layer was extracted with diethyl ether and the pooled organics were washed with saturated brine and dried with Na₂SO₄. The solvent was evaporated to afford the product, (S)-4-(2-fluoro-4-nitrophenyl)-3-methylmorpholine 171-A as a yellow oil (597 mg, 2.484 mmol, 94% yield). $^1$H NMR (CDCl$_3$) δ: 7.84 (dd, J=9.1, 2.6 Hz, 1H), 7.73 (dd, J=13.4, 2.6 Hz, 1H), 6.84 (t, J=8.8 Hz, 1H), 3.93-3.75 (m, 3H), 3.70-3.55 (m, 2H), 3.45-3.34 (m, 1H), 3.03 (dt, J=12.4, 2.8 Hz, 1H), 1.11 (d, J=6.7 Hz, 3H).

Scheme 61, Step 2

In a 20 mL Biotage© microwave vial, a stir bar, (S)-4-(2-fluoro-4-nitrophenyl)-3-methylmorpholine 171-A (663 mg, 2.484 mmol), iron (694 mg, 12.42 mmol), and ammonium chloride (266 mg, 4.97 mmol), were added. The vial was sealed, degassed with Ar for 15 min, and degassed EtOH:H$_2$O (6.21 mL:6.21 mL, 1:1 v/v) injected. The mixture was heated for 0.5 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na$_2$SO$_4$. Solvent was concentrated, redissolved in DCM, dryloaded onto silica and chromatographed on a 12 g silica column, (DCM/MeOH, 0-10%), affording (S)-3-fluoro-4-(3-methylmorpholino)aniline 171-B as a brown solid (462 mg, 2.197 mmol, 88% yield, 5% MeOH). $^1$H NMR (CDCl$_3$) δ: 6.94 (t, J=8.8 Hz, 1H), 6.43-6.38 (m, 2H), 3.90-3.77 (m, 3H), 3.67 (bs, 2H), 3.44-3.35 (m, 1H), 3.29-3.16 (m, 1H), 3.00-2.95 (m, 2H), 0.85 (d, J=6.3 Hz, 3H).

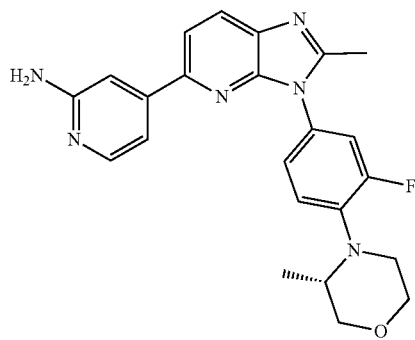

Compound 171 was synthesized in a similar manner as depicted in Scheme 56, using (S)-3-fluoro-4-(3-methylmorpholino)aniline 171-B.

(S)-4-(3-(3-fluoro-4-(3-methylmorpholino)phenyl)-2-methyl-3H-imidazo[4,5-b]pyridin-5-yl)pyridin-2-amine 171.

Red semi-solid (26 mg, 0.062 mmol, 20% yield, 7% MeOH in DCM).

$^1$H NMR (CDCl$_3$) δ: 8.13 (d, J=5.4 Hz, 1H), 8.05 (d, J=8.2 Hz, 1H), 7.72 (d, J=8.3 Hz, 1H), 7.31-7.11 (m, 5H), 4.57 (s, 2H), 4.02-3.92 (m, 2H), 3.87 (ddd, J=11.0, 7.3, 3.0 Hz, 1H), 3.69 (d, J=5.3 Hz, 1H), 3.62 (dd, J=10.9, 5.0 Hz, 1H), 3.39 (ddd, J=11.8, 7.3, 3.1 Hz, 1H), 3.00 (ddd, J=11.9, 5.6, 3.0 Hz, 1H), 2.62 (s, 3H), 1.14 (d, J=6.3 Hz, 3H).

Scheme 62

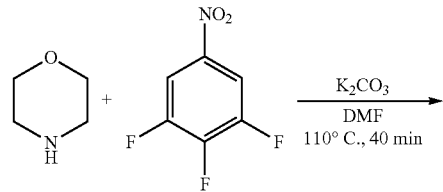

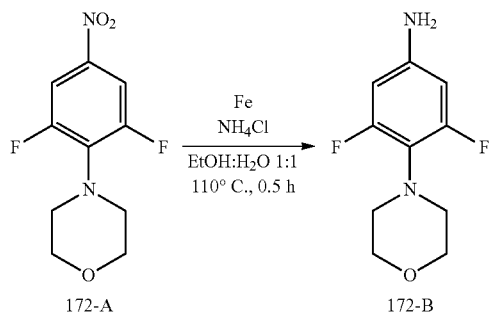

Scheme 62, Step 1

In a 20 mL Biotage© microwave vial, a stir bar, K$_2$CO$_3$ (1.8 g, 13.04 mmol), DMF (5.2 mL) were added, the vial sealed, and purged with Ar for 15 min. 1,2,3-Trifluoro-5-nitrobenzene (0.6 mL, 5.22 mmol), and morpholine (0.5 mL, 5.74 mmol), were injected into the vial and heated at 110° C. for 40 min. Upon cooling, the mixture is poured into 100 mL H$_2$O, filtered, thoroughly washed with H$_2$O, and then hexanes, affording 4-(2,6-difluoro-4-nitrophenyl)morpholine 172-A as a yellow solid (1.05 g, 4.30 mmol, 82% yield) $^1$H NMR (CDCl$_3$) δ: 7.77 (d, J=9.9 Hz, 2H), 3.88-3.77 (m, 4H), 3.43-3.33 (m, 4H).

Scheme 62, Step 2

In a 20 mL Biotage© microwave vial, a stir bar, (4-(2,6-difluoro-4-nitrophenyl)morpholine 172-A (500 mg, 2.048 mmol), iron (572 mg, 10.24 mmol), and ammonium chloride (219 mg, 4.10 mmol), were added. The vial was sealed, degassed with Ar for 15 min, and degassed EtOH:H$_2$O (5.12 mL:5.12 mL, 1:1 v/v) injected. The mixture was heated for 0.5 h at 110° C. in an oil bath. Upon cooling, the mixture was diluted with EtOAc, filtered through celite, transferred to a separatory funnel and 10% NaOH was added. The aq layer was extracted with ethyl acetate and the pooled organics were washed with saturated brine and dried with Na$_2$SO$_4$. Solvent was concentrated, redissolved in DCM, dryloaded onto silica and chromatographed on a 12 g silica column, (DCM/MeOH, 0-5%), affording 3,5-difluoro-4-morpholinoaniline 172-B as a yellow solid (420 mg, 1.961 mmol, 96% yield, 5% MeOH in DCM). $^1$H NMR (CDCl$_3$) δ: 6.18 (d, J=10.8 Hz, 2H), 3.84-3.77 (m, 4H), 3.74 (s, 2H), 3.13-3.05 (m, 4H).

311

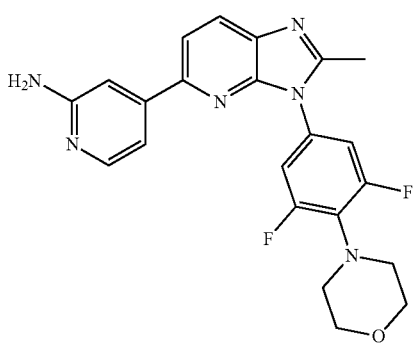 [SMILES: Cc1nc2ccc(-c3ccnc(N)c3)nc2n1-c1cc(F)c(N2CCOCC2)c(F)c1]

Compound 172 was synthesized in a similar manner as depicted in Scheme 56, using 3,5-difluoro-4-morpholinoaniline 172-B.

4-(3-(3,5-difluoro-4-morpholinophenyl)-2-methyl-3H-imidazo[4,5-b]pyridin-5-yl)pyridin-2-amine 172.

Red semi-solid (37 mg, 0.088 mmol, 34% yield, 9% MeOH in DCM).

$^1$H NMR (CDCl$_3$) δ: 8.15 (d, J=5.4 Hz, 1H), 8.06 (d, J=8.3 Hz, 1H), 7.74 (d, J=8.3 Hz, 1H), 7.23 (d, J=5.5 Hz, 1H), 7.14 (s, 1H), 7.07 (d, J=9.0 Hz, 2H), 4.57 (s, 2H), 3.92-3.85 (m, 4H), 3.39-3.32 (m, 4H), 2.64 (s, 3H).

Scheme 63

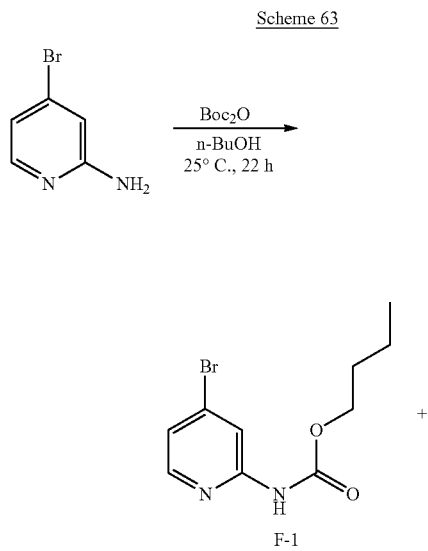

312

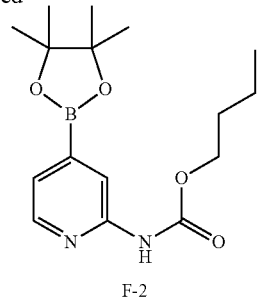

F-2

Scheme 63, Step 1

A 500 mL round bottom flask was loaded with a stir bar, 4-bromopyridin-2-amine (10 g, 57.8 mmol) and n-BuOH (85 mL). Warm Boc$_2$O (16.1 mL, 69.4 mmol) was added dropwise The mixture was sealed with parafilm and stirred at 25° C. for 22 h. Solvent is evaporated and the mixture is azeotroped with hexanes, then heated/cooled repeatedly with Et$_2$O, and the product is filtered, washed with Et$_2$O and hexanes, affording butyl (4-bromopyridin-2-yl)carbamate F-1 as a white solid (12.97 g, 47.5 mmol, 82% yield). $^1$H NMR (DMSO) δ: 10.39 (bs, 1H), 8.17 (d, J=5.3 Hz, 1H), 8.06 (d, J=1.8 Hz, 1H), 7.30 (dd, J=5.3, 1.8 Hz, 1H), 4.12 (t, J=6.6 Hz, 2H), 1.67-1.55 (m, 2H), 1.45-1.31 (m, 2H), 0.92 (t, J=7.4 Hz, 3H). $^{13}$C NMR (DMSO) δ: 154.09, 153.77, 149.69, 133.48, 121.86, 115.14, 64.88, 30.90, 18.98, 14.04.

Scheme 63, Step 2

A 20 mL Biotage© microwave vial loaded with butyl (4-bromopyridin-2-yl)carbamate F-1(1.5 g, 5.49 mmol), 4,4, 4',4',5,5,5',5'-octamethyl-2,2'-bi(1,3,2-dioxaborolane) (2.092 mg, 8.24 mmol), PdCl$_2$(dppf) (403 mg, 0.549 mmol), and KOAc, (1.725 g, 17.57 mmol) was capped, purged with argon, then injected with degassed dioxane (12.2 mL), and heated to 95° C. for 2 h in an oil bath. The reaction was cooled, diluted with EtOAC, poured into a separatory funnel containing EtOAc, saturated ammonium chloride solution, the mixture was shaken, and filtered through celite, (three microwave vials of the above conditions were combined and worked up together). After multiple extractions with EtOAc, the organics were washed with saturated ammonium chloride solution and brine. After concentration, the mixture was dissolved in EtOH and then heated/cooled repeatedly with EtOH and filtered, affording butyl (4-(4,4,5,5-tetramethyl-1,3,2-dioxaborolan-2-yl)pyridin-2-yl)carbamate F-2 as a white solid (4.53 g, 14.15 mmol, 86% yield).

$^1$H NMR (CDCl$_3$) δ: 8.97 (bs, 1H), 8.38 (s, 1H), 8.35 (d, J=4.9 Hz, 1H), 7.33 (d, J=4.9 Hz, 1H), 4.24 (t, J=6.6 Hz, 2H), 1.77-1.66 (m, 2H), 1.52-1.41 (m, 2H), 1.37 (s, 12H), 0.99 (t, J=7.4 Hz, 3H). $^{11}$B NMR (128 MHz, CDCl$_3$) δ 30.32.

Scheme 64

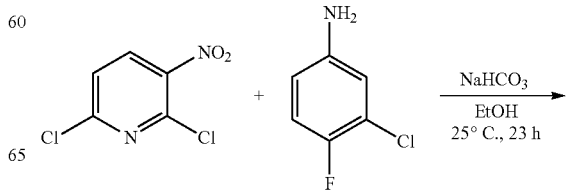

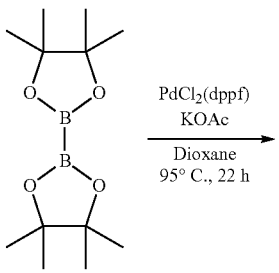

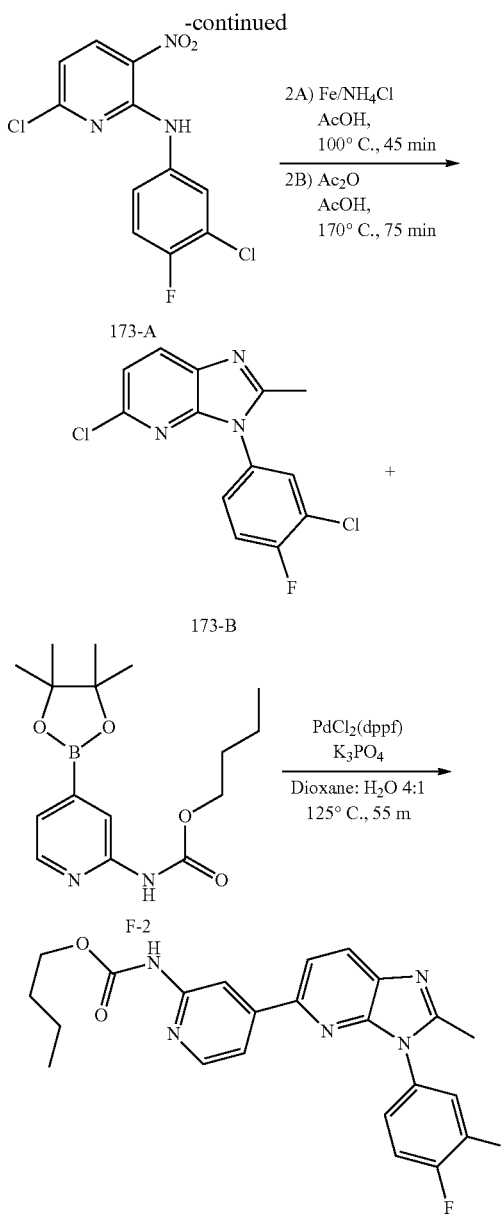

Ar for 15 min, injected with degassed AcOH (12.1 mL each) and purged with Ar for another 5 min. Both vials were heated at 100° C. for 45 min in an oil bath. Upon cooling, both vials were diluted with EtOAc, solids filtered through celite, and the combined mixture concentrated and used in Step 2B.

Scheme 64, Step 2B

The crude residue was dissolved in AcOH (11.4 mL), gently warmed and pipetted repeatedly into one 20 mL Biotage© microwave vial equipped with a stir bar. Ac$_2$O (2.27 mL, 24.0 mmol) was injected and the mixture was purged with Ar for 15 min and heated at 170° C. for 75 min and then cooled. The mixture was poured into a 500 mL RBF and azeotroped with toluene repeatedly. DCM was added followed by 7M NH$_3$ in MeOH (10 mL) with subsequent concentration. The crude freebase was concentrated/dry-loaded onto silica with DCM and purified on a 40 g silica column (DCM), affording 5-chloro-3-(3-chloro-4-fluorophenyl)-2-methyl-3H-imidazo[4,5-b]pyridine 173-B as a white solid (1.4 g, 4.74 mmol, 59% yield, 100% DCM)

$^1$H NMR (CDCl$_3$) δ: 7.94 (d, J=8.2 Hz, 1H), 7.50 (dd, J=6.3, 2.5 Hz, 1H), 7.42-7.30 (m, 2H), 7.26 (d, J=8.3 Hz, 1H), 2.55 (s, 3H).

Scheme 64, Step 3

A 20 mL Biotage© microwave vial loaded with 5-chloro-3-(3-chloro-4-fluorophenyl)-2-methyl-3H-imidazo[4,5-b] pyridine 173-B (300 mg, 1.013 mmol), butyl (4-(4,4,5,5-tetramethyl-1,3,2-dioxaborolan-2-yl)pyridin-2-yl) carbamate F-2 (357 mg, 1.114 mmol), PdCl$_2$(dppf) (82 mg, 0.111 mmol), and K$_3$PO$_4$, (495 mg, 2.33 mmol) was capped, purged with argon, then injected with degassed dioxane:H$_2$O (3.24 mL:0.81 mL, 4:1 v/v), and heated to 125° C. for 55 min in an oil bath. The reaction was cooled, diluted with DCM, filtered through celite, concentrated, dryloaded onto silica gel and purified on a 12 g silica gel column (DCM/MeOH, 0-5%), affording butyl (4-(3-(3-chloro-4-fluorophenyl)-2-methyl-3H-imidazo[4,5-b]pyridin-5-yl)pyridin-2-yl) carbamate 173-C as a White solid (395 mg, 0.870 mmol, 86% yield, 5% MeOH in DCM). $^1$H NMR (DMSO) δ: 10.12 (s, 1H), 8.42 (s, 1H), 8.31 (d, J=5.2 Hz, 1H), 8.18 (d, J=8.3 Hz, 1H), 8.07-8.01 (m, 1H), 7.92 (d, J=8.3 Hz, 1H), 7.79-7.64 (m, 2H), 7.64-7.49 (m, 1H), 4.16-4.06 (m, 2H), 2.55 (s, 3H), 1.67-1.55 (m, 2H), 1.46-1.31 (m, 2H), 0.93 (t, J=7.4 Hz, 3H).

Scheme 64, Step 1

In a 20 mL Biotage© microwave vial, stir bar, 3-chloro-4-fluoroaniline (2.5 g, 17.17 mmol), NaHCO$_3$ (2.89 g, 34.3 mmol) and EtOH (11.45 mL) were added and stirred for 5 min. 2,6-Dichloro-3-nitropyridine (3.31 g, 17.17 mmol) was added and the vial sealed, then stirred at 25° C. for 23 h. The mixture was cooled, filtered and the precipitated product was washed with cold EtOH, H$_2$O, and hexanes, affording 6-chloro-N-(3-chloro-4-fluorophenyl)-3-nitropyridin-2-amine 173-A as a yellow solid (3.41 g, 11.29 mmol, 66% yield). $^1$H NMR (DMSO) δ: 10.12 (s, 1H), 8.53 (d, J=8.6 Hz, 1H), 7.84 (dd, J=6.8, 2.6 Hz, 1H), 7.61-7.52 (m, 1H), 7.44 (t, J=9.0 Hz, 1H), 7.01 (d, J=8.6 Hz, 1H).

Scheme 64, Step 2A

To (2) 20 mL Biotage© microwave vials, stir bars, 6-chloro-N-(3-chloro-4-fluorophenyl)-3-nitropyridin-2-amine 173-A (1.208 g, 4 mmol), iron (1.787 g, 32 mmol), and ammonium chloride (0.856 mg, 16 mmol) were added to each individual vial. The vials were sealed, degassed with Scheme 65

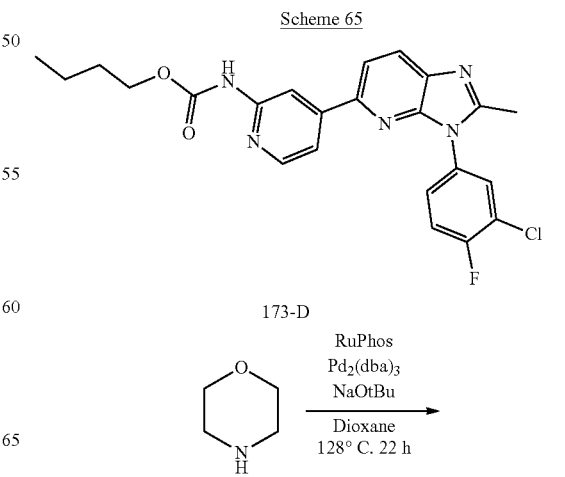

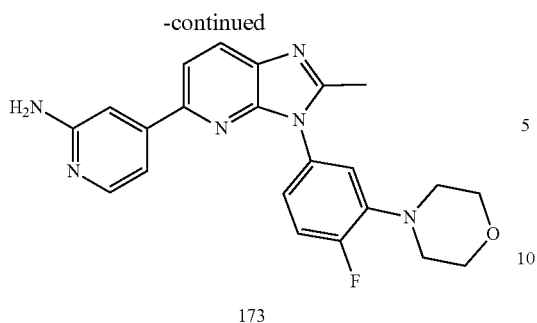

173

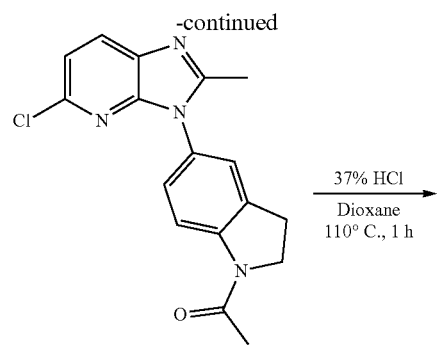

174-B

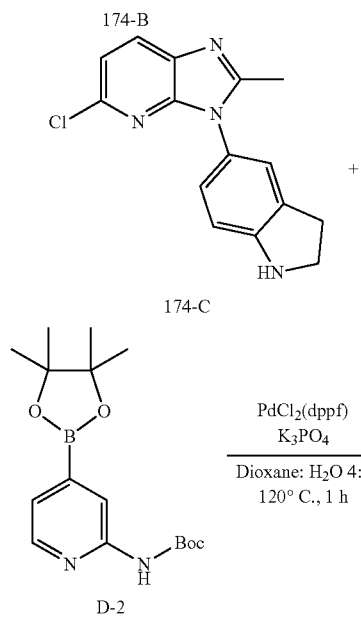

A 2-5 mL Biotage© microwave vial loaded with RuPhos (22.6 mg, 0.048 mmol), Pd₂(dba)₃ (22.19 mg, 0.024 mmol), butyl (4-(3-(3-chloro-4-fluorophenyl)-2-methyl-3H-imidazo[4,5-b]pyridin-5-yl)pyridin-2-yl)carbamate 173-D (100 mg, 0.220 mmol), and sodium tert-butoxide (127 mg, 1.322 mmol) was capped, purged with argon, then injected with morpholine (0.96 mL, 1.102 mmol) dissolved in dioxane (0.734 mL). The vial was heated to 128° C. for 22 h in an oil bath. The reaction was cooled, 37% conc. HCl (0.9 mL) was added, stirred for 1 h and basified with 10% NaOH. The mixture was extracted with ethyl acetate, washed with 10% NaOH, H₂O, brine, and the organic layer was dried over Na₂SO₄, concentrated, dryloaded onto silica gel and purified on a 12 g silica gel column (DCM/MeOH, 0-9%), affording 4-(3-(4-fluoro-3-morpholinophenyl)-2-methyl-3H-imidazo[4,5-b]pyridin-5-yl)pyridin-2-amine 173 as a green semi-solid (6 mg, 0.015 mmol, 7% yield, 9% MeOH in DCM). ¹H NMR (CDCl₃) δ: 8.14 (d, J=5.4 Hz, 1H), 8.07 (d, J=8.3 Hz, 1H), 7.75 (d, J=8.3 Hz, 1H), 7.32-7.21 (m, 2H), 7.17-7.12 (m, 1H), 7.09-7.00 (m, 2H), 4.50 (s, 2H), 3.96-3.89 (m, 4H), 3.24-3.16 (m, 4H), 2.62 (s, 3H).

Scheme 66

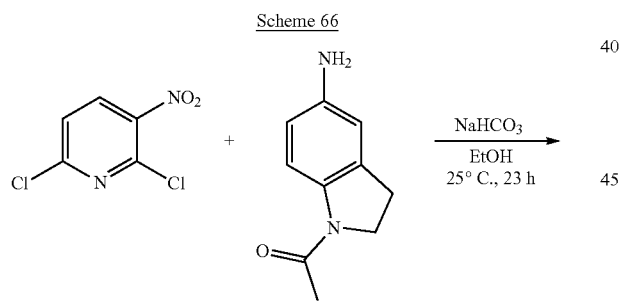

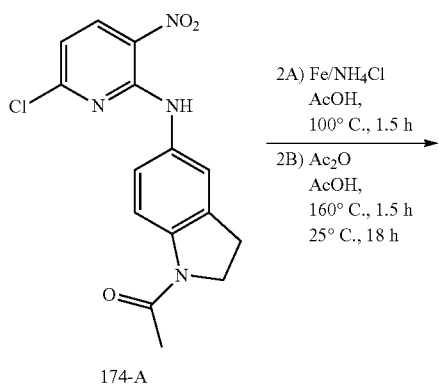

174-A

Scheme 65, Step 1

In a 20 mL Biotage© microwave vial, stir bar, 1-(5-aminoindolin-1-yl)ethan-1-one (1.1 g, 6.24 mmol), NaHCO₃ (1.311 g, 15.61 mmol) and EtOH (4.16 mL) were added and stirred for 5 min. 2,6-Dichloro-3-nitropyridine (1.205 g, 6.24 mmol), was added and the vial sealed, stirred at 25° C. for 23 h. The mixture was cooled, filtered and the precipitated product was washed with cold EtOH, H₂O, and hexanes, affording 1-(5-((6-chloro-3-nitropyridin-2-yl)amino)indolin-1-yl)ethan-1-one 174-A as a black solid (1.58 g, 4.75 mmol, 76% yield). ¹H NMR (DMSO) δ: 10.07 (s, 1H), 8.51 (d, J=8.6 Hz, 1H), 8.02 (d, J=8.6 Hz, 1H), 7.47 (s, 1H), 7.31 (dd, J=8.6, 2.3 Hz, 1H), 6.96 (d, J=8.6 Hz, 1H), 4.12 (t, J=8.5 Hz, 2H), 3.17 (t, J=8.5 Hz, 2H), 2.16 (s, 3H).

Scheme 65, Step 2A

To (2) 20 mL Biotage© microwave vials, stir bars, 1-(5-((6-chloro-3-nitropyridin-2-yl)amino)indolin-1-yl)ethan-1-one 174-A (800 mg, 2.4 mmol), iron (1.074 g, 19.23 mmol), and ammonium chloride (514 mg, 9.62 mmol) were added to each individual vial. The vials were sealed, degassed with Ar for 15 min, injected with degassed AcOH (7.3 mL each) and purged with Ar for another 5 min. Both vials were heated at 100° C. for 1.5 h in an oil bath. Upon cooling, both vials were diluted with EtOAc, solids filtered through celite, and the combined mixture concentrated and used in crude in Step 2B.

Scheme 65, Step 2B

The crude residue was dissolved in AcOH (13.8 mL), gently warmed and pipetted repeatedly into one 20 mL Biotage© microwave vial equipped with a stir bar. Ac$_2$O (1.364 mL, 14.43 mmol) was injected and the mixture was purged with Ar for 15 min and heated at 160° C. for 1.5 h, cooled, and stirred at 25° C. for 18 h. The mixture was poured into a 500 mL RBF and azeotroped with toluene repeatedly. DCM was added followed by 7M NH$_3$ in MeOH (10 mL) with subsequent concentration. The crude freebase was concentrated/dryloaded onto silica with DCM and purified on a 40 g silica column (DCM/MeOH, 0-4%), affording 1-(5-(5-chloro-2-methyl-3H-imidazo[4,5-b]pyridin-3-yl)indolin-1-yl)ethan-1-one 174-B as a white solid (1.22 g, 3.73 mmol, 78% yield, 4% MeOH in DCM). $^1$H NMR (CDCl$_3$) δ: 8.35 (d, J=8.4 Hz, 1H), 7.92 (d, J=8.3 Hz, 1H), 7.25-7.12 (m, 3H), 4.14 (t, J=8.5 Hz, 2H), 3.27 (t, J=8.5 Hz, 2H), 2.50 (s, 3H), 2.26 (s, 3H).

Scheme 65, Step 3

In a 20 mL Biotage© microwave vial, stir bar, 1-(5-(5-chloro-2-methyl-3H-imidazo[4,5-b]pyridin-3-yl)indolin-1-yl)ethan-1-one 174-B (1 g, 3.06 mmol), Dioxane (10.2 mL), and 37% HCl (3.77 mL, 45.9 mmol), were added and the vial was sealed and degassed with Ar for 15 min. The suspension was heated for 1 h at 110° C. for 1 h in an oil bath. The vial was cooled, evaporated completely and 10% NaOH was added. The precipitate is filtered and washed with H$_2$O, affording 5-chloro-3-(indolin-5-yl)-2-methyl-3H-imidazo[4,5-b]pyridine 174-C as a white solid (775 mg, 2.72 mmol, 89% yield). $^1$H NMR (CDCl$_3$) δ: 7.91 (d, J=8.2 Hz, 1H), 7.21 (d, J=8.3 Hz, 1H), 7.05 (s, 1H), 6.95 (d, J=8.2 Hz, 1H), 6.70 (d, J=8.2 Hz, 1H), 4.07 (s, 1H), 3.67 (t, J=8.5 Hz, 2H), 3.12 (t, J=8.5 Hz, 2H), 2.51 (s, 3H). $^{13}$C NMR (CDCl$_3$) δ: 154.57, 152.62, 148.63, 144.90, 133.52, 130.73, 128.51, 126.63, 124.20, 123.74, 118.47, 109.09, 47.62, 29.61, 14.99.

Scheme 65, Step 4

A 5 mL Biotage© microwave vial loaded with 5-chloro-3-(indolin-5-yl)-2-methyl-3H-imidazo[4,5-b]pyridine 174-C (243 mg, 0.852 mmol), tert-butyl (4-(4,4,5,5-tetramethyl-1,3,2-dioxaborolan-2-yl)pyridin-2-yl)carbamate D-2 (300 mg, 0.937 mmol), PdCl$_2$(dppf) (68.7 mg, 0.094 mmol), and K$_3$PO$_4$, (416 mg, 1.959 mmol) was capped, purged with argon, then injected with degassed dioxane:H$_2$O (2.72 mL:0.68 mL, 4:1 v/v), and heated to 120° C. for 1 h in an oil bath. The reaction was cooled, diluted with DCM, filtered through celite, concentrated, dryloaded onto silica gel and purified on a 12 g silica gel column (DCM/MeOH, 0-6%), affording tert-butyl (4-(3-(indolin-5-yl)-2-methyl-3H-imidazo[4,5-b]pyridin-5-yl)pyridin-2-yl)carbamate 174-D as a white solid (111 mg, 0.251 mmol, 29% yield, 6% MeOH in DCM).

$^1$H NMR (CDCl$_3$) δ: 8.56 (d, J=6.4 Hz, 2H), 8.32 (d, J=5.4 Hz, 1H), 8.05 (d, J=8.3 Hz, 1H), 7.86 (d, J=8.3 Hz, 1H), 7.66 (dd, J=5.3, 1.6 Hz, 1H), 7.20 (s, 1H), 7.06 (d, J=8.2 Hz, 1H), 6.77 (d, J=8.2 Hz, 1H), 4.03 (s, 1H), 3.71 (t, J=8.4 Hz, 2H), 3.19 (t, J=8.4 Hz, 2H), 2.60 (s, 3H), 1.58 (s, 9H). $^{13}$C NMR (CDCl$_3$) δ: 155.25, 152.87, 152.66, 152.13, 149.45, 149.25, 148.75, 148.07, 135.15, 130.55, 126.59, 126.52, 125.00, 123.85, 116.43, 116.39, 109.69, 109.02, 80.75, 47.65, 29.67, 28.37, 15.30.

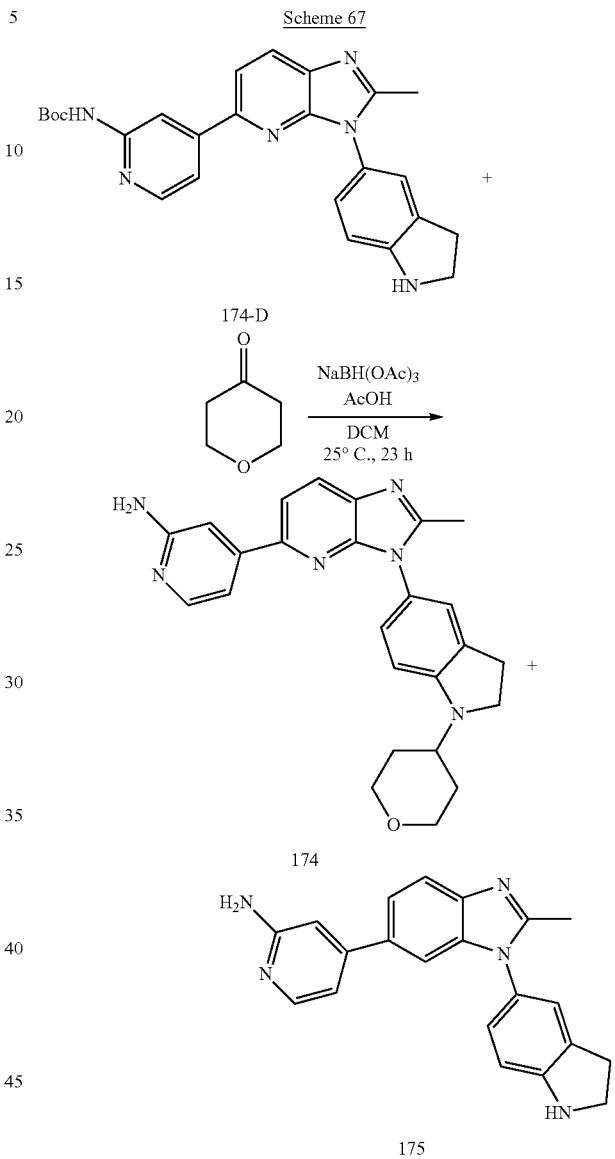

Scheme 67

A 5 mL screw cap vial loaded with tert-butyl (4-(3-(indolin-5-yl)-2-methyl-3H-imidazo[4,5-b]pyridin-5-yl)pyridin-2-yl)carbamate 174-D (30 mg, 0.068 mmol), tetrahydro-4H-pyran-4-one (13.57 mg, 0.136 mmol), DCM (0.678 mL), and AcOH (2 drops) were stirred for 5 minutes. NaBH(OAc)$_3$ (18.68 mg, 0.088 mmol) was added and the mixture was sealed and stirred at 25° C. for 23 h. TFA (0.2 mL, 2.71 mmol) was added and the mixture was stirred for 1.5 h. The vial was diluted with DCM and 10% NaOH, then extracted multiple times with DCM, washed with 10% NaOH, H$_2$O, brine, and the organic layer was dried over Na$_2$SO$_4$, concentrated, dryloaded onto silica gel and purified on a 12 g silica gel column (DCM/MeOH, 0-11%), affording 4-(2-methyl-3-(1-(tetrahydro-2H-pyran-4-yl)indolin-5-yl)-3H-imidazo[4,5-b]pyridin-5-yl)pyridin-2-amine 174 as a clear semi-solid (4 mg, 0.00938 mmol, 14% yield, 11% MeOH in DCM). $^1$H NMR (CDCl$_3$) δ: 8.13 (d, J=5.4 Hz, 1H), 8.04 (d, J=8.2 Hz, 1H), 7.71 (d, J=8.3 Hz, 1H), 7.26 (dd, J=5.4, 1.5 Hz, 1H), 7.19-7.15 (m, 1H), 7.13-7.05 (m, 2H), 6.56 (d, J=8.8 Hz, 1H), 4.48 (s, 2H), 4.20-4.12 (m, 2H), 3.78-3.65 (m, 1H), 3.63-3.49 (m, 4H), 3.11 (t, J=8.5 Hz, 2H), 2.58 (s, 3H), 1.90-1.83 (m, 4H) and 4-(3-(indolin-5-yl)-2-methyl-3H-imidazo[4,5-b]pyridin-5-yl)pyridin-2-amine 175 as a clear semi-solid (17 mg, 0.050 mmol, 73% yield, 10% MeOH in DCM). ¹H NMR (CDCl₃) δ: 8.12 (d, J=5.4 Hz, 1H), 8.04 (d, J=8.2 Hz, 1H), 7.71 (d, J=8.3 Hz, 1H), 7.24 (d, J=5.4 Hz, 1H), 7.17 (s, 1H), 7.13 (s, 1H), 7.04 (d, J=8.2 Hz, 1H), 6.76 (d, J=8.2 Hz, 1H), 4.50 (s, 2H), 4.03 (s, 1H), 3.71 (t, J=8.5 Hz, 2H), 3.16 (t, J=8.4 Hz, 2H), 2.57 (s, 3H).

Scheme 68

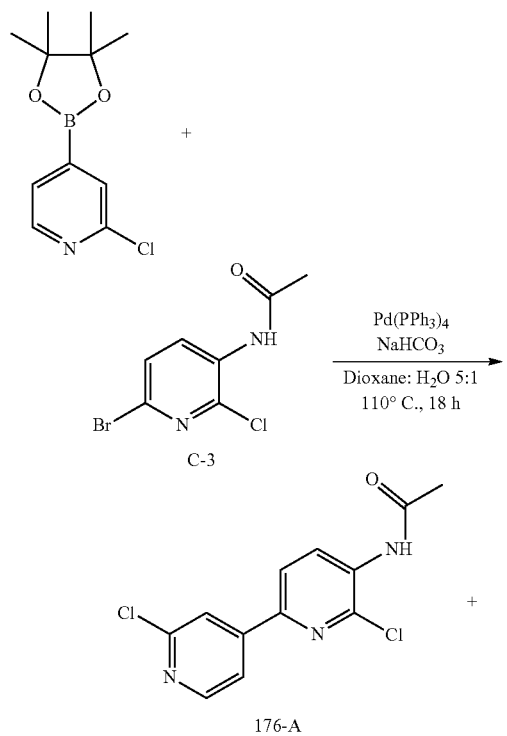

Scheme 68, Step 1

A 20 mL Biotage© microwave vial loaded with (2-chloro-4-(4,4,5,5-tetramethyl-1,3,2-dioxaborolan-2-yl)pyridine (479 mg, 2 mmol), N-(6-bromo-2-chloropyridin-3-yl)acetamide C-3 (499 mg, 2.0 mmol), Pd(PPh₃)₄ (208 mg, 0.180 mmol), and NaHCO₃ (672 mg, 8.0 mmol), was capped, purged with argon, then injected with degassed dioxane:H₂O (9.8 mL:1.961 mL, 5:1 v/v), and heated to 110° C. for 18 h in a Biotage Microwave Reactor. The reaction was cooled, diluted with DCM, filtered through celite, concentrated, dryloaded onto silica gel and purified on a 12 g silica gel column (DCM/MeOH, 0-8%), affording N-(2',6-dichloro-[2,4'-bipyridin]-5-yl)acetamide 176-A as a white semi-solid (40 mg, 0.142 mmol, 7% yield, 8% MeOH). ¹H NMR (DMSO) δ: 9.84 (s, 1H), 8.54 (dd, J=5.2, 0.7 Hz, 1H), 8.45 (d, J=8.4 Hz, 1H), 8.24 (d, J=8.4 Hz, 1H), 8.09 (dd, J=1.6, 0.7 Hz, 1H), 8.03 (dd, J=5.3, 1.6 Hz, 1H), 2.20 (s, 3H).

Scheme 68, Step 2

A 2-5 mL Biotage© microwave vial loaded with Pd₂(dba)₃ (2.5 mg, 0.00273 mmol), XPhos (6.94 mg, 0.015 mmol), N-(2',6-dichloro-[2,4'-bipyridin]-5-yl)acetamide 176-A (61.6 mg, 0.218 mmol), 4-(morpholinomethyl)aniline (35 mg, 0.182 mmol), K₃PO₄ (116 mg, 0.546 mmol), and t-BuOH (0.455 mL) was capped, purged with argon and heated to 110° C. for 18 h in an oil bath. The reaction was cooled, diluted with DCM, filtered through celite, concentrated, dryloaded onto silica gel and purified on a 12 g silica gel column (DCM/MeOH, 0-8%), affording 4-(4-(5-(2-chloropyridin-4-yl)-2-methyl-3H-imidazo[4,5-b]pyridin-3-yl)benzyl)morpholine 176 as a green semi-solid (22 mg, 0.052 mmol, 29% yield, 8% MeOH in DCM). ¹H NMR (CDCl₃) δ: 8.43 (d, J=5.3 Hz, 1H), 8.12 (d, J=8.3 Hz, 1H), 7.93 (s, 1H), 7.86-7.74 (m, 2H), 7.62 (d, J=6.3 Hz, 2H), 7.44 (d, J=8.3 Hz, 2H), 3.86-3.73 (m, 4H), 3.67 (s, 2H), 2.64 (s, 3H), 2.61-2.55 (m, 4H).

Scheme 69

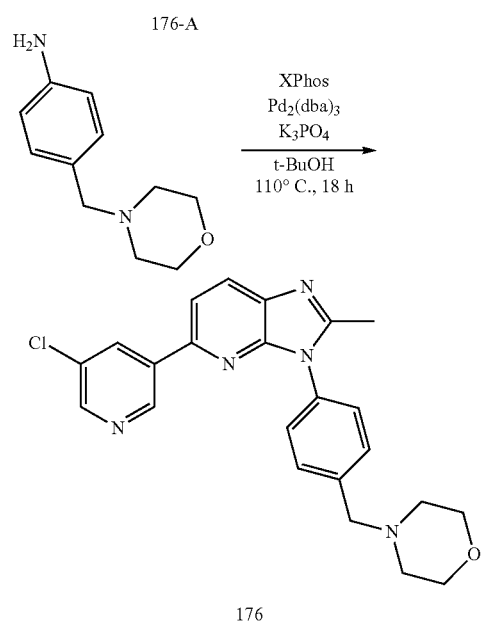

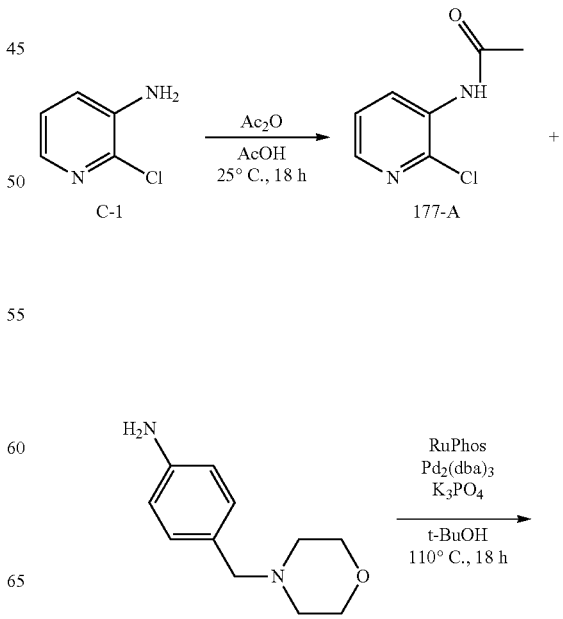

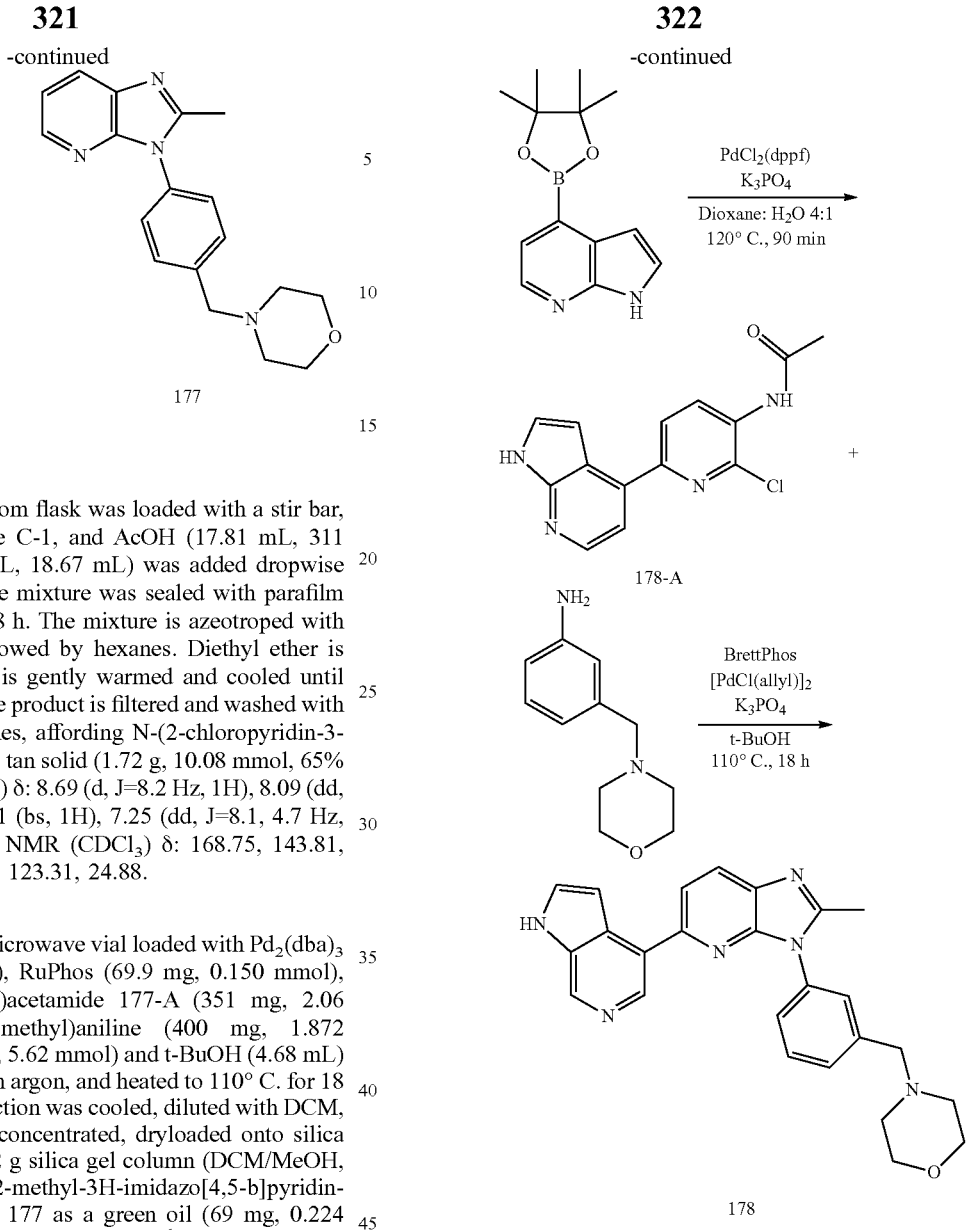

177

Scheme 69, Step 1

A 500 mL round bottom flask was loaded with a stir bar, 2-chloropyridin-3-amine C-1, and AcOH (17.81 mL, 311 mmol). $Ac_2O$ (1.761 mL, 18.67 mL) was added dropwise over 15 minutes and the mixture was sealed with parafilm and stirred at 25° C., 18 h. The mixture is azeotroped with toluene repeatedly, followed by hexanes. Diethyl ether is added and the mixture is gently warmed and cooled until precipitation results. The product is filtered and washed with diethyl ether and hexanes, affording N-(2-chloropyridin-3-yl)acetamide 177-A as a tan solid (1.72 g, 10.08 mmol, 65% yield). $^1$H NMR ($CDCl_3$) δ: 8.69 (d, J=8.2 Hz, 1H), 8.09 (dd, J=4.7, 1.8 Hz, 1H), 7.71 (bs, 1H), 7.25 (dd, J=8.1, 4.7 Hz, 1H), 2.27 (s, 3H). $^{13}$C NMR ($CDCl_3$) δ: 168.75, 143.81, 139.67, 131.90, 129.09, 123.31, 24.88.

Scheme 69, Step 2

A 20 mL Biotage© microwave vial loaded with $Pd_2(dba)_3$ (25.7 mg, 0.028 mmol), RuPhos (69.9 mg, 0.150 mmol), N-(2-chloropyridin-3-yl)acetamide 177-A (351 mg, 2.06 mmol), 4-(morpholinomethyl)aniline (400 mg, 1.872 mmol), $K_3PO_4$ (1.192 g, 5.62 mmol) and t-BuOH (4.68 mL) was capped, purged with argon, and heated to 110° C. for 18 h in an oil bath. The reaction was cooled, diluted with DCM, filtered through celite, concentrated, dryloaded onto silica gel and purified on a 12 g silica gel column (DCM/MeOH, 0-5%), affording 4-(4-(2-methyl-3H-imidazo[4,5-b]pyridin-3-yl)benzyl)morpholine 177 as a green oil (69 mg, 0.224 mmol, 12% yield, 5% MeOH in DCM). $^1$H NMR ($CDCl_3$) δ: 8.28 (dd, J=4.9, 1.3 Hz, 1H), 7.99 (dd, J=8.0, 1.5 Hz, 1H), 7.55 (d, J=8.0 Hz, 2H), 7.36 (d, J=8.0 Hz, 2H), 7.27-7.19 (m, 1H), 3.82-3.71 (m, 4H), 3.58 (s, 2H), 2.55 (s, 3H), 2.53-2.43 (m, 4H).

Scheme 70

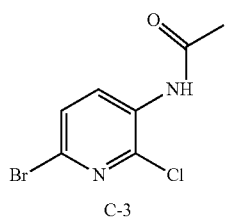

C-3

+

Scheme 70, Step 1

A 20 mL Biotage© microwave vial loaded with N-(6-bromo-2-chloropyridin-3-yl)acetamide C-3 (500 mg, 2.004 mmol), 4-(4,4,5,5-tetramethyl-1,3,2-dioxaborolan-2-yl)-1H-pyrrolo[2,3-b]pyridine (538 mg, 2.204 mmol), $PdCl_2$(dppf) (132 mg, 0.180 mmol), and $K_3PO_4$, (936 mg, 4.41 mmol) was capped, purged with argon, then injected with degassed dioxane:$H_2O$ (6.41 mL:1.6 mL, 4:1 v/v), and heated to 120° C. for 90 min in an oil bath. The reaction was cooled, diluted with DCM, filtered through celite, concentrated, dryloaded onto silica gel and purified on a 12 g silica gel column (DCM/MeOH, 0-9%), affording N-(2-chloro-6-(1H-pyrrolo[2,3-b]pyridin-4-yl)pyridin-3-yl)acetamide 178-A as a white solid (275 mg, 0.959 mmol, 48% yield, 9% MeOH in DCM). $^1$H NMR (DMSO) δ: 11.86 (s, 1H), 9.80 (s, 1H), 8.41 (d, J=8.3 Hz, 1H), 8.34 (d, J=5.0 Hz, 1H), 8.16 (d, J=8.3 Hz, 1H), 7.65-7.57 (m, 2H), 7.08-7.02 (m, 1H), 2.20 (s, 3H).

Scheme 70, Step 2

A 2-5 mL Biotage© microwave vial loaded with [PdCl(allyl)]$_2$ (4.08 mg, 0.011 mmol), BrettPhos (30 mg, 0.056 mmol), and t-BuOH (0.93 mL) was capped, purged with argon, heated to 60° C. for 10 min in an oil bath and cooled. The vial was uncapped, a mixture of N-(2-chloro-6-(1H-pyrrolo[2,3-b]pyridin-4-yl)pyridin-3-yl)acetamide 178-A (80 mg, 0.279 mmol), 3-(morpholinomethyl)aniline (69.7 mg, 0.363 mmol), and K$_3$PO$_4$ (178 mg, 0.837 mmol), added, the vial sealed and heated to 110° C. for 18 h in an oil bath. The reaction was cooled, diluted with DCM, filtered through celite, concentrated, dryloaded onto silica gel and purified on a 12 g silica gel column (DCM/MeOH, 0-9%), affording 4-(3-(2-methyl-5-(1H-pyrrolo[2,3-b]pyridin-4-yl)-3H-imidazo[4,5-b]pyridin-3-yl)benzyl)morpholine 178 as a tan semi-solid (58 mg, 0.137 mmol, 49% yield, 9% MeOH in DCM). $^1$H NMR (CDCl$_3$) δ: 11.59 (s, 1H), 8.35 (s, 1H), 8.13 (d, J=8.3 Hz, 1H), 7.96 (d, J=8.3 Hz, 1H), 7.63-7.36 (m, 6H), 7.02 (s, 1H), 3.75-3.66 (m, 4H), 3.63 (s, 2H), 2.65 (s, 3H), 2.56-2.49 (m, 4H). $^{13}$C NMR (CDCl$_3$) δ: 154.03, 150.80, 150.18, 149.15, 142.48, 139.93, 139.83, 134.73, 134.41, 129.45, 129.33, 127.85, 126.73, 125.99, 125.84, 118.24, 118.15, 114.32, 101.62, 66.96, 62.83, 53.64, 15.41.

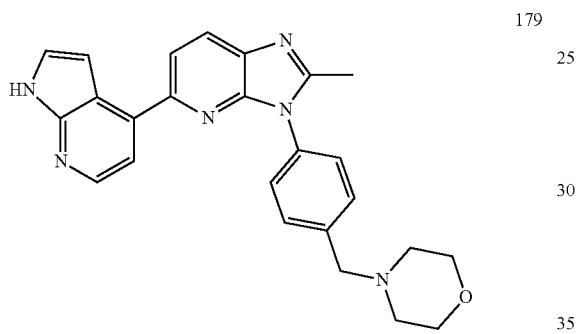

179

Compound 179 was synthesized in a similar manner as depicted in Scheme 70, Step 2, using 4-(morpholinomethyl)aniline.

4-(4-(2-methyl-5-(1H-pyrrolo[2,3-b]pyridin-4-yl)-3H-imidazo[4,5-b]pyridin-3-yl)benzyl)morpholine 179.

Tan solid (45 mg, 0.106 mmol, 43% yield, 10% MeOH in DCM).

$^1$H NMR (CDCl$_3$) δ: 11.10 (bs, 1H), 8.36 (d, J=5.1 Hz, 1H), 8.14 (d, J=8.3 Hz, 1H), 7.96 (d, J=8.3 Hz, 1H), 7.66-7.47 (m, 5H), 7.39 (s, 1H), 7.03 (s, 1H), 3.82-3.76 (m, 4H), 3.65 (s, 2H), 2.65 (s, 3H), 2.59-2.50 (m, 4H). $^{13}$C NMR (CDCl$_3$) δ: 154.13, 150.81, 150.09, 149.26, 142.66, 139.81, 138.86, 134.42, 133.60, 130.15, 127.27, 126.75, 125.68, 118.18, 118.06, 114.41, 101.75, 67.04, 62.87, 53.68, 15.38.

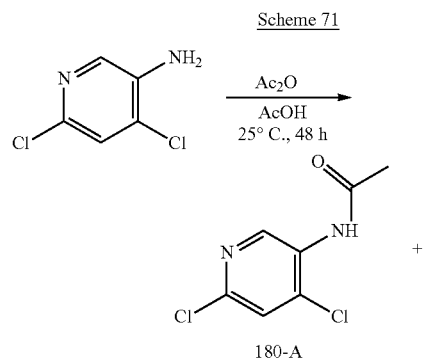

180-A

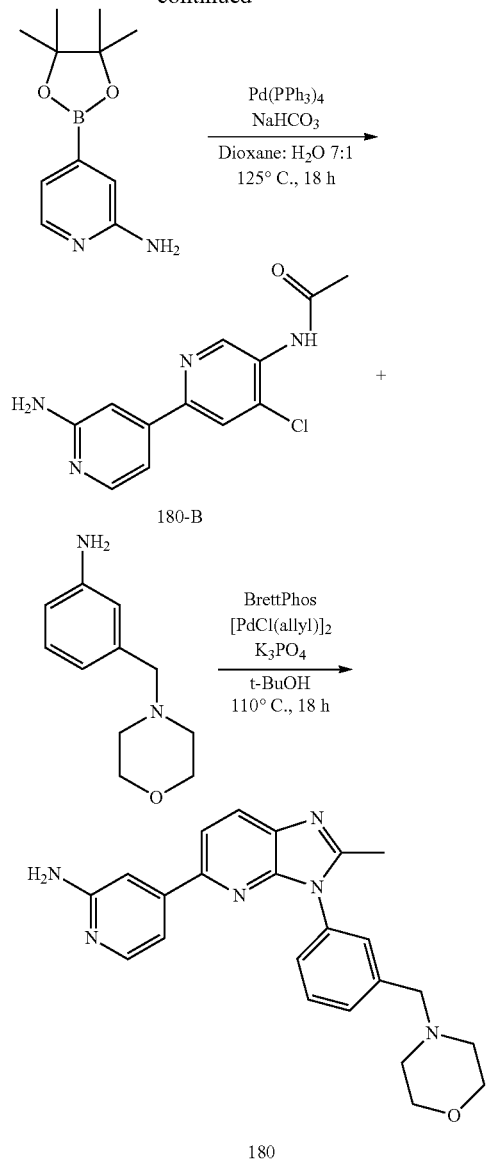

180

Scheme 71, Step 1

A 20 mL dram vial was loaded with a stir bar, 4,6-dichloropyridin-3-amine (652 mg, 4 mmol), AcOH (4.58 mL, 80 mmol) and Ac$_2$O (0.453 mL, 4.8 mmol) was added dropwise over 15 minutes. The mixture was sealed and stirred at 25° C. for 48 h. EtOAc and saturated NaHCO$_3$ solution are added and the mixture is stirred for 0.5 h. The mixture was extracted with ethyl acetate, washed with saturated NaHCO$_3$ solution, H$_2$O, brine, and the organic layer was dried over Na$_2$SO$_4$. The mixture was filtered, concentrated and DCM was added. The precipitated product was filtered and washed with minimal DCM and hexanes, affording N-(4,6-dichloropyridin-3-yl)acetamide 180-A as a white solid (250 mg, 1.219 mmol, 31% yield).

$^1$H NMR (CDCl$_3$) δ: 9.33 (s, 1H), 7.51 (s, 1H), 7.40 (s, 1H), 2.29 (s, 3H). $^{13}$C NMR (CDCl$_3$) δ: 168.12, 145.77, 142.88, 133.94, 131.16, 123.89, 24.45.

Scheme 71, Step 2

A 20 mL Biotage© microwave vial loaded with N-(4,6-dichloropyridin-3-yl)acetamide 180-A (215 mg, 1.049 mmol), 4-(4,4,5,5-tetramethyl-1,3,2-dioxaborolan-2-yl)pyridin-2-amine (231 mg, 1.049 mmol), Pd(PPh$_3$)$_4$ (97 mg, 0.084 mmol), and NaHCO$_3$ (352 mg, 4.19 mmol) was capped, purged with argon, then injected with degassed dioxane:H$_2$O (4.587 mL:0.655 mL, 7:1 v/v), and heated to 120° C. for 18 h in an oil bath. The reaction was cooled, diluted with DCM, filtered through celite, concentrated, dryloaded onto silica gel and purified on a 12 g silica gel column (DCM/MeOH, 0-6%), affording N-(2'-amino-4-chloro-[2,4'-bipyridin]-5-yl)acetamide 180-B as a white solid (80 mg, 0.305 mmol, 29% yield, 6% MeOH in DCM). $^1$H NMR (DMSO) δ: 9.88 (s, 1H), 8.93 (s, 1H), 8.10 (s, 1H), 8.01 (d, J=5.4 Hz, 1H), 7.17 (s, 1H), 7.13 (dd, J=5.4, 1.6 Hz, 1H), 6.05 (s, 2H), 2.16 (s, 3H). $^{13}$C NMR (DMSO) δ: 169.52, 161.02, 152.06, 149.04, 147.40, 145.41, 137.21, 132.53, 121.66, 109.58, 105.34, 23.64.

Scheme 71, Step 3

A 2-5 mL Biotage© microwave vial loaded with [PdCl(allyl)]$_2$ (2.79 mg, 0.00761 mmol), BrettPhos (20.43 mg, 0.038 mmol), and t-BuOH (0.63 mL) was capped, purged with argon, heated to 100° C. for 10 min in an oil bath and cooled. The vial was uncapped, a mixture of N-(2-chloro-N-(2'-amino-4-chloro-[2,4'-bipyridin]-5-yl)acetamide 180-B (80 mg, 0.279 mmol), 3-(morpholinomethyl)aniline (43.9 mg, 0.228 mmol), and K$_3$PO$_4$ (121 mg, 0.571 mmol) was added, the vial sealed and heated to 110° C. for 18 h in an oil bath. The reaction was cooled, diluted with DCM, filtered through celite, concentrated, dryloaded onto silica gel and purified on a 12 g silica gel column (DCM/MeOH, 0-9%), affording 4-(2-methyl-1-(3-(morpholinomethyl)phenyl)-1H-imidazo[4,5-c]pyridin-6-yl)pyridin-2-amine 180 as a green semi-solid (30 mg, 0.075 mmol, 39% yield, 9% MeOH in DCM). $^1$H NMR (CDCl$_3$) δ: 9.11 (s, 1H), 8.11 (d, J=5.4 Hz, 1H), 7.65-7.53 (m, 2H), 7.49 (d, J=1.0 Hz, 1H), 7.43 (s, 1H), 7.31 (dt, J=7.6, 1.8 Hz, 1H), 7.20 (s, 1H), 7.13 (dd, J=5.4, 1.5 Hz, 1H), 4.57 (s, 2H), 3.78-3.71 (m, 4H), 3.65 (s, 2H), 2.58 (s, 3H), 2.55-2.49 (m, 4H). $^{13}$C NMR (CDCl$_3$) δ: 159.21, 154.28, 148.87, 148.57, 148.46, 142.03, 141.44, 140.97, 140.09, 134.93, 130.16, 130.09, 127.04, 125.39, 111.80, 106.10, 102.58, 66.94, 62.62, 53.58, 14.58.

Scheme 72

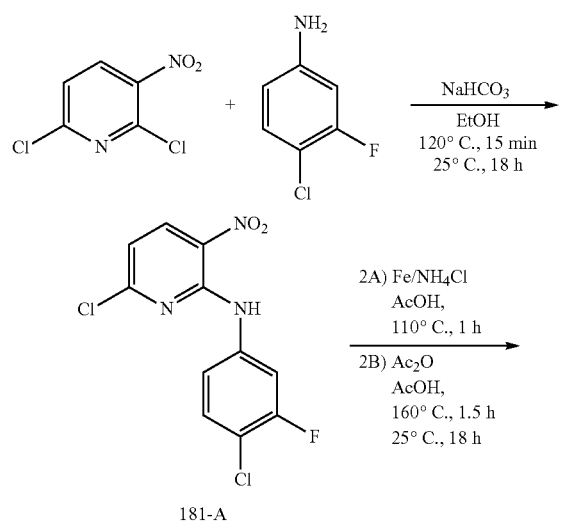

181-A

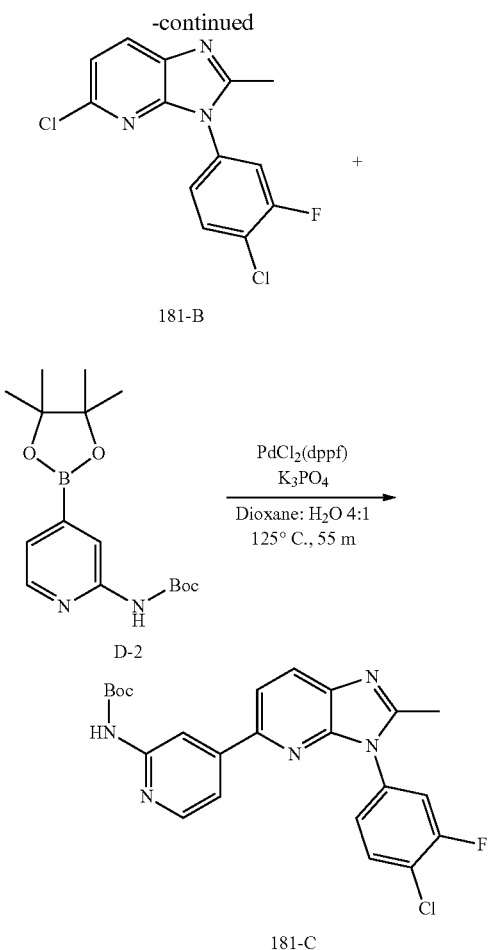

181-C

Scheme 72, Step 1

In a 20 mL Biotage© microwave vial, stir bar, 4-chloro-3-fluoroaniline (0.775 g, 10.36 mmol), NaHCO$_3$ (0.671 g, 7.99 mmol), and EtOH (2.66 mL) were added and stirred for 5 min. 2,6-Dichloro-3-nitropyridine (1.028 g, 5.33 mmol) was added and the vial sealed, then heated at 120° C. for 15 min in an oil bath, ensuring to vent with a needle when necessary. The mixture was then stirred at 25° C. for 18 h, filtered, and the precipitated product was washed with cold EtOH, H$_2$O, and hexanes, affording 6-chloro-N-(4-chloro-3-fluorophenyl)-3-nitropyridin-2-amine 181-A as a yellow solid (705 mg, 2.334 mmol, 44% yield). $^1$H NMR (DMSO-d6) δ: 10.17 (s, 1H), 8.54 (d, J=8.6 Hz, 1H), 7.79 (dd, J=11.7, 2.4 Hz, 1H), 7.57 (t, J=8.6 Hz, 1H), 7.50-7.44 (m, 1H), 7.07 (d, J=8.6 Hz, 1H)

Scheme 72, Step 2A

To (2) 20 mL Biotage© microwave vials, stir bars, 6-chloro-N-(4-chloro-3-fluorophenyl)-3-nitropyridin-2-amine 181-A (1.3 g, 4.3 mmol), iron (1.923 g, 34.4 mmol), and ammonium chloride (0.921 mg, 17.21 mmol) were added to each individual vial. The vials were sealed, degassed with Ar for 15 min, injected with AcOH (13 mL each) and purged with Ar for another 5 min. Both vials were heated at 100° C. for 90 min in an oil bath. Upon cooling, both vials were diluted with EtOAc, solids filtered through celite, and the combined mixture concentrated and used in Step 2B.

Scheme 72, Step 2B

The crude residue was dissolved in AcOH (14.77 mL), gently warmed and pipetted repeatedly into one 20 mL Biotage© microwave vial equipped with a stir bar. Ac$_2$O (1.22 mL, 12.91 mmol) was injected and the mixture was purged with Ar for 15 min and heated at 160° C. for 1.5 h and then at at 25° C. for 18 h. The mixture was poured into a 500 mL RBF and azeotroped with toluene repeatedly. DCM was added followed by 7M NH$_3$ in MeOH (10 mL) with subsequent concentration. The crude freebase was concentrated/dryloaded onto silica with DCM and purified on a 40 g silica column (DCM), affording 5-chloro-3-(4-chloro-3-fluorophenyl)-2-methyl-3H-imidazo[4,5-b]pyridine 181-B as a yellow solid (1.12 g, 3.8 mmol, 72% yield, 100% DCM). $^1$H NMR (CDCl$_3$) δ: 7.95 (d, J=8.3 Hz, 1H), 7.63 (dd, J=8.5, 7.8 Hz, 1H), 7.33-7.24 (m, 2H), 7.23-7.16 (m, 1H), 2.58 (s, 3H).

Scheme 72, Step 3

A 20 mL Biotage© microwave vial loaded with 5-chloro-3-(4-chloro-3-fluorophenyl)-2-methyl-3H-imidazo[4,5-b]pyridine 181-B (700 mg, 2.364 mmol), tert-butyl (4-(4,4,5,5-tetramethyl-1,3,2-dioxaborolan-2-yl)pyridin-2-yl)carbamate D-2 (833 mg, 2.6 mmol), PdCl$_2$(dppf) (191 mg, 0.26 mmol), and K$_3$PO$_4$, (1154 mg, 5.44 mmol) was capped, purged with argon, then injected with degassed dioxane:H$_2$O (7.564 mL:1.891 mL, 4:1 v/v), and heated to 125° C. for 55 min in an oil bath. The reaction was cooled, diluted with DCM, filtered through celite, concentrated, dryloaded onto silica gel and purified on a 40 g silica gel column (DCM/MeOH, 0-5%), affording tert-butyl (4-(3-(4-chloro-3-fluorophenyl)-2-methyl-3H-imidazo[4,5-b]pyridin-5-yl)pyridin-2-yl)carbamate 181-C as a white solid (165 mg, 0.364 mmol, 36% yield, 5% MeOH in DCM). $^1$H NMR (CDCl$_3$) δ: 8.94 (s, 1H), 8.56 (s, 1H), 8.29 (d, J=5.3 Hz, 1H), 8.03 (d, J=8.3 Hz, 1H), 7.87 (d, J=8.3 Hz, 1H), 7.63 (t, J=8.2 Hz, 1H), 7.57 (d, J=5.3 Hz, 1H), 7.37 (dd, J=9.2, 2.4 Hz, 1H), 7.27 (d, J=8.2 Hz, 1H), 2.60 (s, 3H), 1.54 (s, 9H).

Scheme 73

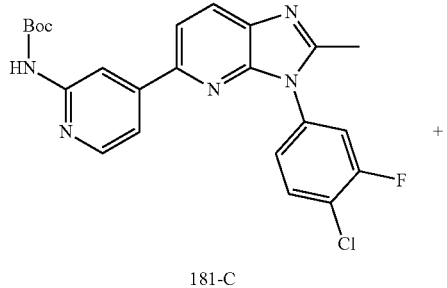

181-C

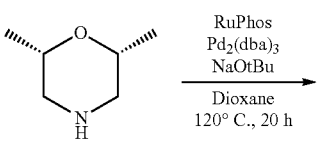

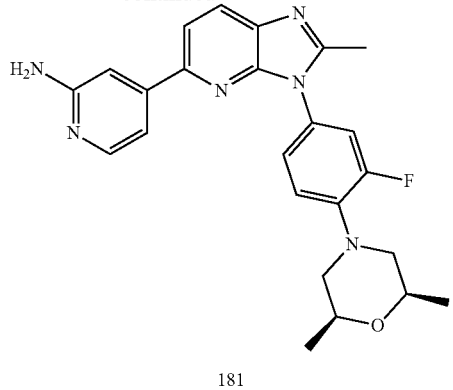

181

A 2-5 mL Biotage© microwave vial loaded with RuPhos (13.88 mg, 0.030 mmol), Pd$_2$(dba)$_3$ (13.62 mg, 0.015 mmol), tert-butyl (4-(3-(4-chloro-3-fluorophenyl)-2-methyl-3H-imidazo[4,5-b]pyridin-5-yl)pyridin-2-yl)carbamate 181-C (75 mg, 0.165 mmol), and sodium tert-butoxide (57.2 mg, 0.595 mmol) was capped, purged with argon, then injected with (2S,6R)-2,6-dimethylmorpholine (41.9 mg, 0.364 mmol) dissolved in dioxane (0.33 mL). The vial was heated to 120° C. for 20 h in an oil bath. The reaction was cooled, 37% conc. HCl (0.7 mL, 50 equiv.) was added, stirred for 1 h and basified with 10% NaOH. The mixture was extracted with ethyl acetate, washed with 10% NaOH, H$_2$O, brine, and the organic layer was dried over Na$_2$SO$_4$, concentrated, dryloaded onto silica gel and purified on a 12 g silica gel column (DCM/MeOH, 0-6%), affording 4-(3-(4-((2S,6R)-2,6-dimethylmorpholino)-3-fluorophenyl)-2-methyl-3H-imidazo[4,5-b]pyridin-5-yl)pyridin-2-amine 181 as a tan solid (33 mg, 0.069 mmol, 42% yield, 6% MeOH in DCM). $^1$H NMR (CDCl$_3$) δ: 8.14 (d, J=5.4 Hz, 1H), 8.07 (dd, J=8.3, 7.0 Hz, 1H), 7.74 (t, J=8.3 Hz, 1H), 7.35-7.07 (m, 5H), 4.52 (s, 2H), 4.01-3.88 (m, 1H), 3.42 (d, J=10.6 Hz, 1H), 2.68-2.54 (m, 7H), 1.32-1.28 (m, 6H).

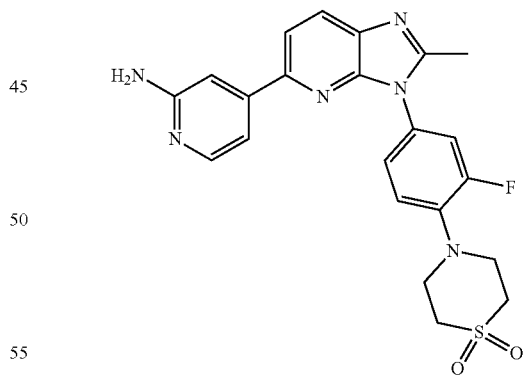

182

182 Was synthesized in a similar manner as depicted in Scheme 73, using thiomorpholine 1,1-dioxide.

4-(4-(5-(2-aminopyridin-4-yl)-2-methyl-3H-imidazo[4,5-b]pyridin-3-yl)-2-fluorophenyl)thiomorpholine 1,1-dioxide 182.

Green semi-solid (20 mg, 0.044 mmol, 22% yield, 8% MeOH in DCM).

$^1$H NMR (CDCl$_3$) δ: 8.15 (d, J=5.4 Hz, 1H), 8.08 (d, J=8.0 Hz, 1H), 7.80-7.71 (m, 1H), 7.34-7.10 (m, 5H), 4.55 (s, 2H), 3.83-3.73 (m, 4H), 3.34-3.26 (m, 4H), 2.64 (s, 3H).

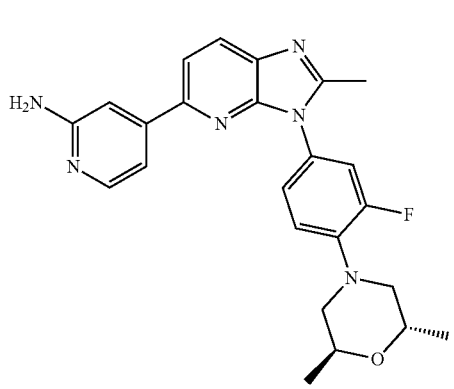

183

183 Was synthesized in a similar manner as depicted in Scheme 73, using (2S,6S)-2,6-dimethylmorpholine.

4-(3-(4-((2S,6S)-2,6-dimethylmorpholino)-3-fluorophenyl)-2-methyl-3H-imidazo[4,5-b]pyridin-5-yl)pyridin-2-amine 183.

Green semi-solid (17 mg, 0.039 mmol, 16% yield, 9% MeOH in DCM).

$^1$H NMR (CDCl$_3$) δ: 8.14 (d, J=5.3 Hz, 1H), 8.08 (d, J=8.3 Hz, 1H), 7.75 (d, J=8.3 Hz, 1H), 7.28-7.11 (m, 5H), 4.56 (s, 2H), 3.48-3.35 (m, 2H), 2.89 (d, J=11.1 Hz, 1H), 2.70-2.57 (m, 3H), 1.53 (s, 3H), 1.32-1.26 (m, 6H).

Scheme 74

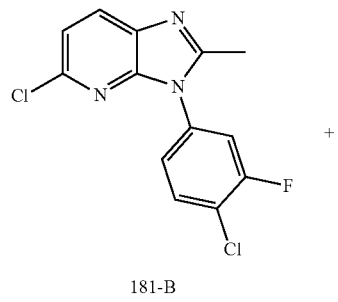

181-B

+

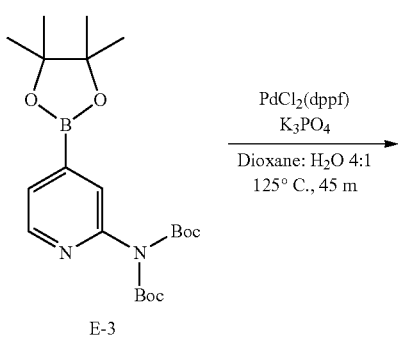

E-3

PdCl$_2$(dppf)
K$_3$PO$_4$
Dioxane: H$_2$O 4:1
125° C., 45 m
→

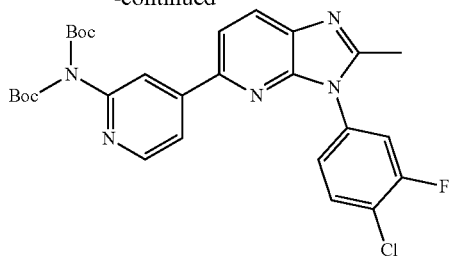

184-A

A 20 mL Biotage© microwave vial loaded with 5-chloro-3-(4-chloro-3-fluorophenyl)-2-methyl-3H-imidazo[4,5-b]pyridine 181-B (600 mg, 2.026 mmol), E-3 (937 mg, 2.23 mmol), PdCl$_2$(dppf) (164 mg, 0.223 mmol), and K$_3$PO$_4$, (1118 mg, 5.27 mmol) was capped, purged with argon, then injected with degassed dioxane:H$_2$O (6.484 mL:1.62 mL, 4:1 v/v), and heated to 125° C. for 45 min in an oil bath. The reaction was cooled, diluted with DCM, filtered through celite, concentrated, dryloaded onto silica gel and purified on a 40 g silica gel column (DCM/MeOH, 0-8%), affording Compound 184-A as a white solid (876 mg, 1.580 mmol, 78% yield, 8% MeOH in DCM)$^1$H NMR (CDCl$_3$) δ: 8.54 (d, J=5.2 Hz, 1H), 8.11 (d, J=8.4 Hz, 1H), 7.87-7.78 (m, 3H), 7.67 (t, J=8.2 Hz, 1H), 7.45-7.27 (m, 2H), 2.65 (s, 3H), 1.46 (s, 18H).

Scheme 75

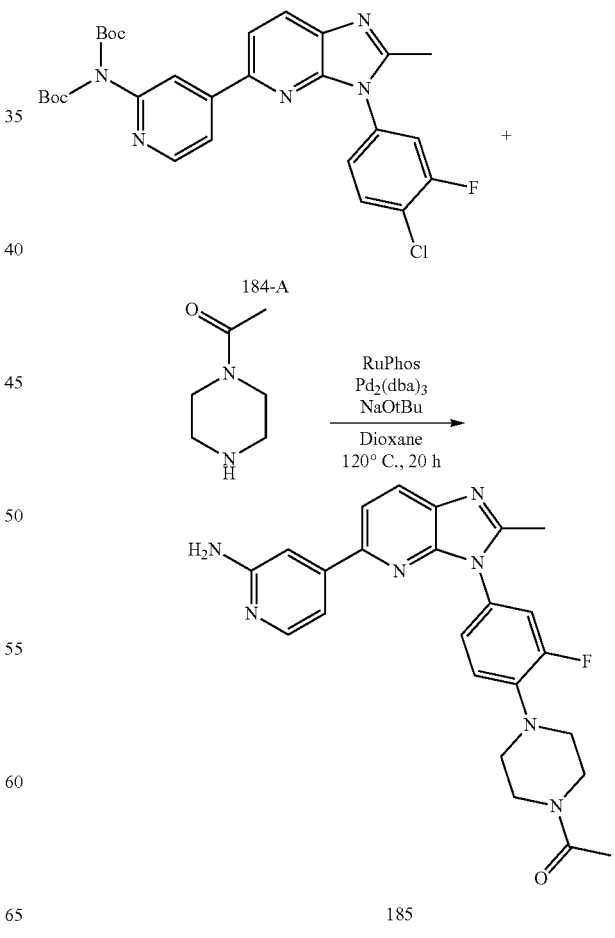

185

A 2-5 mL Biotage© microwave vial loaded with RuPhos (16.94 mg, 0.036 mmol), Pd$_2$(dba)$_3$ (16.62 mg, 0.018 mmol), 184-A (91 mg, 0.165 mmol), and sodium tert-butoxide (63.4 mg, 0.660 mmol) was capped, purged with argon, then injected with 1-(piperazin-1-yl)ethan-1-one (46.5 mg, 0.363 mmol) dissolved in dioxane (0.33 mL). The vial was heated to 120° C. for 20 h in an oil bath. The reaction was cooled, 37% conc. HCl (0.7 mL, 50 equiv.) was added, stirred for 1 h and basified with 10% NaOH. The mixture was extracted with ethyl acetate, washed with 10% NaOH, H$_2$O, brine, and the organic layer was dried over Na$_2$SO$_4$, concentrated, dryloaded onto silica gel and purified on a 12 g silica gel column (DCM/MeOH, 0-15%), affording 1-(4-(4-(5-(2-aminopyridin-4-yl)-2-methyl-3H-imidazo[4,5-b]pyridin-3-yl)-2-fluorophenyl)piperazin-1-yl)ethan-1-one 185 as an orange semi-solid (12 mg, 0.027 mmol, 16% yield, 15% MeOH in DCM). $^1$H NMR (CDCl$_3$) δ: 8.14 (d, J=5.4 Hz, 1H), 8.07 (d, J=8.3 Hz, 1H), 7.74 (d, J=8.3 Hz, 1H), 7.30-7.08 (m, 5H), 4.55 (s, 2H), 3.94-3.81 (m, 2H), 3.77-3.68 (m, 2H), 3.33-3.14 (m, 4H), 2.62 (s, 3H), 2.20 (s, 3H).

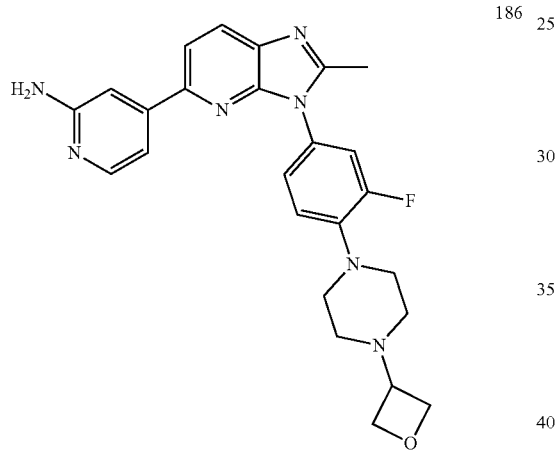

186

186 Was synthesized in a similar manner as depicted in Scheme 73, using 1-(oxetan-3-yl)piperazine.

4-(3-(3-fluoro-4-(4-(oxetan-3-yl)piperazin-1-yl)phenyl)-2-methyl-3H-imidazo[4,5-b]pyridin-5-yl)pyridin-2-amine 186.

Green semi-solid (5.5 mg, 0.012 mmol, 7% yield, 10% MeOH in DCM)

$^1$H NMR (CDCl$_3$) δ: 8.14 (d, J=5.4 Hz, 1H), 8.07 (d, J=8.3 Hz, 1H), 7.74 (d, J=8.3 Hz, 1H), 7.28-7.10 (m, 5H), 4.79-4.68 (m, 5H), 4.56 (s, 2H), 3.35-3.26 (m, 4H), 2.64-2.58 (m, 7H).

INCORPORATION BY REFERENCE

The entire disclosure of each of the patent documents and scientific articles referred to herein is incorporated by reference for all purposes. The following references are herein incorporated by reference in their entireties:

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound selected from:

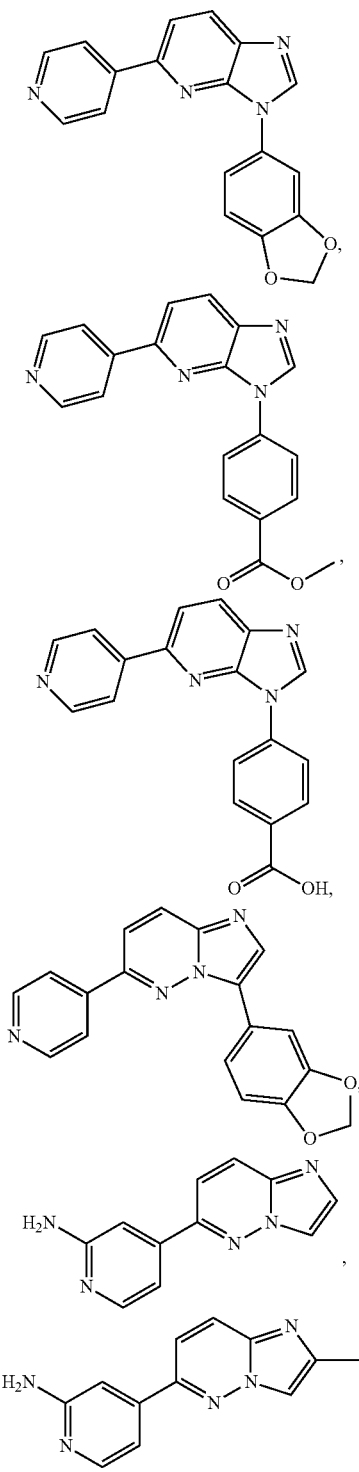

333
-continued
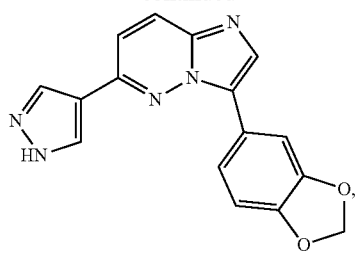
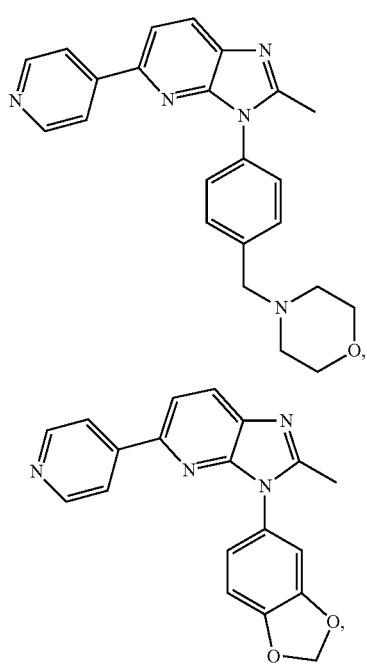
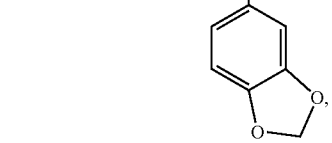
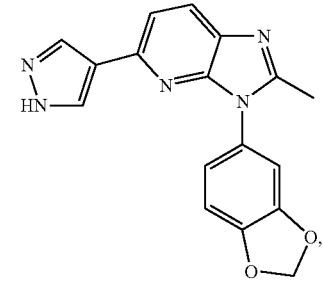
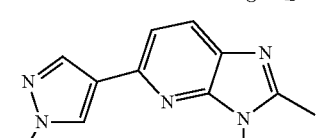
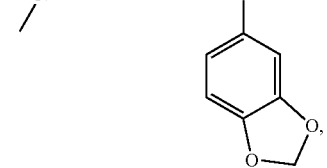
334
-continued
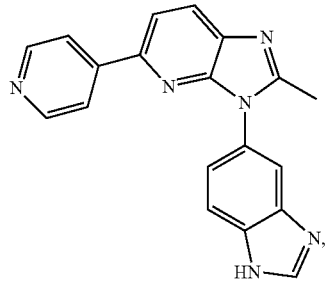
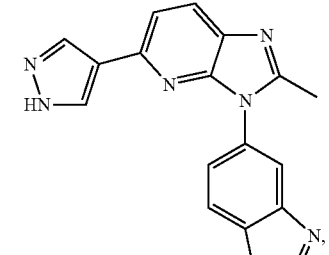
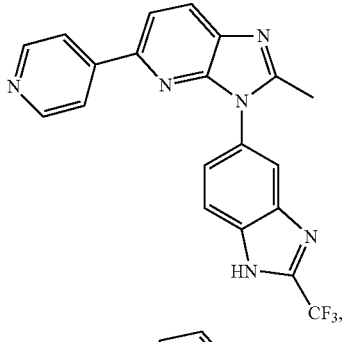
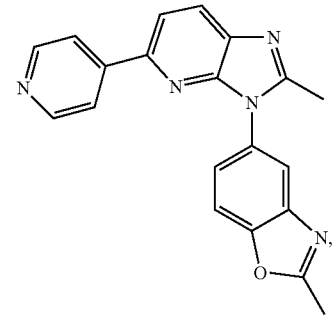
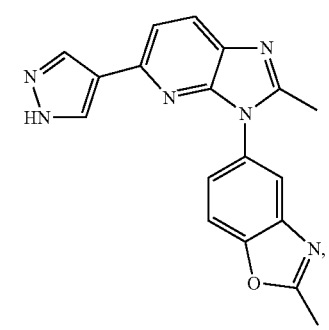

335
-continued
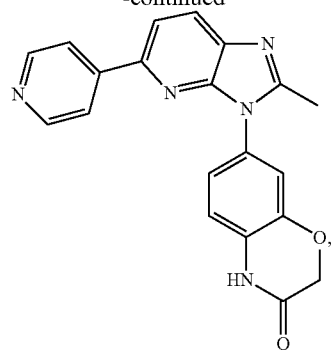
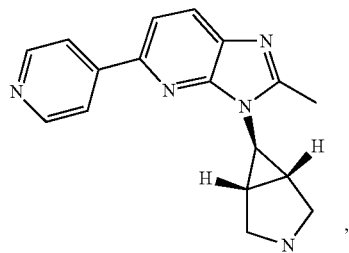
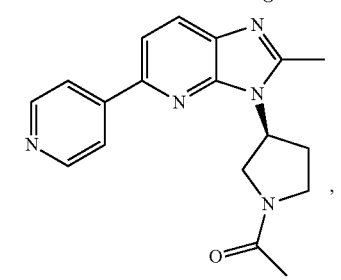
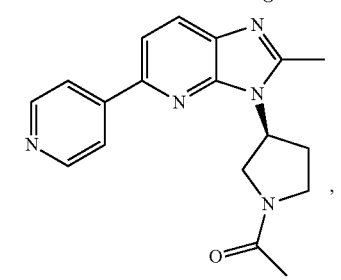
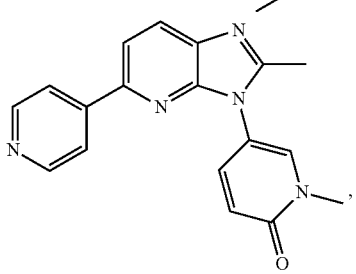
336
-continued
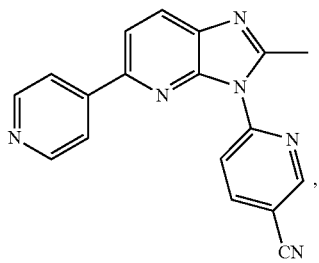
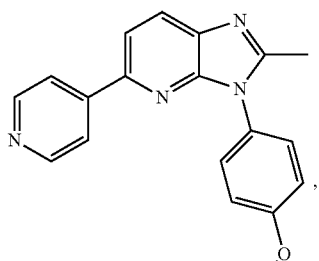
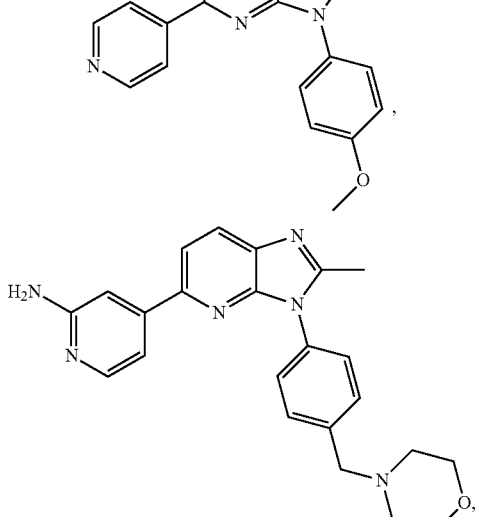
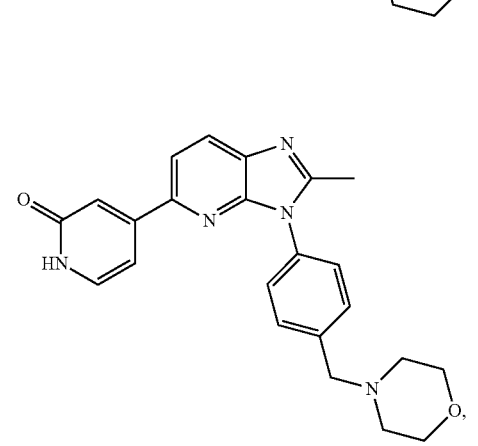
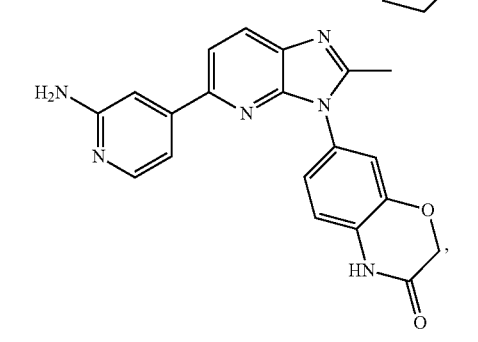

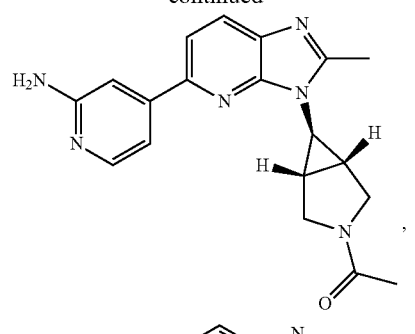
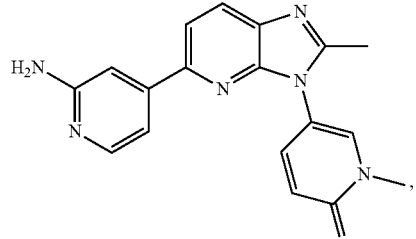
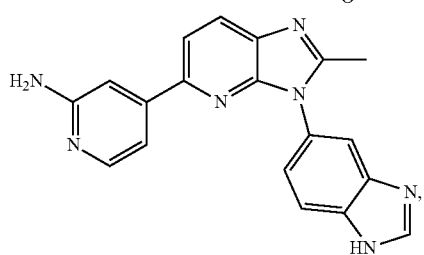
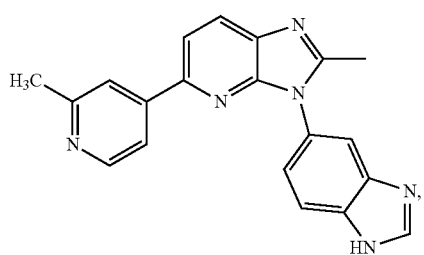
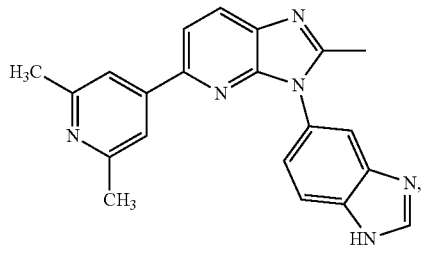
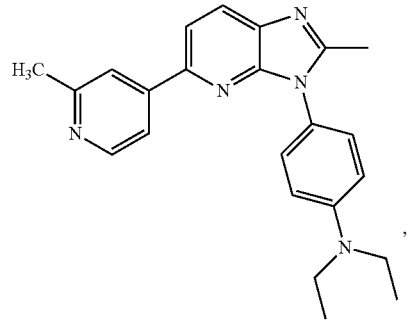
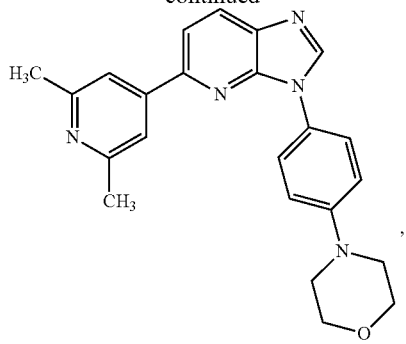
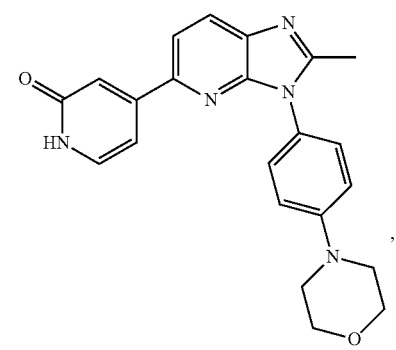
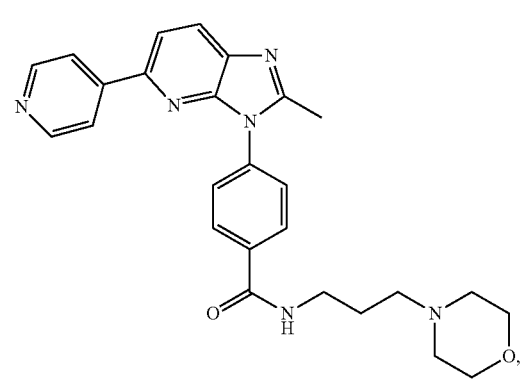
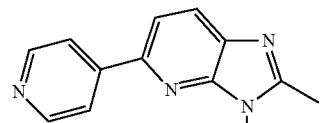
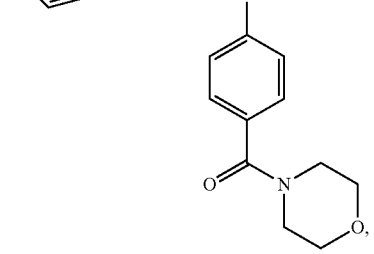

339
-continued
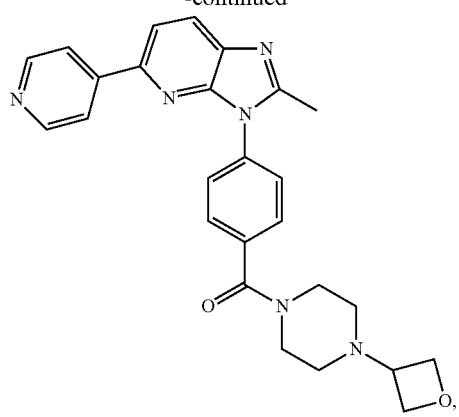
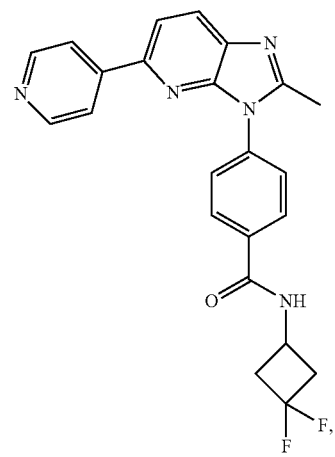
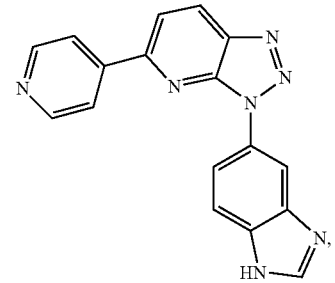
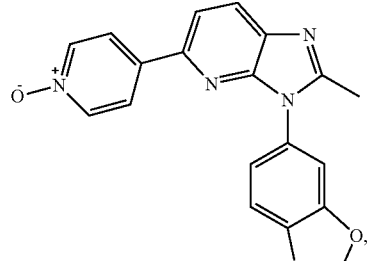
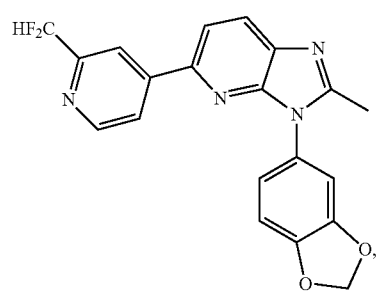
340
-continued
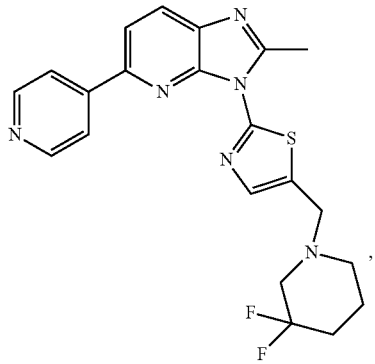
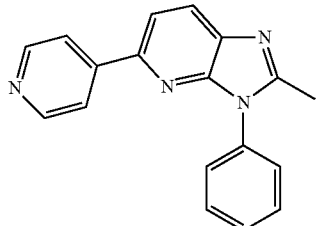
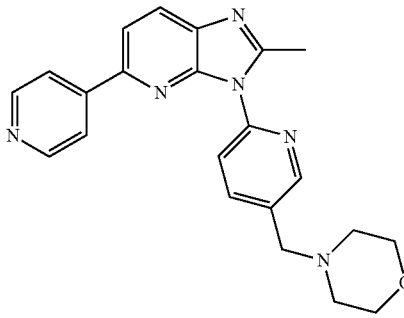
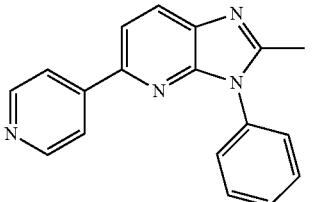
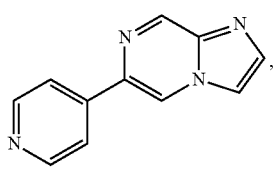

341
-continued
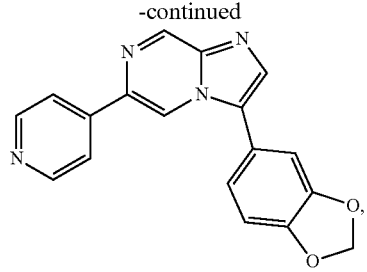
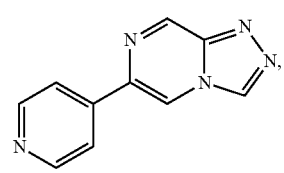
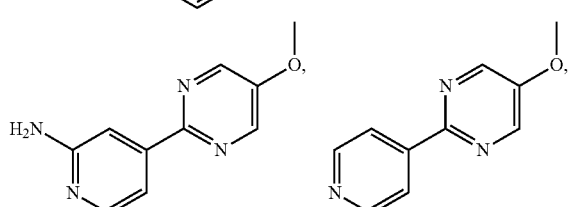
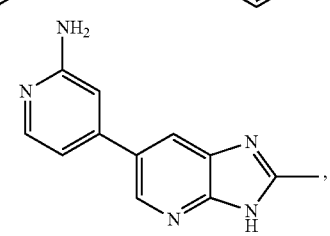
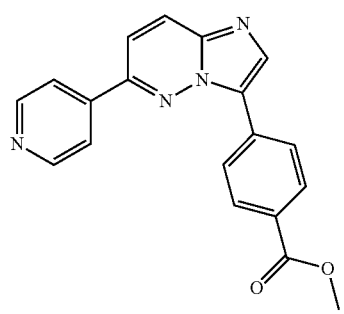
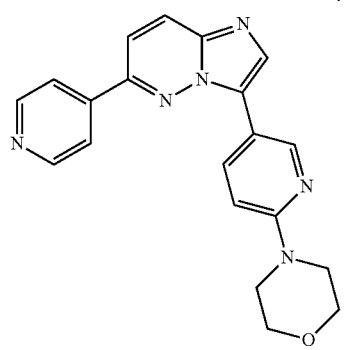
342
-continued
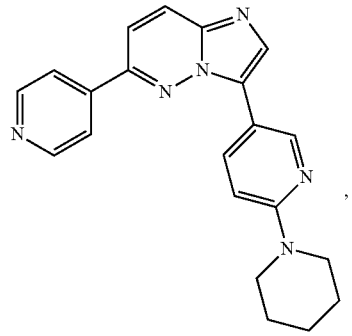
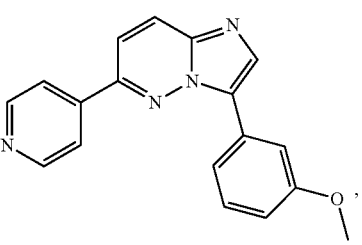
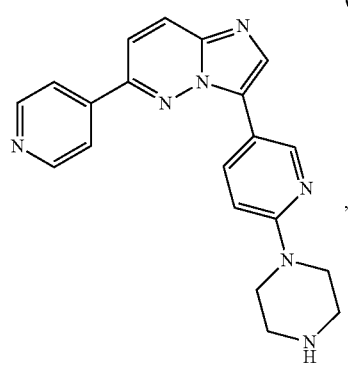
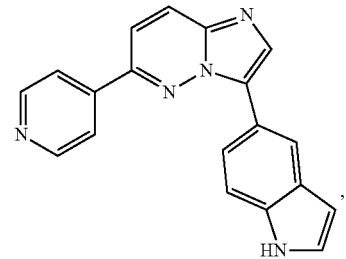
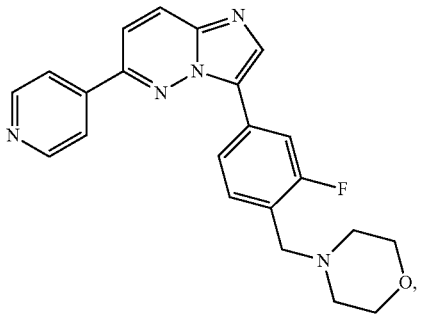

343
-continued

344
-continued

345
-continued
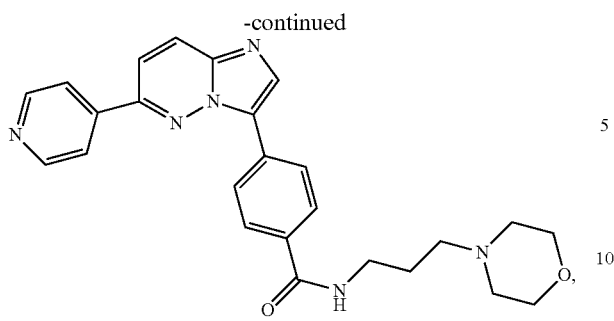
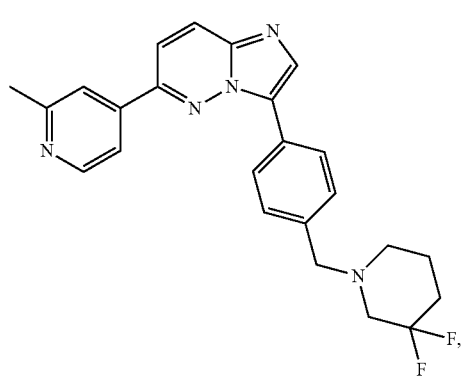
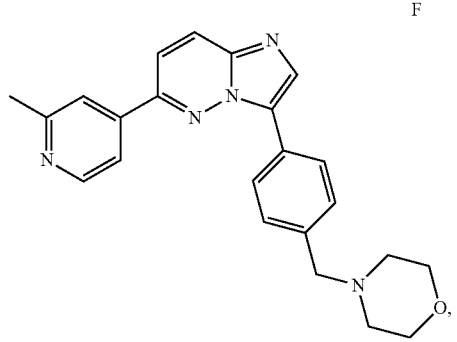
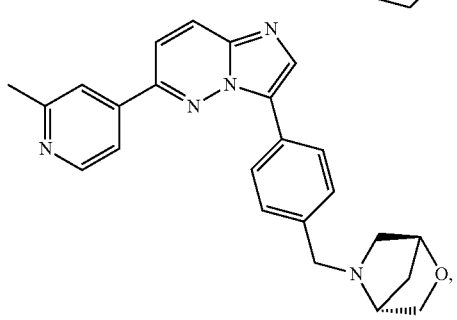
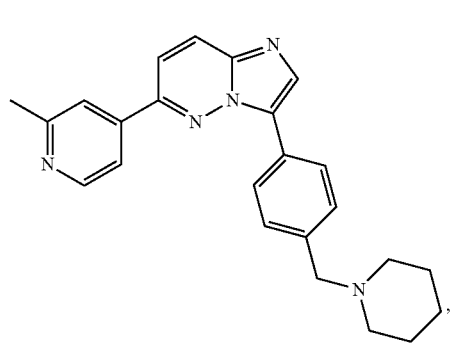
346
-continued
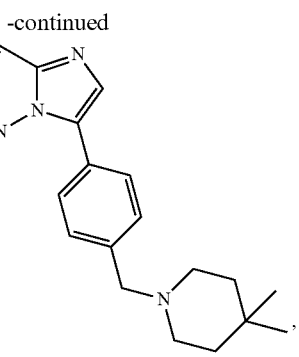
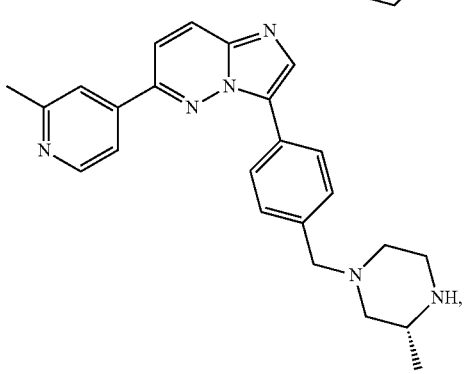
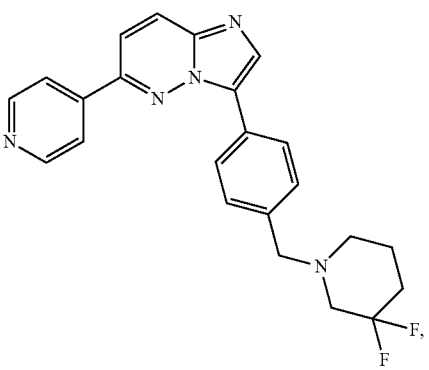
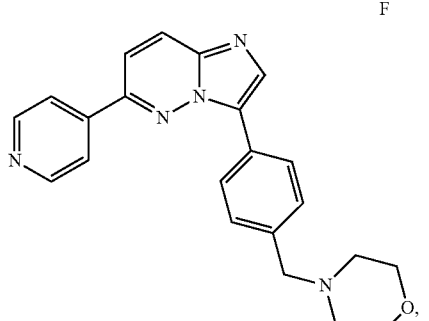
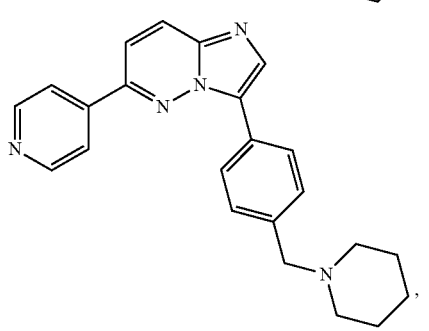

347
-continued
348
-continued
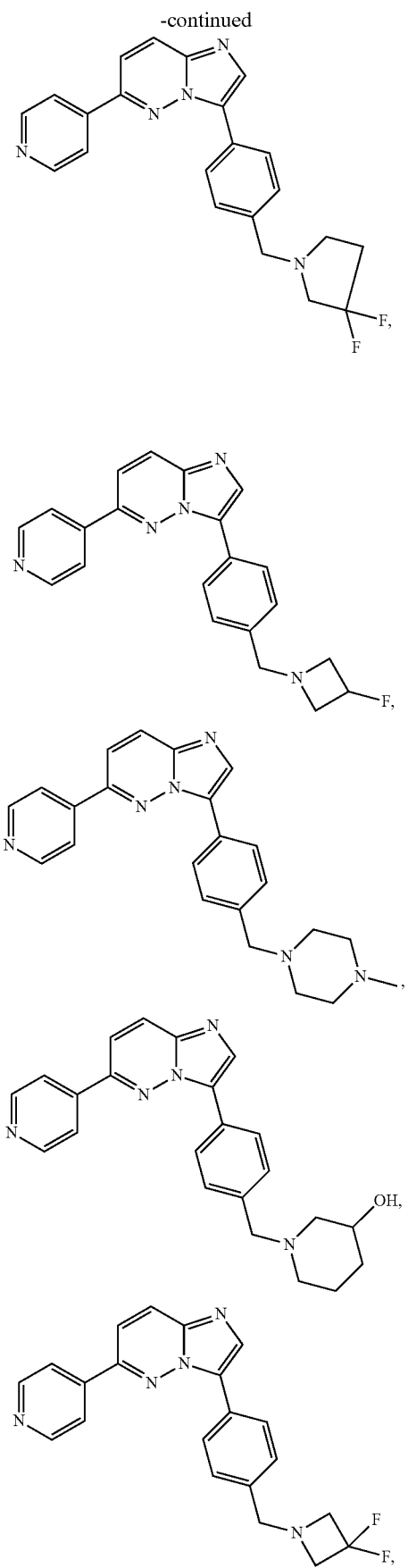
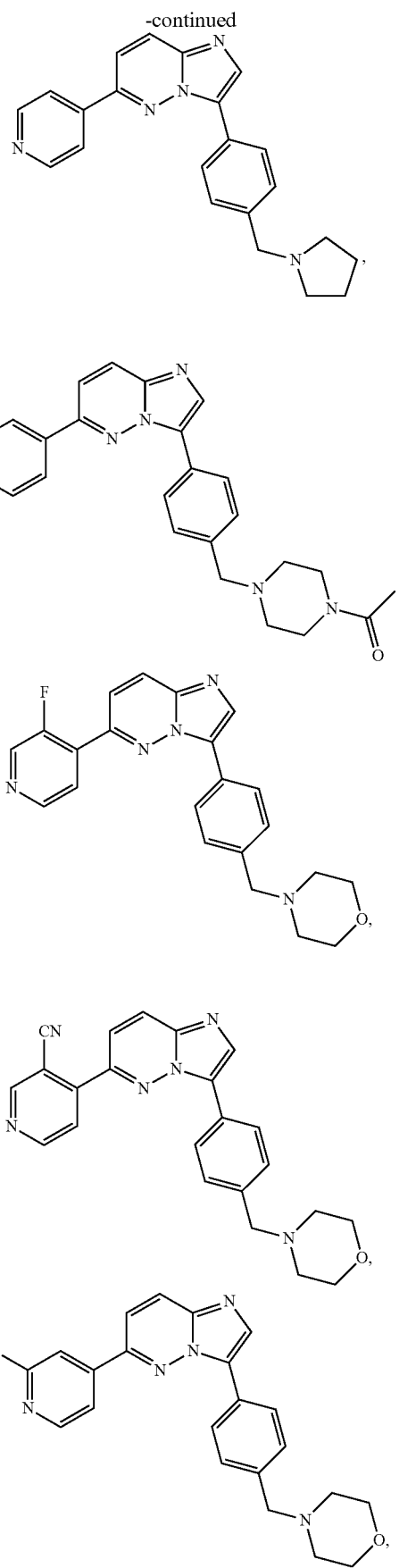

-continued
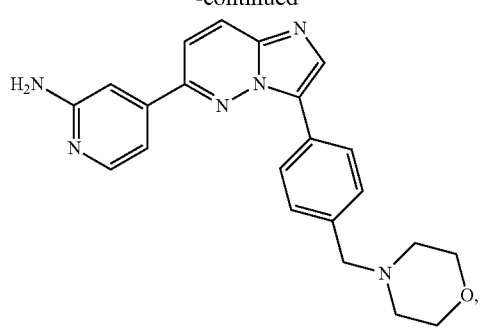
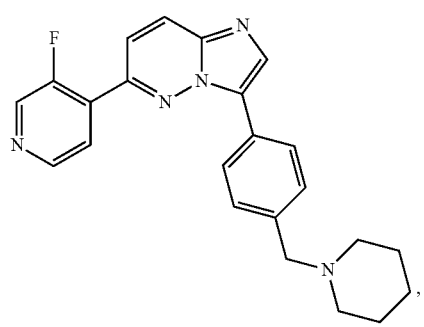
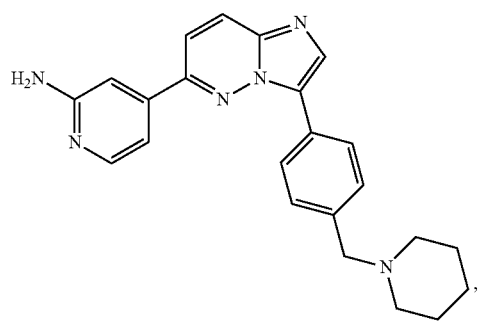
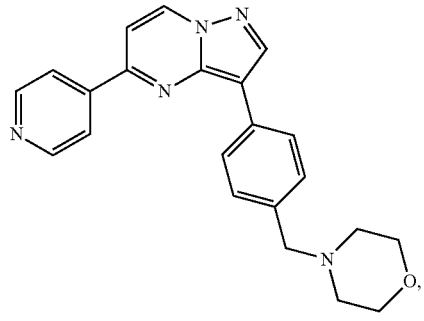
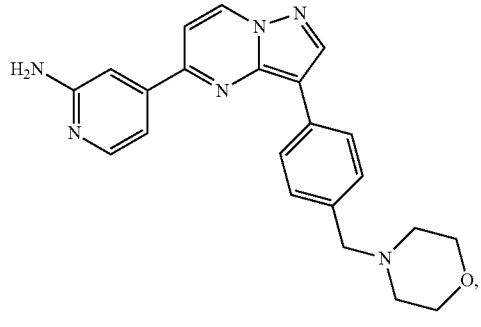
-continued
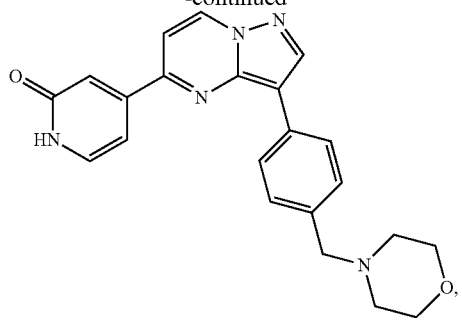
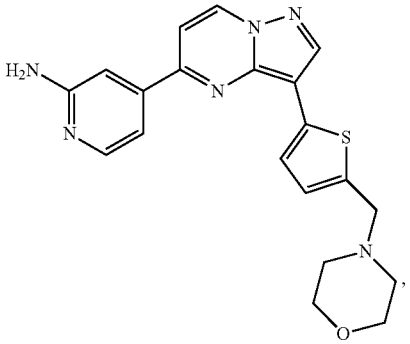
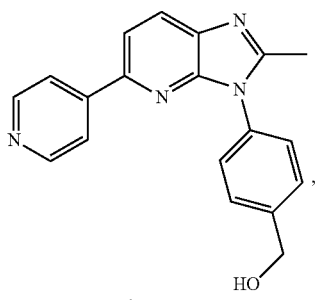
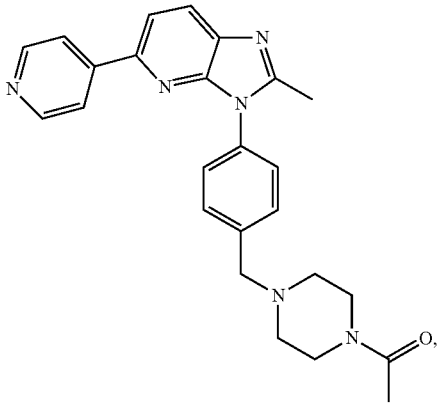
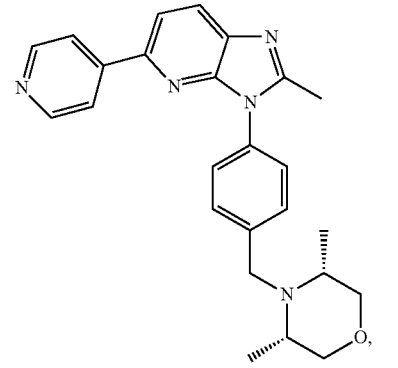

351
-continued
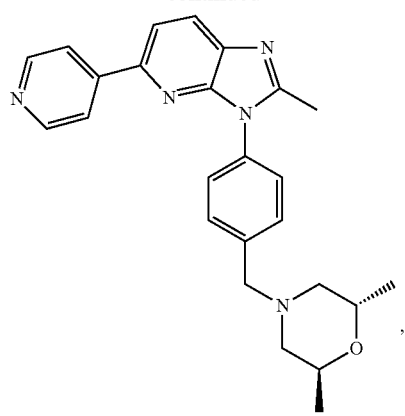
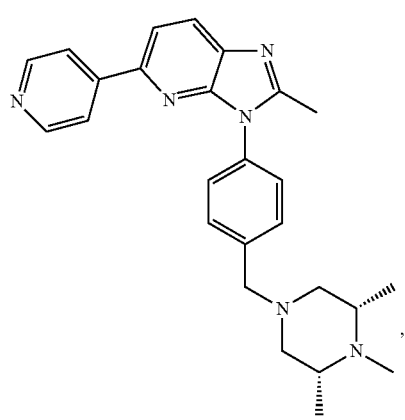
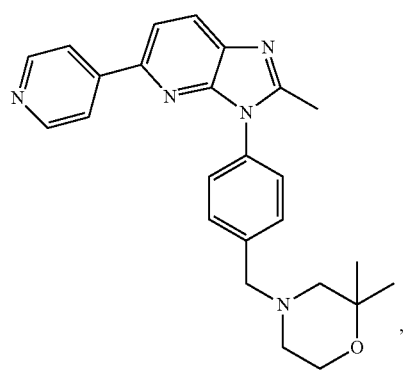
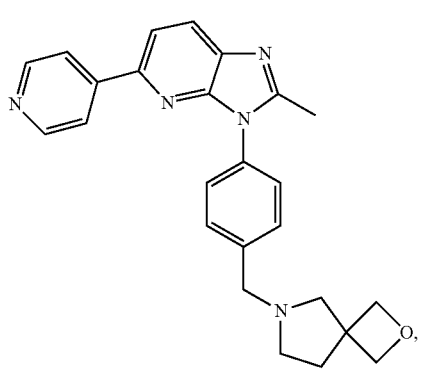
352
-continued
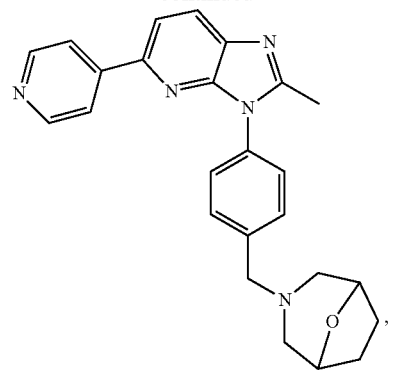
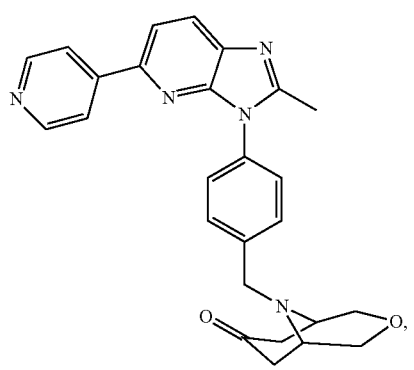
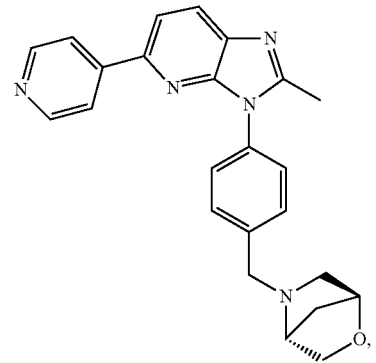
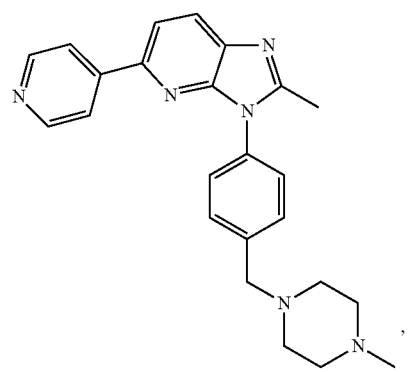

353
-continued
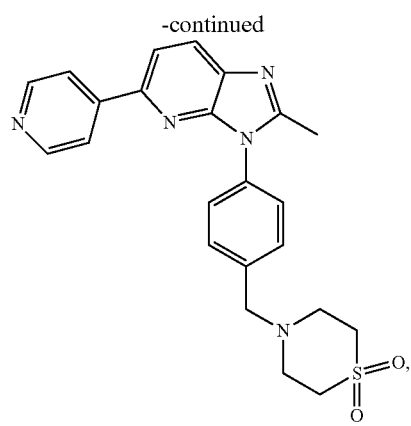
354
-continued
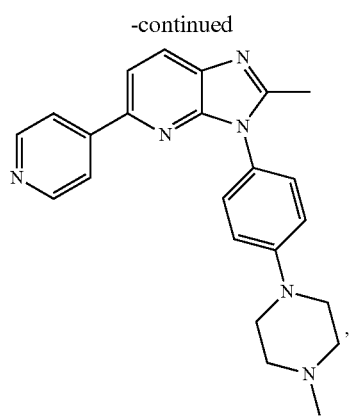
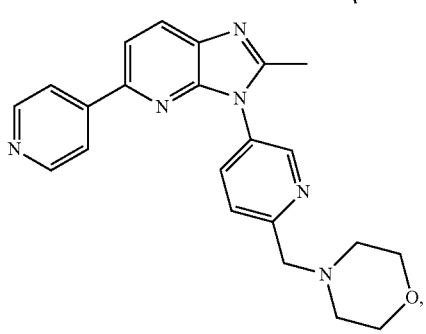
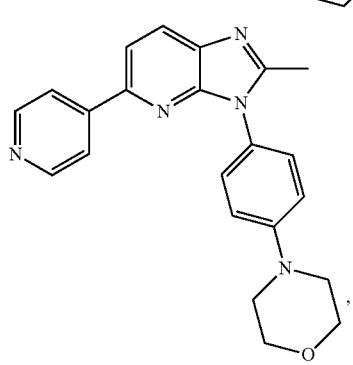
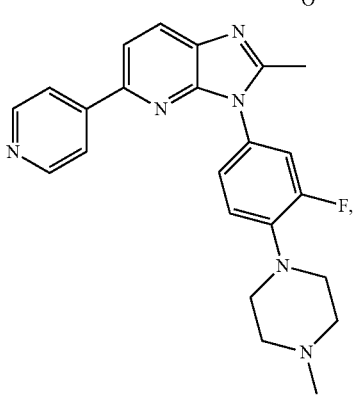
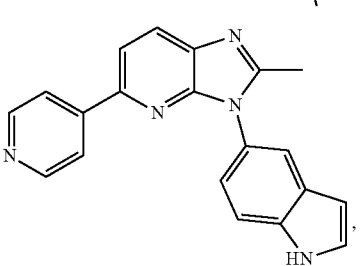

355
-continued
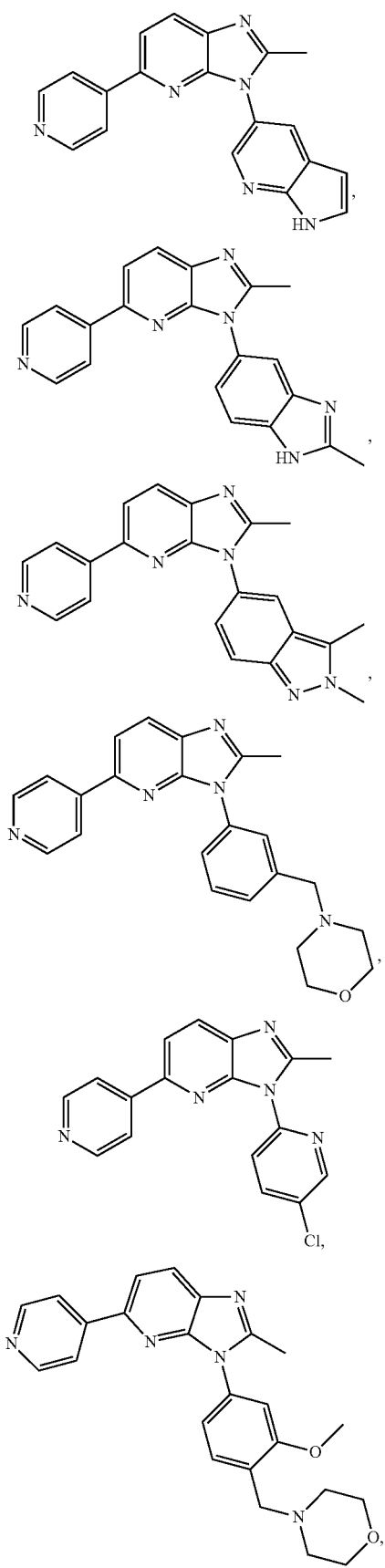
356
-continued
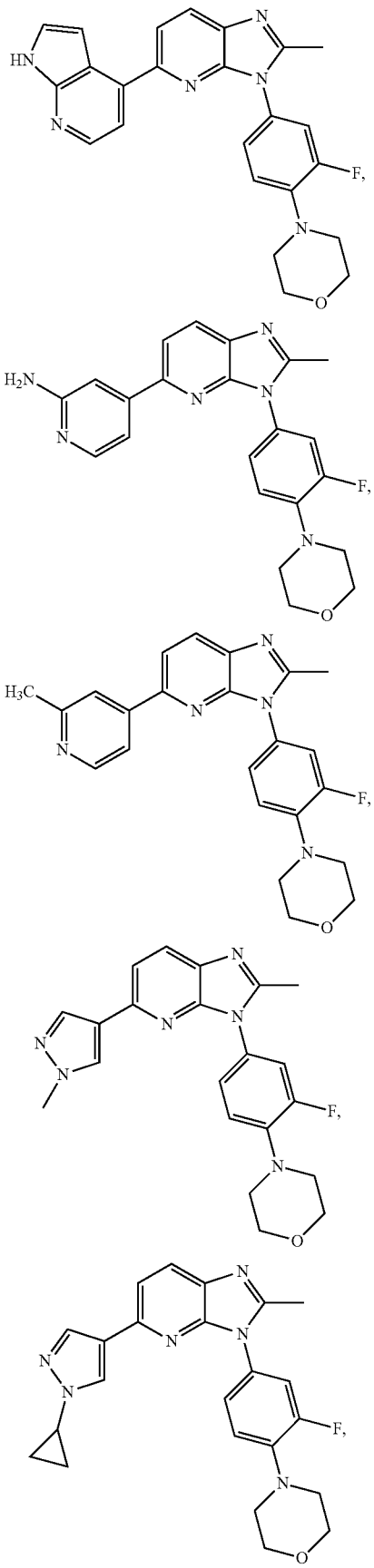

357
-continued
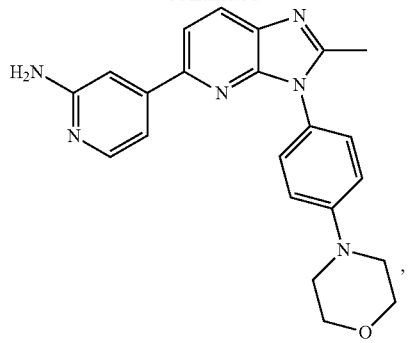
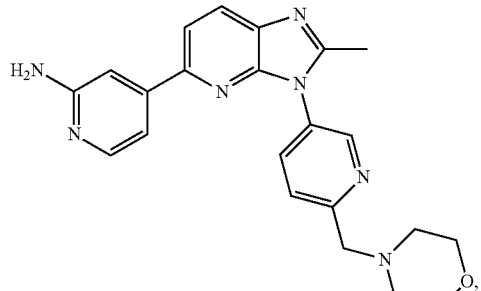
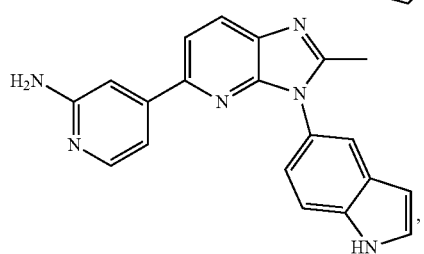
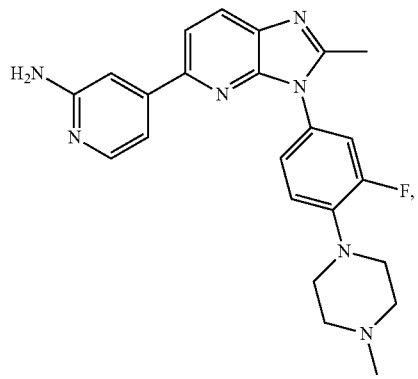
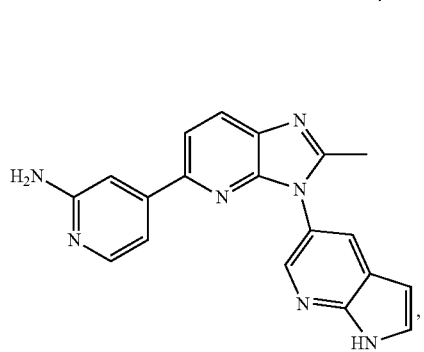
358
-continued
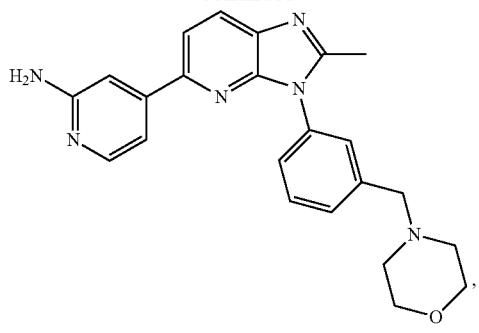
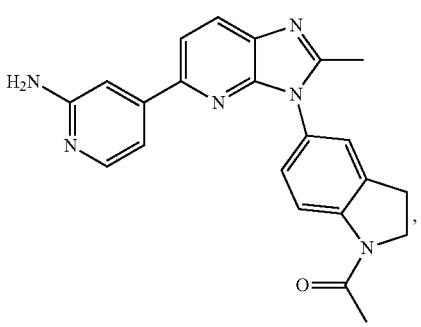
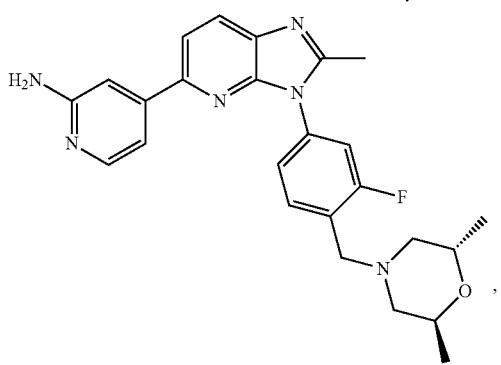
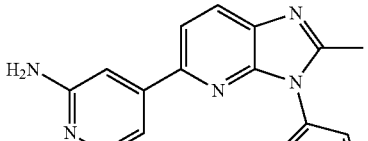
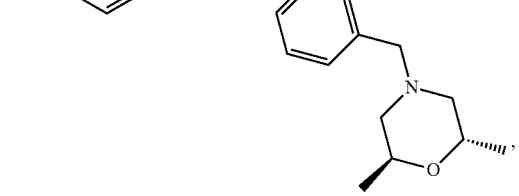
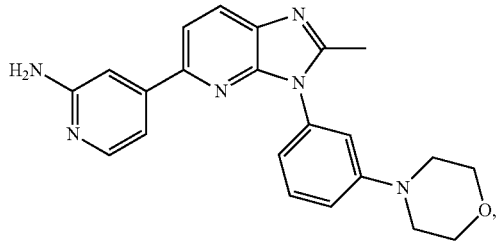

-continued

361
-continued
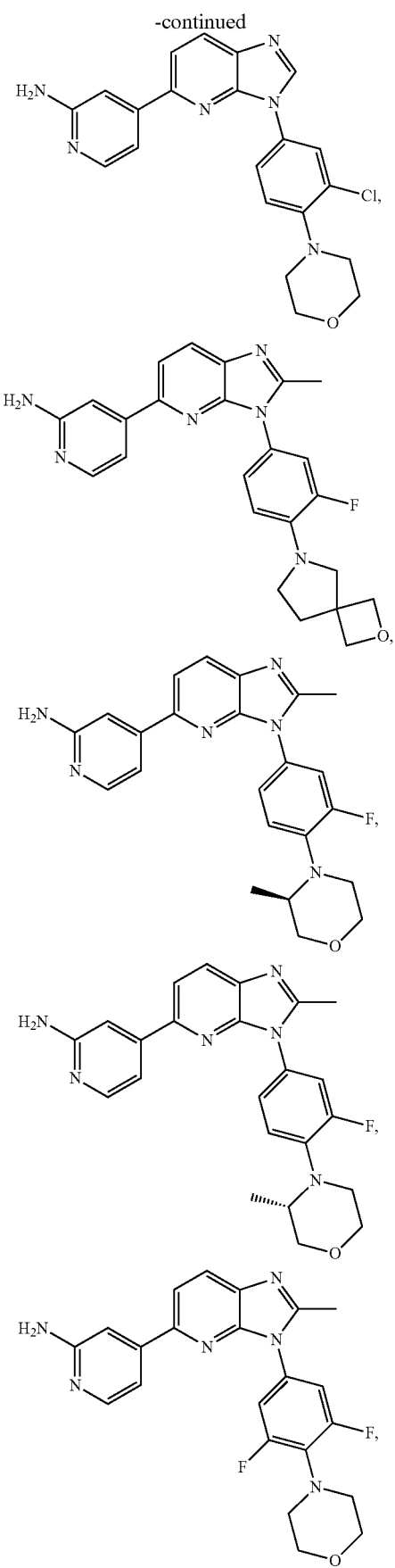
362
-continued
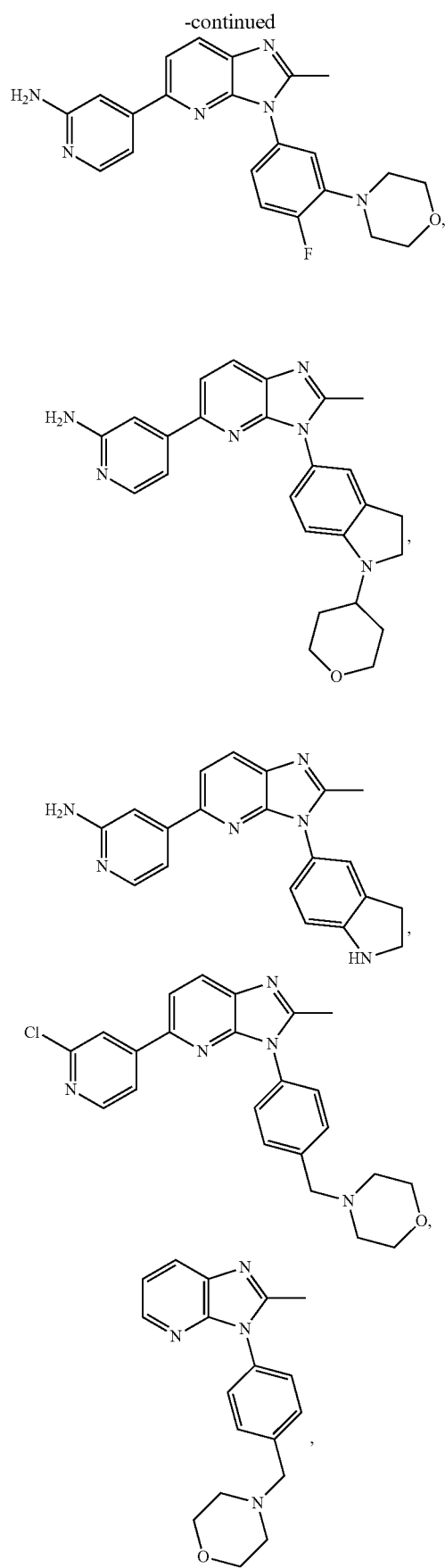

363
-continued
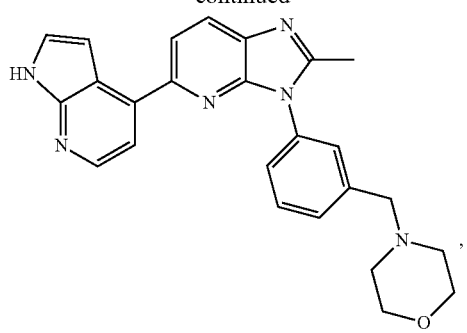
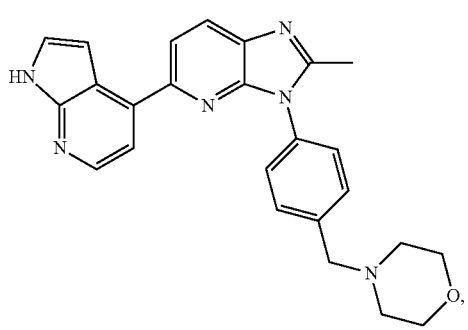
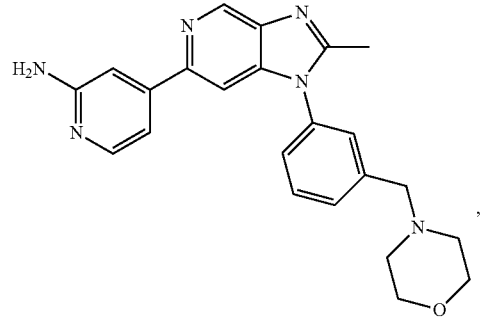
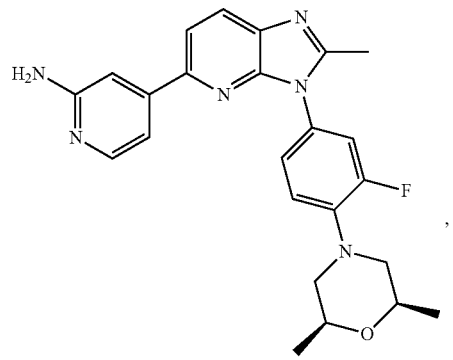
364
-continued
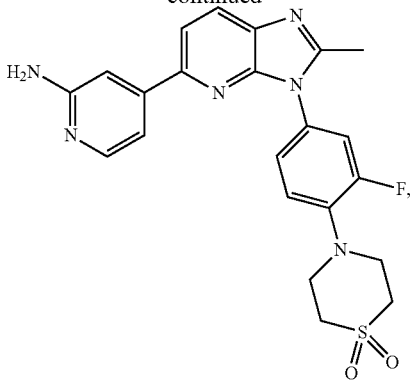
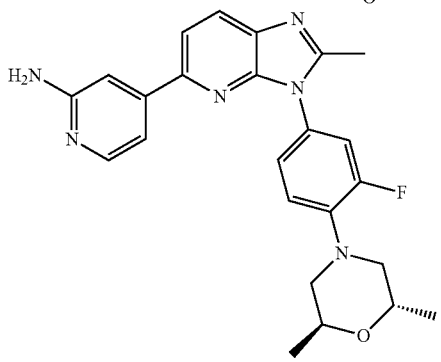
* * * * *